(12) United States Patent
Ashcraft et al.

(10) Patent No.: US 8,969,346 B2
(45) Date of Patent: Mar. 3, 2015

(54) AMINO-PYRIDAZINE SKELETAL MUSCLE MODULATORS

(75) Inventors: Luke W. Ashcraft, San Francisco, CA (US); Gustave Bergnes, Pacifica, CA (US); Scott Collibee, San Carlos, CA (US); Chihyuan Chuang, Millbrae, CA (US); Jeff Gardina, South San Francisco, CA (US); Bradley P. Morgan, Moraga, CA (US); Alex R. Muci, San Francisco, CA (US); Xiangping Qian, Foster City, CA (US); Jeffrey M Warrington, San Mateo, CA (US); Zhe Yang, Daly City, CA (US); Pu-Ping Lu, Foster City, CA (US); Antonio Romero, San Mateo, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 13/642,207

(22) PCT Filed: Apr. 22, 2011

(86) PCT No.: PCT/US2011/033605
§ 371 (c)(1),
(2), (4) Date: Jan. 30, 2013

(87) PCT Pub. No.: WO2011/133882
PCT Pub. Date: Oct. 27, 2011

(65) Prior Publication Data
US 2013/0143862 A1 Jun. 6, 2013

Related U.S. Application Data

(60) Provisional application No. 61/327,538, filed on Apr. 23, 2010, provisional application No. 61/412,302, filed on Nov. 10, 2010.

(51) Int. Cl.
| | | |
|---|---|---|
| A61K 31/50 | (2006.01) |
| C07D 237/20 | (2006.01) |
| C07D 401/12 | (2006.01) |
| C07D 237/24 | (2006.01) |
| C07D 401/04 | (2006.01) |
| C07D 403/04 | (2006.01) |
| C07D 403/06 | (2006.01) |
| C07D 409/14 | (2006.01) |
| C07D 411/04 | (2006.01) |
| C07D 413/04 | (2006.01) |
| C07D 413/14 | (2006.01) |
| C07D 417/14 | (2006.01) |
| C07D 487/04 | (2006.01) |
| C07D 487/10 | (2006.01) |
| C07D 513/04 | (2006.01) |

(Continued)

(52) U.S. Cl.
CPC ............. *C07D 401/12* (2013.01); *A61K 31/50* (2013.01); *C07D 237/20* (2013.01); *C07D 237/24* (2013.01); *C07D 401/04* (2013.01); *C07D 403/04* (2013.01); *C07D 403/06* (2013.01); *C07D 409/14* (2013.01); *C07D 411/04* (2013.01); *C07D 413/04* (2013.01); *C07D 413/14* (2013.01); *C07D 417/14* (2013.01); *C07D 487/04* (2013.01); *C07D 487/10* (2013.01); *C07D 513/04* (2013.01); *C07D 401/14* (2013.01); *C07D 405/14* (2013.01)
USPC .......................................... 514/247; 544/224

(58) Field of Classification Search
CPC .............................. A61K 31/50; C07D 237/20
USPC .......................................... 514/247; 544/224
See application file for complete search history.

(56) References Cited

U.S. PATENT DOCUMENTS

| | | | |
|---|---|---|---|
| 4,157,392 A | 6/1979 | Gullo et al. |
| 4,169,158 A | 9/1979 | Laborit |

(Continued)

FOREIGN PATENT DOCUMENTS

| | | |
|---|---|---|
| CA | 2 757 188 | 10/2010 |
| EP | 0 429 344 | 5/1991 |

(Continued)

OTHER PUBLICATIONS

Refaat, et al. Bulletin of the Faculty of Pharmacy (Cairo University), 42(2), 2004, 415-423.*

(Continued)

*Primary Examiner* — Douglas M Willis

(57) ABSTRACT

Provided are compounds of Formula I:

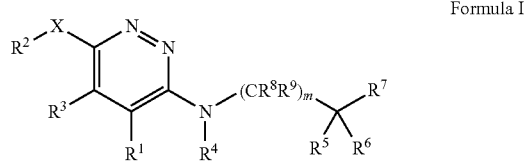

Formula I or a pharmaceutically acceptable salt thereof, wherein $R^1$, $R^2$, $R^3$, $R^4$, $R^5$, $R^6$, $R^7$, $R^8$, $R^9$, X and m are as defined herein.

Also provided is a pharmaceutically acceptable composition comprising a compound of Formula I, or a pharmaceutically acceptable salt thereof.

Also provided are methods of using a compound of Formula I, or a pharmaceutically acceptable salt thereof.

51 Claims, No Drawings

(51) Int. Cl.
*C07D 401/14* (2006.01)
*C07D 405/14* (2006.01)

(56) References Cited

U.S. PATENT DOCUMENTS

| | | | |
|---|---|---|---|
| 4,251,658 | A | 2/1981 | Szilagyi et al. |
| 4,514,397 | A | 4/1985 | Wermuth et al. |
| 5,461,053 | A * | 10/1995 | Boigegrain et al. ............ 514/247 |
| 6,297,375 | B1 | 10/2001 | Boes et al. |
| 6,780,869 | B1 | 8/2004 | Greene et al. |
| 7,157,455 | B2 | 1/2007 | Bartkovitz et al. |
| 7,507,737 | B2 | 3/2009 | Edwards et al. |
| 7,652,009 | B2 | 1/2010 | Kim et al. |
| 2003/0195221 | A1 | 10/2003 | Cai et al. |
| 2007/0173465 | A9 | 7/2007 | Monahan et al. |
| 2007/0197505 | A1 | 8/2007 | Morgan et al. |
| 2007/0197507 | A1 | 8/2007 | Morgan et al. |
| 2008/0318899 | A1 | 12/2008 | Watterson et al. |
| 2009/0029345 | A1 | 1/2009 | Russell et al. |
| 2009/0143385 | A1 * | 6/2009 | Buettelmann et al. ...... 514/236.5 |
| 2009/0264433 | A1 | 10/2009 | Russell et al. |
| 2010/0029942 | A1 | 2/2010 | Cesco-Cancian |
| 2014/0206709 | A1 | 7/2014 | Yang et al. |

FOREIGN PATENT DOCUMENTS

| | | |
|---|---|---|
| EP | 1 078 632 | 2/2001 |
| EP | 2 017 261 | 1/2009 |
| WO | WO 03/044021 | 5/2003 |
| WO | WO 2006/066172 | 6/2006 |
| WO | WO 2006/050389 | 11/2006 |
| WO | WO 2007/048802 | 5/2007 |
| WO | WO 2007/075377 | 7/2007 |
| WO | WO2007-075377 A2 | 7/2007 |
| WO | WO 2007/089336 | 8/2007 |
| WO | WO 2008/071646 | 6/2008 |
| WO | WO 2009/152168 | 12/2009 |
| WO | WO 2010/022121 | 2/2010 |
| WO | WO-2011/133888 A1 | 10/2011 |
| WO | WO-2011/133920 A1 | 10/2011 |
| WO | WO 2013/151938 | 10/2013 |
| WO | WO/2013/155262 | 10/2013 |

OTHER PUBLICATIONS

U.S. Appl. No. 13/642,206, filed Apr. 22, 2011, Yang et al.
U.S. Appl. No. 13/642,227, filed Apr. 22, 2011, Ashcraft et al.
International Search Report & Written Opinion in PCT/US2011/033614 (Jun. 28, 2011).
International Search Report & Written Opinion in PCT/US2011/033650 (Jul. 1, 2011).
Bressi et al., "Adenosine Analogues as Inhibitors of Trypanosoma Brucei Phosphoglycerate Kinase: Elucidation of a Novel Binding Mode for a 2-AMINO-N6-Substituted Adenosine" J. Med. Chem. 43:4135-4150 (2000).
Contreras et al., "Aminopyridazines acetylcholinesterase inhibitors" J. Med. Chem. 42:730-741 (1999).
Cote et al., "Substituted aminopyridines as potent and selective phosphodiesterase-4 inhibitors" Bioorganic & Medicinal Chemistry Letters, 13:741-744 (2003).
Dimauro et al., "Structure-Guided Design of Aminopyrimidine Amides as Potent, Selective Inhibitors of Lymphocyte Specific Kinase: Synthesis, Structure-Activity Relationships, and Inhibition of in Vivo T Cell Activation", J. Med. Chem. 51:1681-1694 (2008).
Hamby et al., "Structure-Activity Relationships for a Novel Series of Pyrid0[2,3-D]Pyrimidine Tyrosine Kinase Inhibitors" J. Med. Chem. 40:2296-2303 (1997).
Hiatt, WR et al. 'Efficacy and Tolerability of the Novel Fast Skeletal Muscle Troponin Activator, CK-2017357, in Patients with Claudication.' 22nd Annual Sessions of the Society for Vascular Medicine, Boston, MA, Jun. 2011 (poster presentation); [Retrieved on Aug. 20, 2013). Retrieved from the Internet at <URL: www.cytokinetics.com/pdf/4022-20110531-rev004.pdf>.
International Search Report & Written Opinion in PCT/US2013/036114 (Nov. 5, 2013).
International Search Report & Written Opinion in PCT/US2013/034824 (Jun. 13, 2013).
Ishida et al. "Novel and orally active 5-(1,3,4-oxadiazol-2-yl)pyrimidine derivatives as selective FLT3 inhibitors" Bioorganic & Medicinal Chemistry Letters, 18:5472-5477 (2008).
March et al. "Antimalarials 3 I,2,4-Triazines" J. Med. Chem. 19:845-848 (1976).
Martyn et al., "Synthesis and antiplasmodial activity of novel 2,4-diaminopyrimidine" Bioorganic & Medicinal Chemistry Letters, 20: 228-231 (2010).
Okumura et al., "Synthesis of Isokinetin, 2-N-furfurylaminopurine and its Leaf-growth Activity (Studies of Isokinetin and its Analogs. Part I)" Bulletin of the Chemical Society of Japan, 33:1471-1472 (1960).
Allingham et al., "The structural basis of blebbistatin inhibition and specificy for myoson II." Nature Structural & Molecular Biology 12:4, pp. 378-379 (Apr. 2005).
PCT/US2011/033605. International Search Report & Written Opinion (Jul. 6, 2011).
Refaat et al. Bulletin of the Faculty of Pharmacy (Cairo University), 42(2), 2004, 415-423.

* cited by examiner

AMINO-PYRIDAZINE SKELETAL MUSCLE MODULATORS

This application is a 35 USC 371 National Stage Entry of PCT/US2011/033605 filed Apr. 22, 2011, and claims the benefit of U.S. Provisional Application Nos. 61/327,538, filed Apr. 23, 2010, and 61/412,302, filed Nov. 10, 2010, each of which is incorporated by reference in its entirety for all purposes.

The cytoskeleton of skeletal and cardiac muscle cells is unique compared to that of all other cells. It consists of a nearly crystalline array of closely packed cytoskeletal proteins called the sarcomere. The sarcomere is elegantly organized as an interdigitating array of thin and thick filaments. The thick filaments are composed of myosin, the motor protein responsible for transducing the chemical energy of ATP hydrolysis into force and directed movement. The thin filaments are composed of actin monomers arranged in a helical array. There are four regulatory proteins bound to the actin filaments, which allows the contraction to be modulated by calcium ions. An influx of intracellular calcium initiates muscle contraction; thick and thin filaments slide past each other driven by repetitive interactions of the myosin motor domains with the thin actin filaments.

Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes. Myosin-II forms homo-dimers resulting in two globular head domains linked together by a long alpha-helical coiled-coiled tail to form the core of the sarcomere's thick filament. The globular heads have a catalytic domain where the actin binding and ATPase functions of myosin take place. Once bound to an actin filament, the release of phosphate (cf. ADP-Pi to ADP) signals a change in structural conformation of the catalytic domain that in turn alters the orientation of the light-chain binding lever arm domain that extends from the globular head; this movement is termed the powerstroke. This change in orientation of the myosin head in relationship to actin causes the thick filament of which it is a part to move with respect to the thin actin filament to which it is bound. Un-binding of the globular head from the actin filament ($Ca^{2+}$ regulated) coupled with return of the catalytic domain and light chain to their starting conformation/orientation completes the catalytic cycle, responsible for intracellular movement and muscle contraction.

Tropomyosin and troponin mediate the calcium effect on the interaction on actin and myosin. The troponin complex is comprised of three polypeptide chains: troponin C, which binds calcium ions; troponin I, which binds to actin; and troponin T, which binds to tropomyosin. The skeletal troponin-tropomyosin complex regulates the myosin binding sites extending over several actin units at once.

Troponin, a complex of the three polypeptides described above, is an accessory protein that is closely associated with actin filaments in vertebrate muscle. The troponin complex acts in conjunction with the muscle form of tropomyosin to mediate the $Ca^{2+}$ dependency of myosin ATPase activity and thereby regulate muscle contraction. The troponin polypeptides T, I, and C, are named for their tropomyosin binding, inhibitory, and calcium binding activities, respectively. Troponin T binds to tropomyosin and is believed to be responsible for positioning the troponin complex on the muscle thin filament. Troponin I binds to actin, and the complex formed by troponins I and T, and tropomyosin inhibits the interaction of actin and myosin. Skeletal troponin C is capable of binding up to four calcium molecules. Studies suggest that when the level of calcium in the muscle is raised, troponin C exposes a binding site for troponin I, recruiting it away from actin. This causes the tropomyosin molecule to shift its position as well, thereby exposing the myosin binding sites on actin and stimulating myosin ATPase activity.

Human skeletal muscle is composed of different types of contractile fibers, classified by their myosin type and termed either slow or fast fibers. Table 1 summarizes the different proteins that make up these types of muscle.

TABLE 1

| | Muscle Fiber Type | |
|---|---|---|
| | Fast skeletal | Slow Skeletal |
| Myosin Heavy Chain | IIa, (IIb*), IIx/d | Cardiac β |
| Troponin I (TnI) | TnI fast SK | TnI slow SK |
| Troponin T (TnT) | TnT fast SK | TnT slow SK |
| Troponin C (TnC) | TnC fast SK | TnC slow/cardiac |
| Tropomyosin | TM-β/TM-α/TPM 3 | TM-β/TM-αs |

*MHC IIb is not expressed in human muscle but is present in rodents and other mammals.

In healthy humans most skeletal muscles are composed of both fast and slow fibers, although the proportions of each vary with muscle type. Slow skeletal fibers, often called type I fibers, have more structural similarity with cardiac muscle and tend to be used more for fine and postural control. They usually have a greater oxidative capacity and are more resistant to fatigue with continued use. Fast skeletal muscle fibers, often called type II fibers, are classified into fast oxidative (IIa) and fast glycolytic (type IIx/d) fibers. While these muscle fibers have different myosin types, they share many components including the troponin and tropomyosin regulatory proteins. Fast skeletal muscle fibers tend to exert greater force but fatigue faster than slow skeletal muscle fibers and are functionally useful for acute, large scale movements such as rising from a chair or correcting falls.

Muscle contraction and force generation is controlled through nervous stimulation by innervating motor neurons. Each motor neuron may innervate many (approximately 100-380) muscle fibers as a contractile whole, termed a motor unit. When a muscle is required to contract, motor neurons send stimuli as nerve impulses (action potentials) from the brain stem or spinal cord to each fiber within the motor unit. The contact region between nerve and muscle fibers is a specialized synapse called the neuromuscular junction (NMJ). Here, membrane depolarizing action potentials in the nerve are translated into an impulse in the muscle fiber through release of the neurotransmitter acetylcholine (ACh). ACh triggers a second action potential in the muscle that spreads rapidly along the fiber and into invaginations in the membrane, termed t-tubules. T-tubules are physically connected to Ca2+ stores within the sarcoplasmic reticulum (SR) of muscle via the dihydropyridine receptor (DHPR). Stimulation of the DHPR activates a second Ca2+ channel in the SR, the ryanodine receptor, to trigger the release of Ca2+ from stores in the SR to the muscle cytoplasm where it can interact with the troponin complex to initiate muscle contraction. If muscle stimulation stops, calcium is rapidly taken back up into the SR through the ATP dependent Ca2+ pump, SERCA.

Muscle function can become compromised in disease by many mechanisms. Examples include the frailty associated with old age (termed sarcopenia) and cachexia syndromes associated with diseases such as cancer, heart failure, chronic obstructive pulmonary disease (COPD), and chronic kidney disease/dialysis. Severe muscular dysfunction can arise from neuromuscular diseases (such as Amyotrophic Lateral Sclerosis (ALS), spinal muscular atrophy (SMA) and myasthenia gravis) or muscular myopathies (such as muscular dystrophies). Additionally, muscle function may become compromised due to rehabilitation-related deficits, such as those associated with recovery from surgery (e.g. post-surgical muscle weakness), prolonged bed rest, or stroke rehabilitation. Additional examples of diseases or conditions where muscle function becomes compromised include peripheral vascular disease (e.g., claudication), chronic fatigue syndrome, metabolic syndrome, and obesity.

Accordingly, there is a need for the development of new compounds that modulate skeletal muscle contractility. There remains a need for agents that exploit new mechanisms of action and which may have better outcomes in terms of relief of symptoms, safety, and patient mortality, both short-term and long-term and an improved therapeutic index.

Provided is a compound of Formula I:

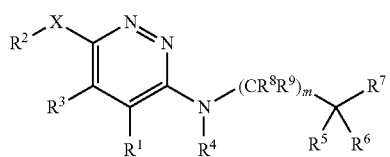

Formula I or a pharmaceutically acceptable salt thereof, wherein $R^1$, $R^2$, $R^3$, $R^4$, $R^5$, $R^6$, $R^7$, $R^8$, $R^9$, X and m are as defined herein.

Also provided is a pharmaceutically acceptable composition comprising a compound of Formula I, or a pharmaceutically acceptable salt thereof.

Also provided are methods for treating a disease or condition responsive to modulation of the contractility of the skeletal sarcomere, for example, modulation of the troponin complex of the fast skeletal muscle sarcomere through one or more of fast skeletal myosin, actin, tropomyosin, troponin C, troponin I, and troponin T, and fragments and isoforms thereof.

As used in the present specification, the following words and phrases are generally intended to have the meanings as set forth below, except to the extent that the context in which they are used indicates otherwise.

Throughout this application, unless the context indicates otherwise, references to a compound of Formula I includes all subgroups of Formula I defined herein, including all substructures, subgenera, preferences, embodiments, examples and particular compounds defined and/or described herein.

References to a compound of Formula I and subgroups thereof include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. "Crystalline form," "polymorph," and "novel form" may be used interchangeably herein, and are meant to include all crystalline and amorphous forms of the compound, including, for example, polymorphs, pseudopolymorphs, solvates (including hydrates), co-crystals, unsolvated polymorphs (including anhydrates), conformational polymorphs, and amorphous forms, as well as mixtures thereof, unless a particular crystalline or amorphous form is referred to. In some embodiments, references to a compound of Formula I and subgroups thereof include polymorphs, solvates, co-crystals, isomers, tautomers and/or oxides thereof. In some embodiments, references to a compound of Formula I and subgroups thereof include polymorphs, salts, solvates, and/or co-crystals thereof. In some embodiments, references to a compound of Formula I and subgroups thereof include isomers, tautomers and/or oxides thereof. In some embodiments, references to a compound of Formula I and subgroups thereof include solvates thereof. Similarly, the term "salts" includes solvates of salts of compounds.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

When a moiety is defined as being optionally substituted, it may be substituted as itself or as part of another moiety. For example, if $R^x$ is defined as "$C_{1-6}$ alkyl or $OC_{1-6}$ alkyl, wherein $C_{1-6}$ alkyl is optionally substituted with halogen", then both the $C_{1-6}$ alkyl group alone and the $C_{1-6}$ alkyl that makes up part of the $OC_{1-6}$ alkyl group may be substituted with halogen.

"Alkyl" encompasses straight and branched carbon chains having the indicated number of carbon atoms, for example, from 1 to 20 carbon atoms, or 1 to 8 carbon atoms, or 1 to 6 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl. "Lower alkyl" refers to alkyl groups having 1 to 6 carbons.

"Haloalkyl" includes straight and branched carbon chains having the indicated number of carbon atoms (e.g., 1 to 6 carbon atoms) substituted with at least one halogen atom. In instances wherein the haloalkyl group contains more than one halogen atom, the halogens may be the same (e.g., dichloromethyl) or different (e.g., chlorofluoromethyl). Examples of haloalkyl groups include, but are not limited to, chloromethyl, dichloromethyl, trichloromethyl, fluoromethyl, difluoromethyl, trifluoromethyl, chlorofluoromethyl, 2-fluoroethyl, 2,2-difluoroethyl, 2,2,2-trifluoroethyl, 1,2-difluoroethyl, 2-chloroethyl, 2,2-dichloroethyl, 2,2,2-trichloroethyl, 1,2-dichloroethyl, pentachloroethyl, and pentafluoroethyl.

"Alkenyl" refers to an unsaturated branched or straight-chain alkyl group having the indicated number of carbon atoms (e.g., 2 to 8, or 2 to 6 carbon atoms) and at least one carbon-carbon double bond derived by the removal of one molecule of hydrogen from adjacent carbon atoms of the corresponding alkyl. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl). "Lower alkenyl" refers to alkenyl groups having 2 to 6 carbons.

"Alkynyl" refers to an unsaturated branched or straight-chain alkyl group having the indicated number of carbon atoms (e.g., 2 to 8 or 2 to 6 carbon atoms) and at least one carbon-carbon triple bond derived by the removal of two molecules of hydrogen from adjacent carbon atoms of the corresponding alkyl. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl). "Lower alkynyl" refers to alkynyl groups having 2 to 6 carbons.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond derived by the removal of one molecule of hydrogen from adjacent carbon atoms of the corresponding cycloalkyl. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Aralkyl" refers to a residue having the indicated number of carbon atoms (e.g., 7 to 12 or 7 to 10 carbon atoms) in which an aryl moiety is attached to the parent structure via an alkyl residue. The alkyl residue may be straight-chain or branched. Examples include, benzyl, phenethyl and 1-phenylethyl.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). When nitrogen is present in a heterocycloalkenyl ring, it may, where the nature of the adjacent atoms and groups permits, exist in an oxidized state (i.e., $N^+$—$O^-$). Additionally, when sulfur is present in a heterocycloalkenyl ring, it may, where the nature of the adjacent atoms and groups permits, exist in an oxidized state (i.e., $S^+$—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group. Examples of polycyclic heterocycloalkenyl groups consisting of a heterocycloalkenyl group fused to an aromatic ring are described below.

Examples of polycyclic rings consisting of an aromatic ring (e.g., aryl or heteroaryl) fused to a non-aromatic ring (e.g., cycloalkyl, cycloalkenyl, heterocycloalkyl, heterocycloalkenyl) include indenyl, 2,3-dihydro-1H-indenyl, 1,2,3,4-tetrahydronaphthalenyl, benzo[1,3]dioxolyl, tetrahydroquinolinyl, 2,3-dihydrobenzo[1,4]dioxinyl, indolinyl, isoindolinyl, 2,3-dihydro-1H-indazolyl, 2,3-dihydro-1H-benzo[d]imidazolyl, 2,3-dihydrobenzofuranyl, 1,3-dihydroisobenzofuranyl, 1,3-dihydrobenzo[c]isoxazolyl, 2,3-dihydrobenzo[d]isoxazolyl, 2,3-dihydrobenzo[d]oxazolyl, 2,3-dihydrobenzo[b]thiophenyl, 1,3-dihydrobenzo[c]thiophenyl, 1,3-dihydrobenzo[c]isothiazolyl, 2,3-dihydrobenzo[d]isothiazolyl, 2,3-dihydrobenzo[d]thiazolyl, 5,6-dihydro-4H-cyclopenta[d]thiazolyl, 4,5,6,7-tetrahydrobenzo[d]thiazolyl, 5,6-dihydro-4H-pyrrolo[3,4-d]thiazolyl, 4,5,6,7-tetrahydrothiazolo[5,4-c]pyridinyl, indolin-2-one, indolin-3-one, isoindolin-1-one, 1,2-dihydroindazol-3-one, 1H-benzo[d]imidazol-2(3H)-one, benzofuran-2(3H)-one, benzofuran-3(2H)-one, isobenzofuran-1(3H)-one, benzo[c]isoxazol-3(1H)-one, benzo[d]isoxazol-3(2H)-one, benzo[d]oxazol-2(3H)-one, benzo[b]thiophen-2(3H)-one, benzo[b]thiophen-3(2H)-one, benzo[c]thiophen-1(3H)-one, benzo[c]isothiazol-3(1H)-one, benzo[d]isothiazol-3(2H)-one, benzo[d]thiazol-2(3H)-one, 4,5-dihydropyrrolo[3,4-d]thiazol-6-one, 1,2-dihydropyrazolo[3,4-d]thiazol-3-one, quinolin-4(3H)-one, quinazolin-4(3H)-one, quinazoline-2,4(1H,3H)-dione, quinoxalin-2(1H)-one, quinoxaline-2,3(1H,4H)- dione, cinnolin-4(3H)-one, pyridin-2(1H)-one, pyrimidin-2 (1H)-one, pyrimidin-4(3H)-one, pyridazin-3(2H)-one, 1H-pyrrolo[3,2-b]pyridin-2(3H)-one, 1H-pyrrolo[3,2-c]pyridin-2(3H)-one, 1H-pyrrolo[2,3-c]pyridin-2(3H)-one, 1H-pyrrolo[2,3-b]pyridin-2(3H)-one, 1,2-dihydropyrazolo[3,4-d]thiazol-3-one and 4,5-dihydropyrrolo[3,4-d]thiazol-6-one. As discussed herein, whether each ring is considered an aryl, heteroaryl, cycloalkyl, cycloalkenyl, heterocycloalkyl or heterocycloalkenyl group is determined by the atom through which the moiety is bound to the parent structure.

"Halogen" or "halo" refers to fluorine, chlorine, bromine or iodine.

"Isomers" are different compounds that have the same molecular formula. "Stereoisomers" are isomers that differ only in the way the atoms are arranged in space. "Enantiomers" are stereoisomers that are non-superimposable mirror images of each other. A 1:1 mixture of a pair of enantiomers is a "racemic" mixture. The symbol "(±)" may be used to designate a racemic mixture where appropriate. "Diastereoisomers" are stereoisomers that have at least two asymmetric atoms, but which are not mirror-images of each other. A "meso compound" or "meso isomer" is a non-optically active member of a set of stereoisomers. Meso isomers contain two or more stereocenters but are not chiral (i.e., a plane of symmetry exists within the molecule). The absolute stereochemistry is specified according to the Cahn-Ingold-Prelog R—S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds disclosed and/or described herein contain one or more asymmetric centers and can thus give rise to enantiomers, diastereomers, meso isomers and other stereoisomeric forms. Unless otherwise indicated, compounds disclosed and/or described herein include all such possible enantiomers, diastereomers, meso isomers and other stereoisomeric forms, including racemic mixtures, optically pure forms and intermediate mixtures. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers.

The stereochemistry depicted in the structures of cyclic meso compounds is not absolute; rather the stereochemistry is intended to indicate the positioning of the substituents relative to one another, e.g., cis or trans.

For example,

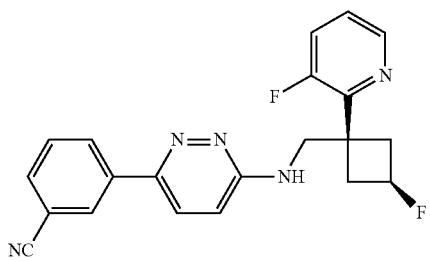 [SMILES: N#Cc1cccc(-c2ccc(NC[C@]3(c4ncccc4F)C[C@@H](F)C3)nn2)c1]

is intended to designate a compound wherein the fluorine and pyridyl substituents on the cyclobutyl ring are in a cis configuration to one another, while

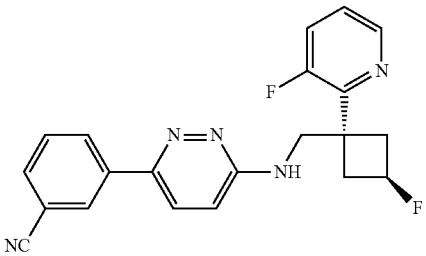 [SMILES: N#Cc1cccc(-c2ccc(NC[C@]3(c4ncccc4F)C[C@H](F)C3)nn2)c1]

is intended to designate a compound wherein the fluorine and pyridyl substituents on the cyclobutyl ring are in a trans configuration to one another.

When a compound can exist as one or more meso isomers, all possible meso isomers are intended to be included. For example, the compound 3-[6-({[3-fluoro-1-(3-fluoro(2-pyridyl))cyclobutyl]methyl}amino)pyridazin-3-yl]benzenecarbonitrile is intended to include both cis and trans meso isomers:

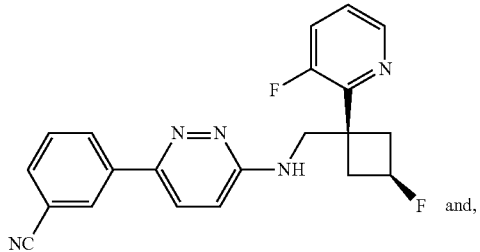

and,

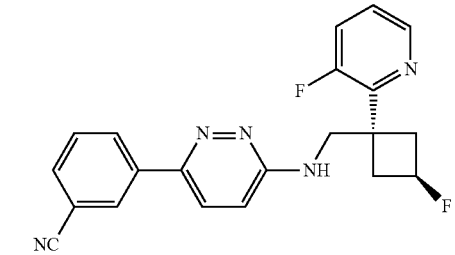

and mixtures thereof. Unless otherwise indicated, compounds disclosed and/or described herein include all possible meso isomers and mixtures thereof.

"Tautomers" are structurally distinct isomers that interconvert by tautomerization. Tautomerization is a form of isomerization and includes prototropic or proton-shift tautomerization, which is considered a subset of acid-base chemistry. Prototropic tautomerization or proton-shift tautomerization involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconverision of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. When the compounds described herein contain moieties capable of tautomerization, and unless specified otherwise, it is intended that the compounds include all possible tautomers.

"Protecting group" has the meaning conventionally associated with it in organic synthesis, i.e., a group that selectively blocks one or more reactive sites in a multifunctional compound such that a chemical reaction can be carried out selectively on another unprotected reactive site, and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a "hydroxy protected form" contains at least one hydroxy group protected with a hydroxy protecting group. Likewise, amines and other reactive groups may similarly be protected.

The term "pharmaceutically acceptable salt" refers to salts that retain the biological effectiveness and properties of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. In many cases, the compounds described herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

A "chelate" is formed by the coordination of a compound to a metal ion at two (or more) points. The term "compound" is intended to include chelates of compounds. Similarly, "salts" includes chelates of salts and "solvates" includes chelates of solvates.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "prodrug" refers to a substance administered in an inactive or less active form that is then transformed (e.g., by metabolic processing of the prodrug in the body) into an active compound. The rationale behind administering a prodrug is to optimize absorption, distribution, metabolism, and/or excretion of the drug. Prodrugs may be obtained by making a derivative of an active compound (e.g., a compound of Formula I or another compound disclosed and/or described herein) that will undergo a transformation under the conditions of use (e.g., within the body) to form the active compound. The transformation of the prodrug to the active compound may proceed spontaneously (e.g., by way of a hydrolysis reaction) or it can be catalyzed or induced by another agent (e.g., an enzyme, light, acid or base, and/or temperature). The agent may be endogenous to the conditions of use (e.g., an enzyme present in the cells to which the prodrug is administered, or the acidic conditions of the stomach) or the agent may be supplied exogenously. Prodrugs can be obtained by converting one or more functional groups in the active compound into another functional group, which is then converted back to the original functional group when administered to the body. For example, a hydroxyl functional group can be converted to a sulfonate, phosphate, ester or carbonate group, which in turn can be hydrolyzed in vivo back to the hydroxyl group. Similarly, an amino functional group can be converted, for example, into an amide, carbamate, imine, urea, phosphenyl, phosphoryl or sulfenyl functional group, which can be hydrolyzed in vivo back to the amino group. A carboxyl functional group can be converted, for example, into an ester (including silyl esters and thioesters), amide or hydrazide functional group, which can be hydrolyzed in vivo back to the carboxyl group. Examples of prodrugs include, but are not limited to, phosphate, acetate, formate and benzoate derivatives of functional groups (such as alcohol or amine groups) present in the compounds of Formula I and other compounds disclosed and/or described herein.

The compounds disclosed and/or described herein can be enriched isotopic forms, e.g., enriched in the content of $^{2}H$, $^{3}H$, $^{11}C$, $^{13}C$ and/or $^{14}C$. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.*, 2000; 6(10); Kabalka, G. et al., The Synthesis of Radiolabeled Compounds via Organometallic Intermediates, *Tetrahedron*, 1989, 45(21), 6601-21; and Evans, E., Synthesis of radiolabeled compounds, *J. Radioanal. Chem.*, 1981, 64(1-2), 9-32.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The term "active agent" is used to indicate a compound that has biological activity. In some embodiments, an "active agent" is a compound having therapeutic utility. In some embodiments, the compound enhances at least one aspect of skeletal muscle function or activity, such as power output, skeletal muscle force, skeletal muscle endurance, oxygen consumption, efficiency, and/or calcium sensitivity. In some embodiments, an active agent is a compound of Formula I, or a pharmaceutically acceptable salt thereof.

The terms "patient" and "subject" refer to an animal, such as a mammal bird or fish. In some embodiments, the patient or subject is a mammal. Mammals include, for example, mice, rats, dogs, cats, pigs, sheep, horses, cows and humans. In some embodiments, the patient or subject is a human, for example a human that has been or will be the object of treatment, observation or experiment. The compounds, compositions and methods described herein can be useful in both human therapy and veterinary applications.

As used herein, "skeletal muscle" includes skeletal muscle tissue as well as components thereof, such as skeletal muscle fibers, the myofibrils comprising the skeletal muscle fibers, the skeletal sarcomere which comprises the myofibrils, and the various components of the skeletal sarcomere described herein, including skeletal myosin, actin, tropomyosin, troponin C, troponin I, troponin T and fragments and isoforms thereof. In some embodiments, "skeletal muscle" includes fast skeletal muscle tissue as well as components thereof, such as fast skeletal muscle fibers, the myofibrils comprising the fast skeletal muscle fibers, the fast skeletal sarcomere which comprises the myofibrils, and the various components of the fast skeletal sarcomere described herein, including fast keletal myosin, actin, tropomyosin, troponin C, troponin I, troponin T and fragments and isoforms thereof. Skeletal muscle does not include cardiac muscle or a combination of sarcomeric components that occurs in such combination in its entirety in cardiac muscle.

As used herein, the term "therapeutic" refers to the ability to modulate the contractility of fast skeletal muscle. As used herein, "modulation" (and related terms, such as "modulate", "modulated", "modulating") refers to a change in function or efficiency of one or more components of the fast skeletal muscle sarcomere, including myosin, actin, tropomyosin, troponin C, troponin I, and troponin T from fast skeletal muscle, including fragments and isoforms thereof, as a direct or indirect response to the presence of a compound described herein, relative to the activity of the fast skeletal sarcomere in the absence of the compound. The change may be an increase in activity (potentiation) or a decrease in activity (inhibition), and may be due to the direct interaction of the compound with the sarcomere, or due to the interaction of the compound with one or more other factors that in turn affect the sarcomere or one or more of its components. In some embodiments, modulation is a potentiation of function or efficiency of one or more components of the fast skeletal muscle sarcomere, including myosin, actin, tropomyosin, troponin C, troponin I, and troponin T from fast skeletal muscle, including fragments and isoforms thereof. Modulation may be mediated by any mechanism and at any physiological level, for example, through sensitization of the fast skeletal sarcomere to contraction at lower $Ca^{2+}$ concentrations. As used herein, "efficiency" or "muscle efficiency" means the ratio of mechanical work output to the total metabolic cost.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease responsive to modulation of fast skeletal muscle. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat", "treated", "treating") includes one or more of: preventing a disease or disorder (i.e., causing the clinical symptoms of the disease or disorder not to develop); inhibiting a disease or disorder; slowing or arresting the development of clinical symptoms of a disease or disorder; and/or relieving a disease or disorder (i.e., causing relief from or regression of clinical symptoms). The term encompasses situations where the disease or disorder is already being experienced by a patient, as well as situations where the disease or disorder is not currently being experienced but is expected to arise. The term covers both complete and partial reduction or prevention of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder. When used in a prophylactic manner, the compounds disclosed and/or described herein may prevent a disease or disorder from developing or lessen the extent of a disease or disorder that may develop.

As used herein, "power output" of a muscle means work/cycle time and may be scaled up from PoLo/cycle time units based on the properties of the muscle. Power output may be modulated by changing, for example, activating parameters during cyclical length changes, including timing of activation (phase of activation) and the period of activation (duty cycle.)

"ATPase" refers to an enzyme that hydrolyzes ATP. ATPases include proteins comprising molecular motors such as the myosins.

As used herein, "selective binding" or "selectively binding" refers to preferential binding to a target protein in one type of muscle or muscle fiber as opposed to other types. For example, a compound selectively binds to fast skeletal troponin C if the compound preferentially binds troponin C in the troponin complex of a fast skeletal muscle fiber or sarcomere in comparison with troponin C in the troponin complex of a slow muscle fiber or sarcomere or with troponin C in the troponin complex of a cardiac sarcomere.

Provided is a compound of Formula I:

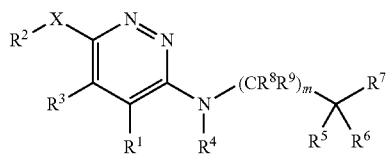

Formula I or a pharmaceutically acceptable salt thereof, wherein:

$R^1$ is selected from hydrogen, halogen, CN, $C_{1-6}$ alkyl, $C_{1-6}$ haloalkyl, $C(O)OR^a$, $C(O)NR^bR^c$, $OR^a$, $NR^bR^c$, $C_{6-10}$ aryl and 5-10 membered heteroaryl;

$R^2$ is selected from $C_{3-8}$ cycloalkyl, $C_{3-8}$ cycloalkenyl, 3-8 membered heterocycloalkyl, 3-8 membered heterocycloalkenyl, $C_{6-10}$ aryl, 5-10 membered heteroaryl and $NR^bR^c$, wherein each of the $C_{3-8}$ cycloalkyl, $C_{3-8}$ cycloalkenyl, 3-8 membered heterocycloalkyl, 3-8 membered heterocycloalkenyl, $C_{6-10}$ aryl and 5-10 membered heteroaryl groups is optionally substituted with 1, 2, 3, 4 or 5 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl groups is optionally substituted with 1, 2, 3, 4 or 5 $R^f$ substituents;

$R^3$ is selected from hydrogen, halogen, CN, $C_{1-6}$ alkyl, $C_{1-6}$ haloalkyl, $C(O)OR^a$, $C(O)NR^bR^c$, $OR^a$, $NR^bR^c$, $C_{6-10}$ aryl and 5-10 membered heteroaryl;

$R^4$ is selected from hydrogen, $C_{1-6}$ alkyl, $C_{1-6}$ haloalkyl, $C(O)R^a$, $C(O)OR^a$, $C(O)NR^bR^c$ and $SO_2R^a$;

$R^5$ and $R^6$ are each independently selected from hydrogen, halogen, $C_{1-6}$ alkyl and $C_{1-6}$ haloalkyl;

or alternatively, $R^5$ and $R^6$ together with the carbon atom to which they are bound form $C_{3-8}$ cycloalkyl, $C_{3-8}$ cycloalkenyl, 3-8 membered heterocycloalkyl or 3-8 membered heterocycloalkenyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl;

$R^7$ is selected from $C_{3-8}$ cycloalkyl, $C_{3-8}$ cycloalkenyl, 3-8 membered heterocycloalkyl, 3-8 membered heterocycloalkenyl, $C_{6-10}$ aryl and 5-10 membered heteroaryl, each optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents;

$R^8$ and $R^9$, at each occurrence, are each independently selected from hydrogen, halogen and $C_{1-6}$ alkyl;

X is selected from a bond, $-(CH_2)_p-$, $-(CH_2)_pC(O)(CH_2)_q-$, $-(CH_2)_pO(CH_2)_q-$, $-(CH_2)_pS(CH_2)_q-$, $-(CH_2)_pNR^d(CH_2)_q-$, $-(CH_2)_pC(O)O(CH_2)_q-$, $-(CH_2)_pOC(O)(CH_2)_q-$, $-(CH_2)_pNR^dC(O)(CH_2)_q-$, $-(CH_2)_pC(O)NR^d(CH_2)_q-$, $-(CH_2)_pNR^dC(O)NR^d(CH_2)_q-$, $-(CH_2)_pNR^dSO_2(CH_2)_q-$, and $-(CH_2)_pSO_2NR^d(CH_2)_q-$;

or alternatively, X, $R^2$ and $R^3$, together with the carbon atoms to which they are bound, form a 5-6 membered ring optionally containing one or more heteroatoms selected from oxygen nitrogen and sulfur, and optionally containing one or more double bonds, and optionally substituted with 1, 2, 3, 4 or 5 $R^f$ substituents;

$R^a$, at each occurrence, is independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents;

$R^b$ and $R^c$, at each occurrence, are each independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, 5-10 membered heteroaryl, $C(O)R^g$, $C(O)OR^g$, $C(O)NR^iR^j$ and $SO_2R^g$, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents;

$R^d$, at each occurrence, is independently selected from hydrogen and $C_{1-6}$ alkyl;

$R^e$, at each occurrence, is independently selected from hydrogen, CN, OH, $C_{1-6}$ alkoxy, $C_{1-6}$ alkyl and $C_{1-6}$ haloalkyl;

$R^f$, at each occurrence, is independently selected from halogen, CN, $OR^h$, $OC(O)R^h$, $OC(O)OR^h$, $OC(O)NR^iR^j$, $NR^iR^j$, $NR^dC(O)R^h$, $NR^dC(O)OR^h$, $NR^dC(O)NR^iR^j$, $NR^dC(O)C(O)NR^iR^j$, $NR^dC(S)R^h$, $NR^dC(S)OR^h$, $NR^dC(S)NR^iR^j$, $NR^dC(NR^e)NR^iR^j$, $NR^dS(O)R^h$, $NR^dSO_2R^h$, $NR^dSO_2NR^iR^j$, $C(O)R^h$, $C(O)OR^h$, $C(O)NR^iR^j$, $C(S)R^h$, $C(S)OR^h$, $C(S)NR^iR^j$, $C(NR^e)NR^iR^j$, $SR^h$, $S(O)R^h$, $SO_2R^h$, $SO_2NR^iR^j$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^k$ substituents;

or two $R^f$ substituents bound to a single carbon atom, together with the carbon atom to which they are both bound, form a group selected from carbonyl, $C_{3-8}$ cycloalkyl and 3-8 membered heterocycloalkyl;

$R^g$, at each occurrence, is independently selected from $C_{1-6}$ alkyl, $C_{1-6}$ haloalkyl, phenyl, naphthyl, and $C_{7-11}$ aralkyl, each optionally substituted with 1, 2, 3, 4 or 5 substituents selected from halogen, CN, OH, $C_{1-6}$ alkoxy, $C_{1-6}$ alkyl and $C_{1-6}$ haloalkyl;

$R^h$, at each occurrence, is independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl, wherein each of the $C_{1-6}$ alkyl, $C_{2-6}$ alkenyl, $C_{2-6}$ alkynyl, cycloalkyl, cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^k$ substituents;

$R^i$ and $R^j$, at each occurrence, are each independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, cycloalkenyl, 3-8 membered heterocycloalkyl, 3-8 membered heterocycloalkenyl, $C_{6-10}$ aryl, $C_{7-11}$ aralkyl, 5-10 membered heteroaryl, $C(O)R^g$, and $C(O)OR^g$, wherein each of the $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 substituents selected from halogen, CN, OH, $C_{1-6}$ alkoxy, $C_{1-6}$ alkyl and $C_{1-6}$ haloalkyl;

$R^k$, at each occurrence, is independently selected from halogen, CN, OH, $C_{1-6}$ alkoxy, $NH_2$, $NH(C_{1-6}$ alkyl), $N(C_{1-6}$ alkyl)$_2$, $NHC(O)C_{1-6}$ alkyl, $NHC(O)C_{7-11}$ aralkyl, $NHC(O)OC_{1-6}$ alkyl, $NHC(O)OC_{7-11}$ aralkyl, $OC(O)C_{1-6}$ alkyl, $OC(O)C_{7-11}$ aralkyl, $OC(O)OC_{1-6}$ alkyl, $OC(O)OC_{7-11}$ aralkyl, $C(O)C_{1-6}$ alkyl, $C(O)C_{7-11}$ aralkyl, $C(O)OC_{1-6}$ alkyl, $C(O)OC_{7-11}$ aralkyl, $C_{1-6}$ alkyl, $C_{1-6}$ haloalkyl, $C_{2-6}$ alkenyl, and $C_{2-6}$ alkynyl, wherein each $C_{1-6}$ alkyl, $C_{2-6}$ alkenyl, $C_{2-6}$ alkynyl, and $C_{7-11}$ aralkyl substituent is optionally substituted with 1, 2 or 3 substituents selected from OH, $C_{1-6}$ alkoxy, $NH_2$, $NH(C_{1-6}$ alkyl), $N(C_{1-6}$ alkyl)$_2$, $NHC(O)C_{1-6}$ alkyl, $NHC(O)C_{7-11}$ aralkyl, $NHC(O)OC_{1-6}$ alkyl, and $NHC(O)OC_{7-11}$ aralkyl;

or two $R^k$ substituents bound to a single carbon atom, together with the carbon atom to which they are both bound, form a carbonyl group;

m is 0, 1 or 2;

n, at each occurrence, independently is 0, 1 or 2;

p is 0, 1 or 2; and q is 0, 1 or 2.

In some embodiments of compounds of Formula I, when m is 1 and $R^5$ and $R^6$ are each methyl, then $R^7$ is not piperidinyl or morpholino. In some embodiments of compounds of Formula I, when m is 1, X is a bond and $R^2$ is optionally substituted phenyl, then $R^7$ is not piperidinyl or morpholino. In some embodiments, the compound of Formula I is not 6-(4-chlorophenyl)-5-methyl-N-(2-methyl-2-(piperidin-1-yl)propyl)pyridazin-3-amine, N-(2-methyl-2-(piperidin-1-yl)propyl)-6-phenyl-5-propylpyridazin-3-amine or N-(2-methyl-2-morpholinopropyl)-6-phenyl-5-propylpyridazin-3-amine.

In some embodiments of compounds of Formula I, m is 0, i.e., a compound of Formula II, or a pharmaceutically acceptable salt thereof:

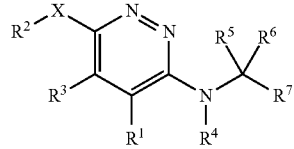

Formula II wherein $R^1$, $R^2$, $R^3$, $R^4$, $R^5$, $R^6$, $R^7$ and X are as defined herein.

In some embodiments of compounds of Formula I, m is 1, i.e., a compound of Formula III, or a pharmaceutically acceptable salt thereof:

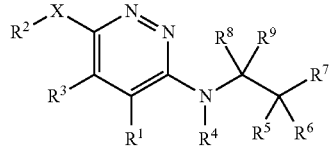

Formula III wherein $R^1$, $R^2$, $R^3$, $R^4$, $R^5$, $R^6$, $R^7$, $R^8$, $R^9$ and X are as defined herein.

In some embodiments of compounds of Formula I, II or III, one of $R^5$ and $R^6$ is hydrogen and the other is $C_{1-6}$ alkyl.

In some embodiments of compounds of Formula I, II or III, $R^5$ and $R^6$ are each independently $C_{1-6}$ alkyl.

In some embodiments of compounds of Formula I, II or III, $R^5$ and $R^6$ are each methyl.

In some embodiments, the compounds are of Formula IV(a) or IV(b), or a pharmaceutically acceptable salt thereof:

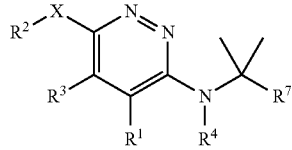

Formula IV(a)

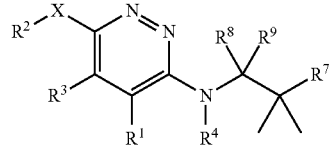

Formula IV(b)

wherein $R^1$, $R^2$, $R^3$, $R^4$, $R^7$, $R^8$, $R^9$ and X are as defined herein.

In some embodiments of compounds of Formula IV(b), $R^7$ is not piperidinyl or morpholinyl.

In some embodiments of compounds of Formula I, II or III, $R^5$ and $R^6$ together with the carbon atom to which they are bound form $C_{3-8}$ cycloalkyl, $C_{3-8}$ cycloalkenyl, 3-8 membered heterocycloalkyl or 3-8 membered heterocycloalkenyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of compounds of Formula I, II or III, $R^5$ and $R^6$, together with the carbon to which they are bound, form $C_{3-6}$ cycloalkyl optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of compounds of Formula I, II or III, $R^5$ and $R^6$, together with the carbon to which they are bound, form cyclopropyl, cyclobutyl, cyclopentyl or cyclohexyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of compounds of Formula I, II or III, $R^5$ and $R^6$, together with the carbon to which they are bound, form cyclobutyl optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of compounds of Formula I, II or III, $R^5$ and $R^6$, together with the carbon to which they are bound, form cyclobutyl substituted with one substituent selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl, wherein the substituent and $R^7$ are in a trans configuration with respect to one another on the cyclobutyl ring.

In some embodiments of compounds of Formula I, II or III, $R^5$ and $R^6$, together with the carbon to which they are bound, form cyclobutyl substituted with one substituent selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl, wherein the substituent and $R^7$ are in a cis configuration with respect to one another on the cyclobutyl ring.

In some embodiments, the compounds are of Formula V(a) or V(b), or a pharmaceutically acceptable salt thereof:

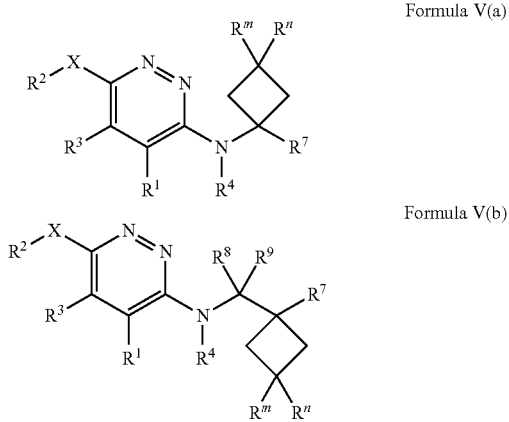

Formula V(a)

Formula V(b)

wherein $R^m$ and $R^n$ are each independently selected from hydrogen, halogen and $C_{1-6}$ alkyl, and $R^1$, $R^2$, $R^3$, $R^4$, $R^7$, $R^8$, $R^9$ and X are as defined herein.

In some embodiments of compounds of Formula V(a) or V(b), $R^m$ and $R^n$ are each hydrogen.

In some embodiments compounds of Formula V(a) or V(b), $R^m$ and $R^n$ are each halogen.

In some embodiments compounds of Formula V(a) or V(b), $R^m$ and $R^n$ are each fluorine.

In some embodiments of compounds of Formula V(a) or V(b), one of $R^m$ and $R^n$ is hydrogen and the other is halogen. In some embodiments of such compounds, the halogen and $R^7$ are in a trans configuration with respect to one another on the cyclobutyl ring. In some embodiments of such compounds, the halogen and $R^7$ are in a cis configuration with respect to one another on the cyclobutyl ring.

In some embodiments compounds of Formula V(a) or V(b), one of $R^m$ and $R^n$ is hydrogen and the other is fluorine. In some embodiments of such compounds, the fluorine and $R^7$ are in a trans configuration with respect to one another on the cyclobutyl ring. In some embodiments of such compounds, the fluorine and $R^7$ are in a cis configuration with respect to one another on the cyclobutyl ring.

In some embodiments of compounds of Formula I, II or III, $R^5$ and $R^6$, together with the carbon atom to which they are bound, form 3-6 membered heterocycloalkyl, each of which is optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of compounds of Formula I, II or III, $R^5$ and $R^6$, together with the carbon atom to which they are bound, form aziridine, azetidine, pyrrolidine, oxirane, oxetane or tetrahydrofuran, each of which is optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of compounds of Formula I, II or III, $R^5$ and $R^6$ are each independently $C_{1-6}$ alkyl, or $R^5$ and $R^6$ together with the carbon atom to which they are bound form $C_{3-8}$ cycloalkyl, $C_{3-8}$ cycloalkenyl, 3-8 membered heterocycloalkyl or 3-8 membered heterocycloalkenyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of compounds of Formula I, II or III, $R^5$ and $R^6$ are each methyl, or $R^5$ and $R^6$ together with the carbon atom to which they are bound form $C_{3-8}$ cycloalkyl, $C_{3-8}$ cycloalkenyl, 3-8 membered heterocycloalkyl or 3-8 membered heterocycloalkenyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of compounds of Formula I, II or III, $R^5$ and $R^6$ are each independently $C_{1-6}$ alkyl, or $R^5$ and $R^6$, together with the carbon to which they are bound, form cyclopropyl, cyclobutyl, cyclopentyl or cyclohexyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of compounds of Formula I, II or III, $R^5$ and $R^6$ are each methyl, or $R^5$ and $R^6$, together with the carbon to which they are bound, form cyclobutyl optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of Formula I, II, III, IV(a), IV(b), V(a) or V(b), $R^7$ is selected from $C_{3-8}$ cycloalkyl, $C_{3-8}$ cycloalkenyl, 3-8 membered heterocycloalkyl, 3-8 membered heterocycloalkenyl, $C_{6-10}$ aryl and 5-10 membered heteroaryl, each optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

In some embodiments of compounds of Formula I, III or IV(b), when $R^5$ and $R^6$ are each methyl, $R^7$ is not piperidinyl or morpholinyl.

In some embodiments of compounds of Formula I, II, III, IV(a), IV(b), V(a) or V(b), $R^7$ is phenyl optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

In some embodiments, the compounds are of Formula VI, or a pharmaceutically acceptable salt thereof:

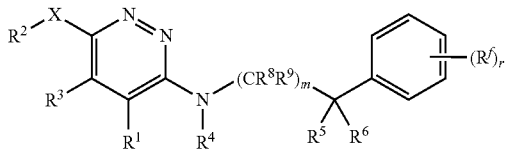

Formula VI wherein r is 0, 1, 2, 3 or 4, and $R^1$, $R^2$, $R^3$, $R^4$, $R^5$, $R^6$, $R^8$, $R^9$, $R^f$, X and m are as defined herein.

In some embodiments, the compounds are of Formula VII(a) or VII(b), or a pharmaceutically acceptable salt thereof:

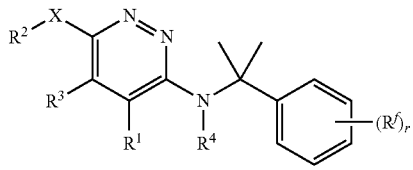

Formula VII(a)

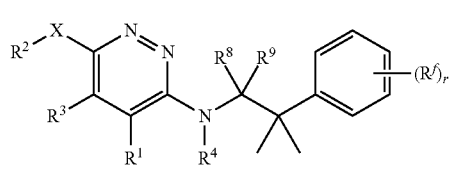

Formula VII(b)

wherein r is 0, 1, 2, 3 or 4, and $R^1$, $R^2$, $R^3$, $R^4$, $R^8$, $R^9$, $R^f$ and X are as defined herein.

In some embodiments, the compounds are of Formula VIII(a) or VIII(b), or a pharmaceutically acceptable salt thereof:

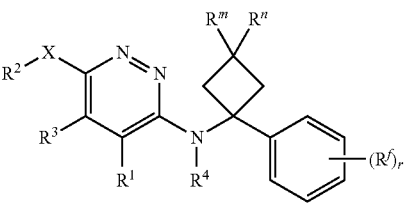

Formula VIII(a)

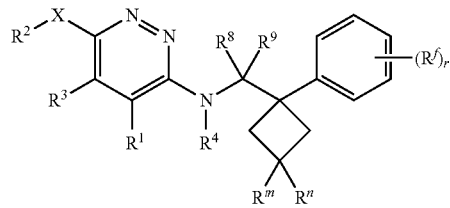

Formula VIII(b)

wherein $R^m$ and $R^n$ are each independently selected from hydrogen, halogen and $C_{1-6}$ alkyl; r is 0, 1, 2, 3 or 4; and $R^1$, $R^2$, $R^3$, $R^4$, $R^8$, $R^9$, $R^f$ and X are as defined herein.

In some embodiments of compounds of Formula VIII(a) or VIII(b), $R^m$ and $R^n$ are each hydrogen.

In some embodiments compounds of Formula VIII(a) or VIII(b), $R^m$ and $R^n$ are each halogen.

In some embodiments compounds of Formula VIII(a) or VIII(b), $R^m$ and $R^n$ are each fluorine.

In some embodiments compounds of Formula VIII(a) or VIII(b), one of $R^m$ and $R^n$ is hydrogen and the other is halogen. In some embodiments of such compounds, the halogen and the phenyl ring are in a trans configuration with respect to one another on the cyclobutyl ring. In some embodiments of such compounds, the halogen and the phenyl ring are in a cis configuration with respect to one another on the cyclobutyl ring.

In some embodiments of compounds of Formula VIII(a) or VIII(b), one of $R^m$ and $R^n$ is hydrogen and the other is fluorine. In some embodiments of such compounds, the fluorine and the phenyl ring are in a trans configuration with respect to one another on the cyclobutyl ring. In some embodiments of such compounds, the fluorine and the phenyl ring are in a cis configuration with respect to one another on the cyclobutyl ring.

In some embodiments of compounds of Formula I, II, III, IV(a), IV(b), V(a) or V(b), $R^7$ is selected from phenyl, 2-fluorophenyl, 3-fluorophenyl, 2,4-difluorophenyl, 3,4-difluorophenyl, 3,5-difluorophenyl, 4-fluorophenyl, 2-chlorophenyl, 3-chlorophenyl, 4-chlorophenyl, 2,4-dichlorophenyl, 3,4-dichlorophenyl, 3,5-dichlorophenyl, 2-methylphenyl, 3-methylphenyl, 2,4-dimethylphenyl, 3,4-dimethylphenyl, 3,5-dimethylphenyl, 2-(hydroxymethyl)phenyl, 3-(hydroxymethyl)phenyl, 4-(hydroxymethyl)phenyl, 2-(aminomethyl)phenyl, 3-(aminomethyl)phenyl, 4-(aminomethyl)phenyl, 2-phenol, 3-phenol, 4-phenol, 2-methoxyphenyl, 3-methoxyphenyl, 4-methoxyphenyl, 2-difluoromethoxyphenyl, 3-difluoromethoxyphenyl, 4-difluoromethoxyphenyl, 2-trifluoromethoxyphenyl, 3-trifluoromethoxyphenyl, 4-trifluoromethoxyphenyl, 2-cyanophenyl, 3-cyanophenyl, 4-cyanophenyl, 2-benzamine, 3-benzamide, 4-benzamide, N-methyl-2-benzamine, N-methyl-3-benzamide, N-methyl-4-benzamide, N,N-dimethyl-2-benzamine, N,N-dimethyl-3-benzamide, and N,N-dimethyl-4-benzamide.

In some embodiments of compounds of Formula I, II, III, IV(a), IV(b), V(a) or V(b), $R^7$ is 5-10 membered heteroaryl optionally substituted with 1, 2, 3, 4 or 5 substituents selected from halogen, ON, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

In some embodiments of compounds of Formula I, II, III, IV(a), IV(b), V(a) or V(b), $R^7$ is pyridyl optionally substituted with 1, 2, 3, 4 or 5 substituents selected from halogen, ON, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

In some embodiments of compounds of Formula I, II, III, IV(a), IV(b), V(a) or V(b), $R^7$ is selected from 2-pyridyl, 3-pyridyl and 4-pyridyl, each optionally substituted with 1, 2, 3, 4 or 5 substituents selected from halogen, ON, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-6}$ cycloalkyl, $C_{3-6}$ cycloalkenyl, 3-6 membered heterocycloalkyl, 3-6 membered heterocycloalkenyl, phenyl, naphthyl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

In some embodiments, the compounds are of Formula IX, or a pharmaceutically acceptable salt thereof:

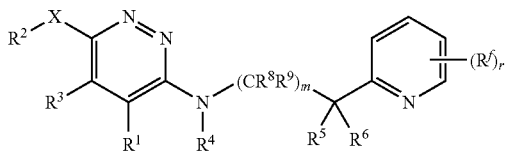

Formula IX wherein r is 0, 1, 2, 3 or 4, and $R^1$, $R^2$, $R^3$, $R^4$, $R^5$, $R^6$, $R^8$, $R^9$, $R^f$, X and m are as defined herein.

In some embodiments, the compounds are of Formula X(a) or X(b), or a pharmaceutically acceptable salt thereof:

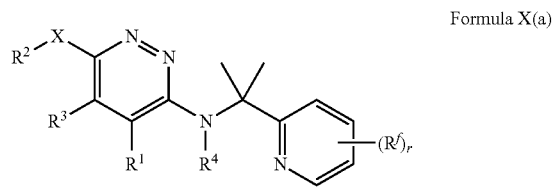

Formula X(a)

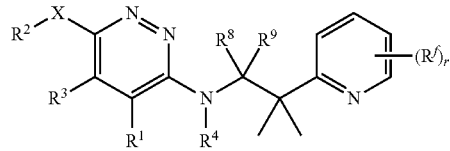

Formula X(b)

wherein r is 0, 1, 2, 3 or 4, and $R^1$, $R^2$, $R^3$, $R^4$, $R^8$, $R^9$, $R^f$ and X are as defined herein.

In some embodiments, the compounds are of Formula XI(a) or XI(b), or a pharmaceutically acceptable salt thereof:

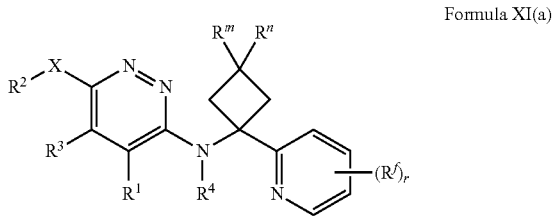

Formula XI(a)

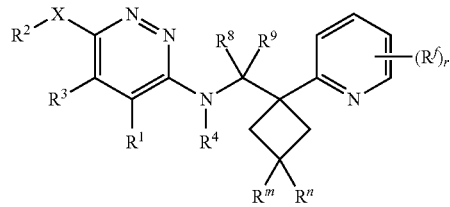

Formula XI(b)

wherein $R^m$ and $R^n$ are each independently selected from hydrogen, halogen and $C_{1-6}$ alkyl; r is 0, 1, 2, 3 or 4; and $R^1$, $R^2$, $R^3$, $R^4$, $R^8$, $R^9$, $R^f$ and X are as defined herein.

In some embodiments of compounds of Formula XI(a) or XI(b), $R^m$ and $R^n$ are each hydrogen.

In some embodiments compounds of Formula XI(a) or XI(b), $R^m$ and $R^n$ are each halogen.

In some embodiments compounds of Formula XI(a) or XI(b), $R^m$ and $R^n$ are each fluorine.

In some embodiments compounds of Formula XI(a) or XI(b), one of $R^m$ and $R^n$ is hydrogen and the other is halogen. In some embodiments of such compounds, the halogen and the pyridyl ring are in a trans configuration with respect to one another on the cyclobutyl ring. In some embodiments of such compounds, the halogen and the pyridyl ring are in a cis configuration with respect to one another on the cyclobutyl ring.

In some embodiments compounds of Formula XI(a) or XI(b), one of $R^m$ and $R^n$ is hydrogen and the other is fluorine. In some embodiments of such compounds, the fluorine and the pyridyl ring are in a trans configuration with respect to one another on the cyclobutyl ring. In some embodiments of such compounds, the fluorine and the pyridyl ring are in a cis configuration with respect to one another on the cyclobutyl ring.

In some embodiments of compounds of Formula I, II, III, IV(a), IV(b), V(a) or V(b), $R^7$ is selected from pyrid-2-yl, 3-fluoro-pyrid-2-yl, 4-fluoro-pyrid-2-yl, 5-fluoro-pyrid-2-yl, 6-fluoro-pyrid-2-yl, 3-chloro-pyrid-2-yl, 4-chloro-pyrid-2-yl, 5-chloro-pyrid-2-yl, 6-chloro-pyrid-2-yl, 3-cyano-pyrid-2-yl, 4-cyano-pyrid-2-yl, 5-cyano-pyrid-2-yl, 6-cyano-pyrid-2-yl, 3-methyl-pyrid-2-yl, 4-methyl-pyrid-2-yl, 5-methyl-pyrid-2-yl, 6-methyl-pyrid-2-yl, 3-difluoromethyl-pyrid-2-yl, 4-difluoromethyl-pyrid-2-yl, 5-difluoromethyl-pyrid-2-yl, 6-difluoromethyl-pyrid-2-yl, 3-trifluoromethyl-pyrid-2-yl, 4-trifluoromethyl-pyrid-2-yl, 5-trifluoromethyl-pyrid-2-yl, 6-trifluoromethyl-pyrid-2-yl, 3-hydroxymethyl-pyrid-2-yl, 4-hydroxymethyl-pyrid-2-yl, 5-hydroxymethyl-pyrid-2-yl, 6-hydroxymethyl-pyrid-2-yl, 3-aminomethyl-pyrid-2-yl, 4-aminomethyl-pyrid-2-yl, 5-aminomethyl-pyrid-2-yl, 6-aminomethyl-pyrid-2-yl, 3-hydroxy-pyrid-2-yl, 4-hydroxy-pyrid-2-yl, 5-hydroxy-pyrid-2-yl, 6-hydroxy-pyrid-2-yl, 3-methoxy-pyrid-2-yl, 4-methoxy-pyrid-2-yl, 5-methoxy-pyrid-2-yl, 6-methoxy-pyrid-2-yl, 3-difluoromethoxy-pyrid-2-yl, 4-difluoromethoxy-pyrid-2-yl, 5-difluoromethoxy-pyrid-2-yl, 6-difluoromethoxy-pyrid-2-yl, 3-trifluoromethoxy-pyrid-2-yl, 4-trifluoromethoxy-pyrid-2-yl, 5-trifluoromethoxy-pyrid-2-yl, 6-trifluoromethoxy-pyrid-2-yl, 3-methylthio-pyrid-2-yl, 4-methylthio-pyrid-2-yl, 5-methylthio-pyrid-2-yl, 6-methylthio-pyrid-2-yl, 3-carboxamide-pyrid-2-yl, 4-carboxamide-pyrid-2-yl, 5-carboxamide-pyrid-2-yl, 6-carboxamide-pyrid-2-yl and 3-fluoro-6-methyl-pyrid-2-yl.

In some embodiments of compounds of Formula I, II, III, IV(a), IV(b), V(a) or V(b), $R^7$ is selected from pyrid-3-yl, 2-fluoro-pyrid-3-yl, 4-fluoro-pyrid-3-yl, 5-fluoro-pyrid-3-yl, 6-fluoro-pyrid-3-yl, 2-chloro-pyrid-3-yl, 4-chloro-pyrid-3-yl, 5-chloro-pyrid-3-yl, 6-chloro-pyrid-3-yl, 2-cyano-pyrid-3-yl, 4-cyano-pyrid-3-yl, 5-cyano-pyrid-3-yl, 6-cyano-pyrid-3-yl, 2-methyl-pyrid-3-yl, 4-methyl-pyrid-3-yl, 5-methyl-pyrid-3-yl, 6-methyl-pyrid-3-yl, 2-difluoromethyl-pyrid-3-yl, 4-difluoromethyl-pyrid-3-yl, 5-difluoromethyl-pyrid-3-yl, 6-difluoromethyl-pyrid-3-yl, 2-trifluoromethyl-pyrid-3-yl, 4-trifluoromethyl-pyrid-3-yl, 5-trifluoromethyl-pyrid-3-yl, 6-trifluoromethyl-pyrid-3-yl, 2-hydroxymethyl-pyrid-3-yl, 4-hydroxymethyl-pyrid-3-yl, 5-hydroxymethyl-pyrid-3-yl, 6-hydroxymethyl-pyrid-3-yl, 2-aminomethyl-pyrid-3-yl, 4-aminomethyl-pyrid-3-yl, 5-aminomethyl-pyrid-3-yl, 6-aminomethyl-pyrid-3-yl, 2-hydroxy-pyrid-3-yl, 4-hydroxy-pyrid-3-yl, 5-hydroxy-pyrid-3-yl, 6-hydroxy-pyrid-3-yl, 2-methoxy-pyrid-3-yl, 4-methoxy-pyrid-3-yl, 5-methoxy-pyrid-3-yl, 6-methoxy-pyrid-3-yl, 2-difluoromethoxy-pyrid-3-yl, 4-difluoromethoxy-pyrid-3-yl, 5-difluoromethoxy-pyrid-3-yl, 6-difluoromethoxy-pyrid-3-yl, 2-trifluoromethoxy-pyrid-3-yl, 4-trifluoromethoxy-pyrid-3-yl, 5-trifluoromethoxy-pyrid-3-yl, 6-trifluoromethoxy-pyrid-3-yl, 2-methylthio-pyrid-3-yl, 4-methylthio-pyrid-3-yl, 5-methylthio-pyrid-3-yl, 6-methylthio-pyrid-3-yl, 2-carboxamide-pyrid-3-yl, 4-carboxamide-pyrid-3-yl, 5-carboxamide-pyrid-3-yl and 6-carboxamide-pyrid-3-yl.

In some embodiments of compounds of Formula I, II, III, IV(a), IV(b), V(a), V(b), VI, VII(a), VII(b), VIII(a), VIII(b), IX, X(a), X(b), XI(a) or XI(b), X is selected from a bond, —(CH$_2$)$_p$—, —(CH$_2$)$_p$C(O)(CH$_2$)$_q$—, —(CH$_2$)$_p$O(CH$_2$)$_q$—, —(CH$_2$)$_p$S(CH$_2$)$_q$—, —(CH$_2$)$_p$NR$^d$(CH$_2$)$_q$—, —(CH$_2$)$_p$C(O)O(CH$_2$)$_q$—, —(CH$_2$)$_p$OC(O)(CH$_2$)$_q$—, —(CH$_2$)$_p$NR$^d$C(O)(CH$_2$)$_q$—, —(CH$_2$)$_p$C(O)NR$^d$(CH$_2$)$_q$—, —(CH$_2$)$_p$NR$^d$C(O)NR$^d$(CH$_2$)$_q$—, —(CH$_2$)$_p$NR$^d$SO$_2$(CH$_2$)$_q$—, and —(CH$_2$)$_p$SO$_2$NR$^d$(CH$_2$)$_q$—.

In some embodiments of compounds of Formula I, II, III, IV(a), IV(b), V(a), V(b), VI, VII(a), VII(b), VIII(a), VIII(b), IX, X(a), X(b), XI(a) or XI(b), X is a bond.

In some embodiments, the compound is of Formula XII(a), XII(b), XII(c), XII(d), XII(e), XII(f), XII(g), XII(h), XII(i), XII(j), XII(k), XII(l), XII(m), XII(n) or XII(o), or a pharmaceutically acceptable salt thereof:

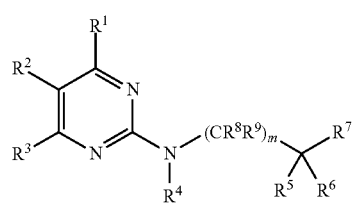

Formula XII(a)

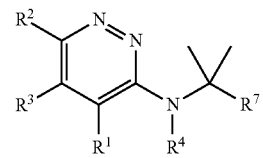

Formula XII(b)

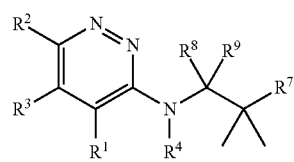

Formula XII(c)

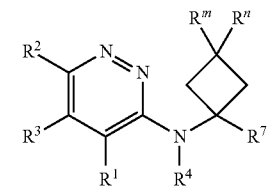

Formula XII(d)

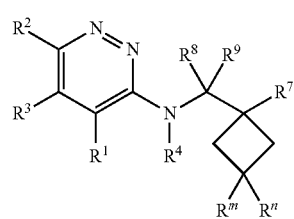

Formula XII(e)

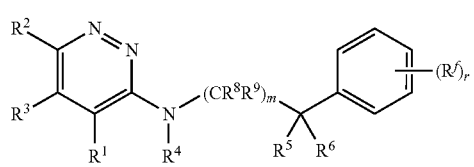

Formula XII(f)

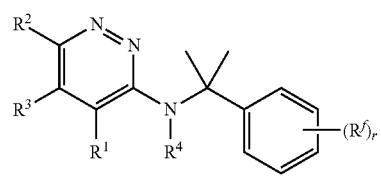

Formula XII(g)

-continued

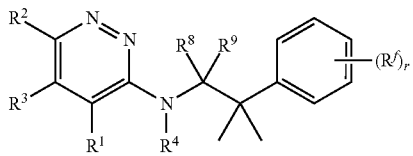
Formula XII(h)

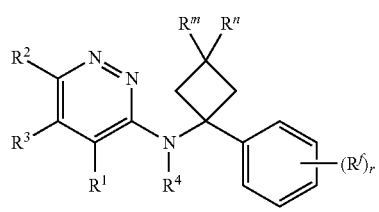
Formula XII(i)

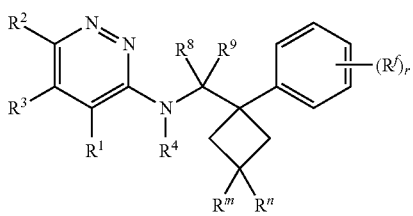
Formula XII(j)

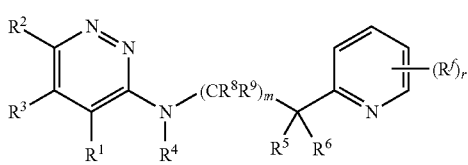
Formula XII(k)

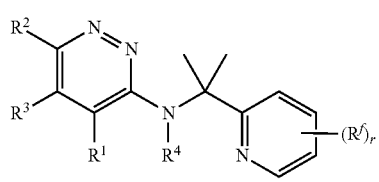
Formula XII(l)

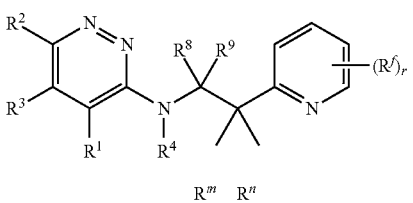
Formula XII(m)

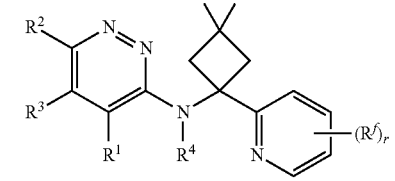
Formula XII(n)

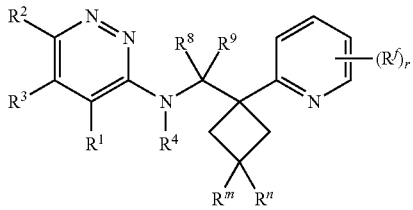
Formula XII(o)

wherein $R^1$, $R^2$, $R^3$, $R^4$, $R^5$, $R^6$, $R^7$, $R^8$, $R^9$, $R^f$, $R^m$, $R^n$, m and r are as defined herein.

In some embodiments of compounds of Formula XII(c), $R^7$ is not piperidinyl or morpholinyl. In some embodiments of compounds of Formula XII(c), when $R^2$ is optionally substituted phenyl, then $R^7$ is not piperidinyl or morpholinyl.

In some embodiments of compounds of Formula I, II, III, IV(a), IV(b), V(a), V(b), VI, VII(a), VII(b), VIII(a), VIII(b), IX, X(a), X(b), XI(a) or XI(b), X is —O—.

In some embodiments of compounds of Formula I, II, III, IV(a), IV(b), V(a), V(b), VI, VII(a), VII(b), VIII(a), VIII(b), IX, X(a), X(b), XI(a) or XI(b), X is selected from —CH$_2$O— and —OCH$_2$—.

In some embodiments of compounds of Formula I, II, III, IV(a), IV(b), V(a), V(b), VI, VII(a), VII(b), VIII(a), VIII(b), IX, X(a), X(b), XI(a) or XI(b), X is —NR$^d$—.

In some embodiments of compounds of Formula I, II, III, IV(a), IV(b), V(a), V(b), VI, VII(a), VII(b), VIII(a), VIII(b), IX, X(a), X(b), XI(a) or XI(b), X is selected from —CH$_2$NR$^d$— and —NR$^d$CH$_2$—.

In some embodiments of compounds of Formula I, II, III, IV(a), IV(b), V(a), V(b), VI, VII(a), VII(b), VIII(a), VIII(b), IX, X(a), X(b), XI(a) or XI(b), X is selected from —NR$^d$C(O)— and —C(O)NR$^d$—.

In some embodiments of compounds of Formula I, II, III, IV(a), IV(b), V(a), V(b), VI, VII(a), VII(b), VIII(a), VIII(b), IX, X(a), X(b), XI(a) or XI(b), X is selected from —CH$_2$NR$^d$C(O)— and —C(O)NR$^d$CH$_2$—.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is selected from $C_{3-8}$ cycloalkyl, $C_{3-8}$ cycloalkenyl, 3-8 membered heterocycloalkyl, 3-8 membered heterocycloalkenyl, $C_{6-10}$ aryl and 5-10 membered heteroaryl, each optionally substituted with 1, 2, 3, 4 or 5 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is phenyl optionally substituted with 1, 2, 3, 4 or 5 substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)

$NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is phenyl substituted with 1, 2, 3, 4 or 5 substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nO(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents; wherein at least one substituent is bonded at the meta position.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is phenyl substituted with a substituent selected from $(CH_2)_nC(O)OR^a$ and $(CH_2)_nC(O)NR^bR^c$; and optionally substituted with 1, 2 or 3 additional substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nO(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is phenyl substituted with a substituent selected from C(O)OH, C(O)NH$_2$, C(O)OC$_{1-6}$ alkyl, C(O)NHC$_{1-6}$ alkyl and C(O)N(C$_{1-6}$ alkyl)$_2$; and optionally substituted with 1, 2 or 3 additional substituents selected from halogen, $C_{1-6}$ alkyl and $C_{1-6}$ haloalkyl.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is phenyl substituted at the meta position with a substituent selected from $(CH_2)_nC(O)OR^a$ and $(CH_2)_nC(O)NR^bR^c$; and optionally substituted with 1, 2 or 3 additional substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is phenyl substituted at the meta position with a substituent selected from $(CH_2)_nC(O)OR^a$ and $(CH_2)_nC(O)NR^bR^c$, and optionally substituted with 1, 2 or 3 additional substituents selected from halogen, hydroxyl, $C_{1-6}$ alkoxy, CN, $C_{1-6}$ alkyl and $C_{1-6}$ haloalkyl.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is phenyl substituted at the meta position with a substituent selected from C(O)OH, C(O)NH$_2$, C(O)OC$_{1-6}$ alkyl, C(O)NHC$_{1-6}$ alkyl and C(O)N(C$_{1-6}$ alkyl)$_2$; and optionally substituted with 1, 2 or 3 additional substituents selected from halogen, hydroxyl, $C_{1-6}$ alkoxy, CN, $C_{1-6}$ alkyl and $C_{1-6}$ haloalkyl.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is phenyl substituted with $(CH_2)_nNR^dC(O)R^a$, wherein $R^a$ is $C_{1-6}$ alkyl or 3-8 membered heterocycloalkyl, each optionally substituted with 1, 2 or 3 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl; and optionally substituted with 1, 2 or 3 additional substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is phenyl substituted with $(CH_2)_nNR^dC(O)R^a$, wherein $R^a$ is selected from $C_{1-6}$ alkyl, $C_{1-6}$ alkyl-OH and $C_{1-6}$ alkyl-NH$_2$, each optionally substituted with 1, 2 or 3 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, and $(CH_2)_n$5-10 membered heteroaryl; and optionally substituted with 1, 2 or 3 additional substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is selected from 3-benzamide, N-methyl-3-benzamide, N,N-dimethyl-3-benzamide, 4-fluoro-3-benzamide, N-methyl-4-fluoro-3-benzamide, N,N-dimethyl-4-fluoro-3-benzamide, 3-benzoic acid, methyl-3-benzoate, 4-fluoro-3-benzoic acid, and methyl-4-fluoro-3-benzoate.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is 5-10 membered heteroaryl optionally substituted with 1, 2, 3, 4 or 5 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is selected from pyridyl, pyrimidyl, pyrazyl, pyridazyl, triazyl, furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with 1, 2, 3 or 4 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is selected from pyridyl, pyrimidyl, pyrazyl, pyridazyl, triazyl, furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with a substituent selected from $(CH_2)_nC(O)OR^a$ and $(CH_2)_nC(O)NR^bR^c$; and optionally substituted with 1, 2 or 3 additional substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is selected from pyridyl, pyrimidyl, pyrazyl, pyridazyl and triazyl, each optionally substituted with $(CH_2)_nC(O)NR^bR^c$.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is selected from furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with $(CH_2)_nC(O)NR^bR^c$.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is selected from pyridyl, pyrimidyl, pyrazyl, pyridazyl and triazyl, each optionally substituted with $(CH_2)_nC(O)NH_2$.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is selected from furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with $(CH_2)_nC(O)NH_2$.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is selected from pyridyl, pyrimidyl, pyrazyl, pyridazyl, triazyl, furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with $(CH_2)_nNR^dC(O)R^a$, wherein $R^a$ is $C_{1-6}$ alkyl or 3-8 membered heterocycloalkyl, each optionally substituted with 1, 2 or 3 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is selected from pyridyl, pyrimidyl, pyrazyl, pyridazyl and triazyl, each optionally substituted with $(CH_2)_nNR^dC(O)R^a$, wherein $R^a$ is selected from $C_{1-6}$ alkyl, $C_{1-6}$ alkyl-OH and $C_{1-6}$ alkyl-NH$_2$, each optionally substituted with 1, 2 or 3 substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is selected furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with $(CH_2)_nNR^dC(O)R^a$, wherein $R^a$ is selected from $C_{1-6}$ alkyl, $C_{1-6}$ alkyl-OH and $C_{1-6}$ alkyl-NH$_2$, each optionally substituted with 1, 2 or 3 substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^2$ is selected from indolyl, indazolyl, benzimidazolyl, benzoxazolyl and benzoisoxazolyl, each optionally substituted with 1, 2, 3 or 4 substituents selected from halogen, ON, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, (CH$_2$)$_n$phenyl, (CH$_2$)$_n$naphthyl and (CH$_2$)$_n$5-10 membered heteroaryl groups is optionally substituted with 1, 2, 3, 4 or 5 R$^f$ substituents.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), R$^2$ is selected from 1H-indazol-6-yl, 1H-indazol-5-yl, 1H-indazol-4-yl, 3-amino(1H-indazol-5-yl), 3-amino(1H-indazol-6-yl), 3-amino(1H-indazol-7-yl), 1-methyl(1H-indazol-6-yl), 3-methyl(1H-indazol-6-yl), 3-amino-1-methyl(1H-indazol-5-yl), 3-cyano(1H-indazol-5-yl), 3-carboxamide(1H-indazol-5-yl), 3-carboxamidine(1H-indazol-5-yl), 3-vinyl(1H-indazol-5-yl), 3-ethyl(1H-indazol-5-yl), 3-acetamide(1H-indazol-5-yl), 3-methylsulfonylamine(1H-indazol-5-yl), 3-methoxycarboxamide(1H-indazol-5-yl), 3-methylamino(1H-indazol-5-yl), 3-dimethylamino(1H-indazol-5-yl), 3-ethylamino(1H-indazol-5-yl), 3-(2-aminoethyl)amino(1H-indazol-5-yl), 3-(2-hydroxyethyl)amino(1H-indazol-5-yl), 3-[(methylethyl)amino](1H-indazol-5-yl), 6-benzimidazol-5-yl, 6-(2-methylbenzimidazol-5-yl), 2-aminobenzimidazol-5-yl, 2-hydroxybenzimidazol-5-yl, 2-acetamidebenzimidazol-5-yl, 3-aminobenzo[3,4-d]isoxazol-5-yl, 3-aminobenzo[d]isoxazol-6-yl, 3-aminobenzo[d]isoxazol-7-yl, 2-methylbenzoxazol-5-yl and 2-methylbenzoxazol-6-yl.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), R$^2$ is selected from 3-6 membered heterocycloalkyl and 3-6 membered heterocycloalkenyl, each optionally substituted with 1, 2, 3, 4 or 5 substituents selected from halogen, CN, oxo, (CH$_2$)$_n$OR$^a$, (CH$_2$)$_n$OC(O) R$^a$, (CH$_2$)$_n$OC(O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O) NR$^b$R$^c$, (CH$_2$)$_n$NR$^d$C(O)C(O)NR$^b$R$^c$, (CH$_2$)$_n$NR$^d$C(S)R$^a$, (CH$_2$)$_n$NR$^d$C(S)OR$^a$, (CH$_2$)$_n$NR$^d$C(S)NR$^b$R$^c$, (CH$_2$)$_n$NR$^d$C(NR$^e$)NR$^b$R$^c$, (CH$_2$)$_n$NR$^d$S(O)R$^a$, (CH$_2$)$_n$NR$^d$SO$_2$R$^a$, (CH$_2$)$_n$NR$^d$SO$_2$NR$^b$R$^c$, (CH$_2$)$_n$C(O)R$^a$, (CH$_2$)$_n$C(O)OR$^a$, (CH$_2$)$_n$C(O)NR$^b$R$^c$, (CH$_2$)$_n$C(S)R$^a$, (CH$_2$)$_n$C(S)OR$^a$, (CH$_2$)$_n$C(S)NR$^b$R$^c$, (CH$_2$)$_n$C(NR$^e$)NR$^b$R$^c$, (CH$_2$)$_n$SR$^a$, (CH$_2$)$_n$S(O)R$^a$, (CH$_2$)$_n$SO$_2$R$^a$, (CH$_2$)$_n$SO$_2$NR$^b$R$^c$, C$_{1-6}$ alkyl, C$_{1-6}$ haloalkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl, wherein each of the C$_{1-6}$ alkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl groups is optionally substituted with 1, 2, 3, 4 or 5 R$^f$ substituents.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), R$^2$ is selected from aziridinyl, azetidinyl, pyrrolidinyl, piperidinyl, piperazinyl and morpholinyl, each optionally substituted with 1, 2, 3, 4 or 5 substituents selected from halogen, CN, oxo, (CH$_2$)$_n$OR$^a$, (CH$_2$)$_n$OC(O) R$^a$, (CH$_2$)$_n$OC(O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O) NR$^b$R$^c$, (CH$_2$)$_n$NR$^d$C(O)C(O)NR$^b$R$^c$, (CH$_2$)$_n$NR$^d$C(S)R$^a$, (CH$_2$)$_n$NR$^d$C(S)OR$^a$, (CH$_2$)$_n$NR$^d$C(S)NR$^b$R$^c$, (CH$_2$)$_n$NR$^d$C(NR$^e$)NR$^b$R$^c$, (CH$_2$)$_n$NR$^d$S(O)R$^a$, (CH$_2$)$_n$NR$^d$SO$_2$R$^a$, (CH$_2$)$_n$NR$^d$SO$_2$NR$^b$R$^c$, (CH$_2$)$_n$C(O)R$^a$, (CH$_2$)$_n$C(O)OR$^a$, (CH$_2$)$_n$C(O)NR$^b$R$^c$, (CH$_2$)$_n$C(S)R$^a$, (CH$_2$)$_n$C(S)OR$^a$, (CH$_2$)$_n$C(S)NR$^b$R$^c$, (CH$_2$)$_n$C(NR$^e$)NR$^b$R$^c$, (CH$_2$)$_n$SR$^a$, (CH$_2$)$_n$S(O)R$^a$, (CH$_2$)$_n$SO$_2$R$^a$, (CH$_2$)$_n$SO$_2$NR$^b$R$^c$, C$_{1-6}$ alkyl, C$_{1-6}$ haloalkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl, wherein each of the C$_{1-6}$ alkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl groups is optionally substituted with 1, 2, 3, 4 or 5 R$^f$ substituents.

In some embodiments of compounds of Formula I, II, III, IV(a), IV(b), V(a), V(b), VI, VII(a), VII(b), VIII(a), VIII(b), IX, X(a), X(b), XI(a) or XI(b), R$^2$ is NR$^b$R$^c$, wherein R$^b$ and R$^c$ are as defined herein.

In some embodiments of compounds of Formula I, II, III, IV(a), IV(b), V(a), V(b), VI, VII(a), VII(b), VIII(a), VIII(b), IX, X(a), X(b), XI(a) or XI(b), R$^2$ is NR$^b$R$^c$, wherein one of R$^b$ and R$^c$ is hydrogen and the other is C$_{1-6}$ alkyl optionally substituted with 1, 2, 3, 4 or 5 R$^f$ substituents.

In some embodiments of compounds of Formula I, II, III, IV(a), IV(b), V(a), V(b), VI, VII(a), VII(b), VIII(a), VIII(b), IX, X(a), X(b), XI(a) or XI(b), X is —C(O)— and R$^2$ is NR$^b$R$^c$, wherein R$^b$ and R$^c$ are as defined herein.

In some embodiments of compounds of Formula I, II, III, IV(a), IV(b), V(a), V(b), VI, VII(a), VII(b), VIII(a), VIII(b), IX, X(a), X(b), XI(a) or XI(b), X is —C(O)— and R$^2$ is NR$^b$R$^c$, wherein one of R$^b$ and R$^c$ is hydrogen and the other is C$_{1-6}$ alkyl optionally substituted with 1, 2, 3, 4 or 5 R$^f$ substituents.

In some embodiments of compounds of Formula I, II, III, IV(a), IV(b), V(a), V(b), VI, VII(a), VII(b), VIII(a), VIII(b), IX, X(a), X(b), XI(a) or XI(b), X is —(CH$_2$)$_p$— and R$^2$ is NR$^b$R$^c$, wherein R$^b$ and R$^c$ are as defined herein.

In some embodiments of compounds of Formula I, II, III, IV(a), IV(b), V(a), V(b), VI, VII(a), VII(b), VIII(a), VIII(b), IX, X(a), X(b), XI(a) or XI(b), X is —(CH$_2$)$_p$— and R$^2$ is NR$^b$R$^c$, wherein one of R$^b$ and R$^c$ is hydrogen and the other is C$_{1-6}$ alkyl optionally substituted with 1, 2, 3, 4 or 5 R$^f$ substituents.

In some embodiments, X, R$^2$ and R$^3$, together with the carbon atoms to which they are bound, form a 5-6 membered ring optionally containing one or more heteroatoms selected from oxygen nitrogen and sulfur, and optionally containing one or more double bonds, and optionally substituted with 1, 2, 3, 4 or 5 R$^f$ substituents.

In some embodiments, the compound is of Formula XIII, or a pharmaceutically acceptable salt thereof:

Formula XIII

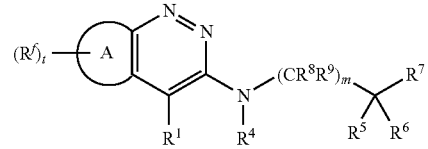

wherein A is a 5 or 6 membered ring optionally containing one or more heteroatoms selected from oxygen nitrogen and sulfur, and optionally containing one or more double bonds; t is 0, 1, 2, 3 or 4; and R$^1$, R$^4$, R$^5$, R$^6$, R$^7$, R$^8$, R$^9$, R$^f$ and m are as defined herein.

In some embodiments of compounds of Formula XIII, ring A together with the pyridazine ring to which it is bound form a group selected from cinnoline, pyrido[2,3-c]pyridazine, pyrido[3,4-c]pyridazine, pyrido[4,3-c]pyridazine, pyrido[3,2-c]pyridazine, 5,6,7,8-tetrahydrocinnoline, 5,6,7,8-tetrahydropyrido[2,3-c]pyridazine, 5,6,7,8-tetrahydropyrido[3,4-c]pyridazine, 5,6,7,8-tetrahydropyrido[4,3-c]pyridazine, 5,6,7,8-tetrahydropyrido[3,2-c]pyridazine, thieno[2,3-c]pyridazine, thiazolo[5,4-c]pyridazine, 7H-pyrrolo[2,3-c]pyridazine, 7H-imidazo[4,5-c]pyridazine, thieno[3,2-c]pyridazine, thiazolo[4,5-c]pyridazine, 5H-pyrrolo[3,2-c]pyridazine, 5H-imidazo[4,5-c]pyridazine, 1H-pyrazolo[4,3-c]pyridazine, 1H-pyrazolo[3,4-c]pyridazine, 3H-[1,2,3]triazolo[4,5-c]pyridazine, 6,7-dihydro-5H-pyrrolo[2,3-c]pyridazine, 6,7-dihydro-5H-pyrrolo[3,4-c]pyridazine, 6,7-dihydro-5H-pyrrolo[3,2-c]pyridazine and 6,7-dihydro-5H-cyclopenta[c]pyridazine, each optionally substituted with 1, 2, 3, 4 or 5 $R^f$ substituents.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n), XII(o) or XIII, $R^1$ is selected from hydrogen, halogen, CN, $C_{1-6}$ alkyl, $C_{1-6}$ haloalkyl, $C(O)OR^a$, $C(O)NR^bR^c$, $OR^a$, $NR^bR^c$, $C_{6-10}$ aryl and 5-10 membered heteroaryl.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n), XII(o) or XIII, $R^1$ is selected from hydrogen, halogen, CN, $C_{1-6}$ alkyl, $C_{1-6}$ haloalkyl, hydroxyl, $C_{1-6}$ alkoxy, $NH_2$, $NHC_{1-6}$ alkyl, and $N(C_{1-6}$ alkyl$)_2$.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n), XII(o) or XIII, $R^1$ is selected from hydrogen, halogen, CN, $CF_3$ and methyl.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n), XII(o) or XIII, $R^1$ is hydrogen.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^3$ is selected from hydrogen, halogen, CN, $C_{1-6}$ alkyl, $C_{1-6}$ haloalkyl, $C(O)OR^a$, $C(O)NR^bR^c$, $OR^a$, $NR^bR^c$, $C_{6-10}$ aryl and 5-10 membered heteroaryl.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^3$ is selected from hydrogen, halogen, CN, $C_{1-6}$ alkyl, $C_{1-6}$ haloalkyl, hydroxyl, $C_{1-6}$ alkoxy, $NH_2$, $NHC_{1-6}$ alkyl, and $N(C_{1-6}$ alkyl$)_2$.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^3$ is selected from hydrogen, halogen, CN, $CF_3$ and methyl.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^3$ is hydrogen.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^1$ and $R^3$ are each hydrogen.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n), XII(o), or XIII, $R^4$ is selected from hydrogen, $C_{1-6}$ alkyl, $C_{1-6}$ haloalkyl, $C(O)R^a$, $C(O)OR^a$, $C(O)NR^bR^c$ and $SO_2R^a$.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n) or XII(o), $R^4$ is hydrogen.

In some embodiments of compounds of Formula I, II, III, IV(a), IV(b), V(a), V(b), VI, VII(a), VII(b), VIII(a), VIII(b), IX, X(a), X(b), XI(a), XI(b), XII(a), XII(b), XII(c), XII(d), XII(e), XII(f), XII(g), XII(h), XII(i), XII(j), XII(k), XII(l), XII(m), XII(n), XII(o), or XIII, $R^1$, $R^3$ and $R^4$ are each hydrogen.

In some embodiments of compounds of Formula I, III, IV(b), V(b), VI, VII(b), VIII(b), IX, X(b), XI(b), XII(a), XII(c), XII(e), XII(f), XII(h), XII(j), XII(k), XII(m), XII(o) or XIII, $R^8$ and $R^9$, at each occurrence, are each independently selected from hydrogen, halogen and $C_{1-6}$ alkyl.

In some embodiments of compounds of Formula I, III, IV(b), V(b), VI, VII(b), VIII(b), IX, X(b), XI(b), XII(a), XII(c), XII(e), XII(f), XII(h), XII(j), XII(k), XII(m), XII(o) or XIII, $R^8$ and $R^9$, at each occurrence, are each hydrogen.

In some embodiments, the compound is selected from the compounds in Table 2, or a pharmaceutically acceptable salt thereof.

The compounds and compositions described and/or disclosed herein modulate the contractility of the skeletal sarcomere. Specifically, the compounds modulate the troponin complex of the fast skeletal muscle sarcomere through one or more of fast skeletal myosin, actin, tropomyosin, troponin C, troponin I, and troponin T, and fragments and isoforms thereof. As used in this context, "modulate" means either increasing or decreasing activity. In some instances, the compounds described and/or disclosed herein potentiate (i.e., increase activity) of one or more of fast skeletal myosin, actin, tropomyosin, troponin C, troponin I, and troponin T, and fragments and isoforms thereof. In other instances, the compounds described and/or disclosed herein inhibit (i.e., decrease activity) of one or more of fast skeletal myosin, actin, tropomyosin, troponin C, troponin I, and troponin T, and fragments and isoforms thereof.

In both preclinical and clinical settings, activators of the fast skeletal troponin complex have been shown to amplify the response of fast skeletal muscle to nerve stimulation, resulting in an increase in muscle force development at sub-maximal muscle activation (see, e.g., Russell et al., "The Fast Skeletal Troponin Activator, CK-2017357, Increases Skeletal Muscle Force in vitro and in situ", 2009 Experimental Biology Conference, New Orleans, La., April 2009). Activators of the fast skeletal troponin complex have been shown to increase the sensitivity of skinned skeletal muscle fibers to calcium, and in living muscle to the frequency of stimulation, each of which results in an increase in muscle force development at sub-maximal muscle activation. Such activators have also been shown to reduce muscle fatigue and/or to increase the overall time to fatigue in normal and low oxygenated conditions (see, e.g., Russell et al., "The Fast Skeletal Troponin Activator, CK-2017357, Increases Skeletal Muscle Force and Reduces Muscle Fatigue in vitro and in situ", 5th Cachexia Conference, Barcelona, Spain, December 2009;

Hinken et al., "The Fast Skeletal Troponin Activator, CK-2017357, Reduces Muscle Fatigue in an in situ Model of Vascular Insufficiency", Society for Vascular Medicine's 2010 Annual Meeting: 21st Annual Scientific Sessions, Cleveland, Ohio, April 2010). The increase in muscle force in response to nerve input has been demonstrated in healthy human volunteers as well (see, e.g., Hansen et al., "CK-2017357, a Novel Activator of Fast Skeletal Muscle, Increases Isometric Force Evoked by Electrical Stimulation of the Anterior Tibialis Muscle in Healthy Male Subjects", Society for Neuroscience 40th Annual Meeting: Neuroscience 2010, November 2010). Work in additional preclinical models of muscle function suggests that activators of the fast skeletal troponin complex also cause an increase in muscle power and/or endurance. These pharmacological properties suggest this mechanism of action could have application in conditions, for example, where neuromuscular function is impaired.

Provided are methods for enhancing fast skeletal muscle efficiency in a patient in need thereof, comprising administering to said patient an effective amount of a compound or composition described and/or disclosed herein that selectively binds the troponin complex of fast skeletal muscle fiber or sarcomere. In some embodiments, the compound disclosed and/or described herein activates fast skeletal muscle fibers or sarcomeres. In some embodiments, administration of a compound disclosed and/or described herein results in an increase in fast skeletal muscle power output. In some embodiments, administration of a compound disclosed and/or described herein results in increased sensitivity of fast skeletal muscle fibers or sarcomeres to calcium ion, as compared to fast skeletal muscle fibers or sarcomeres untreated with the compound. In some embodiments, administration of a compound disclosed and/or described herein results in a lower concentration of calcium ions causing fast skeletal muscle myosin to bind to actin. In some embodiments, administration of a compound disclosed and/or described herein results in the fast skeletal muscle fiber generating force to a greater extent at submaximal levels of muscle activation.

Also provided is a method for sensitizing a fast skeletal muscle fiber to produce force in response to a lower concentration of calcium ion, comprising contacting the fast skeletal muscle fiber with a compound or composition described and/or disclosed herein that selectively binds to troponin complexes in the fast skeletal muscle sarcomere. In some embodiments, contacting the fast skeletal muscle fiber with the compound results in activation of the fast skeletal muscle fiber at a lower calcium ion concentration than in an untreated fast skeletal muscle fiber. In some embodiments, contacting the fast skeletal muscle fiber with the compound results in the production of increased force at a lower calcium ion concentration in comparison with an untreated fast skeletal muscle fiber.

Also provided is a method for increasing time to fast skeletal muscle fatigue in a patient in need thereof, comprising contacting fast skeletal muscle fibers with a compound or composition described and/or disclosed herein that selectively binds to the troponin complexes of the fast skeletal muscle fibers. In some embodiments, the compound binds to form ligand-troponin-calcium ion complexes that activate the fast skeletal muscle fibers. In some embodiments, formation of the complexes and/or activation of the fast skeletal muscle fibers results in enhanced force and/or increased time to fatigue as compared to untreated fast skeletal muscle fibers contacted with a similar calcium ion concentration.

The compounds and pharmaceutical compositions described and/or disclosed herein are capable of modulating the contractility of the fast skeletal sarcomere in vivo, and can have application in both human and animal disease. Modulation would be desirable in a number of conditions or diseases, including, but not limited to, 1) neuromuscular disorders, such as Amyotrophic Lateral Sclerosis (ALS), Spinal Muscular Atrophy (SMA), peripheral neuropathies and myasthenia gravis; 2) disorders of voluntary muscle, including muscular dystrophies, myopathies and conditions of muscle wasting, such as sarcopenia and cachexia syndromes (e.g., cachexia syndromes caused by diseases such as cancer, heart failure, chronic obstructive pulmonary disease (COPD), and chronic kidney disease/dialysis), and rehabilitation-related deficits, such as those associated with recovery from surgery (e.g. post-surgical muscle weakness) prolonged bed rest or stroke rehabilitation; 3) central nervous system (CNS) disorders in which muscle weakness, atrophy and fatigue are prominent symptoms, such as multiple sclerosis, Parkinson's disease, stroke and spinal cord injury; and 4) muscle symptoms stemming from systemic disorders, including Peripheral Vascular Disease (PVD) or Peripheral Arterial Disease (PAD) (e.g., claudication), metabolic syndrome, chronic fatigue syndrome, obesity and frailty due to aging.

The compounds and compositions described and/or disclosed herein may be used to treat neuromuscular diseases, i.e., diseases that affect any part of the nerve-muscle unit. Neuromuscular diseases include, for example: 1) diseases of the motor unit, including but not limited to Amyotrophic Lateral Sclerosis (ALS) including bulbar and primary lateral sclerosis (PLS) variants; spinal muscular atrophy types 1-4; Kennedy syndrome; post-polio syndrome; motor neuropathies including, for example, critical illness polyneuropathy; multifocal motor neuropathy with conduction block; Charcot-Marie-Tooth disease and other hereditary motor and sensory neuropathies; and Guillain-Barre Syndrome, 2) disorders of the neuromuscular junction, including myasthenia gravis, Lambert-Eaton myasthenic syndrome, and prolonged neuromuscular blockade due to drugs or toxins; and 3) peripheral neuropathies, such as acute inflammatory demyelinating polyradiculoneuropathy, diabetic neuropathy, chronic inflammatory demyelinating polyradiculoneuropathy, traumatic peripheral nerve lesions, neuropathy of leprosy, vasculitic neuropathy, dermatomyositis/polymyositis and neuropathy of Friedreich Ataxia.

The compounds and compositions described and/or disclosed herein may be used to treat disorders of voluntary muscle. Disorders of voluntary muscle include 1) muscular dystrophies (including, for example, Duchenne, Becker, Limb-Girdle, Facioscapulohumeral, limb girdle, Emery-Dreyfus, oculopharyngeal and congenital muscular dystrophies); and 2) myopathies, such as nemaline myopathy, central core disease, congenital myopathies, mitochondrial myopathies, acute myopathy; inflammatory myopathies (such as dermatomyositis/polymyositis and inclusion body myositis), endocrine myopathies (such as those associated with hyper- or hypothyroidism), Cushing's or Addison's syndrome or disease and pituitary gland disorders, metabolic myopathies (such as glycogen storage diseases, e.g., McArdle's disease, Pompe disease, etc), drug-induced myopathy (statins, anti-retroviral drugs, steroid myopathy) restrictive lung disease, sarcoidosis, Schwartz-Jampel Syndrome, focal muscular atrophies, and distal myopathies.

The compounds and compositions described and/or disclosed herein may be used to treat or Amyotrophic Lateral Sclerosis (ALS). ALS is a disease that generally arises later in life (Age 50+) and has a rapid progression from initial limb weakness to paralysis and death. Common life expectancy after diagnosis is 3-5 years. The cause of disease for most ALS patients is unknown (termed the spontaneous form) while a small proportion of patients have an inherited form (familial) of disease. The condition causes progressive death of motor neurons through causes that are not clear. Surviving motor units attempt to compensate for dying ones by innervating more fibers (termed sprouting) but this can only partially correct muscle function, as muscles are subsequently more prone to problems of coordination and fatigue. Eventually, surviving motor neurons die, resulting in complete paralysis of the affected muscle. The disease is commonly fatal through the eventual loss of innervation to the diaphragm, resulting in respiratory failure. Current treatment options for ALS are limited.

The compounds and compositions described and/or disclosed herein may be used to treat Spinal Muscular Atrophy (SMA). SMA is a genetic disorder that arises through the mutation of a protein, SMN1, that appears to be required for the survival and health of motor neurons. The disease is most common in children as the majority of patients only survive until 11-12 years of age. There is currently no available treatment for SMA.

The compounds and compositions described and/or disclosed herein may be used to treat myasthenia gravis. Myasthenia gravis is a chronic autoimmune neuromuscular disease wherein the body produces antibodies that block, alter, or destroy proteins involved in signaling at the neuromuscular junction, thus preventing muscle contraction from occurring. These proteins include nicotinic acetylcholine receptor (AChR) or, less frequently, a muscle-specific tyrosine kinase (MuSK) involved in AChR clustering (see, e.g., Drachman, N. Eng. J. of Med., 330:1797-1810, 1994). The disease is characterized by varying degrees of weakness of the skeletal (voluntary) muscles of the body. The hallmark of myasthenia gravis is muscle weakness that increases during periods of activity and improves after periods of rest. Although myasthenia gravis may affect any voluntary muscle, certain muscles, such as those that control eye and eyelid movement, facial expression, chewing, talking, and swallowing are often, but not always, involved in the disorder. The muscles that control breathing and neck and limb movements may also be affected. In most cases, the first noticeable symptom is weakness of the eye muscles. In others, difficulty in swallowing and slurred speech may be the first signs. The degree of muscle weakness involved in myasthenia gravis varies greatly among patients, ranging from a localized form, limited to eye muscles (ocular myasthenia), to a severe or generalized form in which many muscles—sometimes including those that control breathing—are affected. Symptoms, which vary in type and severity, may include a drooping of one or both eyelids (ptosis), blurred or double vision (diplopia) due to weakness of the muscles that control eye movements, unstable or waddling gait, weakness in arms, hands, fingers, legs, and neck, a change in facial expression, difficulty in swallowing and shortness of breath, and impaired speech (dysarthria). Generalized weakness develops in approximately 85% of patients.

The compounds and compositions described and/or disclosed herein may be used to treat sarcopenia, e.g., sarcopenia associated with aging or disease (e.g. HIV infection). Sarcopenia is characterized by a loss of skeletal muscle mass, quality, and strength. Clinically, a decline in skeletal muscle tissue mass (muscle atrophy) contributes to frailty in older individuals. In human males, muscle mass declines by one-third between the ages of 50 and 80. In older adults, extended hospitalization can result in further disuse atrophy leading to a potential loss of the ability for independent living and to a cascade of physical decline. Moreover, the physical aging process profoundly affects body composition, including significant reductions in lean body mass and increases in central adiposity. The changes in overall adiposity and fat distribution appear to be important factors in many common age-related diseases such as hypertension, glucose intolerance and diabetes, dyslipidemia, and atherosclerotic cardiovascular disease. In addition, it is possible that the age-associated decrement in muscle mass, and subsequently in strength and endurance, may be a critical determinant for functional loss, dependence and disability. Muscle weakness is also a major factor predisposing the elderly to falls and the resulting morbidity and mortality.

The compounds and compositions described and/or disclosed herein may be used to treat cachexia. Cachexia is a state often associated with cancer or other serious diseases or conditions, (e.g, chronic obstructive pulmonary disease, heart failure, chronic kidney disease, kidney dialysis), that is characterized by progressive weight loss, muscle atrophy and fatigue, due to the deletion of adipose tissue and skeletal muscle.

The compounds and compositions described and/or disclosed herein may be used to treat muscular dystrophies. Muscular dystrophy can be characterized by progressive muscle weakness, destruction and regeneration of the muscle fibers, and eventual replacement of the muscle fibers by fibrous and fatty connective tissue.

The compounds and compositions described and/or disclosed herein may be used to treat post-surgical muscle weakness, which is a reduction in the strength of one or more muscles following surgical procedure. Weakness may be generalized (i.e. total body weakness) or localized to a specific area, side of the body, limb, or muscle.

The compounds and compositions described and/or disclosed herein may be used to treat post-traumatic muscle weakness, which is a reduction in the strength of one or more muscles following a traumatic episode (e.g. bodily injury). Weakness may be generalized (i.e. total body weakness) or localized to a specific area, side of the body, limb, or muscle.

The compounds and compositions described and/or disclosed herein may be used to treat muscle weakness and fatigue produced by peripheral vascular disease (PVD) or peripheral artery disease (PAD). Peripheral vascular disease is a disease or disorder of the circulatory system outside of the brain and heart. Peripheral artery disease (PAD), also known as peripheral artery occlusive disease (PAOD), is a form of PVD in which there is partial or total blockage of an artery, usually one leading to a leg or arm. PVD and/or PAD can result from, for example, atherosclerosis, inflammatory processes leading to stenosis, embolus/thrombus formation, or damage to blood vessels due to disease (e.g., diabetes), infection or injury. PVD and/or PAD can cause either acute or chronic ischemia, typically of the legs. The symptoms of PVD and/or PAD include pain, weakness, numbness, or cramping in muscles due to decreased blood flow (claudication), muscle pain, ache, cramp, numbness or fatigue that occurs during exercise and is relieved by a short period of rest (intermittent claudication), pain while resting (rest pain) and biological tissue loss (gangrene). The symptoms of PVD and/or PAD often occur in calf muscles, but symptoms may also be observed in other muscles such as the thigh or hip. Risk factors for PVD and/or PAD include age, obesity, sedentary lifestyle, smoking, diabetes, high blood pressure, and high cholesterol (i.e., high LDL, and/or high triglycerides and/or low HDL). People who have coronary heart disease or a history of heart attack or stroke generally also have an increased frequency of having PVD and/or PAD. Activators of the fast skeletal troponin complex have been shown to reduce muscle fatigue and/or to increase the overall time to fatigue in in vitro and in situ models of vascular insufficiency (see, e.g., Russell et al., "The Fast Skeletal Troponin Activator, CK-2017357, Increases Skeletal Muscle Force and Reduces Muscle Fatigue in vitro and in situ", 5th Cachexia Conference, Barcelona, Spain, December 2009; Hinken et al., "The Fast Skeletal Troponin Activator, CK-2017357, Reduces Muscle Fatigue in an in situ Model of Vascular Insufficiency", Society for Vascular Medicine's 2010 Annual Meeting: 21st Annual Scientific Sessions, Cleveland, Ohio, April 2010).

The compounds and compositions described and/or disclosed herein may be used to treat symptoms of frailty, e.g., frailty associated with aging. Frailty is characterized by one or more of unintentional weight loss, muscle weakness, slow walking speed, exhaustion, and low physical activity.

The compounds and compositions described and/or disclosed herein may be used to treat muscle weakness and/or fatigue due to wasting syndrome, which is a condition characterized by involuntary weight loss associated with chronic fever and diarrhea. In some instances, patients with wasting syndrome lose 10% of baseline body weight within one month.

The compounds and compositions described and/or disclosed herein may be used to treat muscular diseases and conditions caused by structural and/or functional abnormalities of skeletal muscle tissue, including muscular dystrophies, congenital muscular dystrophies, congenital myopathies, distal myopathies, other myopathies (e.g., myofibrillar, inclusion body), myotonic syndromes, ion channel muscle diseases, malignant hyperthermias, metabolic myopathies, congenital myasthenic syndromes, sarcopenia, muscle atrophy and cachexia.

The compounds and compositions described and/or disclosed herein also may be used to treat diseases and conditions caused by muscle dysfunction originating from neuronal dysfunction or transmission, including amyotrophic lateral sclerosis, spinal muscular atrophies, hereditary ataxias, hereditary motor and sensory neuropathies, hereditary paraplegias, stroke, multiple sclerosis, brain injuries with motor deficits, spinal cord injuries, Alzheimer's disease, Parkinson's disease with motor deficits, myasthenia gravis and Lambert-Eaton syndrome.

The compounds and compositions described and/or disclosed herein also may be used to treat diseases and conditions caused by CNS, spinal cord or muscle dysfunction originating from endocrine and/or metabolic dysregulation, including claudication secondary to peripheral artery disease, hypothyroidism, hyper- or hypo-parathyroidism, diabetes, adrenal dysfunction, pituitary dysfunction and acid/base imbalances.

The compounds and compositions described and/or disclosed herein may be administered alone or in combination with other therapies and/or therapeutic agents useful in the treatment of the aforementioned disorders.

The compounds and compositions described and/or disclosed herein may be combined with one or more other therapies to treat ALS. Examples of suitable therapies include riluzole, baclofen, diazepam, trihexyphenidyl and amitriptyline. In some embodiments, the compounds and compositions described and/or disclosed herein are combined with riluzole to treat a subject suffering from ALS.

The compounds and compositions described and/or disclosed herein may be combined with one or more other therapies to treat myasthenia gravis. Examples of suitable therapies include administration of anticholinesterase agents (e.g., neostigmine, pyridostigmine), which help improve neuromuscular transmission and increase muscle strength; administration of immunosuppressive drugs (e.g., prednisone, cyclosporine, azathioprine, mycophenolate mofetil) which improve muscle strength by suppressing the production of abnormal antibodies; thymectomy (i.e., the surgical removal of the thymus gland, which often is abnormal in myasthenia gravis patients); plasmapheresis; and intravenous immune globulin.

The compounds and compositions described and/or disclosed herein may be combined with one or more other therapies to treat PVD or PAD (e.g., claudication). Treatment of PVD and PAD is generally directed to increasing arterial blood flow, such as by smoking cessation, controlling blood pressure, controlling diabetes, and exercising. Treatment can also include medication, such as medicines to help improve walking distance (e.g., cilostazol, pentoxifylline), antiplatelet agents (e.g., aspirin, ticlopidine, clopidogrel), anticoagulents (e.g., heparin, low molecular weight heparin, warfarin, enoxaparin) throbmolytics, antihypertensive agents (e.g., diuretics, ACE inhibitors, calcium channel blockers, beta blockers, angiotensin II receptor antagonists), and cholesterol-lowering agents (e.g., statins). In some patients, angioplasty, stenting, or surgery (e.g., bypass surgery or surgery to remove an atherosclerotic plaque) may be necessary.

Suitable therapeutic agents include, for example, anti-obesity agents, anti-sarcopenia agents, anti-wasting syndrome agents, anti-frailty agents, anti-cachexia agents, anti-muscle spasm agents, agents against post-surgical and post-traumatic muscle weakness, and anti-neuromuscular disease agents.

Suitable additional therapeutic agents include, for example: orlistat, sibramine, diethylpropion, phentermine, benzaphetamine, phendimetrazine, estrogen, estradiol, levonorgestrel, norethindrone acetate, estradiol valerate, ethinyl estradiol, norgestimate, conjugated estrogens, esterified estrogens, medroxyprogesterone acetate, testosterone, insulin-derived growth factor, human growth hormone, riluzole, cannabidiol, prednisone, albuterol, non-steroidal anti-inflammatory drugs, and botulinum toxin.

Other suitable therapeutic agents include TRH, diethylstilbesterol, theophylline, enkephalins, E series prostaglandins, compounds disclosed in U.S. Pat. No. 3,239,345 (e.g., zeranol), compounds disclosed in U.S. Pat. No. 4,036,979 (e.g., sulbenox), peptides disclosed in U.S. Pat. No. 4,411,890, growth hormone secretagogues such as GHRP-6, GHRP-1 (disclosed in U.S. Pat. No. 4,411,890 and publications WO 89/07110 and WO 89/07111), GHRP-2 (disclosed in WO 93/04081), NN703 (Novo Nordisk), LY444711 (Lilly), MK-677 (Merck), CP424391 (Pfizer) and B-HT920, growth hormone releasing factor and its analogs, growth hormone and its analogs and somatomedins including IGF-1 and IGF-2, alpha-adrenergic agonists, such as clonidine or serotonin 5-$HT_D$ agonists, such as sumatriptan, agents which inhibit somatostatin or its release, such as physostigmine, pyridostigmine, parathyroid hormone, PTH(1-34), and bisphosphonates, such as MK-217 (alendronate).

Still other suitable therapeutic agents include estrogen, testosterone, selective estrogen receptor modulators, such as tamoxifen or raloxifene, other androgen receptor modulators, such as those disclosed in Edwards, J. P. et. al., Bio. Med. Chem. Let., 9, 1003-1008 (1999) and Hamann, L. G. et. al., J. Med. Chem., 42, 210-212 (1999), and progesterone receptor agonists ("PRA"), such as levonorgestrel, medroxyprogesterone acetate (MPA).

Other suitable therapeutic agents include anabolic agents, such as selective androgen receptor modulators (SARMs); antagonists of the activin receptor pathway, such as anti-myostatin antibodies or soluble activin receptor decoys, including ACE-031 (Acceleron Pharmaceuticals, a soluble activin receptor type IIB antagonist), MYO-027/PFE-3446879 (Wyeth/Pfizer, an antibody myostatin inhibitor), AMG-745 (Amgen, a peptibody myostatin inhibitor), and an ActRIIB decoy receptor (see Zhou et al., Cell, 142, 531-543, Aug. 20, 2010); and anabolic steroids.

Still other suitable therapeutic agents include aP2 inhibitors, such as those disclosed in U.S. Pat. No. 6,548,529, PPAR gamma antagonists, PPAR delta agonists, beta 3 adrenergic agonists, such as AJ9677 (Takeda/Dainippon), L750355 (Merck), or CP331648 (Pfizer), other beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993, WO 99/00353, and GB98/284425, and anorectic agents, such as dexamphetamine, phentermine, phenylpropanolamine or mazindol.

Still other suitable therapeutic agents include HIV and AIDS therapies, such as indinavir sulfate, saquinavir, saquinavir mesylate, ritonavir, lamivudine, zidovudine, lamivudine/zidovudine combinations, zalcitabine, didanosine, stavudine, and megestrol acetate.

Still other suitable therapeutic agents include antiresorptive agents, hormone replacement therapies, vitamin D analogues, elemental calcium and calcium supplements, cathepsin K inhibitors, MMP inhibitors, vitronectin receptor antagonists, Src SH.sub.2 antagonists, vacuolar $H^+$-ATPase inhibitors, ipriflavone, fluoride, Tibo lone, pro stanoids, 17-beta hydroxysteroid dehydrogenase inhibitors and Src kinase inhibitors.

The above therapeutic agents, when employed in combination with the compounds and compositions disclosed and/or described herein, may be used, for example, in those amounts indicated in the Physicians' Desk Reference (PDR) or as otherwise determined by one of ordinary skill in the art.

The compounds and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.05 to 100 mg/kg of body weight; in some embodiments, from about 0.10 to 10.0 mg/kg of body weight, and in some embodiments, from about 0.15 to 1.0 mg/kg of body weight. Thus, for administration to a 70 kg person, in some embodiments, the dosage range would be about from 3.5 to 7000 mg per day; in some embodiments, about from 7.0 to 700.0 mg per day, and in some embodiments, about from 10.0 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 70 mg to about 700 mg per day, and an exemplary intravenous administration dosage is from about 70 mg to about 700 mg per day, each depending upon the compound pharmacokinetics.

Administration of the compounds and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound or composition is administered orally or intravenously. In some embodiments, the compound or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The compounds disclosed and/or described herein can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see *Remington's Pharmaceutical Sciences*, Mack Publishing Company, Easton, Pa.

In some embodiments, the compositions will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

The following examples serve to more fully describe the invention described herein. It is understood that these examples in no way serve to limit the true scope of this invention, but rather are presented for illustrative purposes.

EXAMPLE 1

Preparation of N-(5-(6-(2-(4-Fluorophenyl)-2-methylpropylamino)pyridazin-3-yl)-1H-indazol-3-yl)acetamide

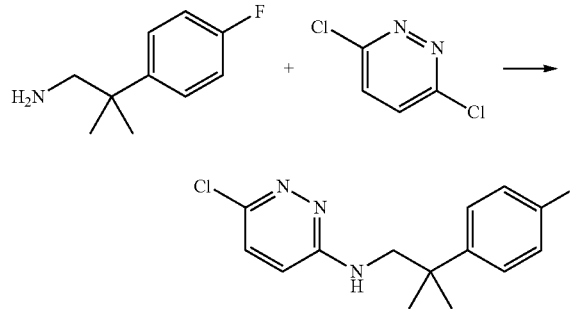

6-Chloro-N-(2-(4-fluorophenyl)-2-methylpropyl)pyridazin-3-amine

A solution of (2-(4-fluorophenyl)-2-methylpropan-1-amine (27 g, 160 mmol, 1.6 equiv), 3,6-dichloropyridazine (15 g, 100 mmol, 1.0 equiv) and $K_2CO_3$ (42 g, 302 mmol, 3.0 equiv) in isopropanol (15 mL) was stirred at 100° C. for 36 hours. The cooled mixture was partitioned between water and EtOAc and the organic fraction was dried over $Na_2SO_4$ and concentrated in vacuo. Partial purification over silica gel using a 30-75% gradient of EtOAc/hexanes gave the desired product (29.6 g, 103%) which was used without further purification.

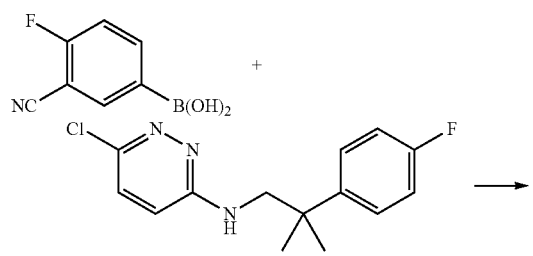

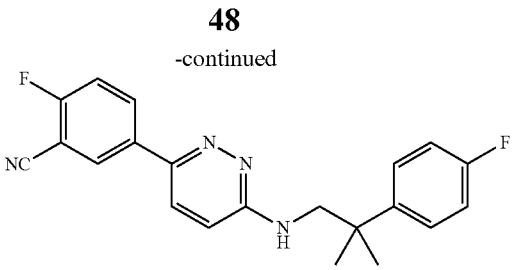

2-Fluoro-5-(6-(2-(4-fluorophenyl)-2-methylpropylamino)pyridazin-3-yl)benzonitrile To a solution of 6-chloro-N-(2-(4-fluorophenyl)-2-methylpropyl)pyridazin-3-amine (5.0 g, 23 mmol, 1.0 equiv) and $K_2CO_3$ (9.4 g, 68 mmol, 3.0 equiv) in dioxane (35 mL) was added Pd(dppf)Cl$_2$ (1.7 g, 2.3 mmol, 0.1 equiv) and 3-cyano-4-fluorophenylboronic acid (5.0 g, 30 mmol, 1.3 equiv). The mixture was stirred at 80° C. for 3 hours after which it was allowed to cool to room temperature and concentrated in vacuo. The residue was diluted with EtOAc, washed with saturated NaHCO$_3$, dried over Na$_2$SO$_4$ and evaporated to dryness. The residue was purified by reverse phase HPLC using a CH$_3$CN/water gradient to give the desired product (5.3 g, 63%).

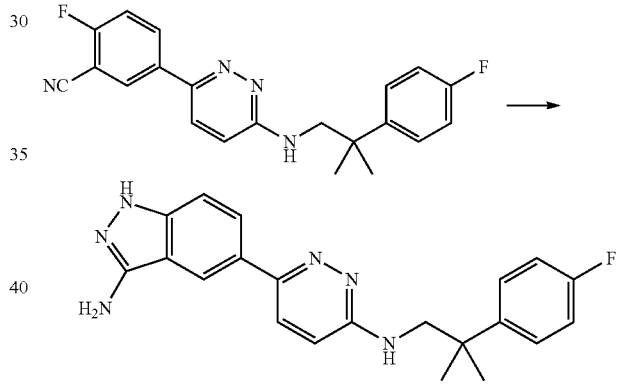

5-(6-(2-(4-Fluorophenyl)-2-methylpropylamino)pyridazin-3-yl)-1H-indazol-3-amine

To a solution of 2-fluoro-5-(6-(2-(4-fluorophenyl)-2-methylpropylamino)pyridazin-3-yl)benzonitrile (0.53 g, 1.5 mmol, 1.0 equiv) in n-butanol (10 mL) was added hydrazine monohydrate (1.0 mL, 32 mmol, 20 equiv). The mixture was stirred at 110° C. for two hours followed by evaporation of the solvents in vacuo. Purification on a preparatory TLC plate using 5% MeOH/DCM as eluent gave the desired product (195 mg, 36%), m/z=377.1 [M+H].

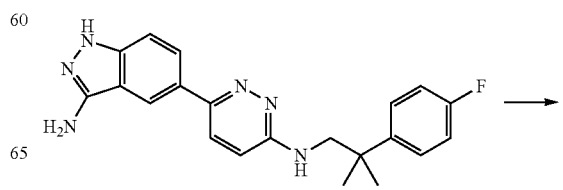

-continued

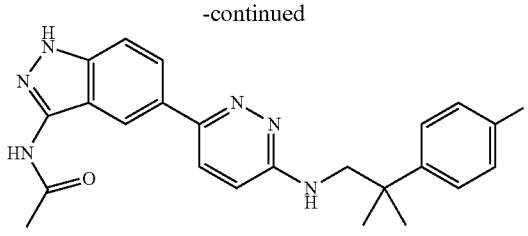

N-(5-(6-(2-(4-Fluorophenyl)-2-methylpropylamino)pyridazin-3-yl)-1H-indazol-3-yl)acetamide To a solution of 5-(6-(2-(4-fluorophenyl)-2-methylpropylamino)pyridazin-3-yl)-1H-indazol-3-amine (50 mg, 133 μmol) in pyridine (1 mL) was added acetyl chloride (9.5 μL, 133 μmol). The mixture was stirred for 15 min, concentrated, purified by reverse phase chromatography using a CH$_3$CN/water gradient to afford 25 mg of white solid, m/z=419.9 [M+H].

EXAMPLE 2

Preparation of N-(2-(4-Fluorophenyl)-2-methylpropyl)-6-(1H-pyrazol-1-yl)pyridazin-3-amine

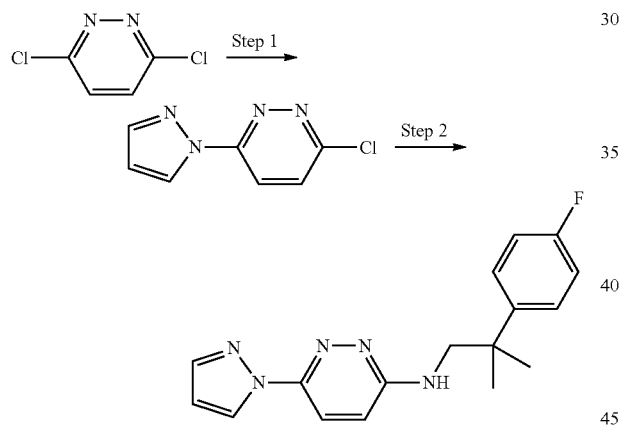

Step 1

To a solution of pyrazole (3.69 g, 25 mmol, 1.0 equiv) in NMP (25 mL) was added sodium hydride (60% dispersion in mineral oil, 1.5 g, 38 mmol, 1.5 equiv). The mixture was stirred for 15 min, followed by the addition of 3,6-dichloropyridazine (3.02 g, 25 mmol, 1.0 equiv). The reaction mixture was stirred for 1.5 h and then diluted with water (50 mL) and ethyl acetate (100 mL). After transferring to a separatory funnel and shaking, the organic layer was separated from the aqueous layer and then washed with brine (3×50 mL). The organic layer was then dried over Na$_2$SO$_4$, filtered, and concentrated to give 3.89 g of 3-chloro-6-(1H-pyrazol-1-yl)pyridazine as a crude tan solid that was used directly in the next step.

Step 2

To a 5 mL microwave vial was added 3-chloro-6-(1H-pyrazol-1-yl)pyridazine (320 mg, 1.8 mmol, 1.0 equiv), 2-(4-fluorophenyl)-2-methylpropan-1-amine (386 mg, 2.3 mmol, 1.3 equiv), diisopropylethylamine (620 μL, 3.6 mmol, 2.0 equiv), and NMP (4 mL). The reaction was heated in a microwave reactor to 250° C. and stirred for 15 min. A portion (roughly a third) of the reaction was purified by reverse phase chromatography and then silica gel chromatography (10% MeOH/DCM) to give 61 mg of N-(2-(4-fluorophenyl)-2-methylpropyl)-6-(1H-pyrazol-1-yl)pyridazin-3-amine, m/z=312.1 [M+H].

EXAMPLE 3

Preparation of 5-(6-(2-(4-fluorophenyl)-2-methylpropylamino) pyridazin-3-yl)-1,3,4-oxadiazol-2(3H)-one

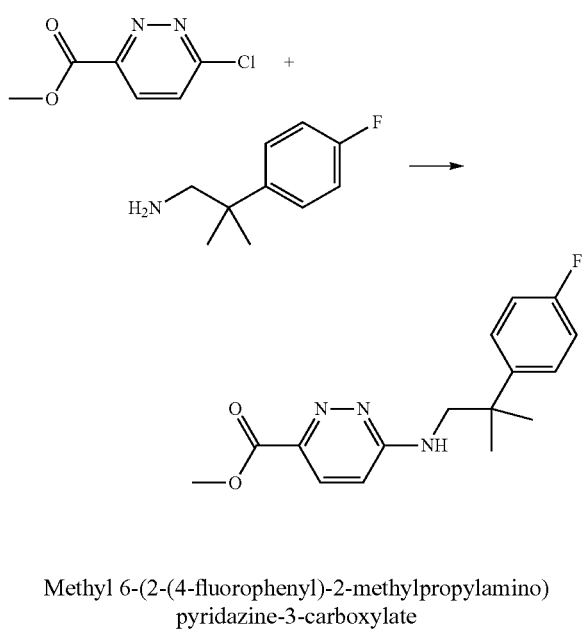

Methyl 6-(2-(4-fluorophenyl)-2-methylpropylamino)pyridazine-3-carboxylate

To a 25 mL round bottom flask was added methyl 6-chloropyridazine-3-carboxylate (0.50 g, 2.90 mmol, 1.0 equiv), 2-(4-fluorophenyl)-2-methylpropan-1-amine (0.60 g, 3.6 mmol, 1.2 equiv), potassium carbonate (300 mg, 2.2 mmol, 0.75 equiv), and isopropanol (3 mL). The reaction mixture was stirred and heated at 120° C. for 12 h. The reaction was then filtered through celite, concentrated, and purified by silica gel chromatography (0-40% EtOAC/hexanes) to afford 360 mg (43%) of methyl 6-(2-(4-fluorophenyl)-2-methylpropylamino)pyridazine-3-carboxylate as an off-white foam.

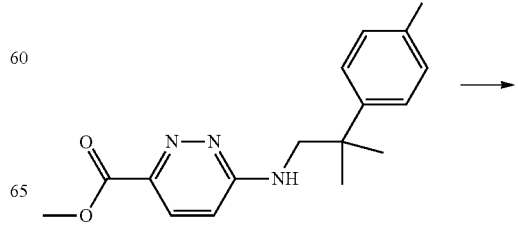

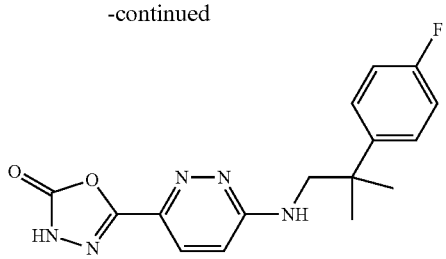

5-(6-(2-(4-Fluorophenyl)-2-methylpropylamino)
pyridazin-3-yl)-1,3,4-oxadiazol-2(3H)-one To a 25 mL round bottom flask was added methyl 6-(2-(4-fluorophenyl)-2-methylpropylamino)pyridazine-3-carboxylate (100 mg, 0.3 mmol, 1.0 equiv), hydrazine hydrate (1 mL), and ethanol (5 mL)). The reaction was refluxed for 2 h and concentrated. N,N'-Carbonyldiimidazole (100 mg, 0.6 mmol, 2.0 equiv) and DMF (1 mL) were then added to the crude product and the reaction was heated to 90° C. for 1.5 h. The reaction mixture was directly purified by reverse phase column chromatography to afford 72 mg (67%) of 5-(6-(2-(4-fluorophenyl)-2-methylpropylamino)pyridazin-3-yl)-1,3,4-oxadiazol-2(3H)-one as a white solid, m/z=330.0 [M+H].

EXAMPLE 4

Preparation of 6-(2-Amino-1H-imidazol-4-yl)-N-(2-(4-fluorophenyl)-2-methylpropyl)pyridazin-3-amine

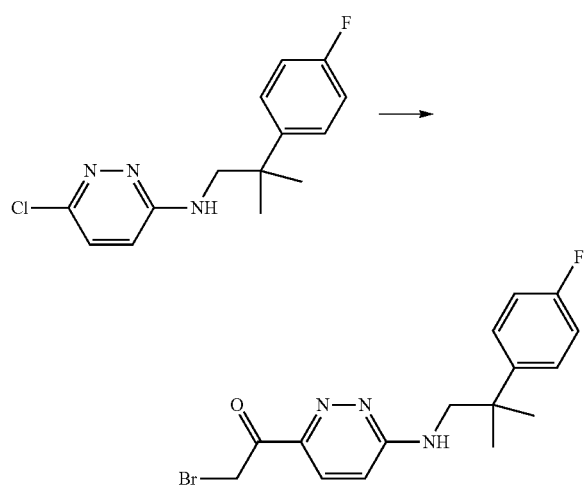

2-Bromo-1-(6-(2-(4-fluorophenyl)-2-methylpropylamino)pyridazin-3-yl)ethanone 6-chloro-N-(2-(4-fluorophenyl)-2-methylpropyl)pyridazin-3-amine (300 mg, 1.1 mmol, 1.0 equiv) and dioxane (5 mL) were added to a microwave vial and sonication was applied until the mixture was homogeneous. Tributyl(1-ethoxyvinyl)stannane (475 µL, 1.4 mmol, 1.3 equiv) and trans-dichlorobis(triphenylphosphine)palladium (30 mg, 0.04 mmol, 0.03 equiv) were then added, and the reaction was heated in a microwave reactor at 150° C. for 20 min. The reaction was concentrated, dissolved in EtOAc (25 mL), and mixed with 2.0 M potassium fluoride (5 mL). The mixture was filtered through celite, and then washed with water, dried over Na$_2$SO$_4$, filtered, and concentrated. The crude solid was redissolved in 50% THF/water (4 mL), followed by the addition of NBS (300 mg, 1.7 mmol, 1.5 equiv). The reaction mixture was stirred for 1 h and then diluted with brine (20 mL) and ethyl acetate (20 mL). After transferring to a separatory funnel and shaking, the organic layer was separated from the aqueous layer. The organic layer was then dried over Na$_2$SO$_4$, filtered, and concentrated to give a brown oil that was purified by silica gel chromatography (0-100% EtOAC/hexanes) to afford 270 mg of 2-bromo-1-(6-(2-(4-fluorophenyl)-2-methylpropylamino)pyridazin-3-yl)ethanone as an orange oil.

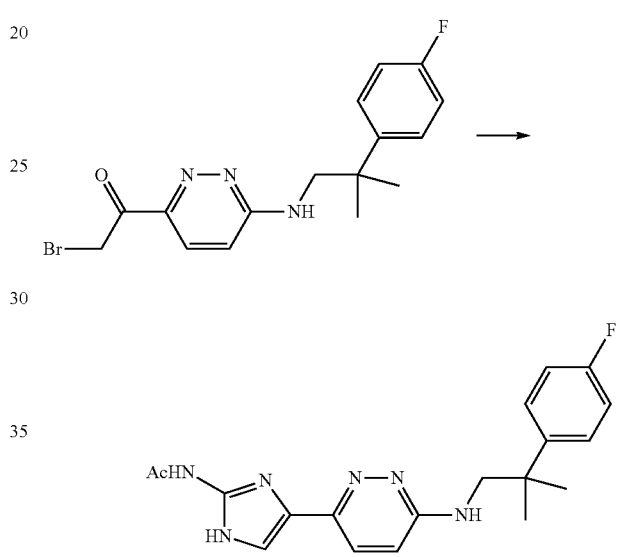

N-(4-(6-(2-(4-Fluorophenyl)-2-methylpropylamino)
pyridazin-3-yl)-1H-imidazol-2-yl)acetamide To a 3 mL microwave reaction vial was added 2-bromo-1-(6-(2-(4-fluorophenyl)-2-methylpropylamino)pyridazin-3-yl)ethanone (125 mg, 0.3 mmol, 1.0 equiv), acetyl guanidine (90 mg, 0.6 mmol, 2.0 equiv) and acetonitrile (2 mL). The reaction was heated in a microwave reactor at 100° C. for 13 min. The reaction was filtered and directly purified by reverse phase column chromatography to afford N-(4-(6-(2-(4-fluorophenyl)-2-methylpropylamino)pyridazin-3-yl)-1H-imidazol-2-yl)acetamide (70 mg) as an white solid. m/z=369.2 [M+H]+.

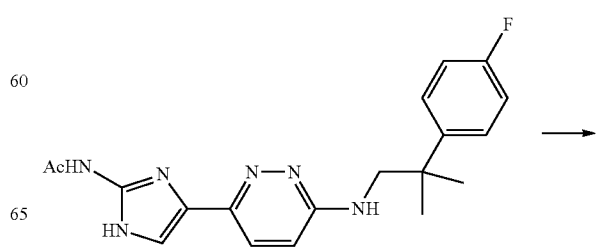

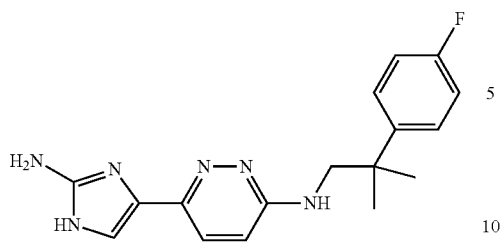

6-(2-Amino-1H-imidazol-4-yl)-N-(2-(4-fluorophenyl)-2-methylpropyl)pyridazin-3-amine To a 10 mL round bottom flask was added N-(4-(6-(2-(4-fluorophenyl)-2-methylpropylamino)pyridazin-3-yl)-1H-imidazol-2-yl)acetamide (22 mg, 59 μmol), concentrated HCl (100 μL) and methanol (1 mL). The reaction was refluxed for 12 h and then concentrated, redissolved in EtOAc (10 mL), washed with saturated sodium carbonate (2×10 mL) and brine (1×10 mL), dried (Na$_2$SO$_4$) and concentrated to yield 8 mg (42%) of 6-(2-amino-1H-imidazol-4-yl)-N-(2-(4-fluorophenyl)-2-methylpropyl)pyridazin-3-amine as a pale yellow solid, m/z=327.2 [M+H].

EXAMPLE 5

Preparation of 6-(5-Amino-1H-pyrazol-3-yl)-N-(2-(4-fluorophenyl)-2-methylpropyl)pyridazin-3-amine

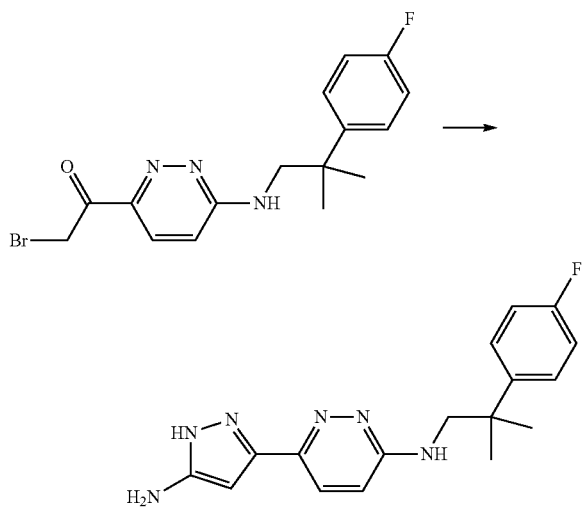

To a 20 dram vial was added 2-bromo-1-(6-(2-(4-fluorophenyl)-2-methylpropylamino)pyridazin-3-yl)ethanone (13 mg, 35 μmol, 1.0 equiv), sodium cyanide (25 mg, 500 μmol, 15.0 equiv) and ethanol (1 mL). The reaction mixture was heated to 60° C. for 30 min. After cooling to room temperature, the reaction was filtered. Hydrazine hydrate (250 μL) was then added, and the reaction mixture was heated to 100° C. for 2 h. The reaction was filtered and directly purified by reverse phase column chromatography to afford 6-(5-amino-1H-pyrazol-3-yl)-N-(2-(4-fluorophenyl)-2-methylpropyl)pyridazin-3-amine (2 mg) as an white solid, m/z=327.2 [M+H].

EXAMPLE 6

Preparation of 6-Ethyl-N-(2-(4-fluorophenyl)-2-methylpropyl)pyridazin-3-amine

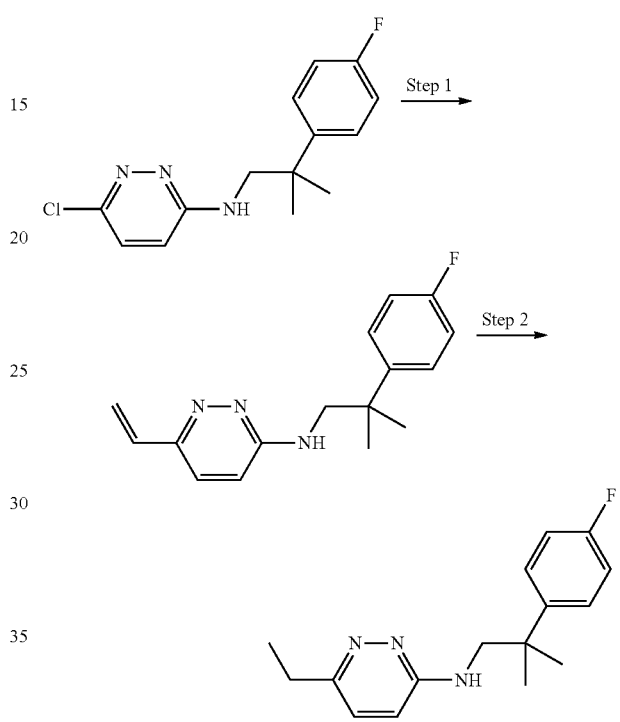

Step 1

To a 5 mL microwave reaction vial was added 6-chloro-N-(2-(4-fluorophenyl)-2-methylpropyl)pyridazin-3-amine (123 mg, 441 μmol, 1.0 equiv), 2,4,6-trivinyl-1,3,5,2,4,6-trioxatriborinane (159 mg, 661 μmol, 1.5 equiv), Cl$_2$Pd(dppf) (54 mg, 66 μmol, 0.15 equiv), potassium carbonate (182 mg, 1.32 mmol, 3 equiv), and dioxane (21 mL). The reaction was heated in a microwave reactor at 140° C. for 12 min and then diluted with water (20 mL) and ethyl acetate (50 mL). After transferring to a separatory funnel and shaking, the organic layer was separated from the aqueous layer and then washed with brine (1×20 mL). The organic layer was then dried over Na$_2$SO$_4$, filtered, and concentrated to give a crude solid that was purified by silica gel column chromatography (20-50% EtOAc/hexanes) to give 50 mg (46%) of N-(2-(4-fluorophenyl)-2-methylpropyl)-6-vinylpyridazin-3-amine as a white solid.

Step 2

The isolated product from Step 1 was dissolved in ethanol (10 mL) and transferred to a 20 dram vial. Palladium (10% on carbon, 10 mg) was then added, and the reaction was stirred under 60 psi of hydrogen for 3 days. The reaction was then filtered, concentrated, and purified by reverse phase column chromatography to afford 3 mg (10%) of 6-ethyl-N-(2-(4-fluorophenyl)-2-methylpropyl)pyridazin-3-amine as a clear oil, m/z=274 [M+H].

EXAMPLE 7

Preparation of 2-(6-((1-(3-Fluoropyridin-2-yl)cyclobutyl)methylamino)pyridazin-3-yl)propan-2-ol

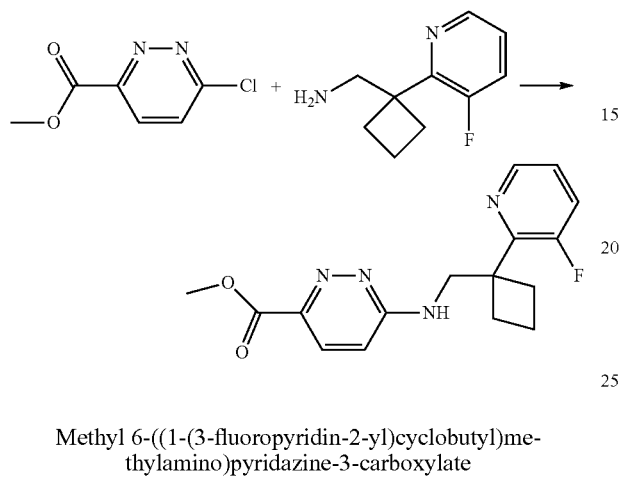

Methyl 6-((1-(3-fluoropyridin-2-yl)cyclobutyl)methylamino)pyridazine-3-carboxylate To a 20 dram vial was added methyl 6-chloropyridazine-3-carboxylate (510 mg, 2.7 mmol, 1.0 equiv), (1-(3-fluoropyridin-2-yl)cyclobutyl)methanamine (738 mg, 4 mmol, 1.5 equiv), DIPEA (0.7 mL, 4 mmol, 1.5 equiv), and NMP (2 mL). The reaction was heated at 120° C. for 40 min and then diluted with water (20 mL) and ethyl acetate (50 mL). After transferring to a separatory funnel and shaking, the organic layer was separated from the aqueous layer and then washed with brine (1×20 mL). The organic layer was then dried over Na$_2$SO$_4$, filtered, and concentrated to give a crude solid that was purified by silica gel column chromatography (20-100% EtOAc/hexanes) to give 440 mg (48%) of methyl 6-((1-(3-fluoropyridin-2-yl)cyclobutyl)methylamino)pyridazine-3-carboxylate as a white solid. m/z=331.1 [M+H]+.

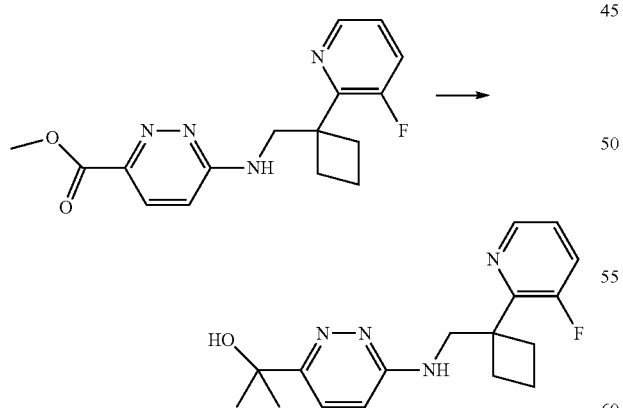

2-(6-((1-(3-Fluoropyridin-2-yl)cyclobutyl)methylamino)pyridazin-3-yl)propan-2-ol A portion of the isolated methyl 6-((1-(3-fluoropyridin-2-yl)cyclobutyl)methylamino)pyridazine-3-carboxylate (99 mg, 0.3 mmol, 1.0 equiv) was dissolved in THF (10 mL) and transferred to a 20 dram vial. The mixture was cooled to 0° C. and MeMgBr (3M in Et$_2$O, 0.5 mL, 1.5 mmol, 5 equiv) was added. The reaction was allowed to warm to rt and then stirred for 15 min. The reaction mixture was poured into a mixture of EtOAc (30 mL) and saturated ammonium chloride (15 mL). The organic layer was separated, dried over Na$_2$SO$_4$, filtered, and concentrated to give a crude solid that was purified by silica gel column chromatography (0-20% MeOH/CH$_2$Cl$_2$) to give 42 mg (43%) of 2-(6-((1-(3-fluoropyridin-2-yl)cyclobutyl)methylamino)pyridazin-3-yl)propan-2-ol as a white powder. m/z=317 [M+H]+.

EXAMPLE 8

Preparation of 1-(6-((1-(3-Fluoropyridin-2-yl)cyclobutyl)methylamino)pyridazin-3-yl)ethanone

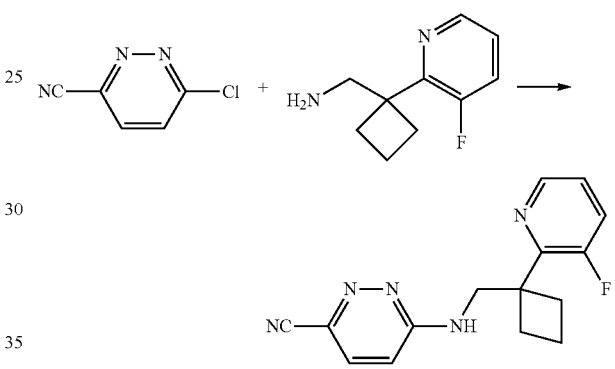

6-((1-(3-Fluoropyridin-2-yl)cyclobutyl)methylamino)pyridazine-3-carbonitrile

To a 20 dram vial was added 6-chloropyridazine-3-carbonitrile (1.0 g, 7.2 mmol, 1.0 equiv), (1-(3-fluoropyridin-2-yl)cyclobutyl)methanamine (1.36 g, 7.6 mmol, 1.05 equiv), triethylamine (2.1 mL, 14.4 mmol, 2.0 equiv), and NMP (2 mL). The reaction was heated at 130° C. for 12 h and then diluted with water (20 mL) and ethyl acetate (50 mL). After transferring to a separatory funnel and shaking, the organic layer was separated from the aqueous layer and then washed with brine (1×20 mL). The organic layer was then dried over Na$_2$SO$_4$, filtered, and concentrated to give a crude solid that was purified by silica gel column chromatography (20-30% EtOAc/hexanes) to give 507 mg (25%) of 6-((1-(3-fluoropyridin-2-yl)cyclobutyl)methylamino)pyridazine-3-carbonitrile. m/z=284 [M+H]+.

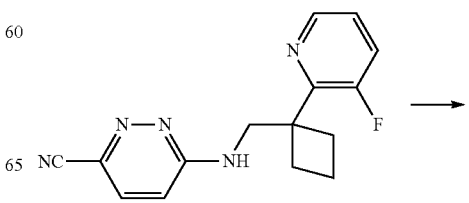

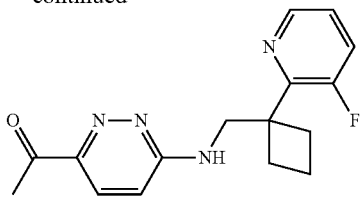

1-(6-((1-(3-Fluoropyridin-2-yl)cyclobutyl)methylamino)pyridazin-3-yl)ethanone 6-((1-(3-Fluoropyridin-2-yl)cyclobutyl)methylamino)pyridazine-3-carbonitrile (500 mg, 1.8 mmol, 1.0 equiv) was dissolved in THF (4.5 mL) and transferred to a 20 dram vial. The mixture was cooled to 0° C. and MeMgBr (1.8 mL, 5.3 mmol of a 3M solution in Et$_2$O, 2.9 equiv) was added. The reaction was stirred at this temperature for 15 min. The reaction mixture was poured into ice water, acidified to pH of 2 with 2N aqueous hydrochloric acid, and then extracted EtOAc (30 mL). The organic layer was then separated, dried over Na$_2$SO$_4$, filtered, and concentrated to give a crude solid that was purified by silica gel column chromatography (50% EtOAc/hexanes) to give 104 mg (18%) of 1-(6-((1-(3-fluoropyridin-2-yl)cyclobutyl)methylamino)pyridazin-3-yl)ethanone as a white powder. m/z=301.1 [M+H]+.

EXAMPLE 9

Preparation of N-(2-(4-fluorophenyl)-2-methylpropyl)-6-(pyridin-2-yl)pyridazin-3-amine

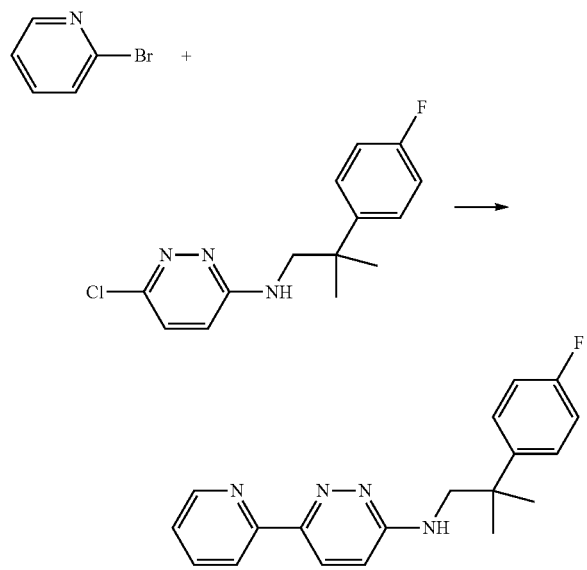

To a 25 mL round bottom flask was added 2-bromopyridine (500 mg, 3.2 mmol, 1.0 equiv), triisopropylborate (654 mg, 3.5 mmol, 1.1 equiv), and an 80% toluene/THF mixture (16 mL). The mixture was cooled to −78° C. After stirring for 10 min, n-BuLi (1.7 mL, 3.48 mmol, 1.1 equiv of a 2.0 M/hexanes solution) was slowly added over an hour. After the addition was complete, the reaction mixture was stirred for 30 min and allowed to warm to rt and stirred overnight. The reaction was then concentrated at 100° C. and dried in vacuo for 2 h. To 100 mg of this crude solid in a microwave vial was added 6-chloro-N-(2-(4-fluorophenyl)-2-methylpropyl)pyridazin-3-amine (70 mg, 0.25 mmol), Pd$_2$dba$_3$ (10 mg, 0.011 mmol), PO(tBu)$_3$ (5 mg, 0.030 mmol), potassium fluoride (43 mg, 0.75 mmol), and dioxane (0.75 mL). The reaction was degassed with nitrogen for 5 minutes and then heated in a microwave reactor at 160° C. for 15 min. The reaction was then concentrated, dissolved in EtOAc (25 mL), washed with water, dried over Na$_2$SO$_4$, filtered, concentrated, and purified by reverse phase column chromatography to give 5 mg of N-(2-(4-fluorophenyl)-2-methylpropyl)-6-(pyridin-2-yl)pyridazin-3-amine as a white solid. m/z=323.1 [M+H]+.

EXAMPLE 10

Preparation of 6-(6-(2-(4-fluorophenyl)-2-methylpropylamino)pyridazin-3-yl)nicotinamide

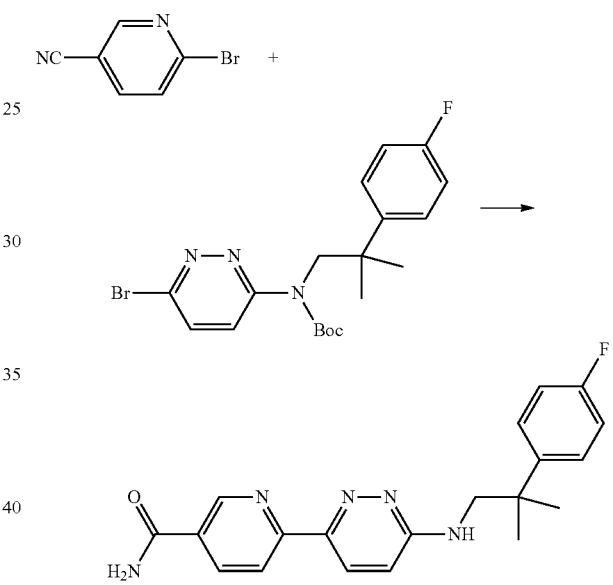

To a 20 dram vial was added 2-bromo-5-cyanopyridine (182 mg, 1.0 mmol, 1.0 equiv), hexamethylditin (639 mg, 1.1 mmol, 1.1 equiv), Cl$_2$Pd(Ph$_3$P)$_2$ (91 mg, 0.13 mmol, 0.13 equiv), triphenylarsine (34 mg, 0.11 mmol, 0.11 equiv), and dioxane (7 mL). The reaction mixture was stirred and heated to 80° C. for 12 h. The reaction was then concentrated, followed by the addition of tert-butyl 6-bromopyridazin-3-yl(2-(4-fluorophenyl)-2-methylpropyl)carbamate (423 mg, 1.0 mmol, 1.0 equiv), Pd(Ph$_3$P)$_4$ (172 mg, 0.15 mmol, 0.15 equiv), and DMF (3.3 mL). The reaction was stirred and heated to 100° C. for 3 h. After cooling to room temperature, the reaction was diluted with aqueous potassium fluoride (5 mL), extracted with ethyl acetate (20 mL) and washed with brine (20 mL). The organic layer was then dried (Na$_2$SO$_4$), filtered, and concentrated to give crude tert-butyl 6-(5-cyanopyridin-2-yl)pyridazin-3-yl(2-(4-fluorophenyl)-2-methylpropyl)carbamate.

To a 20 dram vial was added crude tert-butyl 6-(5-cyanopyridin-2-yl)pyridazin-3-yl(2-(4-fluorophenyl)-2-methylpropyl)carbamate, hydrogen peroxide (2 mL), and potassium carbonate (150 mg). The reaction was stirred for 30 min and then diluted with water (20 mL) and ethyl acetate (50 mL). After transferring to a separatory funnel and shaking, the organic layer was separated from the aqueous layer and then washed with brine (20 mL). The organic layer was then dried over Na₂SO₄, filtered, and concentrated to give a crude solid that was subsequently treated with 4N HCl/dioxane (1 mL). The reaction was stirred for 1 h at room temperature, concentrated, quenched with aqueous sodium bicarbonate, and extracted with ethyl acetate (20 mL). The organic layer was then dried (Na₂SO₄), filtered, and concentrated to give a crude solid that was purified by reverse phase column chromatography to afford 10 mg of 6-(6-(2-(4-fluorophenyl)-2-methylpropylamino)pyridazin-3-yl)nicotinamide, m/z=366.1 [M+H].

EXAMPLE 11

Preparation of 6-(2-aminopyridin-3-yl)-N-((1-(3-fluoropyridin-2-yl)cyclobutyl)methyl)pyridazin-3-amine

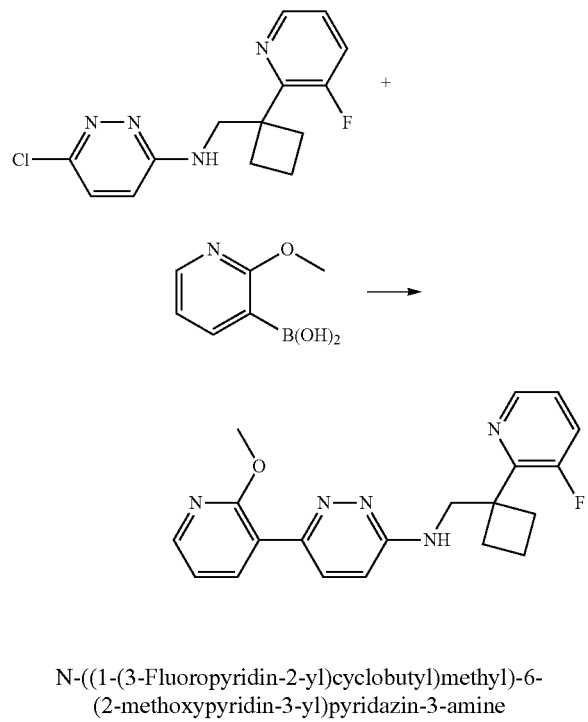

N-((1-(3-Fluoropyridin-2-yl)cyclobutyl)methyl)-6-(2-methoxypyridin-3-yl)pyridazin-3-amine To a 20 dram vial was added 6-chloro-N-((1-(3-fluoropyridin-2-yl)cyclobutyl)methyl)pyridazin-3-amine (1.8 g, 6.23 mmol, 1.0 equiv), 2-methoxypyridin-3-ylboronic acid (1.0 g, 6.54 mmol, 1.1 equiv), Cl₂Pd(dppf) (350 mg, 0.43 mmol, 0.07 equiv), 2M potassium carbonate (8 mL, 15.5 mmol, 2.5 equiv), and dioxane (21 mL). The reaction was stirred and heated to 90° C. for 2 h and then diluted with water (20 mL) and ethyl acetate (50 mL). After transferring to a separatory funnel and shaking, the organic layer was separated from the aqueous layer and then washed with lithium chloride (1×20 mL). The organic layer was then dried over Na₂SO₄, filtered, and concentrated to give a crude solid that was purified by silica gel column chromatography to give N-((1-(3-fluoropyridin-2-yl)cyclobutyl)methyl)-6-(2-methoxypyridin-3-yl)pyridazin-3-amine (1.7 g, 77%) as an off-white solid.

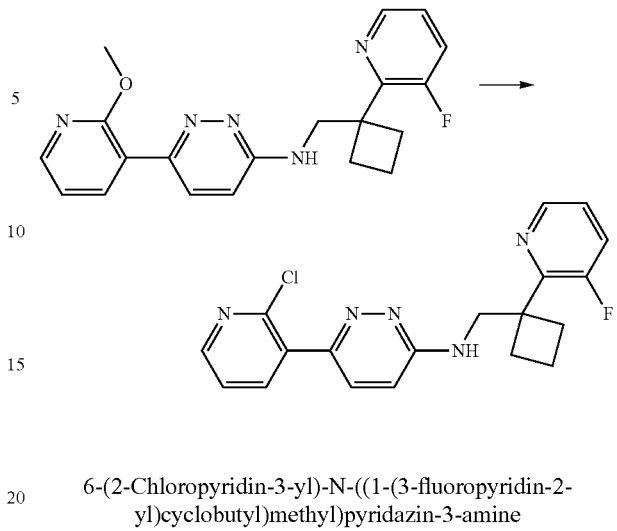

6-(2-Chloropyridin-3-yl)-N-((1-(3-fluoropyridin-2-yl)cyclobutyl)methyl)pyridazin-3-amine To a 50 mL round bottom flask was added N-((1-(3-fluoropyridin-2-yl)cyclobutyl)methyl)-6-(2-methoxypyridin-3-yl)pyridazin-3-amine (1.7 g, 4.7 mmol), concentrated hydrochloric acid (15 mL), and methanol (15 mL). The reaction was heated to 90° C. and stirred for 12 h. The reaction was concentrated, brought to pH of 11 through the addition of saturated potassium carbonate (20 mL), and then diluted with ethyl acetate (50 mL). After transferring to a separatory funnel and shaking, the organic layer was separated from the aqueous layer and washed with lithium chloride (1×20 mL). The organic layer was then dried over Na₂SO₄, filtered, and concentrated to give 3-(6-((1-(3-fluoropyridin-2-yl)cyclobutyl)methylamino)pyridazin-3-yl)pyridin-2-ol (1.6 g, 95%) as a tan powder. The isolated product (1.3 g, 3.7 mmol, 1.0 equiv) was transferred to a 100 mL round bottom flask, followed by the addition of a mixture of phosphorous oxytrichloride (24 mL) and DMF (8 mL). The reaction was heated to 90° C. and stirred for 6 h. The reaction was concentrated and carefully quenched with a 50% mixture of saturated sodium bicarbonate and lithium chloride until gas evolution ceased. The mixture was extracted with ethyl acetate (100 mL). The combined organic layers were then dried over Na₂SO₄, filtered, concentrated, and purified by silica gel column chromatography to give 1.2 g (88%) of 6-(2-chloropyridin-3-yl)-N-((1-(3-fluoropyridin-2-yl)cyclobutyl)methyl)pyridazin-3-amine as an off-white solid.

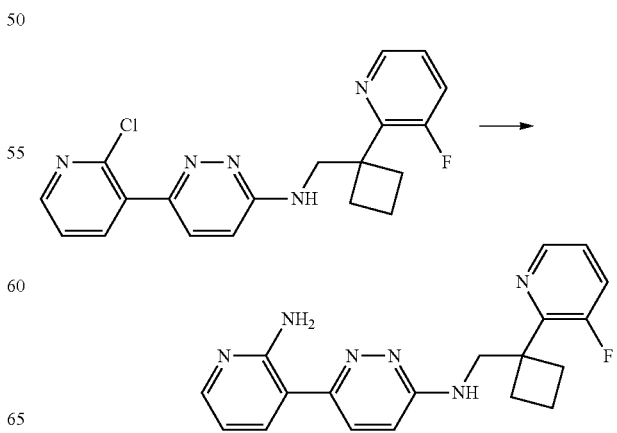

6-(2-Aminopyridin-3-yl)-N-((1-(3-fluoropyridin-2-yl)cyclobutyl)methyl)pyridazin-3-amine To a 5 mL microwave reaction vessel was added 6-(2-chloropyridin-3-yl)-N-((1-(3-fluoropyridin-2-yl)cyclobutyl)methyl)pyridazin-3-amine (750 mg, 2.0 mmol), hydrazine hydrate (1 mL), and dioxane (4 mL). The reaction was heated in a microwave reactor to 160° C. for 15 min, then diluted with ethyl acetate (50 mL), and washed with brine (20 mL). The organic layer was dried over Na$_2$SO$_4$, filtered, and concentrated to give a crude solid that was purified by reverse phase column chromatography to give 150 mg of N-((1-(3-fluoropyridin-2-yl)cyclobutyl)methyl)-6-(2-hydrazinylpyridin-3-yl)pyridazin-3-amine as an off-white solid. The isolated product was then dissolved in methanol and added to a vial containing ~1 mL of Raney Nickel suspension in water. The mixture was then stirred under 50 psi of hydrogen for 2 h. The reaction was then filtered, concentrated, and purified by reverse phase column chromatography to give 10 mg (88%) of 6-(2-aminopyridin-3-yl)-N-((1-(3-fluoropyridin-2-yl)cyclobutyl)methyl)pyridazin-3-amine as an off-white solid, m/z=351.1 [M+H].

EXAMPLE 12

Preparation of N1-(5-(6-((1-(3-Fluoropyridin-2-yl)cyclobutyl)methylamino)pyridazin-3-yl)-1H-indazol-3-yl)ethane-1,2-diamine

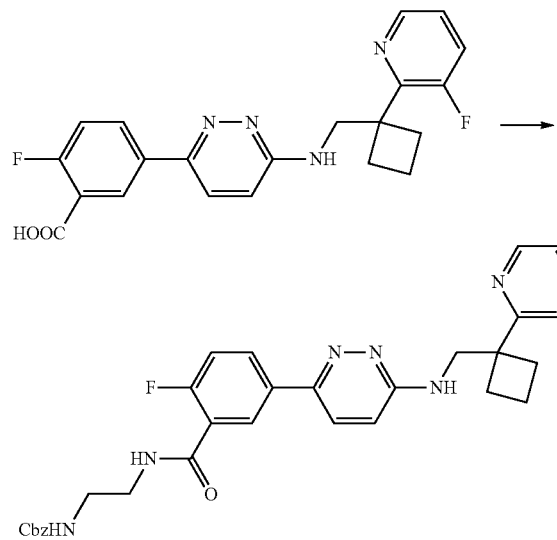

Benzyl 2-(2-Fluoro-5-(6-((1-(3-fluoropyridin-2-yl)cyclobutyl)methylamino)pyridazin-3-yl)benzamido)ethylcarbamate To a 20 dram vial was added 2-fluoro-5-(6-((1-(3-fluoropyridin-2-yl)cyclobutyl)methylamino)pyridazin-3-yl)benzoic acid (320 mg, 0.8 mmol, 1.0 equiv), benzyl 2-aminoethylcarbamate (242 mg, 1.0 mmol, 1.3 equiv), HOBt (141 mg, 1.0 mmol, 1.3 equiv), EDC HCl (200 mg, 1.0 mmol, 1.3 equiv), DIPEA (550 µL, 3.8 equiv) and CH$_2$Cl$_2$ (5 mL). The reaction was stirred for 4 h and then concentrated and then purified using a silica gel column (50%-100% EtOAc/hexanes) to afford 230 mg (50%) of benzyl 2-(2-fluoro-5-(6-((1-(3-fluoropyridin-2-yl)cyclobutyl)methylamino)pyridazin-3-yl)benzamido)ethylcarbamate as a white foam.

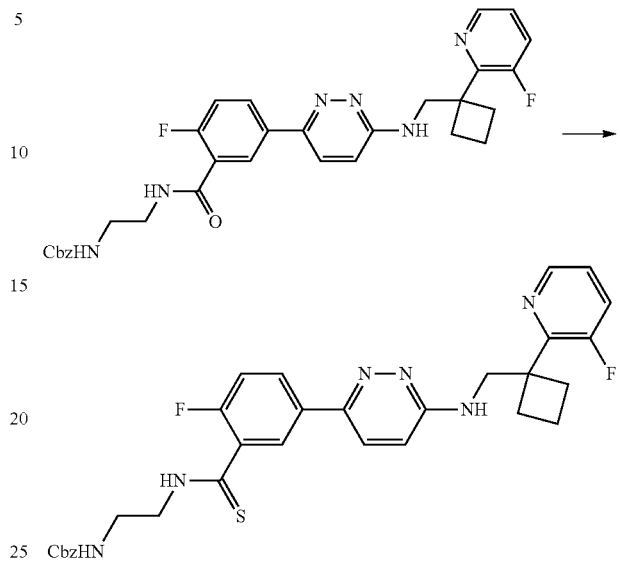

Benzyl 2-(2-fluoro-5-(6-((1-(3-fluoropyridin-2-yl)cyclobutyl)methylamino)pyridazin-3-yl)phenylthioamido)ethylcarbamate In a 20 dram vial containing benzyl 2-(2-fluoro-5-(6-((1-(3-fluoropyridin-2-yl)cyclobutyl)methylamino)pyridazin-3-yl)benzamido)ethylcarbamate (230 mg, 0.5 mmol, 1 equiv) was added Lawesson's reagent (162 mg, 0.4 mmol, 0.8 equiv) and dioxane (10 mL). The reaction was heated to 100° C. and stirred for 1 h, concentrated, and then purified using a silica gel column (35%-100% EtOAc/hexanes) to give 203 mg (86%) of benzyl 2-(2-fluoro-5-(6((1-(3-fluoropyridin-2-yl)cyclobutyl)methylamino)pyridazin-3-yl)phenylthioamido)ethylcarbamate as a pale yellow oil.

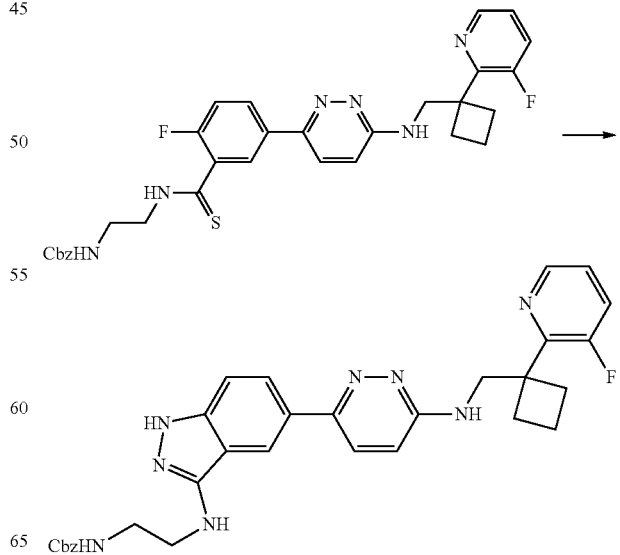

Benzyl 2-(5-(6-((1-(3-fluoropyridin-2-yl)cyclobutyl)methylamino)pyridazin-3-yl)-1H-indazol-3-ylamino)ethylcarbamate The isolated benzyl 2-(2-fluoro-5-(6-((1-(3-fluoropyridin-2-yl)cyclobutyl)methylamino)pyridazin-3-yl)phenylthioamido)ethyl-carbamate was transferred to a 20 dram vial, followed by the addition of hydrazine hydrate (0.1 mL) and dioxane (2 mL). The reaction was heated to 100° C. and stirred for 12 h, concentrated, and then purified using a silica gel column (5%-10% MeOH/EtOAc) to yield 48 mg (25%) of benzyl 2-(5-(6-((1-(3-fluoropyridin-2-yl)cyclobutyl)methylamino)pyridazin-3-yl)-1H-indazol-3-ylamino)ethylcarbamate as a pale yellow oil.

N1-(5-(6-((1-(3-Fluoropyridin-2-yl)cyclobutyl)methylamino)pyridazin-3-yl)-1H-indazol-3-yl)ethane-1,2-diamine Benzyl 2-(5-(6-((1-(3-fluoropyridin-2-yl)cyclobutyl)methylamino)pyridazin-3-yl)-1H-indazol-3-ylamino)ethylcarbamate (48 mg, 84 μmol) was dissolved in acetonitrile (5 mL), and TMSI (0.5 mL) was added. The reaction was stirred for 15 min, diluted with methanol (15 mL), concentrated, and was directly purified by reverse phase column chromatography to yield 20 mg (88%) of N1-(5-(6-((1-(3-fluoropyridin-2-yl)cyclobutyl)methylamino)pyridazin-3-yl)-1H-indazol-3-yl)ethane-1,2-diamine as a yellow solid, m/z=433 [M+H].

EXAMPLE 13

Preparation of 6-(5-Aminopyridin-2-yl)-N-((1-(3-fluoropyridin-2-yl)cyclobutyl)methyl)pyridazin-3-amine

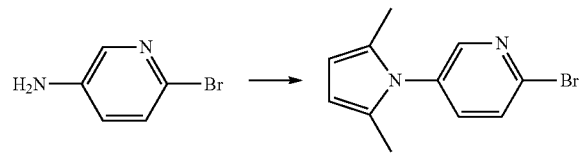

2-Bromo-5-(2,5-dimethyl-1H-pyrrol-1-yl)pyridine

To a 25 mL round bottom flask was added 5-amino-2-bromopyridine (600 mg, 3.5 mmol, 1.0 equiv), hexane-2,5-dione (420 mg, 4.2 mmol, 1.2 equiv), p-toluenesulfonic acid (5 mg), and toluene (3.5 mL). A Dean-Stark trap was fitted on top of the round bottom flask and the reaction mixture was heated to reflux for 2 h. The reaction was then concentrated and purified by silica gel column chromatography (5% ethyl acetate/hexanes) to give 660 mg (76%) of 2-bromo-5-(2,5-dimethyl-1H-pyrrol-1-yl)pyridine.

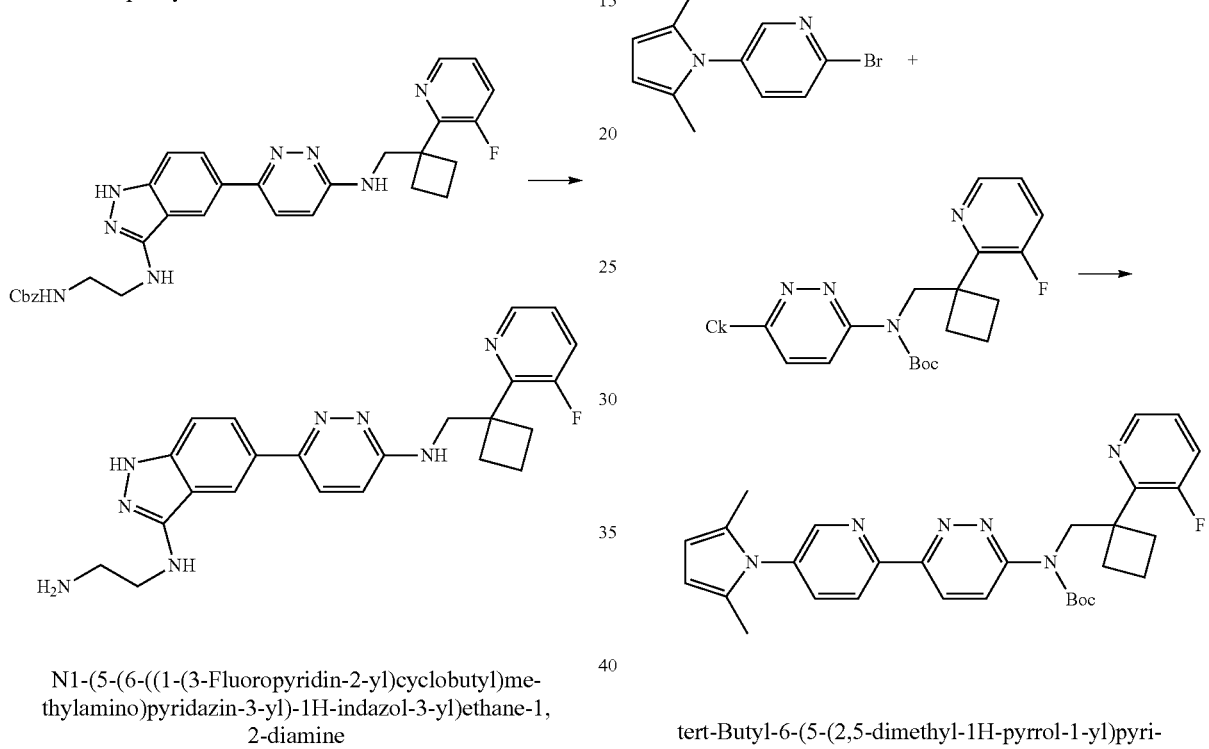

tert-Butyl-6-(5-(2,5-dimethyl-1H-pyrrol-1-yl)pyridin-2-yl)pyridazin-3-yl((1-(3-fluoropyridin-2-yl)cyclobutyl)methyl)carbamate THF (8.5 mL) was cooled to −78° C. under a nitrogen atmosphere. tBuLi (1.7 mL, 2.9 mmol, 2.0 equiv) was added, followed by the addition of 2-bromo-5-(2,5-dimethyl-1H-pyrrol-1-yl)pyridine (370 mg, 1.47 mmol, 1.0 equiv dissolved in 2 mL THF) over 2 min. The reaction as stirred for 45 min at −78° C. Zinc chloride (510 mg, 3.75 mmol, 2.5 equiv dissolved in 5 mL of THF) was added and the reaction was allowed to warm to rt and stirred for 3 h. (t-Bu₃P)₂Pd (41 mg, 0.015 mmol, 0.10 equiv dissolved in 5 mL of THF) and t-butyl 6-chloropyridazin-3-yl((1-(3-fluoropyridin-2-yl)cyclobutyl)methyl)carbamate (393 mg, 0.1 mmol, 0.07 equiv dissolved in 5 mL of THF) were added and the reaction was refluxed for 4 h followed by dilution with sodium bicarbonate (20 mL), and extraction with ethyl acetate (40 mL). The organic layer was dried over Na₂SO₄, filtered, and concentrated to give a crude solid that was purified by silica gel column chromatography (35% EtOAc/hexanes) to give 245 mg (46%) of tert-butyl 6-(5-(2,5-dimethyl-1H-pyrrol-1-yl)pyridin-2-yl)pyridazin-3-yl((1-(3-fluoropyridin-2-yl)cyclobutyl)methyl)carbamate.

6-(5-Aminopyridin-2-yl)-N-((1-(3-fluoropyridin-2-yl)cyclobutyl)methyl)pyridazin-3-amine

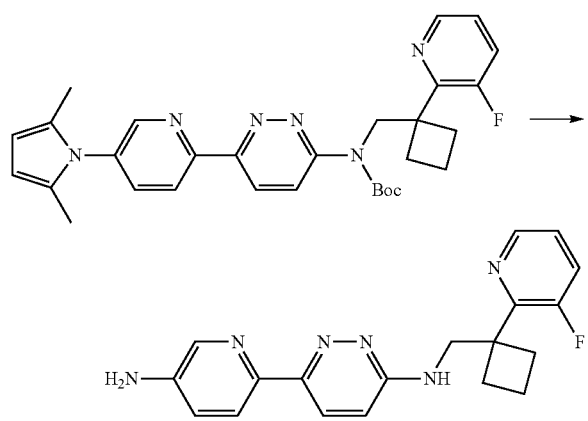

To a 20 dram vial was added tert-butyl 6-(5-(2,5-dimethyl-1H-pyrrol-1-yl)pyridin-2-yl)pyridazin-3-yl((1-(3-fluoropyridin-2-yl)cyclobutyl)methyl)carbamate (245 mg, 0.5 mmol) and a 5 mL of a 50% mixture of TFA and $CH_2Cl_2$. The reaction was stirred for 15 min, concentrated, and then diluted with sodium bicarbonate (20 mL) and extracted with ethyl acetate (40 mL). The organic layer was dried over $Na_2SO_4$, filtered, and concentrated to give a crude solid that was purified by silica gel column chromatography (60% EtOAc/hexanes) to give 91 mg (46%) of 6-(5-(2,5-dimethyl-1H-pyrrol-1-yl)pyridin-2-yl)-N-((1-(3-fluoropyridin-2-yl)cyclobutyl)methyl)pyridazin-3-amine. This product was transferred to a 100 mL round bottom flask to which was added hydroxylamine hydrochloride (270 mg), triethylamine (5 mL), and ethanol (20 mL). The reaction mixture was heated to reflux overnight and then concentrated, diluted with sodium bicarbonate (20 mL) and extracted with ethyl acetate (40 mL). The organic layer was dried over $Na_2SO_4$, filtered, and concentrated to give a crude solid that was purified by reverse phase column chromatography to afford 28 mg of 6-(5-aminopyridin-2-yl)-N-((1-(3-fluoropyridin-2-yl)cyclobutyl)methyl)pyridazin-3-amine, m/z=351.2 [M+H].

EXAMPLE 14

Preparation of 3-(6-(2-(4-Fluorophenyl)-2-methylpropylamino)-4-methylpyridazin-3-yl)benzamide

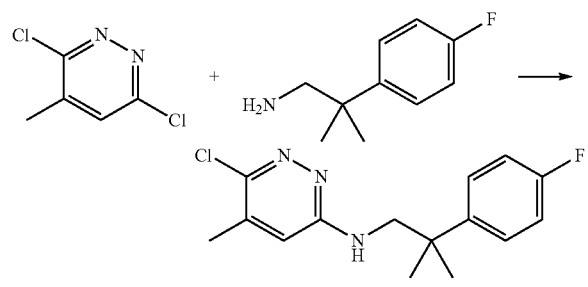

6-Chloro-N-(2-(4-fluorophenyl)-2-methylpropyl)-5-methylpyridazin-3-amine

A solution of (2-(4-fluorophenyl)-2-methylpropan-1-amine (5.5 g, 33 mmol, 1.8 equiv), 3,6-dichloro-4-methylpyridazine (3.0 g, 18 mmol, 1.0 equiv) and $K_2CO_3$ (5.1 g, 37 mmol, 2.0 equiv) in isopropanol (7.5 mL) was stirred at 100° C. under a blanket of nitrogen for 18 hours. The cooled mixture was partitioned between water and EtOAc and the organic fraction was concentrated in vacuo. Purification over silica gel using a 20-35% gradient of EtOAc/hexanes gave the desired product (0.80 g, 15%) of a yellow oil which was determined by HPLC to be a 5:1 mixture of regioisomers by HPLC.

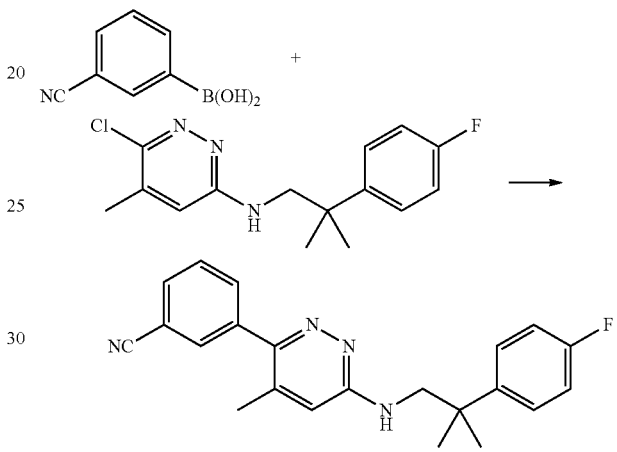

2-Fluoro-5-(6-(2-(4-fluorophenyl)-2-methylpropylamino)-4-methylpyridazin-3-yl)benzonitrile To a solution of 6-chloro-N-(2-(4-fluorophenyl)-2-methylpropyl)-5-methylpyridazin-3-amine (0.8 g, 2.7 mmol, 1.0 equiv) and 2 M aqueous $K_2CO_3$ (2.0 mL, 8.2 mmol, 3.0 equiv) in dioxane (14 mL) was added $Pd(dppf)Cl_2$ (0.11 g, 0.14 mmol, 0.05 equiv) and 3-cyanophenylboronic acid (0.48 g, 3.3 mmol, 1.2 equiv). The mixture was stirred at 80° C. for 2 hours under a blanket of nitrogen. This was followed by addition of another 100 mg (0.68 mmol, 0.25 equiv) of the boronic acid and 30 mg (0.037 mmol, 0.013 equiv) of Pd(dppf)Cl$_2$ and another 1 h of heating at 100° C. The mixture was allowed to cool to room temperature and then was diluted with EtOAc. The solution was washed with 50% NaCl solution, dried over $Na_2SO_4$ and evaporated to dryness. The residue was purified by over silica gel using a 20-50% EtOAc/hexanes stepwise gradient to give the desired product (850 mg, 86%) as a single regioisomer.

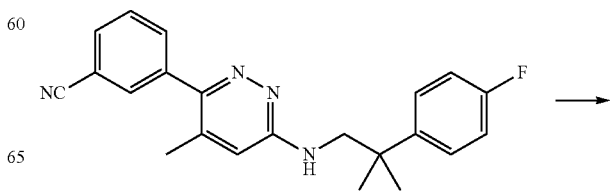

-continued

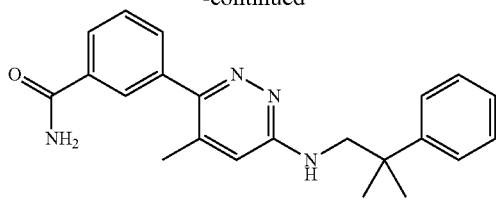

3-(6-(2-(4-Fluorophenyl)-2-methylpropylamino)-4-methylpyridazin-3-yl)benzamide

A 0° C. solution of 2-fluoro-5-(6-(2-(4-fluorophenyl)-2-methylpropylamino)-4-methylpyridazin-3-yl)benzonitrile (0.80 g, 2.2 mmol, 1.0 equiv), 30% hydrogen peroxide (0.45 mL, 4.4 mmol, 2.0 equiv), and $K_2CO_3$ (600 mg, 4.4 mmol, 2.0 equiv) in DMSO (9.0 mL) was stirred for 1 hour. The mixture was diluted with EtOAc, washed with saturated NaCl, water and saturated NaCl again, and then dried over $Na_2SO_4$. Purification by reverse phase HPLC using a gradient of 20-70% $CH_3CN$/water gave the desired product (420 mg, 51%) as a yellow solid. m/z=379.1 [M+H]+.

EXAMPLE 15

Preparation of 3-(5-Cyano-6-(2-(4-fluorophenyl)-2-methylpropylamino)pyridazin-3-yl)benzamide

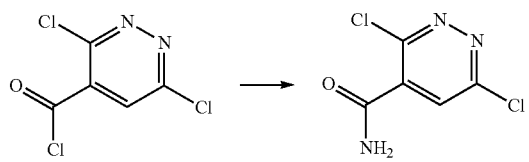 [SMILES: O=C(Cl)c1cc(Cl)nnc1Cl ; NC(=O)c1cc(Cl)nnc1Cl]

3,6-Dichloropyridazine-4-carboxamide

A solution of $NH_4OH$ (1.1 mL, 17 mmol, 1.2 equiv) and diisopropylethylamine (6.2 mL, 36 mmol, 2.1 equiv) in THF (57 mL) was sonicated until homogeneous after which was added DMAP (1.0 g, 14 mmol, 1.0 equiv). 3,6-dichloropyridazine-4-carbonyl chloride (3.0 g, 14 mmol, 1.0 equiv) was then added and the solution was stirred at room temperature for 20 minutes. The solution was filtered and partitioned between EtOAc and 1M $KHSO_4$ solution. The organic layer was washed once more with 1M $KHSO_4$ and saturated NaCl, dried over $Na_2SO_4$, and evaporated to dryness to give the desired product (2.6 g, 96%).

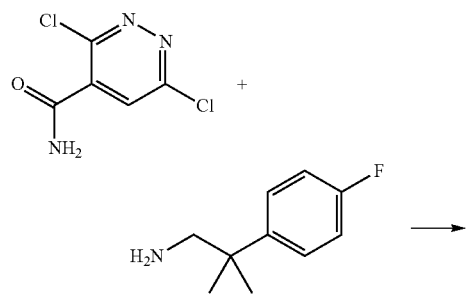

-continued

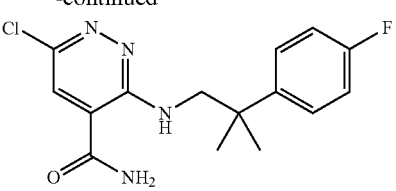

6-Chloro-3-(2-(4-fluorophenyl)-2-methylpropylamino)pyridazine-4-carboxamide

Using a similar procedure as was used for 6-chloro-N-(2-(4-fluorophenyl)-2-methylpropyl)-5-methylpyridazin-3-amine in example 14, 3,6-dichloropyridazine-4-carboxamide (2.6 g, 13 mmol, 1.0 equiv), (2-(4-fluorophenyl)-2-methylpropan-1-amine (2.5 g, 15 mmol, 1.1 equiv), and diisopropylethylamine (2.8 mL, 16 mmol, 1.2 equiv) in $CH_3CN$ (54 mL) was heated at 60-90° C. for 48 hours. The product was purified over silica gel with 100% EtOAc to give the desired product (3.4 g, 78%) as a yellow foamy solid.

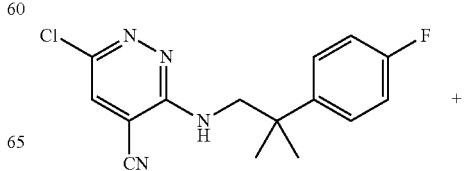

6-Chloro-3-(2-(4-fluorophenyl)-2-methylpropylamino)pyridazine-4-carbonitrile

To a portion of 6-chloro-3-(2-(4-fluorophenyl)-2-methylpropylamino)pyridazine-4-carboxamide (3.4 g, 11 mmol, 1.0 equiv) was added $POCl_3$ (10 mL) at room temperature. The mixture was stirred at reflux for 3 hours and then quenched by pouring it into ice water containing $NaHCO_3$. Dioxane and EtOAc were added to facilitate mixing of the layers. The layers were allowed to separate and the aqueous layer was extracted with EtOAc and the combined organic phases were washed with saturated NaCl. The organics were dried over $Na_2SO_4$ and evaporated to dryness in vacuo. Purification over silica gel using a gradient of 10-20% EtOAc/hexanes yielded the desired product (0.60 g, 19%) as a yellow oil.

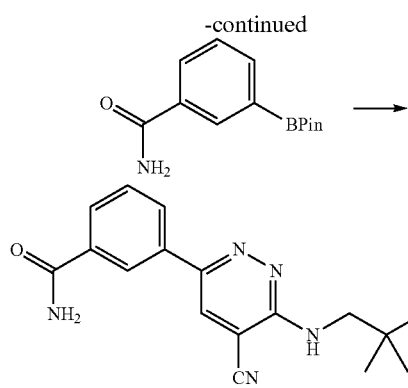

3-(5-Cyano-6-(2-(4-fluorophenyl)-2-methylpropylamino)pyridazin-3-yl)benzamide

To a solution of 6-chloro-3-(2-(4-fluorophenyl)-2-methylpropylamino)pyridazine-4-carbonitrile (550 mg, 1.8 mmol, 1.0 equiv), 3-aminocarbonylphenylboronic acid, pinacol ester (330 mg, 2.0 mmol, 1.1 equiv) and aqueous $K_2CO_3$ (2.0 M, 5.0 mL, 5.4 mmol, 3.0 equiv) in dioxane (18 mL) was added $Pd(dppf)Cl_2$ (150 mg, 0.18 mmol, 0.1 equiv). The mixture was stirred at 120° C. for 10 minutes in a microwave and allowed to cool to room temperature. The solvents were evaporated in vacuo, and the residue was dissolved in dichloromethane. The solution was filtered and the solvent dried over $Na_2SO_4$. Purification over silica gel using a gradient of 40-80% EtOAc/hexanes gave a yellow solid that was slurried with $CH_3CN$ to give the desired product (30 mg, 4.3%) as a yellow solid. m/z=390.2 [M+H]+.

EXAMPLE 16

Preparation of (S)-2-(4-Fluorophenyl)propan-1-amine

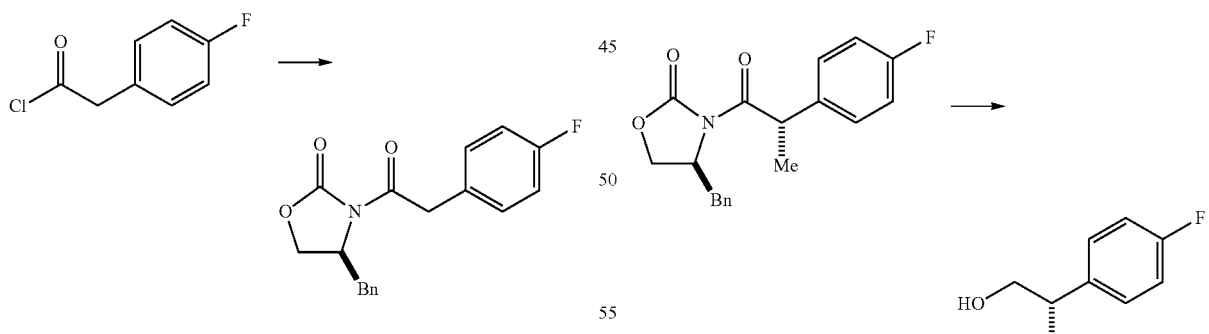

(S)-4-Benzyl-3-(2-(4-fluorophenyl)acetyl)oxazolidin-2-one

To a cooled (−78° C.) solution of (S)-4-benzyloxazolidin-2-one (10 g, 58 mmol, 1.0 equiv) in 100 mL THF was added dropwise n-BuLi (40 mL, 1.6 M in hexanes, 64 mmol, 1.1 equiv). After stirring for 30 minutes, 4-fluorophenylacetyl chloride (10 g, 0.58 mmol, 1.0 equiv) was added dropwise. After stirring for an additional 30 minutes, the reaction mixture was allowed to warm to room temperature. The reaction was quenched with saturated aq. $NH_4Cl$, extracted with dichloromethane, and washed with brine. The organic layer was then dried over sodium sulfate, filtered, and concentrated in vacuo. Purification by silica gel (10-20% EtOAc/hexanes) provided the title compound as a thick oil (14.7 g, 81%).

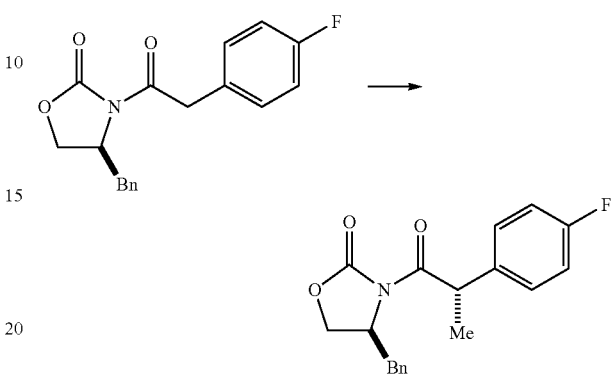

(S)-4-Benzyl-3((S)-2-(4-fluorophenyl)propanoyl)oxazolidin-2-one

To a room-temperature solution of (S)-4-benzyl-3-(2-(4-fluorophenyl)acetyl)oxazolidin-2-one (5.1 g, 16.3 mmol, 1.0 equiv) in dry THF (100 mL) was added iodomethane (1.0 mL, 16.2 mmol, 1.0 equiv) by syringe. The resulting mixture was cooled to −78° C., and NaHMDS (8.15 mL, 2M in THF, 16.3 mmol, 1.0 equiv) was added dropwise by syringe. After stirring for 15 minutes at −78° C., the reaction mixture was allowed to warm to room temperature. The reaction was quenched with saturated aq. $NH_4Cl$, and diluted with EtOAc. The organic layer was washed with brine, dried over $Na_2SO_4$, filtered and concentrated in vacuo. Purification by silica gel chromatography (7-20% EtOAc/hexanes) provided the title compound (2.6 g, 49%).

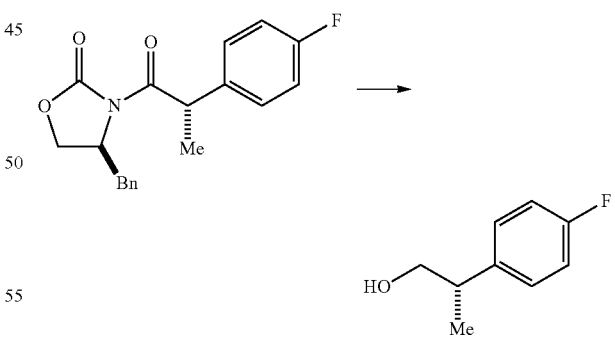

(S)-2-(4-Fluorophenyl)propan-1-ol

To a room-temperature solution of (S)-4-benzyl-3-((S)-2-(4-fluorophenyl)propanoyl)oxazolidin-2-one (1.8 g, 5.5 mmol, 1.0 equiv) in THF (18 mL) was added a solution of $NaBH_4$ (1.0 g, 26.4 mmol, 4.8 equiv) in water (6.0 mL). The reaction mixture was stirred for 3 h at room temperature and then quenched by the careful addition of aq. 1M HCl. The reaction mixture was diluted with water and ethyl acetate. The layers were separated and the organic layer was subsequently washed with brine, dried over Na₂SO₄, filtered and concentrated in vacuo. Purification by silica gel chromatography (10-75% EtOAc/Hexanes) provided the title compound (0.824 g, 97%).

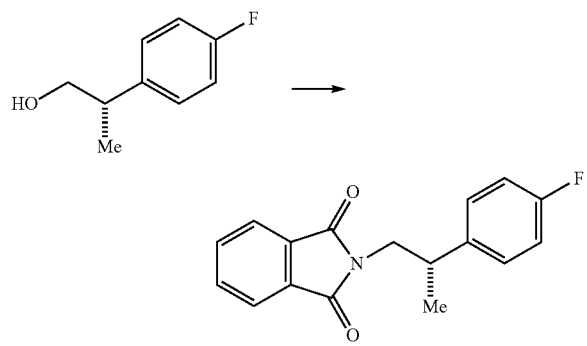

(S)-2-(2-(4-Fluorophenyl)propyl)isoindoline-1,3-dione

To a solution of (S)-2-(4-fluorophenyl)propan-1-ol (0.82 g, 5.35 mmol, 1.0 equiv), phthalimide (0.82 g, 5.6 mmol, 1.05 equiv), and triphenyl phosphine (2.1 g, 8.03 mmol, 1.5 equiv) in dry THF (18 mL) was added dropwise diethylazodicarboxylate (3.6 mL, 15% in toluene, 8.0 mmol, 1.5 equiv). The reaction mixture was stirred over 72 h and then concentrated in vacuo. Purification by silica gel chromatography (15-25% EtOAc/Hexanes) provided the title compound (0.9 g, 59%).

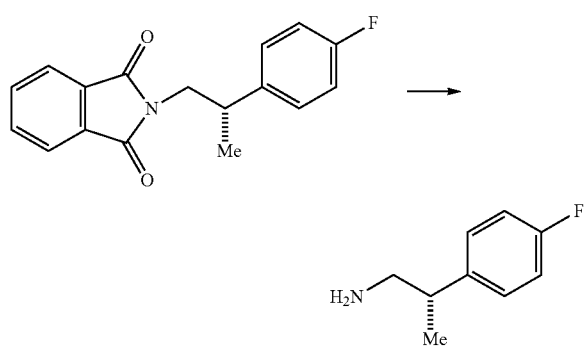

(S)-2-(4-Fluorophenyl)propan-1-amine

To a room-temperature solution of (S)-2-(2-(4-fluorophenyl)propyl)isoindoline-1,3-dione (900 mg, 3.2 mmol, 1.0 equiv) in toluene (14 mL) was added hydrazine hydrate (1.4 mL, 45 mmol, 14 equiv) by syringe. The resulting mixture was heated to 80° C. for 30 minutes and then cooled to room temperature. The resulting solution was decanted from the solid in the reaction mixture, and the solid was washed with additional toluene. The combined organic layers were combined and concentrated in vacuo to provide the title compound (491 mg, 99%), which was used without further purification.

EXAMPLE 17

Preparation of 2-(4-Fluorophenyl)-2-methylpropan-1-amine

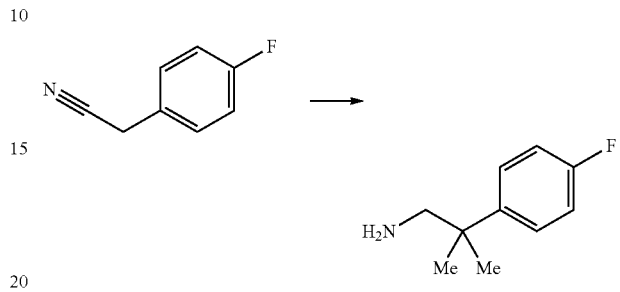

To a solution of 4-fluorophenylacetonitrile (50 g, 370 mmol, 1.0 equiv) and iodomethane (70 mL, 1.1 mol, 3 equiv) in THF (370 mL) was added KOt-Bu (124 g, 1.1 mol, 3 equiv) as a solid in portions such that the reaction mixture did not exceed 50° C. The reaction mixture was stirred overnight and then quenched by the addition of brine. The mixture was diluted with EtOAc and washed twice with brine. The organic layer was dried over Na₂SO₄, filtered, and concentrated in vacuo to provide 2-(4-fluorophenyl)-2-methylpropanenitrile as a yellow oil (57 g, 94%), which was used without further purification in the next step. To a solution of the nitrile in dry THF (800 mL) was added a solution of lithium aluminum hydride (210 mL, 2 M in ether, 420 mmol, 1.2 equiv). After the mixture was heated at reflux overnight, the reaction was allowed to cool to room temperature, and a Fieser and Fieser work-up (300 uL water/mmol, 1.0 mL 3N NaOH/mmol, 300 uL water/mmol) was performed. Filtration of the resulting solids provided the title compound as an orange oil (57 g, 92%).

EXAMPLE 18

Preparation (1-(4-Fluorophenyl)cyclobutyl)methanamine

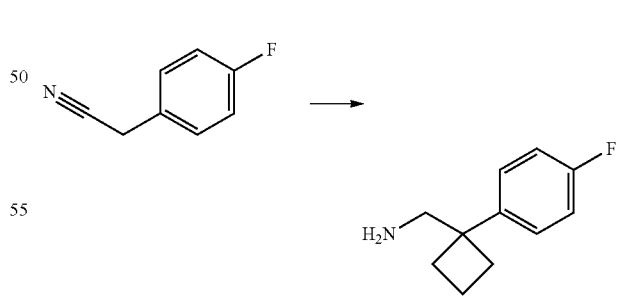

A solution of 4-fluorophenylacetonitrile (6.7 g, 75 mmol, 1.5 equiv), 1,3-dibromopropane (10 mL, 50 mmol, 1 equiv), KOH (27 g, 150 mmol, 3.0 equiv), and tetrabutylammonium bromide (100 mg) in toluene (135 mL) was heated to 100° C. for 3 hours. The organic layer was separated and concentrated to dryness. Silica gel chromatography using a gradient of 0-30% EtOAc/hexanes resulted in partially purified product which was further purified by Kugelrohr distillation at 200° C. to provide 3.76 g (22 mmol) of the intermediate nitrile product as an oil. The residue was dissolved in dry THF (22 mL) and treated with a solution of LAH (27 mL, 2 M in ether, 55 mmol, 2.5 equiv). The mixture was stirred at 0° C. for 2 hours followed by a Fieser and Fieser work-up (38 uL water/mmol, 118 uL 3N NaOH/mmol, 38 uL water/mmol). The organic layer was concentrated to dryness to provide the desired product (3.6 g, 40% overall) as a yellow oil.

EXAMPLE 19

Preparation of (1-(6-Methoxypyridin-2-yl)cyclobutyl)methanamine

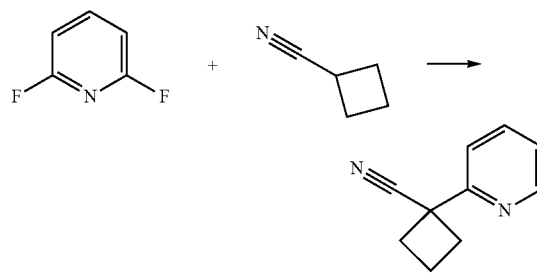

1-(6-Fluoropyridin-2-yl)cyclobutanecarbonitrile

Following the same procedure as described for 2-(3-fluoropyridin-2-yl)acetonitrile (Example 18), 2,6-difluoropyridine (5.0 g, 43 mmol, 1.0 equiv), cyclobutylcarbonitrile (3.5 g, 43 mmol, 1.0 equiv) and NaHMDS (2.0 M in THF, 24 mL, 47 mmol, 1.1 equiv) in toluene (100 mL) gave the desired product (4.9 g, 64%) as a colorless oil following purification over silica gel using 25% EtOAc/hexanes as eluent.

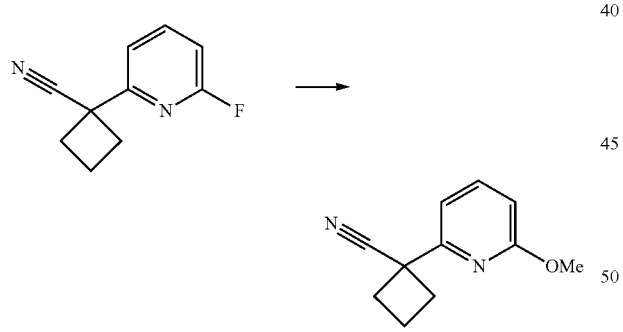

1-(6-Methoxypyridin-2-yl)cyclobutanecarbonitrile

To stirred 6.0 mL of anhydrous methanol at 0° C. under nitrogen was added sodium metal (~1 g) and the mixture stirred for 30 minutes. To this was added 1-(6-fluoropyridin-2-yl)cyclobutanecarbonitrile (1.6 g, 9.1 mmol) and the resulting mixture heated to 75° C. for 45 minutes. The solution was cooled to room temperature and partitioned between water and EtOAc. The layers were separated, the aqueous phase was extracted with EtOAc, and the combined organic phases were washed with saturated NaCl, dried over Na₂SO₄ and concentrated in vacuo to give the desired product (1.7 g, 97%) as a colorless oil.

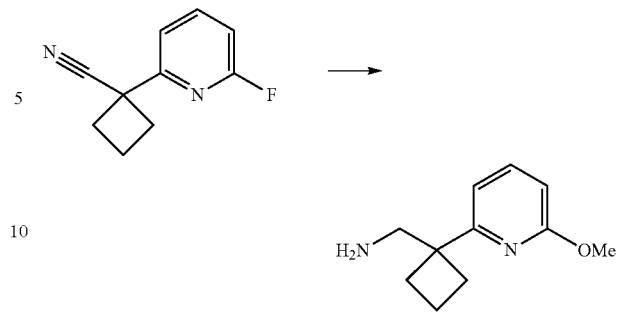

(1-(6-Methoxypyridin-2-yl)cyclobutyl)methanamine

To a stirred solution of 1-(6-methoxypyridin-2-yl)cyclobutanecarbonitrile (1.7 g, 8.8 mmol, 1.0 equiv) in THF (20 mL) was added lithium aluminum hydride solution (1.0 M in THF, 11 mL, 11 mmol, 1.1 equiv). The mixture was refluxed for 1.5 hours and allowed to cool to room temperature. Water (0.43 mL) was added slowly followed by 0.43 mL of 3 M NaOH and then three additions of 0.43 mL of water (Fieser and Fieser workup). The resulting mixture was filtered through diatomaceous earth and rinsed with THF. The combined organics were dried over Na₂SO₄ and concentrated to dryness to give the desired product (1.6 g, 97%) as a viscous oil.

EXAMPLE 20

Preparation of 1-(3-Fluoropyridin-2-yl)cyclobutanamine

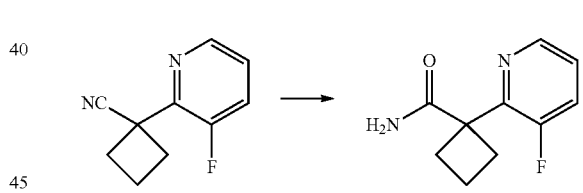

1-(3-Fluoropyridin-2-yl)cyclobutanecarboxamide

To a 250 mL round bottom flask containing DMSO (60 mL), 1-(3-fluoropyridin-2-yl)cyclobutanecarbonitrile (2.96 g, 16.8 mmol, 1.0 equiv) was added and the mixture was stirred until homogenous. Potassium carbonate (7.0 g, 50.4 mmol, 3.0 equiv) was then added and the reaction mixture was cooled to 0° C., followed by the addition of 35% hydrogen peroxide (6.5 mL). The reaction was stirred at 0° C. for 30 min and then warmed to room temperature. At this time, the reaction was diluted with water (50 mL) and ethyl acetate (100 mL). After transferring to a separatory funnel and shaking, the organic layer was separated from the aqueous layer and then washed with brine (3×50 mL). The organic layer was then dried over Na₂SO₄, filtered, and concentrated to give a crude solid that was purified by silica gel chromatography (10% EtOAC/hexanes) to afford 1.92 g (59%) of 1-(3-fluoropyridin-2-yl)cyclobutanecarboxamide as a white solid.

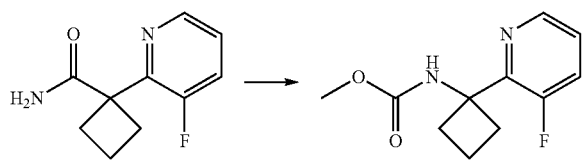 [SMILES: NC(=O)C1(c2ncccc2F)CCC1 ; COC(=O)NC1(c2ncccc2F)CCC1]

Methyl 1-(3-fluoropyridin-2-yl)cyclobutylcarbamate 1-(3-fluoropyridin-2-yl)cyclobutanecarboxamide (1.92 g, 9.88 mmol, 1.0 equiv) was dissolved in methanol (20 mL) and potassium hydroxide (1.11 g, 19.8 mmol, 2.0 equiv) was added. The mixture was sonicated until homogeneous, followed by the addition of iodosobenzene diacetate (4.77 g, 14.8 mmol, 1.5 equiv). The reaction was stirred for 20 min and then diluted with water (100 mL) and ethyl acetate (125 mL). After transferring to a separatory funnel and shaking, the organic layer was separated from the aqueous layer, and the aqueous layer was extracted with EtOAc (50 mL). The combined organic layers were then dried over $Na_2SO_4$, filtered, and concentrated to give a crude oil that was purified by silica gel chromatography (40% EtOAC/hexanes) to afford 1.47 g (67%) of methyl 1-(3-fluoropyridin-2-yl)cyclobutylcarbamate as a white solid.

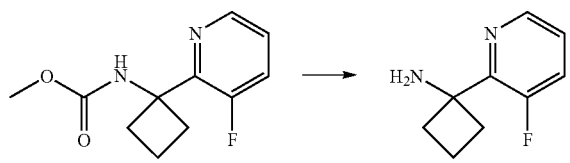 [SMILES: COC(=O)NC1(c2ncccc2F)CCC1 ; NC1(c2ncccc2F)CCC1]

1-(3-Fluoropyridin-2-yl)cyclobutanamine

To a 20 mL microwave reaction vial was added methyl 1-(3-fluoropyridin-2-yl)cyclobutylcarbamate (1.47 g, 6.56 mmol), ethanol (12 mL) and 3N aqueous sodium hydroxide (7 mL). The reaction mixture was heated in the microwave reactor at 150° C. for 30 min. The ethanol was evaporated under reduced pressure and the mixture was extracted with ethyl acetate (30 mL). The aqueous layer was then extracted with ethyl acetate (2×30 mL). The organic layers were combined, dried over $Na_2SO_4$, filtered, and concentrated to give 1-(3-fluoropyridin-2-yl)cyclobutanamine (1.01 g, 93%) as a crude yellow oil that was used in the next reaction step without further purification.

EXAMPLE 21

Preparation of 2-(3-Fluoropyridin-2yl)acetonitrile

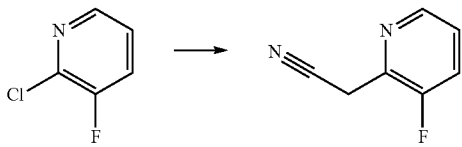 [SMILES: Fc1cccnc1Cl ; N#CCc1ncccc1F]

To a 0° C. solution of 2-chloro-3-fluoropyridine (3.0 g, 23 mmol, 1.0 equiv) and acetonitrile (1.3 mL, 25 mmol, 1.1 equiv) in toluene (50 mL) was added sodium hexamethyldisilazide (NaHMDS) (2.0 M in THF, 13 mL, 25 mmol, 1.1 equiv). The resulting mixture was stirred for 2 hours at 0° C. and then partitioned between EtOAc and water. The aqueous layer was extracted with EtOAc and the combined organic phases were washed with saturated NaCl, dried over $Na_2SO_4$ and concentrated in vacuo to provide the crude desired product as an oil which was used without further purification.

EXAMPLE 22

Preparation of 6-Chloro-N-(2-phenylpropan-2-yl)pyridazin-3-amine

To a 5 mL microwave reaction vial was added 3,6-dichloropyridazine (544 mg, 3.7 mmol, 1.0 equiv), cumylamine (500 mg, 3.7 mmol, 1.0 equiv), and DIPEA (640 μL, 3.7 mmol, 1.0 equiv). The reaction was heated in a microwave reactor to 225° C. for 15 min and then diluted with brine (20 mL) and extracted with ethyl acetate (40 mL). The organic layer was dried over $Na_2SO_4$, filtered, and concentrated to give a crude solid that was purified by silica gel column chromatography (20% EtOAc/hexanes) to yield 48 mg (5%) of 6-chloro-N-(2-phenylpropan-2-yl)pyridazin-3-amine as a white solid.

EXAMPLE 23

Preparation of 2-(2-(6-((1-(3-fluoropyridin-2-yl)cyclobutyl)methylamino)pyridazin-3-yl)thiazol-5-yl)acetamide 5-((t-Butyldimethylsilyloxy)methyl)thiazole Thiazole-5-methanol (65 g, 0.56 mol), imidazole (58 g, 0.85 mol), and $CH_2Cl_2$ (700 mL) were added to a round bottom flask, followed by TBSCI (93 g, 0.62 mol). The reaction was stirred for 20 min and the resultant white solid was filtered off. The filtrate was washed with saturated sodium bicarbonate, dried over sodium sulfate, concentrated, and purified by silica gel chromatography (10% EtOAC/hexanes) to afford 140 g of 5-((t-butyldimethylsilyloxy)methyl)thiazole as a clear oil.

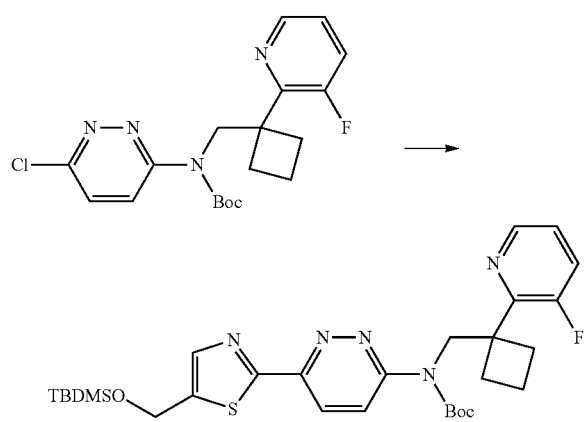

t-butyl 6-(5-((t-butyldimethylsilyloxy)methyl)thiazol-2-yl)pyridazin-3-yl((1-(3-fluoropyridin-2-yl)cyclobutyl)methyl)carbamate To a stirring mixture of THF (2000 mL) and diisopropylamine (79.3 mL, 0.56 mol) at −78° C. was added n-BuLi (244 mL, 0.56 mol) dropwise. After stirring for 20 min at −78° C., a solution of 5-((t-butyldimethylsilyloxy)methyl)thiazole (110.9 g, 0.49 mol in 300 mL of THF) was added dropwise to the reaction mixture while maintaining a temperature less than −70° C. After the addition was complete, the reaction was stirred for an additional 30 min and a solution of zinc bromide (126.6 g, 0.56 mol in 300 mL of THF) was added dropwise to the reaction mixture while maintaining a temperature less than −65° C. The reaction was warmed to 0° C., stirred for 30 min, and added to a stirring mixture of t-butyl 6-chloropyridazin-3-yl((1-(3-fluoropyridin-2-yl)cyclobutyl)methyl)carbamate (100 g, 0.26 mol), tetrakis(triphenylphosphine)palladium(0) (56 g, 0.05 mol), and THF (2000 mL) heated to 80° C. The reaction mixture was stirred overnight at 80° C. The reaction was concentrated and then slurried in ethyl acetate and brine. The resultant solid was filtered off, and the filtrate was dried over sodium sulfate, concentrated, and purified twice by silica gel chromatography (EtOAc/hexanes) to afford 112.5 g of t-butyl 6-(5-((tert-butyldimethylsilyloxy)methyl)thiazol-2-yl)pyridazin-3-yl((1-(3-fluoropyridin-2-yl)cyclobutyl)methyl)carbamate as a dark oil.

t-butyl (1-(3-fluoropyridin-2-yl)cyclobutyl)methyl(6-(5-(hydroxymethyl)thiazol-2-yl)pyridazin-3-yl)carbamate To a solution of t-butyl 6-(5-(((tert-butyldimethylsilyloxy)methyl)thiazol-2-yl)pyridazin-3-yl((1-(3-fluoropyridin-2-yl)cyclobutyl)methyl)carbamate (112.5 g, 0.19 mol) in THF (1000 mL) was added TBAF (105 mL, 0.29 mol, 75% w/w). The reaction was stirred for 30 min followed by the addition of ammonium chloride (200 mL). The organic layer was separated, washed with brine (300 mL×3), and concentrated (this wash was repeated once). Ethyl acetate was added to the oil, resulting in a white solid. Filtration of the solid afforded 44 g of t-butyl (1-(3-fluoropyridin-2-yl)cyclobutyl)methyl(6-(5-(hydroxymethyl)thiazol-2-yl)pyridazin-3-yl)carbamate.

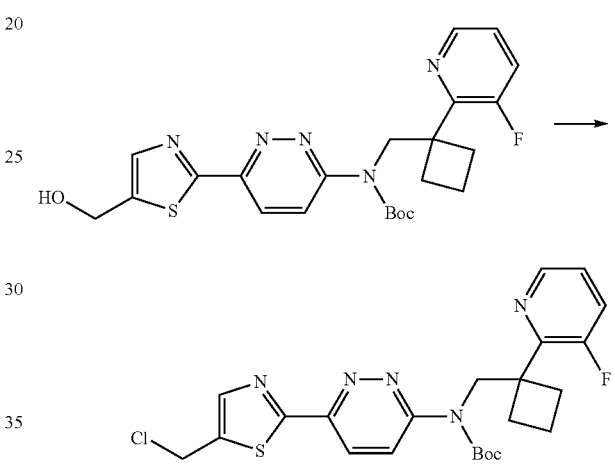

t-butyl 6-(5-(chloromethyl)thiazol-2-yl)pyridazin-3-yl((1-(3-fluoropyridin-2-yl)cyclobutyl)methyl)carbamate To a solution of t-butyl (1-(3-fluoropyridin-2-yl)cyclobutyl)methyl(6-(5-(hydroxymethyl)thiazol-2-yl)pyridazin-3-yl)carbamate (44.1 g, 93.8 mmol) in dioxane (235 mL) was added thionyl chloride (27.3 mL, 375.3 mmol). The reaction was stirred until it was homogeneous. The reaction was then slowly quenched by pouring into a mixture of saturated potassium carbonate solution and ethyl acetate. The organic layer was then separated, dried over Na₂SO₄, filtered, concentrated, and purified by silica gel chromatography (EtOAC/hexanes) to afford 33.1 g of t-butyl 6-(5-(chloromethyl)thiazol-2-yl)pyridazin-3-yl((1-(3-fluoropyridin-2-yl)cyclobutyl)methyl)carbamate as a white solid.

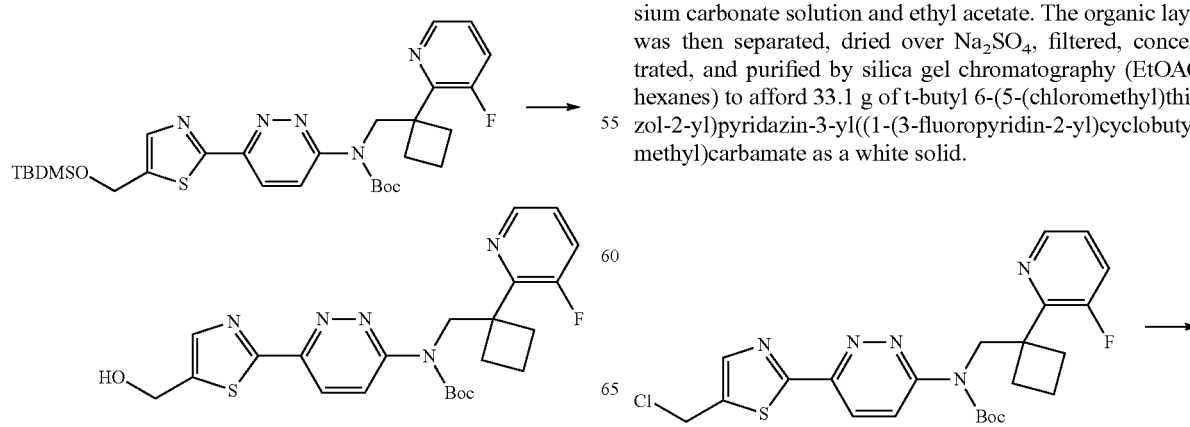

-continued

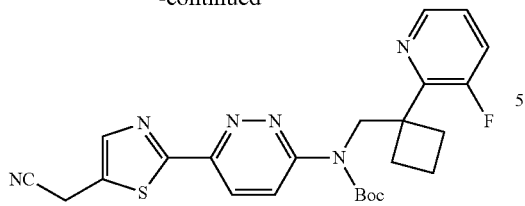

t-butyl 6-(5-(cyanomethyl)thiazol-2-yl)pyridazin-3-yl((1-(3-fluoropyridin-2-yl)cyclobutyl)methyl)carbamate To a solution of t-butyl 6-(5-(chloromethyl)thiazol-2-yl)pyridazin-3-yl((1-(3-fluoropyridin-2-yl)cyclobutyl)methyl)carbamate (33.1 g, 68 mmol) in $CH_2Cl_2$ (450 mL) was added tetrabutylammonium cyanide (36 g, 135 mmol). The reaction was heated to 45° C. and stirred for 1 h, followed by concentration and purification by silica gel chromatography (EtOAc/hexanes) to afford 13.4 g of t-butyl 6-(5-(cyanomethyl)thiazol-2-yl)pyridazin-3-yl((1-(3-fluoropyridin-2-yl)cyclobutyl)methyl)carbamate as an off-white solid.

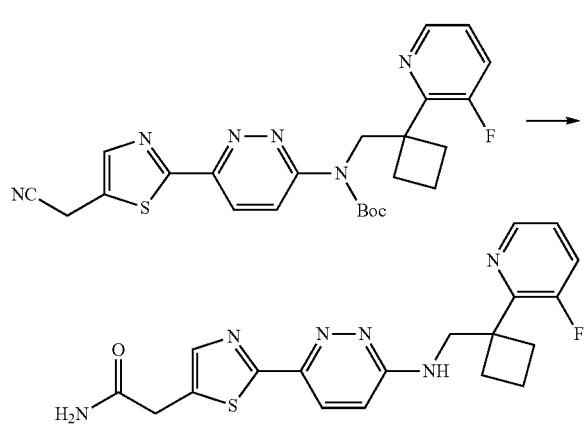

2-(2-(6-((1-(3-fluoropyridin-2-yl)cyclobutyl)methylamino)pyridazin-3-yl)thiazol-5-yl)acetamide To a solution of t-butyl 6-(5-(cyanomethyl)thiazol-2-yl)pyridazin-3-yl((1-(3-fluoropyridin-2-yl)cyclobutyl)methyl)carbamate (12.5 g, 26.0 mmol) in DMSO (260 mL) was added potassium carbonate (14.4 g, 104.1 mmol). The mixture was cooled to 0° C. and hydrogen peroxide (86 mL) was slowly added. The reaction was warmed to rt and stirred for 90 min. The reaction was diluted with EtOAc (200 mL) and water (500 mL), and the organic layer was washed three times with brine (150 mL). The organic layer was then dried over $Na_2SO_4$, filtered, and concentrated to give a crude solid that was purified by silica gel chromatography ($CH_3CN/CH_2Cl_2$) to afford 6.2 g of t-butyl 6-(5-(2-amino-2-oxoethyl)thiazol-2-yl)pyridazin-3-yl((1-(3-fluoropyridin-2-yl)cyclobutyl)methyl)carbamate as a reddish solid. This compound was combined with other batches (15.5 g overall), dissolved in 25% TFA/$CH_2Cl_2$, and stirred for 1 h. The reaction was then concentrated, dissolved in ethyl acetate (75 mL), and washed three times with potassium carbonate. The organic layer was then dried over $Na_2SO_4$, filtered, and concentrated to give a crude solid that was recrystallized with THF to give 10.8 g of 1-(2-((-3-fluoro-1-(3-fluoropyridin-2-yl)cyclobutyl)methylamino)pyrimidin-5-yl)-1H-pyrrole-3-carboxamide as an off-white solid (M+H=399.1).

EXAMPLE 24

Preparation of 2-(2-(6-((1-(3-fluoropyridin-2-yl)cyclobutyl)methylamino)pyridazin-3-yl)thiazol-5-yl)-N-methylacetamide

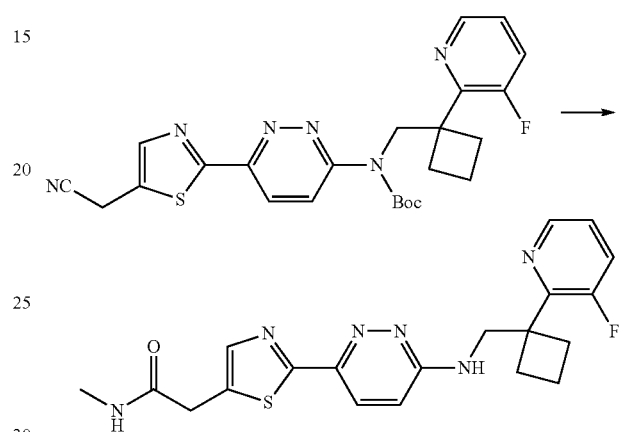

A solution of t-butyl 6-(5-(cyanomethyl)thiazol-2-yl)pyridazin-3-yl((1-(3-fluoropyridin-2-yl)cyclobutyl)methyl)carbamate (1 g, 2 mmol) in HCl (30 mL, conc) was heated to 105° C. in a microwave reactor and stirred for 15 min. The reaction was concentrated to give 900 mg (2.3 mmol) of a crude reddish solid. To this solid was added methylamine hydrochloride (183 mg, 2.7 mmol), HOBt (365 mg, 2.7 mmol), EDC (516 mg, 2.7 mmol), DMF (30 mL), and TEA (1.3 mL, 9 mmol). The reaction was stirred at rt overnight. The reaction was then poured into ethyl acetate (200 mL), washed with water (3×100 mL), and the organic layer was separated, dried over $Na_2SO_4$, filtered, concentrated, and recrystallized from EtOAc to give 408 mg of 2-(2-(6-((1-(3-Fluoropyridin-2-yl)cyclobutyl)methylamino)pyridazin-3-yl)thiazol-5-yl)-N-methylacetamide as a white solid (M+H=413.3).

EXAMPLE 25

Preparation of N-((2-(6-((1-(3-fluoropyridin-2-yl)cyclobutyl)methylamino)pyridazin-3-yl)thiazol-5-yl)methyl)-2-hydroxyacetamide

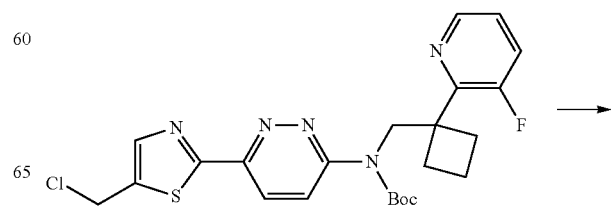

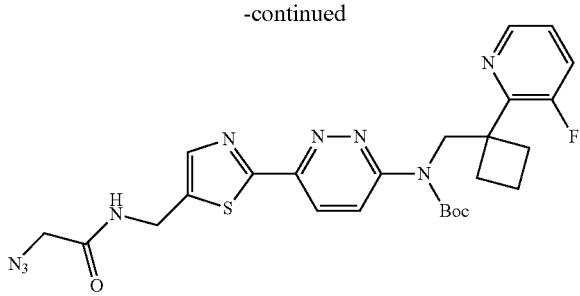

t-butyl 6-(5-(Azidomethyl)thiazol-2-yl)pyridazin-3-yl((1-(3-fluoropyridin-2-yl)cyclobutyl)methyl)carbamate To a stirring solution of t-butyl 6-(5-(chloromethyl)thiazol-2-yl)pyridazin-3-yl((1-(3-fluoropyridin-2-yl)cyclobutyl)methyl)carbamate (60.7 g, 124 mmol) in DMF (800 mL) was added sodium azide (22.2 g, 341 mmol) and DIPEA (31.1 mL, 171 mmol). The reaction was heated to 60° C. and stirred for 1 h. The reaction was poured into ethyl acetate (2000 mL), washed with water (3×400 mL), and the combined organic layers were separated, dried over Na$_2$SO$_4$, filtered, concentrated, and purified by silica gel chromatography (EtOAC/hexanes) to afford 20.0 g of t-butyl 6-(5-(azidomethyl)thiazol-2-yl)pyridazin-3-yl((1-(3-fluoropyridin-2-yl)cyclobutyl)methyl)carbamate as a yellow oil.

t-butyl 6-(5-(Aminomethyl)thiazol-2-yl)pyridazin-3-yl((1-(3-fluoropyridin-2-yl)cyclobutyl)methyl)carbamate Tin(II) chloride dihydrate (15.5 g, 80 mmol) was added to a solution of t-butyl 6-(5-(azidomethyl)thiazol-2-yl)pyridazin-3-yl((1-(3-fluoropyridin-2-yl)cyclobutyl)methyl)carbamate (20 g, 40 mmol) in methanol (400 mL) and the reaction was stirred at rt for 30 min. The reaction was poured into ethyl acetate (1000 mL), washed with water (3×200 mL), and the combined organic layers were separated, dried over Na$_2$SO$_4$, filtered, concentrated, and purified using silica gel column chromatography (9% MeOH/90% EtOAc/1% TEA) to give 35 g of t-butyl 6-(5-(aminomethyl)thiazol-2-yl)pyridazin-3-yl((1-(3-fluoropyridin-2-yl)cyclobutyl)methyl)carbamate as a yellow oil.

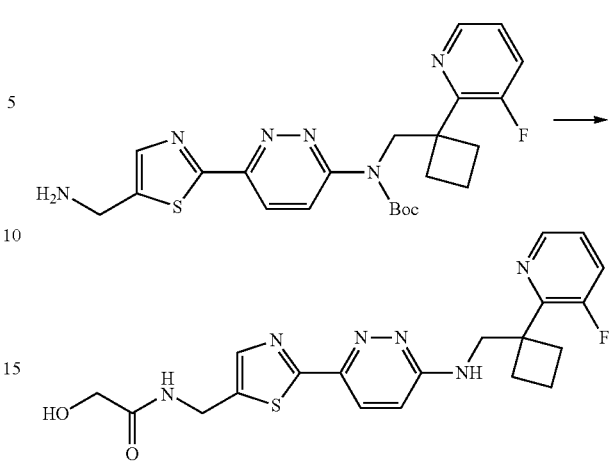

N-((2-(6-((1-(3-fluoropyridin-2-yl)cyclobutyl)methylamino)pyridazin-3-yl)thiazol-5-yl)methyl)-2-hydroxyacetamide t-butyl 6-(5-(aminomethyl)thiazol-2-yl)pyridazin-3-yl((1-(3-fluoropyridin-2-yl)cyclobutyl)methyl)carbamate (4.8 g, 10 mmol), glycolic acid (0.9 g, 12 mmol), HOBt (1.6 g, 12 mmol), EDC (2.3 g, 12 mmol), DMF (50 mL), and TEA (5.9 mL) were added to a 250 mL round bottom flask and the reaction was heated to 60° C. and stirred for 1 h. The reaction was poured into ethyl acetate (400 mL), washed with water (3×100 mL), and the combined organic layers were separated, dried over Na$_2$SO$_4$, filtered, concentrated, and purified by silica gel chromatography (EtOAC/hexanes) to afford 3.9 g of t-butyl (1-(3-fluoropyridin-2-yl)cyclobutyl)methyl(6-(5-((2-hydroxyacetamido)methyl)thiazol-2-yl)pyridazin-3-yl)carbamate as a white solid. This compound was dissolved in 30% TFA/CH$_2$Cl$_2$ (30 mL) and stirred for 1 h. The reaction was concentrated, dissolved in EtOAc (200 mL), washed with potassium carbonate (3×30 mL), concentrated, and then recrystallized with ethanol to give a white solid that was further purified with reverse phase chromatography to give 305 mg of N-((2-(6-((1-(3-fluoropyridin-2-yl)cyclobutyl)methylamino)pyridazin-3-yl)thiazol-5-yl)methyl)-2-hydroxyacetamide as a white solid (M+H=429.1).

EXAMPLE 26

Preparation of 1-(6-((1-(3-fluoropyridin-2-yl)cyclobutyl)methylamino)pyridazin-3-yl)-1H-pyrrole-3-carboxamide

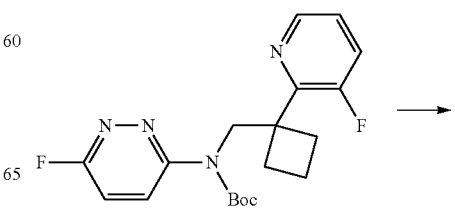

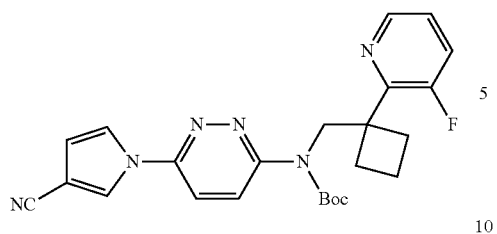

t-butyl 6-(3-Cyano-1H-pyrrol-1-yl)pyridazin-3-yl((1-(3-fluoropyridin-2-yl)cyclobutyl)methyl)carbamate To a stirring solution of t-butyl 6-fluoropyridazin-3-yl((1-(3-fluoropyridin-2-yl)cyclobutyl)methyl)carbamate (200 mg, 551 μmol) in DMF (2 mL) was added 3-cyanopyrrole (61 mg, 661 μmol) and potassium carbonate (152 mg, 1.1 mmol). The reaction was heated to 110° C. and stirred for 30 min. The reaction was then poured into ethyl acetate (100 mL), washed with water (3×25 mL), and the organic layer was separated, dried over $Na_2SO_4$, filtered, concentrated, and purified by silica gel chromatography (EtOAC/hexanes) to afford 130 mg of t-butyl 6-(3-cyano-1H-pyrrol-1-yl)pyridazin-3-yl((1-(3-fluoropyridin-2-yl)cyclobutyl)methyl)carbamate as a pale yellow solid.

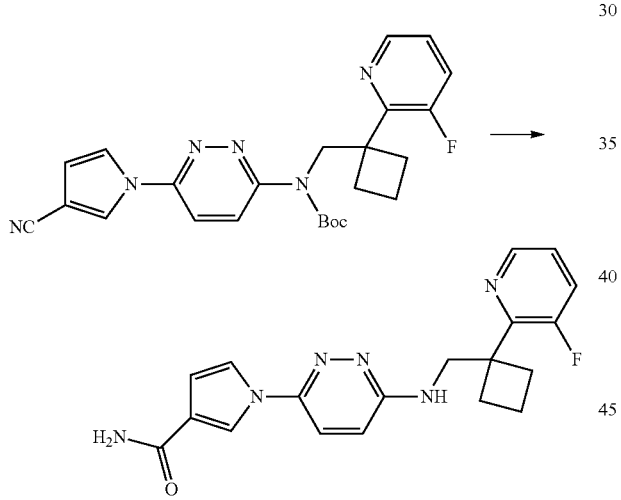

1-(6-((1-(3-Fluoropyridin-2-yl)cyclobutyl)methylamino)pyridazin-3-yl)-1H-pyrrole-3-carboxamide t-butyl 6-(3-cyano-1H-pyrrol-1-yl)pyridazin-3-yl((1-(3-fluoropyridin-2-yl)cyclobutyl)methyl)carbamate (120 mg, 267 μmol), potassium carbonate (147 mg, 1.1 mmol), and DMSO (3 mL) were combined in a vial and cooled to 0° C. Hydrogen peroxide (700 uL) was added dropwise, and the reaction was warmed to rt and stirred for 1 h. The reaction was then poured into ethyl acetate (50 mL), washed with water (3×20 mL), and the organic layer was separated, dried over $Na_2SO_4$, filtered, and concentrated. The crude solid was dissolved in 50% $TFA/CH_2Cl_2$ (2 mL) and stirred for 30 min. The reaction was then concentrated and purified using reverse phase chromatography to give 29 mg of 1-(6-((1-(3-fluoropyridin-2-yl)cyclobutyl)methylamino)pyridazin-3-yl)-1H-pyrrole-3-carboxamide as a tan solid (M+H=367.1).

EXAMPLE 27

Preparation of 2-(6-((1-(3-fluoropyridin-2-yl)cyclobutyl)methylamino)pyridazin-3-yl)-4-hydroxy-2,5-dihydrothiazole-5-carboxamide

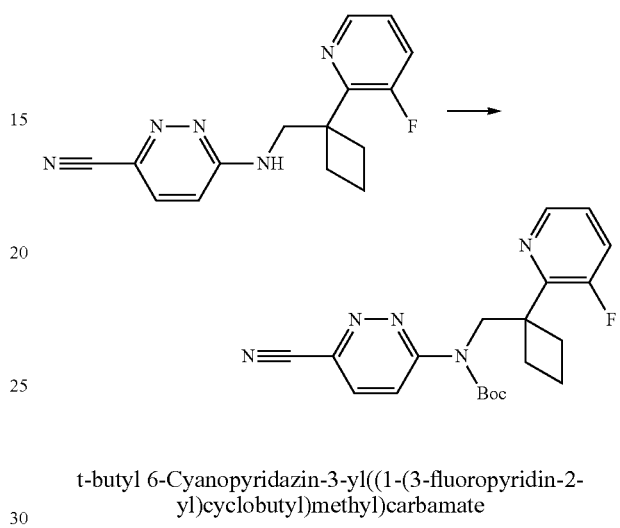

t-butyl 6-Cyanopyridazin-3-yl((1-(3-fluoropyridin-2-yl)cyclobutyl)methyl)carbamate To a solution of 6-((1-(3-fluoropyridin-2-yl)cyclobutyl)methylamino)pyridazine-3-carbonitrile (3.3 g, 4.7 mmol) in THF (30 mL) was added di-t-butyl dicarbonate (2.8 g, 13 mmol), and DMAP (0.5 g, 4.3 mmol). The reaction mixture was refluxed for 2 h. The reaction was concentrated and then poured into ethyl acetate (150 mL) and washed with 0.1M HCl (50 mL, aq) and brine (50 mL). The organic layer was separated, dried over $Na_2SO_4$, filtered, and concentrated to give a crude oil that was purified by silica gel column chromatography (EtOAC/hexanes) to afford 3.9 g of t-butyl 6-cyanopyridazin-3-yl((1-(3-fluoropyridin-2-yl)cyclobutyl)methyl)carbamate as a white solid.

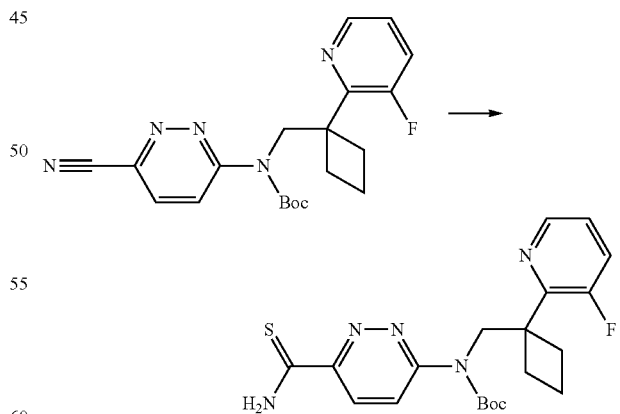

t-butyl 6-Carbamothioylpyridazin-3-yl((1-(3-fluoropyridin-2-yl)cyclobutyl)methyl)carbamate NMP (40 mL) and DIPEA (10 mL) were added to t-butyl 6-cyanopyridazin-3-yl((1-(3-fluoropyridin-2-yl)cyclobutyl)

methyl)carbamate (3.9 g, 10 mmol), and hydrogen sulfide was bubbled through the reaction mixture for 2 h. The reaction was diluted with water, and the resultant yellow solid was filtered and dried under vacuum to give 2.1 g of t-butyl 6-carbamothioylpyridazin-3-yl((1-(3-fluoropyridin-2-yl)cyclobutyl)methyl)carbamate as a yellow solid.

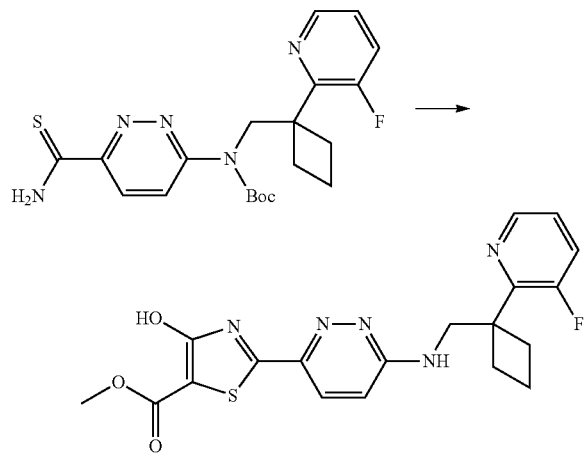

Ethyl 2-(6-(t-butoxycarbonyl((1-(3-fluoropyridin-2-yl)cyclobutyl)methyl)amino)pyridazin-3-yl)-4-hydroxy-2,5-dihydrothiazole-5-carboxylate t-Butyl 6-carbamothioylpyridazin-3-yl((1-(3-fluoropyridin-2-yl)cyclobutyl)methyl)carbamate (1.0 g, 2.4 mmol), diethylbromomalonate (2 mL, 12 mmol), and toluene were added to a round bottom flask, heated to 90° C., and stirred for 40 min. The reaction was concentrated and purified using reverse phase chromatography to yield 219 mg of ethyl 2-(6-(t-butoxycarbonyl((1-(3-fluoropyridin-2-yl)cyclobutyl)methyl)amino)pyridazin-3-yl)-4-hydroxy-2,5-dihydrothiazole-5-carboxylate as an off-white solid.

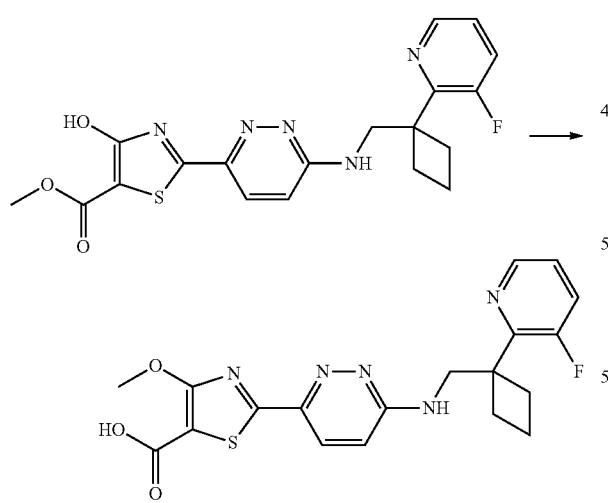

2-(6-(t-Butoxycarbonyl((1-(3-fluoropyridin-2-yl)cyclobutyl)methyl)amino)pyridazin-3-yl)-4-methoxy-2,5-dihydrothiazole-5-carboxylic acid To a stirring solution of ethyl 2-(6-(t-butoxycarbonyl((1-(3-fluoropyridin-2-yl)cyclobutyl)methyl)amino)pyridazin-3-yl)-4-hydroxy-2,5-dihydrothiazole-5-carboxylate (350 mg, 0.7 mmol) in DMF (4 mL) was added methyl iodide (200 μL, 3.3 mmol) and sodium hydride (60% dispersion in mineral oil, 40 mg, 1 mmol). The reaction was stirred at rt for 1 h and at 40° C. for 45 min. The reaction was then concentrated and quenched with water (5 mL), poured into ethyl acetate (150 mL), and washed with 0.1M HCl (50 mL, aq) and brine (50 mL). The organic layer was separated, dried over $Na_2SO_4$, filtered, concentrated and purified by silica gel column chromatography (EtOAC/hexanes) to afford 205 mg of ethyl 2-(6-(tert-butoxycarbonyl((1-(3-fluoropyridin-2-yl)cyclobutyl)methyl)amino)pyridazin-3-yl)-4-methoxy-2,5-dihydrothiazole-5-carboxylate. This compound was dissolved in methanol (4 mL) and 1M KOH (aq, 2 mL). The reaction mixture was heated to 75° C. and stirred for 45 min. The reaction was cooled and the pH was adjusted to 4 using 1M HCl. The reaction was then poured into ethyl acetate (50 mL), washed with brine (15 mL), dried over $Na_2SO_4$, filtered, and concentrated to give 175 mg of 2-(6-(t-butoxycarbonyl((1-(3-fluoropyridin-2-yl)cyclobutyl)methyl)amino)pyridazin-3-yl)-4-methoxy-2,5-dihydrothiazole-5-carboxylic acid as a white foam.

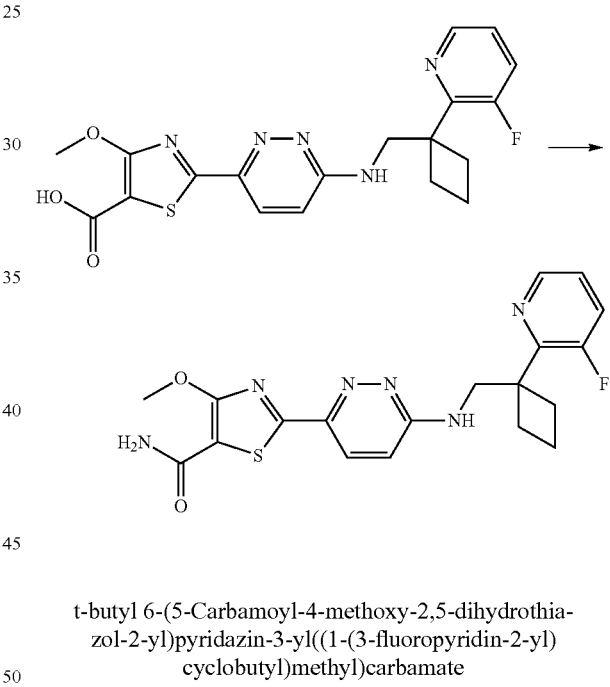

t-butyl 6-(5-Carbamoyl-4-methoxy-2,5-dihydrothiazol-2-yl)pyridazin-3-yl((1-(3-fluoropyridin-2-yl)cyclobutyl)methyl)carbamate To a 50 dram vial was added 2-(6-(t-butoxycarbonyl((1-(3-fluoropyridin-2-yl)cyclobutyl)methyl)amino)pyridazin-3-yl)-4-methoxy-2,5-dihydrothiazole-5-carboxylic acid (175 mg, 0.34 mmol), HATU (194 mg, 0.51 mmol), HOAt (70 mg, 0.51 mmol), DIPEA (296 μL, 1.7 mmol), NMP (2 mL), and ammonium chloride (180 mg, 3.4 mmol). The reaction was stirred overnight at rt. The reaction was then poured into ethyl acetate (50 mL), washed with aqueous sodium bicarbonate, and brine (50 mL). The organic layer was separated, dried over $Na_2SO_4$, filtered, concentrated and purified by silica gel column chromatography (EtOAC/hexanes) to afford 120 mg of t-butyl 6-(5-carbamoyl-4-methoxy-2,5-dihydrothiazol-2-yl)pyridazin-3-yl((1-(3-fluoropyridin-2-yl)cyclobutyl)methyl)carbamate.

87

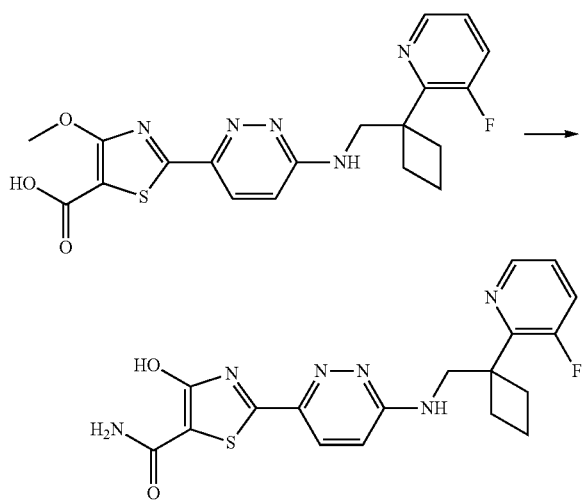

2-(6-((1-(3-Fluoropyridin-2-yl)cyclobutyl)methylamino)pyridazin-3-yl)-4-hydroxy-2,5-dihydrothiazole-5-carboxamide To a stirring mixture of t-butyl 6-(5-carbamoyl-4-methoxy-2,5-dihydrothiazol-2-yl)pyridazin-3-yl((1-(3-fluoropyridin-2-yl)cyclobutyl)methyl)carbamate (60 mg, 0.12 μmol) in CH$_2$Cl$_2$ (2 mL) was added BBr$_3$ (140 μL, 1.2 mmol). The reaction was stirred at rt for 2 h and then at 60° C. for 15 min. The reaction was cooled to rt and carefully diluted with methanol (2 mL). The reaction was concentrated, diluted with ethyl acetate (20 mL), and saturated sodium bicarbonate (10 mL) was added. The mixture was agitated and then filtered. The subsequent crude solid was then purified using reverse phase chromatography to give 15 mg of 2-(6-((1-(3-fluoropyridin-2-yl)cyclobutyl)methylamino)pyridazin-3-yl)-4-hydroxy-2,5-dihydrothiazole-5-carboxamide as a yellow solid (M+H=401.3)

EXAMPLE 28

Preparation of 4-fluoro-3-(6-(((trans)-3-fluoro-1-(3-fluoropyridin-2-yl)cyclobutyl)methylamino)pyridazin-3-yl)-2-hydroxybenzamide

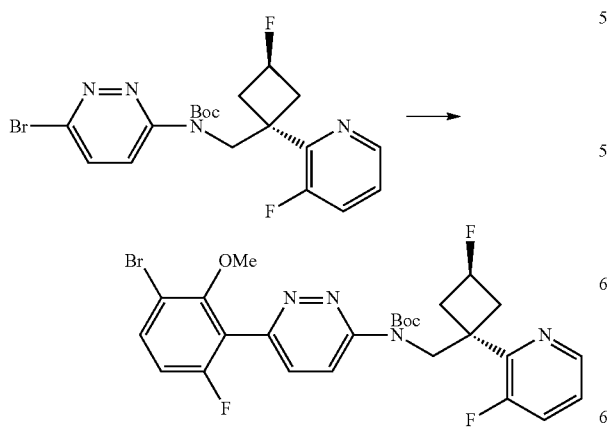

88 t-butyl 6-(3-Bromo-6-fluoro-2-methoxyphenyl)pyridazin-3-yl(((trans)-3-fluoro-1-(3-fluoropyridin-2-yl)cyclobutyl)methyl)carbamate t-Butyl 6-Bromopyridazin-3-yl(((trans)-3-fluoro-1-(3-fluoropyridin-2-yl)cyclobutyl)methyl)carbamate (3.0 g, 6.61 mmol), 3-bromo-6-fluoro-2-methoxyphenylboronic acid (1.64 g, 6.61 mmol), (dppf)PdCl$_2$ (0.48 g, 0.66 mmol), nitrogen-sparged dioxane (13.2 mL) and aq. 2 N K$_2$CO$_3$ (0.6 mL) were combined and heated in a microwave reactor at 125° C. The reaction mixture was diluted with EtOAc and washed with satd. aq. NaHCO$_3$ and brine. The organic layer was dried over sodium sulfate, filtered, and concentrated. Silica gel chromatography afforded the title compound as a yellow solid (1.4 g, 37%), (m/z [M+H]=579.1).

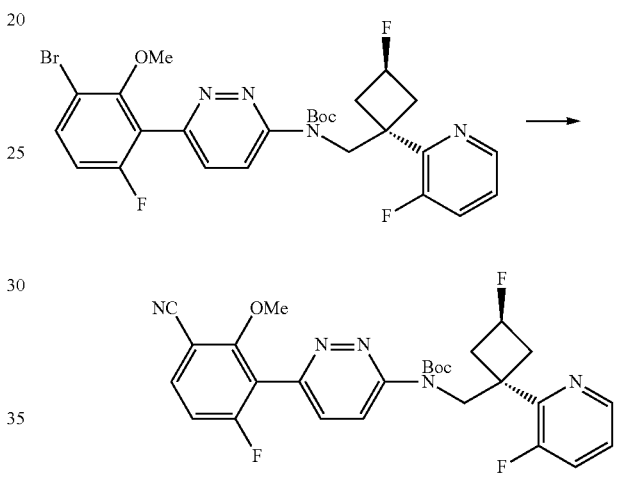

t-butyl 6-(3-cyano-6-fluoro-2-methoxyphenyl)pyridazin-3-yl(((trans)-3-fluoro-1-(3-fluoropyridin-2-yl)cyclobutyl)methyl)carbamate t-Butyl 6-(3-Bromo-6-fluoro-2-methoxyphenyl)pyridazin-3-yl(((trans)-3-fluoro-1-(3-fluoropyridin-2-yl)cyclobutyl)methyl)carbamate (1.4 g, 3.0 mmol), zinc cyanide (0.42 g, 3.6 mmol), Pd(PPh$_3$)$_4$ (1.0 g, 0.9 mmol), DMF (3 mL) were combined and heated to 100° C. The reaction mixture was diluted with EtOAc and washed with satd. aq. NaHCO$_3$ and brine. The organic layer was dried over sodium sulfate, filtered, and concentrated. Silica gel chromatography afforded the title compound as a yellow solid (1.0 g, 63%), (m/z [M+H]=526.2).

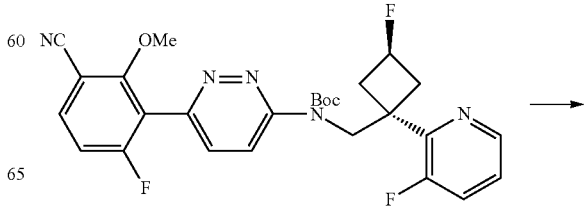

-continued

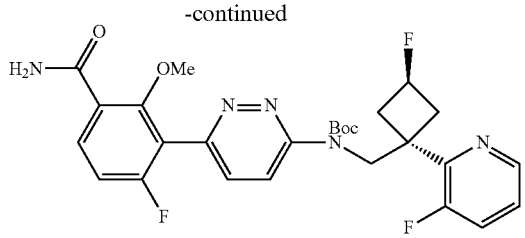

t-butyl 6-(3-carbamoyl-6-fluoro-2-methoxyphenyl)pyridazin-3-yl(((trans)-3-fluoro-1-(3-fluoropyridin-2-yl)cyclobutyl)methyl)carbamate t-Butyl 6-(3-cyano-6-fluoro-2-methoxyphenyl)pyridazin-3-yl(((trans)-3-fluoro-1-(3-fluoropyridin-2-yl)cyclobutyl)methyl)carbamate (1.0 g, 1.9 mmol), $K_2CO_3$ (0.8 g, 5.8 mmol), and DMSO (10 mL) were combined in a round bottom flask, cooled to 0° C., and $H_2O_2$ (2 mL of 35% solution) was added dropwise. The reaction mixture was diluted with EtOAc and washed with satd. aq. $NaHCO_3$ and brine. The organic layer was dried over sodium sulfate, filtered, and concentrated. Silica gel chromatography afforded the title compound as a white solid (0.32 g, 33%), (m/z [M+H] =545.1).

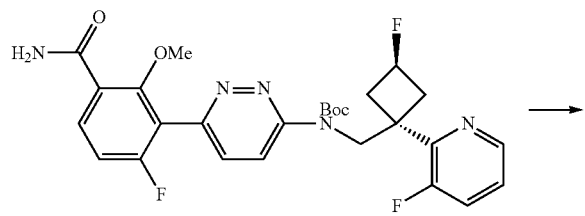

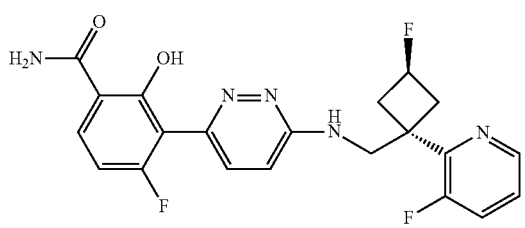

4-Fluoro-3-(6-(((trans)-3-fluoro-1-(3-fluoropyridin-2-yl)cyclobutyl)methylamino)pyridazin-3-yl)-2-hydroxybenzamide t-Butyl 6-(3-carbamoyl-6-fluoro-2-methoxyphenyl)pyridazin-3-yl(((trans)-3-fluoro-1-(3-fluoropyridin-2-yl)cyclobutyl)methyl)carbamate (0.32 g, 0.59 mmol), lithium iodide (0.71 g, 5.34 mmol), and pyridine (5 mL) were combined in a microwave reactor and heated to 125° C. The reaction mixture was diluted with EtOAc and washed with satd. aq. $NaHCO_3$ and brine. The organic layer was dried over sodium sulfate, filtered, and concentrated. Reverse phase chromatography provided 4-fluoro-3-(6-(((E)-3-fluoro-1-(3-fluoropyridin-2-yl)cyclobutyl)methylamino)pyridazin-3-yl)-2-hydroxybenzamide as a white solid (0.024 g, 10%), (m/z [M+H]=430.1).

EXAMPLE 29

Preparation of 4-fluoro-5-(6-(((trans)-3-fluoro-1-(3-fluoropyridin-2-yl)cyclobutyl)methylamino)pyridazin-3-yl)-2-hydroxybenzamide

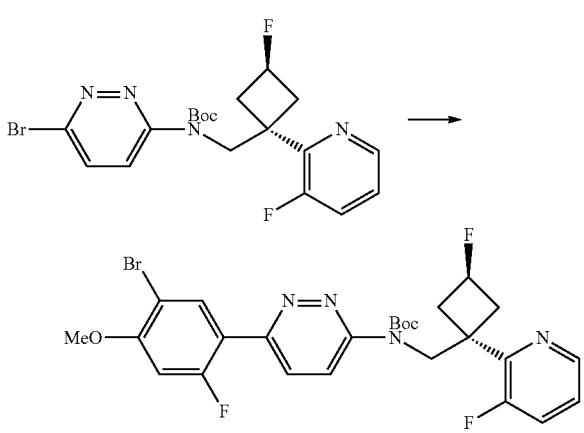

t-Butyl 6-(5-bromo-2-fluoro-4-methoxyphenyl)pyridazin-3-yl(((trans)-3-fluoro-1-(3-fluoropyridin-2-yl)cyclobutyl)methyl)carbamate t-Butyl 6-bromopyridazin-3-yl(((trans)-3-fluoro-1-(3-fluoropyridin-2-yl)cyclobutyl)methyl)carbamate (3.0 g, 6.61 mmol), 2-(5-bromo-2-fluoro-4-methoxyphenyl)-4,4,5,5-tetramethyl-1,3,2-dioxaborolane (2.2 g, 6.61 mmol), (dppf)PdCl$_2$ (0.48 g, 0.66 mmol), nitrogen-sparged dioxane (13.2 mL) and aq. 2 N $K_2CO_3$ (0.6 mL) were combined and heated to 90° C. The reaction mixture was diluted with EtOAc and washed with satd. aq. $NaHCO_3$ and brine. The organic layer was dried over sodium sulfate, filtered, and concentrated. Silica gel chromatography provided a light yellow solid (1.7 g, 44%), (m/z [M+H]=579.1).

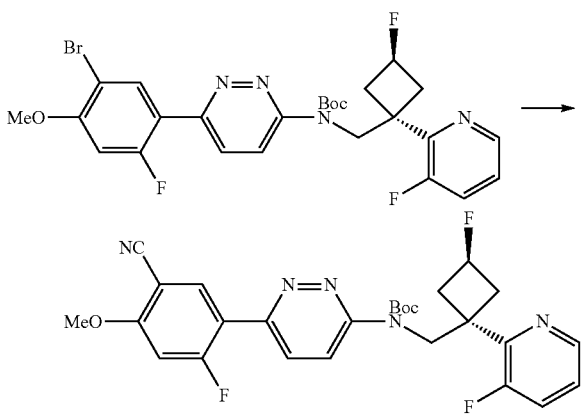

t-Butyl 6-(5-cyano-2-fluoro-4-methoxyphenyl)pyridazin-3-yl(((trans)-3-fluoro-1-(3-fluoropyridin-2-yl)cyclobutyl)methyl)carbamate t-Butyl 6-(5-bromo-2-fluoro-4-methoxyphenyl)pyridazin-3-yl(((trans)-3-fluoro-1-(3-fluoropyridin-2-yl)cyclobutyl)methyl)carbamate (1.7 g, 3.6 mmol), zinc cyanide (0.51 g, 4.3 mmol), Pd(PPh$_3$)$_4$ (1.26 g, 1.0 mmol), DMF (5 mL) were combined and heated to 100° C. The reaction mixture was diluted with EtOAc and washed with satd. aq. NaHCO$_3$ and brine. The organic layer was dried over sodium sulfate, filtered, and concentrated. Silica gel chromatography provided a yellow solid (1.1 g, 66%), (m/z [M+H]=526.2).

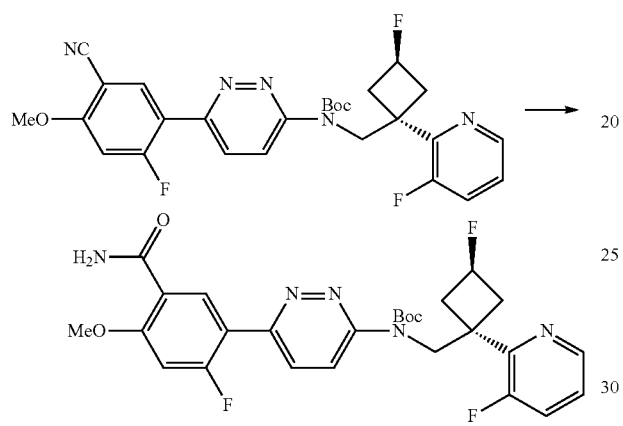

t-Butyl 6-(5-carbamoyl-2-fluoro-4-methoxyphenyl)pyridazin-3-yl(((trans)-3-fluoro-1-(3-fluoropyridin-2-yl)cyclobutyl)methyl)carbamate t-Butyl 6-(5-cyano-2-fluoro-4-methoxyphenyl)pyridazin-3-yl(((trans)-3-fluoro-1-(3-fluoropyridin-2-yl)cyclobutyl)methyl)carbamate (0.21 g, 0.4 mmol), K$_2$CO$_3$ (0.22 g, 1.6 mmol), and DMSO (4 mL) were combined in a round bottom flask, cooled to 0° C., and H$_2$O$_2$ (1.3 mL of 35%) was added dropwise. The reaction mixture was diluted with EtOAc and washed with satd. aq. NaHCO$_3$ and brine. The organic layer was dried over sodium sulfate, filtered, and concentrated. Silica gel chromatography provided a white solid (0.10 g, 46%), (m/z [M+H]=545.1).

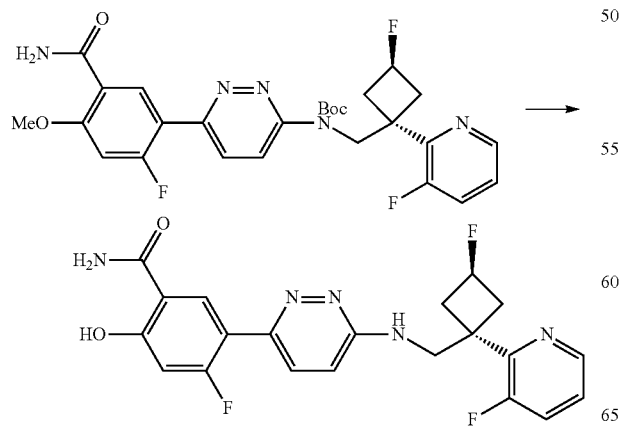

4-Fluoro-5-(6-(((trans)-3-fluoro-1-(3-fluoropyridin-2-yl)cyclobutyl)methylamino)pyridazin-3-yl)-2-hydroxybenzamide t-Butyl 6-(5-carbamoyl-2-fluoro-4-methoxyphenyl)pyridazin-3-yl(((trans)-3-fluoro-1-(3-fluoropyridin-2-yl)cyclobutyl)methyl)carbamate (0.10 g, 0.18 mmol), lithium iodide (0.22 g, 1.65 mmol) and pyridine (3 mL) were combined in a microwave reactor and heated to 125° C. The reaction mixture was diluted with EtOAc and washed with satd. aq. NaHCO$_3$ and brine. The organic layer was dried over sodium sulfate, filtered, and concentrated. Reverse phase chromatography provided the title compound as a white solid (0.023 g, 30%), (m/z [M+H]=430.1).

EXAMPLE 30

Preparation of 5-(6-((1-(3-fluoropyridin-2-yl)cyclobutyl)methylamino)pyridazin-3-yl)-1H-pyrazole-3-carboxamide

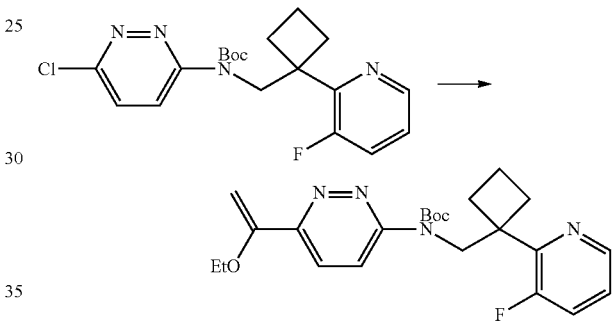

t-Butyl 6(1-ethoxyvinyl)pyridazin-3-yl((1-(3-fluoropyridin-2-yl)cyclobutyl)methyl)carbamate t-Butyl 6-chloropyridazin-3-yl((1-(3-fluoropyridin-2-yl)cyclobutyl)methyl)carbamate (5.1 g, 13.0 mmol), tributyl(1-ethoxyvinyl)stannane (6.1 g, 16.9 mmol), (PPh$_3$)$_2$PdCl$_2$ (2.3 g, 3.2 mmol), and nitrogen-sparged dioxane (18 mL) were combined and heated in a microwave reactor at 150° C. The reaction mixture was diluted with EtOAc and washed with satd. aq. NaHCO$_3$ and brine. The organic layer was dried over sodium sulfate, filtered, and concentrated. Silica gel chromatography provided a light yellow solid (3.9 g, 71%), (m/z [M+H]=429.2).

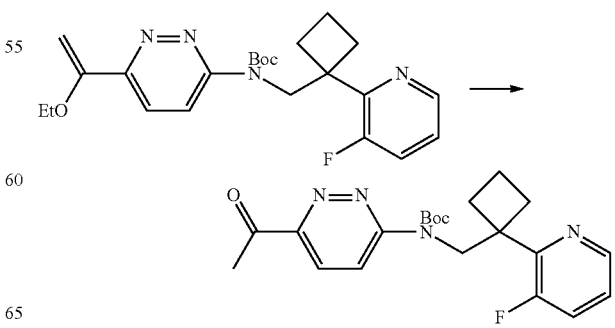

t-Butyl 6-acetylpyridazin-3-yl((1-(3-fluoropyridin-2-yl)cyclobutyl)methyl)carbamate t-Butyl 6-(1-ethoxyvinyl)pyridazin-3-yl((1-(3-fluoropyridin-2-yl)cyclobutyl)methyl)carbamate (1.0 g, 2.3 mmol), EtOH (75 mL), and 1N HCl (15 mL) were combined at 0° C., warmed to 25° C., and stirred for 1 h. The reaction mixture was concentrated and silica gel chromatography provided a colorless oil (0.6 g, 64%), (m/z [M+H]=401.1).

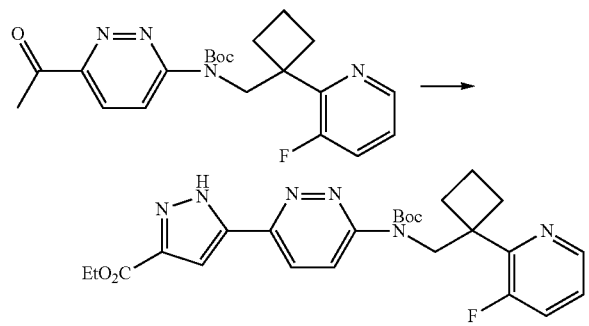

Ethyl 5-(6-(tert-butoxycarbonyl((1-(3-fluoropyridin-2-yl)cyclobutyl)methyl)amino)pyridazin-3-yl)-1H-pyrazole-3-carboxylate t-Butyl 6-acetylpyridazin-3-yl((1-(3-fluoropyridin-2-yl)cyclobutyl)methyl)carbamate (2.5 g, 6.2 mmol) in THF (150 mL) was treated with NaOEt (3.44 g, 10.6 mmol, 21% in EtOH). The resulting mixture was then treated with diethyl oxalate (1.7 mL, 12.5 mmol), heated to 45° C., and stirred for 4 h. The reaction mixture was added to 1N HCl, extracted with EtOAc, and washed with satd. aq. NaHCO₃ and brine. The organic layer was dried over sodium sulfate, filtered, and concentrated. A portion of the resultant oil was dissolved in AcOH and hydrazine (0.41 g, 13.2 mmol) was added and stirred at 80° C. Concentration afforded a yellow oil which was purified by reverse-phase chromatography to give solid (0.285 g, 62%), (m/z [M+H]=497.2).

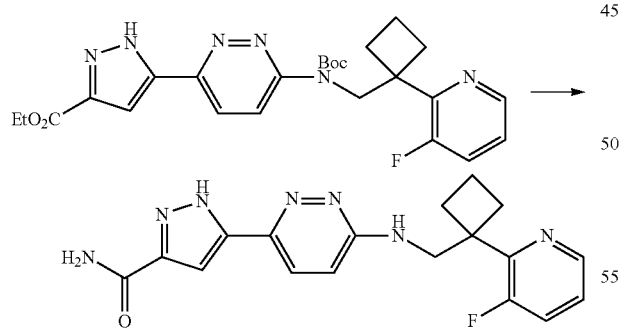

5-(6-((1-(3-Fluoropyridin-2-yl)cyclobutyl)methylamino)pyridazin-3-yl)-1H-pyrazole-3-carboxamide Ethyl 5-(6-(t-butoxycarbonyl((1-(3-fluoropyridin-2-yl)cyclobutyl)methyl)amino)pyridazin-3-yl)-1H-pyrazole-3-carboxylate (0.28 g, 0.56 mmol) and 7N ammonia in MeOH were combined in a microwave reactor and heated to 110° C. for 1 h. The reaction mixture was then concentrated, diluted with EtOAc, and washed with satd. aq. NaHCO₃ and brine. The organic layer was dried over sodium sulfate, filtered, and concentrated. The resultant oil was diluted in 10 mL of DCM and TFA (15 mL) was added. The reaction mixture was then concentrated and purified by reverse phase chromatography to give the title compound as a white solid (18 mg, 12%), (m/z [M+H]=368.1).

EXAMPLE 31

Preparation of 3-(6-((1-(3-fluoropyridin-2-yl)cyclobutyl)methylamino)pyridazin-3-yl)isoxazole-5-carboxamide

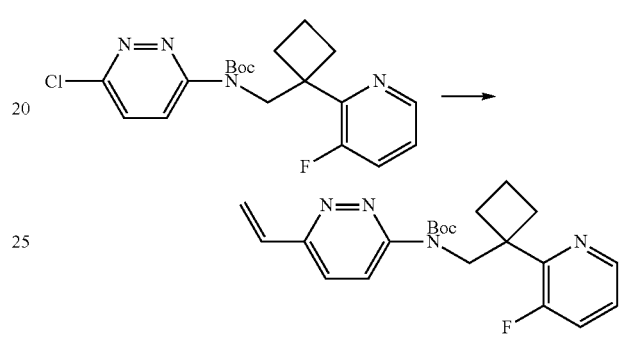

t-Butyl (1-(3-fluoropyridin-2-yl)cyclobutyl)methyl (6-vinylpyridazin-3-yl)carbamate t-Butyl 6-chloropyridazin-3-yl((1-(3-fluoropyridin-2-yl)cyclobutyl)methyl)carbamate (2.5 g, 6.36 mmol), triethenylboroxin pyridine complex (1.0 g, 4.13 mmol), Pd(PPh₃)₄ (0.3 g, 0.25 mmol), nitrogen-sparged dioxane (13.2 mL) and aq. 2 N K₂CO₃ (0.9 mL) were combined and heated to 110° C. for 25 min. The reaction mixture was diluted with EtOAc and washed with satd. aq. NaHCO₃ and brine. The organic layer was dried over sodium sulfate, filtered, and concentrated. Silica gel chromatography provided a light yellow oil (2.1 g, 86%), (m/z [M+H]=385.2).

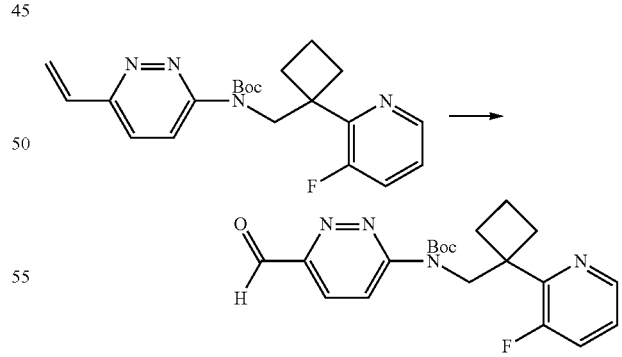

t-Butyl (1-(3-fluoropyridin-2-yl)cyclobutyl)methyl (6-formylpyridazin-3-yl)carbamate t-Butyl (1-(3-fluoropyridin-2-yl)cyclobutyl)methyl(6-vinylpyridazin-3-yl)carbamate (3.4 g, 8.84 mmol) was added as a dioxane (100 mL) solution to a mixture of sodium periodate (10.8 g, 50.5 mmol) and 4% osmium tetraoxide solution (6.5 mL) in H₂O (30 mL) at 0° C. The reaction was stirred for 2 h. The reaction mixture was filtered through a pad of celite and washed with EtOAc. The organic layer was washed with satd. aq. NaHCO₃, brine and dried over sodium sulfate, filtered, and concentrated. Silica gel chromatography provided a colorless oil (1.4 g, 41%), (m/z [M+H]=387.2).

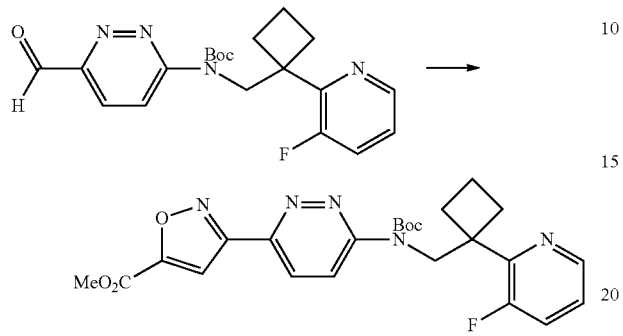

Methyl-3-(6-(tert-butoxycarbonyl((1-(3-fluoropyridin-2-yl)cyclobutyl)methyl)amino)pyridazin-3-yl)isoxazole-5-carboxylate To t-butyl (1-(3-fluoropyridin-2-yl)cyclobutyl)methyl(6-formylpyridazin-3-yl)carbamate (1.4 g, 3.6 mmol) in ethanol (10 mL) and water (2 mL) was added hydroxylamine hydrochloride (0.27 g, 3.8 mmol) followed by sodium acetate (0.32 g, 3.8 mmol) and stirred at 24° C. for 30 min. The crude reaction mixture was concentrated and diluted with EtOAc. The organic layer was washed with satd. aq. NaHCO₃ and brine, then dried over sodium sulfate, filtered, and concentrated. The crude mixture was then diluted in THF (2 mL) and pyridine (57 mg, 0.72 mmol) then treated with NCS (0.58 g, 4.35 mmol) and heated to 40° C. for 1.5 h. The crude mixture was then treated with methyl propiolate (0.30 g, 3.56 mmol) and TEA (0.36, 3.56 mmol), and the reaction was stirred for 45 min. The reaction mixture was concentrated and diluted with EtOAc, and then washed with satd. aq. NaHCO₃ and brine. The organic layer was dried over sodium sulfate, filtered, concentrated, and purified by reverse phase chromatography to give a white solid (0.53 g, 31%).

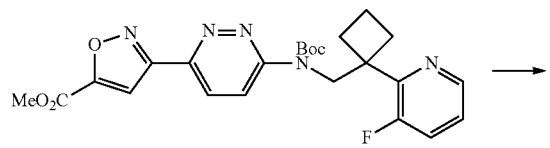

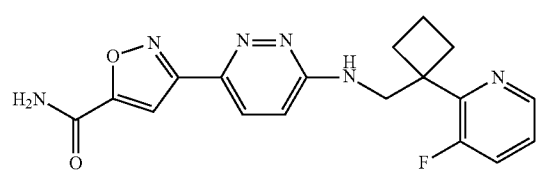

3-(6-((1-(3-Fluoropyridin-2-yl)cyclobutyl)methylamino)pyridazin-3-yl)isoxazole-5-carboxamide Methyl 3-(6-(tert-butoxycarbonyl((1-(3-fluoropyridin-2-yl)cyclobutyl)methyl)amino)pyridazin-3-yl)isoxazole-5-carboxylate (0.53 g, 1.1 mmol), methanol (5 mL) and concentrated ammonium hydroxide (8 mL) were combined in a microwave reactor and heated to 100° C. for 60 min. The reaction mixture was then concentrated and diluted with EtOAc and washed with satd. aq. NaHCO₃ and brine. The organic layer was dried over sodium sulfate, filtered, and concentrated. Resultant oil was diluted in 10 mL of DCM and TFA (6 mL) was added and the reaction was stirred for 35 min. The reaction mixture was then concentrated and purified by reverse phase chromatography to give the title compound as a white solid (144 mg, 36%), (m/z [M+H]=369.1).

EXAMPLE 32

Preparation of 2-(6-((1-(3-fluoropyridin-2-yl)cyclobutyl)methylamino)pyridazin-3-yl)thiazole-5-carboxamide

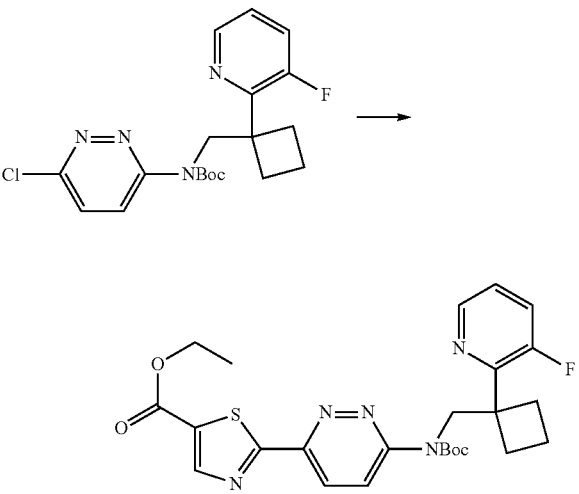

Ethyl 2-(6-(tert-butoxycarbonyl((1-(3-fluoropyridin-2-yl)cyclobutyl)methyl)amino)pyridazin-3-yl)thiazole-5-carboxylate tert-butyl 6-chloropyridazin-3-yl((1-(3-fluoropyridin-2-yl)cyclobutyl)methyl)carbamate (500 mg, 1.27 mmol), ethyl thiazole-5-carboxylate (300 mg, 1.91 mmol), Pd(OAc)₂ (86 mg, 0.13 mmol), JohnPhos (92 mg, 0.26 mmol) and Cs₂CO₃ (827 mg, 2.54 mmol) in toluene (10 mL) were combined and heated in a microwave reactor for 30 min at 145° C. The reaction mixture was filtered through a celite plug and the filtrate was concentrated. The resulting residue was purified on silica gel using a mixture of ethyl acetate and hexanes to provide the title compound as yellow oil (162 mg, 82% pure, 21%), LRMS (M+H⁺) m/z 514.3.

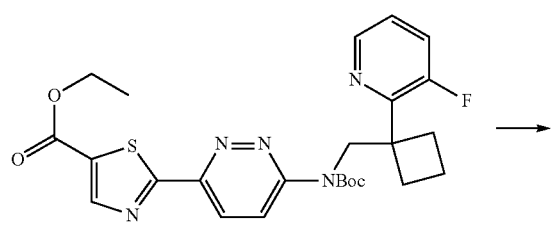

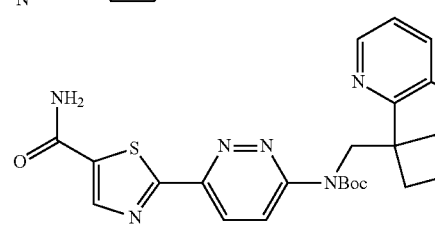

t-Butyl 6-(5-carbamoylthiazol-2-yl)pyridazin-3-yl ((1-(3-fluoropyridin-2-yl)cyclobutyl)methyl)carbamate To a solution of ethyl 2-(6-(tert-butoxycarbonyl((1-(3-fluoropyridin-2-yl)cyclobutyl)methyl)amino)pyridazin-3-yl)thiazole-5-carboxylate (162 mg, 0.32 mmol) in MeOH (8 mL) was purged with $NH_3$ gas for 5 min. The reaction mixture was sealed and heated in a microwave reactor for 30 min at 120° C. The reaction mixture was concentrated and used in next step without purification, LRMS (M+H$^+$) m/z 484.2.

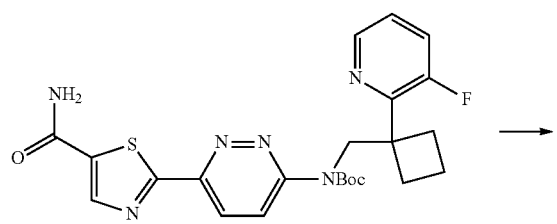

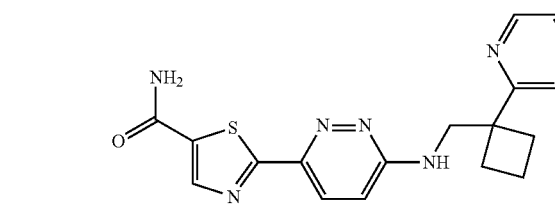

2-(6-((1-(3-Fluoropyridin-2-yl)cyclobutyl)methylamino)pyridazin-3-yl)thiazole-5-carboxamide To a crude mixture of t-butyl 6-(5-carbamoylthiazol-2-yl)pyridazin-3-yl((1-(3-fluoropyridin-2-yl)cyclobutyl)methyl)carbamate (141 mg, crude) in DCM (6 mL) was added TFA (2 mL) at rt. The reaction mixture was further stirred at rt for 2 hr followed by concentration to dryness. The crude mixture was purified on RP-HPLC using a mixture of acetonitrile and $H_2O$ to provide the title compound as a pale yellow solid (98.5 mg, 99% for 2 steps), LRMS (M+H$^+$) m/z 385.2.

EXAMPLE 33

Preparation of 5-(6-((1-(3-fluoropyridin-2-yl)cyclobutyl)methylamino)pyridazin-3-yl)isoxazole-3-carboxamide

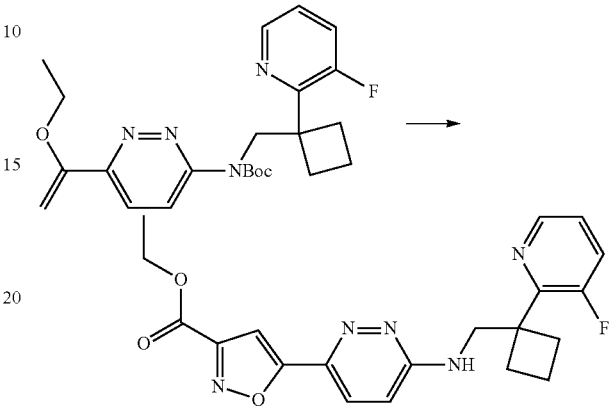

Ethyl 5-(6-((1-(3-fluoropyridin-2-yl)cyclobutyl)methylamino)pyridazin-3-yl)isoxazole-3-carboxylate To t-butyl 6-(1-ethoxyvinyl)pyridazin-3-yl((1-(3-fluoropyridin-2-yl)cyclobutyl)methyl)carbamate (439 mg, 1.02 mmol) in THF (5.0 mL) was added (E)-ethyl 2-chloro-2-(hydroxyimino)acetate (465 mg, 3.06 mmol) and TEA (1.4 mL, 10.2 mmol). The reaction mixture was stirred at rt for 30 min followed by addition of TFA (5 mL) and then heated to reflux overnight. The mixture was then concentrated and purified by reverse phase chromatography to give 415 mg of the title compound as a colorless oil, LRMS (M+H$^+$) m/z 398.3.

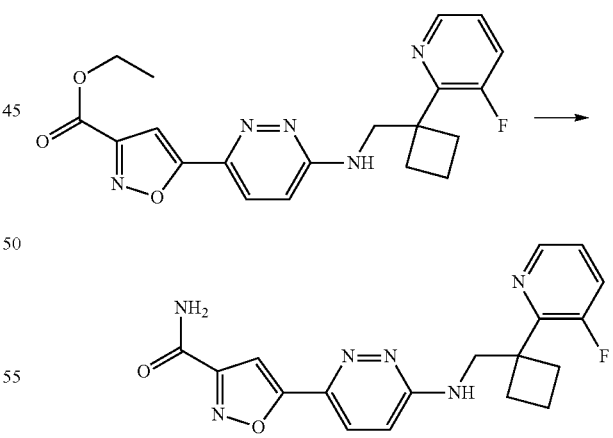

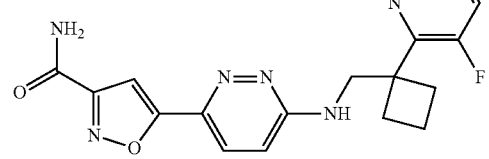

5-(6-((1-(3-Fluoropyridin-2-yl)cyclobutyl)methylamino)pyridazin-3-yl)isoxazole-3-carboxamide To a solution of ethyl 5-(6((1-(3-fluoropyridin-2-yl)cyclobutyl)methylamino)pyridazin-3-yl)isoxazole-3-carboxylate (200 mg, 0.40 mmol) in THF/MeOH mixture (12 mL, 5:1) was added LiOH (1M, 1.2 mL) at rt. The reaction mixture was stirred overnight and concentrated. To this crude mixture was added NH₄Cl (60 mg, 1.2 mmol), HBTU (246 mg, 0.65 mmol), DIEA (132 uL, 0.8 mmol), and DMF (5.0 mL). The mixture was stirred at rt overnight, filtered, and purified by reverse phase chromatography to provide the title compound as a white solid (23.2 mg, 16%), LRMS (M+H⁺) m/z 369.2.

EXAMPLE 34

Preparation of 5-(5-(6-((1-(3-Fluoropyridin-2-yl)cyclobutyl)methylamino)pyridazin-3-yl)thiophen-2-yl)-2H-1,2,4-triazol-3(4H)-one

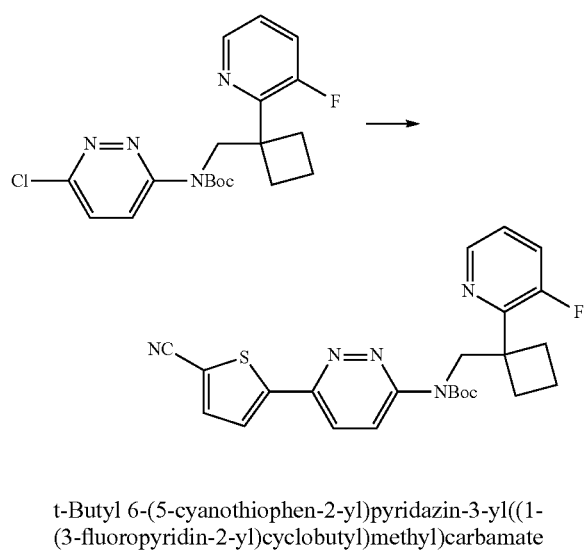

t-Butyl 6-(5-cyanothiophen-2-yl)pyridazin-3-yl((1-(3-fluoropyridin-2-yl)cyclobutyl)methyl)carbamate t-Butyl 6-chloropyridazin-3-yl((1-(3-fluoropyridin-2-yl)cyclobutyl)methyl)carbamate (900 mg, 2.29 mmol, 1 equiv), 5-cyanothiophen-2-ylboronic acid (390 mg, 2.52 mmol, 1.1 equiv), (dppf)PdCl₂ (164 mg, 0.23 mmol, 0.1 equiv), nitrogen-sparged dioxane (6.0 mL) and aq. 2 N K₂CO₃ (2.3 mL) were combined and heated in a microwave reactor for 30 min at 140° C. The reaction mixture was filtered through a Celite plug and the filtrate was concentrated. The resulting residue was purified on silica gel using a mixture of ethyl acetate and hexanes to provide the title compound as a yellow oil (340 mg, 32%), LRMS (M+H⁺) m/z 466.3.

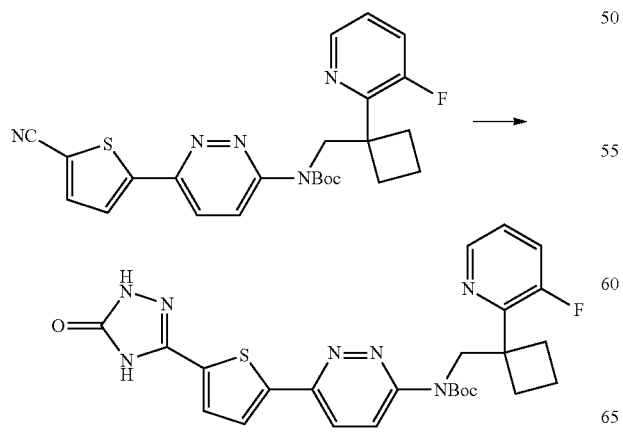

tert-butyl (1-(3-fluoropyridin-2-yl)cyclobutyl)methyl (6-(5-(5-oxo-4,5-dihydro-1H-1,2,4-triazol-3-yl)thiophen-2-yl)pyridazin-3-yl)carbamate To a solution of tert-butyl 6-(5-cyanothiophen-2-yl)pyridazin-3-yl((1-(3-fluoropyridin-2-yl)cyclobutyl)methyl)carbamate (340 mg, 0.73 mmol, 1 equiv) in MeOH (10 mL) was added sodium methoxide (0.59 g, 1.1 mmol, 1.5 equiv). The reaction mixture was stirred at rt overnight followed by addition of hydrazine (0.5 mL). The mixture was then heated to reflux for 2 h and concentrated to dryness. The crude mixture was partitioned between EtOAc and water. The organic layer was washed with brine, dried over Na₂SO₄, filtered, and concentrated. The crude product was dissolved in dioxane (3 mL), combined with CU (137 mg, 1.46 mmol, 2 equiv), and heated for 4 h at 100° C. The mixture was cooled, filtered, and purified by reverse phase chromatography to give the title compound as a yellow solid (86 mg, 23% over 3 steps), LRMS (M+H⁺) m/z 524.3.

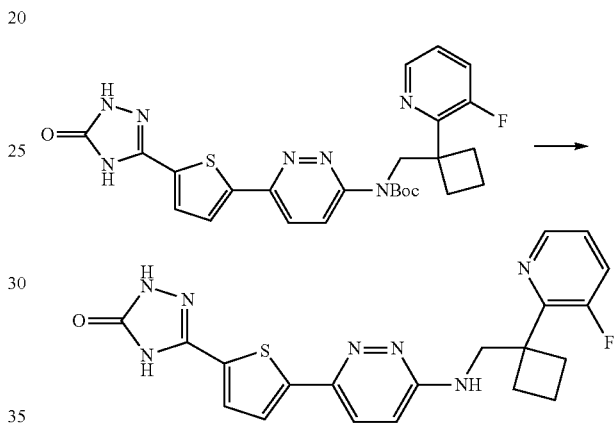

5-(5-(6-((1-(3-Fluoropyridin-2-yl)cyclobutyl)methylamino)pyridazin-3-yl)thiophen-2-yl)-2H-1,2,4-triazol-3(4H)-one To tert-butyl (1-(3-fluoropyridin-2-yl)cyclobutyl)methyl (6-(5-(5-oxo-4,5-dihydro-1H-1,2,4-triazol-3-yl)thiophen-2-yl)pyridazin-3-yl)carbamate (86 mg, 0.16 mmol) in DCM (6 mL) was added TFA (2 mL) at rt. The reaction mixture was stirred at rt for 2 hr followed by concentration to dryness. The crude mixture was purified by reverse phase chromatography to provide the title compound as a pale yellow solid (73.6 mg, quantitative). LRMS (M+H⁺) m/z 424.2.

EXAMPLE 35

Preparation of 4-fluoro-3-(6-(((trans)-3-fluoro-1-(3-fluoropyridin-2-yl)cyclobutyl)methylamino)pyridazin-3-yl)-N-methylbenzamide

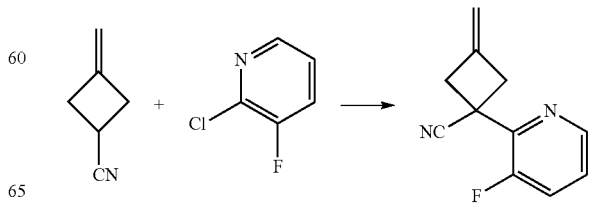

1-(3-Fluoropyridin-2-yl)-3-methylenecyclobutan-ecarbonitrile

To a solution of 3-methylenecyclobutanecarbonitrile (150 g, 1.61 mol, 1 equiv) and 2-chloro-3-fluoropyridine (212 g, 1.61 mmol, 1 equiv) in toluene (1 L) was added NaHMDS (2 M in THF, 885 mL, 1.1 equiv) dropwise at 0-10° C. Upon completion of addition, the reaction mixture was warmed to rt, stirred overnight, and quenched with $NH_4C_{(sat.)}$ solution. The organic layer was washed with water (500 mL×2) and brine (500 mL), dried over $Na_2SO_4$, filtered, and concentrated to give a crude title compound (272 g, 90%), which was used in the next step without further purification, LRMS (M+H$^+$) m/z 189.1.

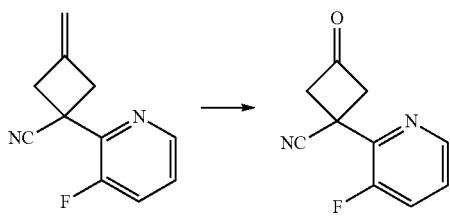

1-(3-Fluoropyridin-2-yl)-3-oxocyclobutanecarbonitrile

To a mixture of 1-(3-fluoropyridin-2-yl)-3-methylenecyclobutanecarbonitrile (272 g, 1.45 mol) and $RuCl_3.H_2O$ (9.0 g, 0.044 mol) in DCM (1 L), acetonitrile (1 L), and water (1.5 L) was added solid $NaIO_4$ (1235 g, 5.8 mol) portionwise at 10-30° C. Upon completion of the addition, the reaction was stirred 1 h at 15° C. and overnight at rt. The solid precipitate was filtered off and washed with DCM (1 L×2). The organic layer was washed with water (500 mL×2) and brine (500 mL), dried over $Na_2SO_4$, and concentrated to provide the title compound as a crude dark solid (238 g, 86.3%), LRMS (M+H$^+$) m/z 191.1.

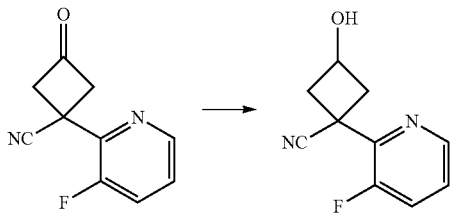 [SMILES: N#CC1(c2ncccc2F)CC(=O)C1 ; N#CC1(c2ncccc2F)CC(O)C1]

1-(3-Fluoropyridin-2-yl)-3-hydroxycyclobutanecarbonitrile

To a solution of 1-(3-fluoropyridin-2-yl)-3-oxocyclobutanecarbonitrile (231 g, 1.22 mol) in a mixture of DCM (2 L) and MeOH (200 mL) was added $NaBH_4$ portion-wise at −78° C. The reaction mixture was stirred 1 h at −78° C. and then quenched with a mixture of methanol and water (1/1). The organic layer was washed with water (500 mL×3), dried over $Na_2SO_4$, and concentrated. The residue was purified on silica gel (50% EtOAc in Hexanes) to provide the title compound as an amber oil (185.8 g, 77.5%), LRMS (M+H$^+$) m/z 193.2.

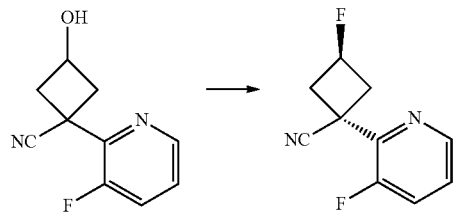 [SMILES: N#CC1(c2ncccc2F)CC(O)C1 ; N#C[C@]1(c2ncccc2F)C[C@H](F)C1]

trans-3-Fluoro-1-(3-fluoropyridin-2-yl)cyclobutan-ecarbonitrile

To a solution of 1-(3-fluoropyridin-2-yl)-3-hydroxycyclobutanecarbonitrile (185 g, 0.96 mol) in DCM (1 L) was added DAST portion-wise at 0-10° C. Upon the completion of addition, the reaction was refluxed for 6 h. The reaction was cooled to rt and poured onto sat. $NaHCO_3$ solution. The mixture was separated and the organic layer was washed with water, dried over $Na_2SO_4$, and concentrated. The residue was purified on silica gel (100% DCM) to provide the title compound as a brown oil (116 g, 62%) with a trans/cis ratio of 8:1 as determined by $^1$H NMR. The above brown oil (107 g) was dissolved in a mixture of toluene (110 mL) and hexanes (330 mL) at 70° C. The solution was cooled to 0° C. and stirred at 0° C. overnight. The precipitate was filtered and washed with hexanes to provide a single trans-isomer white solid (87.3 g, 81.6%), LRMS (M+H$^+$) m/z 195.1.

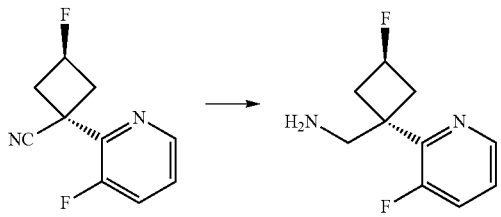 [SMILES: N#C[C@]1(c2ncccc2F)C[C@H](F)C1 ; NC[C@]1(c2ncccc2F)C[C@H](F)C1]

trans-3-Fluoro-1-(3-fluoropyridin-2-yl)cyclobutyl) methanamine

A mixture of trans-3-fluoro-1-(3-fluoropyridin-2-yl)cyclobutanecarbonitrile (71 g, 0.37 mol) and Raney nickel (~7 g) in 7N ammonia in methanol (700 mL) was charged with hydrogen (60 psi) for 2 days. The reaction was filtered through a celite pad and washed with methanol. The filtrate was concentrated under high vacuum to provide the title compound as a light green oil (70 g, 98%), LRMS (M+H$^+$) m/z 199.2.

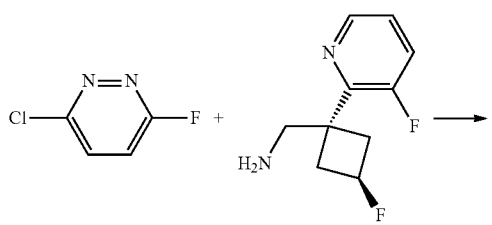

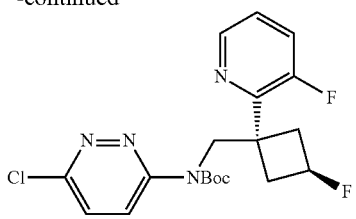

t-Butyl 6-chloropyridazin-3-yl(((trans)-3-fluoro-1-(3-fluoropyridin-2-yl)cyclobutyl)methyl)carbamate 3-Chloro-6-fluoropyridazine (10.11 g, 76.30 mmol, 1 equiv), trans-3-fluoro-1-(3-fluoropyridin-2-yl)cyclobutyl)methanamine (15.10 g, 76.30 mmol, 4:1 trans/cis ratio), and K$_2$CO$_3$ (29.27 g, 304.9 mmol) in CH$_3$CN (20 mL) were refluxed overnight. Upon cooling, water was added into the mixture. The precipitate was collected and dried to give 9.2 g (39%) of desired product with ratio of trans:cis greater than 20:1. To this solid (9.2 g) and DMAP (353 mg, 2.9 mmol) in THF (100 mL) was added (Boc)$_2$O (12.8 g, 58.7 mmol). The mixture was then refluxed for 2 h, cooled, and concentrated. The residue was purified on silica gel to provide the title compound as a white solid (9 g, 75%), LRMS (M+H$^+$) m/z 411.2.

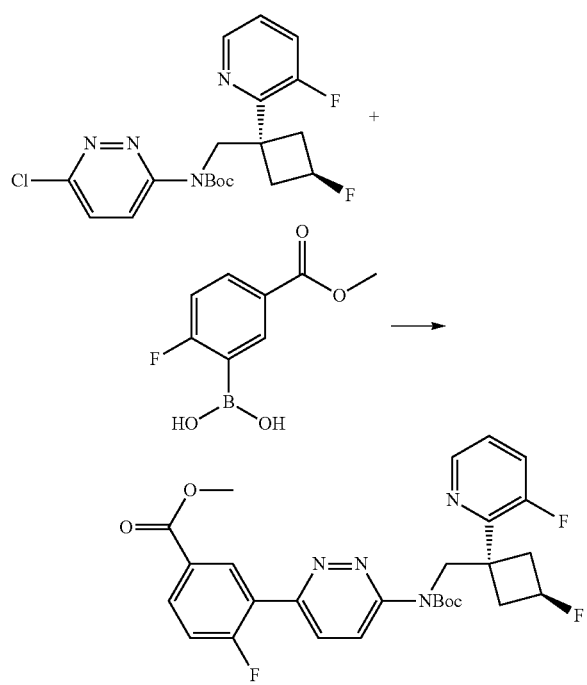

Methyl 3-(6-(t-butoxycarbonyl(((trans)-3-fluoro-1-(3-fluoropyridin-2-yl)cyclobutyl)methyl)amino)pyridazin-3-yl)-4-fluorobenzoate To t-butyl 6-chloropyridazin-3-yl((trans)-3-fluoro-1-(3-fluoropyridin-2-yl)cyclobutyl)methyl)carbamate (30.3 g, 73.9 mmol, 1 equiv), 2-fluoro-5-(methoxycarbonyl)phenylboronic acid (16.1 g, 81.3 mmol, 1.1 equiv), (dppf)PdCl$_2$ (6.0 g, 7.39 mmol, 0.1 equiv), K$_2$CO$_3$ (40.8 g, 296 mmol, 4 equiv) were added dioxane (160 mL) and water (40 mL). The mixture was heated 2 h at 80° C., cooled and diluted with EtOAc. The organic layer was washed with brine, dried over Na$_2$SO$_4$, filtered, and concentrated. The residue was purified on silica gel to provide the title compound as pale orange solid (29.4 g, 75%), LRMS (M+H$^+$) m/z 529.2.

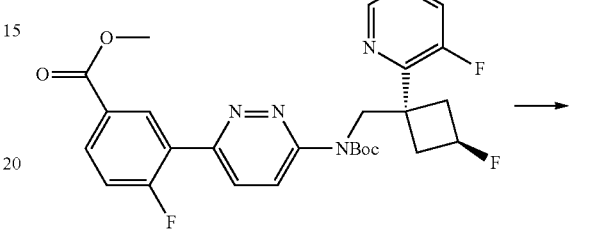

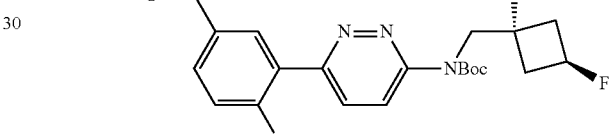

3-(6-(t-butoxycarbonyl(((trans)-3-fluoro-1-(3-fluoropyridin-2-yl)cyclobutyl)methyl)amino)pyridazin-3-yl)-4-fluorobenzoic acid To a 500 mL round bottom flask was added methyl 3-(6-(t-butoxycarbonyl(((trans)-3-fluoro-1-(3-fluoropyridin-2-yl)cyclobutyl)methyl)amino)pyridazin-3-yl)-4-fluorobenzoate (29.4 g, 55.7 mmol, 1 equiv), THF (200 mL), MeOH (100 mL), and NaOH (74.2 mL of a 3N aqueous solution, 222 mmol). The mixture was heated 30 min at 60° C., cooled, acidified to pH 3 with NaHSO$_4$ (1N), and concentrated. The residue was partitioned between EtOAc and water. The organic layer was washed with brine, dried over Na$_2$SO$_4$, filtered, and concentrated to provide the title compound as a pale orange solid (29 g, crude), LRMS (M+H$^+$) m/z 515.2.

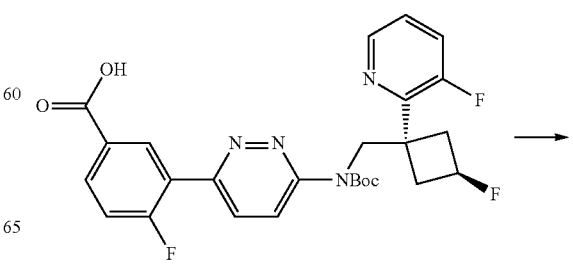

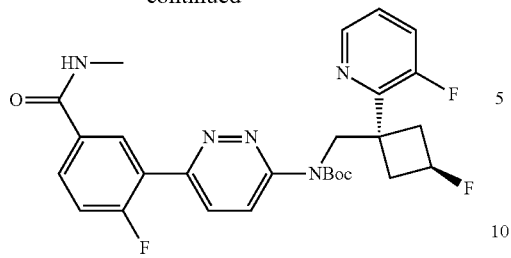

t-Butyl((trans)-3-fluoro-1-(3-fluoropyridin-2-yl)cyclobutyl)methyl(6-(2-fluoro-5-(methylcarbamoyl)phenyl)pyridazin-3-yl)carbamate To 3-(6-(t-butoxycarbonyl(((trans)-3-fluoro-1-(3-fluoropyridin-2-yl)cyclobutyl)methyl)amino)pyridazin-3-yl)-4-fluorobenzoic acid (29 g, 55.7 mmol, 1 equiv) in DCM (200 mL) was added oxalyl chloride (19.4 mL, 222 mmol, 4 equiv). The reaction was stirred for 1 h, concentrated, and azeotroped twice with toluene. The crude product was then dissolved in DCM and cooled to 0° C. To this mixture was added NH$_2$Me (2 M/THF, 278 mL, 556.8 mmol). The mixture was warmed to rt and stirred at rt for 30 min. The solid was filtered off and the filtrate was concentrated. The crude product was purified on silica gel to provide the title compound as pale yellow solid (28.1 g, 96%), LRMS (M+H$^+$) m/z 528.2.

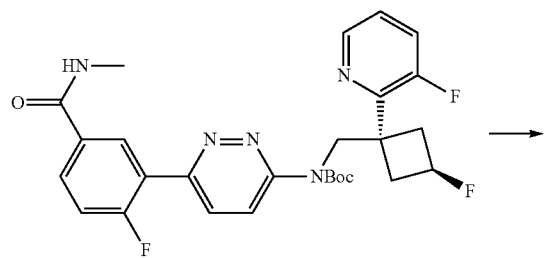

4-fluoro-3-(6-(((trans)-3-fluoro-1-(3-fluoropyridin-2-yl)cyclobutyl)methylamino)pyridazin-3-yl)-N-methylbenzamide To tert-butyl((trans)-3-fluoro-1-(3-fluoropyridin-2-yl)cyclobutyl)methyl(6-(2-fluoro-5-(methylcarbamoyl)phenyl)pyridazin-3-yl)carbamate (28.1 g, 53.3 mmol) in DCM (100 mL) was added TFA (40 mL, 533 mmol, 10 equiv) at rt. The reaction mixture was further stirred at rt for 2 h followed by concentration to dryness. The residue was partitioned between EtOAc and NaHCO$_3$. The pH was further adjusted to pH 9 with NaOH (1N). The organic layer was washed with brine, dried over Na$_2$SO$_4$, filtered, and concentrated to give 25.2 g of a pale yellow solid. The solid was dissolved in EtOH (80 mL), warmed to 66° C. and diluted with water (80 mL) at 66° C. The mixture was slowly cooled to rt with stirring. The precipitate was filtered, washed with water, and dried to provide the title compound as a white solid (21.2 g, 93%), LRMS (M+H$^+$) m/z 428.2.

EXAMPLE 36

Preparation of 6-(5-(1H-pyrazol-3-yl)thiazol-2-yl)-N-((1-(3-fluoropyridin-2-yl)cyclobutyl)methyl)pyridazin-3-amine

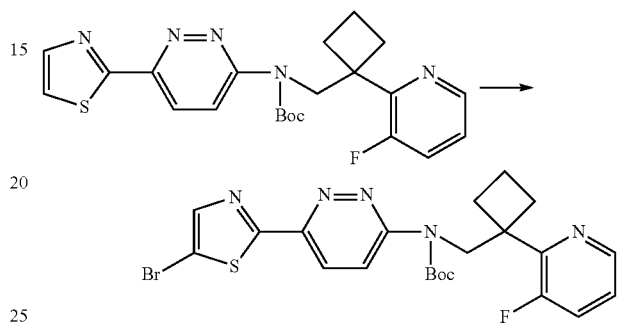

t-Butyl 6-(5-bromothiazol-2-yl)pyridazin-3-yl((1-(3-fluoropyridin-2-yl)cyclobutyl)methyl)carbamate To a 100 mL round bottom flask was added t-butyl (1-(3-fluoropyridin-2-yl)cyclobutyl)methyl(6-(thiazol-2-yl)pyridazin-3-yl)carbamate (2.0 g, 4.6 mmol), NBS (1.6 g, 9.1 mmol), and DMF (20 mL). The reaction was heated to 100° C. and stirred overnight. The reaction mixture was then was poured into ethyl acetate (200 mL), washed with water (100 mL), dried over Na$_2$SO$_4$, filtered, concentrated, and purified by silica gel chromatography (EtOAc/hex) to afford 1.8 g of t-butyl 6-(5-bromothiazol-2-yl)pyridazin-3-yl((1-(3-fluoropyridin-2-yl)cyclobutyl)methyl)carbamate.

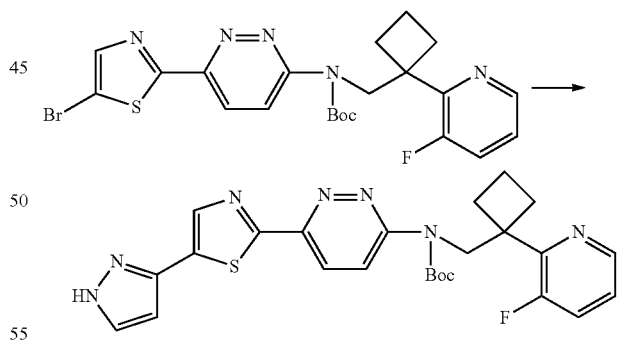

6-(5-(1H-pyrazol-3-yl)thiazol-2-yl)-N-((1-(3-fluoropyridin-2-yl)cyclobutyl)methyl)pyridazin-3-amine To a microwave vial was added t-butyl 6-(5-bromothiazol-2-yl)pyridazin-3-yl((1-(3-fluoropyridin-2-yl)cyclobutyl)methyl)carbamate (100 mg, 0.19 mmol), 1H-pyrazol-5-ylboronic acid (32 mg, 0.29 mmol), (dppf)PdCl$_2$ (16 mg, 0.02 mmol), dioxane (2 mL), and K$_2$CO$_3$ (0.2 mL of a 2M aqueous solution, 38 mmol). The mixture was heated to 140° C. in a microwave reactor and stirred for 20 min. The reaction mixture was then poured into ethyl acetate (50 mL), washed with water (20 mL), dried over Na$_2$SO$_4$, filtered, concentrated, and purified by silica gel chromatography (EtOAc/hex) to afford 38 mg of t-butyl 6-(5-(1H-pyrazol-3-yl)thiazol-2-yl)pyridazin-3-yl((1-(3-fluoropyridin-2-yl)cyclobutyl)methyl) carbamate. This compound was dissolved in CH$_2$Cl$_2$ (5 mL) and TFA (1 mL). The reaction was stirred for 30 min at rt, concentrated, and then purified using reverse phase chromatography to give 15 mg of 6-(5-(1H-pyrazol-3-yl)thiazol-2-yl)-N-((1-(3-fluoropyridin-2-yl)cyclobutyl)methyl)pyridazin-3-amine, (M+H=408.3).

EXAMPLE 37

Preparation of 6-(6-(((trans-3-fluoro-1-(3-fluoropyridin-2-yl)cyclobutyl)methylamino)pyridazin-3-yl)imidazo[2,1-b]thiazole-3-carboxamide

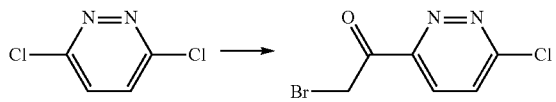

2-Bromo-1-(6-chloropyridazin-3-yl)ethanone

To a stirring solution of dioxane (100 mL, degassed) was added 3,6-dichloropyridazine (5.0 g, 34 mmol), Cl$_2$Pd (PPh$_3$)$_2$ (2.4 g, 3.4 mmol), and tributyl(1ethoxyvinyl)tin (18.2 g, 50 mmol). The reaction was heated to 100° C. and stirred for 1 h. The reaction was then concentrated, followed by the addition of EtOAc (100 mL) and potassium fluoride (50 mL of a saturated aqueous solution). The mixture was stirred for 30 min and then filtered through a pad of Celite. The filtrate was concentrated and then dissolved in THF (80 mL) and water (80 mL). NBS (18.1 g, 102 mmol) was then added, and the reaction was stirred for 20 min at rt. The reaction mixture was poured into ethyl acetate (200 mL), washed twice with brine (50 mL), dried over Na$_2$SO$_4$, filtered, concentrated, and purified by silica gel chromatography to afford 4.2 g of 2-bromo-1-(6-chloropyridazin-3-yl)ethanone.

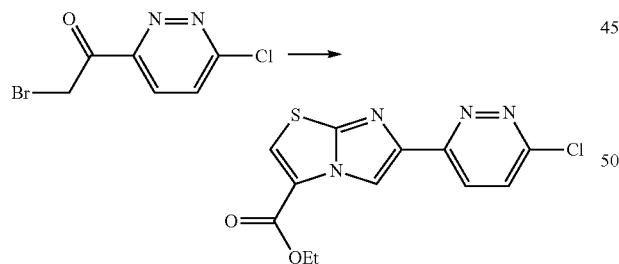

Ethyl 6-(6-chloropyridazin-3-yl)imidazo[2,1-b]thiazole-3-carboxylate

To a 20 dram vial was added 2-bromo-1-(6-chloropyridazin-3-yl)ethanone (4.2 g, 18 mmol), ethyl-2-aminothiazole-4-carboxylate (3.1 g, 18 mmol), and methylethylketone (40 mL). The mixture was heated to 90° C. and stirred overnight. The reaction was then concentrated and purified by silica gel chromatography (EtOAc/hex) to afford 1.0 g of ethyl 6-(6-chloropyridazin-3-yl)imidazo[2,1-b]thiazole-3-carboxylate as a yellow solid.

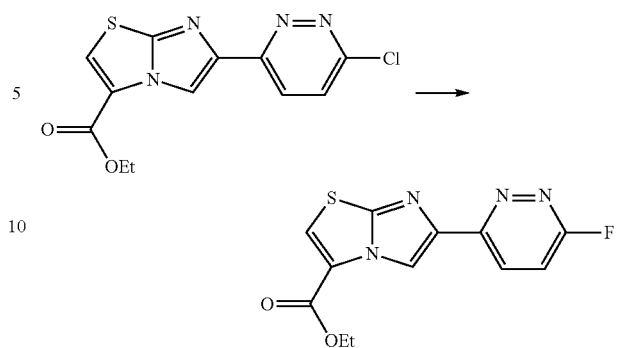

Ethyl 6-(6-fluoropyridazin-3-yl)imidazo[2,1-b]thiazole-3-carboxylate

To a 20 dram vial was added ethyl 6-(6-chloropyridazin-3-yl)imidazo[2,1-b]thiazole-3-carboxylate (1.0 g, 3.2 mmol), 1,8-bis(dimethylamino)naphthalene (1.4 g, 6.4 mmol), and Et$_3$N.3HF (30 mL). The reaction was heated in a microwave to 140° C. and stirred for 1.5 h. The reaction mixture was poured into ethyl acetate (100 mL), washed with water (50 mL), dried over Na$_2$SO$_4$, filtered, concentrated, and purified by silica gel chromatography to afford 760 mg of ethyl 6-(6-fluoropyridazin-3-yl)imidazo[2,1-b]thiazole-3-carboxylate as a yellow solid.

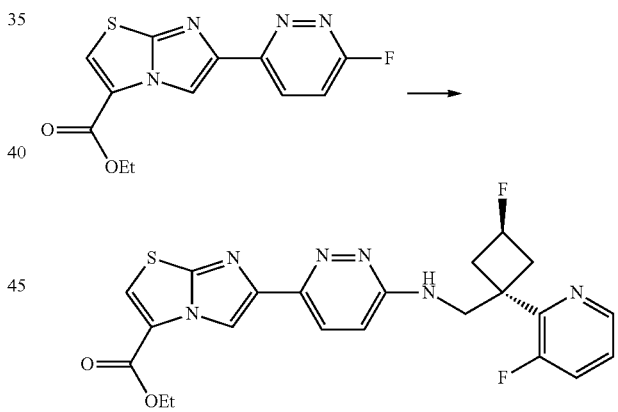

Ethyl 6-(6-(((trans)-3-fluoro-1-(3-fluoropyridin-2-yl)cyclobutyl)methylamino)pyridazin-3-yl)imidazo[2,1-b]thiazole-3-carboxylate Ethyl 6-(6-fluoropyridazin-3-yl)imidazo[2,1-b]thiazole-3-carboxylate (65 mg, 0.2 mmol), (trans-3-fluoro-1-(3-fluoropyridin-2-yl)cyclobutyl)methanamine (56 mg, 0.29 mmol), DIPEA (114 µL, 0.66 mmol), and NMP (3 mL). The reaction was heated to 165° C. and stirred for 2 h. The reaction was then purified directly using reverse phase chromatography to give 15 mg of ethyl 6-(6-(((trans)-3-fluoro-1-(3-fluoropyridin-2-yl)cyclobutyl)methylamino)pyridazin-3-yl)imidazo[2,1-b]thiazole-3-carboxylate.

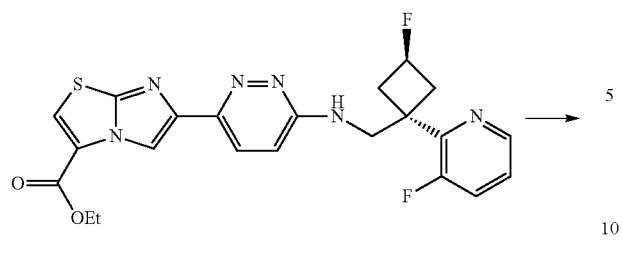

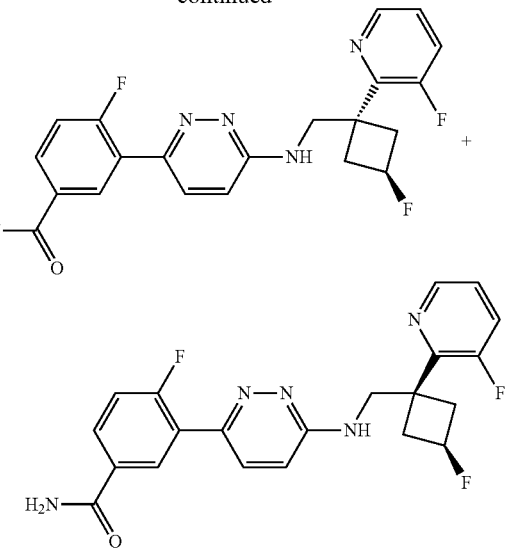

6-(6-(((trans)-3-fluoro-1-(3-fluoropyridin-2-yl)cyclobutyl)methylamino)pyridazin-3-yl)imidazo[2,1-b]thiazole-3-carboxamide To a solution of ethyl 6-(6-(((trans)-3-fluoro-1-(3-fluoropyridin-2-yl)cyclobutyl)methylamino)pyridazin-3-yl)imidazo[2,1-b]thiazole-3-carboxylate (20 mg, 0.05 mmol) in dioxane (0.5 mL) was added LiOH (1M, 0.15 mL, 0.15 mmol). The reaction mixture was stirred at rt for 1 h and then concentrated. To this crude mixture was added NH₄Cl (28 mg, 0.5 mmol), HATU (28 mg, 0.075 mmol), HOAt (10 mg, 0.075 mmol), DIEA (19 mg, 0.15 mmol), and DMF (1 mL). The mixture was stirred at 50° C. for 30 min and then was purified directly by reverse phase chromatography to provide 2 mg of 6-(6-(((trans)-3-fluoro-1-(3-fluoropyridin-2-yl)cyclobutyl)methylamino)pyridazin-3-yl)imidazo[2,1-b]thiazole-3-carboxamide as a white solid, (M+H=442.1).

EXAMPLE 38

Preparation of 4-Fluoro-3-(6-(((trans)-3-fluoro-1-(3-fluoropyridin-2-yl)cyclobutyl)methylamino)pyridazin-3-yl)benzamide and 4-fluoro-3-(6-(((cis)-3-fluoro-1-(3-fluoropyridin-2-yl)cyclobutyl)methylamino)pyridazin-3-yl)benzamide

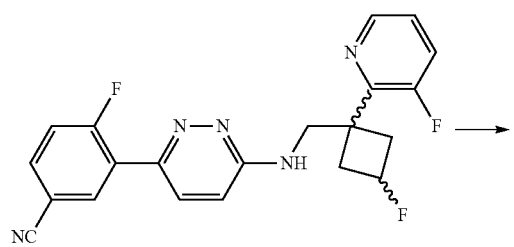

To a solution of 4-fluoro-3-(6((3-fluoro-1-(3-fluoropyridin-2-yl)cyclobutyl)methylamino)pyridazin-3-yl)benzonitrile (482 mg, 1.22 mmol, 95:5 cis/trans ratio) in DMSO (3 mL) was added potassium carbonate (673 mg, 4.88 mmol). The mixture was cooled to 0° C. and hydrogen peroxide (0.6 mL) was slowly added. The reaction was warmed to rt and stirred for 2 h. The reaction was diluted with EtOAc (75 mL) and water (50 mL), and the organic layer was washed three times with brine (50 mL). The organic layer was then dried over Na₂SO₄, filtered, concentrated, and purified by reverse phase chromatography to afford 470 mg of 4-fluoro-3-(6-(((trans)-3-fluoro-1-(3-fluoropyridin-2-yl)cyclobutyl)methylamino)pyridazin-3-yl)benzamide and 6 mg of 4-fluoro-3-(6-(((cis)-3-fluoro-1-(3-fluoropyridin-2-yl)cyclobutyl)methylamino)pyridazin-3-yl)benzamide as white solids (M+H=414.3).

EXAMPLE 39

Preparation and Assay of Fast Skeletal Myofibrils

Preparation of Fast Skeletal Myofibrils.

Rabbit skeletal myofibrils were prepared based upon the method of Herrmann et al. (Biochem. 32(28):7255-7263 (1993). Myofibrils were prepared from rabbit psoas muscle purchased from Pel-Freez Biologicals (Arkansas) within 2 days of ordering, stored on ice. Minced muscle was homogenized in 10 volumes of ice-cold "standard" buffer (50 mM Tris, pH 7.4, 0.1M potassium acetate, 5 mM KCl, 2 mM DTT, 0.2 mM PMSF, 10 µM leupeptin, 5 µM pepstatin, and 0.5 mM sodium azide) containing 5 mM EDTA and 0.5% Triton X-100 using an Omni-Macro homogenizer. Myofibrils were recovered by low speed centrifugation (3000 rpm for 10 minutes) and washed 2 times in the Triton X-100 containing buffer to ensure removal of cellular membrane. Following the Triton washes, myofibrils were washed 3 times in "standard" buffer containing 2 mM magnesium acetate. A final wash in assay buffer (12 mM PIPES, pH 6.8, 60 mM KCl, 1 mM DTT) was performed and brought to 10% sucrose for flash freezing in liquid nitrogen and storage at −80° C.

Activation of Fast Skeletal Myofibrils.

Fast fiber activators were identified by measuring the enzymatic activity of muscle myofibril preparations using the proprietary PUMA™ (see, e.g., U.S. Pat. Nos. 6,410,254, 6,743,599, 7,202,051, and 7,378,254) assay system. Myofibril preparations consisted of rabbit skeletal muscle (approximately 90% fast fibers) that had been mechanically homogenized and washed with a detergent (triton X-100) to remove cellular membranes. This preparation retained all of the sarcomeric components in a native conformation and the enzymatic activity was still regulated by calcium. Compounds were tested using a myofibril suspension and a level of calcium sufficient to increase enzymatic activity of the myofibrils to 25% of their maximal rate (termed pCa25). Enzymatic activity was tracked via a pyruvate kinase and lactate dehydrogenase-coupled enzyme system. This assay regenerates myosin-produced ADP into ATP by oxidizing NADH, producing an absorbance change at 340 nm. The buffering system was 12 mM Pipes, 2 mM $MgCl_2$, 1 mM DTT at pH 6.8 (PM12 buffer). Data was reported as AC1.4, which is the concentration at which the compound increased the enzymatic activity by 40%. The results are summarized in Table 2 below.

EXAMPLE 40

Preparation and Assay of Sarcomeric Proteins from Skeletal Muscle

Powder Preparation
1. Volumes are given per about 1000 g of the minced muscle.
2. Pre-cut and boil cheesecloth for 10 min in water. Drain and dry.
3. Mince chicken breast in a prechilled meat grinder.
4. Extract with stirring in 2 L of 0.1M KCl, 0.15 M K-phosphate, pH 6.5 for 10 min at 4° C. Spin 5000 rpm, 10 min, 4° C. in JLA. Collect the pellet.
5. Extract pellets with stirring with 2 L of 0.05 M $NaHCO_3$ for 5 min. Spin 5000 rpm, 10 min, 4° C. in JLA. Collect the pellet. Repeat the extraction once more.
6. Extract the filtered residue with 2 L of 1 mM EDTA, pH 7.0 for 10 min with stirring.
7. Extract with 2 L of $H_2O$ for 5 min with stirring. Spin 10000 rpm, 15 min, 4° C. in JLA. Carefully collect the pellet, part of which will be loose and gelatinous.
8. Extract 5 times with acetone (2 L of acetone for 10 min each with stirring). Squeeze through cheesecloth gently. All acetone extractions are performed at room temperature. Acetone should be prechilled to 4° C.
9. Drying: Place the filtered residue spread on a cheesecloth in a large glass tray and leave in a hood overnight. When the residue is dry, put in a wide mouth plastic bottle and store at 20° C.
Alternate Powder Preparation
(See Zot & Potter (1981) Prep. Biochem. 11(4) pp. 381-395)
1. Dissect left ventricles of the cardiac muscle. Remove as much of the pericardial tissue and fat as possible. Grind in a prechilled meat grinder. Weigh.
2. Prepare 5 volumes of Extract buffer (see below). Homogenize the meat in a blender, 4 times 15 sec on blend with 15 secs in between. Do this with 1 volume (weight/volume) of buffer taken from the 5 volumes already prepared. Add the homogenate back to the extract buffer and stir until well mixed (5 minutes).
3. Filter through one layer of cheesecloth in large polypropylene strainer. Resuspend back into 5 volumes of extract buffer as above.
4. Repeat Step 3 four more times. At the end, do not resuspend in extraction buffer but proceed to Step 5. The pellets should be yellow white.
5. Resuspend in 3 volumes (according to original weight) of 95% cold ethanol. Stir for 5 min and squeeze through cheesecloth as above, repeat two more times.
6. Weigh squeezed residue and then resuspend in 3 volumes (new weight/volume) of cold diethyl ether.
7. Repeat Step 6 a total of three times.
8. Leave overnight in a single layer on a cheesecloth in a glass tray.
9. When dry, collect the powder, weigh and store in a wide-mouth jar at 4° C.
EXTRACT BUFFER: 50 mM KCl, 5 mM Tris pH 8.0 Prepare as 50 times concentrate. For 2 L: 250 mM Tris pH 8.0. Tris Base (121.14 g/mol, 60.6 g), pH to 8.0 with conc. HCl, then add 2.5 M KCl (74.55 g/mol, 372 g).
Actin Preparation
1. Extract powder (as described above) with 20 ml buffer A (see below, add BME and ATP just prior to use in each of the following steps) per gram of powder (200 ml per 10 g). Use a large 4 L beaker for 150 g of powder. Mix vigorously to dissolve powder. Stir at 4° C. for 30 min.
2. Separate extract from the hydrated powder by squeezing through several layers of cheesecloth. Cheesecloth should be pre-sterilized by microwaving damp for 1-2 min.
3. Re-extract the residue with the same volume of buffer A and combine extracts.
4. Spin in JLA10 rotor(s) for 1 hr at 10K rpm (4° C.). Collect supernatant through 2 layers of cheesecloth.
5. Add ATP to 0.2 mM and $MgCl_2$ to 50 mM. Stir on stir plate at 4° C. for 60 minutes to allow actin to polymerize/form para-crystals.
6. Slowly add solid KCl to 0.6 M (45 g/l). Stir at 4° C. for 30 min.
7. Spin in JLA10 rotor(s) at 10K rpm for 1 hr.
8. Depolymerization: Quickly rinse surface of pellets with buffer A and dispose of wash. Soften the pellets by pre-incubation on ice with small amount of buffer A in each tube (use less than half of final resuspension volume total in all tubes). Resuspend by hand first with cell scraper and combine pellets. Wash tubes with extra buffer using a 25 ml pipette and motorized pipettor, aggressively removing actin from sides of tubes. Homogenize in large dounce in cold buffer A on ice. Use 3 ml per gram of powder originally extracted.
9. Dialyze against buffer A with 4 changes over 48 hour period.
10. Collect dialyzed actin and spin in the 45Ti rotor at 40K rpm for 1.5 hr (4° C.).
11. Collect supernatant (G-Actin). Save a sample for gel analysis and determination of protein concentration.
12. To polymerize G-actin for storage, add KCl to 50 mM (from 3 M stock), $MgCl_2$ to 1 mM, and $NaN_3$ to 0.02% (from 10% stock). Store at 4° C. Do not freeze.
Buffer A: 2 mM tris/HCl, 0.2 mM $CaCl_2$, 0.5 mM (36 μl/L) 2-mercaptoethanol, 0.2 mM $Na_2$ ATP (added fresh), and 0.005% Na-azide; pH 8.0.
Purification of Skeletal Muscle Myosin
(See Margossian, S. S, and Lowey, S. (1982) Methods Enzymol. 85, 55-123; and Goldmann, W. H. and Geeves, M. A. (1991) Anal. Biochem. 192, 55-58)
Solution A: 0.3 M KCl, 0.15 M potassium phosphate, 0.02 M EDTA, 0.005 M $MgCl_2$, 0.001M ATP, pH 6.5.
Solution B: 1M KCl, 0.025 M EDTA, 0.06 M potassium phosphate, pH 6.5.
Solution C, 0.6 M KCl, 0.025 M potassium phosphate, pH 6.5.
Solution D: 0.6 M KCl, 0.05 M potassium phosphate, pH 6.5.
Solution E: 0.15 M potassium phosphate, 0.01M EDTA, pH 7.5.

Solution F: 0.04 M KCl, 0.01M potassium phosphate, 0.001M DTT, pH 6.5.
Solution G: 3 M KCl, 0.01M potassium phosphate, pH 6.5.
All procedures are carried out at 4° C.
1. Obtain approx. 1000 g skeletal muscle, such as rabbit skeletal muscle.
2. Grind twice; extract with 2 L solution A for 15 min while stirring; add 4 L cold H₂O, filter through gauze; dilute with cold H₂O to ionic strength of 0.04, (about 10-fold); let settle for 3 h; collect precipitate at 7,000 rpm in GSA rotor for 15 min.
3. Disperse pellet in 220 ml solution B; dialyze overnight against 6 L solution C; slowly add ~400 ml equal volume cold distilled H₂O; stir for 30 min; centrifuge at 10,000 rpm for 10 min in GSA rotor.
4. Centrifuge supernatant at 19,000 rpm for 1 h.
5. Dilute supernatant to ionic strength of 0.04 (~8-fold); let myosin settle overnight; collect about 5-6 L fluffy myosin precipitate by centrifuging at 10,000 rpm for 10 min in GSA rotor.
6. Resuspend pellet in minimal volume of solution G; dialyze overnight against 2 L solution D; centrifuge at 19,000 rpm for 2 h, in cellulose nitrate tubes; puncture tubes and separate myosin from fat and insoluble pellet.
7. Dilute supernatant to 5-10 mg/ml and dialyze against solution E extensively, load onto DEAE-sephadex column.
8. Pre-equilibrate with solution E; apply 500-600 g myosin at 30 ml/h; wash with 350 ml solution E; elute with linear gradient of 0-0.5 M KCl in solution E (2×1 liter); collect 10 ml fractions; pool myosin fractions (>0.1M KCl); concentrate by overnight dialysis against solution F; centrifuge at 25,000 rpm for 30 min; store as above.
9. The myosin is then cut with chymotrypsin or papain in the presence of EDTA to generate the S1 fragment which is soluble at the low salt conditions optimal for ATPase activity (Margossian, supra).

Preparation and Assay

Myosin is prepared by precipitation from salt extracts of rabbit psoas muscle, and a soluble S1 fraction is prepared by digestion with chymotrypsin (Margossian and Lowey, 1982).

Actin is purified by first preparing an ether powder of cardiac muscle (Zot H G and Potter J D. (1981) Preparative Biochemistry 11:381-395) as described above. Subsequently, actin is cycled between the filamentous and soluble state through rounds of centrifugation and dialysis (Spudich J A and Watt S. (1971) J. Biol. Chem. 246:4866-4871).

Tropomyosin is extracted from the ether powder and separated from the other proteins based on pH dependent precipitations followed by successive ammonium sulfate cuts at 53% and 65% (Smillie L B. (1981) Methods Enzymol 85 Pt B:234-41). The troponins are isolated as an intact complex of TnC, TnT, and TnI. Ether powder is extracted in a high salt buffer. Successive ammonium sulfate cuts of 30% and 45% are done; the precipitate is solubilized by dialysis into a low salt buffer and then further purified on a DEAE Toyopearl column with a 25-350 mM KCl gradient. There is no measurable ATPase in any of the components except for myosin which naturally had a very low basal ATPase in the absence of actin.

Prior to screening, the actin, tropomyosin, and troponin complex are mixed together in the desired ratio (e.g., 7:1:1) to achieve maximal calcium regulation of the actin filament. The screen is conducted at a concentration that gives 25% activation. This calcium concentration is in the physiological range during muscle contraction.

To measure the generation of ADP during the reaction, a pyruvate kinase/lactate dehydrogenase/NADH coupled enzyme system (PK/LDH) is added to the actin. The myosin is kept separately, and added to the regulated thin filaments to initiate the reaction. Oxidation of NADH is monitored in real time, so that kinetic curves are obtained. Compounds are dissolved in DMSO and spotted onto the bottoms of 384 well plates at 10 to 40 μg/ml final concentration.

Using procedures similar to those described herein, utilizing reagents and intermediates commercially available (e.g., Sigma-Aldrich, St. Louis, Mo.) or readily synthesized by one of skill in the art, the compounds in Table 2 were synthesized, characterized and tested. AC1.4 values were determined according to the procedure described in Example 39, and the reported median AC1.4 values are as follows: A=<1 uM; B=1-10 uM; C=10-20 uM; D=>20 uM.

TABLE 2

| Compound | Structure | m/z (M + H) | Mean AC1.4 |
|---|---|---|---|
| 3-(6-{[2-(4-fluorophenyl)-2-methylpropyl]amino}pyridazin-3-yl)benzamide | 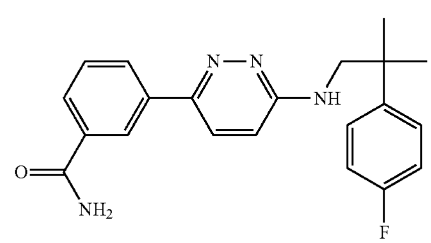 [SMILES: CC(C)(CNc1ccc(-c2cccc(C(N)=O)c2)nn1)c1ccc(F)cc1] | 365.2 | A |
| 4-(6-{[2-(4-fluorophenyl)-2-methylpropyl]amino}pyridazin-3-yl)benzamide | 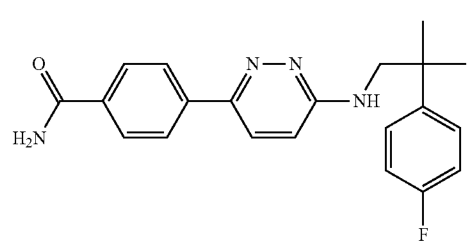 [SMILES: CC(C)(CNc1ccc(-c2ccc(C(N)=O)cc2)nn1)c1ccc(F)cc1] | 365.1 | B |

TABLE 2-continued

| Compound | Structure | m/z (M + H) | Mean AC1.4 |
|---|---|---|---|
| 5-(6-{[2-(4-fluorophenyl)-2-methylpropyl]amino}pyridazin-3-yl)pyridine-3-carbonitrile | 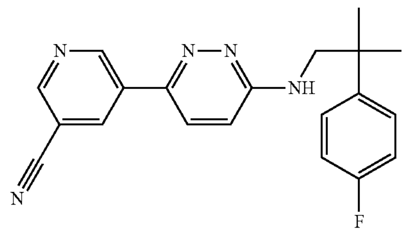 [SMILES: CC(C)(CNc1ccc(-c2cncc(C#N)c2)nn1)c1ccc(F)cc1] | 348.1 | B |
| methyl 5-(6-{[2-(4-fluorophenyl)-2-methylpropyl]amino}pyridazin-3-yl)pyridine-3-carboxylate | 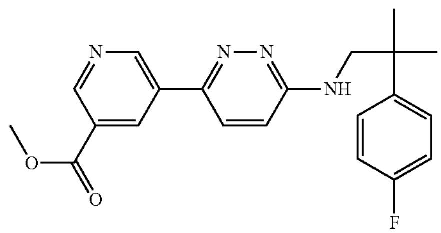 [SMILES: COC(=O)c1cncc(-c2ccc(NCC(C)(C)c3ccc(F)cc3)nn2)c1] | 381.1 | B |
| 5-(6-{[2-(4-fluorophenyl)-2-methylpropyl]amino}pyridazin-3-yl)pyridine-3-carboxamide | 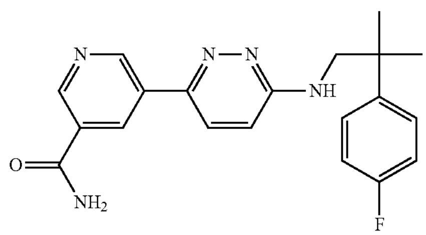 [SMILES: CC(C)(CNc1ccc(-c2cncc(C(N)=O)c2)nn1)c1ccc(F)cc1] | 366.1 | B |
| [2-(4-fluorophenyl)-2-methylpropyl](6-pyrazol-4-ylpyridazin-3-yl)amine | 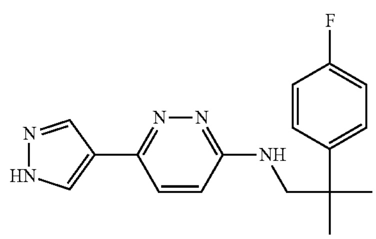 [SMILES: CC(C)(CNc1ccc(-c2cn[nH]c2)nn1)c1ccc(F)cc1] | 312.1 | B |
| [2-(4-fluorophenyl)-2-methylpropyl](6-prop-2-enylpyridazin-3-yl)amine | 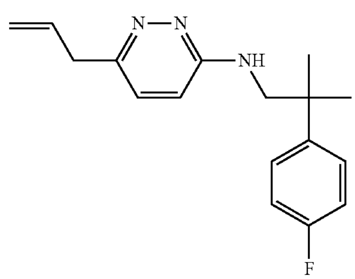 [SMILES: C=CCc1ccc(NCC(C)(C)c2ccc(F)cc2)nn1] | 281.6 | B |
| [6-((1E)prop-1-enyl)pyridazin-3-yl][2-(4-fluorophenyl)-2-methylpropyl]amine | 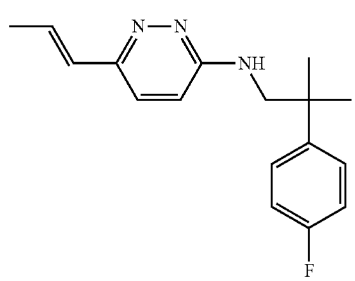 [SMILES: C/C=C/c1ccc(NCC(C)(C)c2ccc(F)cc2)nn1] | 286.1 | B |

TABLE 2-continued

| Compound | Structure | m/z (M + H) | Mean AC1.4 |
|---|---|---|---|
| 3-(6-{[(2S)-2-(4-fluorophenyl)propyl]amino}pyridazin-3-yl)benzamide | 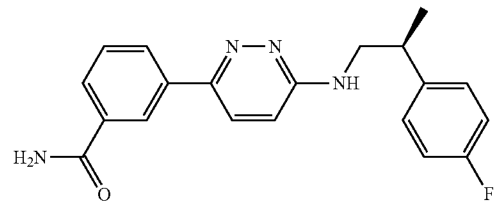 [SMILES: C[C@H](CNc1ccc(-c2cccc(C(N)=O)c2)nn1)c1ccc(F)cc1] | 351.0 | B |
| 3-(6-{[(2R)-2-(4-fluorophenyl)propyl]amino}pyridazin-3-yl)benzamide | 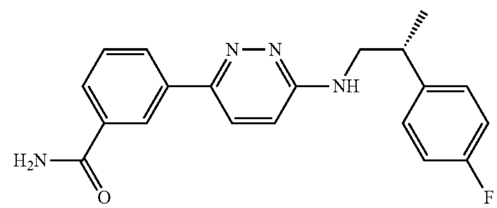 [SMILES: C[C@@H](CNc1ccc(-c2cccc(C(N)=O)c2)nn1)c1ccc(F)cc1] | 351.0 | B |
| 3-(6-{[2-(4-chlorophenyl)ethyl]amino}pyridazin-3-yl)benzamide | 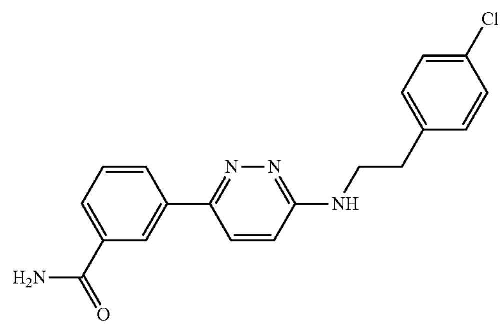 [SMILES: NC(=O)c1cccc(-c2ccc(NCCc3ccc(Cl)cc3)nn2)c1] | 353.1 | D |
| 3-(6-{[2-(3-chlorophenyl)ethyl]amino}pyridazin-3-yl)benzamide | 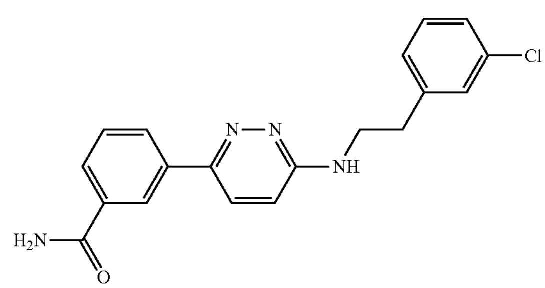 [SMILES: NC(=O)c1cccc(-c2ccc(NCCc3cccc(Cl)c3)nn2)c1] | 353.1 | B |
| 3-(6-{[2-(2-chlorophenyl)ethyl]amino}pyridazin-3-yl)benzamide | 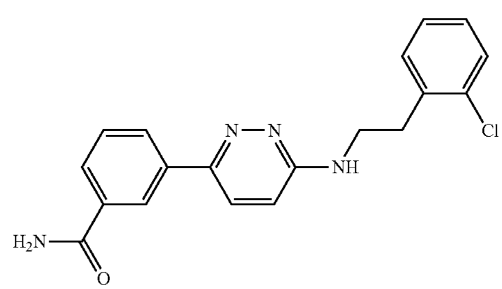 [SMILES: NC(=O)c1cccc(-c2ccc(NCCc3ccccc3Cl)nn2)c1] | 353.1 | B |

TABLE 2-continued

| Compound | Structure | m/z (M + H) | Mean AC1.4 |
|---|---|---|---|
| 3-(6-{[2-(4-methylphenyl)ethyl]amino}pyridazin-3-yl)benzamide | 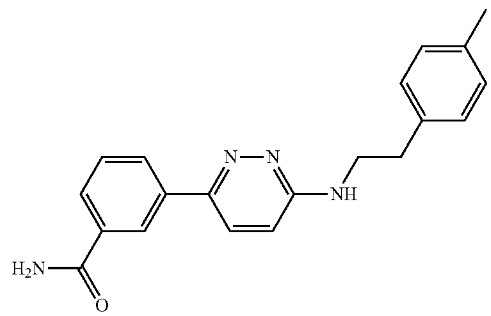 [SMILES: Cc1ccc(CCNc2ccc(-c3cccc(C(N)=O)c3)nn2)cc1] | 333.2 | C |
| 3-(6-{[2-(4-fluorophenyl)ethyl]amino}pyridazin-3-yl)benzamide | 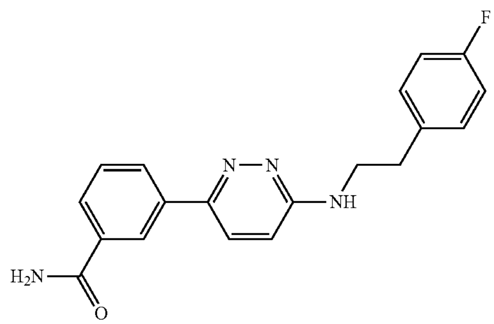 [SMILES: NC(=O)c1cccc(-c2ccc(NCCc3ccc(F)cc3)nn2)c1] | 337.1 | D |
| 3-(6-{[2-(4-methoxyphenyl)ethyl]amino}pyridazin-3-yl)benzamide | 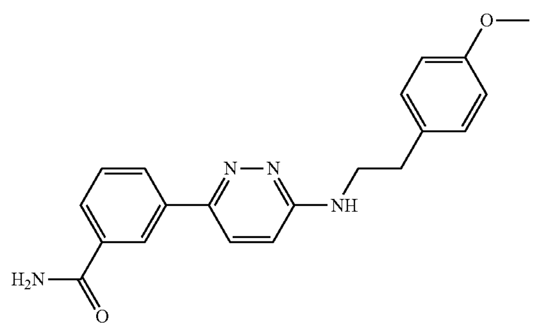 [SMILES: COc1ccc(CCNc2ccc(-c3cccc(C(N)=O)c3)nn2)cc1] | 349.1 | D |
| (6-{[2-(4-fluorophenyl)-2-methylpropyl]amino}pyridazin-3-yl)methan-1-ol | 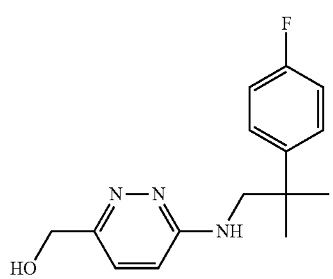 [SMILES: CC(C)(CNc1ccc(CO)nn1)c1ccc(F)cc1] | 276.1 | D |
| methyl 6-{[2-(4-fluorophenyl)-2-methylpropyl]amino}pyridazine-3-carboxylate | 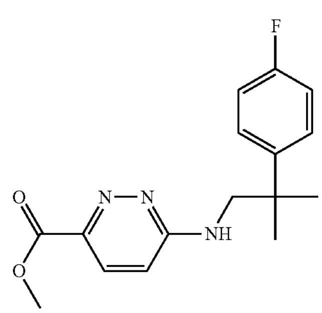 [SMILES: COC(=O)c1ccc(NCC(C)(C)c2ccc(F)cc2)nn1] | 304.2 | C |

TABLE 2-continued

| Compound | Structure | m/z (M + H) | Mean AC1.4 |
|---|---|---|---|
| 3-(6-{[2-(2,4-dichlorophenyl)ethyl]amino}pyridazin-3-yl)benzenecarbonitrile | 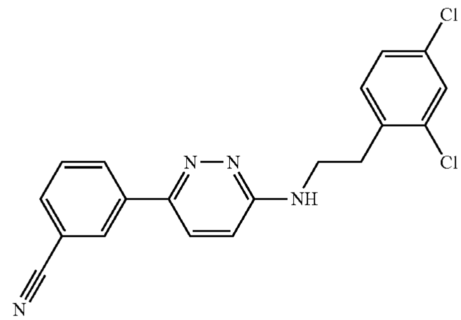 [SMILES: N#Cc1cccc(-c2ccc(NCCc3ccc(Cl)cc3Cl)nn2)c1] | 369.0 | D |
| 3-(6-{[2-(2,4-dichlorophenyl)ethyl]amino}pyridazin-3-yl)benzamide | 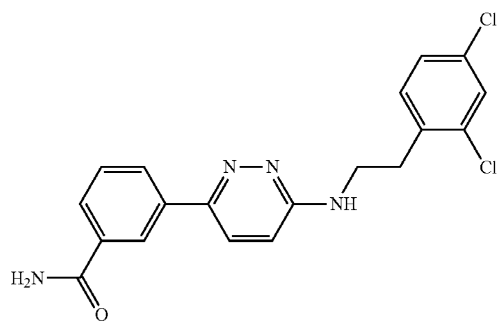 [SMILES: NC(=O)c1cccc(-c2ccc(NCCc3ccc(Cl)cc3Cl)nn2)c1] | 387.0 | C |
| 3-(6-{[2-(3,4-dichlorophenyl)ethyl]amino}pyridazin-3-yl)benzamide | 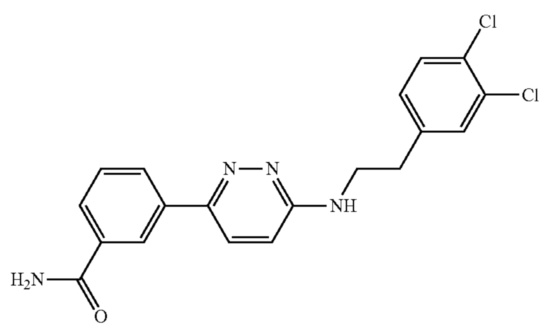 [SMILES: NC(=O)c1cccc(-c2ccc(NCCc3ccc(Cl)c(Cl)c3)nn2)c1] | 387.0 | C |
| 3-(6-{[2-(2,4-difluorophenyl)ethyl]amino}pyridazin-3-yl)benzamide | 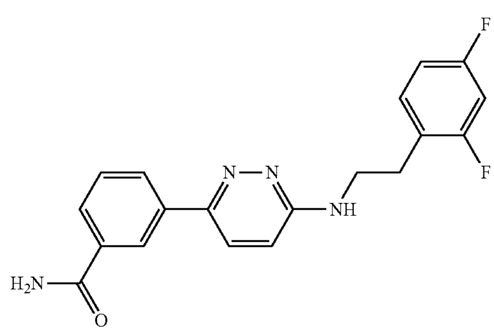 [SMILES: NC(=O)c1cccc(-c2ccc(NCCc3ccc(F)cc3F)nn2)c1] | 355.1 | D |

TABLE 2-continued

| Compound | Structure | m/z (M + H) | Mean AC1.4 |
|---|---|---|---|
| 3-(6-{[2-(3,4-difluorophenyl)ethyl]amino}pyridazin-3-yl)benzamide | 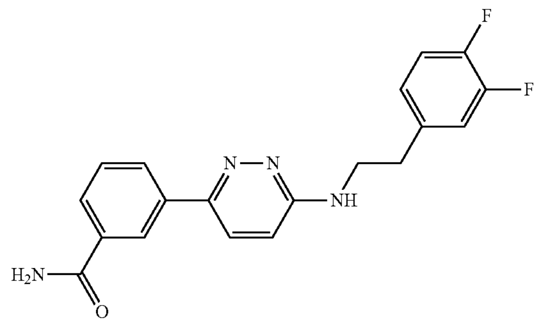 [SMILES: NC(=O)c1cccc(-c2ccc(NCCc3ccc(F)c(F)c3)nn2)c1] | 355.1 | C |
| 3-(6-{[2-(3,5-difluorophenyl)ethyl]amino}pyridazin-3-yl)benzamide | 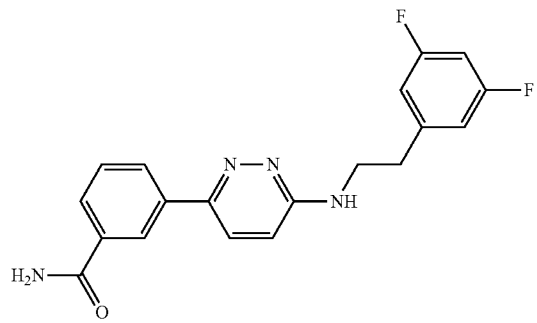 [SMILES: NC(=O)c1cccc(-c2ccc(NCCc3cc(F)cc(F)c3)nn2)c1] | 355.1 | D |
| 3-{6-[(2-(4-pyridyl)ethyl)amino]pyridazin-3-yl}benzamide | 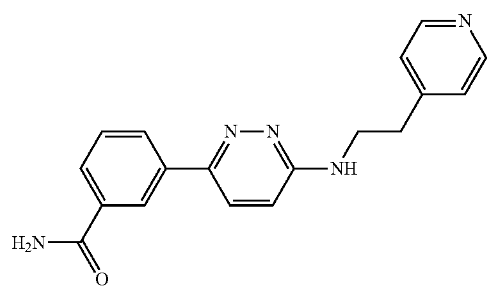 [SMILES: NC(=O)c1cccc(-c2ccc(NCCc3ccncc3)nn2)c1] | 320.1 | D |
| 3-{6-[(2-(3-pyridyl)ethyl)amino]pyridazin-3-yl}benzamide | 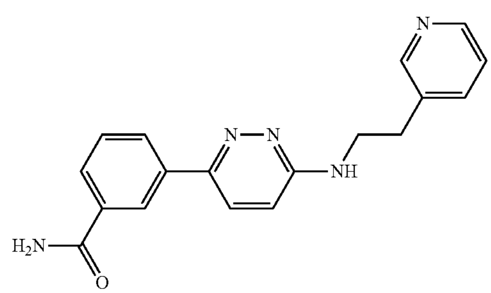 [SMILES: NC(=O)c1cccc(-c2ccc(NCCc3cccnc3)nn2)c1] | 320.1 | D |
| 3-{6-[(2-(2-pyridyl)ethyl)amino]pyridazin-3-yl}benzamide | 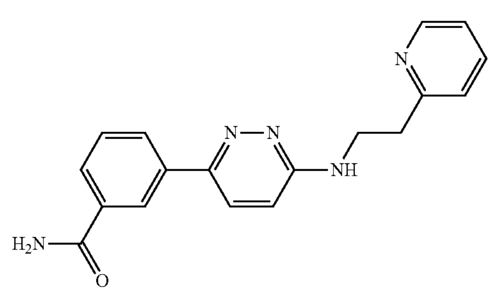 [SMILES: NC(=O)c1cccc(-c2ccc(NCCc3ccccn3)nn2)c1] | 320.1 | D |

TABLE 2-continued

| Compound | Structure | m/z (M + H) | Mean AC1.4 |
|---|---|---|---|
| 3-{6-[(2-phenylethyl)amino]pyridazin-3-yl}benzamide | 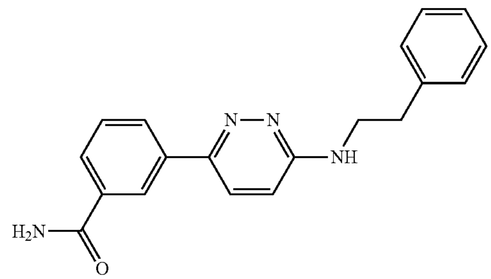 [SMILES: NC(=O)c1cccc(-c2ccc(NCCc3ccccc3)nn2)c1] | 319.1 | D |
| 3-{6-[(3-methylbutyl)amino]pyridazin-3-yl}benzamide | 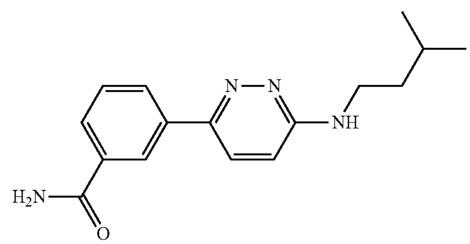 [SMILES: CC(C)CCNc1ccc(-c2cccc(C(N)=O)c2)nn1] | 319.1 | D |
| 3-{6-[(2-phenylpropyl)amino]pyridazin-3-yl}benzamide | 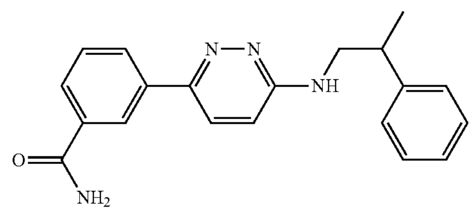 [SMILES: CC(CNc1ccc(-c2cccc(C(N)=O)c2)nn1)c1ccccc1] | 333.1 | B |
| 3-(6-{[(4-fluorophenyl)ethyl]amino}pyridazin-3-yl)benzamide | 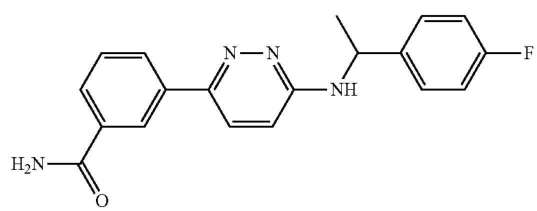 [SMILES: CC(Nc1ccc(-c2cccc(C(N)=O)c2)nn1)c1ccc(F)cc1] | 337.1 | C |
| 3-{6-[(phenylethyl)amino]pyridazin-3-yl}benzamide | 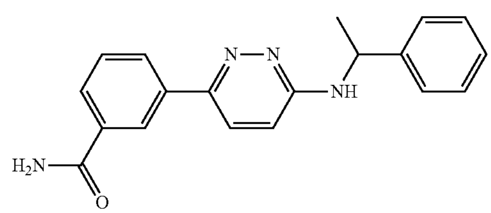 [SMILES: CC(Nc1ccc(-c2cccc(C(N)=O)c2)nn1)c1ccccc1] | 319.1 | D |
| 3-{6-[(3,3-dimethylbutyl)amino]pyridazin-3-yl}benzamide | | 299.2 | D |

TABLE 2-continued

| Compound | Structure | m/z (M + H) | Mean AC1.4 |
|---|---|---|---|
| 3-{6-[(2-pyrazin-2-ylethyl)amino]pyridazin-3-yl}benzamide | 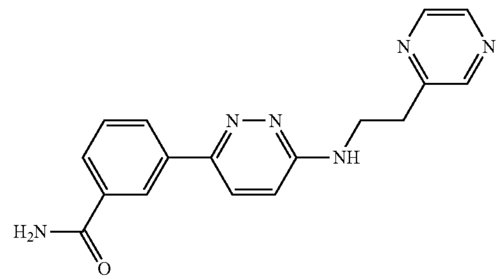 [SMILES: NC(=O)c1cccc(-c2ccc(NCCc3cnccn3)nn2)c1] | 321.1 | D |
| 3-(6-{[2-(2-chlorophenyl)-2-methylpropyl]amino}pyridazin-3-yl)benzamide | 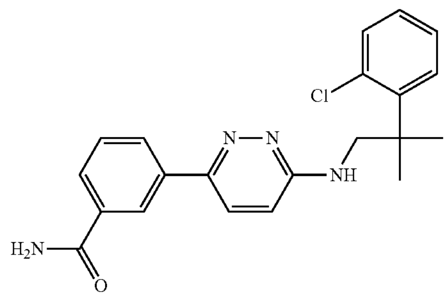 [SMILES: CC(C)(CNc1ccc(-c2cccc(C(N)=O)c2)nn1)c1ccccc1Cl] | 381.1 | A |
| 3-(6-{[2-(4-chlorophenyl)-2-methylpropyl]amino}pyridazin-3-yl)benzamide | 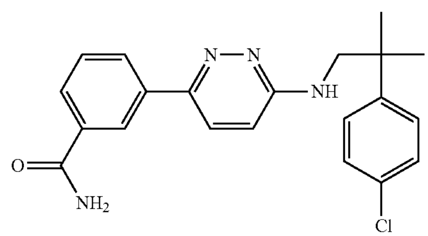 | 381.1 | B |
| 3-(6-{[2-(2,4-difluorophenyl)-2-methylpropyl]amino}pyridazin-3-yl)benzamide | 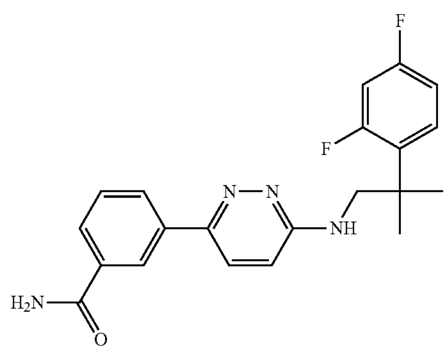 [SMILES: CC(C)(CNc1ccc(-c2cccc(C(N)=O)c2)nn1)c1ccc(F)cc1F] | 383.1 | B |
| 3-[6-({[(4-fluorophenyl)cyclopropyl]methyl}amino)pyridazin-3-yl]benzamide | 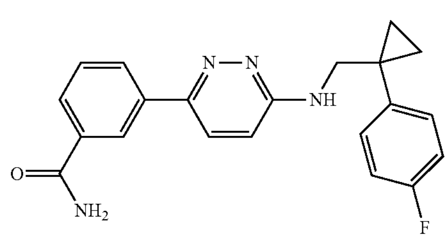 [SMILES: NC(=O)c1cccc(-c2ccc(NCC3(c4ccc(F)cc4)CC3)nn2)c1] | 362.2 | A |

TABLE 2-continued

| Compound | Structure | m/z (M + H) | Mean AC1.4 |
|---|---|---|---|
| (6-(1H-indazol-6-yl)pyridazin-3-yl)[2-(4-fluorophenyl)-2-methylpropyl]amine | 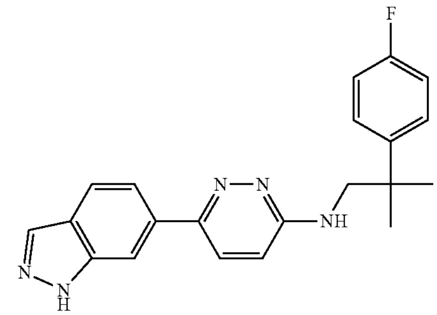 [SMILES: CC(C)(CNc1ccc(-c2ccc3cn[nH]c3c2)nn1)c1ccc(F)cc1] | 362.1 | A |
| 3-(6-{[2-(4-fluorophenyl)-2-methylpropyl]amino}pyridazin-3-yl)benzenecarbonitrile | 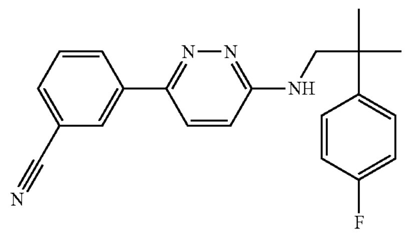 [SMILES: CC(C)(CNc1ccc(-c2cccc(C#N)c2)nn1)c1ccc(F)cc1] | 347.1 | B |
| (6-(1H-indazol-5-yl)pyridazin-3-yl)[2-(4-fluorophenyl)-2-methylpropyl]amine | 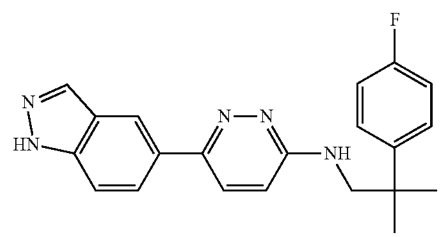 [SMILES: CC(C)(CNc1ccc(-c2ccc3[nH]ncc3c2)nn1)c1ccc(F)cc1] | 362.2 | A |
| 3-(6-{[2-(2-fluorophenyl)-2-methylpropyl]amino}pyridazin-3-yl)benzamide | 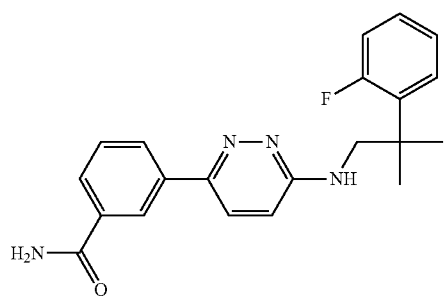 [SMILES: CC(C)(CNc1ccc(-c2cccc(C(N)=O)c2)nn1)c1ccccc1F] | 365.1 | A |
| (6-(1H-indazol-4-yl)pyridazin-3-yl)[2-(4-fluorophenyl)-2-methylpropyl]amine | 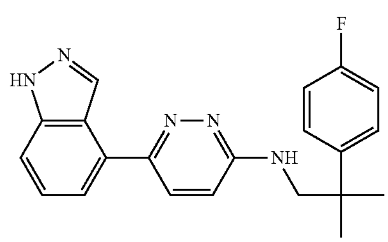 [SMILES: CC(C)(CNc1ccc(-c2cccc3[nH]ncc23)nn1)c1ccc(F)cc1] | 362.1 | A |
| 5-[6-({[(4-fluorophenyl)cyclopropyl]methyl}amino)pyridazin-3-yl]pyridine-3-carboxamide | 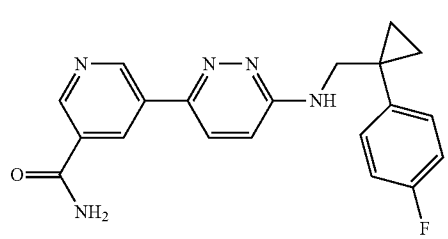 [SMILES: NC(=O)c1cncc(-c2ccc(NCC3(c4ccc(F)cc4)CC3)nn2)c1] | 364.1 | B |

TABLE 2-continued

| Compound | Structure | m/z (M + H) | Mean AC1.4 |
|---|---|---|---|
| 5-[6-({[(4-fluorophenyl)cyclopropyl]methyl}amino)pyridazin-3-yl]pyridine-3-carbonitrile | 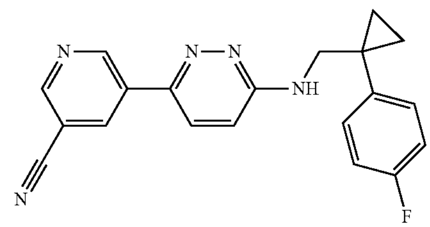 [SMILES: N#Cc1cncc(-c2ccc(NCC3(c4ccc(F)cc4)CC3)nn2)c1] | 346.1 | B |
| 6-{[2-(4-fluorophenyl)-2-methylpropyl]amino}pyridazine-3-carbonitrile | 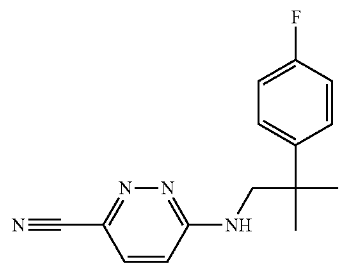 [SMILES: CC(C)(CNc1ccc(C#N)nn1)c1ccc(F)cc1] | 271.1 | D |
| 6-{[2-(4-fluorophenyl)-2-methylpropyl]amino}pyridazine-3-carboxamide | 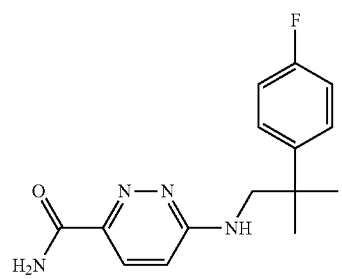 [SMILES: CC(C)(CNc1ccc(C(N)=O)nn1)c1ccc(F)cc1] | 289.1 | C |
| 5-(6-{[2-(4-fluorophenyl)-2-methylpropyl]amino}pyridazin-3-yl)-3-hydrobenzimidazol-2-one | 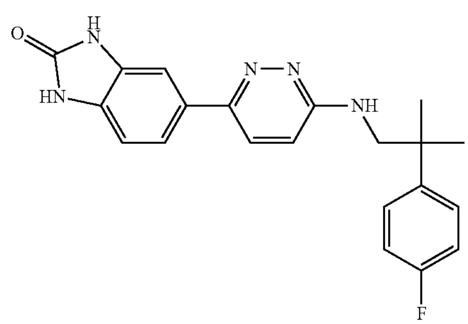 [SMILES: CC(C)(CNc1ccc(-c2ccc3[nH]c(=O)[nH]c3c2)nn1)c1ccc(F)cc1] | 378.1 | A |
| 3-(6-{[2-(3-fluorophenyl)-2-methylpropyl]amino}pyridazin-3-yl)benzamide | 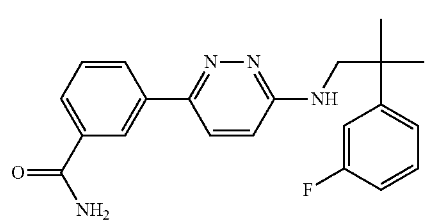 [SMILES: CC(C)(CNc1ccc(-c2cccc(C(N)=O)c2)nn1)c1cccc(F)c1] | 365.1 | A |

TABLE 2-continued

| Compound | Structure | m/z (M + H) | Mean AC1.4 |
|---|---|---|---|
| (6-(1H-1,2,3,4-tetraazol-5-yl)pyridazin-3-yl)[2-(4-fluorophenyl)-2-methylpropyl]amine | 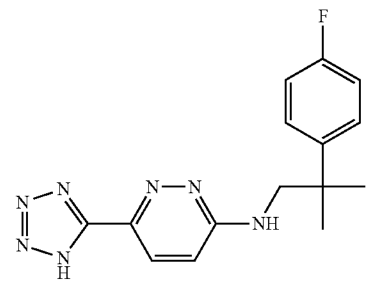 [SMILES: CC(C)(CNc1ccc(-c2nnn[nH]2)nn1)c1ccc(F)cc1] | 314.1 | D |
| 5-(6-{[2-(2-chlorophenyl)-2-methylpropyl]amino}pyridazin-3-yl)pyridine-3-carboxamide | 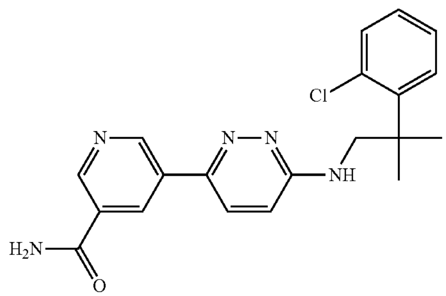 [SMILES: CC(C)(CNc1ccc(-c2cncc(C(N)=O)c2)nn1)c1ccccc1Cl] | 382.1 | B |
| 5-(6-{[2-(2-chlorophenyl)-2-methylpropyl]amino}pyridazin-3-yl)pyridine-3-carbonitrile | 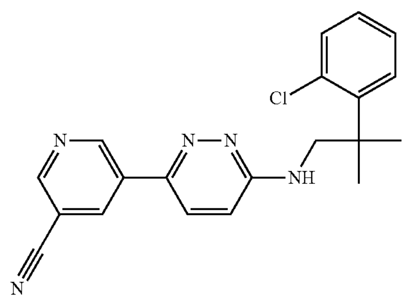 [SMILES: CC(C)(CNc1ccc(-c2cncc(C#N)c2)nn1)c1ccccc1Cl] | 364.1 | B |
| [(6-{[2-(4-fluorophenyl)-2-methylpropyl]amino}pyridazin-3-yl)methyl](methylsulfonyl)amine | 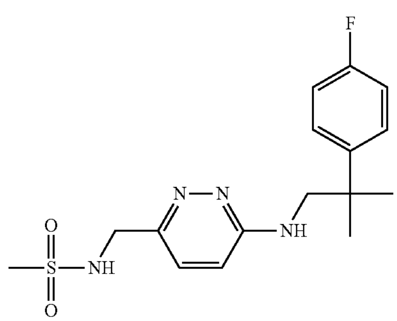 [SMILES: CC(C)(CNc1ccc(CNS(C)(=O)=O)nn1)c1ccc(F)cc1] | 353.1 | B |
| N-[(6-{[2-(4-fluorophenyl)-2-methylpropyl]amino}pyridazin-3-yl)methyl]methoxycarboxamide | 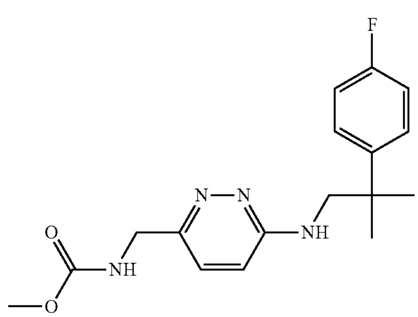 [SMILES: COC(=O)NCc1ccc(NCC(C)(C)c2ccc(F)cc2)nn1] | 333.2 | D |

TABLE 2-continued

| Compound | Structure | m/z (M + H) | Mean AC1.4 |
|---|---|---|---|
| [6-(3-amino(1H-indazol-5-yl))pyridazin-3-yl][2-(4-fluorophenyl)-2-methylpropyl]amine | 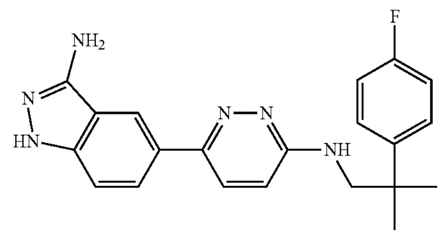 | 377.1 | A |
| [6-(3-amino(1H-indazol-7-yl))pyridazin-3-yl][2-(4-fluorophenyl)-2-methylpropyl]amine | 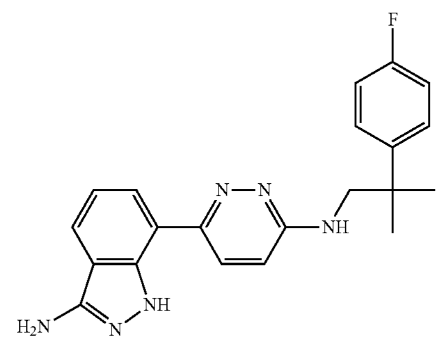 [SMILES: CC(C)(CNc1ccc(-c2cccc3c(N)n[nH]c23)nn1)c1ccc(F)cc1] | 377.0 | B |
| [6-(3-aminobenzo[3,4-d]isoxazol-5-yl)pyridazin-3-yl][2-(4-fluorophenyl)-2-methylpropyl]amine | 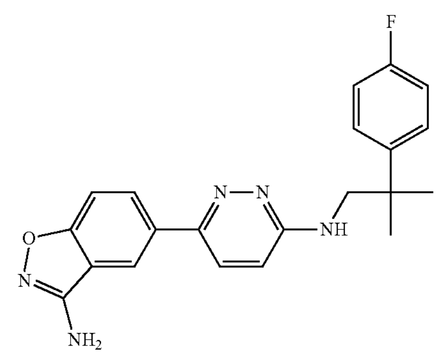 [SMILES: CC(C)(CNc1ccc(-c2ccc3onc(N)c3c2)nn1)c1ccc(F)cc1] | 378.0 | B |
| [6-(3-aminobenzo[d]isoxazol-7-yl)pyridazin-3-yl][2-(4-fluorophenyl)-2-methylpropyl]amine | 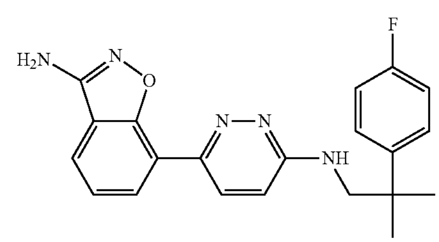 [SMILES: CC(C)(CNc1ccc(-c2cccc3c(N)noc23)nn1)c1ccc(F)cc1] | 388.0 | B |
| [2-(2-chlorophenyl)-2-methylpropyl](6-(3-pyridyl)pyridazin-3-yl)amine | 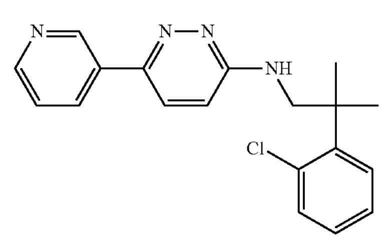 | 339.1 | B |

TABLE 2-continued

| Compound | Structure | m/z (M + H) | Mean AC1.4 |
|---|---|---|---|
| [2-(2-chlorophenyl)-2-methylpropyl](6-pyrimidin-5-ylpyridazin-3-yl)amine | 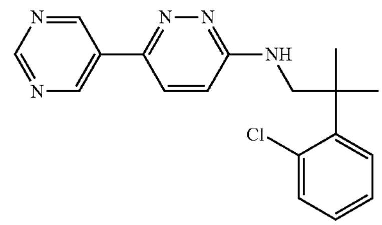 [SMILES: CC(C)(CNc1ccc(-c2cccnc2)nn1)c1ccccc1Cl] | 340.1 | B |
| 3-[6-({[(2-chlorophenyl)cyclopropyl]methyl}amino)pyridazin-3-yl]benzamide | 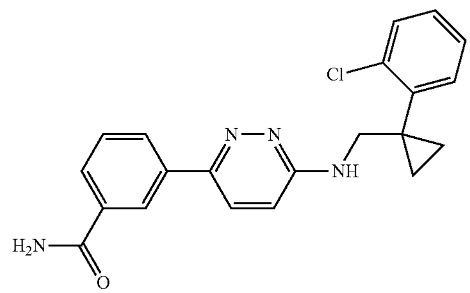 [SMILES: NC(=O)c1cccc(-c2ccc(NCC3(c4ccccc4Cl)CC3)nn2)c1] | 379.1 | A |
| 3-(6-{[2-(4-fluorophenyl)-2-methylpropyl]amino}-5-methylpyridazin-3-yl)benzenecarbonitrile | 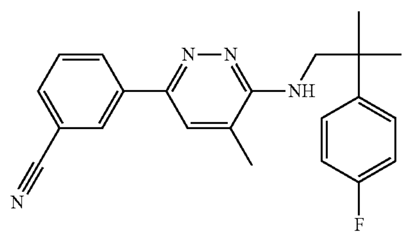 [SMILES: Cc1cc(-c2cccc(C#N)c2)nnc1NCC(C)(C)c1ccc(F)cc1] | 361.1 | C |
| 3-(6-{[2-(4-fluorophenyl)-2-methylpropyl]amino}-5-methylpyridazin-3-yl)benzamide | 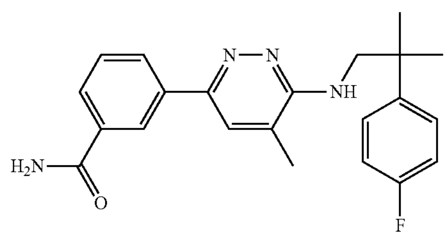 [SMILES: Cc1cc(-c2cccc(C(N)=O)c2)nnc1NCC(C)(C)c1ccc(F)cc1] | 379.1 | B |
| 3-(6-{[2-(4-fluorophenyl)-2-methylpropyl]amino}-4-methylpyridazin-3-yl)benzenecarbonitrile | 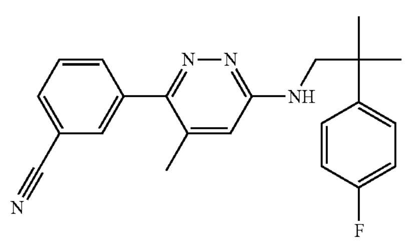 | 361.1 | B |
| 3-(6-{[2-(4-fluorophenyl)-2-methylpropyl]amino}-4-methylpyridazin-3-yl)benzamide | 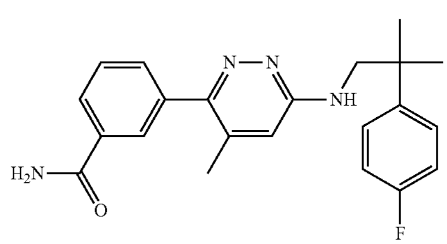 [SMILES: Cc1cc(NCC(C)(C)c2ccc(F)cc2)nnc1-c1cccc(C(N)=O)c1] | 379.1 | B |

TABLE 2-continued

| Compound | Structure | m/z (M + H) | Mean AC1.4 |
|---|---|---|---|
| [3-(6-{[2-(4-fluorophenyl)-2-methylpropyl]amino}pyridazin-3-yl)phenyl]-N-(2-hydroxyethyl)carboxamide | 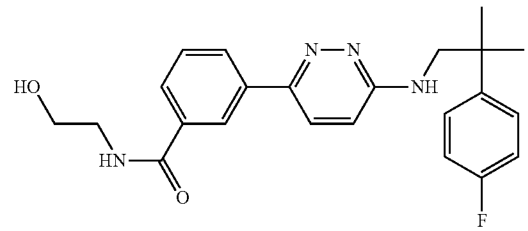 [SMILES: CC(C)(CNc1ccc(-c2cccc(C(=O)NCCO)c2)nn1)c1ccc(F)cc1] | 409.1 | B |
| N-(2,3-dihydroxypropyl)[3-(6-{[2-(4-fluorophenyl)-2-methylpropyl]amino}pyridazin-3-yl)phenyl]carboxamide | 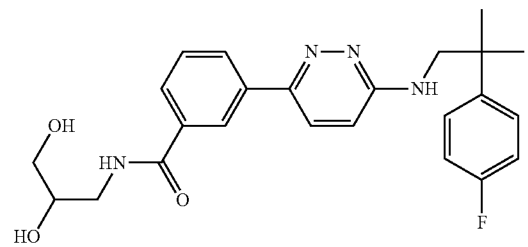 [SMILES: CC(C)(CNc1ccc(-c2cccc(C(=O)NCC(O)CO)c2)nn1)c1ccc(F)cc1] | 439.1 | B |
| 3-(6-{[2-(4-fluorophenyl)-2-methylpropyl]amino}pyridazin-3-yl)phenyl piperidyl ketone | 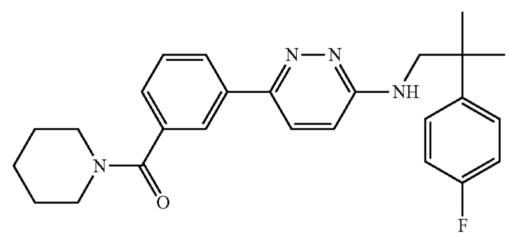 [SMILES: CC(C)(CNc1ccc(-c2cccc(C(=O)N3CCCCC3)c2)nn1)c1ccc(F)cc1] | 433.2 | B |
| 3-(6-{[2-(4-fluorophenyl)-2-methylpropyl]amino}pyridazin-3-yl)phenyl morpholin-4-yl ketone | 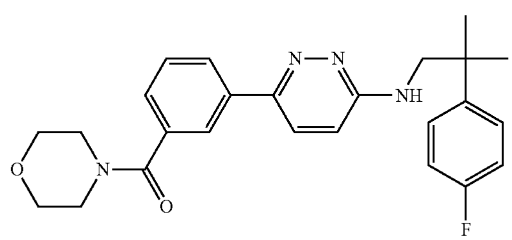 [SMILES: CC(C)(CNc1ccc(-c2cccc(C(=O)N3CCOCC3)c2)nn1)c1ccc(F)cc1] | 435.1 | B |
| N-(2-aminoethyl)[3-(6-{[2-(4-fluorophenyl)-2-methylpropyl]amino}pyridazin-3-yl)phenyl]carboxamide | 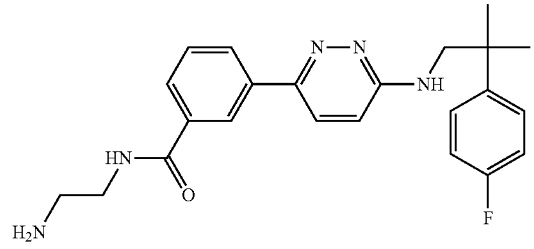 [SMILES: CC(C)(CNc1ccc(-c2cccc(C(=O)NCCN)c2)nn1)c1ccc(F)cc1] | 408.2 | A |

TABLE 2-continued

| Compound | Structure | m/z (M + H) | Mean AC1.4 |
|---|---|---|---|
| [3-(6-{[2-(4-fluorophenyl)-2-methylpropyl]amino}pyridazin-3-yl)phenyl]-N-(2-{[3-(6-{[2-(4-fluorophenyl)-2-methylpropyl]amino}pyridazin-3-yl)phenyl]carbonylamino}ethyl)carboxamide | 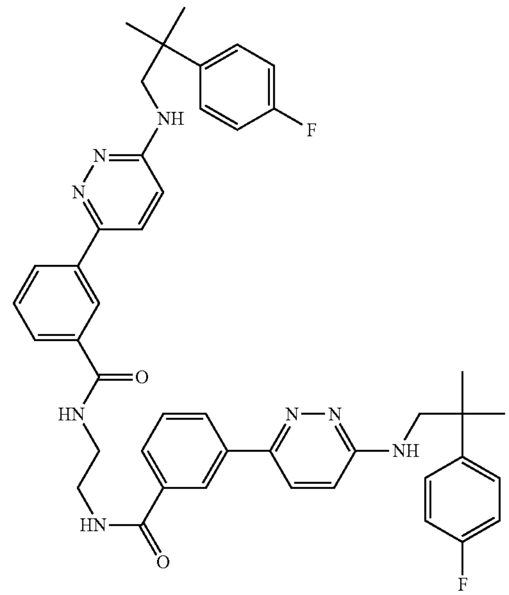 [SMILES: CC(C)(CNc1ccc(-c2cccc(C(=O)NCCNC(=O)c3cccc(-c4ccc(NCC(C)(C)c5ccc(F)cc5)nn4)c3)c2)nn1)c1ccc(F)cc1] | 755.3 | B |
| tert-butyl 4-{[3-(6-{[2-(4-fluorophenyl)-2-methylpropyl]amino}pyridazin-3-yl)phenyl]carbonyl}piperazinecarboxylate | 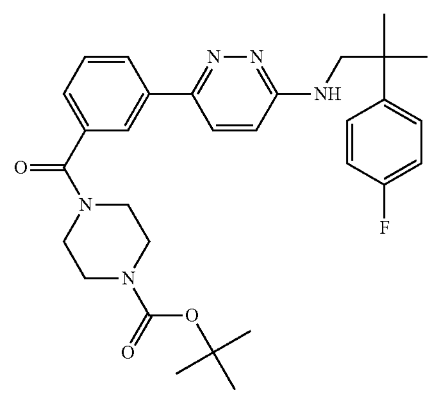 [SMILES: CC(C)(C)OC(=O)N1CCN(C(=O)c2cccc(-c3ccc(NCC(C)(C)c4ccc(F)cc4)nn3)c2)CC1] | 534.2 | B |
| 2-(6-{[2-(4-fluorophenyl)-2-methylpropyl]amino}pyridazin-3-yl)benzamide | 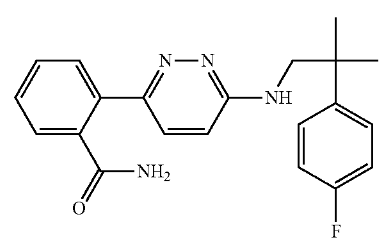 [SMILES: CC(C)(CNc1ccc(-c2ccccc2C(N)=O)nn1)c1ccc(F)cc1] | 365.0 | B |
| 5-[6-({[(4-fluorophenyl)cyclopropyl]methyl}amino)pyridazin-3-yl]-3-hydrobenzimidazol-2-one | 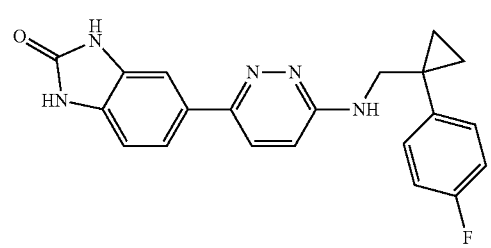 [SMILES: O=c1[nH]c2ccc(-c3ccc(NCC4(c5ccc(F)cc5)CC4)nn3)cc2[nH]1] | 376.1 | A |

TABLE 2-continued

| Compound | Structure | m/z (M + H) | Mean AC1.4 |
|---|---|---|---|
| [2-(4-fluorophenyl)-2-methylpropyl][6-(1-methyl(1H-indazol-6-yl))pyridazin-3-yl]amine | 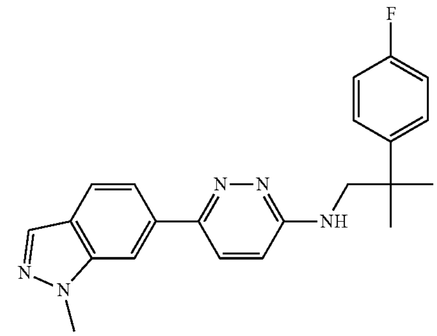 [SMILES: Cn1ncc2ccc(-c3ccc(NCC(C)(C)c4ccc(F)cc4)nn3)cc21] | 376.2 | B |
| 3-(6-{[2-(4-fluorophenyl)-2-methylpropyl]amino}pyridazin-3-yl)phenyl piperazinyl ketone | 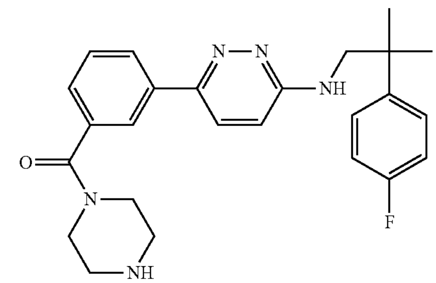 [SMILES: CC(C)(CNc1ccc(-c2cccc(C(=O)N3CCNCC3)c2)nn1)c1ccc(F)cc1] | 434.2 | B |
| 1-[(6-{[2-(4-fluorophenyl)-2-methylpropyl]amino}pyridazin-3-yl)carbonyl]pyrrolidine-2-carboxamide | 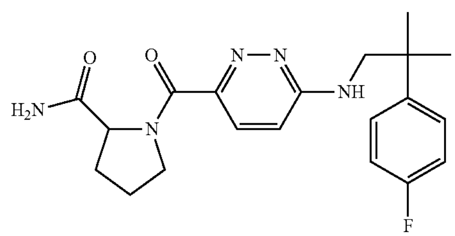 [SMILES: CC(C)(CNc1ccc(C(=O)N2CCCC2C(N)=O)nn1)c1ccc(F)cc1] | 386.1 | D |
| ethyl 1-[(6-{[2-(4-fluorophenyl)-2-methylpropyl]amino}pyridazin-3-yl)carbonylamino]cyclopropanecarboxylate | 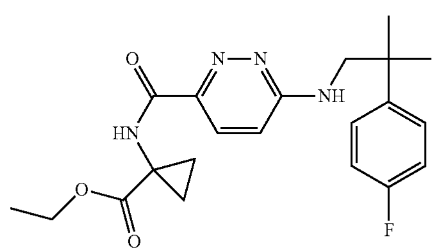 [SMILES: CCOC(=O)C1(NC(=O)c2ccc(NCC(C)(C)c3ccc(F)cc3)nn2)CC1] | 401.1 | D |
| 6-{[2-(4-fluorophenyl)-2-methylpropyl]amino}pyridazine-3-carboxylic acid | 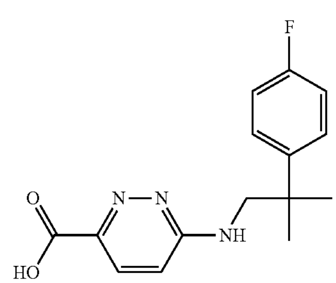 [SMILES: CC(C)(CNc1ccc(C(=O)O)nn1)c1ccc(F)cc1] | 290.1 | D |

TABLE 2-continued

| Compound | Structure | m/z (M + H) | Mean AC1.4 |
|---|---|---|---|
| 1-[(6-{[2-(4-fluorophenyl)-2-methylpropyl]amino}pyridazin-3-yl)carbonylamino]cyclopropanecarboxylic acid | 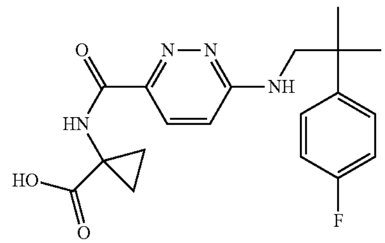 [SMILES: CC(C)(CNc1ccc(C(=O)NC2(C(=O)O)CC2)nn1)c1ccc(F)cc1] | 373.1 | D |
| 3-(6-{[2-(2-chlorophenyl)pentyl]amino}pyridazin-3-yl)benzamide | 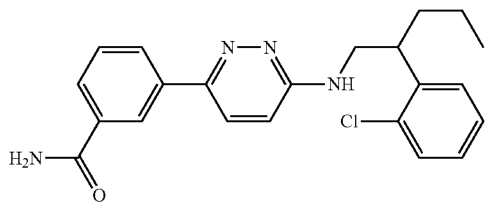 [SMILES: CCCC(CNc1ccc(-c2cccc(C(N)=O)c2)nn1)c1ccccc1Cl] | 395.1 | B |
| [6-(3-amino-1-methyl(1H-indazol-5-yl))pyridazin-3-yl][2-(4-fluorophenyl)-2-methylpropyl]amine | 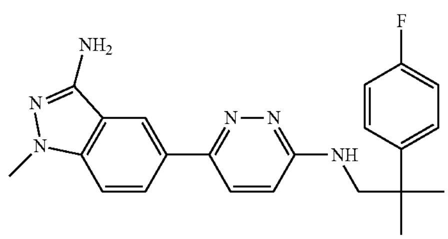 [SMILES: Cn1nc(N)c2cc(-c3ccc(NCC(C)(C)c4ccc(F)cc4)nn3)ccc21] | 391.0 | B |
| 3-(6-{[2-(2-fluorophenyl)-4-methoxybutyl]amino}pyridazin-3-yl)benzamide | 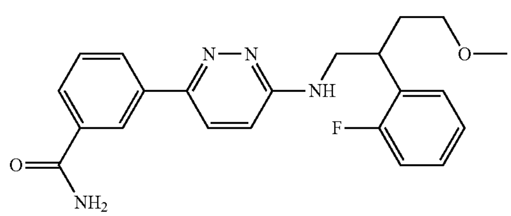 [SMILES: COCCC(CNc1ccc(-c2cccc(C(N)=O)c2)nn1)c1ccccc1F] | 395.1 | D |
| 6-{[2-(4-fluorophenyl)-2-methylpropyl]amino}pyridazin-3-yl morpholin-4-yl ketone | 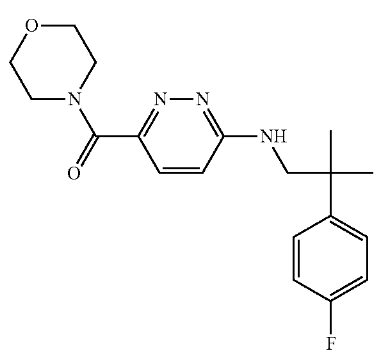 [SMILES: CC(C)(CNc1ccc(C(=O)N2CCOCC2)nn1)c1ccc(F)cc1] | 359.1 | D |

TABLE 2-continued

| Compound | Structure | m/z (M + H) | Mean AC1.4 |
|---|---|---|---|
| 6-{[2-(4-fluorophenyl)-2-methylpropyl]amino}pyridazin-3-yl 4-methylpiperazinyl ketone | 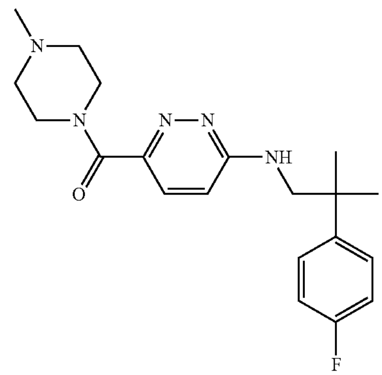 [SMILES: CN1CCN(C(=O)c2ccc(NCC(C)(C)c3ccc(F)cc3)nn2)CC1] | 372.1 | D |
| tert-butyl 4-[(6-{[2-(4-fluorophenyl)-2-methylpropyl]amino}pyridazin-3-yl)carbonyl]piperazinecarboxylate | 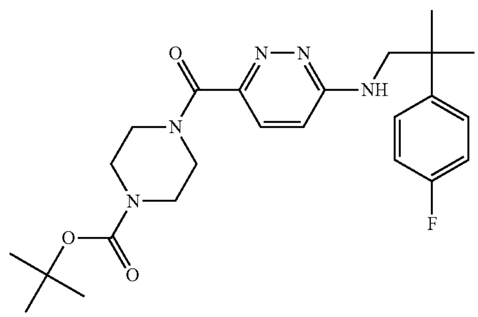 [SMILES: CC(C)(C)OC(=O)N1CCN(C(=O)c2ccc(NCC(C)(C)c3ccc(F)cc3)nn2)CC1] | 458.2 | D |
| tert-butyl 4-[(6-{[2-(4-fluorophenyl)-2-methylpropyl]amino}pyridazin-3-yl)carbonyl]-3-(hydroxymethyl)piperazinecarboxylate | | 488.2 | D |
| 1-[(6-{[2-(4-fluorophenyl)-2-methylpropyl]amino}pyridazin-3-yl)carbonyl]azetidine-2-carboxamide | 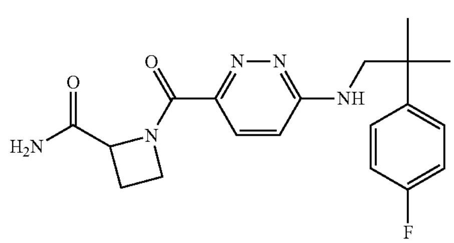 [SMILES: CC(C)(CNc1ccc(C(=O)N2CCC2C(N)=O)nn1)c1ccc(F)cc1] | 372.1 | D |
| 1-[(6-{[2-(4-fluorophenyl)-2-methylpropyl]amino}pyridazin-3-yl)carbonyl]piperidine-2-carboxamide | 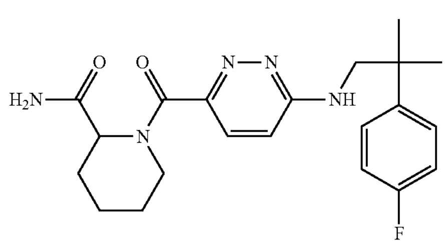 [SMILES: CC(C)(CNc1ccc(C(=O)N2CCCCC2C(N)=O)nn1)c1ccc(F)cc1] | 400.1 | D |

TABLE 2-continued

| Compound | Structure | m/z (M + H) | Mean AC1.4 |
|---|---|---|---|
| 4-[(6-{[2-(4-fluorophenyl)-2-methylpropyl]amino}pyridazin-3-yl)carbonyl]piperazin-2-one | 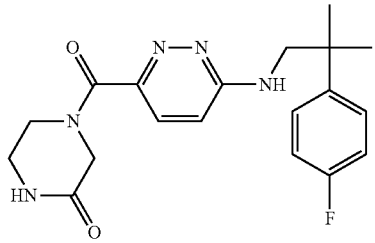 [SMILES: CC(C)(CNc1ccc(C(=O)N2CCNC(=O)C2)nn1)c1ccc(F)cc1] | 372.1 | D |
| 5-(6-{[2-(2-fluorophenyl)-2-methylpropyl]amino}pyridazin-3-yl)-3-hydrobenzimidazol-2-one | 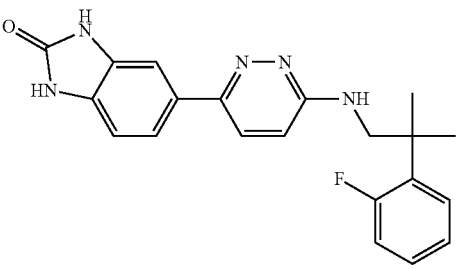 [SMILES: CC(C)(CNc1ccc(-c2ccc3[nH]c(=O)[nH]c3c2)nn1)c1ccccc1F] | 378.2 | A |
| [6-(3-amino(1H-indazol-6-yl))pyridazin-3-yl][2-(4-fluorophenyl)-2-methylpropyl]amine | 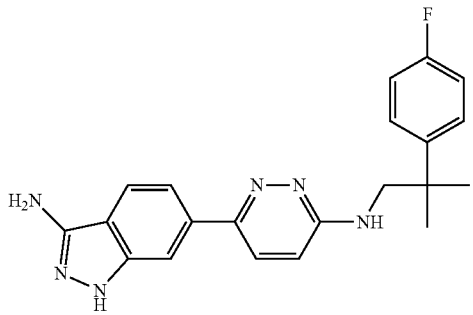 | 377.0 | A |
| [6-(3-aminobenzo[d]isoxazol-6-yl)pyridazin-3-yl][2-(4-fluorophenyl)-2-methylpropyl]amine | 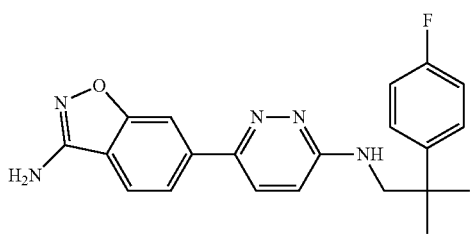 [SMILES: CC(C)(CNc1ccc(-c2ccc3c(N)noc3c2)nn1)c1ccc(F)cc1] | 378.0 | A |
| 3-fluoro-5-(6-{[2-(4-fluorophenyl)-2-methylpropyl]amino}pyridazin-3-yl)benzamide | 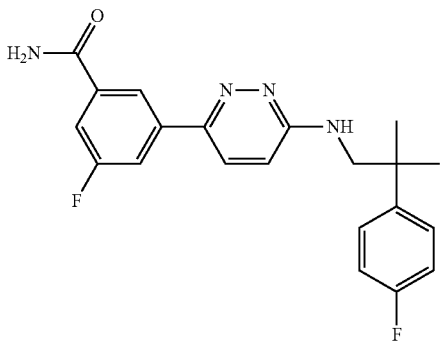 [SMILES: CC(C)(CNc1ccc(-c2cc(F)cc(C(N)=O)c2)nn1)c1ccc(F)cc1] | 383.1 | B |

TABLE 2-continued

| Compound | Structure | m/z (M + H) | Mean AC1.4 |
|---|---|---|---|
| N-(1-carbamoyl-3-methylbutyl)(6-{[2-(4-fluorophenyl)-2-methylpropyl]amino}pyridazin-3-yl)carboxamide | 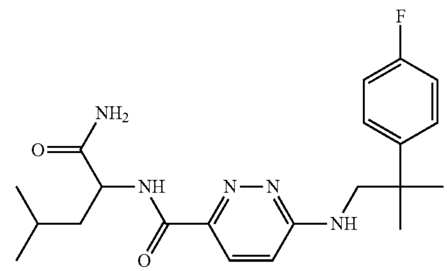 [SMILES: CC(C)CC(NC(=O)c1ccc(NCC(C)(C)c2ccc(F)cc2)nn1)C(N)=O] | 402.2 | C |
| N-((1S)-1-carbamoyl-2-hydroxyethyl)(6-{[2-(4-fluorophenyl)-2-methylpropyl]amino}pyridazin-3-yl)carboxamide | 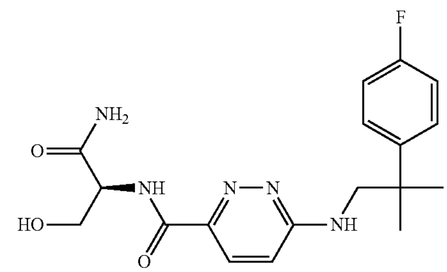 [SMILES: CC(C)(CNc1ccc(C(=O)N[C@@H](CO)C(N)=O)nn1)c1ccc(F)cc1] | 376.1 | D |
| (6-{[2-(4-fluorophenyl)-2-methylpropyl]amino}pyridazin-3-yl)-N-(pyrazol-3-ylmethyl)carboxamide | 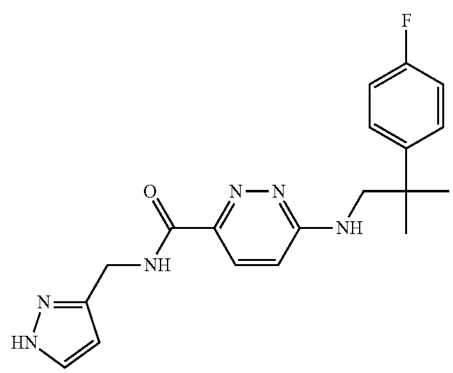 [SMILES: CC(C)(CNc1ccc(C(=O)NCc2cc[nH]n2)nn1)c1ccc(F)cc1] | 369.1 | C |
| 3-(5-cyano-6-{[2-(4-fluorophenyl)-2-methylpropyl]amino}pyridazin-3-yl)benzamide | 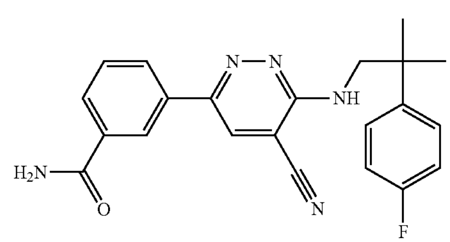 [SMILES: CC(C)(CNc1nnc(-c2cccc(C(N)=O)c2)cc1C#N)c1ccc(F)cc1] | 390.2 | C |
| 6-(3-carbamoylphenyl)-3-{[2-(4-fluorophenyl)-2-methylpropyl]amino}pyridazine-4-carboxamide | 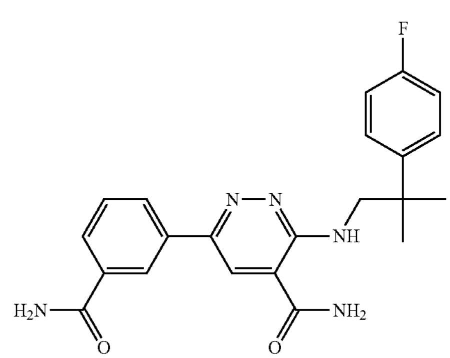 [SMILES: CC(C)(CNc1nnc(-c2cccc(C(N)=O)c2)cc1C(N)=O)c1ccc(F)cc1] | 408.2 | B |

TABLE 2-continued

| Compound | Structure | m/z (M + H) | Mean AC1.4 |
|---|---|---|---|
| 5-[6-({2-[2-(hydroxymethyl)phenyl]-2-methylpropyl}amino)pyridazin-3-yl]-3-hydrobenzimidazol-2-one | 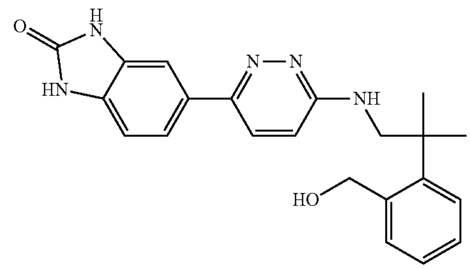 [SMILES: CC(C)(CNc1ccc(-c2ccc3[nH]c(=O)[nH]c3c2)nn1)c1ccccc1CO] | 390.1 | B |
| 1-[(6-{[2-(4-fluorophenyl)-2-methylpropyl]amino}pyridazin-3-yl)carbonyl]piperidine-3-carboxamide | 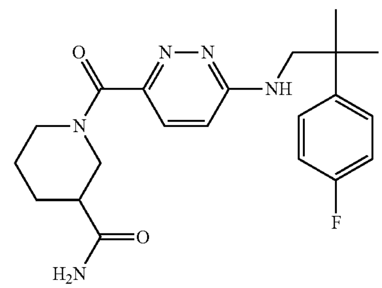 [SMILES: CC(C)(CNc1ccc(C(=O)N2CCCC(C(N)=O)C2)nn1)c1ccc(F)cc1] | 400.1 | D |
| (2S,1R)-2-[(6-{[2-(4-fluorophenyl)-2-methylpropyl]amino}pyridazin-3-yl)carbonylamino]cyclopentanecarboxamide | 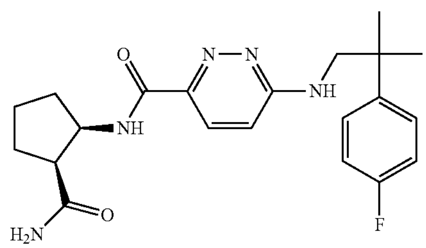 [SMILES: CC(C)(CNc1ccc(C(=O)N[C@@H]2CCC[C@@H]2C(N)=O)nn1)c1ccc(F)cc1] | 400.1 | D |
| N-(2-carbamoylethyl)(6-{[2-(4-fluorophenyl)-2-methylpropyl]amino}pyridazin-3-yl)carboxamide | 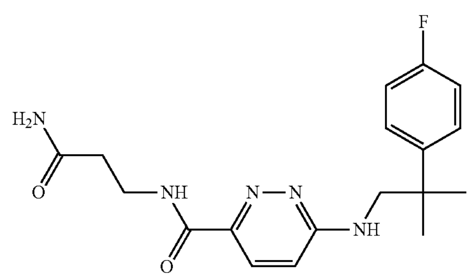 [SMILES: CC(C)(CNc1ccc(C(=O)NCCC(N)=O)nn1)c1ccc(F)cc1] | 360.1 | D |
| 4-[(6-{[2-(4-fluorophenyl)-2-methylpropyl]amino}pyridazin-3-yl)carbonyl]piperazine-2-carboxamide | 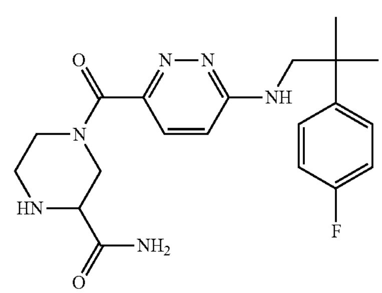 [SMILES: CC(C)(CNc1ccc(C(=O)N2CCNC(C(N)=O)C2)nn1)c1ccc(F)cc1] | 401.1 | D |

TABLE 2-continued

| Compound | Structure | m/z (M + H) | Mean AC1.4 |
|---|---|---|---|
| 1-[(6-{[2-(4-fluorophenyl)-2-methylpropyl]amino}pyridazin-3-yl)carbonyl]pyrrolidine-3-carboxamide | 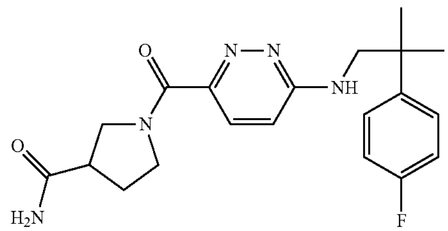 [SMILES: CC(C)(CNc1ccc(C(=O)N2CCC(C(N)=O)C2)nn1)c1ccc(F)cc1] | 386.1 | D |
| 1-[(6-{[2-(4-fluorophenyl)-2-methylpropyl]amino}pyridazin-3-yl)carbonylamino]cyclopropanecarboxamide | 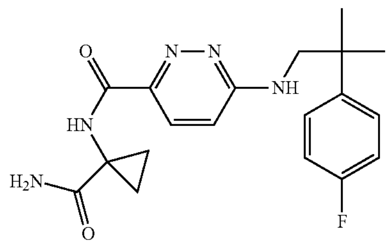 [SMILES: CC(C)(CNc1ccc(C(=O)NC2(C(N)=O)CC2)nn1)c1ccc(F)cc1] | 372.1 | D |
| 5-{6-[(2,2-dimethylpropyl)amino]pyridazin-3-yl}-3-hydrobenzimidazol-2-one | 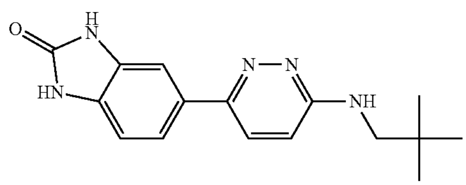 [SMILES: CC(C)(C)CNc1ccc(-c2ccc3[nH]c(=O)[nH]c3c2)nn1] | 298.2 | D |
| 3-(6-{[3-(1,3-dioxolan-2-yl)-2-(2-fluorophenyl)propyl]amino}pyridazin-3-yl)benzamide | 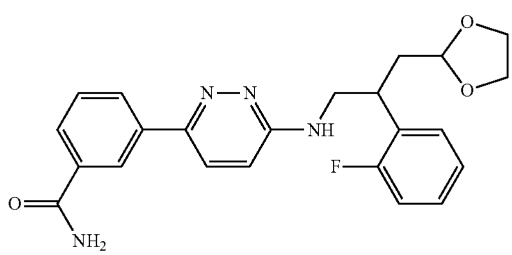 [SMILES: NC(=O)c1cccc(-c2ccc(NCC(CC3OCCO3)c3ccccc3F)nn2)c1] | 423.1 | D |
| 6-{[2-(4-fluorophenyl)-2-methylpropyl]amino}pyridazin-3-yl piperazinyl ketone | 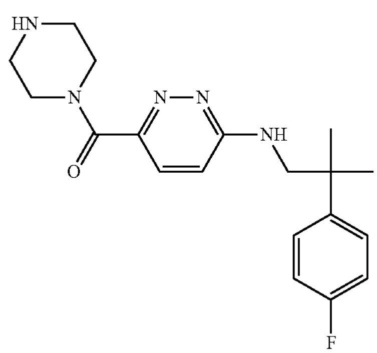 [SMILES: CC(C)(CNc1ccc(C(=O)N2CCNCC2)nn1)c1ccc(F)cc1] | 358.0 | D |
| 4-[(6-{[2-(4-fluorophenyl)-2-methylpropyl]amino}pyridazin-3-yl)carbonyl]piperazinecarboxamide | 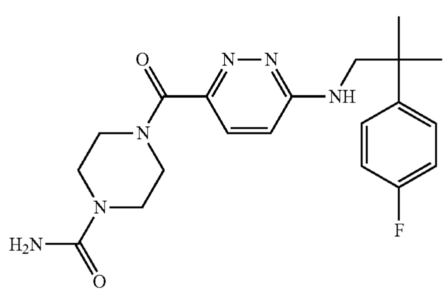 [SMILES: CC(C)(CNc1ccc(C(=O)N2CCN(C(N)=O)CC2)nn1)c1ccc(F)cc1] | 401.0 | D |

TABLE 2-continued

| Compound | Structure | m/z (M + H) | Mean AC1.4 |
|---|---|---|---|
| 5-{6-[(2-methyl-2-phenylpropyl)amino]pyridazin-3-yl}-3-hydrobenzimidazol-2-one | 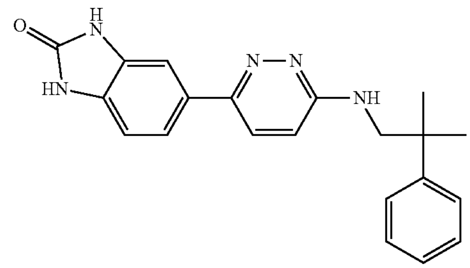 [SMILES: CC(C)(CNc1ccc(-c2ccc3[nH]c(=O)[nH]c3c2)nn1)c1ccccc1] | 360.1 | A |
| 5-(6-{[2-(4-fluorophenyl)-tert-butyl]amino}pyridazin-3-yl)-3-hydrobenzimidazol-2-one | 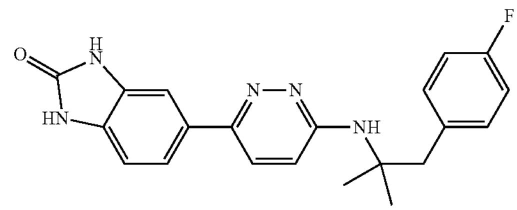 [SMILES: CC(C)(Cc1ccc(F)cc1)Nc1ccc(-c2ccc3[nH]c(=O)[nH]c3c2)nn1] | 378.1 | D |
| (6-{[2-(4-fluorophenyl)-2-methylpropyl]amino}pyridazin-3-yl)-N-pyrazol-5-ylcarboxamide | | 355.1 | D |
| (6-{[2-(4-fluorophenyl)-2-methylpropyl]amino}pyridazin-3-yl)-N-(2-oxo(3-piperidyl))carboxamide | 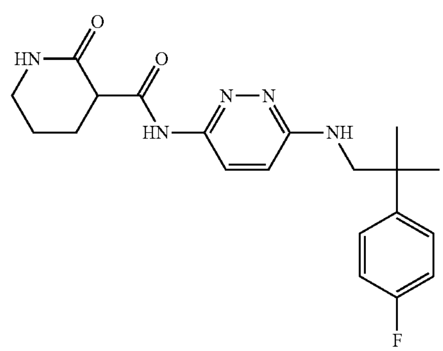 [SMILES: CC(C)(CNc1ccc(NC(=O)C2CCCNC2=O)nn1)c1ccc(F)cc1] | 386.1 | D |
| 4-[(6-{[2-(4-fluorophenyl)-2-methylpropyl]amino}pyridazin-3-yl)carbonylamino)piperidinecarboxamide | | 401.1 | D |

TABLE 2-continued

| Compound | Structure | m/z (M + H) | Mean AC1.4 |
|---|---|---|---|
| (6-{[2-(4-fluorophenyl)-2-methylpropyl]amino}pyridazin-3-yl)-N-[(5-oxopyrrolidin-2-yl)methyl]carboxamide | 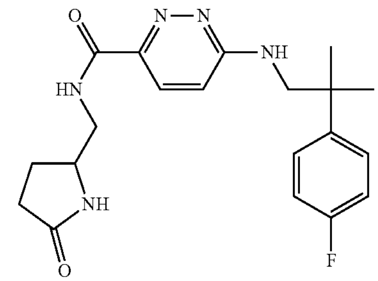 [SMILES: CC(C)(CNc1ccc(C(=O)NCC2CCC(=O)N2)nn1)c1ccc(F)cc1] | 386.2 | C |
| 3-(6-{[2-(2-fluorophenyl)butyl]amino}pyridazin-3-yl)benzamide | 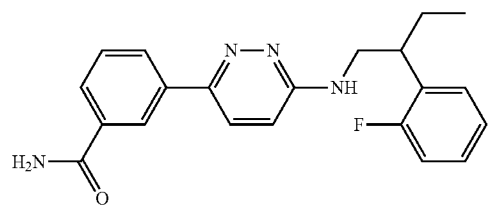 [SMILES: CCC(CNc1ccc(-c2cccc(C(N)=O)c2)nn1)c1ccccc1F] | 365.1 | B |
| (6-{[2-(4-fluorophenyl)-2-methylpropyl]amino}pyridazin-3-yl)-N-(2-oxopyrrolidin-3-yl)carboxamide | 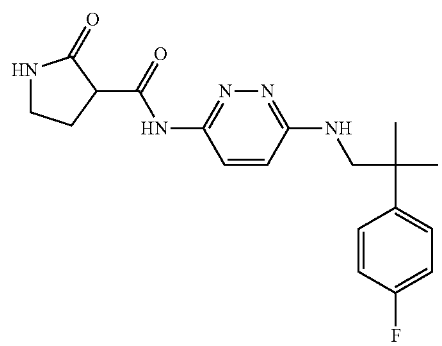 [SMILES: CC(C)(CNc1ccc(NC(=O)C2CCNC2=O)nn1)c1ccc(F)cc1] | 372.1 | C |
| N-{3-[(tert-butoxy)carbonylamino]propyl}[3-(6-{[2-(4-fluorophenyl)-2-methylpropyl]amino}pyridazin-3-yl)phenyl]carboxamide | 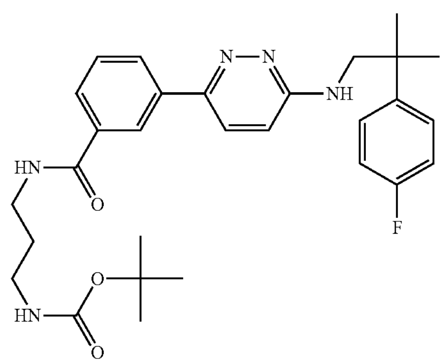 [SMILES: CC(C)(C)OC(=O)NCCCNC(=O)c1cccc(-c2ccc(NCC(C)(C)c3ccc(F)cc3)nn2)c1] | 522.2 | B |
| N-(3-aminopropyl)[3-(6-{[2-(4-fluorophenyl)-2-methylpropyl]amino}pyridazin-3-yl)phenyl]carboxamide | 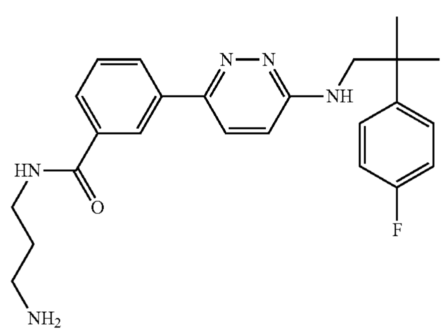 [SMILES: CC(C)(CNc1ccc(-c2cccc(C(=O)NCCCN)c2)nn1)c1ccc(F)cc1] | 422.2 | B |

TABLE 2-continued

| Compound | Structure | m/z (M + H) | Mean AC1.4 |
|---|---|---|---|
| (6-benzimidazol-5-ylpyridazin-3-yl)[2-(4-fluorophenyl)-2-methylpropyl]amine | 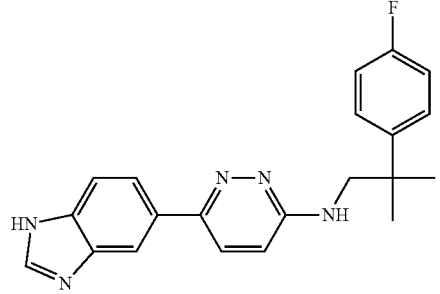 [SMILES: CC(C)(CNc1ccc(-c2ccc3[nH]cnc3c2)nn1)c1ccc(F)cc1] | 362.2 | A |
| [2-(4-fluorophenyl)-2-methylpropyl][6-(2-methylbenzimidazol-5-yl)pyridazin-3-yl]amine | 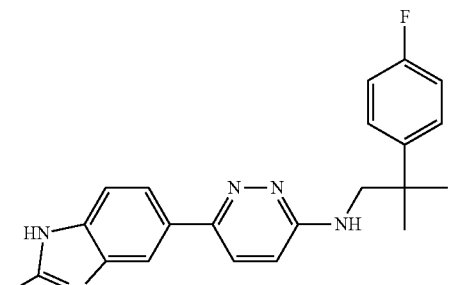 | 376.2 | B |
| [6-(2-aminobenzimidazol-5-yl)pyridazin-3-yl][2-(4-fluorophenyl)-2-methylpropyl]amine | 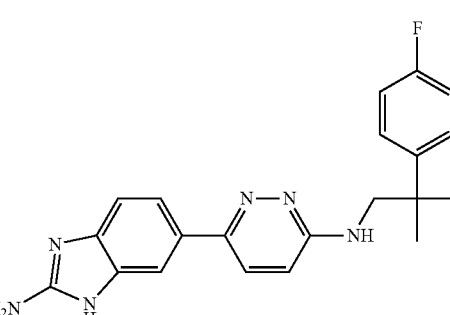 | 377.2 | A |
| [3-(6-{[2-(4-fluorophenyl)-2-methylpropyl]amino}pyridazin-3-yl)phenyl]-N-methylcarboxamide | 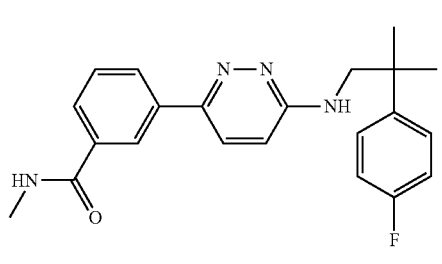 [SMILES: CNC(=O)c1cccc(-c2ccc(NCC(C)(C)c3ccc(F)cc3)nn2)c1] | 379.1 | B |
| 3-(6-{[2-(2-oxopyrrolidinyl)propyl]amino}pyridazin-3-yl)benzamide | 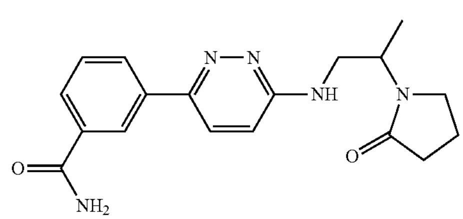 [SMILES: CC(CNc1ccc(-c2cccc(C(N)=O)c2)nn1)N1CCCC1=O] | 340.1 | D |
| 3-(6-{[2-(2-oxopiperidyl)propyl]amino}pyridazin-3-yl)benzamide | 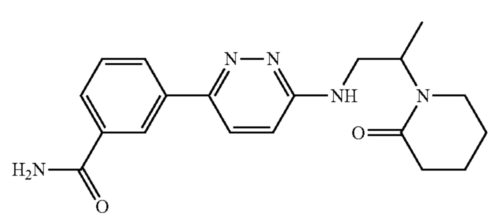 [SMILES: CC(CNc1ccc(-c2cccc(C(N)=O)c2)nn1)N1CCCCC1=O] | 354.1 | D |

TABLE 2-continued

| Compound | Structure | m/z (M + H) | Mean AC1.4 |
|---|---|---|---|
| N-[5-(6-{[2-(4-fluorophenyl)-2-methylpropyl]amino}pyridazin-3-yl)-2-pyridyl]acetamide | 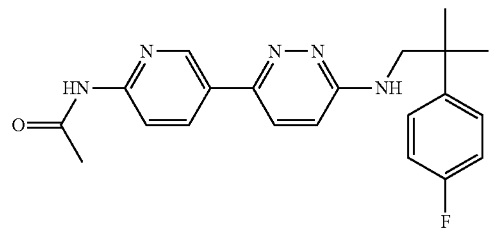 [SMILES: CC(=O)Nc1ccc(-c2ccc(NCC(C)(C)c3ccc(F)cc3)nn2)cn1] | 380.2 | B |
| [2-(4-fluorophenyl)-2-methylpropyl][6-(2-methylbenzoxazol-5-yl)pyridazin-3-yl]amine | 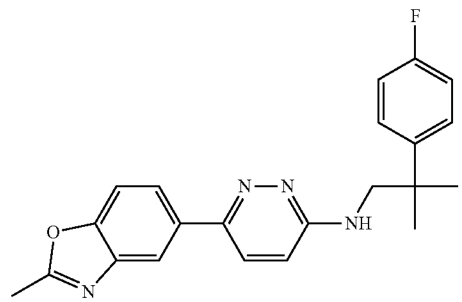 [SMILES: Cc1nc2cc(-c3ccc(NCC(C)(C)c4ccc(F)cc4)nn3)ccc2o1] | 377.2 | B |
| [2-(4-fluorophenyl)-2-methylpropyl][6-(2-methylbenzoxazol-6-yl)pyridazin-3-yl]amine | 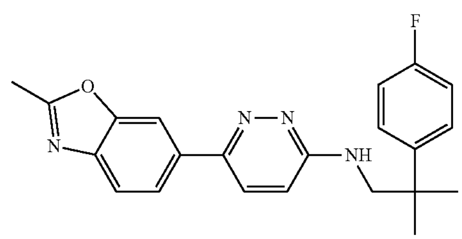 [SMILES: Cc1nc2ccc(-c3ccc(NCC(C)(C)c4ccc(F)cc4)nn3)cc2o1] | 377.2 | B |
| 1-[(6-{[2-(4-fluorophenyl)-2-methylpropyl]amino}pyridazin-3-yl)carbonyl]piperidine-4-carboxamide | 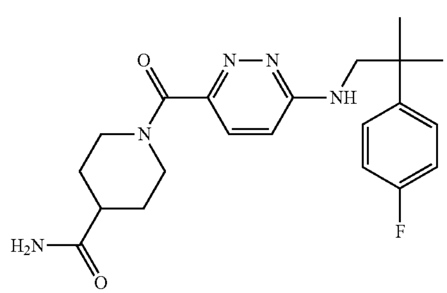 | 400.2 | D |
| N-((1S)-1-carbamoyl-2-phenylethyl)(6-{[2-(4-fluorophenyl)-2-methylpropyl]amino}pyridazin-3-yl)carboxamide | 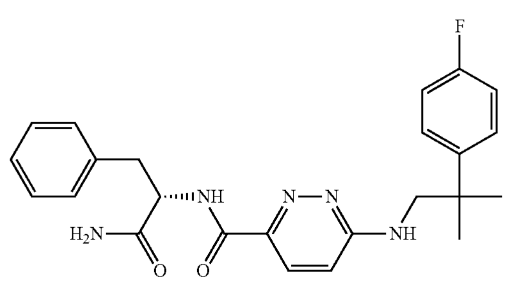 [SMILES: CC(C)(CNc1ccc(C(=O)N[C@@H](Cc2ccccc2)C(N)=O)nn1)c1ccc(F)cc1] | 436.1 | C |

TABLE 2-continued

| Compound | Structure | m/z (M + H) | Mean AC1.4 |
|---|---|---|---|
| N-((1R)-1-carbamoyl-2-phenylethyl)(6-{[2-(4-fluorophenyl)-2-methylpropyl]amino}pyridazin-3-yl)carboxamide | 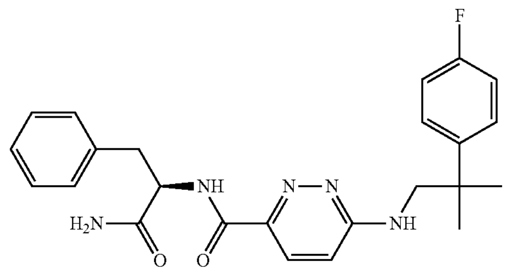 [SMILES: CC(C)(CNc1ccc(C(=O)N[C@H](Cc2ccccc2)C(N)=O)nn1)c1ccc(F)cc1] | 436.1 | C |
| N-(carbamoylmethyl)(6-{[2-(4-fluorophenyl)-2-methylpropyl]amino}pyridazin-3-yl)carboxamide | 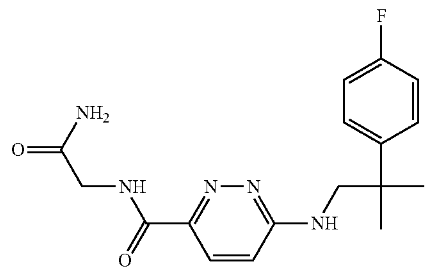 [SMILES: CC(C)(CNc1ccc(C(=O)NCC(N)=O)nn1)c1ccc(F)cc1] | 346.1 | D |
| N-(1,3-dicarbamoylpropyl)(6-{[2-(4-fluorophenyl)-2-methylpropyl]amino}pyridazin-3-yl)carboxamide | 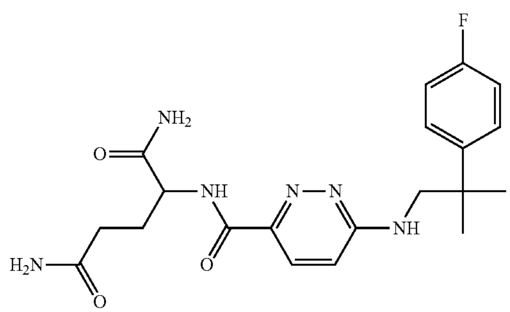 [SMILES: CC(C)(CNc1ccc(C(=O)NC(CCC(N)=O)C(N)=O)nn1)c1ccc(F)cc1] | 417.1 | D |
| 3-(6-{[2-(2-fluorophenyl)propyl]amino}pyridazin-3-yl)benzamide | 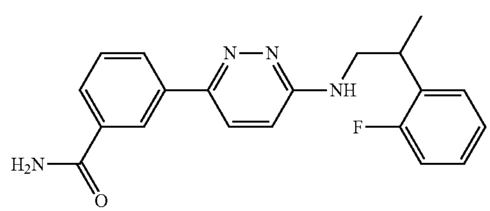 [SMILES: CC(CNc1ccc(-c2cccc(C(N)=O)c2)nn1)c1ccccc1F] | 351.1 | B |
| 3-(6-{[2-(3-fluoro(2-pyridyl))-2-methylpropyl]amino}pyridazin-3-yl)benzamide | 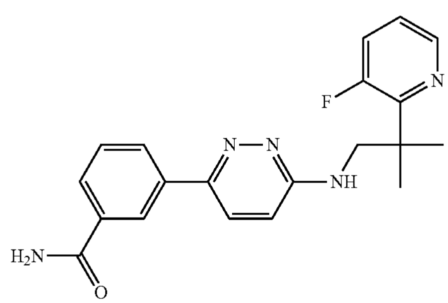 [SMILES: CC(C)(CNc1ccc(-c2cccc(C(N)=O)c2)nn1)c1ncccc1F] | 366.1 | B |

TABLE 2-continued

| Compound | Structure | m/z (M + H) | Mean AC1.4 |
|---|---|---|---|
| 3-(6-{[2-(5-fluoro(2-pyridyl))-2-methylpropyl]amino}pyridazin-3-yl)benzamide | 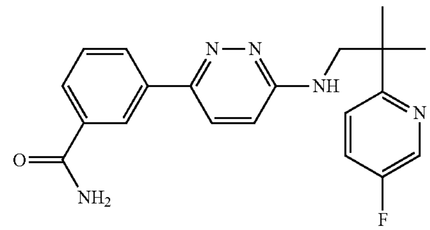 [SMILES: CC(C)(CNc1ccc(-c2cccc(C(N)=O)c2)nn1)c1ccc(F)cn1] | 366.1 | C |
| 3-[6-(3,3-dimethylindolinyl)pyridazin-3-yl]benzamide | 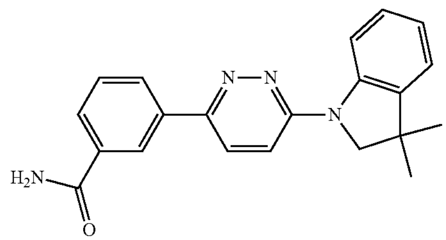 [SMILES: CC1(C)CN(c2ccc(-c3cccc(C(N)=O)c3)nn2)c2ccccc21] | 345.2 | D |
| 6-(6-{[2-(4-fluorophenyl)-2-methylpropyl]amino}pyridazin-3-yl)-3-hydrobenzoxazol-2-one | 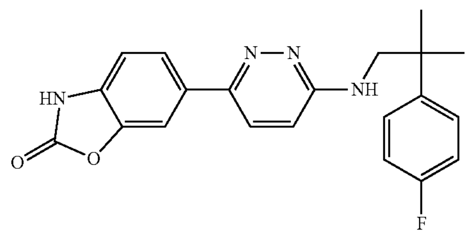 [SMILES: CC(C)(CNc1ccc(-c2ccc3[nH]c(=O)oc3c2)nn1)c1ccc(F)cc1] | 379.2 | A |
| 3-(6-{[2-(4-fluorophenyl)-2-methylpropyl]amino}pyridazin-3-yl)phenyl phenyl ketone | 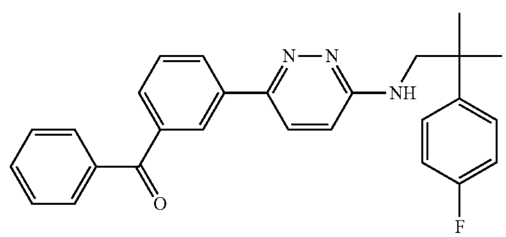 [SMILES: CC(C)(CNc1ccc(-c2cccc(C(=O)c3ccccc3)c2)nn1)c1ccc(F)cc1] | 426.2 | D |
| 4-(6-{[2-(4-fluorophenyl)-2-methylpropyl]amino}pyridazin-3-yl)phenyl phenyl ketone | 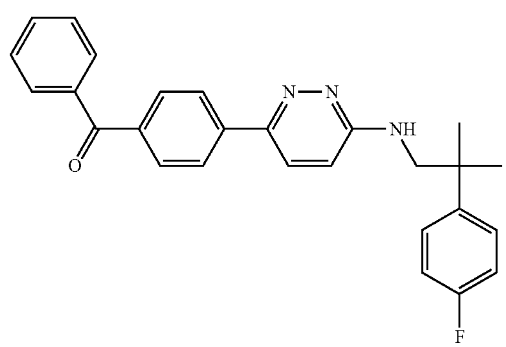 [SMILES: CC(C)(CNc1ccc(-c2ccc(C(=O)c3ccccc3)cc2)nn1)c1ccc(F)cc1] | 426.2 | D |
| [6-(3-amino(1H-indazol-5-yl))pyridazin-3-yl]{[(4-fluorophenyl)cyclopropyl)methyl}amine | | 375.3 | A |

TABLE 2-continued

| Compound | Structure | m/z (M + H) | Mean AC1.4 |
|---|---|---|---|
| [2-(4-fluorophenyl)-2-methylpropyl][6-(3-iodo(1H-indazol-5-yl))pyridazin-3-yl]amine | 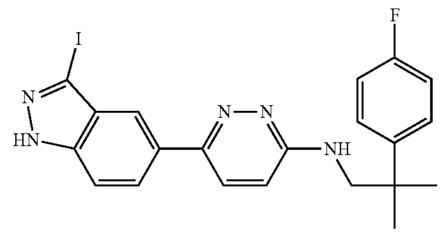 [SMILES: CC(C)(CNc1ccc(-c2ccc3[nH]nc(I)c3c2)nn1)c1ccc(F)cc1] | 488.0 | B |
| [2-(4-fluorophenyl)-2-methylpropyl](6-(4-1,2,5,6-tetrahydropyridyl)pyridazin-3-yl)amine | 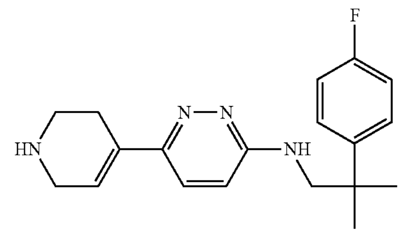 [SMILES: CC(C)(CNc1ccc(C2=CCNCC2)nn1)c1ccc(F)cc1] | 327.2 | B |
| [2-(4-fluorophenyl)-2-methylpropyl](6-pyrazol-3-ylpyridazin-3-yl)amine | 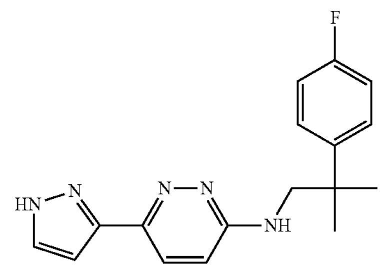 [SMILES: CC(C)(CNc1ccc(-c2cc[nH]n2)nn1)c1ccc(F)cc1] | 312.1 | B |
| 1-acetyl-4-(6-{[2-(4-fluorophenyl)-2-methylpropyl]amino}pyridazin-3-yl)-1,2,5,6-tetrahydropyridine | 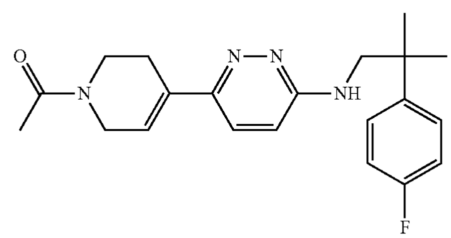 [SMILES: CC(=O)N1CC=C(c2ccc(NCC(C)(C)c3ccc(F)cc3)nn2)CC1] | 369.1 | D |
| methyl 4-(6-{[2-(4-fluorophenyl)-2-methylpropyl]amino}pyridazin-3-yl)-1,2,5,6-tetrahydropyridine-carboxylate | 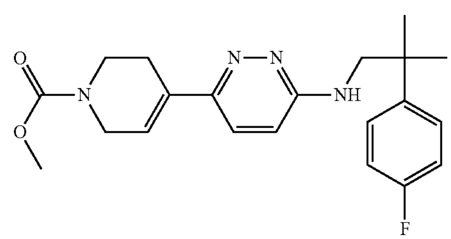 [SMILES: COC(=O)N1CC=C(c2ccc(NCC(C)(C)c3ccc(F)cc3)nn2)CC1] | 385.1 | C |
| 4-(6-{[2-(4-fluorophenyl)-2-methylpropyl]amino}pyridazin-3-yl)-1-(methylsulfonyl)-1,2,5,6-tetrahydropyridine | 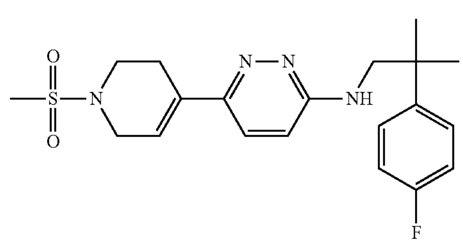 [SMILES: CC(C)(CNc1ccc(C2=CCN(S(C)(=O)=O)CC2)nn1)c1ccc(F)cc1] | 405.1 | B |

TABLE 2-continued

| Compound | Structure | m/z (M + H) | Mean AC1.4 |
|---|---|---|---|
| 4-(6-{[2-(4-fluorophenyl)-2-methylpropyl]amino}pyridazin-3-yl)-1,2,5,6-tetrahydropyridinecarboxamide | 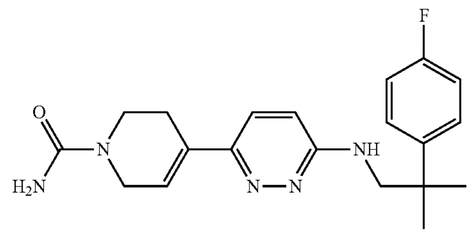 [SMILES: CC(C)(CNc1ccc(C2=CCN(C(N)=O)CC2)nn1)c1ccc(F)cc1] | 370.1 | B |
| 3-{6-[(2-piperidylpropyl)amino]pyridazin-3-yl}benzamide | 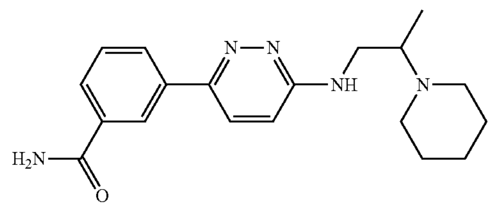 [SMILES: CC(CNc1ccc(-c2cccc(C(N)=O)c2)nn1)N1CCCCC1] | 340.1 | D |
| [6-(3-amino(1H-indazol-5-yl))pyridazin-3-yl](2-piperidylpropyl)amine | 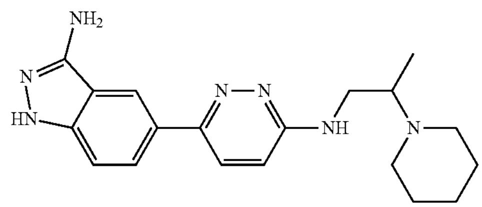 [SMILES: CC(CNc1ccc(-c2ccc3[nH]nc(N)c3c2)nn1)N1CCCCC1] | 352.2 | D |
| 3-{6-[(1,2,3,4-tetrahydronaphthylmethyl)amino]pyridazin-3-yl}benzamide | 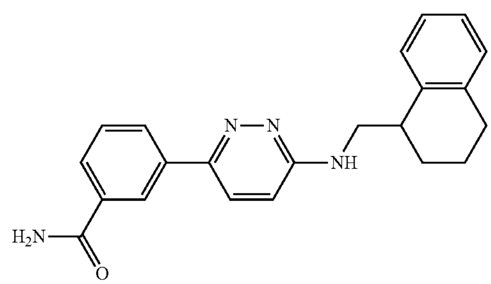 [SMILES: NC(=O)c1cccc(-c2ccc(NCC3CCCc4ccccc43)nn2)c1] | 359.0 | B |
| (tert-butoxy)-N-(2-{[5-(6-{[2-(4-fluorophenyl)-2-methylpropyl]amino}pyridazin-3-yl)(1H-indazol-3-yl)]amino}ethyl)carboxamide | 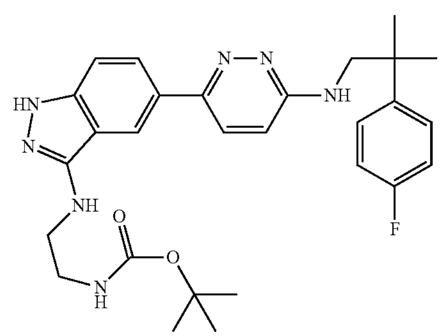 [SMILES: CC(C)(C)OC(=O)NCCNc1n[nH]c2ccc(-c3ccc(NCC(C)(C)c4ccc(F)cc4)nn3)cc12] | 520.2 | A |
| [2-(4-fluorophenyl)-2-methylpropyl](6-pyrrolo[3,2-b]pyridin-6-ylpyridazin-3-yl)amine | 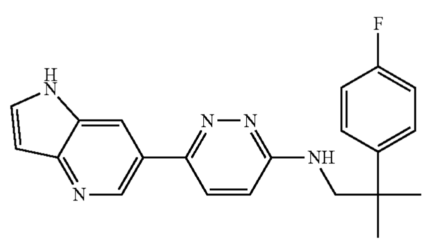 [SMILES: CC(C)(CNc1ccc(-c2cnc3cc[nH]c3c2)nn1)c1ccc(F)cc1] | 362.2 | A |

TABLE 2-continued

| Compound | Structure | m/z (M + H) | Mean AC1.4 |
|---|---|---|---|
| [2-(4-fluorophenyl)-2-methylpropyl](6-pyrazolo[5,4-b]pyridin-5-ylpyridazin-3-yl)amine | 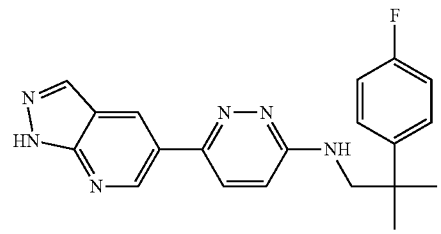 [SMILES: CC(C)(CNc1ccc(-c2cnc3[nH]ncc3c2)nn1)c1ccc(F)cc1] | 363.2 | B |
| 5-(6-{[2-(4-fluorophenyl)-2-methylpropyl]amino}pyridazin-3-yl)-3-hydrobenzoxazol-2-one | 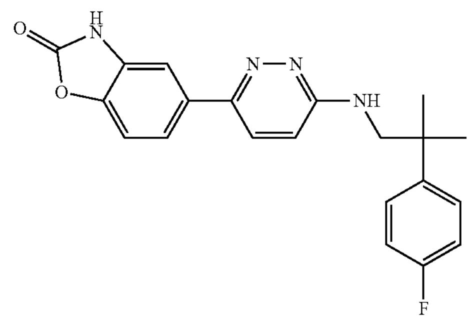 [SMILES: CC(C)(CNc1ccc(-c2ccc3oc(=O)[nH]c3c2)nn1)c1ccc(F)cc1] | 379.2 | B |
| [6-(3-amino(1H-indazol-5-yl))pyridazin-3-yl]{[(2-fluorophenyl)cyclopropyl]methyl}amine | 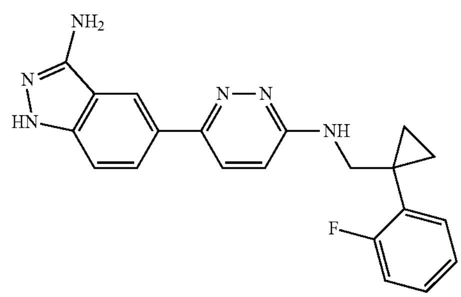 [SMILES: Nc1n[nH]c2ccc(-c3ccc(NCC4(c5ccccc5F)CC4)nn3)cc12] | 375.1 | A |
| [6-(3-amino(1H-indazol-5-yl))pyridazin-3-yl]{[(2-fluorophenyl)cyclobutyl]methyl}amine | 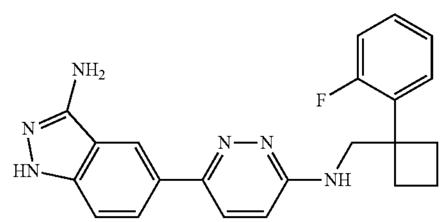 | 389.1 | A |
| [6-(3-amino(1H-indazol-5-yl))pyridazin-3-yl][2,2-difluoro-2-(4-fluorophenyl)ethyl]amine | 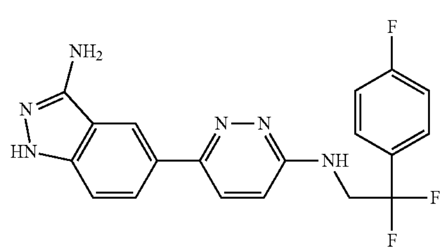 [SMILES: Nc1n[nH]c2ccc(-c3ccc(NCC(F)(F)c4ccc(F)cc4)nn3)cc12] | 385.0 | B |
| 3-[6-(indan-2-ylamino)pyridazin-3-yl]benzamide | 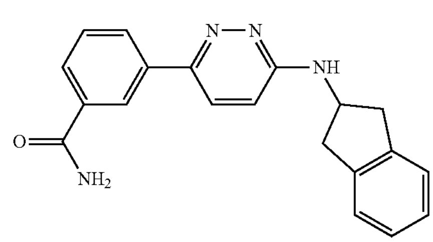 [SMILES: NC(=O)c1cccc(-c2ccc(NC3Cc4ccccc4C3)nn2)c1] | 331.0 | D |

TABLE 2-continued

| Compound | Structure | m/z (M + H) | Mean AC1.4 |
|---|---|---|---|
| 3-{6-[(indanylmethyl)amino]pyridazin-3-yl}benzamide | 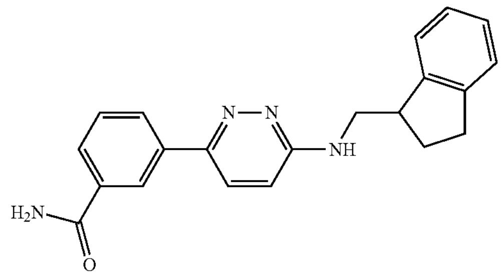 [SMILES: NC(=O)c1cccc(-c2ccc(NCC3CCc4ccccc43)nn2)c1] | 345.0 | B |
| (6-{3-[(2-aminoethyl)amino](1H-indazol-5-yl)}pyridazin-3-yl)[2-(4-fluorophenyl)-2-methylpropyl]amine | 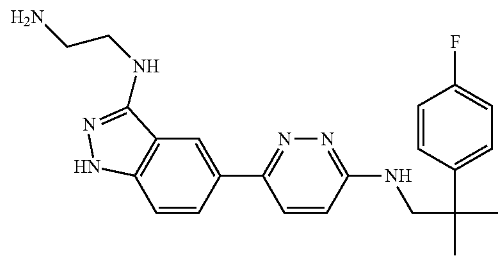 [SMILES: CC(C)(CNc1ccc(-c2ccc3[nH]nc(NCCN)c3c2)nn1)c1ccc(F)cc1] | 420.1 | A |
| 1-(6-{[2-(4-fluorophenyl)-2-methylpropyl]amino}pyridazin-3-yl)ethan-1-one | 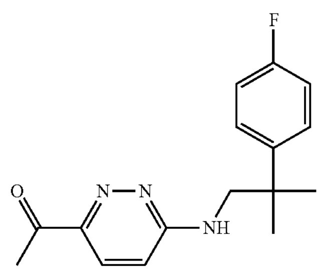 [SMILES: CC(=O)c1ccc(NCC(C)(C)c2ccc(F)cc2)nn1] | 288.1 | D |
| 4-fluoro-3-(6-{[2-(4-fluorophenyl)-2-methylpropyl]amino}pyridazin-3-yl)benzamide | 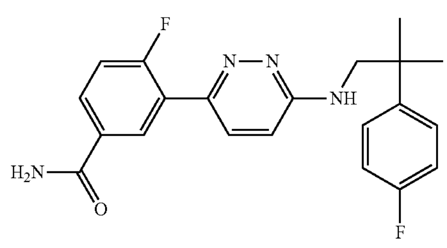 [SMILES: CC(C)(CNc1ccc(-c2cc(C(N)=O)ccc2F)nn1)c1ccc(F)cc1] | 283.1 | A |
| 3-{6-[((2S,1R)-2-phenylcyclopropyl)amino]pyridazin-3-yl}benzamide | 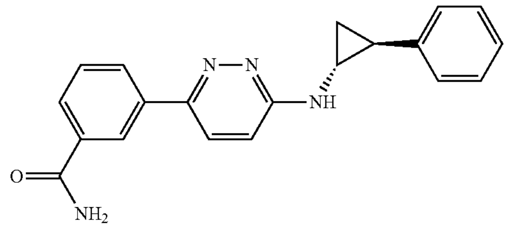 [SMILES: NC(=O)c1cccc(-c2ccc(N[C@@H]3C[C@H]3c3ccccc3)nn2)c1] | 331.0 | D |

TABLE 2-continued

| Compound | Structure | m/z (M + H) | Mean AC1.4 |
|---|---|---|---|
| [2-(4-fluorophenyl)-2-methylpropyl][6-(3-methyl(1H-indazol-6-yl))pyridazin-3-yl]amine | 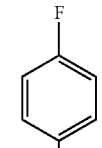 | 376.0 | B |
| [6-(3-amino(1H-indazol-5-yl))pyridazin-3-yl]{[(4-fluorophenyl)cyclobutyl]methyl}amine | 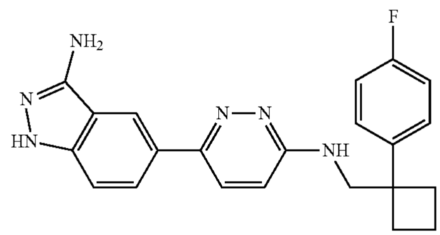 [SMILES: Nc1n[nH]c2ccc(-c3ccc(NCC4(c5ccc(F)cc5)CCC4)nn3)cc12] | 389.1 | A |
| [6-(3-amino(1H-indazol-5-yl))pyridazin-3-yl]{[(2-fluorophenyl)cyclopentyl]methyl}amine | 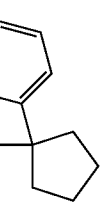 | 403.1 | A |
| [6-(3-amino(1H-indazol-5-yl))pyridazin-3-yl][2-methyl-2-(2-methylphenyl)propyl]amine | 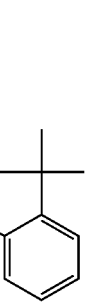 | 373.2 | A |
| [6-(3-amino(1H-indazol-5-yl))pyridazin-3-yl]{[(4-fluorophenyl)cyclohexyl]methyl}amine | 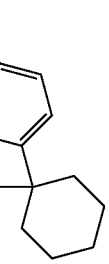 | 417.2 | A |
| [6-(3-amino(1H-indazol-5-yl))pyridazin-3-yl][(phenylcyclopropyl)methyl]amine | 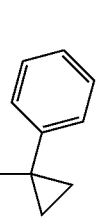 | 357.1 | A |

TABLE 2-continued

| Compound | Structure | m/z (M + H) | Mean AC1.4 |
|---|---|---|---|
| [6-(3-amino(1H-indazol-5-yl))pyridazin-3-yl][(phenylcyclobutyl)methyl]amine | 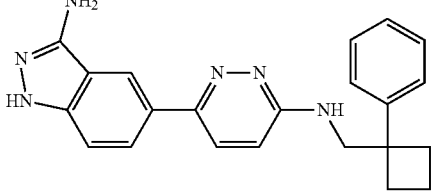 | 371.1 | A |
| [6-(3-amino(1H-indazol-5-yl))pyridazin-3-yl][(2,2-dimethyl-1-phenylcyclopropyl)methyl]amine | 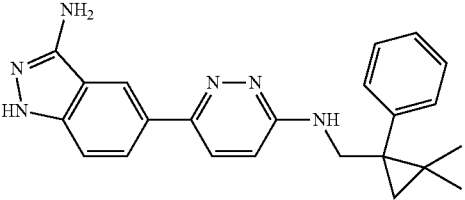 [SMILES: CC1(C)CC1(CNc1ccc(-c2ccc3[nH]nc(N)c3c2)nn1)c1ccccc1] | 385.2 | A |
| 5-(6-{[2-(4-fluorophenyl)-2-methylpropyl]amino}pyridazin-3-yl)-1H-indazole-3-carbonitrile | 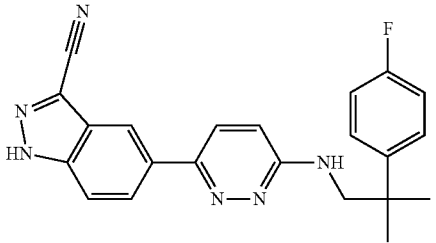 [SMILES: CC(C)(CNc1ccc(-c2ccc3[nH]nc(C#N)c3c2)nn1)c1ccc(F)cc1] | 387.1 | D |
| [6-(3-amino(1H-indazol-5-yl))pyridazin-3-yl]{[(4-fluorophenyl)cyclopentyl]methyl}amine | 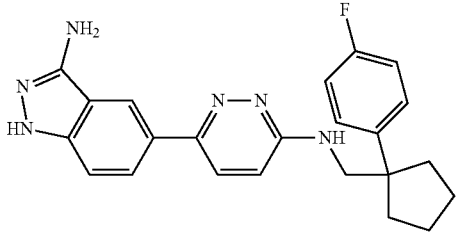 [SMILES: Nc1n[nH]c2ccc(-c3ccc(NCC4(c5ccc(F)cc5)CCCC4)nn3)cc12] | 403.1 | A |
| 5-(6-{[2-(4-fluorophenyl)-2-methylpropyl]amino}pyridazin-3-yl)-1H-indazole-3-carboxamide | 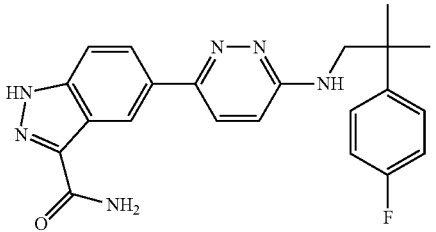 [SMILES: CC(C)(CNc1ccc(-c2ccc3[nH]nc(C(N)=O)c3c2)nn1)c1ccc(F)cc1] | 405.1 | A |
| [4-(2-{[6-(3-amino(1H-indazol-5-yl))pyridazin-3-yl]amino}-tert-butyl)phenyl]methan-1-ol | 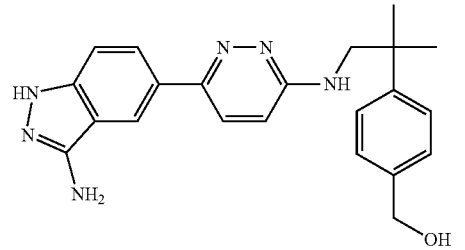 [SMILES: CC(C)(CNc1ccc(-c2ccc3[nH]nc(N)c3c2)nn1)c1ccc(CO)cc1] | 389.2 | D |

TABLE 2-continued

| Compound | Structure | m/z (M + H) | Mean AC1.4 |
|---|---|---|---|
| {[4-(2-{[6-(3-amino(1H-indazol-5-yl))pyridazin-3-yl]amino}-tert-butyl)phenyl]methyl}dimethylamine | 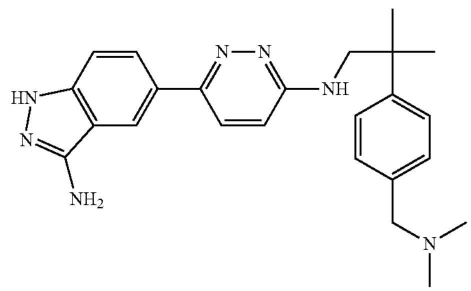 [SMILES: CN(C)Cc1ccc(C(C)(C)CNc2ccc(-c3ccc4[nH]nc(N)c4c3)nn2)cc1] | 416.2 | D |
| [2-(4-fluorophenyl)-2-methylpropyl][6-(3-vinyl(1H-indazol-5-yl))pyridazin-3-yl]amine | 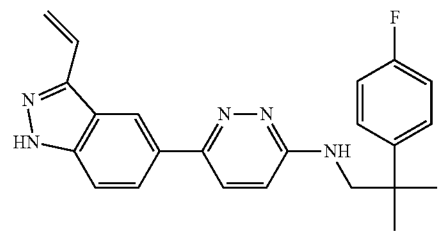 [SMILES: C=Cc1n[nH]c2ccc(-c3ccc(NCC(C)(C)c4ccc(F)cc4)nn3)cc12] | 388.1 | A |
| [6-(3-ethyl(1H-indazol-5-yl))pyridazin-3-yl][2-(4-fluorophenyl)-2-methylpropyl]amine | 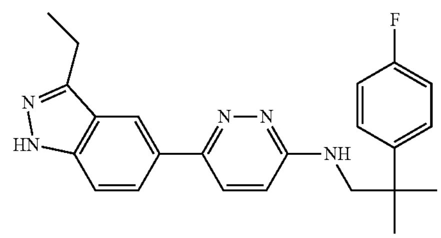 [SMILES: CCc1n[nH]c2ccc(-c3ccc(NCC(C)(C)c4ccc(F)cc4)nn3)cc12] | 390.2 | B |
| 3-(6-{[2-(4-fluorophenyl)-2-methylpropyl]amino}pyridazin-3-yl)-1,2,4-oxadiazole-5-carboxamide | 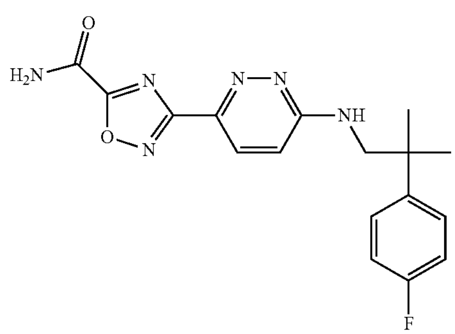 [SMILES: CC(C)(CNc1ccc(-c2noc(C(N)=O)n2)nn1)c1ccc(F)cc1] | 357.1 | C |
| [6-(3-amino(1H-indazol-5-yl))pyridazin-3-yl][2-(3-fluoro(2-pyridyl))-2-methylpropyl]amine | 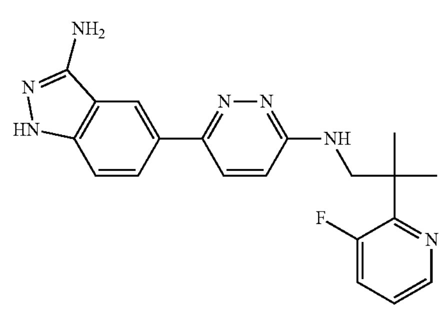 [SMILES: CC(C)(CNc1ccc(-c2ccc3[nH]nc(N)c3c2)nn1)c1ncccc1F] | 378.1 | B |

TABLE 2-continued

| Compound | Structure | m/z (M + H) | Mean AC1.4 |
|---|---|---|---|
| [6-(3-amino(1H-indazol-6-yl))pyridazin-3-yl][2-(3-fluoro(2-pyridyl))-2-methylpropyl]amine | 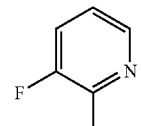 | 378.1 | B |
| [6-(3-amino(1H-indazol-5-yl))pyridazin-3-yl][2-(5-fluoro(2-pyridyl))-2-methylpropyl]amine | 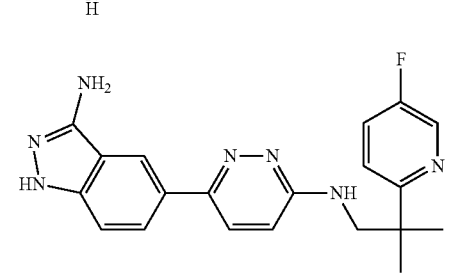 | 378.1 | B |
| [6-(3-amino(1H-indazol-6-yl))pyridazin-3-yl][2-(5-fluoro(2-pyridyl))-2-methylpropyl]amine | 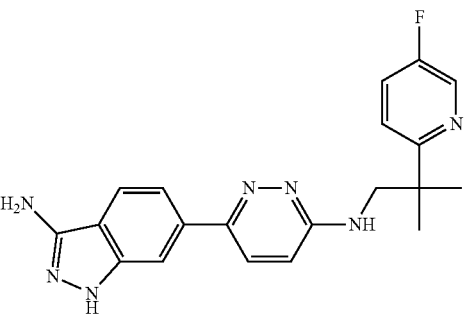 [SMILES: CC(C)(CNc1ccc(-c2ccc3c(N)n[nH]c3c2)nn1)c1ccc(F)cn1] | 378.1 | C |
| 1-[5-(6-{[2-(4-fluorophenyl)-2-methylpropyl]amino}pyridazin-3-yl)-1H-indazol-3-yl]ethane-1,2-diol | 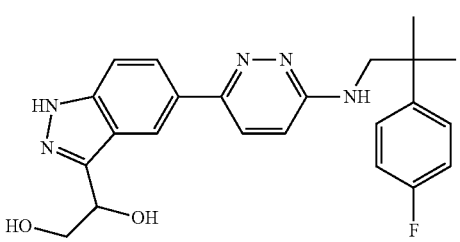 [SMILES: CC(C)(CNc1ccc(-c2ccc3[nH]nc(C(O)CO)c3c2)nn1)c1ccc(F)cc1] | 422.1 | B |
| 2-amino-6-(6-{[2-(4-fluorophenyl)-2-methylpropyl]amino}pyridazin-3-yl)-3-hydropyrimidin-4-one | 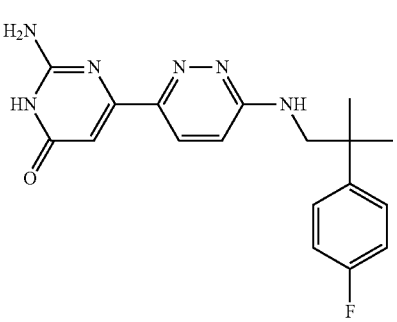 [SMILES: CC(C)(CNc1ccc(-c2cc(=O)[nH]c(N)n2)nn1)c1ccc(F)cc1] | 355.1 | B |

TABLE 2-continued

| Compound | Structure | m/z (M + H) | Mean AC1.4 |
|---|---|---|---|
| N-[6-(2-amino-6-oxohydropyrimidin-4-yl)pyridazin-3-yl](tert-butoxy)-N-[2-(4-fluorophenyl)-2-methylpropyl]carboxamide | 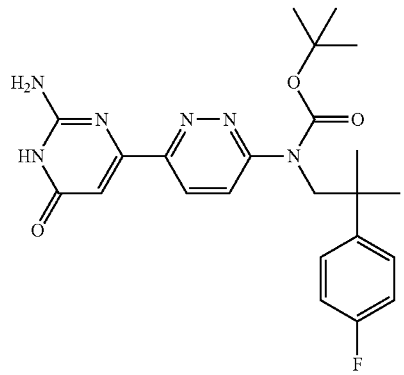 [SMILES: CC(C)(C)OC(=O)N(CC(C)(C)c1ccc(F)cc1)c1ccc(-c2cc(=O)[nH]c(N)n2)nn1] | 455.1 | B |
| 6-(6-{[2-(4-fluorophenyl)-2-methylpropyl]amino}pyridazin-3-yl)-3-hydroquinazolin-4-one | 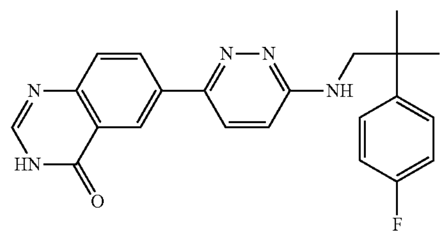 [SMILES: CC(C)(CNc1ccc(-c2ccc3nc[nH]c(=O)c3c2)nn1)c1ccc(F)cc1] | 390.1 | B |
| [6-(3-amino(1H-indazol-5-yl))pyridazin-3-yl](2-methyl-2-(1,3-oxazol-2-yl)propyl)amine | 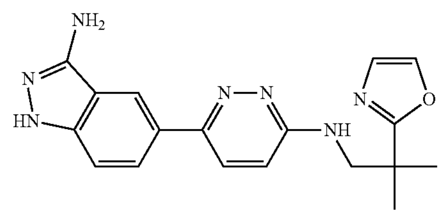 [SMILES: CC(C)(CNc1ccc(-c2ccc3[nH]nc(N)c3c2)nn1)c1ncco1] | 350.3 | D |
| ethyl 2-fluoro-5-(6-{[2-(4-fluorophenyl)-2-methylpropyl]amino}pyridazin-3-yl)benzoate | 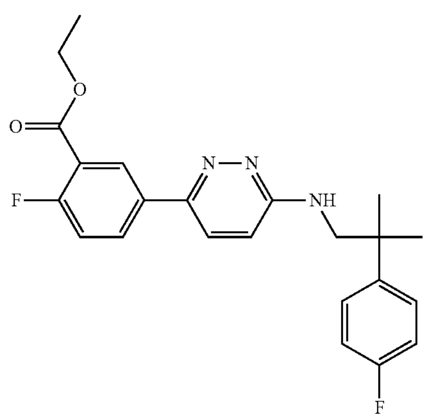 [SMILES: CCOC(=O)c1cc(-c2ccc(NCC(C)(C)c3ccc(F)cc3)nn2)ccc1F] | 412.2 | B |
| 2-amino-6-(6-{[2-(4-fluorophenyl)-2-methylpropyl]amino}pyridazin-3-yl)-3-hydroquinazolin-4-one | 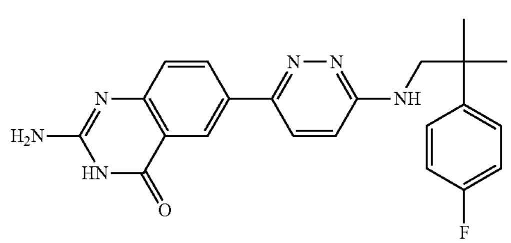 [SMILES: CC(C)(CNc1ccc(-c2ccc3nc(N)[nH]c(=O)c3c2)nn1)c1ccc(F)cc1] | 405.1 | A |

TABLE 2-continued

| Compound | Structure | m/z (M + H) | Mean AC1.4 |
|---|---|---|---|
| 4-(2-{[6-(3-amino(1H-indazol-5-yl))pyridazin-3-yl]amino}-tert-butyl)benzenecarbonitrile | 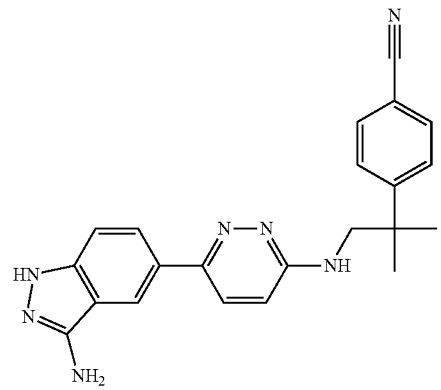 [SMILES: CC(C)(CNc1ccc(-c2ccc3[nH]nc(N)c3c2)nn1)c1ccc(C#N)cc1] | 384.1 | A |
| 4-(2-{[6-(3-amino(1H-indazol-5-yl))pyridazin-3-yl]amino}-tert-butyl)benzamide | 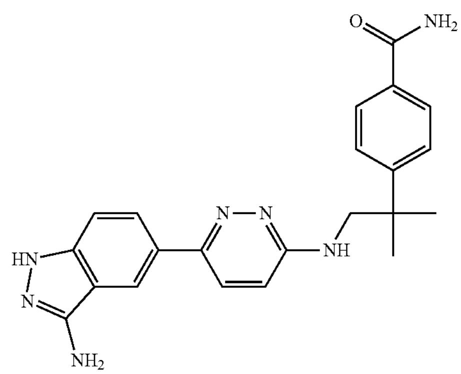 [SMILES: CC(C)(CNc1ccc(-c2ccc3[nH]nc(N)c3c2)nn1)c1ccc(C(N)=O)cc1] | 402.2 | D |
| [6-(3-amino(1H-indazol-5-yl))pyridazin-3-yl]{2-[4-(aminomethyl)phenyl]-2-methylpropyl}amine | | 388.2 | D |
| 5-(6-{[2-(4-fluorophenyl)-2-methylpropyl]amino}pyridazin-3-yl)-1H-indazole-3-carboxamidine | 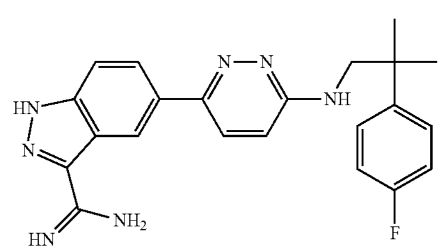 | 404.1 | B |

TABLE 2-continued

| Compound | Structure | m/z (M + H) | Mean AC1.4 |
|---|---|---|---|
| 2-[4-(2-{[6-(3-amino(1H-indazol-5-yl))pyridazin-3-yl]amino}-tert-butyl)phenyl]propan-2-ol | 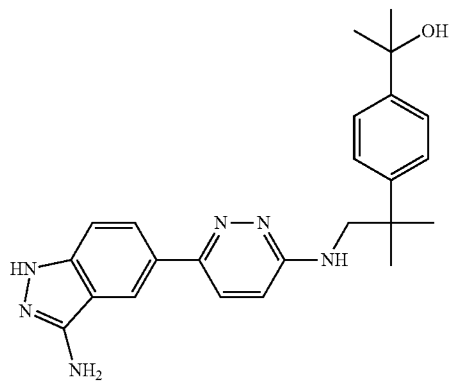 [SMILES: CC(C)(O)c1ccc(C(C)(C)CNc2ccc(-c3ccc4[nH]nc(N)c4c3)nn2)cc1] | 417.2 | D |
| [3-(2-{[6-(3-amino(1H-indazol-5-yl))pyridazin-3-yl]amino}-tert-butyl)phenyl]methan-1-ol | 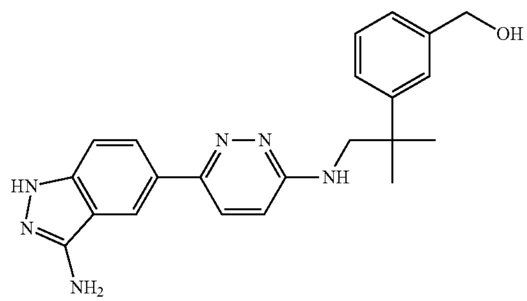 [SMILES: CC(C)(CNc1ccc(-c2ccc3[nH]nc(N)c3c2)nn1)c1cccc(CO)c1] | 389.2 | B |
| 2-[5-(6-{[2-(4-fluorophenyl)-2-methylpropyl]amino}pyridazin-3-yl)-1H-indazol-3-yl]propan-2-ol | 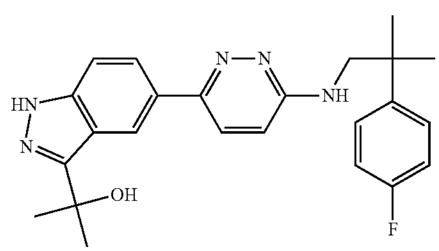 [SMILES: CC(C)(O)c1n[nH]c2ccc(-c3ccc(NCC(C)(C)c4ccc(F)cc4)nn3)cc12] | 420.1 | B |
| 3-(6-{[2-(3,5-difluoro(2-pyridyl))-2-methylpropyl]amino}pyridazin-3-yl)benzamide | 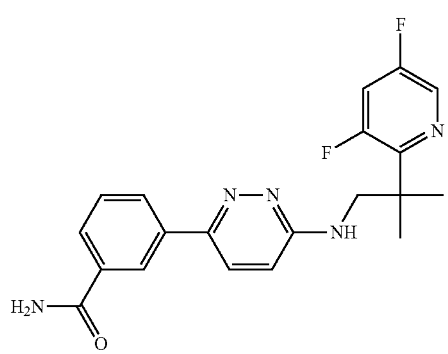 [SMILES: CC(C)(CNc1ccc(-c2cccc(C(N)=O)c2)nn1)c1ncc(F)cc1F] | 384.0 | B |
| [5-(6-{[2-(4-fluorophenyl)-2-methylpropyl]amino}pyridazin-3-yl)-1H-indazol-3-yl]methan-1-ol | 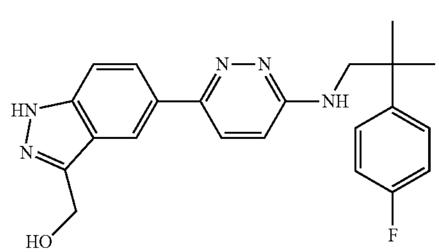 [SMILES: CC(C)(CNc1ccc(-c2ccc3[nH]nc(CO)c3c2)nn1)c1ccc(F)cc1] | 392.1 | A |

TABLE 2-continued
| Compound | Structure | m/z (M + H) | Mean AC1.4 |
|---|---|---|---|
| {[3-(2-{[6-(3-amino(1H-indazol-5-yl))pyridazin-3-yl]amino}-tert-butyl)phenyl]methyl}dimethyl-amine | 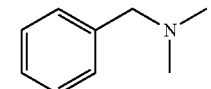 | 416.3 | D |
| 3-(2-{[6-(3-amino(1H-indazol-5-yl))pyridazin-3-yl]amino}-tert-butyl)benzenecarbonitrile | 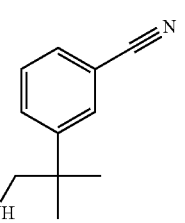 | 384.2 | A |
| 3-(2-{[6-(3-amino(1H-indazol-5-yl))pyridazin-3-yl]amino}-tert-butyl)benzamide | 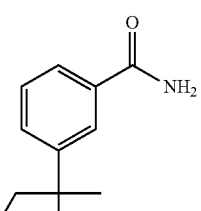 | 402.2 | D |
| 2-[3-(2-{[6-(3-amino(1H-indazol-5-yl))pyridazin-3-yl]amino}-tert-butyl)phenyl]propan-2-ol | 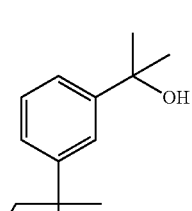 | 417.2 | C |

TABLE 2-continued

| Compound | Structure | m/z (M + H) | Mean AC1.4 |
|---|---|---|---|
| [6-(3-amino(1H-indazol-5-yl))pyridazin-3-yl][2-(3,5-difluoro(2-pyridyl))-2-methylpropyl]amine | 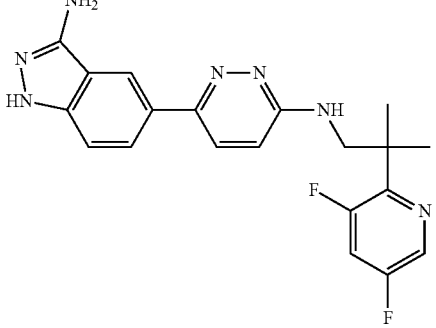 | 396.0 | A |
| [6-(3-amino(1H-indazol-5-yl))pyridazin-3-yl]{[(3-fluoro(2-pyridyl))cyclobutyl]methyl}amine | 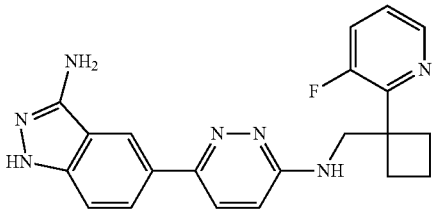 [SMILES: Nc1n[nH]c2ccc(-c3ccc(NCC4(c5ncccc5F)CCC4)nn3)cc12] | 390.0 | A |
| 3-[6-({[(3-fluoro-2-pyridyl)cyclobutyl]methyl}amino)pyridazin-3-yl]benzamide | 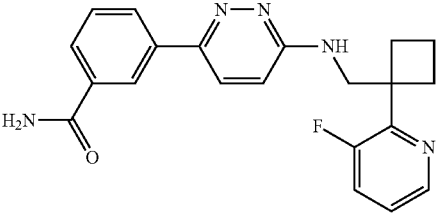 | 378.2 | A |
| N-[5-(6-{[2-(4-fluorophenyl)-2-methylpropyl]amino}pyridazin-3-yl)-1H-indazol-3-yl]acetamide | 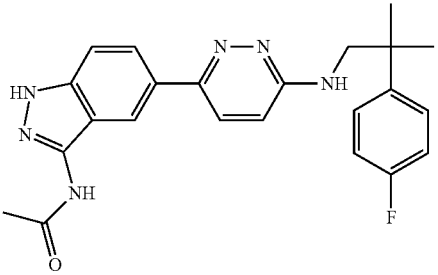 [SMILES: CC(=O)Nc1n[nH]c2ccc(-c3ccc(NCC(C)(C)c4ccc(F)cc4)nn3)cc12] | 419.1 | A |
| [6-(3-aminopyrazolo[5,4-b]pyridin-5-yl)pyridazin-3-yl][2-(4-fluorophenyl)-2-methylpropyl]amine | 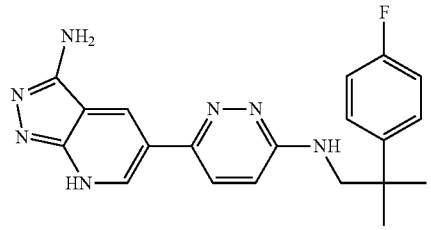 [SMILES: CC(C)(CNc1ccc(-c2c[nH]c3nnc(N)c-3c2)nn1)c1ccc(F)cc1] | 387.3 | A |
| [3-(2-{[6-(3-amino(1H-indazol-5-yl))pyridazin-3-yl]amino}-tert-butyl)phenyl]-N-methylcarboxamide | 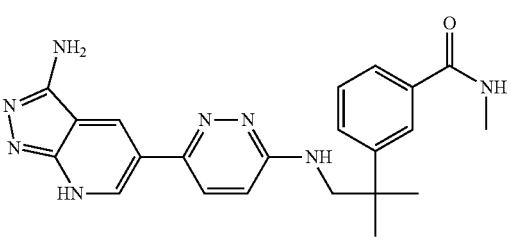 [SMILES: CNC(=O)c1cccc(C(C)(C)CNc2ccc(-c3c[nH]c4nnc(N)c-4c3)nn2)c1] | 416.2 | D |

TABLE 2-continued

| Compound | Structure | m/z (M + H) | Mean AC1.4 |
|---|---|---|---|
| [3-(2-{[6-(3-amino(1H-indazol-5-yl))pyridazin-3-yl]amino}-tert-butyl)phenyl)-N,N-dimethylcarboxamide | 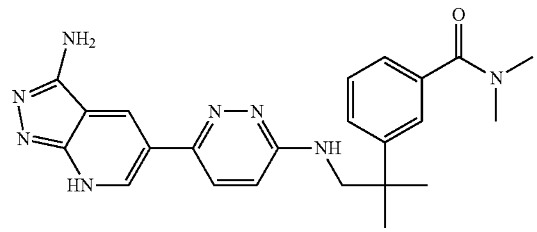 [SMILES: CN(C)C(=O)c1cccc(C(C)(C)CNc2ccc(-c3c[nH]c4nnc(N)c-4c3)nn2)c1] | 430.2 | C |
| [5-(6-{[2-(4-fluorophenyl)-2-methylpropyl]amino}pyridazin-3-yl)(1H-indazol-3-yl)](methylsulfonyl(amine | 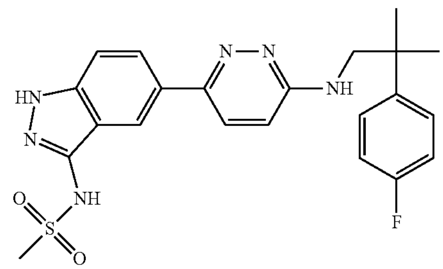 [SMILES: CC(C)(CNc1ccc(-c2ccc3[nH]nc(NS(C)(=O)=O)c3c2)nn1)c1ccc(F)cc1] | 455.1 | A |
| [2-(2-{[6-(3-amino(1H-indazol-5-yl))pyridazin-3-yl]amino}-tert-butyl)phenyl]methan-1-ol | 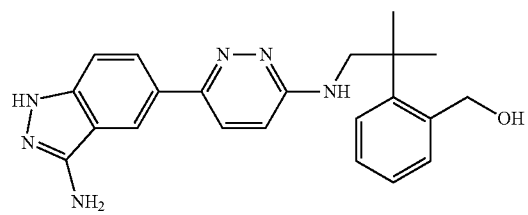 [SMILES: CC(C)(CNc1ccc(-c2ccc3[nH]nc(N)c3c2)nn1)c1ccccc1CO] | 389.1 | B |
| [6-(3-amino(1H-indazol-5-yl))pyridazin-3-yl]{2-[3-(aminomethyl)phenyl]-2-methylpropyl}amine | 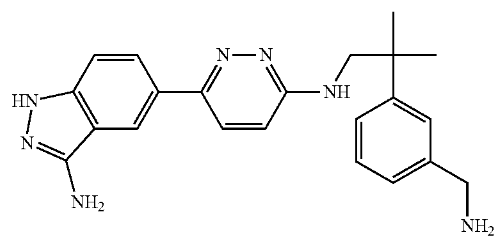 [SMILES: CC(C)(CNc1ccc(-c2ccc3[nH]nc(N)c3c2)nn1)c1cccc(CN)c1] | 388.2 | C |
| {[(4-fluorophenyl)cyclobutyl]methyl}[6-(2-methoxypyrimidin-5-yl)pyridazin-3-yl]amine | 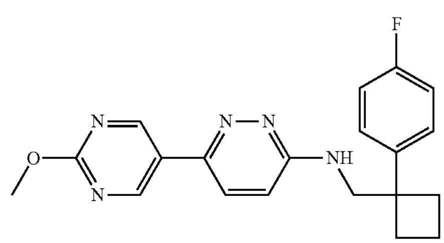 [SMILES: COc1ncc(-c2ccc(NCC3(c4ccc(F)cc4)CCC3)nn2)cn1] | 366.1 | B |
| 5-[6-({[(4-fluorophenyl)cyclobutyl]methyl}amino)pyridazin-3-yl]-3-hydropyrimidin-2-one | 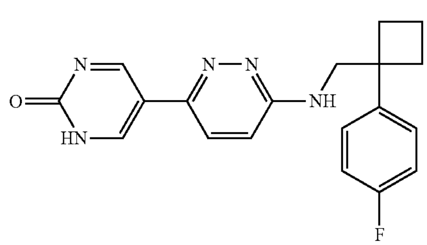 [SMILES: O=c1ncc(-c2ccc(NCC3(c4ccc(F)cc4)CCC3)nn2)c[nH]1] | 352.1 | B |

TABLE 2-continued

| Compound | Structure | m/z (M + H) | Mean AC1.4 |
|---|---|---|---|
| 5-(6-{[2-(4-fluorophenyl)-2-methylpropyl]amino}pyridazin-3-yl)-1H-indazole-7-carboxamide | 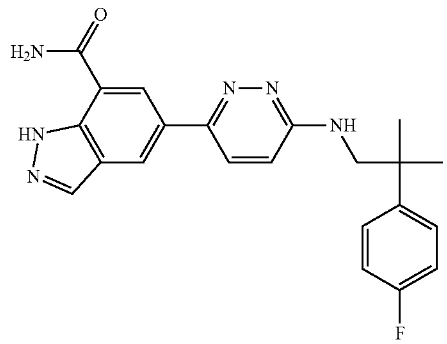 [SMILES: CC(C)(CNc1ccc(-c2cc(C(N)=O)c3[nH]ncc3c2)nn1)c1ccc(F)cc1] | 405.1 | B |
| [6-(3-amino(1H-indazol-5-yl))pyridazin-3-yl][2-(3-methoxyphenyl)-2-methylpropyl]amine | 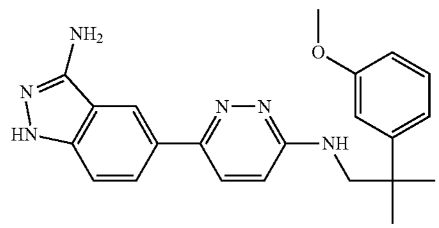 [SMILES: COc1cccc(C(C)(C)CNc2ccc(-c3ccc4[nH]nc(N)c4c3)nn2)c1] | 389.1 | A |
| [6-(3-amino(1H-indazol-5-yl))pyridazin-3-yl][2-methyl-2-(4-methylphenyl)propyl]amine | 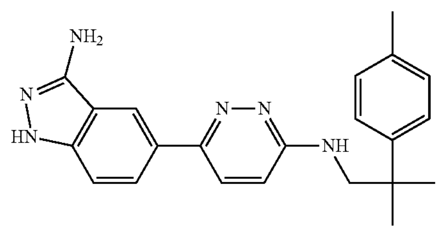 [SMILES: Cc1ccc(C(C)(C)CNc2ccc(-c3ccc4[nH]nc(N)c4c3)nn2)cc1] | 373.1 | A |
| 2-[3-(2-{[6-(3-amino(1H-indazol-5-yl))pyridazin-3-yl]amino}-tert-butyl)phenyl]ethan-1-ol | 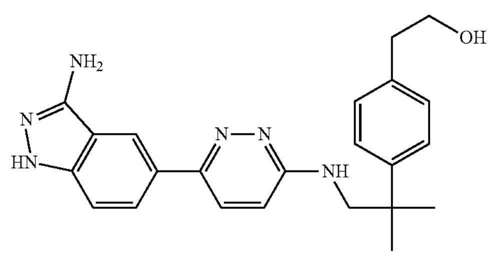 [SMILES: CC(C)(CNc1ccc(-c2ccc3[nH]nc(N)c3c2)nn1)c1ccc(CCO)cc1] | 403.2 | B |
| [6-(3-amino(1H-indazol-5-yl))pyridazin-3-yl]{[(5-fluoro(2-pyridyl))cyclobutyl]methyl}amine | 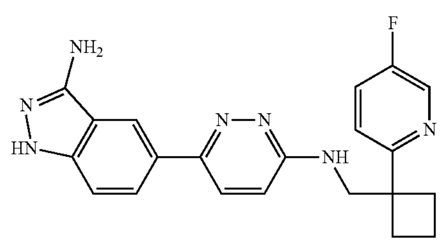 [SMILES: Nc1n[nH]c2ccc(-c3ccc(NCC4(c5ccc(F)cn5)CCC4)nn3)cc12] | 390.0 | A |
| 3-[6-({[(5-fluoro-2-pyridyl)cyclobutyl]methyl}amino)pyridazin-3-yl]benzamide | 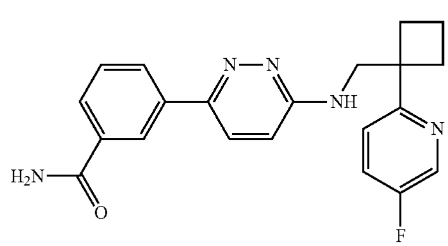 [SMILES: NC(=O)c1cccc(-c2ccc(NCC3(c4ccc(F)cn4)CCC3)nn2)c1] | 378.0 | B |

TABLE 2-continued

| Compound | Structure | m/z (M + H) | Mean AC1.4 |
|---|---|---|---|
| (tert-butoxy)-N-[6-(2,3-dioxo(1,4-dihydroquinoxalin-6-yl))pyridazin-3-yl]-N-[2-(4-fluorophenyl)-2-methylpropyl]carboxamide | 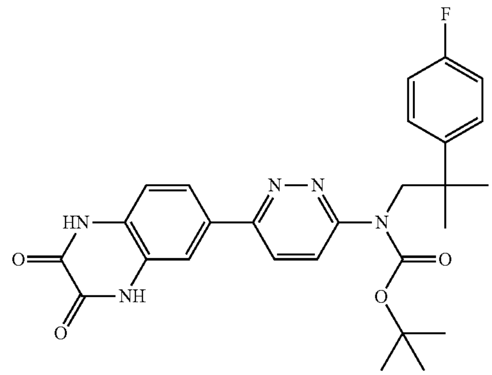 [SMILES: CC(C)(C)OC(=O)N(CC(C)(C)c1ccc(F)cc1)c1ccc(-c2ccc3[nH]c(=O)c(=O)[nH]c3c2)nn1] | 506.1 | D |
| {2-[3-(2-{[6-(3-amino(1H-indazol-5-yl))pyridazin-3-yl]amino}-tert-butyl)phenyl]ethyl}dimethylamine | 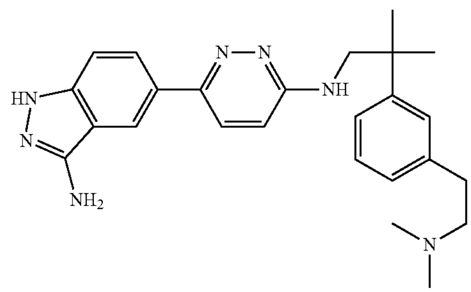 [SMILES: CN(C)CCc1cccc(C(C)(C)CNc2ccc(-c3ccc4[nH]nc(N)c4c3)nn2)c1] | 430.2 | D |
| 3-(2-{[6-(3-amino(1H-indazol-5-yl))pyridazin-3-yl]amino}-tert-butyl)phenol | 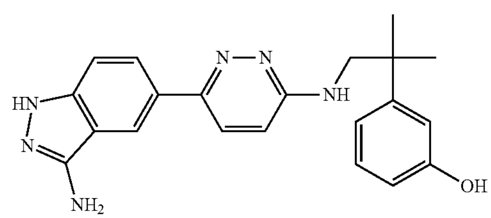 [SMILES: CC(C)(CNc1ccc(-c2ccc3[nH]nc(N)c3c2)nn1)c1cccc(O)c1] | 375.1 | B |
| 6-(6-{[2-(4-fluorophenyl)-2-methylpropyl]amino}pyridazin-3-yl)-1,4-dihydroquinoxaline-2,3-dione | 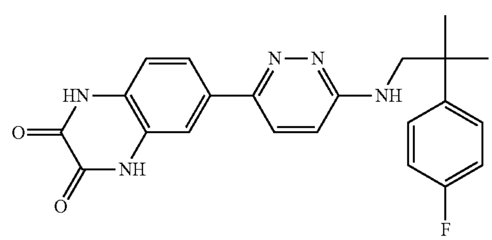 [SMILES: CC(C)(CNc1ccc(-c2ccc3[nH]c(=O)c(=O)[nH]c3c2)nn1)c1ccc(F)cc1] | 406.1 | A |
| [6-(3-amino(1H-indazol-5-yl))pyridazin-3-yl]{2-[2-(methoxymethyl)phenyl]-2-methylpropyl}amine | 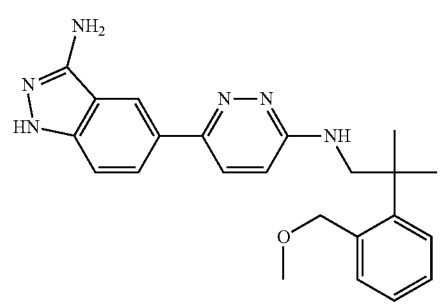 [SMILES: COCc1ccccc1C(C)(C)CNc1ccc(-c2ccc3[nH]nc(N)c3c2)nn1] | 403.2 | C |

TABLE 2-continued

| Compound | Structure | m/z (M + H) | Mean AC1.4 |
|---|---|---|---|
| 3-(6-{(tert-butoxy)-N-[2-(3-fluoro(2-pyridyl))-2-methylpropyl]carbonylamino}pyridazin-3-yl)benzamide | 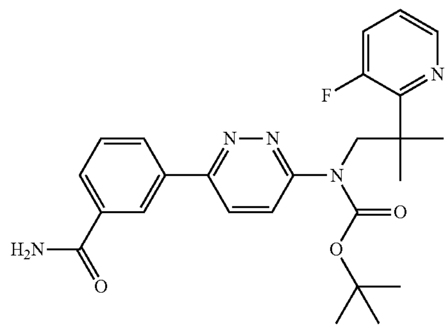 [SMILES: CC(C)(C)OC(=O)N(CC(C)(C)c1ncccc1F)c1ccc(-c2cccc(C(N)=O)c2)nn1] | 466.1 | D |
| (tert-butoxy)-N-[2-(3-fluoro(2-pyridyl))-2-methylpropyl]-N-[6-(2-hydroxybenzimidazol-5-yl)pyridazin-3-yl]carboxamide | 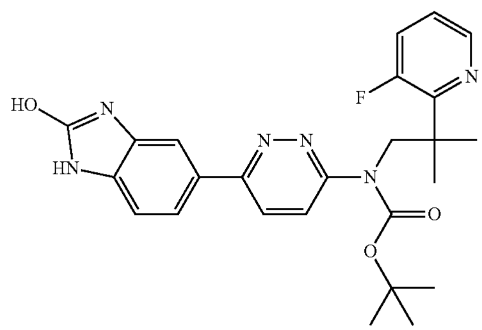 [SMILES: CC(C)(C)OC(=O)N(CC(C)(C)c1ncccc1F)c1ccc(-c2ccc3[nH]c(O)nc3c2)nn1] | 479.1 | D |
| 5-(6-{[2-(3-fluoro(2-pyridyl))-2-methylpropyl]amino}pyridazin-3-yl)benzimidazol-2-ol | 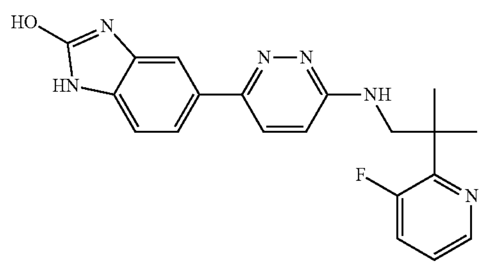 [SMILES: CC(C)(CNc1ccc(-c2ccc3[nH]c(O)nc3c2)nn1)c1ncccc1F] | 379.1 | A |
| (6-(1H-indazol-5-yl)pyridazin-3-yl)[2-(3-fluoro(2-pyridyl))-2-methylpropyl]amine | 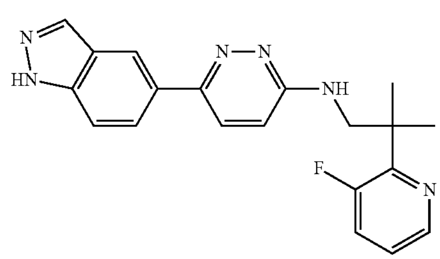 [SMILES: CC(C)(CNc1ccc(-c2ccc3[nH]ncc3c2)nn1)c1ncccc1F] | 363.1 | B |
| N-[6-(6-{[2-(4-fluorophenyl)-2-methylpropyl]amino}pyridazin-3-yl)benzimidazol-2-yl]acetamide | 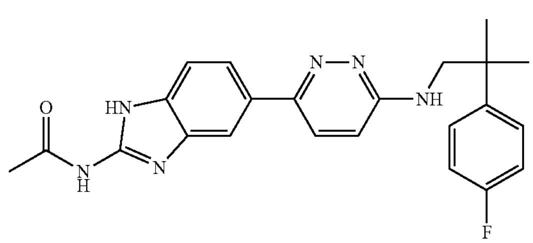 [SMILES: CC(=O)Nc1nc2cc(-c3ccc(NCC(C)(C)c4ccc(F)cc4)nn3)ccc2[nH]1] | 419.1 | A |

TABLE 2-continued

| Compound | Structure | m/z (M + H) | Mean AC1.4 |
|---|---|---|---|
| 6-(6-{[2-(4-fluorophenyl)-2-methylpropyl]amino}pyridazin-3-yl)-1,3-dihydroquinazoline-2,4-dione | 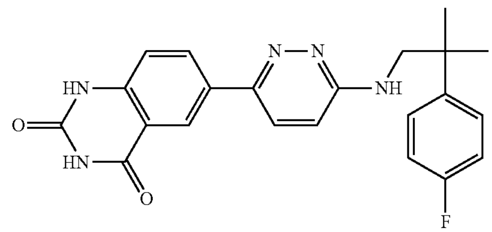 [SMILES: CC(C)(CNc1ccc(-c2ccc3[nH]c(=O)[nH]c(=O)c3c2)nn1)c1ccc(F)cc1] | 406.1 | B |
| 4-[6-({[(3-fluoro-2-pyridyl)cyclobutyl]methyl}amino)pyridazin-3-yl]benzamide | 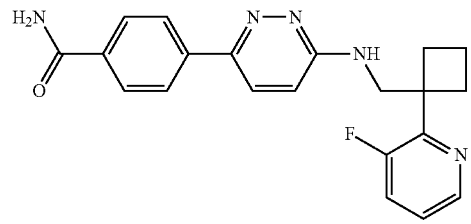 [SMILES: NC(=O)c1ccc(-c2ccc(NCC3(c4ncccc4F)CCC3)nn2)cc1] | 378.0 | B |
| 4-fluoro-3-[6-({[(3-fluoro(2-pyridyl))cyclobutyl]methyl}amino)pyridazin-3-yl]benzamide | 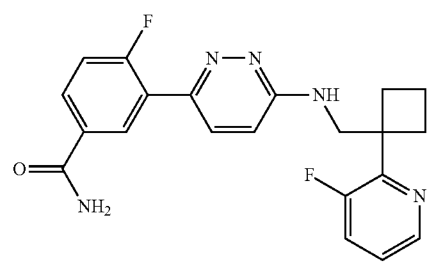 [SMILES: NC(=O)c1ccc(F)c(-c2ccc(NCC3(c4ncccc4F)CCC3)nn2)c1] | 396.2 | A |
| (6-(1H-indazol-5-yl)pyridazin-3-yl){[(3-fluoro(2-pyridyl))cyclobutyl]methyl}amine | 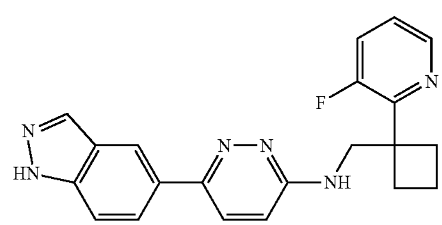 [SMILES: Fc1cccnc1C1(CNc2ccc(-c3ccc4[nH]ncc4c3)nn2)CCC1] | 375.0 | A |
| 2-(6-{[2-(4-fluorophenyl)-2-methylpropyl]amino}pyridazin-3-yl)pyridine-4-carboxamide | 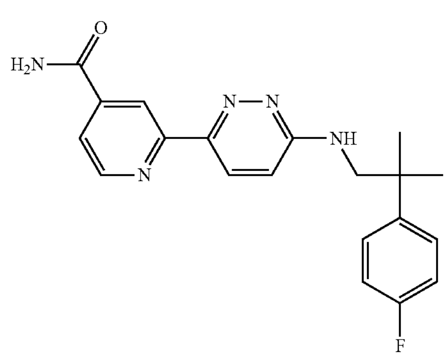 | 366.0 | A |

TABLE 2-continued

| Compound | Structure | m/z (M + H) | Mean AC1.4 |
|---|---|---|---|
| 6-(6-{[2-(4-fluorophenyl)-2-methylpropyl]amino}pyridazin-3-yl)pyridine-2-carboxamide | 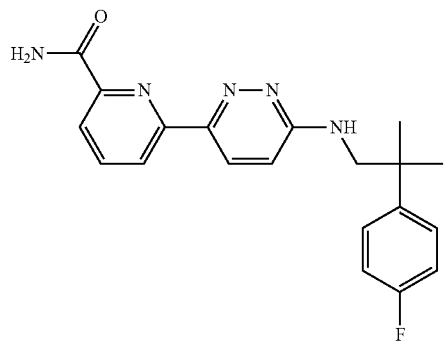 [SMILES: CC(C)(CNc1ccc(-c2cccc(C(N)=O)n2)nn1)c1ccc(F)cc1] | 366.1 | B |
| 3-(6-{(tert-butoxy)-N-[2-(4-fluorophenyl)-2-methylpropyl]carbonylamino}pyridazin-3-yl)benzamide | 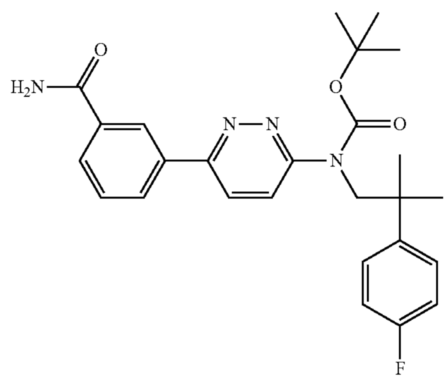 [SMILES: CC(C)(C)OC(=O)N(CC(C)(C)c1ccc(F)cc1)c1ccc(-c2cccc(C(N)=O)c2)nn1] | 465.3 | D |
| 3-(6-{(tert-butoxy)-N-[2-(4-fluorophenyl)-2-methylpropyl]carbonylamino}pyridazin-3-yl)-4-fluorobenzamide | 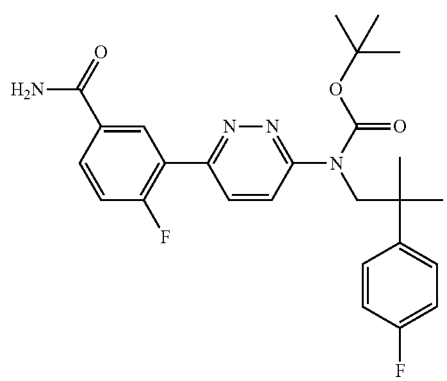 [SMILES: CC(C)(C)OC(=O)N(CC(C)(C)c1ccc(F)cc1)c1ccc(-c2cc(C(N)=O)ccc2F)nn1] | 483.3 | D |
| (6-(1H-indazol-6-yl)pyridazin-3-yl){[(3-fluoro(2-pyridyl))cyclobutyl]methyl}amine | 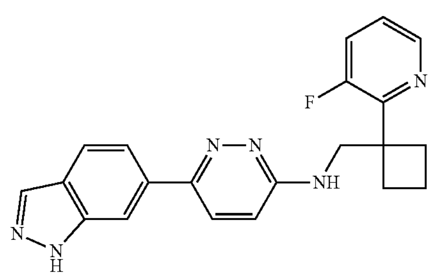 [SMILES: Fc1cccnc1C1(CNc2ccc(-c3ccc4cn[nH]c4c3)nn2)CCC1] | 375.0 | A |

TABLE 2-continued

| Compound | Structure | m/z (M + H) | Mean AC1.4 |
|---|---|---|---|
| (6-(1H-indazol-6-yl)pyridazin-3-yl){[(6-methoxy(2-pyridyl))cyclobutyl]methyl}amine | 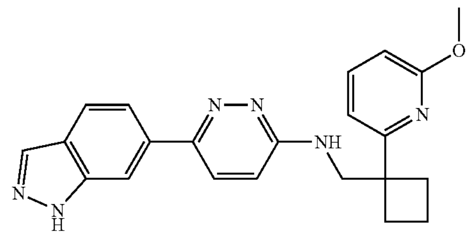 [SMILES: COc1cccc(C2(CNc3ccc(-c4ccc5cn[nH]c5c4)nn3)CCC2)n1] | 387.1 | A |
| (6-(1H-indazol-5-yl)pyridazin-3-yl){[(6-methoxy(2-pyridyl))cyclobutyl]methyl}amine | 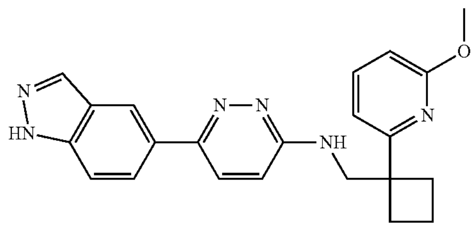 [SMILES: COc1cccc(C2(CNc3ccc(-c4ccc5[nH]ncc5c4)nn3)CCC2)n1] | 387.1 | A |
| 4-fluoro-3-[6-({[(6-methoxy(2-pyridyl))cyclobutyl]methyl}amino)pyridazin-3-yl]benzamide | 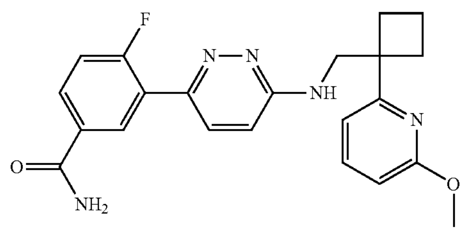 [SMILES: COc1cccc(C2(CNc3ccc(-c4cc(C(N)=O)ccc4F)nn3)CCC2)n1] | 408.1 | A |
| 4-fluoro-3-(6-{[(2-pyridylcyclobutyl)methyl]amino}pyridazin-3-yl)benzamide | 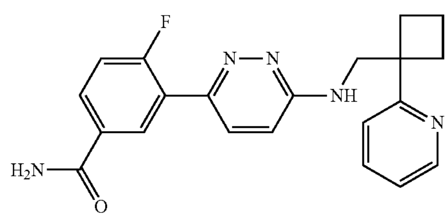 [SMILES: NC(=O)c1ccc(F)c(-c2ccc(NCC3(c4ccccn4)CCC3)nn2)c1] | 378.1 | A |
| (6-(1H-indazol-5-yl)pyridazin-3-yl)[(2-pyridylcyclobutyl)methyl]amine | 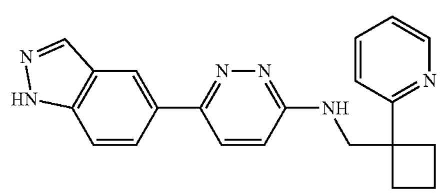 [SMILES: c1ccc(C2(CNc3ccc(-c4ccc5[nH]ncc5c4)nn3)CCC2)nc1] | 357.2 | A |
| (6-(1H-indazol-6-yl)pyridazin-3-yl)[(2-pyridylcyclobutyl)methyl]amine | 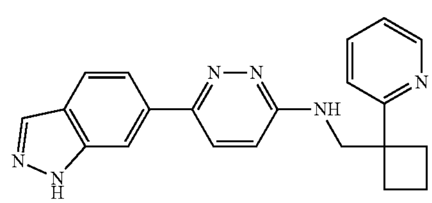 [SMILES: c1ccc(C2(CNc3ccc(-c4ccc5cn[nH]c5c4)nn3)CCC2)nc1] | 357.2 | A |
| 2-fluoro-3-[6-({[(3-fluoro(2-pyridyl))cyclobutyl]methyl}amino)pyridazin-3-yl]benzamide | 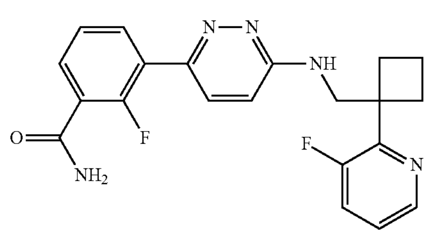 [SMILES: NC(=O)c1cccc(-c2ccc(NCC3(c4ncccc4F)CCC3)nn2)c1F] | 396.0 | B |

TABLE 2-continued

| Compound | Structure | m/z (M + H) | Mean AC1.4 |
|---|---|---|---|
| 3-fluoro-4-[6-({[(3-fluoro(2-pyridyl))cyclobutyl]methyl}amino)pyridazin-3-yl]benzamide | 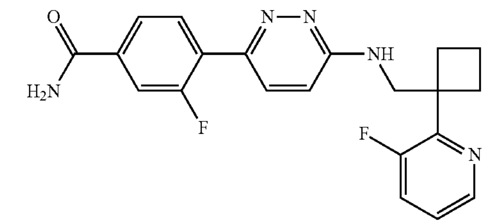 [SMILES: NC(=O)c1ccc(-c2ccc(NCC3(c4ncccc4F)CCC3)nn2)c(F)c1] | 396.0 | B |
| 2-fluoro-4-(6-{[2-(4-fluorophenyl)-2-methylpropyl]amino}pyridazin-3-yl)benzoic acid | 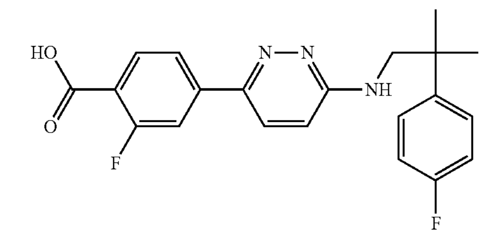 [SMILES: CC(C)(CNc1ccc(-c2ccc(C(=O)O)c(F)c2)nn1)c1ccc(F)cc1] | 384.1 | D |
| methyl 3-amino-5-(6-{[2-(4-fluorophenyl)-2-methylpropyl]amino}pyridazin-3-yl)-1H-indazolecarboxylate | 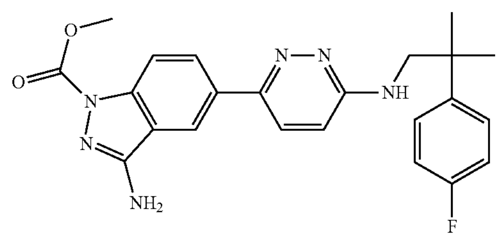 [SMILES: COC(=O)n1nc(N)c2cc(-c3ccc(NCC(C)(C)c4ccc(F)cc4)nn3)ccc21] | 435.1 | B |
| methyl 5-(6-{[2-(4-fluorophenyl)-2-methylpropyl]amino}pyridazin-3-yl)-3-(methoxycarbonylamino)-1H-indazolecarboxylate | 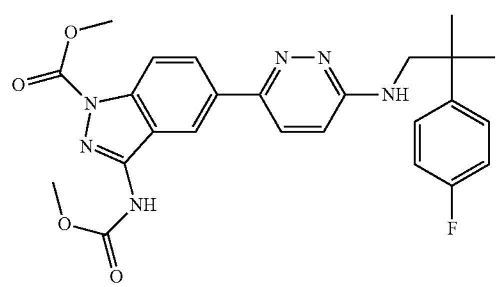 [SMILES: COC(=O)Nc1nn(C(=O)OC)c2ccc(-c3ccc(NCC(C)(C)c4ccc(F)cc4)nn3)cc12] | 493.1 | C |
| N-[5-(6-{[2-(4-fluorophenyl)-2-methylpropyl]amino}pyridazin-3-yl)(1H-indazol-3-yl)]methoxycarboxamide | 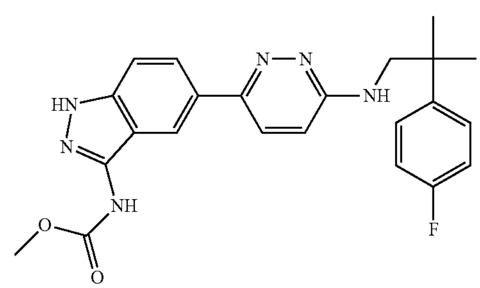 [SMILES: COC(=O)Nc1n[nH]c2ccc(-c3ccc(NCC(C)(C)c4ccc(F)cc4)nn3)cc12] | 435.1 | A |
| [3-amino-5-(6-{[2-(4-fluorophenyl)-2-methylpropyl]amino}pyridazin-3-yl)(1H-indazolyl)]-N,N-dimethylcarboxamide | 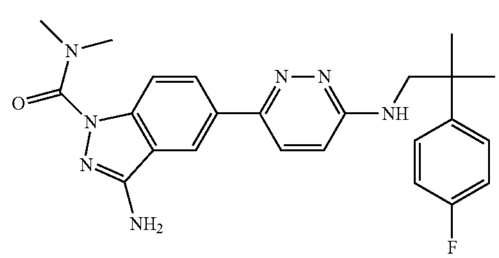 [SMILES: CN(C)C(=O)n1nc(N)c2cc(-c3ccc(NCC(C)(C)c4ccc(F)cc4)nn3)ccc21] | 448.1 | B |

TABLE 2-continued

| Compound | Structure | m/z (M + H) | Mean AC1.4 |
|---|---|---|---|
| 6-({[(6-(1H-indazol-5-yl)pyridazin-3-yl)amino]methyl}cyclobutyl)pyridin-2-ol | 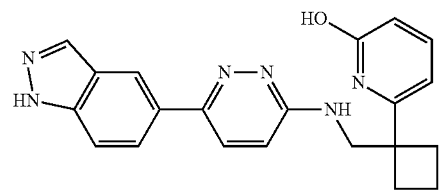 [SMILES: Oc1cccc(C2(CNc3ccc(-c4ccc5[nH]ncc5c4)nn3)CCC2)n1] | 373.1 | D |
| 6-({[(6-(1H-indazol-6-yl)pyridazin-3-yl)amino]methyl}cyclobutyl)pyridin-2-ol | 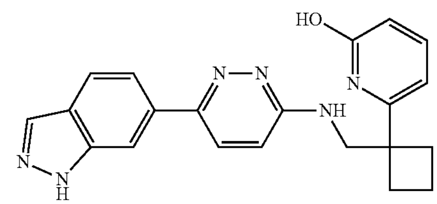 | 373.1 | D |
| 4-fluoro-3-[6-({[(6-hydroxy(2-pyridyl))cyclobutyl]methyl}amino)pyridazin-3-yl]benzamide | 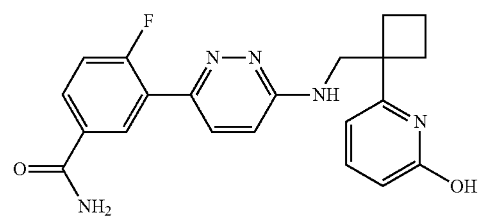 [SMILES: NC(=O)c1ccc(F)c(-c2ccc(NCC3(c4cccc(O)n4)CCC3)nn2)c1] | 394.1 | D |
| 2-({[(6-(1H-indazol-5-yl)pyridazin-3-yl)amino]methyl}cyclobutyl)pyridin-4-ol | 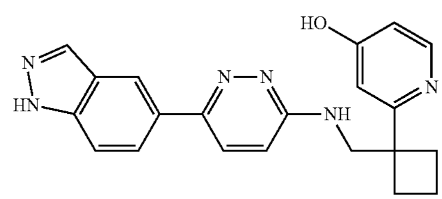 [SMILES: Oc1ccnc(C2(CNc3ccc(-c4ccc5[nH]ncc5c4)nn3)CCC2)c1] | 373.1 | D |
| 4-fluoro-3-[6-({[(4-methoxy(2-pyridyl))cyclobutyl]methyl}amino)pyridazin-3-yl]benzamide | 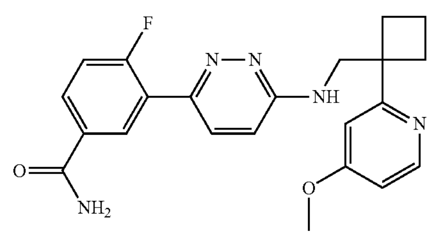 [SMILES: COc1ccnc(C2(CNc3ccc(-c4cc(C(N)=O)ccc4F)nn3)CCC2)c1] | 408.2 | B |
| (6-(1H-indazol-5-yl)pyridazin-3-yl){[(4-methoxy(2-pyridyl))cyclobutyl]methyl}amine | 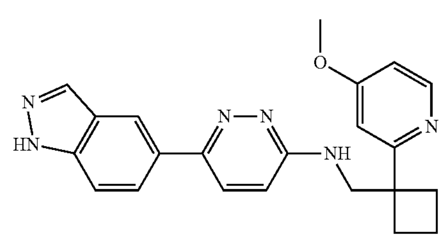 [SMILES: COc1ccnc(C2(CNc3ccc(-c4ccc5[nH]ncc5c4)nn3)CCC2)c1] | 387.2 | A |
| (6-(1H-indazol-6-yl)pyridazin-3-yl){[(4-methoxy(2-pyridyl))cyclobutyl]methyl}amine | 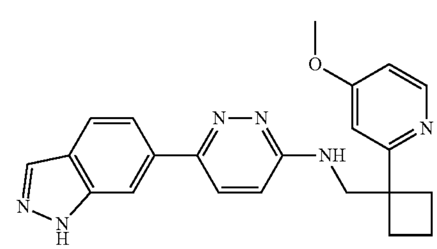 [SMILES: COc1ccnc(C2(CNc3ccc(-c4ccc5cn[nH]c5c4)nn3)CCC2)c1] | 387.2 | A |

TABLE 2-continued

| Compound | Structure | m/z (M + H) | Mean AC1.4 |
|---|---|---|---|
| 2-({[(6-(1H-indazol-6-yl)pyridazin-3-yl)amino]methyl}cyclobutyl)pyridin-4-ol | 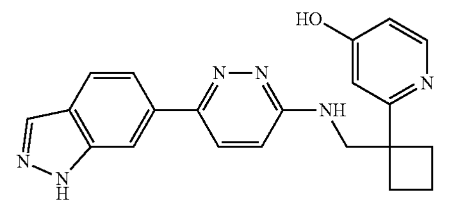 [SMILES: Oc1ccnc(C2(CNc3ccc(-c4ccc5cn[nH]c5c4)nn3)CCC2)c1] | 373.2 | D |
| 4-fluoro-3-[6-({[(4-hydroxy(2-pyridyl))cyclobutyl]methyl}amino)pyridazin-3-yl]benzamide | 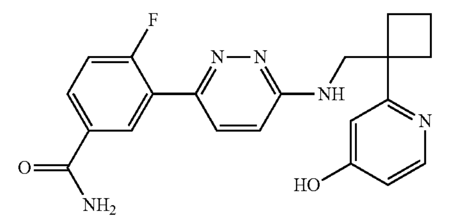 [SMILES: NC(=O)c1ccc(F)c(-c2ccc(NCC3(c4cc(O)ccn4)CCC3)nn2)c1] | 394.2 | D |
| 5-[6-({[(3-fluoro-2-pyridyl)cyclobutyl]methyl}amino)pyridazin-3-yl]-3-hydrobenzimidazol-2-one | 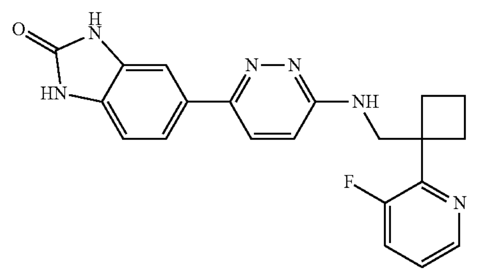 [SMILES: O=c1[nH]c2ccc(-c3ccc(NCC4(c5ncccc5F)CCC4)nn3)cc2[nH]1] | 391.0 | B |
| {[(3-fluoro(2-pyridyl))cyclobutyl]methyl}(6-pyrazol-4-ylpyridazin-3-yl)amine | 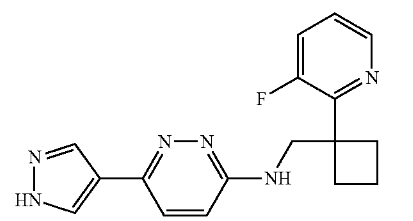 [SMILES: Fc1cccnc1C1(CNc2ccc(-c3cn[nH]c3)nn2)CCC1] | 325.0 | C |
| {[(3-fluoro(2-pyridyl))cyclobutyl]methyl}[6-(1-methylpyrazol-4-yl)pyridazin-3-yl]amine | 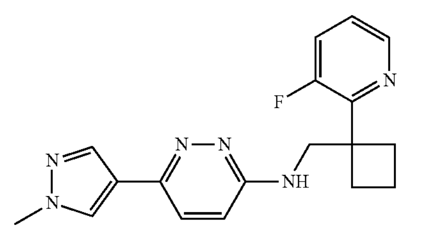 [SMILES: Cn1cc(-c2ccc(NCC3(c4ncccc4F)CCC3)nn2)cn1] | 339.0 | D |
| 6-(6-{[2-(4-fluorophenyl)-2-methylpropyl]amino}pyridazin-3-yl)-3,3-dimethylindolin-2-one | 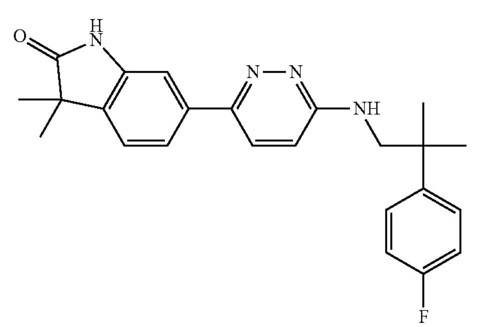 [SMILES: CC(C)(CNc1ccc(-c2ccc3c(c2)NC(=O)C3(C)C)nn1)c1ccc(F)cc1] | 405.0 | D |

TABLE 2-continued

| Compound | Structure | m/z (M + H) | Mean AC1.4 |
|---|---|---|---|
| 2-amino-7-(6-{[2-(4-fluorophenyl)-2-methylpropyl]amino}pyridazin-3-yl)-3-hydroquinazolin-4-one | 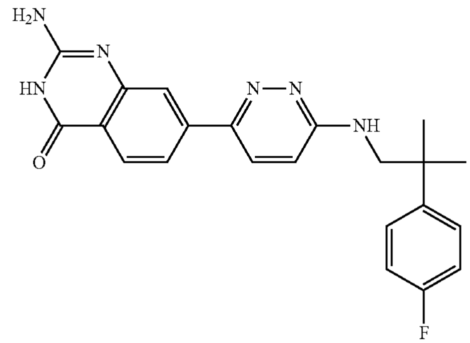 [SMILES: CC(C)(CNc1ccc(-c2ccc3c(=O)[nH]c(N)nc3c2)nn1)c1ccc(F)cc1] | 405.1 | C |
| 3-[6-({[(3-fluoro-2-pyridyl)cyclobutyl]methyl}amino)pyridazin-3-yl]benzenesulfonamide | 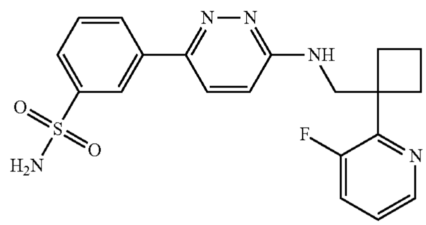 [SMILES: NS(=O)(=O)c1cccc(-c2ccc(NCC3(c4ncccc4F)CCC3)nn2)c1] | 414.4 | A |
| {4-[6-({[(3-fluoro(2-pyridyl))cyclobutyl]methyl}amino)pyridazin-3-yl]phenyl}(methylsulfonyl)amine | 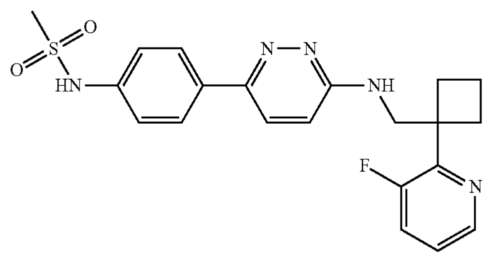 [SMILES: CS(=O)(=O)Nc1ccc(-c2ccc(NCC3(c4ncccc4F)CCC3)nn2)cc1] | 428.3 | B |
| {3-[6-({[(3-fluoro(2-pyridyl))cyclobutyl]methyl}amino)pyridazin-3-yl]phenyl}(methylsulfonyl)amine | 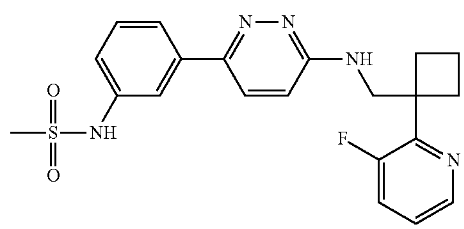 [SMILES: CS(=O)(=O)Nc1cccc(-c2ccc(NCC3(c4ncccc4F)CCC3)nn2)c1] | 428.3 | B |
| 3-{6-[(2-methyl-2-pyrimidin-2-ylpropyl)amino]pyridazin-3-yl}benzamide | 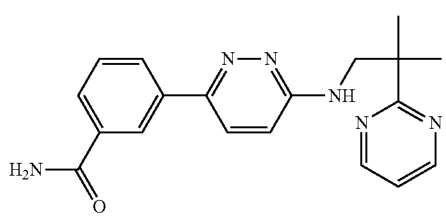 [SMILES: CC(C)(CNc1ccc(-c2cccc(C(N)=O)c2)nn1)c1ncccn1] | 349.0 | D |
| 4-fluoro-3-[6-({[(3-methoxy(2-pyridyl))cyclobutyl]methyl}amino)pyridazin-3-yl]benzamide | 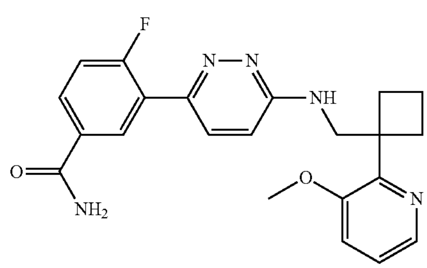 [SMILES: COc1cccnc1C1(CNc2ccc(-c3cc(C(N)=O)ccc3F)nn2)CCC1] | 408.2 | B |

TABLE 2-continued

| Compound | Structure | m/z (M + H) | Mean AC1.4 |
|---|---|---|---|
| (6-(1H-indazol-5-yl)pyridazin-3-yl){[(3-methoxy(2-pyridyl))cyclobutyl]methyl}amine | 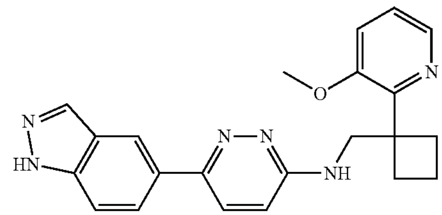 [SMILES: COc1cccnc1C1(CNc2ccc(-c3ccc4[nH]ncc4c3)nn2)CCC1] | 387.2 | B |
| (6-(1H-indazol-6-yl)pyridazin-3-yl){[(3-methoxy(2-pyridyl))cyclobutyl]methyl}amine | 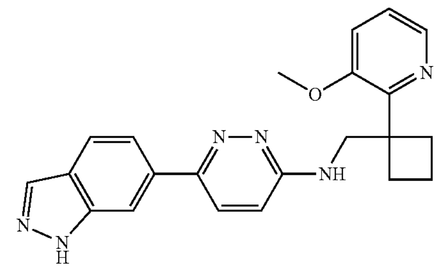 [SMILES: COc1cccnc1C1(CNc2ccc(-c3ccc4cn[nH]c4c3)nn2)CCC1] | 387.1 | B |
| 4-fluoro-3-[6-({[(5-methoxy(2-pyridyl))cyclobutyl]methyl}amino)pyridazin-3-yl]benzamide | 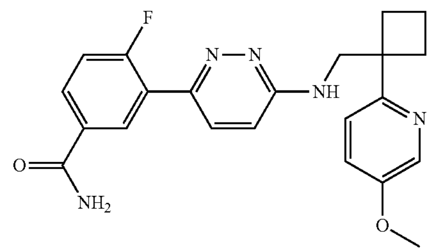 [SMILES: COc1ccc(C2(CNc3ccc(-c4cc(C(N)=O)ccc4F)nn3)CCC2)nc1] | 408.1 | D |
| (6-(1H-indazol-5-yl)pyridazin-3-yl){[(5-methoxy(2-pyridyl))cyclobutyl]methyl}amine | 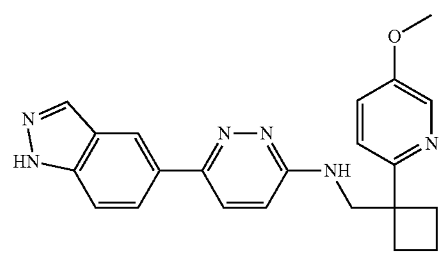 [SMILES: COc1ccc(C2(CNc3ccc(-c4ccc5[nH]ncc5c4)nn3)CCC2)nc1] | 387.2 | B |
| (6-(1H-indazol-6-yl)pyridazin-3-yl){[(5-methoxy(2-pyridyl))cyclobutyl]methyl}amine | 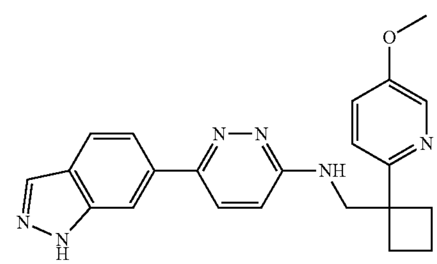 [SMILES: COc1ccc(C2(CNc3ccc(-c4ccc5cn[nH]c5c4)nn3)CCC2)nc1] | 387.2 | B |
| 3-{[(6-(1H-indazol-6-yl)pyridazin-3-yl)amino]methyl}-3-(2-pyridyl)cyclobutan-1-ol | 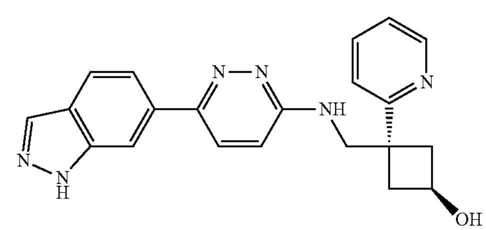 [SMILES: O[C@H]1C[C@](CNc2ccc(-c3ccc4cn[nH]c4c3)nn2)(c2ccccn2)C1] | 373.1 | D |

TABLE 2-continued

| Compound | Structure | m/z (M + H) | Mean AC1.4 |
|---|---|---|---|
| 3-{[(6-(1H-indazol-6-yl)pyridazin-3-yl)amino]methyl}-3-(2-pyridyl)cyclobutan-1-ol | 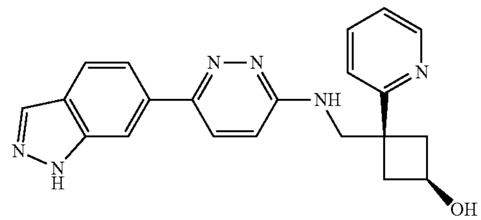 [SMILES: O[C@H]1C[C@@](CNc2ccc(-c3ccc4cn[nH]c4c3)nn2)(c2ccccn2)C1] | 373.2 | D |
| 3-[6-({[(4-fluorophenyl)cyclobutyl]methyl}amino)pyridazin-3-yl]benzamide | 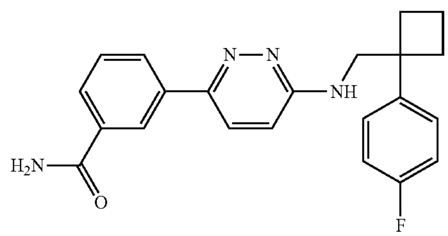 [SMILES: NC(=O)c1cccc(-c2ccc(NCC3(c4ccc(F)cc4)CCC3)nn2)c1] | 377.3 | A |
| 3-[6-({[(3-fluoro(2-pyridyl))cyclobutyl]methyl}amino)pyridazin-3-yl]-4-methylbenzamide | 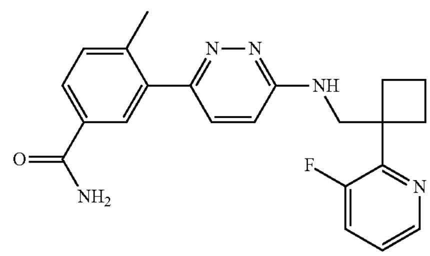 [SMILES: Cc1ccc(C(N)=O)cc1-c1ccc(NCC2(c3ncccc3F)CCC2)nn1] | 392.3 | B |
| 6-({[(6-(1H-indazol-5-yl)pyridazin-3-yl)amino]methyl}cyclobutyl)pyridine-3-carbonitrile | 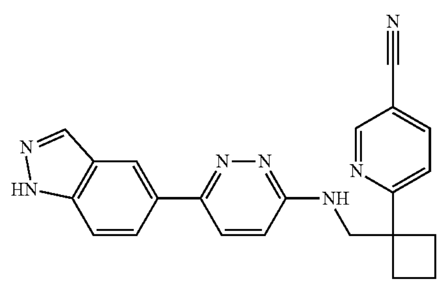 [SMILES: N#Cc1ccc(C2(CNc3ccc(-c4ccc5[nH]ncc5c4)nn3)CCC2)nc1] | 382.2 | B |
| 6-[6-({[(3-fluoro(2-pyridyl))cyclobutyl]methyl}amino)pyridazin-3-yl]-3,3-dimethylindolin-2-one | 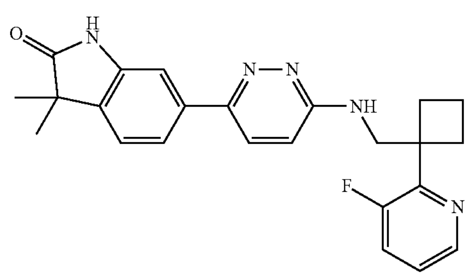 [SMILES: CC1(C)C(=O)Nc2cc(-c3ccc(NCC4(c5ncccc5F)CCC4)nn3)ccc21] | 418.0 | D |
| 3-[6-({[(4-cyano-2-pyridyl)cyclobutyl]methyl}amino)pyridazin-3-yl]benzamide | 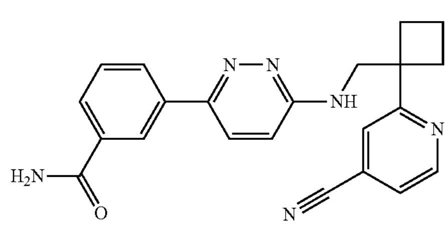 [SMILES: N#Cc1ccnc(C2(CNc3ccc(-c4cccc(C(N)=O)c4)nn3)CCC2)c1] | 385.1 | B |

TABLE 2-continued

| Compound | Structure | m/z (M + H) | Mean AC1.4 |
|---|---|---|---|
| 2-[({[6-(3-carbamoylphenyl)pyridazin-3-yl]amino}methyl)cyclobutyl]pyridine-4-carboxamide | 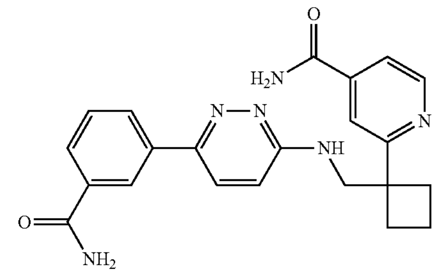 [SMILES: NC(=O)c1cccc(-c2ccc(NCC3(c4cc(C(N)=O)ccn4)CCC3)nn2)c1] | 403.2 | D |
| 3-[6-({[(4-cyano(2-pyridyl))cyclobutyl]methyl}amino)pyridazin-3-yl]-4-fluorobenzamide | | 403.1 | B |
| 2-[({[6-(3-carbamoyl-6-fluorophenyl)pyridazin-3-yl]amino}methyl)cyclobutyl]pyridine-4-carboxamide | 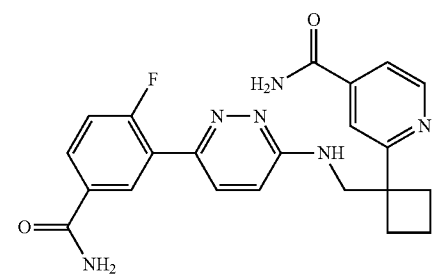 [SMILES: NC(=O)c1ccnc(C2(CNc3ccc(-c4cc(C(N)=O)ccc4F)nn3)CCC2)c1] | 421.2 | D |
| 2-({[(6-(1H-indazol-5-yl)pyridazin-3-yl)amino]methyl}cyclobutyl)pyridine-4-carbonitrile | 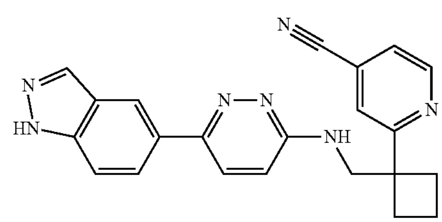 [SMILES: N#Cc1ccnc(C2(CNc3ccc(-c4ccc5[nH]ncc5c4)nn3)CCC2)c1] | 382.1 | A |
| 2-({[(6-(1H-indazol-5-yl)pyridazin-3-yl)amino]methyl}cyclobutyl)pyridine-4-carboxamide | 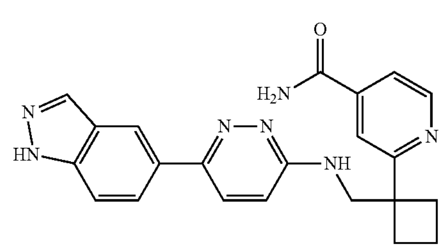 [SMILES: NC(=O)c1ccnc(C2(CNc3ccc(-c4ccc5[nH]ncc5c4)nn3)CCC2)c1] | 400.2 | C |
| 3-[6-({[(6-cyano-2-pyridyl)cyclobutyl]methyl}amino)pyridazin-3-yl]benzamide | 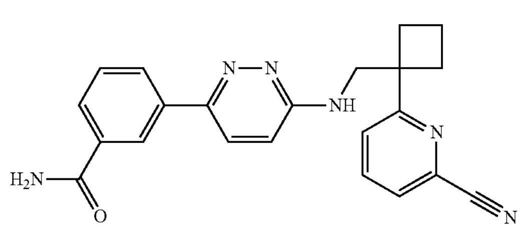 [SMILES: N#Cc1cccc(C2(CNc3ccc(-c4cccc(C(N)=O)c4)nn3)CCC2)n1] | 385.1 | B |

TABLE 2-continued

| Compound | Structure | m/z (M + H) | Mean AC1.4 |
|---|---|---|---|
| 6-[({[6-(3-carbamoylphenyl)pyridazin-3-yl]amino}methyl)cyclobutyl]pyridine-2-carboxamide | 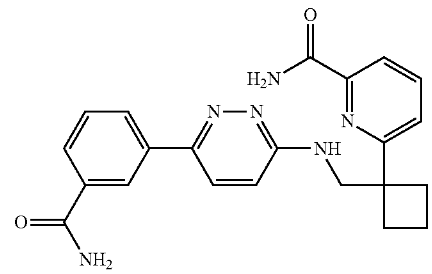 [SMILES: NC(=O)c1cccc(-c2ccc(NCC3(c4cccc(C(N)=O)n4)CCC3)nn2)c1] | 403.2 | D |
| 6-({[(6-(1H-indazol-5-yl)pyridazin-3-yl)amino]methyl}cyclobutyl)pyridine-2-carbonitrile | 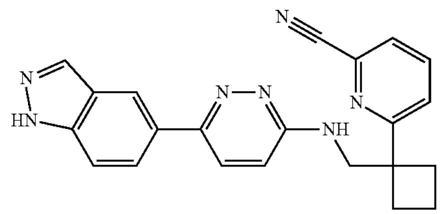 | 382.1 | B |
| 6-({[(6-(1H-indazol-5-yl)pyridazin-3-yl)amino]methyl}cyclobutyl)pyridine-2-carboxamide | 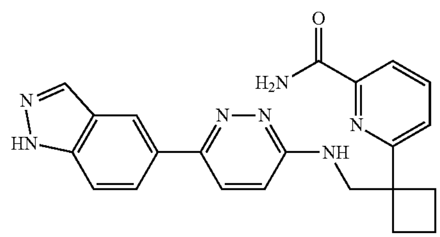 | 400.1 | B |
| (6-(1H-indazol-6-yl)pyridazin-3-yl){[(4-fluorophenyl)cyclobutyl]methyl}amine | 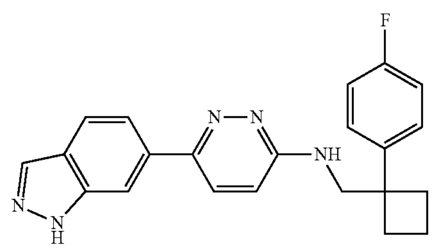 [SMILES: Fc1ccc(C2(CNc3ccc(-c4ccc5cn[nH]c5c4)nn3)CCC2)cc1] | 374.1 | A |
| (6-(1H-indazol-5-yl)pyridazin-3-yl){[(4-fluorophenyl)cyclobutyl]methyl}amine | 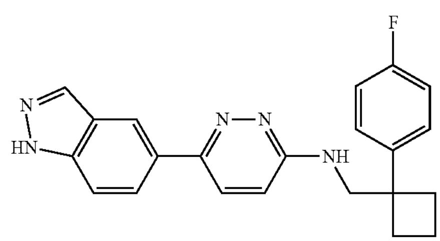 [SMILES: Fc1ccc(C2(CNc3ccc(-c4ccc5[nH]ncc5c4)nn3)CCC2)cc1] | 374.1 | A |
| 4-fluoro-3-[6-({[(1-methyl-6-oxo(2-hydropyridyl))cyclobutyl]methyl}amino)pyridazin-3-yl]benzamide | 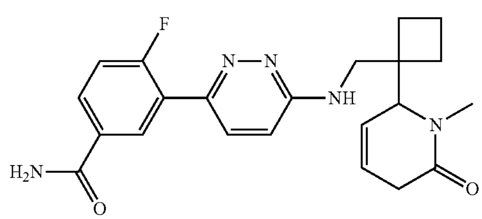 [SMILES: CN1C(=O)CC=CC1C1(CNc2ccc(-c3cc(C(N)=O)ccc3F)nn2)CCC1] | 408.1 | D |

TABLE 2-continued

| Compound | Structure | m/z (M + H) | Mean AC1.4 |
|---|---|---|---|
| 3-(6-{[(2-pyridylcyclobutyl)methyl]amino}pyridazin-3-yl)benzamide | 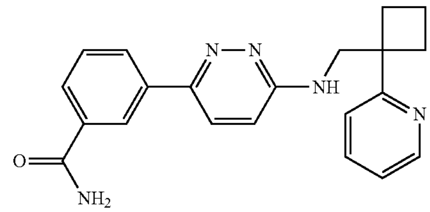 | 360.2 | A |
| ({[(6-(1H-indazol-5-yl)pyridazin-3-yl)amino]methyl}cyclobutyl)methan-1-ol | 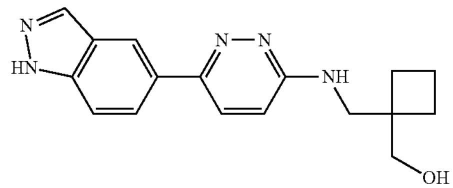 [SMILES: OCC1(CNc2ccc(-c3ccc4[nH]ncc4c3)nn2)CCC1] | 310.2 | D |
| 1-({[6-(3-cyanophenyl)pyridazin-3-yl]amino}methyl)cyclobutanecarboxylic acid | 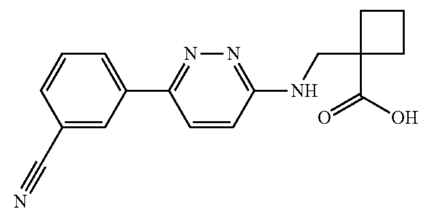 [SMILES: N#Cc1cccc(-c2ccc(NCC3(C(=O)O)CCC3)nn2)c1] | 309.2 | D |
| 1-({[6-(3-carbarnoylphenyl)pyridazin-3-yl]amino}methyl)cyclobutanecarboxylic acid | 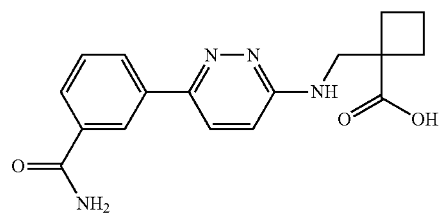 [SMILES: NC(=O)c1cccc(-c2ccc(NCC3(C(=O)O)CCC3)nn2)c1] | 327.2 | D |
| 1-({[6-(3-cyanophenyl)pyridazin-3-yl]amino}methyl)cyclobutanecarboxamide | 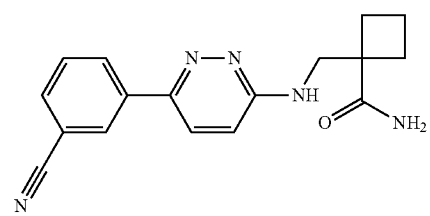 [SMILES: N#Cc1cccc(-c2ccc(NCC3(C(N)=O)CCC3)nn2)c1] | 308.2 | D |
| 3-(6-{[(carbamoylcyclobutyl)methyl]amino}pyridazin-3-yl)benzamide | 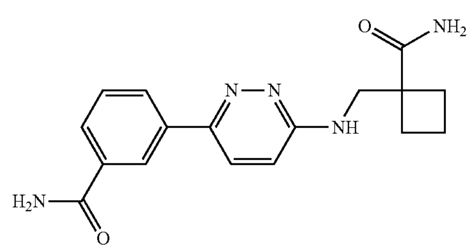 [SMILES: NC(=O)c1cccc(-c2ccc(NCC3(C(N)=O)CCC3)nn2)c1] | 326.2 | D |
| methyl 3-(3-fluoro(2-pyridyl))-3-{[(6-(1H-indazol-5-yl)pyridazin-3-yl)amino]methyl}azetidinecarboxylate | 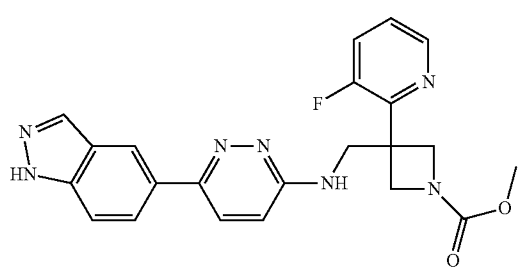 [SMILES: COC(=O)N1CC(CNc2ccc(-c3ccc4[nH]ncc4c3)nn2)(c2ncccc2F)C1] | 434.2 | D |

TABLE 2-continued

| Compound | Structure | m/z (M + H) | Mean AC1.4 |
|---|---|---|---|
| methyl 3-({[6-(3-carbamoylphenyl)pyridazin-3-yl]amino}methyl)-3-(3-fluoro(2-pyridyl))azetidinecarboxylate | 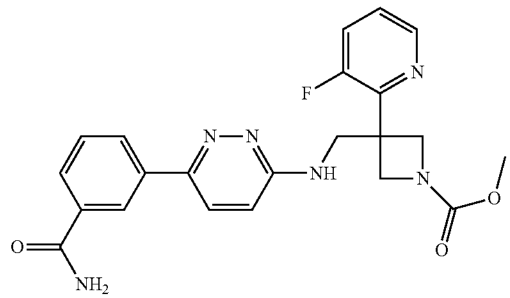 [SMILES: COC(=O)N1CC(CNc2ccc(-c3cccc(C(N)=O)c3)nn2)(c2ncccc2F)C1] | 437.2 | D |
| {[(3-fluoro(2-pyridyl))cyclobutyl]methyl}{6-[3-(methylamino)(1H-indazol-5-yl)]pyridazin-3-yl}amine | 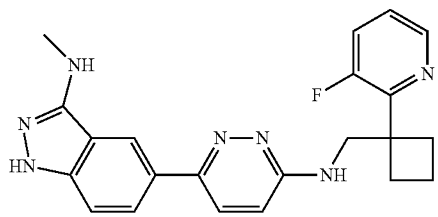 | 404.1 | A |
| 2-fluoro-5-[6-({[(3-fluoro(2-pyridyl))cyclobutyl]methyl}amino)pyridazin-3-yl]benzoic acid | 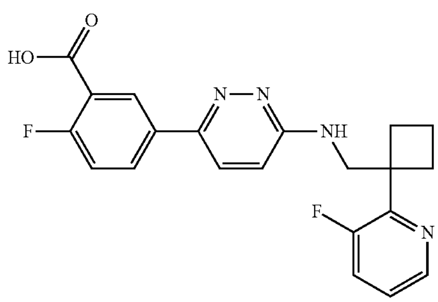 [SMILES: O=C(O)c1cc(-c2ccc(NCC3(c4ncccc4F)CCC3)nn2)ccc1F] | 397.0 | B |
| {2-fluoro-5-[6-({[(3-fluoro(2-pyridyl))cyclobutyl]methyl}amino)pyridazin-3-yl]phenyl}-N-methylcarboxamide | 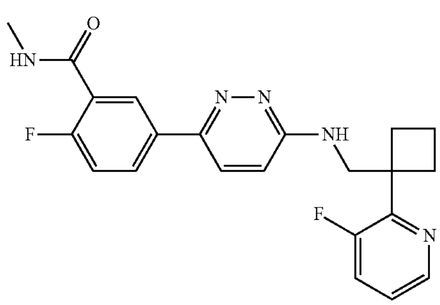 [SMILES: CNC(=O)c1cc(-c2ccc(NCC3(c4ncccc4F)CCC3)nn2)ccc1F] | 410.0 | B |
| N-{5-[6-({[(3-fluoro-2-pyridyl)cyclobutyl]methyl}amino)pyridazin-3-yl]-1H-indazol-3-yl}acetamide | 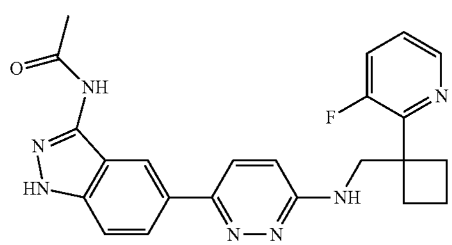 [SMILES: CC(=O)Nc1n[nH]c2ccc(-c3ccc(NCC4(c5ncccc5F)CCC4)nn3)cc12] | 432.2 | B |

TABLE 2-continued

| Compound | Structure | m/z (M + H) | Mean AC1.4 |
|---|---|---|---|
| 2-amino-N-{5-[6-({[(3-fluoro(2-pyridyl))cyclobutyl]methyl}amino)pyridazin-3-yl](1H-indazol-3-yl)}acetamide | 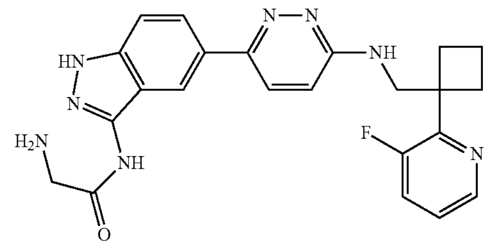 [SMILES: NCC(=O)Nc1n[nH]c2ccc(-c3ccc(NCC4(c5ncccc5F)CCC4)nn3)cc12] | 447.2 | B |
| {5-[6-({[(3-fluoro(2-pyridyl))cyclobutyl]methyl}amino)pyridazin-3-yl](1H-indazol-3-yl)}(methylsulfonyl)amine | 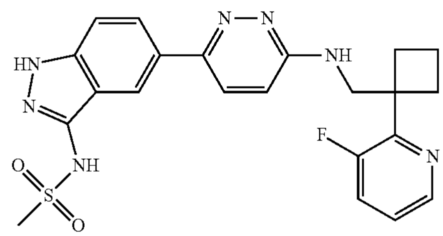 [SMILES: CS(=O)(=O)Nc1n[nH]c2ccc(-c3ccc(NCC4(c5ncccc5F)CCC4)nn3)cc12] | 468.2 | A |
| 3-amino-5-[6-({[(3-fluoro(2-pyridyl))cyclobutyl]methyl}amino)pyridazin-3-yl]-1H-indazolecarboxamide | 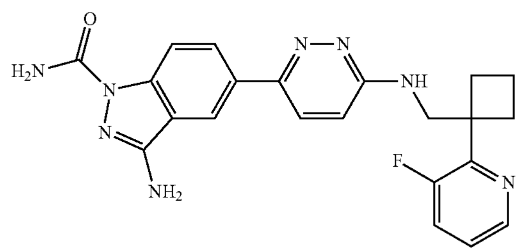 [SMILES: NC(=O)n1nc(N)c2cc(-c3ccc(NCC4(c5ncccc5F)CCC4)nn3)ccc21] | 433.3 | B |
| [6-(3-aminophenyl)pyridazin-3-yl]{[(3-fluoro(2-pyridyl))cyclobutyl]methyl}amine | 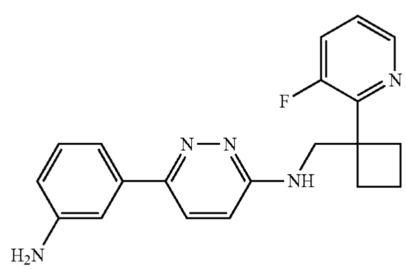 [SMILES: Nc1cccc(-c2ccc(NCC3(c4ncccc4F)CCC3)nn2)c1] | 350.2 | A |
| [6-(4-aminophenyl)pyridazin-3-yl]{[(3-fluoro(2-pyridyl))cyclobutyl]methyl}amine | 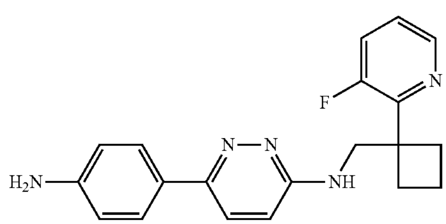 | 350.2 | A |
| (6-{3-[(2-aminoethyl)amino](1H-indazol-5-yl)}pyridazin-3-yl){[(3-fluoro(2-pyridyl))cyclobutyl]methyl}amine | | 433.0 | A |

TABLE 2-continued

| Compound | Structure | m/z (M + H) | Mean AC1.4 |
|---|---|---|---|
| amino{3-[6-({[(3-fluoro(2-pyridyl))cyclobutyl]methyl}amino)pyridazin-3-yl]phenyl}carboxamidine | | 392.2 | B |
| amino{4-[6-({[(3-fluoro(2-pyridyl))cyclobutyl]methyl}amino)pyridazin-3-yl]phenyl}carboxamidine | 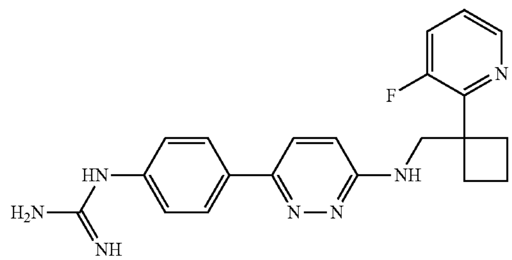 [SMILES: N=C(N)Nc1ccc(-c2ccc(NCC3(c4ncccc4F)CCC3)nn2)cc1] | 392.2 | B |
| 3-(6-{[(pyrazin-2-ylcyclobutyl)methyl]amino}pyridazin-3-yl)benzamide | 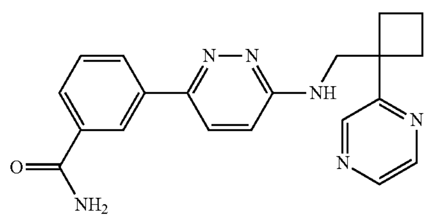 | 361.3 | D |
| (6-(1H-indazol-6-yl)pyridazin-3-yl)[(pyrazin-2-ylcyctobutyl)methyl]amine | 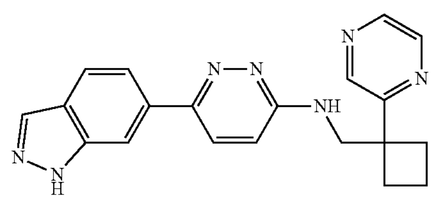 | 358.3 | C |
| (6-(1H-indazol-5-yl)pyridazin-3-yl)[(pyrazin-2-ylcyclobutyl)methyl]amine | 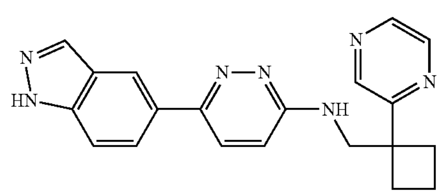 | 358.3 | C |
| amino-N-{3-[6-({[(3-fluoro(2-pyridyl))cyclobutyl]methyl}amino)pyridazin-3-yl]phenyl}amide | 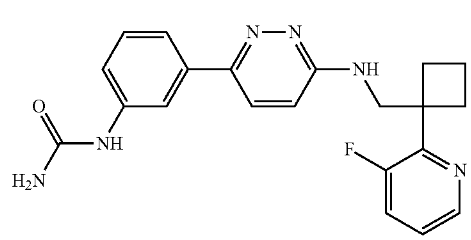 [SMILES: NC(=O)Nc1cccc(-c2ccc(NCC3(c4ncccc4F)CCC3)nn2)c1] | 393.2 | A |

TABLE 2-continued

| Compound | Structure | m/z (M + H) | Mean AC1.4 |
|---|---|---|---|
| 5-[6-({[(3-fluoro-2-pyridyl)cyclobutyl]methyl}amino)pyridazin-3-yl]benzene-1,3-dicarboxylic acid | 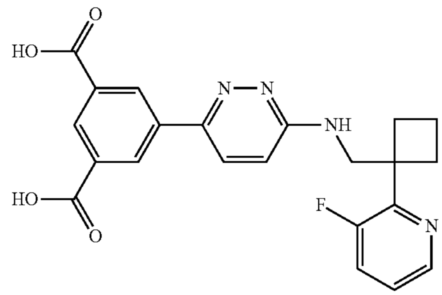 [SMILES: O=C(O)c1cc(C(=O)O)cc(-c2ccc(NCC3(c4ncccc4F)CCC3)nn2)c1] | 423.2 | D |
| 5-[6-({[(3-fluoro-2-pyridyl)cyclobutyl]methyl}amino)pyridazin-3-yl]benzene-1,3-dicarboxamide | 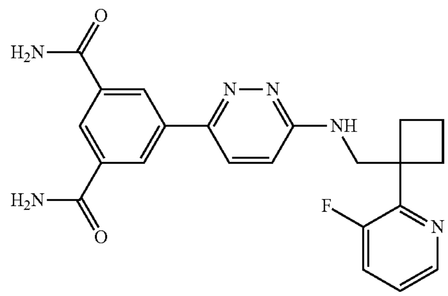 [SMILES: NC(=O)c1cc(C(N)=O)cc(-c2ccc(NCC3(c4ncccc4F)CCC3)nn2)c1] | 421.2 | B |
| 3-[6-({[(3-fluoro-2-pyridyl)cyclobutyl]methyl}amino)pyridazin-3-yl]benzenecarboxamidine | 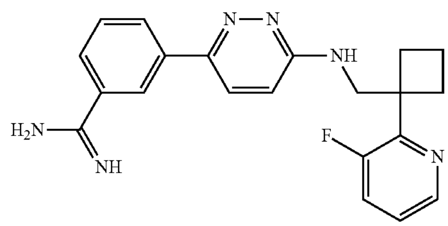 [SMILES: N=C(N)c1cccc(-c2ccc(NCC3(c4ncccc4F)CCC3)nn2)c1] | 377.2 | D |
| 3-[6-({[1-acetyl-3-(3-fluoro(2-pyridyl))azetidin-3-yl]methyl}amino)pyridazin-3-yl]benzamide | 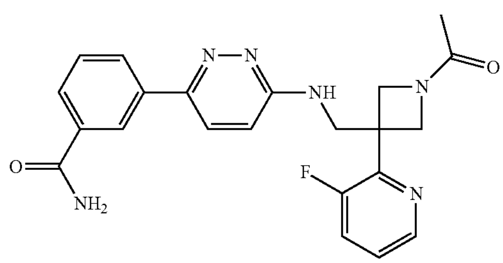 [SMILES: CC(=O)N1CC(CNc2ccc(-c3cccc(C(N)=O)c3)nn2)(c2ncccc2F)C1] | 421.2 | D |
| 1-acetyl-3-(3-fluoro(2-pyridyl))-3-{[(6-(1H-indazol-5-yl)pyridazin-3-yl)amino]methyl}azetidine | 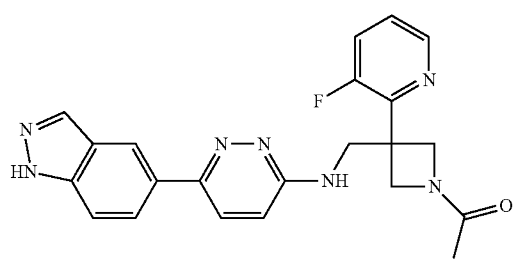 [SMILES: CC(=O)N1CC(CNc2ccc(-c3ccc4[nH]ncc4c3)nn2)(c2ncccc2F)C1] | 418.2 | D |
| (6-(1H-indazol-5-yl)pyridazin-3-yl){[3-(3-fluoro(2-pyridyl))azetidin-3-yl]methyl}amine | 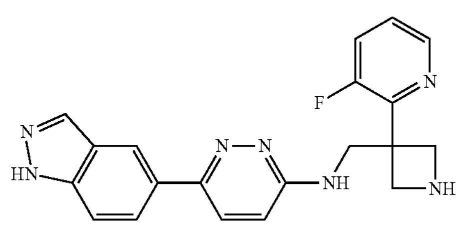 [SMILES: Fc1cccnc1C1(CNc2ccc(-c3ccc4[nH]ncc4c3)nn2)CNC1] | 376.2 | D |

TABLE 2-continued

| Compound | Structure | m/z (M + H) | Mean AC1.4 |
|---|---|---|---|
| 3-[6-({[3-(3-fluoro-2-pyridyl)azetidin-3-yl]methyl}amino)pyridazin-3-yl]benzamide | 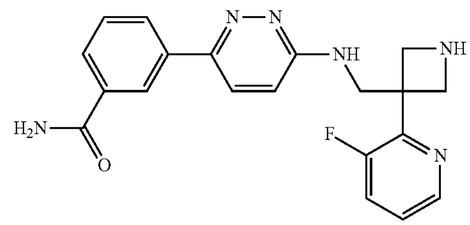 [SMILES: NC(=O)c1cccc(-c2ccc(NCC3(c4ncccc4F)CNC3)nn2)c1] | 379.2 | D |
| 3-(3-fluoro(2-pyridyl))-3-{[(6-(1H-indazol-5-yl)pyridazin-3-yl)amino]methyl}-1-(methylsulfonyl)azetidine | 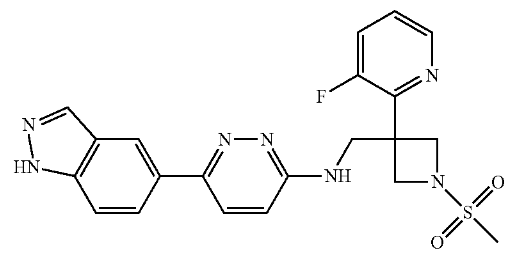 [SMILES: CS(=O)(=O)N1CC(CNc2ccc(-c3ccc4[nH]ncc4c3)nn2)(c2ncccc2F)C1] | 454.2 | D |
| 3-[6-({[3-(3-fluoro(2-pyridyl))-1-(methylsulfonyl)azetidin-3-yl]methyl}amino)pyridazin-3-yl]benzamide | 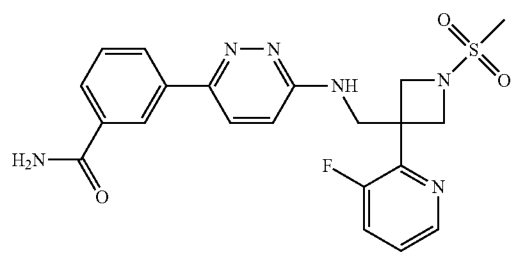 [SMILES: CS(=O)(=O)N1CC(CNc2ccc(-c3cccc(C(N)=O)c3)nn2)(c2ncccc2F)C1] | 457.2 | D |
| (6-(1H-indazol-5-yl)pyridazin-3-yl){[3-(3-fluoro(2-pyridyl))azetidin-3-yl]methyl}(methylsulfonyl)amine | 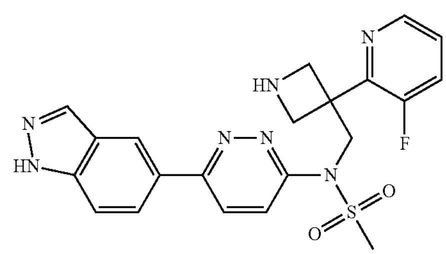 [SMILES: CS(=O)(=O)N(CC1(c2ncccc2F)CNC1)c1ccc(-c2ccc3[nH]ncc3c2)nn1] | 454.2 | D |
| amino{5-[6-({[(3-fluoro(2-pyridyl))cyclobutyl]methyl}amino)pyridazin-3-yl](1H-indazol-3-yl)}carboxamidine | 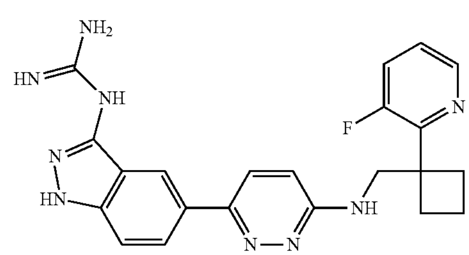 [SMILES: N=C(N)Nc1n[nH]c2ccc(-c3ccc(NCC4(c5ncccc5F)CCC4)nn3)cc12] | 432.2 | B |
| 3-[6-({[3-(4-fluorophenyl)oxetan-3-yl]methyl}amino)pyridazin-3-yl]benzamide | 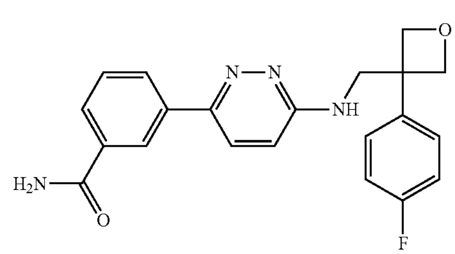 [SMILES: NC(=O)c1cccc(-c2ccc(NCC3(c4ccc(F)cc4)COC3)nn2)c1] | 379.0 | D |

TABLE 2-continued

| Compound | Structure | m/z (M + H) | Mean AC1.4 |
|---|---|---|---|
| [2-(4-fluorophenyl)-2-methylpropyl](6-{3-[(methylethyl)amino](1H-indazol-5-yl)}pyridazin-3-yl)amine | 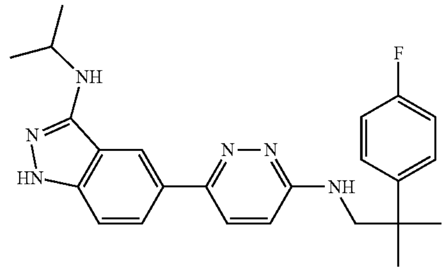 [SMILES: CC(C)Nc1n[nH]c2ccc(-c3ccc(NCC(C)(C)c4ccc(F)cc4)nn3)cc12] | 419.3 | A |
| [6-(2-aminopyrimidin-5-yl)pyridazin-3-yl][2-(4-fluorophenyl)-2-methylpropyl]amine | 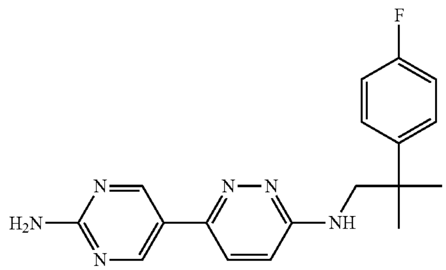 [SMILES: CC(C)(CNc1ccc(-c2cnc(N)nc2)nn1)c1ccc(F)cc1] | 339.2 | B |
| [2-(4-fluorophenyl)-2-methylpropyl]{6-[3-(methylamino)(1H-indazol-5-yl)]pyridazin-3-yl}amine | 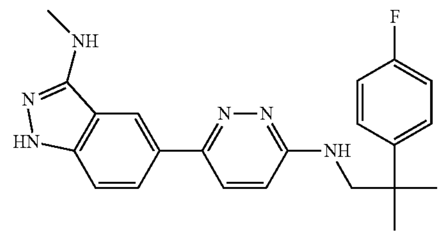 [SMILES: CNc1n[nH]c2ccc(-c3ccc(NCC(C)(C)c4ccc(F)cc4)nn3)cc12] | 391.3 | B |
| [2-(4-fluorophenyl)-2-methylpropyl][6-(2-methoxypyrimidin-5-yl)pyridazin-3-yl]amine | 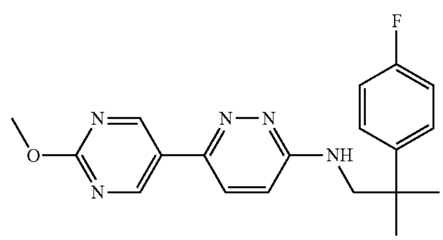 [SMILES: COc1ncc(-c2ccc(NCC(C)(C)c3ccc(F)cc3)nn2)cn1] | 354.2 | C |
| [2-(4-fluorophenyl)-2-methylpropyl][6-(2-methoxy(3-pyridyl))pyridazin-3-yl]amine | 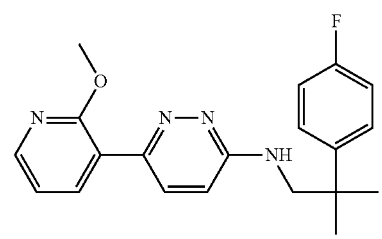 [SMILES: COc1ncccc1-c1ccc(NCC(C)(C)c2ccc(F)cc2)nn1] | 353.1 | A |
| {6-[3-(ethylamino)(1H-indazol-5-yl)]pyridazin-3-yl}[2-(4-fluorophenyl)-2-methylpropyl]amine | 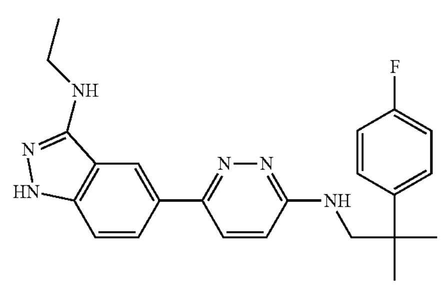 [SMILES: CCNc1n[nH]c2ccc(-c3ccc(NCC(C)(C)c4ccc(F)cc4)nn3)cc12] | 405.2 | A |

TABLE 2-continued

| Compound | Structure | m/z (M + H) | Mean AC1.4 |
|---|---|---|---|
| [2-(4-fluorophenyl)-2-methylpropyl](6-phenylpyridazin-3-yl)amine | 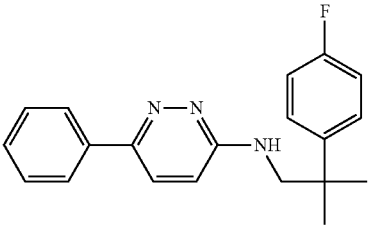 [SMILES: CC(C)(CNc1ccc(-c2ccccc2)nn1)c1ccc(F)cc1] | 322.2 | A |
| 5-(6-{[2-(4-fluorophenyl)-2-methylpropyl]amino}pyridazin-3-yl)hydropyridin-2-one | 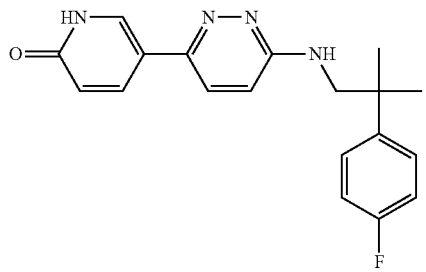 [SMILES: CC(C)(CNc1ccc(-c2ccc(=O)[nH]c2)nn1)c1ccc(F)cc1] | 339.2 | B |
| [6-(2-amino(4-pyridyl))pyridazin-3-yl][2-(4-fluorophenyl)-2-methylpropyl]amine | 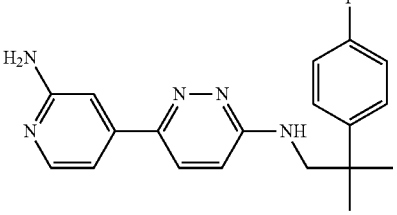 | 338.2 | B |
| [6-(4-aminophenyl)pyridazin-3-yl][2-(4-fluorophenyl)-2-methylpropyl]amine | 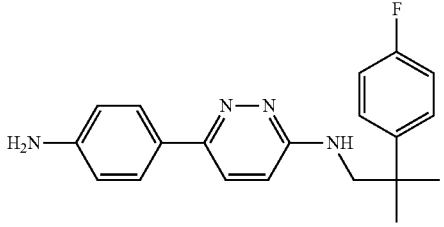 [SMILES: CC(C)(CNc1ccc(-c2ccc(N)cc2)nn1)c1ccc(F)cc1] | 337.1 | A |
| [6-(3-aminophenyl)pyridazin-3-yl][2-(4-fluorophenyl)-2-methylpropyl]amine | 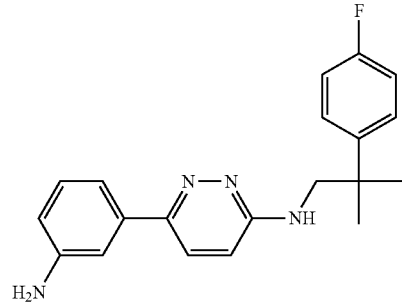 [SMILES: CC(C)(CNc1ccc(-c2cccc(N)c2)nn1)c1ccc(F)cc1] | 337.1 | A |
| 3-(6-{[2-(4-fluorophenyl)-2-methylpropyl]amino}pyridazin-3-yl)pyridin-2-ol | 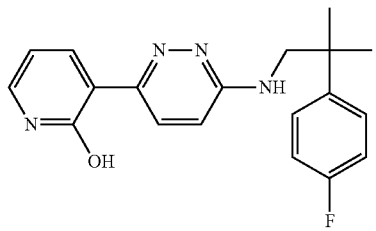 [SMILES: CC(C)(CNc1ccc(-c2cccnc2O)nn1)c1ccc(F)cc1] | 339.1 | B |

TABLE 2-continued

| Compound | Structure | m/z (M + H) | Mean AC1.4 |
|---|---|---|---|
| 5-(6-{[2-(4-fluorophenyl)-2-methylpropyl]amino}pyridazin-3-yl)-3-hydropyrimidin-2-one | 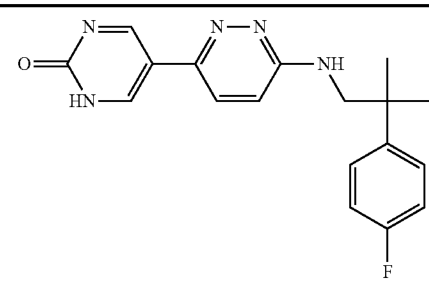 | 340.1 | D |
| 5-(6-{[2-(4-fluorophenyl)-2-methylpropyl]amino}pyridazin-3-yl)-1,3,4-oxadiazolin-2-one | 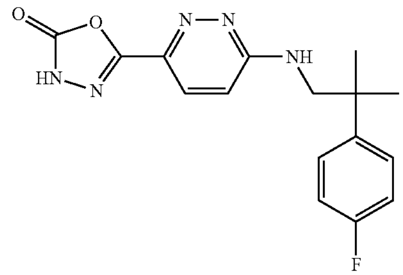 [SMILES: CC(C)(CNc1ccc(-c2n[nH]c(=O)o2)nn1)c1ccc(F)cc1] | 330.0 | C |
| [6-(6-amino(3-pyridyl))pyridazin-3-yl][2-(4-fluorophenyl)-2-methylpropyl]amine | 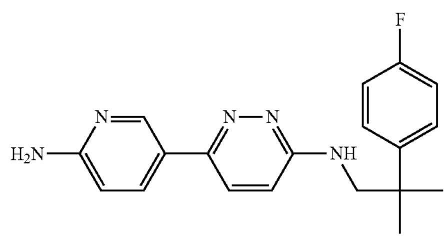 [SMILES: CC(C)(CNc1ccc(-c2ccc(N)nc2)nn1)c1ccc(F)cc1] | 338.2 | A |
| [2-(4-fluorophenyl)-2-methylpropyl](6-vinylpyridazin-3-yl)amine | 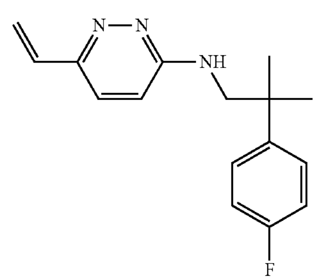 [SMILES: C=Cc1ccc(NCC(C)(C)c2ccc(F)cc2)nn1] | 272.0 | B |
| [6-(5-aminopyrazol-3-yl)pyridazin-3-yl][2-(4-fluorophenyl)-2-methylpropyl]amine | 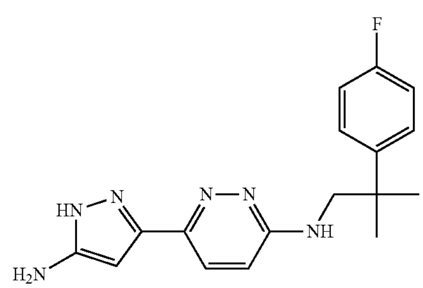 [SMILES: CC(C)(CNc1ccc(-c2cc(N)[nH]n2)nn1)c1ccc(F)cc1] | 327.2 | B |
| [2-(4-fluorophenyl)-2-methylpropyl][6-(6-methoxy(2-pyridyl))pyridazin-3-yl]amine | 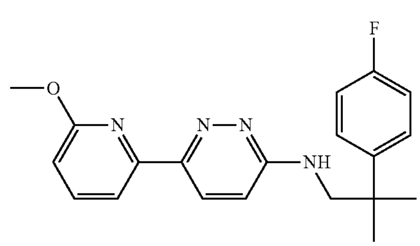 [SMILES: COc1cccc(-c2ccc(NCC(C)(C)c3ccc(F)cc3)nn2)n1] | 353.1 | A |

TABLE 2-continued

| Compound | Structure | m/z (M + H) | Mean AC1.4 |
|---|---|---|---|
| N-[4-(6-{[2-(4-fluorophenyl)-2-methylpropyl]amino}pyridazin-3-yl)imidazol-2-yl]acetamide | 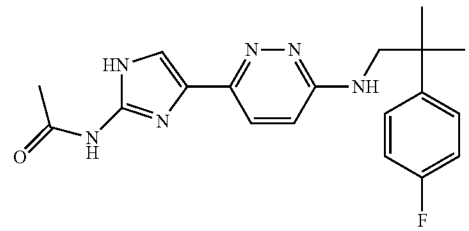 [SMILES: CC(=O)Nc1nc(-c2ccc(NCC(C)(C)c3ccc(F)cc3)nn2)c[nH]1] | 369.2 | C |
| 5-(6-{[2-(4-fluorophenyl)-2-methylpropyl]amino}pyridazin-3-yl)pyridine-2-carbonitrile | 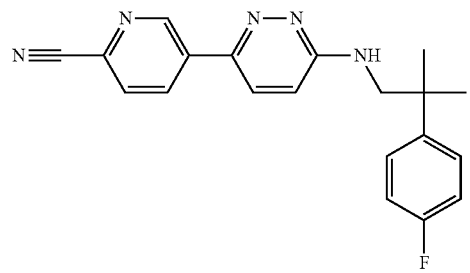 [SMILES: CC(C)(CNc1ccc(-c2ccc(C#N)nc2)nn1)c1ccc(F)cc1] | 348.0 | C |
| [6-(2-aminoimidazol-4-yl)pyridazin-3-yl][2-(4-fluorophenyl)-2-methylpropyl]amine | 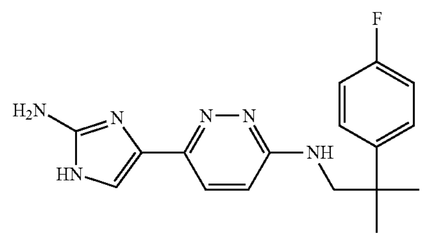 [SMILES: CC(C)(CNc1ccc(-c2c[nH]c(N)n2)nn1)c1ccc(F)cc1] | 327.2 | B |
| 5-(6-{[2-(4-fluorophenyl)-2-methylpropyl]amino}pyridazin-3-yl)pyridine-2-carboxamide | 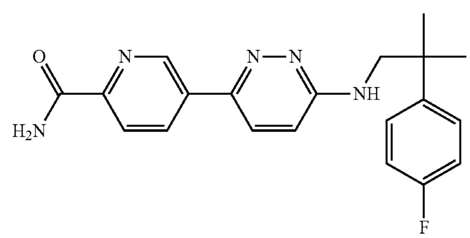 [SMILES: CC(C)(CNc1ccc(-c2ccc(C(N)=O)nc2)nn1)c1ccc(F)cc1] | 366.1 | B |
| 6-(6-{[2-(4-fluorophenyl)-2-methylpropyl]amino}pyridazin-3-yl)pyridin-2-ol | 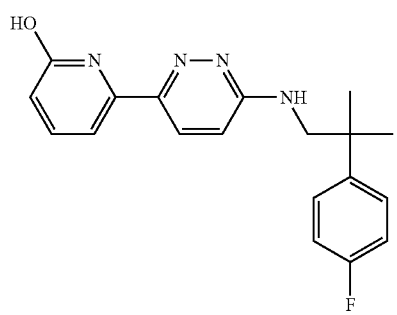 [SMILES: CC(C)(CNc1ccc(-c2cccc(O)n2)nn1)c1ccc(F)cc1] | 339.1 | B |
| {6-[6-(aminomethyl)(3-pyridyl)]pyridazin-3-yl}[2-(4-fluorophenyl)-2-methylpropyl]amine | 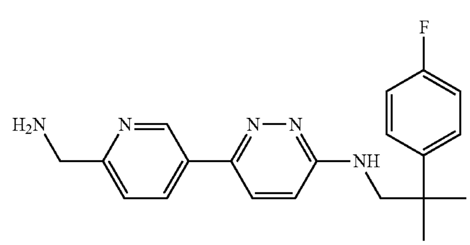 [SMILES: CC(C)(CNc1ccc(-c2ccc(CN)nc2)nn1)c1ccc(F)cc1] | 352.2 | B |

TABLE 2-continued

| Compound | Structure | m/z (M + H) | Mean AC1.4 |
|---|---|---|---|
| [2-(4-fluorophenyl)-2-methylpropyl][6-(2-fluorophenyl)pyridazin-3-yl]amine | 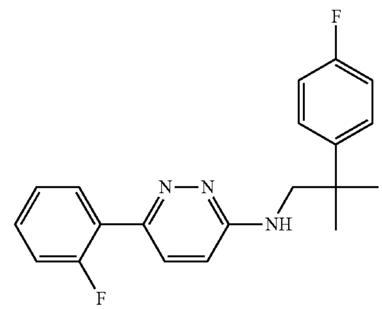 | 340.1 | A |
| [2-(4-fluorophenyl)-2-methylpropyl][6-(3-fluorophenyl)pyridazin-3-yl]amine | 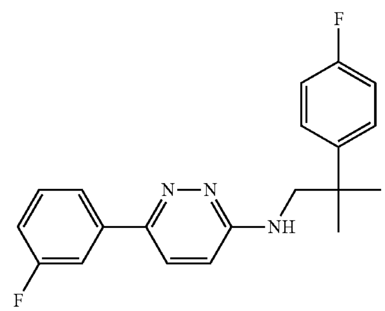 [SMILES: CC(C)(CNc1ccc(-c2cccc(F)c2)nn1)c1ccc(F)cc1] | 340.1 | A |
| [2-(4-fluorophenyl)-2-methylpropyl][6-(4-fluorophenyl)pyridazin-3-yl]amine | 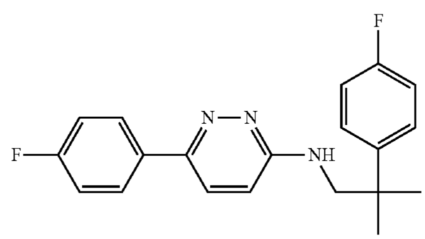 [SMILES: CC(C)(CNc1ccc(-c2ccc(F)cc2)nn1)c1ccc(F)cc1] | 340.1 | B |
| [6-(2-chlorophenyl)pyridazin-3-yl][2-(4-fluorophenyl)-2-methylpropyl]amine | 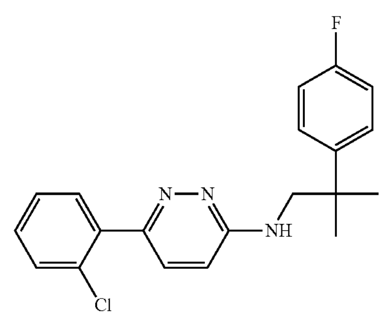 [SMILES: CC(C)(CNc1ccc(-c2ccccc2Cl)nn1)c1ccc(F)cc1] | 356.1 | A |
| [6-(3-chlorophenyl)pyridazin-3-yl][2-(4-fluorophenyl)-2-methylpropyl]amine | 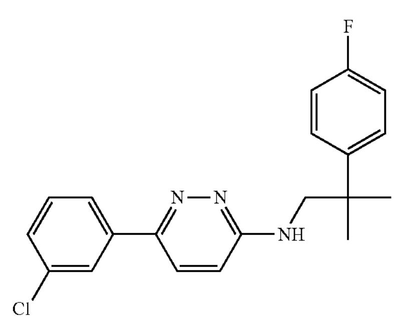 [SMILES: CC(C)(CNc1ccc(-c2cccc(Cl)c2)nn1)c1ccc(F)cc1] | 356.1 | A |

TABLE 2-continued

| Compound | Structure | m/z (M + H) | Mean AC1.4 |
|---|---|---|---|
| [6-(4-chlorophenyl)pyridazin-3-yl][2-(4-fluorophenyl)-2-methylpropyl]amine | 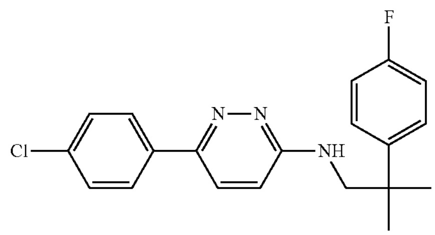 [SMILES: CC(C)(CNc1ccc(-c2ccc(Cl)cc2)nn1)c1ccc(F)cc1] | 356.1 | B |
| 4-(6-{[2-(4-fluorophenyl)-2-methylpropyl]amino}pyridazin-3-yl)benzenecarbonitrile | 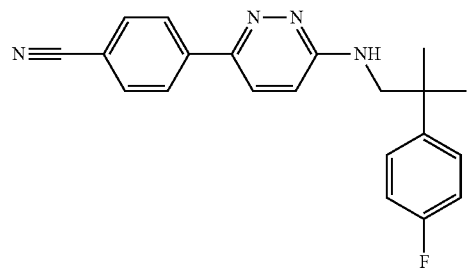 | 347.1 | B |
| [2-(4-fluorophenyl)-2-methylpropyl](6-(3-pyridyl)pyridazin-3-yl)amine | 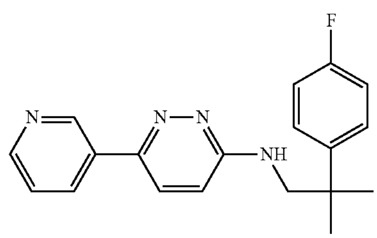 [SMILES: CC(C)(CNc1ccc(-c2cccnc2)nn1)c1ccc(F)cc1] | 323.1 | B |
| [6-(6-amino(2-pyridyl))pyridazin-3-yl][2-(4-fluorophenyl)-2-methylpropyl]amine | 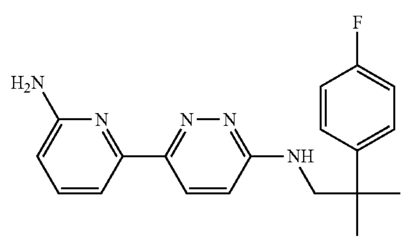 [SMILES: CC(C)(CNc1ccc(-c2cccc(N)n2)nn1)c1ccc(F)cc1] | 338.2 | B |
| N-{[5-(6-{[2-(4-fluorophenyl)-2-methylpropyl]amino}pyridazin-3-yl)-2-pyridyl]methyl}acetamide | 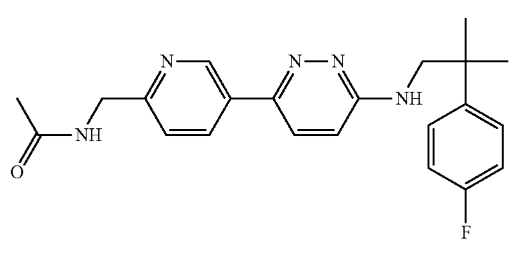 [SMILES: CC(=O)NCc1ccc(-c2ccc(NCC(C)(C)c3ccc(F)cc3)nn2)cn1] | 394.2 | C |
| N-{[5-(6-{[2-(4-fluorophenyl)-2-methylpropyl]amino}pyridazin-3-yl)(2-pyridyl)]methyl}methoxycarboxamide | 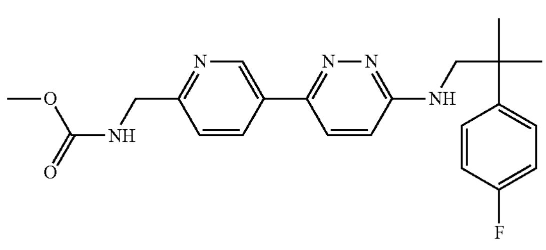 [SMILES: COC(=O)NCc1ccc(-c2ccc(NCC(C)(C)c3ccc(F)cc3)nn2)cn1] | 410.2 | C |

TABLE 2-continued

| Compound | Structure | m/z (M + H) | Mean AC1.4 |
|---|---|---|---|
| {6-[3-(ethylamino)(1H-indazol-5-yl)]pyridazin-3-yl}{[(3-fluoro(2-pyridyl))cyclobutyl]methyl}amine | 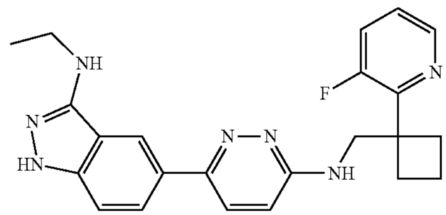 [SMILES: CCNc1n[nH]c2ccc(-c3ccc(NCC4(c5ncccc5F)CCC4)nn3)cc12] | 418.2 | A |
| 3-(6-{[2-methyl-2-(phenylmethoxy)propyl]amino}pyridazin-3-yl)benzamide | 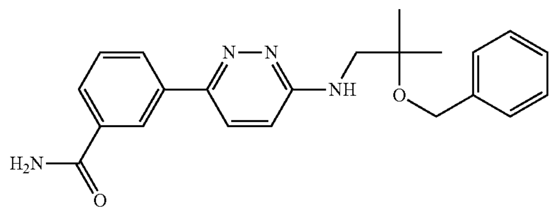 [SMILES: CC(C)(CNc1ccc(-c2cccc(C(N)=O)c2)nn1)OCc1ccccc1] | 377.0 | D |
| 3-(6-{[2-methyl-2-(phenylmethoxy)propyl]amino}pyridazin-3-yl)benzenecarbonitrile | 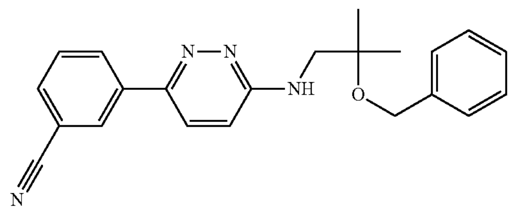 [SMILES: CC(C)(CNc1ccc(-c2cccc(C#N)c2)nn1)OCc1ccccc1] | 359.0 | D |
| [2-(4-fluorophenyl)-2-methylpropyl](6-(2-pyridyl)pyridazin-3-yl)amine | 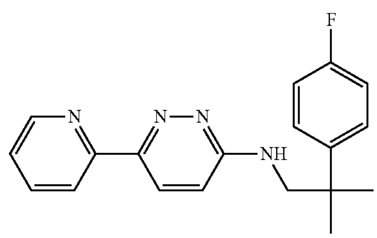 [SMILES: CC(C)(CNc1ccc(-c2ccccn2)nn1)c1ccc(F)cc1] | 323.1 | B |
| N-{4-[6-({[(3-fluoro-2-pyridyl)cyclobutyl]methyl}amino)pyridazin-3-yl]imidazol-2-yl}acetamide | | 382.1 | D |
| [6-(2-aminoimidazol-4-yl)pyridazin-3-yl]{[(3-fluoro(2-pyridyl))cyclobutyl]methyl}amine | 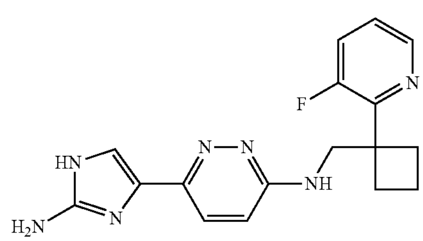 [SMILES: Nc1nc(-c2ccc(NCC3(c4ncccc4F)CCC3)nn2)c[nH]1] | 340.1 | D |
| {[(3-fluoro(2-pyridyl))cyclobutyl]methyl}(6-{3-[(methylethyl)amino](1H-indazol-5-yl)}pyridazin-3-yl)amine | 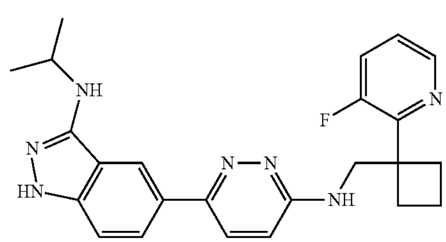 [SMILES: CC(C)Nc1n[nH]c2ccc(-c3ccc(NCC4(c5ncccc5F)CCC4)nn3)cc12] | 432.2 | A |

TABLE 2-continued

| Compound | Structure | m/z (M + H) | Mean AC1.4 |
|---|---|---|---|
| {6-[3-(ethylamino)(1H-indazol-5-yl)]pyridazin-3-yl}[(2-pyridylcyclobutyl)methyl]amine | 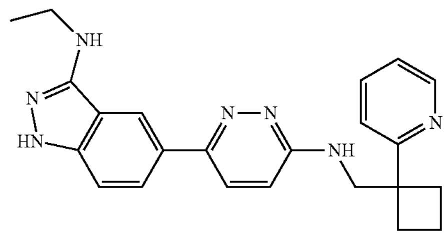 [SMILES: CCNc1n[nH]c2ccc(-c3ccc(NCC4(c5ccccn5)CCC4)nn3)cc12] | 400.2 | A |
| [6-((1E)prop-1-enyl)pyridazin-3-yl][2-(4-fluorophenyl)-2-methylpropyl]amine | | 286.0 | B |
| [2-(4-fluorophenyl)-2-methylpropyl][6-(2-methylprop-1-enyl)pyridazin-3-yl]amine | 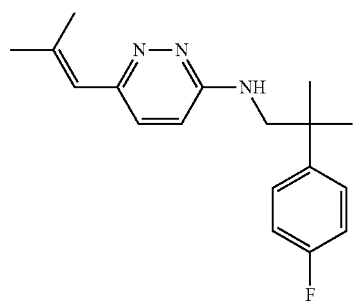 [SMILES: CC(C)=Cc1ccc(NCC(C)(C)c2ccc(F)cc2)nn1] | 300.0 | B |
| [2-(4-fluorophenyl)-2-methylpropyl][6-(2-methylpropyl)pyridazin-3-yl]amine | 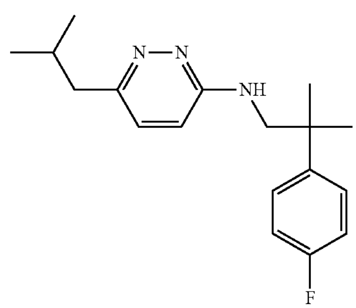 [SMILES: CC(C)Cc1ccc(NCC(C)(C)c2ccc(F)cc2)nn1] | 302.0 | B |
| ethyl 3-(6-{[2-(4-fluorophenyl)-2-methylpropyl]amino}pyridazin-3-yl)propanoate | 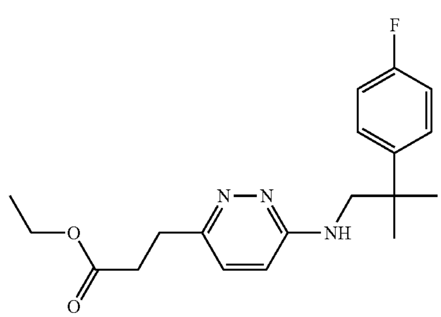 [SMILES: CCOC(=O)CCc1ccc(NCC(C)(C)c2ccc(F)cc2)nn1] | 346.0 | D |

TABLE 2-continued

| Compound | Structure | m/z (M + H) | Mean AC1.4 |
|---|---|---|---|
| 6-(6-{[2-(4-fluorophenyl)-2-methylpropyl]amino}pyridazin-3-yl)pyridine-3-carboxamide | 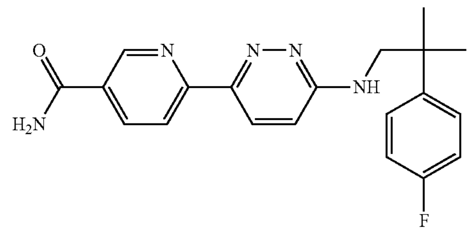 [SMILES: CC(C)(CNc1ccc(-c2ccc(C(N)=O)cn2)nn1)c1ccc(F)cc1] | 366.1 | B |
| (6-ethylpyridazin-3-yl)[2-(4-fluorophenyl)-2-methylpropyl]amine | 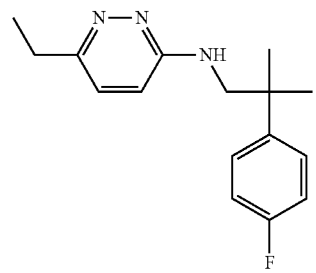 [SMILES: CCc1ccc(NCC(C)(C)c2ccc(F)cc2)nn1] | 274.0 | C |
| [3-(6-{[2-(4-fluorophenyl)-2-methylpropyl]amino}pyridazin-3-yl)phenyl]methan-1-ol | 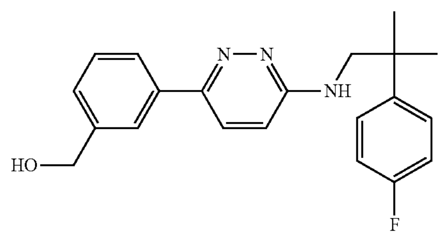 [SMILES: CC(C)(CNc1ccc(-c2cccc(CO)c2)nn1)c1ccc(F)cc1] | 352.2 | B |
| (tert-butoxy)-N-{[3-(6-{[2-(4-fluorophenyl)-2-methylpropyl]amino}pyridazin-3-yl)phenyl]methyl}carboxamide | 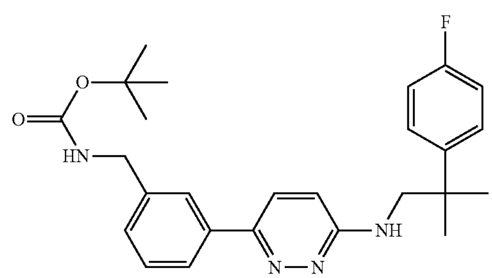 [SMILES: CC(C)(C)OC(=O)NCc1cccc(-c2ccc(NCC(C)(C)c3ccc(F)cc3)nn2)c1] | 451.1 | B |
| {6-[3-(aminomethyl)phenyl]pyridazin-3-yl}[2-(4-fluorophenyl)-2-methylpropyl]amine | 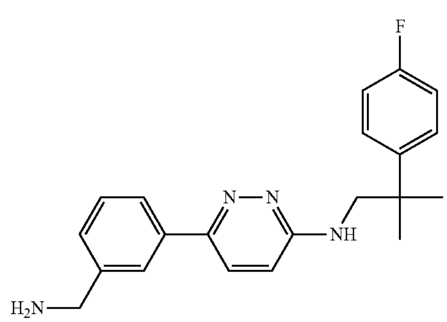 [SMILES: CC(C)(CNc1ccc(-c2cccc(CN)c2)nn1)c1ccc(F)cc1] | 351.2 | B |

TABLE 2-continued

| Compound | Structure | m/z (M + H) | Mean AC1.4 |
|---|---|---|---|
| {[(3-fluoro(2-pyridyl))cyclobutyl]methyl}{6-[2-(trifluoromethoxy)phenyl]pyridazin-3-yl}amine | 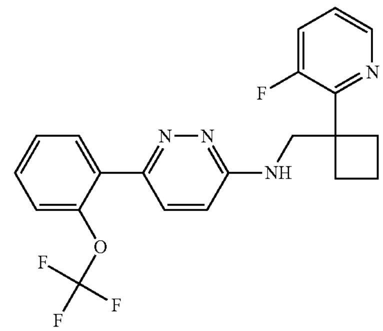 [SMILES: Fc1cccnc1C1(CNc2ccc(-c3ccccc3OC(F)(F)F)nn2)CCC1] | 419.1 | A |
| {2-[6-({[(3-fluoro-2-pyridyl)cyclobutyl]methyl}amino)pyridazin-3-yl]phenyl}methan-1-ol | 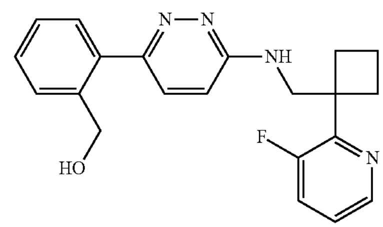 | 365.2 | B |
| [2-(4-fluorophenyl)-2-methylpropyl][6-(5-methoxy(2-pyridyl))pyridazin-3-yl]amine | 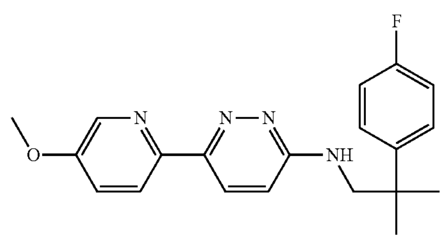 [SMILES: COc1ccc(-c2ccc(NCC(C)(C)c3ccc(F)cc3)nn2)nc1] | 353.2 | B |
| 6-(6-{[2-(4-fluorophenyl)-2-methylpropyl]amino}pyridazin-3-yl)pyridin-3-ol | 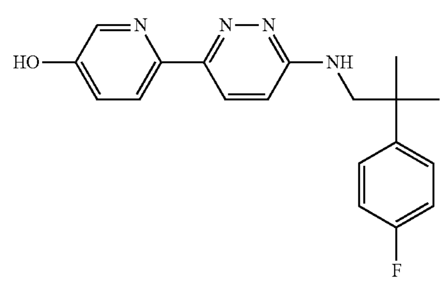 [SMILES: CC(C)(CNc1ccc(-c2ccc(O)cn2)nn1)c1ccc(F)cc1] | 339.1 | A |
| [6-(5-amino(2-pyridyl))pyridazin-3-yl]{[(3-fluoro(2-pyridyl))cyclobutyl]methyl}amine | 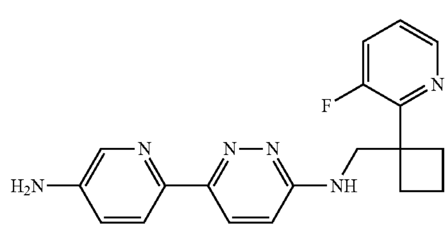 [SMILES: Nc1ccc(-c2ccc(NCC3(c4ncccc4F)CCC3)nn2)nc1] | 351.2 | A |

TABLE 2-continued

| Compound | Structure | m/z (M + H) | Mean AC1.4 |
|---|---|---|---|
| [2-(4-fluorophenyl)-2-methylpropyl](6-{3-[(2,2,2-trifluoroethyl)amino](1H-indazol-5-yl)}pyridazin-3-yl)amine | 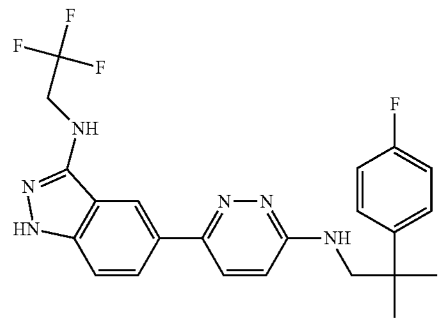 [SMILES: CC(C)(CNc1ccc(-c2ccc3[nH]nc(NCC(F)(F)F)c3c2)nn1)c1ccc(F)cc1] | 459.2 | A |
| [6-(6-amino(3-pyridyl))pyridazin-3-yl]{[(3-fluoro(2-pyridyl))cyclobutyl]methyl}amine | 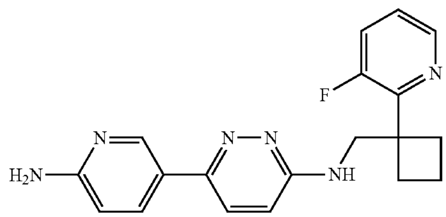 [SMILES: Nc1ccc(-c2ccc(NCC3(c4ncccc4F)CCC3)nn2)cn1] | 351.2 | A |
| [6-(4-amino-3-fluorophenyl)pyridazin-3-yl]{[(3-fluoro(2-pyridyl))cyclobutyl]methyl}amine | 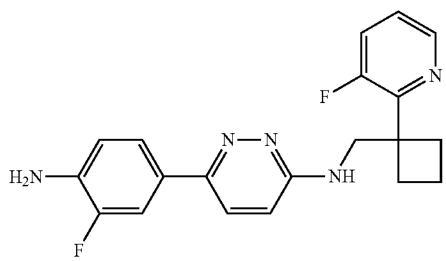 [SMILES: Nc1ccc(-c2ccc(NCC3(c4ncccc4F)CCC3)nn2)cc1F] | 368.1 | A |
| (6-benzotriazol-6-ylpyridazin-3-yl){[(3-fluoro(2-pyridyl))cyclobutyl]methyl}amine | 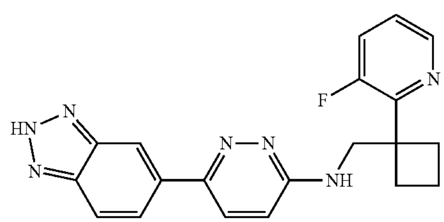 [SMILES: Fc1cccnc1C1(CNc2ccc(-c3ccc4n[nH]nc4c3)nn2)CCC1] | 376.1 | A |
| 4-[6-({[(3-fluoro-2-pyridyl)cyclobutyl]methyl}amino)pyridazin-3-yl]indolin-2-one | 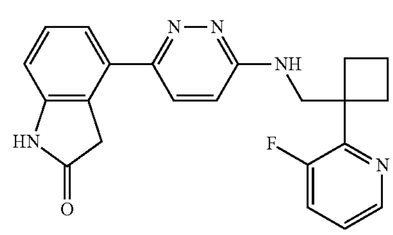 [SMILES: O=C1Cc2c(cccc2-c2ccc(NCC3(c4ncccc4F)CCC3)nn2)N1] | 390.1 | B |
| (6-benzimidazol-5-ylpyridazin-3-yl){[(3-fluoro(2-pyridyl))cyclobutyl]methyl}amine | 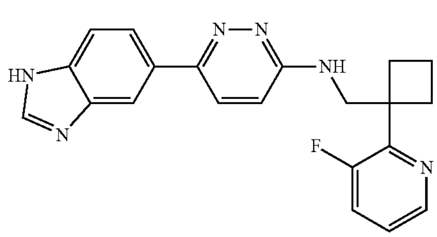 [SMILES: Fc1cccnc1C1(CNc2ccc(-c3ccc4[nH]cnc4c3)nn2)CCC1] | 375.1 | A |

TABLE 2-continued

| Compound | Structure | m/z (M + H) | Mean AC1.4 |
|---|---|---|---|
| N-{3-[6-({[(3-fluoro-2-pyridyl)cyclobutyl]methyl}amino)pyridazin-3-yl]phenyl}acetamide | | 392.2 | B |
| {[(3-fluoro(2-pyridyl))cyclobutyl]methyl}[6-(4-morpholin-4-ylphenyl)pyridazin-3-yl]amine | 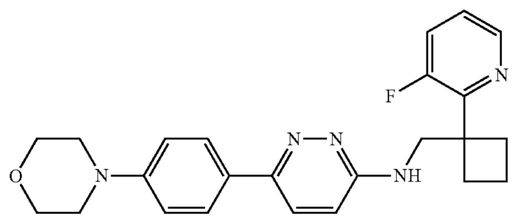 [SMILES: Fc1cccnc1C1(CNc2ccc(-c3ccc(N4CCOCC4)cc3)nn2)CCC1] | 420.2 | D |
| {[(3-fluoro(2-pyridyl))cyclobutyl]methyl}[6-(2-methylpyrimidin-5-yl)pyridazin-3-yl]amine | 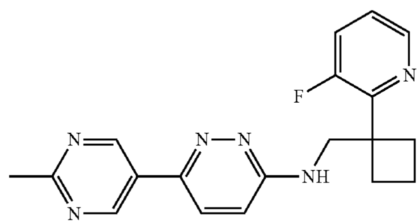 [SMILES: Cc1ncc(-c2ccc(NCC3(c4ncccc4F)CCC3)nn2)cn1] | 351.2 | D |
| [5-(6-{[2-(4-fluorophenyl)-2-methylpropyl]amino}pyridazin-3-yl)(1H-indazol-3-yl)]dimethylamine | 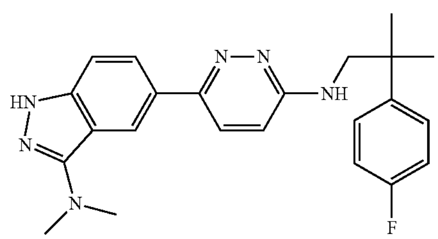 [SMILES: CN(C)c1n[nH]c2ccc(-c3ccc(NCC(C)(C)c4ccc(F)cc4)nn3)cc12] | 405.2 | B |
| [2-(4-fluorophenyl)-2-methylpropyl][6-(3-{[2-(phenylmethoxy)ethyl]amino}(1H-indazol-5-yl))pyridazin-3-yl]amine | 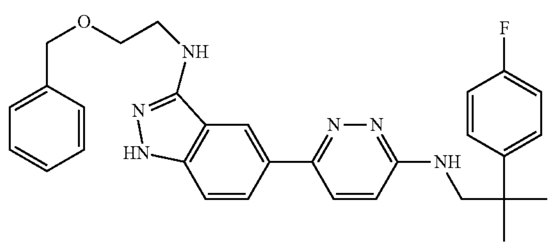 [SMILES: CC(C)(CNc1ccc(-c2ccc3[nH]nc(NCCOCc4ccccc4)c3c2)nn1)c1ccc(F)cc1] | 511.2 | A |
| 2-{[5-(6-{[2-(4-fluorophenyl)-2-methylpropyl]amino}pyridazin-3-yl)-1H-indazol-3-yl]amino}ethan-1-ol | 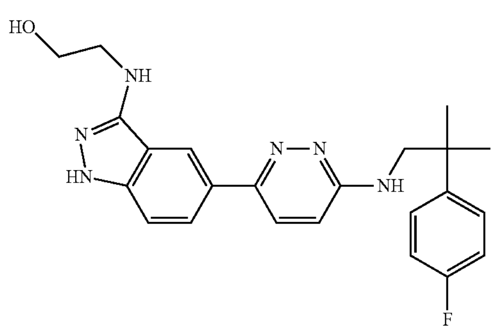 [SMILES: CC(C)(CNc1ccc(-c2ccc3[nH]nc(NCCO)c3c2)nn1)c1ccc(F)cc1] | 421.2 | A |

TABLE 2-continued

| Compound | Structure | m/z (M + H) | Mean AC1.4 |
|---|---|---|---|
| {[(3-fluoro(2-pyridyl))cyclobutyl]methyl}(6-pyrimidin-2-ylpyridazin-3-yl)amine | 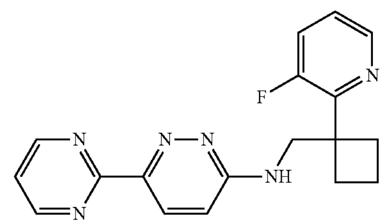 | 337.0 | B |
| {[(3-fluoro(2-pyridyl))cyclobutyl]methyl}(6-pyrazin-2-ylpyridazin-3-yl)amine | 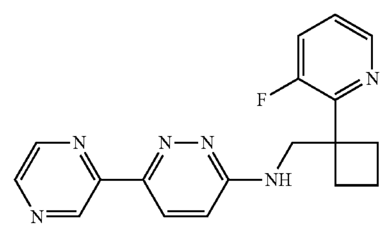 [SMILES: Fc1cccnc1C1(CNc2ccc(-c3ncccn3)nn2)CCC1] | 337.0 | B |
| ethyl 6-({[(3-fluoro-2-pyridyl)cyclobutyl]methyl}amino)pyridazine-3-carboxylate | 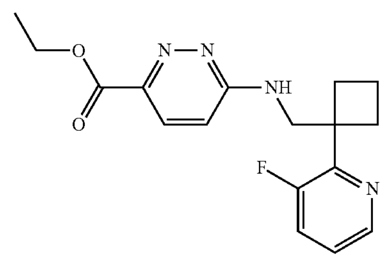 [SMILES: CCOC(=O)c1ccc(NCC2(c3ncccc3F)CCC2)nn1] | 331.0 | D |
| 2-[6-({[(3-fluoro-2-pyridyl)cyclobutyl]methyl}amino)pyridazin-3-yl]propan-2-ol | 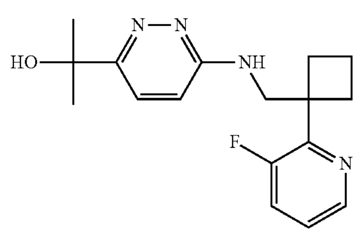 [SMILES: CC(C)(O)c1ccc(NCC2(c3ncccc3F)CCC2)nn1] | 317.0 | D |
| {[(3-fluoro(2-pyridyl))cyclobutyl]methyl}(6-phenylpyridazin-3-yl)amine | 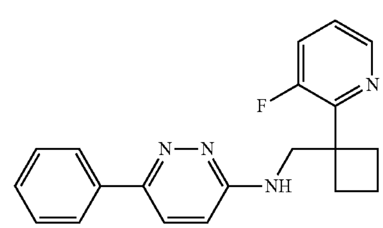 | 335.1 | A |
| {[(3-fluoro(2-pyridyl))cyclobutyl]methyl}(6-vinylpyridazin-3-yl)amine | 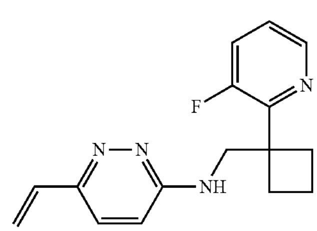 [SMILES: C=Cc1ccc(NCC2(c3ncccc3F)CCC2)nn1] | 285.1 | D |

TABLE 2-continued

| Compound | Structure | m/z (M + H) | Mean AC1.4 |
|---|---|---|---|
| (6-ethylpyridazin-3-yl){[(3-fluoro(2-pyridyl))cyclobutyl]methyl}amine | 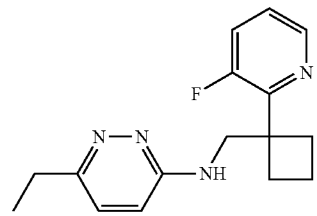 [SMILES: CCc1ccc(NCC2(c3ncccc3F)CCC2)nn1] | 287.1 | D |
| N-{4-[6-({[(3-fluoro-2-pyridyl)cyclobutyl]methyl}amino)pyridazin-3-yl]phenyl}acetamide | 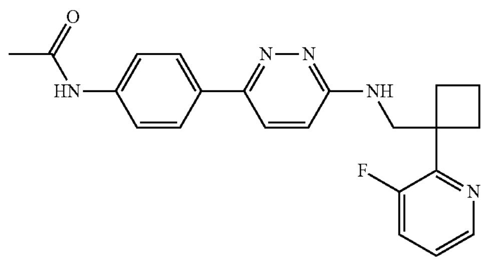 [SMILES: CC(=O)Nc1ccc(-c2ccc(NCC3(c4ncccc4F)CCC3)nn2)cc1] | 392.2 | A |
| [6-(2-aminopyrimidin-5-yl)pyridazin-3-yl]{[(3-fluoro(2-pyridyl))cyclobutyl]methyl}amine | 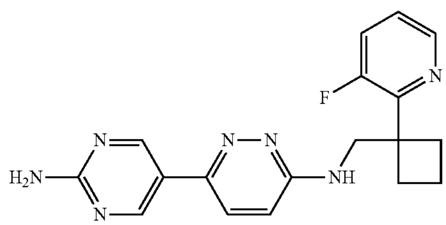 [SMILES: Nc1ncc(-c2ccc(NCC3(c4ncccc4F)CCC3)nn2)cn1] | 352.1 | B |
| N-{5-[6-({[(3-fluoro-2-pyridyl)cyclobutyl]methyl}amino)pyridazin-3-yl]pyrimidin-2-yl}acetamide | 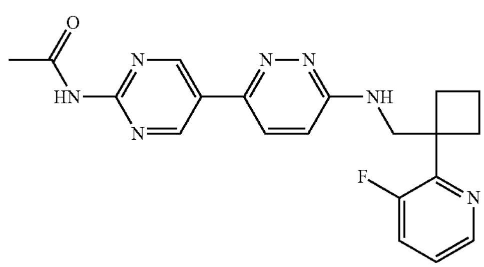 | 394.2 | C |
| N-{5-[6-({[(3-fluoro(2-pyridyl))cyclobutyl]methyl}amino)pyridazin-3-yl]pyrimidin-2-yl}methoxycarboxamide | 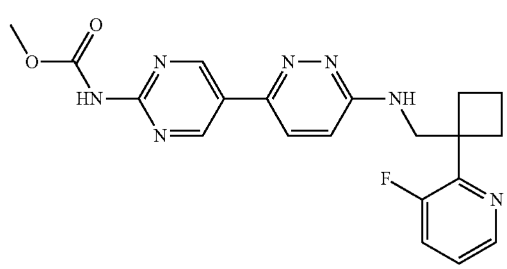 [SMILES: COC(=O)Nc1ncc(-c2ccc(NCC3(c4ncccc4F)CCC3)nn2)cn1] | 410.1 | D |
| {[(3-fluoro(2-pyridyl))cyclobutyl]methyl}[6-(5-methoxy(2-pyridyl))pyridazin-3-yl]amine | 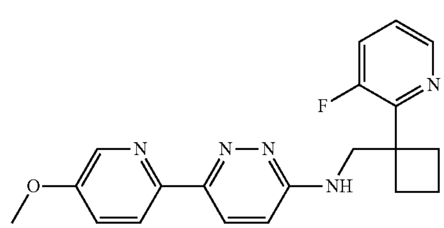 [SMILES: COc1ccc(-c2ccc(NCC3(c4ncccc4F)CCC3)nn2)nc1] | 366.2 | B |

TABLE 2-continued

| Compound | Structure | m/z (M + H) | Mean AC1.4 |
|---|---|---|---|
| 6-[6-({[(3-fluoro-2-pyridyl)cyclobutyl]methyl}amino)pyridazin-3-yl]pyridin-3-ol | 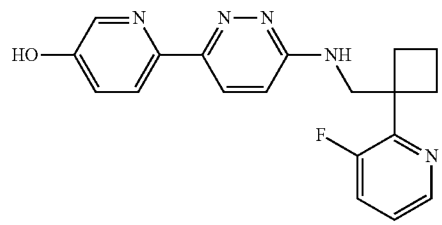 [SMILES: Oc1ccc(-c2ccc(NCC3(c4ncccc4F)CCC3)nn2)nc1] | 352.1 | A |
| {5-[6-({[(3-fluoro(2-pyridyl))cyclobutyl]methyl}amino)pyridazin-3-yl]pyrimidin-2-yl}(methylsulfonyl)amine | 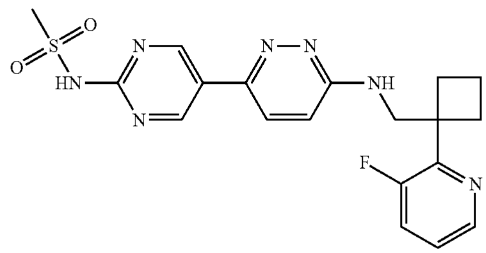 [SMILES: CS(=O)(=O)Nc1ncc(-c2ccc(NCC3(c4ncccc4F)CCC3)nn2)cn1] | 430.0 | D |
| [6-(2,3-difluorophenyl)pyridazin-3-yl]{[(3-fluoro(2-pyridyl))cyclobutyl]methyl}amine | 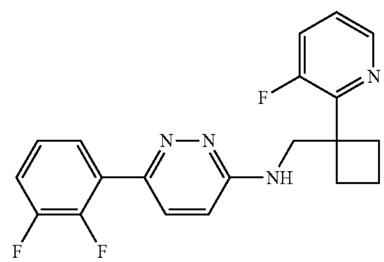 [SMILES: Fc1cccnc1C1(CNc2ccc(-c3cccc(F)c3F)nn2)CCC1] | 371.0 | A |
| {[(3-fluoro(2-pyridyl))cyclobutyl]methyl}[6-(3-fluoro(2-pyridyl))pyridazin-3-yl]amine | 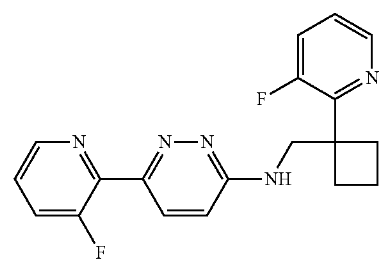 | 354.0 | B |
| 3-{6-[(1-methyl-1-phenylethyl)amino]pyridazin-3-yl}benzamide | 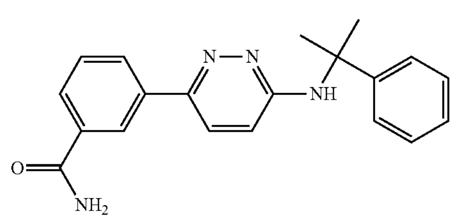 [SMILES: CC(C)(Nc1ccc(-c2cccc(C(N)=O)c2)nn1)c1ccccc1] | 333.2 | B |
| 5-[6-({[(3-fluoro-2-pyridyl)cyclobutyl]methyl}amino)pyridazin-3-yl]indolin-2-one | 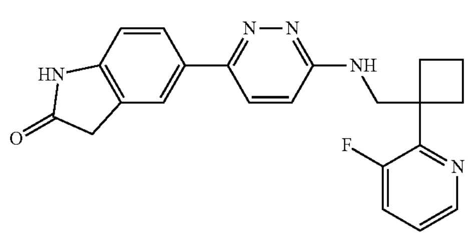 [SMILES: O=C1Cc2cc(-c3ccc(NCC4(c5ncccc5F)CCC4)nn3)ccc2N1] | 390.1 | B |

TABLE 2-continued

| Compound | Structure | m/z (M + H) | Mean AC1.4 |
|---|---|---|---|
| 5-[6-({[(3-fluoro-2-pyridyl)cyclobutyl]methyl}amino)pyridazin-3-yl]-1H-2-hydroindazol-3-one | 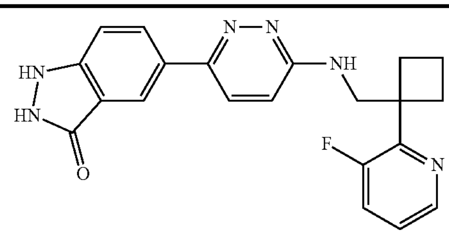 | 391.1 | A |
| N-{3-[6-({[(3-fluoro(2-pyridyl))cyclobutyl]methyl}amino)pyridazin-3-yl]phenyl}(methylamino)carboxamide | 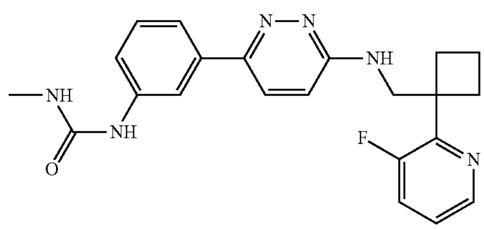 [SMILES: CNC(=O)Nc1cccc(-c2ccc(NCC3(c4ncccc4F)CCC3)nn2)c1] | 407.2 | A |
| N-{4-[6-({[(3-fluoro(2-pyridyl))cyclobutyl]methyl}amino)pyridazin-3-yl]phenyl}(methylamino)carboxamide | 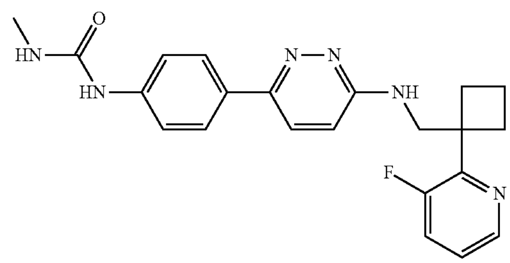 [SMILES: CNC(=O)Nc1ccc(-c2ccc(NCC3(c4ncccc4F)CCC3)nn2)cc1] | 407.2 | A |
| tert-butyl 4-{5-[6-({[(3-fluoro-2-pyridyl)cyclobutyl]methyl}amino)pyridazin-3-yl]pyrimidin-2-yl}piperazinecarboxylate | 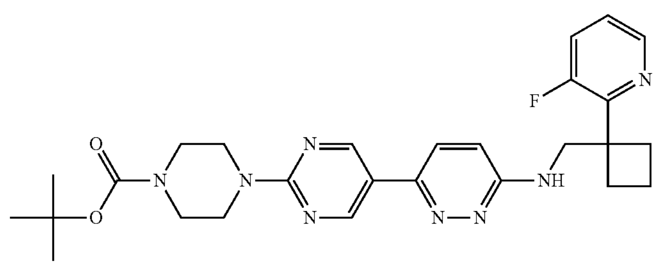 [SMILES: CC(C)(C)OC(=O)N1CCN(c2ncc(-c3ccc(NCC4(c5ncccc5F)CCC4)nn3)cn2)CC1] | 521.3 | D |
| 2-({5-[6-({[(3-fluoro-2-pyridyl)cyclobutyl]methyl}amino)pyridazin-3-yl]pyrimidin-2-yl}amino)acetamide | 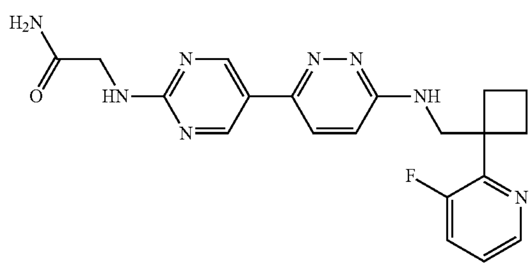 [SMILES: NC(=O)CNc1ncc(-c2ccc(NCC3(c4ncccc4F)CCC3)nn2)cn1] | 409.1 | C |
| {6-[2-(aminomethyl)-5-fluorophenyl]pyridazin-3-yl}{[(3-fluoro(2-pyridyl))cyclobutyl]methyl}amine | 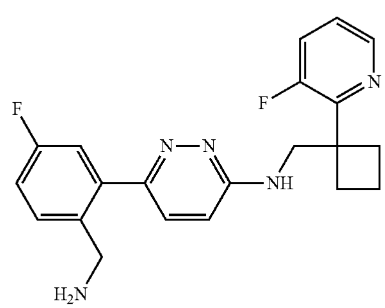 [SMILES: NCc1ccc(F)cc1-c1ccc(NCC2(c3ncccc3F)CCC2)nn1] | 382.2 | C |

TABLE 2-continued

| Compound | Structure | m/z (M + H) | Mean AC1.4 |
|---|---|---|---|
| {6-[2-(aminomethyl)phenyl]pyridazin-3-yl}{[(3-fluoro(2-pyridyl))cyclobutyl]methyl}amine | 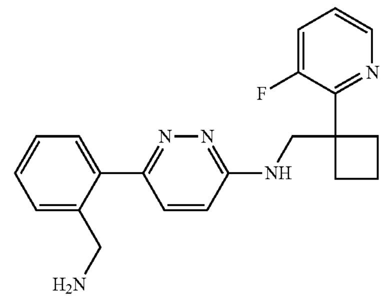 [SMILES: NCc1ccccc1-c1ccc(NCC2(c3ncccc3F)CCC2)nn1] | 364.2 | D |
| {6-[4-(aminomethyl)phenyl]pyridazin-3-yl}{[(3-fluoro(2-pyridyl))cyclobutyl]methyl}amine | 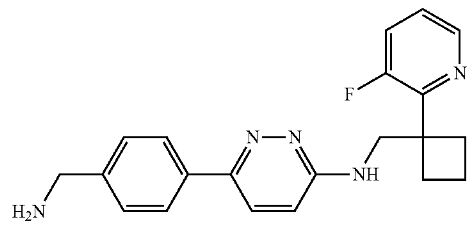 [SMILES: NCc1ccc(-c2ccc(NCC3(c4ncccc4F)CCC3)nn2)cc1] | 364.2 | B |
| {[(3-fluoro(2-pyridyl))cyclobutyl]methyl}[6-(2-piperazinylpyrimidin-5-yl)pyridazin-3-yl]amine | 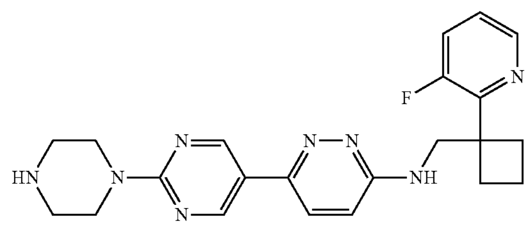 [SMILES: Fc1cccnc1C1(CNc2ccc(-c3cnc(N4CCNCC4)nc3)nn2)CCC1] | 421.2 | D |
| (6-(1H-indazol-6-yl)pyridazin-3-yl)(2,2-difluoro-2-(2-pyridyl)ethyl)amine | 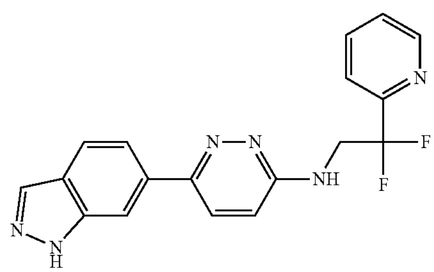 [SMILES: FC(F)(CNc1ccc(-c2ccc3cn[nH]c3c2)nn1)c1ccccn1] | 353.1 | D |
| 3-{6-[(2,2-difluoro-2-(2-pyridyl)ethyl)amino]pyridazin-3-yl}benzamide | 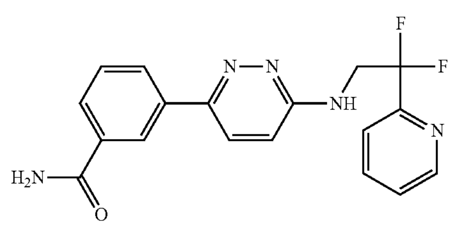 [SMILES: NC(=O)c1cccc(-c2ccc(NCC(F)(F)c3ccccn3)nn2)c1] | 356.1 | D |
| [6-(3-chloro(2-pyridyl))pyridazin-3-yl]{[(3-fluoro(2-pyridyl))cyclobutyl]methyl}amine | 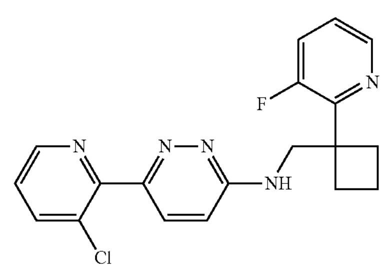 [SMILES: Fc1cccnc1C1(CNc2ccc(-c3ncccc3Cl)nn2)CCC1] | 370.1 | C |

TABLE 2-continued

| Compound | Structure | m/z (M + H) | Mean AC1.4 |
|---|---|---|---|
| 6-({[(3-fluoro-2-pyridyl)cyclobutyl]methyl}amino)pyridazine-3-carbonitrile | 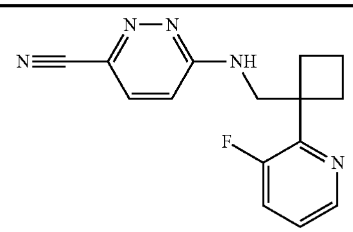 | 284.0 | D |
| 1-[6-({[(3-fluoro-2-pyridyl)cyclobutyl]methyl}amino)pyridazin-3-yl]ethan-1-one | 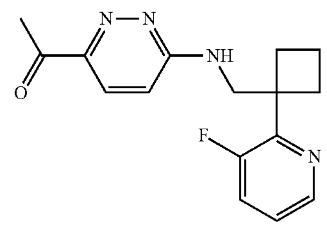 [SMILES: CC(=O)c1ccc(NCC2(c3ncccc3F)CCC2)nn1] | 301.1 | D |
| {[(3-fluoro(2-pyridyl))cyclobutyl]methyl}[6-(2-methyl(3-pyridyl))pyridazin-3-yl]amine | 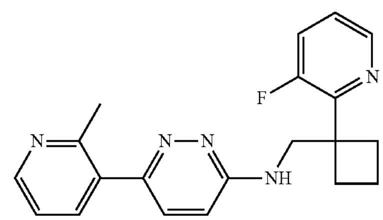 [SMILES: Cc1ncccc1-c1ccc(NCC2(c3ncccc3F)CCC2)nn1] | 350.2 | C |
| 3-[6-({[(3-fluoro-2-pyridyl)cyclobutyl]methyl}amino)pyridazin-3-yl]pyridine-2-carbonitrile | 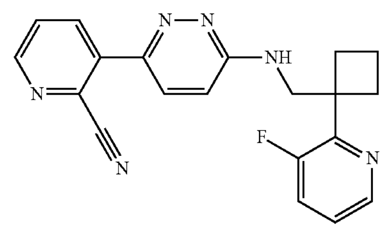 [SMILES: N#Cc1ncccc1-c1ccc(NCC2(c3ncccc3F)CCC2)nn1] | 361.1 | C |
| 3-[6-({[(3-fluoro-2-pyridyl)cyclobutyl]methyl}amino)pyridazin-3-yl]pyridine-2-carboxamide | 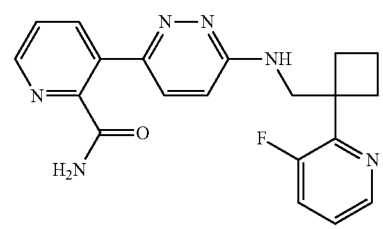 [SMILES: NC(=O)c1ncccc1-c1ccc(NCC2(c3ncccc3F)CCC2)nn1] | 379.2 | C |
| methyl 3-[6-({[(3-fluoro-2-pyridyl)cyclobutyl]methyl}amino)pyridazin-3-yl]pyridine-2-carboxylate | 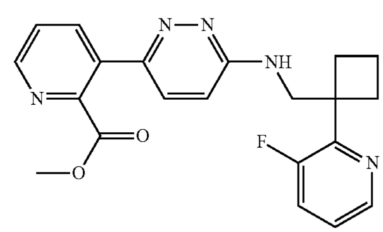 [SMILES: COC(=O)c1ncccc1-c1ccc(NCC2(c3ncccc3F)CCC2)nn1] | 394.2 | C |
| 2-{3-[6-({[(3-fluoro-2-pyridyl)cyclobutyl]methyl}amino)pyridazin-3-yl]-2-pyridyl}propan-2-ol | 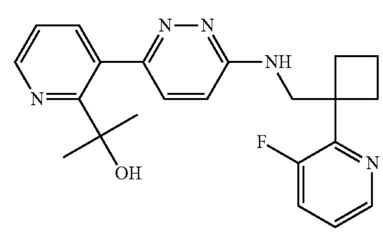 [SMILES: CC(C)(O)c1ncccc1-c1ccc(NCC2(c3ncccc3F)CCC2)nn1] | 394.2 | D |

TABLE 2-continued

| Compound | Structure | m/z (M + H) | Mean AC1.4 |
|---|---|---|---|
| amino-N-{4-[6-({[(3-fluoro(2-pyridyl))cyclobutyl]methyl}amino)pyridazin-3-yl]phenyl}amide | 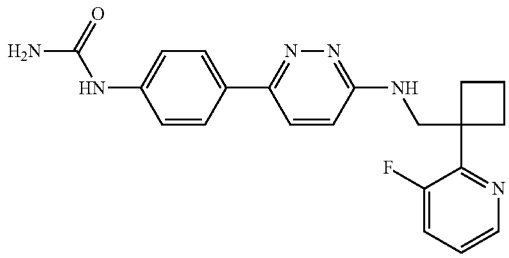 [SMILES: NC(=O)Nc1ccc(-c2ccc(NCC3(c4ncccc4F)CCC3)nn2)cc1] | 393.0 | A |
| 2-amino-2-{3-[6-({[(3-fluoro(2-pyridyl))cyclobutyl]methyl}amino)pyridazin-3-yl]phenyl}acetamide | 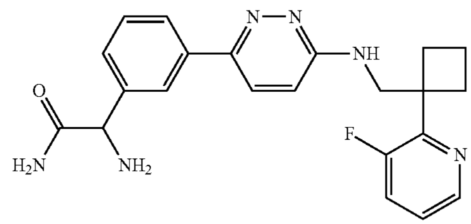 [SMILES: NC(=O)C(N)c1cccc(-c2ccc(NCC3(c4ncccc4F)CCC3)nn2)c1] | 407.0 | C |
| {[(3-fluoro(2-pyridyl))cyclobutyl]methyl}(6-pyridazin-4-ylpyridazin-3-yl)annine | 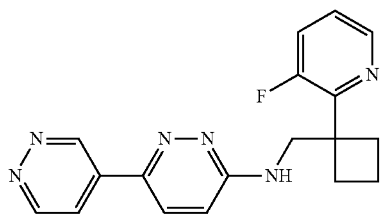 [SMILES: Fc1cccnc1C1(CNc2ccc(-c3ccnnc3)nn2)CCC1] | 337.2 | D |
| 3-[6-({[3,3-difluoro-1-(3-fluoro(2-pyridyl))cyclobutyl]methyl}amino)pyridazin-3-yl]benzamide | 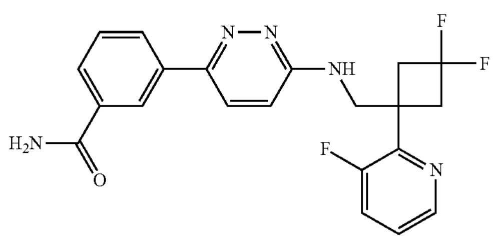 [SMILES: NC(=O)c1cccc(-c2ccc(NCC3(c4ncccc4F)CC(F)(F)C3)nn2)c1] | 414.0 | B |
| (6-(1H-indazol-5-yl)pyridazin-3-yl){[3,3-difluoro-1-(3-fluoro(2-pyridyl))cyclobutyl]methyl}amine | 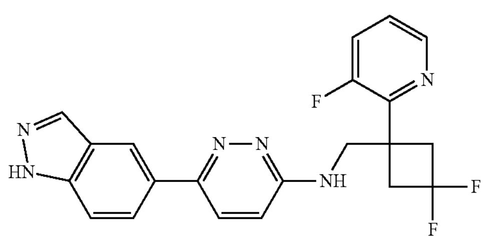 [SMILES: Fc1cccnc1C1(CNc2ccc(-c3ccc4[nH]ncc4c3)nn2)CC(F)(F)C1] | 411.0 | B |
| 5-[6-({[(3-fluoro(2-pyridyl))cyclobutyl]methyl}amino)pyridazin-3-yl]-2-(methylethyl)-1H-2-hydroindazol-3-one | 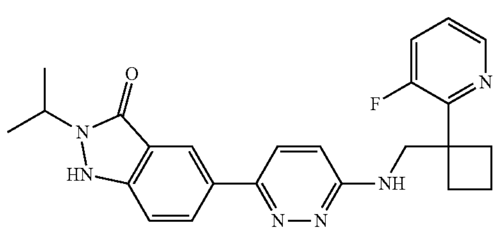 [SMILES: CC(C)n1[nH]c2ccc(-c3ccc(NCC4(c5ncccc5F)CCC4)nn3)cc2c1=O] | 433.1 | B |

TABLE 2-continued

| Compound | Structure | m/z (M + H) | Mean AC1.4 |
|---|---|---|---|
| 5-[6-({[(3-fluoro(2-pyridyl))cyclobutyl]methyl}amino)pyridazin-3-yl]-1-(methylethyl)-1H-2-hydroindazol-3-one | 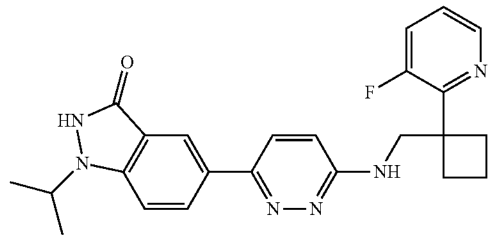 [SMILES: CC(C)n1[nH]c(=O)c2cc(-c3ccc(NCC4(c5ncccc5F)CCC4)nn3)ccc21] | 433.1 | C |
| 3-{6-[(1-methyl-1-phenylethyl)amino]pyridazin-3-yl}benzenecarbonitrile | 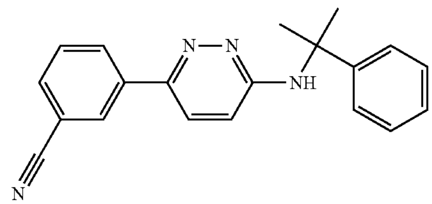 [SMILES: CC(C)(Nc1ccc(-c2cccc(C#N)c2)nn1)c1ccccc1] | 315.0 | B |
| 3-{6-[(tert-butyl)amino]pyridazin-3-yl}benzamide | 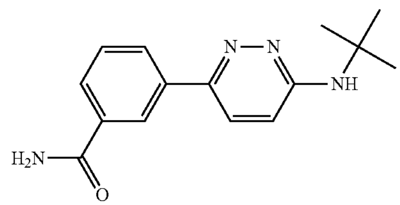 [SMILES: CC(C)(C)Nc1ccc(-c2cccc(C(N)=O)c2)nn1] | 271.1 | C |
| 3-[6-(phenylcarbonylamino)pyridazin-3-yl]benzamide | 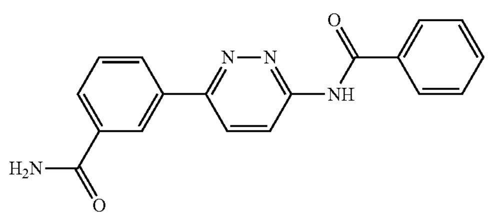 [SMILES: NC(=O)c1cccc(-c2ccc(NC(=O)c3ccccc3)nn2)c1] | 319.1 | D |
| {[(3-fluoro(2-pyridyl))cyclobutyl]methyl}(6-(2-pyridyl)pyridazin-3-yl)amine | 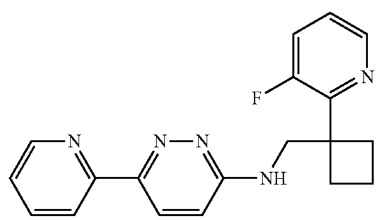 [SMILES: Fc1cccnc1C1(CNc2ccc(-c3ccccn3)nn2)CCC1] | 336.1 | B |
| 3-{6-[(1-methyl-1-(2-pyridyl)ethyl)amino]pyridazin-3-yl}benzamide | 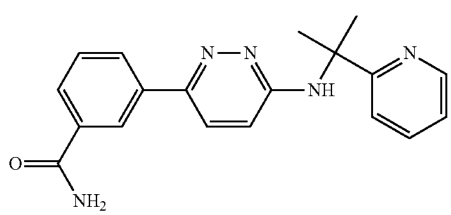 [SMILES: CC(C)(Nc1ccc(-c2cccc(C(N)=O)c2)nn1)c1ccccn1] | 334.1 | D |
| {3-[6-({[(3-fluoro-2-pyridyl)cyclobutyl]methyl}amino)pyridazin-3-yl]-2-pyridyl}methan-1-ol | 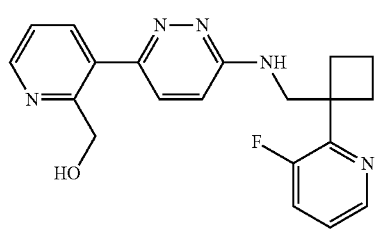 | 366.2 | C |

TABLE 2-continued

| Compound | Structure | m/z (M + H) | Mean AC1.4 |
|---|---|---|---|
| 3-(6-{[(4-fluorophenyl)cyclobutyl]amino}pyridazin-3-yl)benzamide | 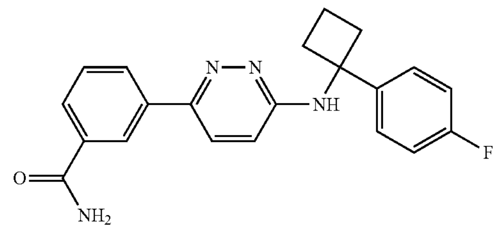 | 363.1 | A |
| (6-(1H-indazol-5-yl)pyridazin-3-yl)[(4-fluorophenyl)cyclobutyl]amine | 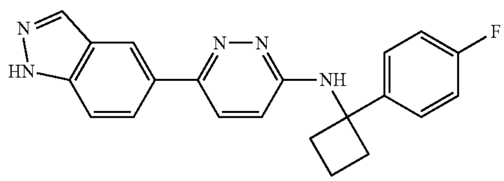 [SMILES: Fc1ccc(C2(Nc3ccc(-c4ccc5[nH]ncc5c4)nn3)CCC2)cc1] | 360.1 | A |
| 4-{6-[(1-methyl-1-phenylethyl)amino]pyridazin-3-yl}benzamide | 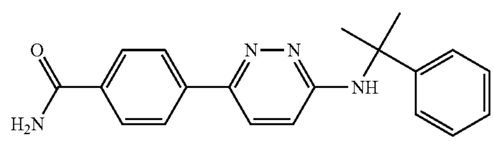 [SMILES: CC(C)(Nc1ccc(-c2ccc(C(N)=O)cc2)nn1)c1ccccc1] | 333.1 | C |
| (6-(1H-indazol-5-yl)pyridazin-3-yl)(1-methyl-1-phenylethyl)amine | 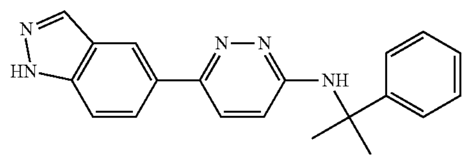 [SMILES: CC(C)(Nc1ccc(-c2ccc3[nH]ncc3c2)nn1)c1ccccc1] | 330.2 | B |
| [6-(6-amino(3-pyridyl))pyridazin-3-yl](1-methyl-1-phenylethyl)amine | 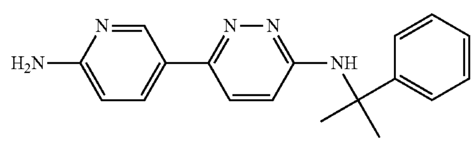 [SMILES: CC(C)(Nc1ccc(-c2ccc(N)nc2)nn1)c1ccccc1] | 306.2 | B |
| amino-N-{5-[6-({[(3-fluoro(2-pyridyl))cyclobutyl]methyl}amino)pyridazin-3-yl](2-pyridyl)}amide | 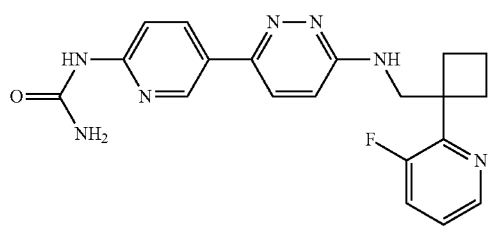 [SMILES: NC(=O)Nc1ccc(-c2ccc(NCC3(c4ncccc4F)CCC3)nn2)cn1] | 394.2 | B |
| (1-methyl-1-phenylethyl)(6-phenylpyridazin-3-yl)amine | 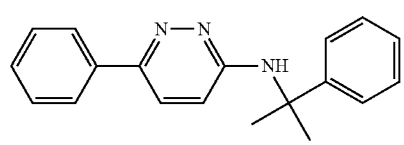 [SMILES: CC(C)(Nc1ccc(-c2ccccc2)nn1)c1ccccc1] | 290.1 | B |
| 1-amino-1-{4-[6-({[(3-fluoro(2-pyridyl))cyclobutyl]methyl}amino)pyridazin-3-yl]phenyl}-2-methylpropan-2-ol | 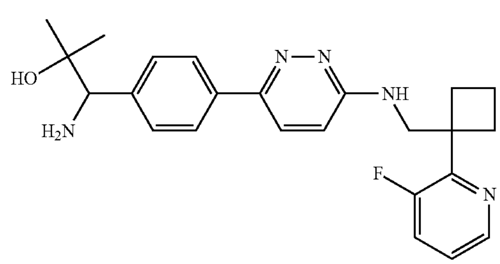 [SMILES: CC(C)(O)C(N)c1ccc(-c2ccc(NCC3(c4ncccc4F)CCC3)nn2)cc1] | 422.2 | D |

TABLE 2-continued

| Compound | Structure | m/z (M + H) | Mean AC1.4 |
|---|---|---|---|
| amino-N-{5-[6-({[(3-fluoro(2-pyridyl))cyclobutyl]methyl}amino)pyridazin-3-yl]pyrimidin-2-yl}amide | 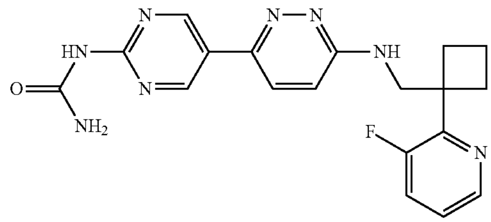 [SMILES: NC(=O)Nc1ncc(-c2ccc(NCC3(c4ncccc4F)CCC3)nn2)cn1] | 395.2 | D |
| (6-(1H-indazol-6-yl)pyridazin-3-yl){[3,3-difluoro-1-(3-fluoro(2-pyridyl))cyclobutyl]methyl}amine | 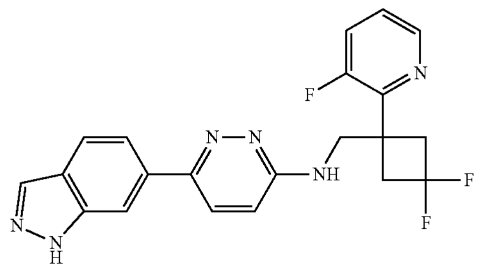 [SMILES: Fc1cccnc1C1(CNc2ccc(-c3ccc4cn[nH]c4c3)nn2)CC(F)(F)C1] | 411.1 | B |
| [6-(2-amino(3-pyridyl))pyridazin-3-yl]{[(3-fluoro(2-pyridyl))cyclobutyl]methyl}amine | 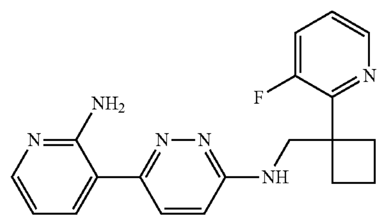 | 351.1 | B |
| [6-(6-amino-5-fluoro(3-pyridyl))pyridazin-3-yl]{[(3-fluoro(2-pyridyl))cyclobutyl]methyl}amine | 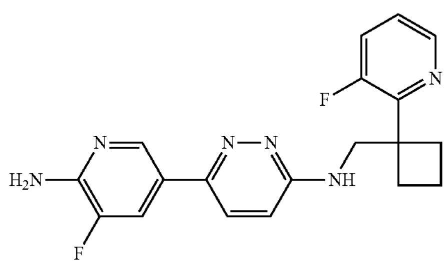 [SMILES: Nc1ncc(-c2ccc(NCC3(c4ncccc4F)CCC3)nn2)cc1F] | 369.1 | A |
| 6-[6-({[(3-fluoro-2-pyridyl)cyclobutyl]methyl}amino)pyridazin-3-yl]indolin-2-one | 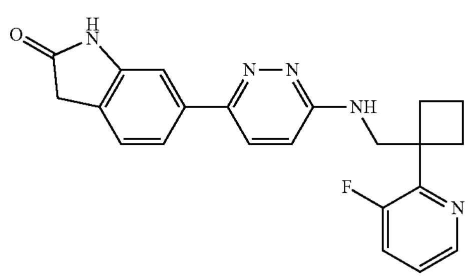 [SMILES: O=C1Cc2ccc(-c3ccc(NCC4(c5ncccc5F)CCC4)nn3)cc2N1] | 390.1 | B |
| [6-(2-aminopyrimidin-5-yl)pyridazin-3-yl][(4-fluorophenyl)cyclobutyl]amine | 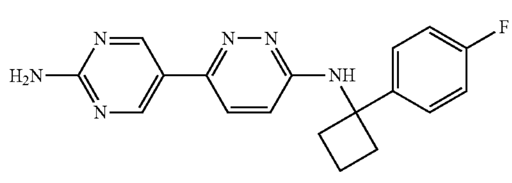 [SMILES: Nc1ncc(-c2ccc(NC3(c4ccc(F)cc4)CCC3)nn2)cn1] | 337.0 | B |

TABLE 2-continued

| Compound | Structure | m/z (M + H) | Mean AC1.4 |
|---|---|---|---|
| amino-N-[4-(6-{[(4-fluorophenyl)cyclobutyl]amino}pyridazin-3-yl)phenyl]amide | 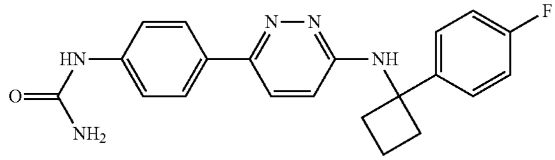 [SMILES: NC(=O)Nc1ccc(-c2ccc(NC3(c4ccc(F)cc4)CCC3)nn2)cc1] | 378.2 | A |
| amino-N-{4-[6-({[3,3-difluoro-1-(3-fluoro(2-pyridyl))cyclobutyl]methyl}amino)pyridazin-3-yl]phenyl}amide | 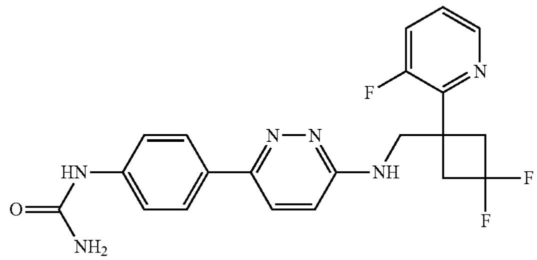 [SMILES: NC(=O)Nc1ccc(-c2ccc(NCC3(c4ncccc4F)CC(F)(F)C3)nn2)cc1] | 429.0 | A |
| 3-(6-{[1-(4-fluorophenyl)-isopropyl]amino}pyridazin-3-yl)benzamide | 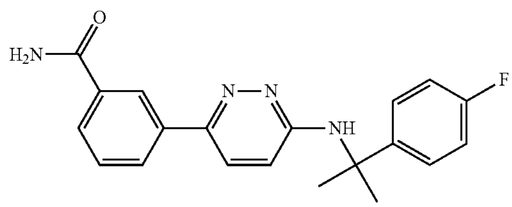 [SMILES: CC(C)(Nc1ccc(-c2cccc(C(N)=O)c2)nn1)c1ccc(F)cc1] | 351.1 | B |
| 3-(6-{[(2-fluorophenyl)cyclobutyl]amino}pyridazin-3-yl)benzamide | 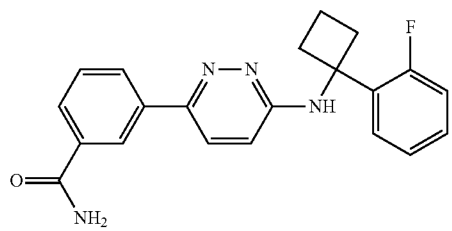 [SMILES: NC(=O)c1cccc(-c2ccc(NC3(c4ccccc4F)CCC3)nn2)c1] | 363.2 | A |
| 3-(6-{[1-(3-fluorophenyl)-isopropyl]amino}pyridazin-3-yl)benzamide | 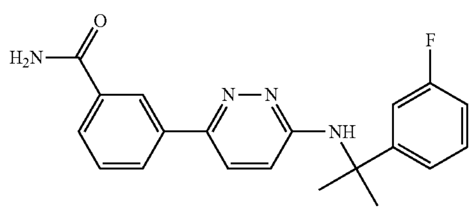 [SMILES: CC(C)(Nc1ccc(-c2cccc(C(N)=O)c2)nn1)c1cccc(F)c1] | 351.1 | B |
| 3-(6-{[(3-fluorophenyl)cyclobutyl]amino}pyridazin-3-yl)benzamide | 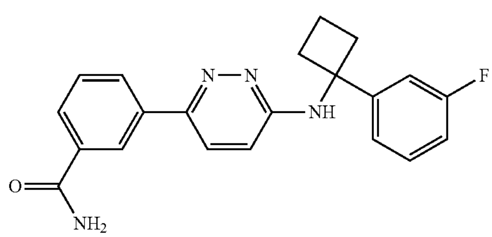 | 363.2 | B |
| 3-{6-[(2-hydroxy-tert-butyl)amino]pyridazin-3-yl}benzamide | 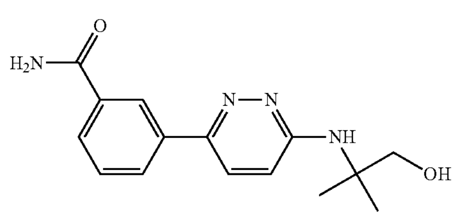 [SMILES: CC(C)(CO)Nc1ccc(-c2cccc(C(N)=O)c2)nn1] | 287.1 | D |

TABLE 2-continued

| Compound | Structure | m/z (M + H) | Mean AC1.4 |
|---|---|---|---|
| 3-{6-[(2-pyridylcyclobutyl)amino]pyridazin-3-yl}benzamide | 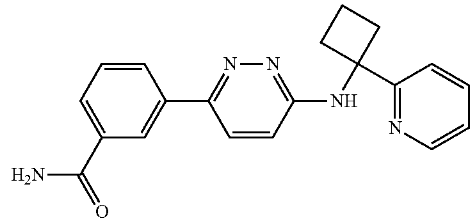 [SMILES: NC(=O)c1cccc(-c2ccc(NC3(c4ccccn4)CCC3)nn2)c1] | 346.1 | D |
| (phenylcyclobutyl)(6-phenylpyridazin-3-yl)amine | 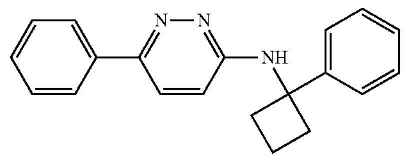 [SMILES: c1ccc(-c2ccc(NC3(c4ccccc4)CCC3)nn2)cc1] | 302.2 | B |
| 3-{6-[(phenylcyclobutyl)amino]pyridazin-3-yl}benzamide | 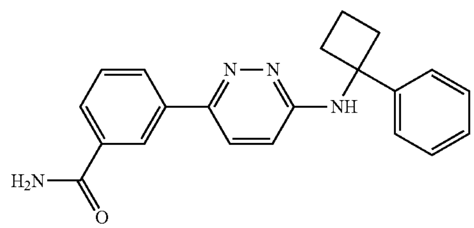 [SMILES: NC(=O)c1cccc(-c2ccc(NC3(c4ccccc4)CCC3)nn2)c1] | 345.1 | B |
| 3-(6-{[(3-fluoro-2-pyridyl)cyclobutyl]amino}pyridazin-3-yl)benzamide | | 364.1 | B |
| 3-(6-{[(5-fluoro-2-pyridyl)cyclobutyl]amino}pyridazin-3-yl)benzamide | 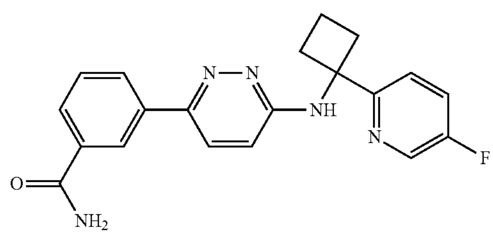 | 364.1 | B |
| 4-fluoro-3-(6-{[(4-fluorophenyl)cyclobutyl]amino}pyridazin-3-yl)benzamide | 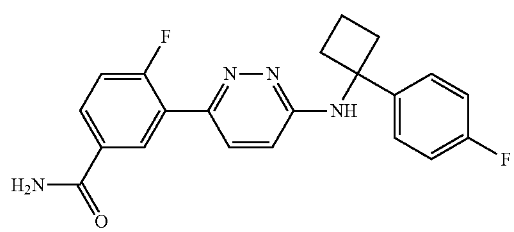 [SMILES: NC(=O)c1ccc(F)c(-c2ccc(NC3(c4ccc(F)cc4)CCC3)nn2)c1] | 381.1 | A |
| [(4-fluorophenyl)cyclobutyl][6-(6-methoxy(2-pyridyl))pyridazin-3-yl]amine | 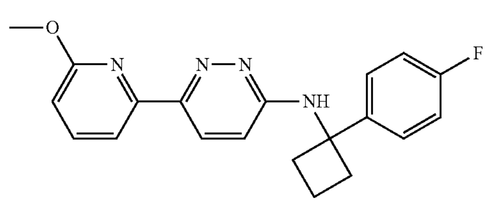 [SMILES: COc1cccc(-c2ccc(NC3(c4ccc(F)cc4)CCC3)nn2)n1] | 351.1 | B |

TABLE 2-continued

| Compound | Structure | m/z (M + H) | Mean AC1.4 |
|---|---|---|---|
| (6-benzimidazol-5-ylpyridazin-3-yl)[(4-fluorophenyl)cyclobutyl]amine | 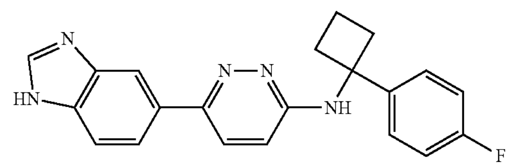 [SMILES: Fc1ccc(C2(Nc3ccc(-c4ccc5[nH]cnc5c4)nn3)CCC2)cc1] | 360.1 | A |
| [(4-fluorophenyl)cyclobutyl](6-pyrazol-4-ylpyridazin-3-yl)amine | 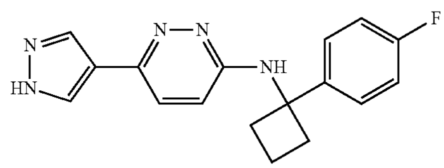 [SMILES: Fc1ccc(C2(Nc3ccc(-c4cn[nH]c4)nn3)CCC2)cc1] | 310.1 | B |
| 3-{6-[(1,3-thiazol-2-ylcyclobutyl)amino]pyridazin-3-yl}benzamide | 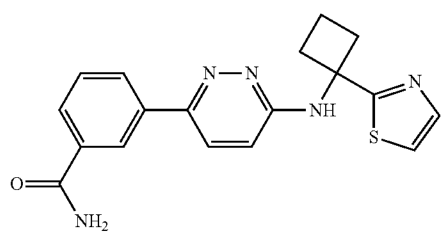 [SMILES: NC(=O)c1cccc(-c2ccc(NC3(c4nccs4)CCC3)nn2)c1] | 352.2 | D |
| 4-fluoro-3-(6-{[(3-fluoro(2-pyridyl))cyclobutyl]amino}pyridazin-3-yl)benzamide | 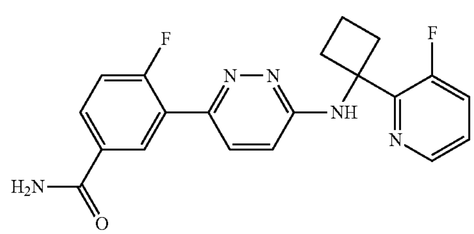 [SMILES: NC(=O)c1ccc(F)c(-c2ccc(NC3(c4ncccc4F)CCC3)nn2)c1] | 382.1 | B |
| 4-fluoro-3-(6-{[1-(4-fluorophenyl)-isopropyl]amino}pyridazin-3-yl)benzamide | 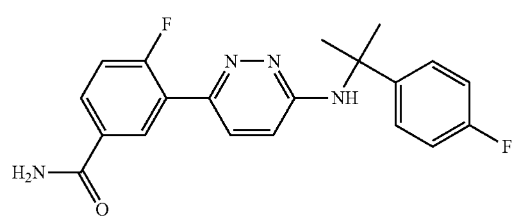 [SMILES: CC(C)(Nc1ccc(-c2cc(C(N)=O)ccc2F)nn1)c1ccc(F)cc1] | 369.1 | A |
| 3-(6-{[(4-methoxy-2-pyridyl)cyclobutyl]amino}pyridazin-3-yl)benzamide | 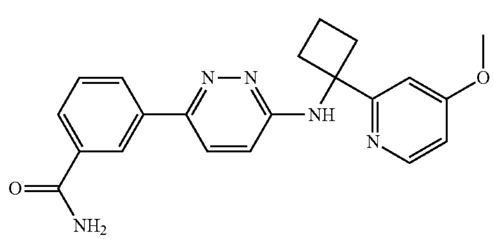 [SMILES: COc1ccnc(C2(Nc3ccc(-c4cccc(C(N)=O)c4)nn3)CCC2)c1] | 376.0 | D |
| [6-(3-fluoro(4-pyridyl))pyridazin-3-yl][(4-fluorophenyl)cyclobutyl]amine | 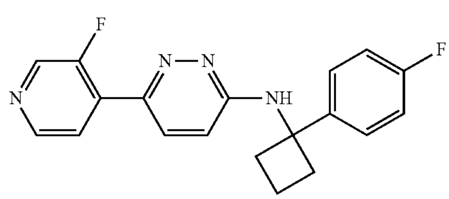 [SMILES: Fc1ccc(C2(Nc3ccc(-c4ccncc4F)nn3)CCC2)cc1] | 339.2 | B |

TABLE 2-continued

| Compound | Structure | m/z (M + H) | Mean AC1.4 |
|---|---|---|---|
| [(4-fluorophenyl)cyclobutyl](6-(4-pyridyl)pyridazin-3-yl)amine | 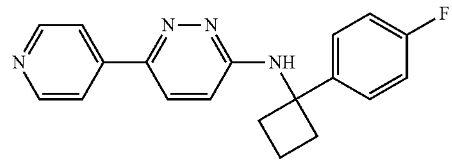 [SMILES: Fc1ccc(C2(Nc3ccc(-c4ccncc4)nn3)CCC2)cc1] | 321.2 | B |
| 4-(6-{[(4-fluorophenyl)cyclobutyl]amino}pyridazin-3-yl)pyridine-2-carbonitrile | 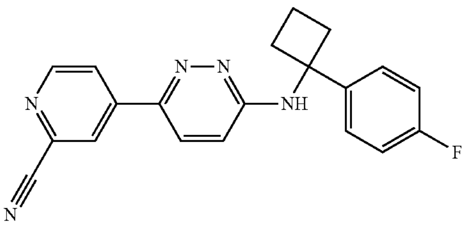 [SMILES: N#Cc1cc(-c2ccc(NC3(c4ccc(F)cc4)CCC3)nn2)ccn1] | 346.2 | B |
| 4-(6-{[(4-fluorophenyl)cyclobutyl]amino}pyridazin-3-yl)pyridine-2-carboxamide | 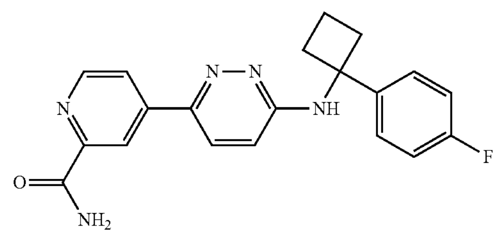 [SMILES: NC(=O)c1cc(-c2ccc(NC3(c4ccc(F)cc4)CCC3)nn2)ccn1] | 364.2 | B |
| [4-(6-{[(4-fluorophenyl)cyclobutyl]amino}pyridazin-3-yl)phenyl](methylsulfonyl)amine | 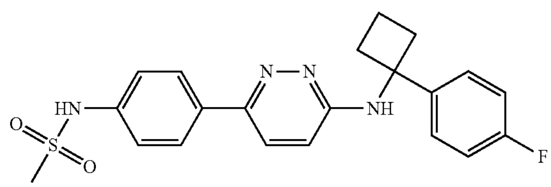 [SMILES: CS(=O)(=O)Nc1ccc(-c2ccc(NC3(c4ccc(F)cc4)CCC3)nn2)cc1] | 413.1 | B |
| [(4-fluorophenyl)cyclobutyl][6-(2-methoxy(3-pyridyl))pyridazin-3-yl]amine | 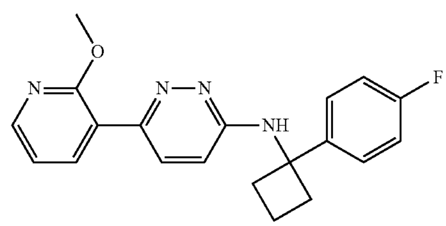 [SMILES: COc1ncccc1-c1ccc(NC2(c3ccc(F)cc3)CCC2)nn1] | 351.2 | A |
| [(4-fluorophenyl)cyclobutyl]{6-[2-(2,2,2-trifluoroethoxy)(3-pyridyl)]pyridazin-3-yl}amine | 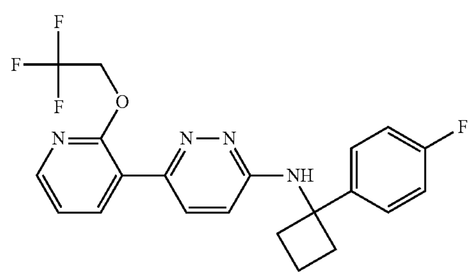 [SMILES: Fc1ccc(C2(Nc3ccc(-c4cccnc4OCC(F)(F)F)nn3)CCC2)cc1] | 419.2 | B |
| 3-(6-{[(4-chlorophenyl)cyclobutyl]amino}pyridazin-3-yl)benzamide | 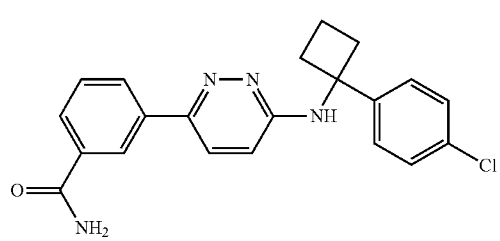 [SMILES: NC(=O)c1cccc(-c2ccc(NC3(c4ccc(Cl)cc4)CCC3)nn2)c1] | 379.1 | B |

TABLE 2-continued

| Compound | Structure | m/z (M + H) | Mean AC1.4 |
|---|---|---|---|
| 3-(6-{[(4-cyanophenyl)cyclobutyl]amino}pyridazin-3-yl)benzamide | 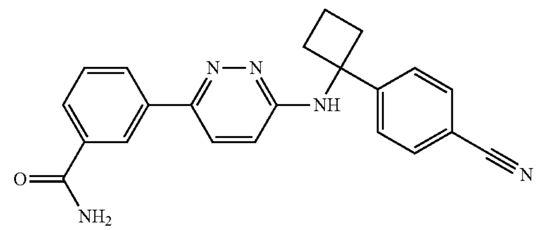 [SMILES: N#Cc1ccc(C2(Nc3ccc(-c4cccc(C(N)=O)c4)nn3)CCC2)cc1] | 370.1 | D |
| 3-(6-{[(3-chloro(2-pyridyl))cyclobutyl]amino}pyridazin-3-yl)-4-fluorobenzamide | 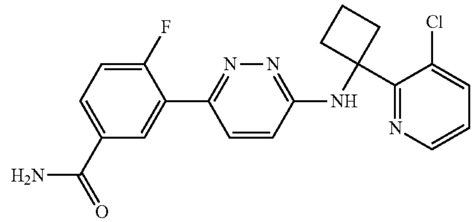 [SMILES: NC(=O)c1ccc(F)c(-c2ccc(NC3(c4ncccc4Cl)CCC3)nn2)c1] | 398.1 | A |
| [3-(6-{[(4-fluorophenyl)cyclobutyl]amino}pyridazin-3-yl)phenyl](methylsulfonyl)amine | 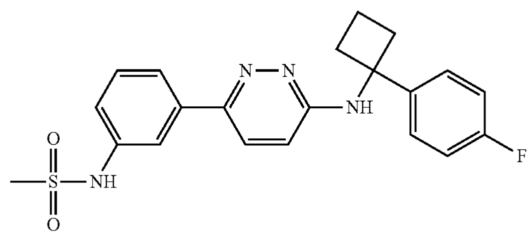 [SMILES: CS(=O)(=O)Nc1cccc(-c2ccc(NC3(c4ccc(F)cc4)CCC3)nn2)c1] | 413.0 | A |
| 3-(6-{[(4-carbamoylphenyl)cyclobutyl]amino}pyridazin-3-yl)benzamide | 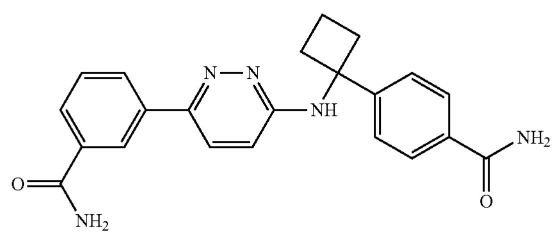 [SMILES: NC(=O)c1ccc(C2(Nc3ccc(-c4cccc(C(N)=O)c4)nn3)CCC2)cc1] | 388.2 | D |
| [(4-fluorophenyl)cyclobutyl][6-(2-methyl(4-pyridyl))pyridazin-3-yl]amine | 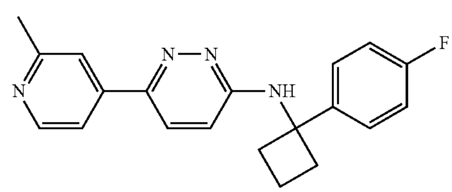 [SMILES: Cc1cc(-c2ccc(NC3(c4ccc(F)cc4)CCC3)nn2)ccn1] | 335.2 | B |
| [(4-fluorophenyl)cyclobutyl][6-(2-methoxy(4-pyridyl))pyridazin-3-yl]amine | 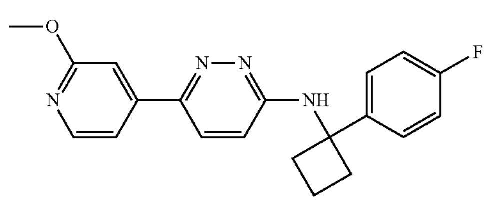 | 351.2 | B |
| 3-(6-{[(6-methoxy-2-pyridyl)cyclobutyl]amino}pyridazin-3-yl)benzamide | | 376.1 | B |

TABLE 2-continued

| Compound | Structure | m/z (M + H) | Mean AC1.4 |
|---|---|---|---|
| 4-fluoro-3-(6-{[(6-methoxy(2-pyridyl))cyclobutyl]amino}pyridazin-3-yl)benzamide | 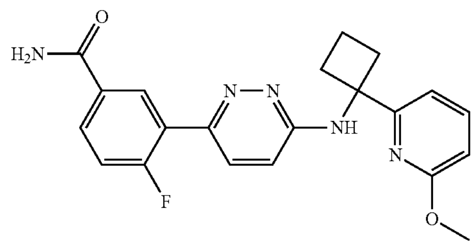 [SMILES: COc1cccc(C2(Nc3ccc(-c4cc(C(N)=O)ccc4F)nn3)CCC2)n1] | 394.1 | A |
| [3-(6-{[(6-methoxy(2-pyridyl))cyclobutyl]amino}pyridazin-3-yl)phenyl](methylsulfonyl)amine | 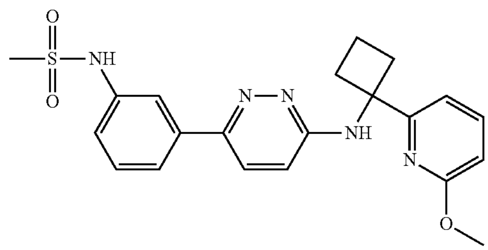 | 426.1 | B |
| [3-(6-{[(3-fluoro(2-pyridyl))cyclobutyl]amino}pyridazin-3-yl)phenyl](methylsulfonyl)amine | 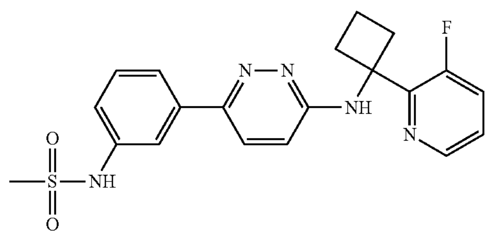 [SMILES: CS(=O)(=O)Nc1cccc(-c2ccc(NC3(c4ncccc4F)CCC3)nn2)c1] | 414.1 | B |
| amino-N-[4-(6-{[(3-fluoro(2-pyridyl))cyclobutyl]amino}pyridazin-3-yl)phenyl]amide | 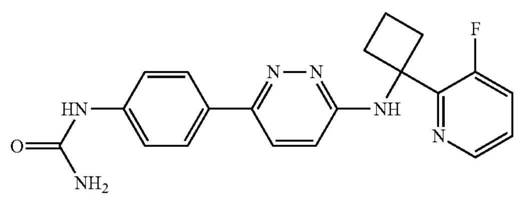 | 379.2 | B |
| (6-(1H-indazol-6-yl)pyridazin-3-yl)[(3-fluoro(2-pyridyl))cyclobutyl]amine | 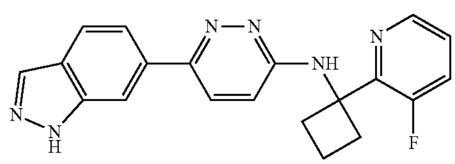 [SMILES: Fc1cccnc1C1(Nc2ccc(-c3ccc4cn[nH]c4c3)nn2)CCC1] | 361.1 | B |
| (6-benzimidazol-6-ylpyridazin-3-yl)[(3-fluoro(2-pyridyl))cyclobutyl]amine | 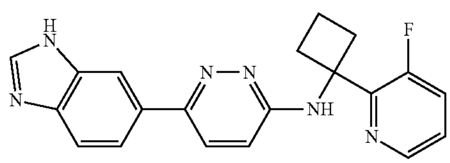 [SMILES: Fc1cccnc1C1(Nc2ccc(-c3ccc4nc[nH]c4c3)nn2)CCC1] | 361.2 | B |
| 3-[6-({[6-(difluoromethoxy)-2-pyridyl]cyclobutyl}amino)pyridazin-3-yl]benzamide | 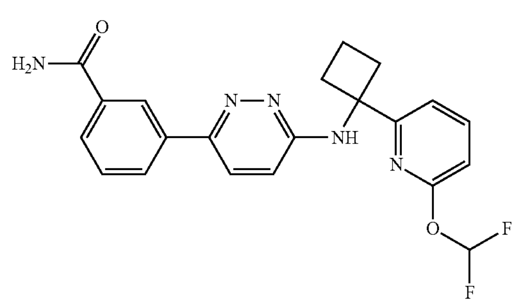 [SMILES: NC(=O)c1cccc(-c2ccc(NC3(c4cccc(OC(F)F)n4)CCC3)nn2)c1] | 412.0 | A |

TABLE 2-continued

| Compound | Structure | m/z (M + H) | Mean AC1.4 |
|---|---|---|---|
| 3-[6-({[6-(difluoromethoxy)(2-pyridyl)]cyclobutyl}amino)pyridazin-3-yl]-4-fluorobenzamide | 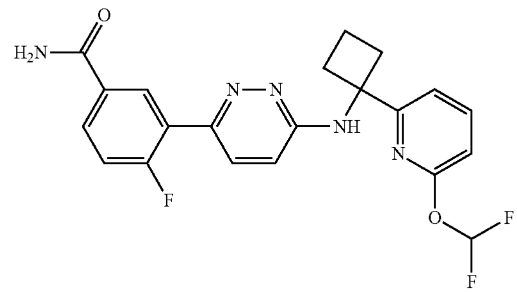 [SMILES: NC(=O)c1ccc(F)c(-c2ccc(NC3(c4cccc(OC(F)F)n4)CCC3)nn2)c1] | 430.1 | A |
| {3-[6-({[6-(difluoromethoxy)(2-pyridyl)]cyclobutyl}amino)pyridazin-3-yl]phenyl}(methylsulfonyl)amine | 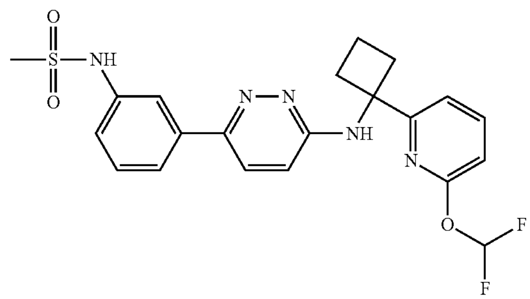 [SMILES: CS(=O)(=O)Nc1cccc(-c2ccc(NC3(c4cccc(OC(F)F)n4)CCC3)nn2)c1] | 462.1 | A |
| 4-fluoro-3-(6-{[(4-fluorophenyl)cyclobutyl]amino}pyridazin-3-yl)benzoic acid | 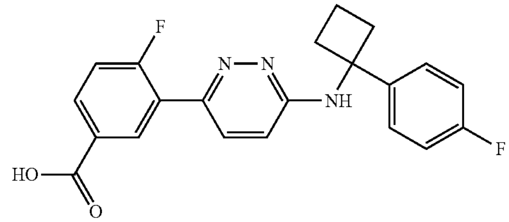 [SMILES: O=C(O)c1ccc(F)c(-c2ccc(NC3(c4ccc(F)cc4)CCC3)nn2)c1] | 382.2 | B |
| [4-fluoro-3-(6-{[(4-fluorophenyl)cyclobutyl]amino}pyridazin-3-yl)phenyl]-N-(2-hydroxy-2-methylpropyl)carboxamide | 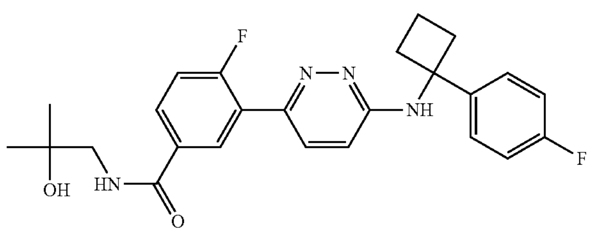 [SMILES: CC(C)(O)CNC(=O)c1ccc(F)c(-c2ccc(NC3(c4ccc(F)cc4)CCC3)nn2)c1] | 453.2 | B |
| 3-(6-{[(3-bromo(2-pyridyl))cyclobutyl]amino}pyridazin-3-yl)-4-fluorobenzamide | 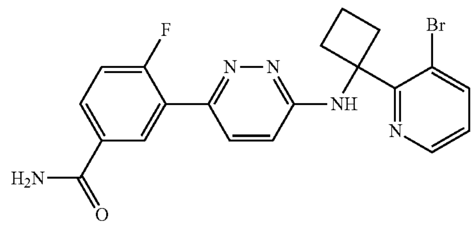 | 442.1 | A |
| 3-(6-{[1-(3-chloro(2-pyridyl))-isopropyl]amino}pyridazin-3-yl)-4-fluorobenzamide | 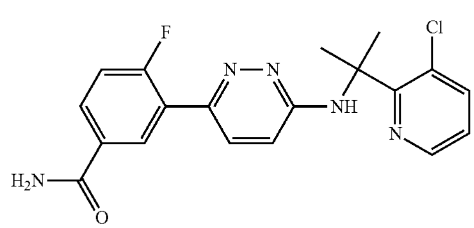 [SMILES: CC(C)(Nc1ccc(-c2cc(C(N)=O)ccc2F)nn1)c1ncccc1Cl] | 386.1 | B |

TABLE 2-continued

| Compound | Structure | m/z (M + H) | Mean AC1.4 |
|---|---|---|---|
| 4-chloro-3-(6-{[(3-fluoro(2-pyridyl))cyclobutyl]amino}pyridazin-3-yl)benzamide | 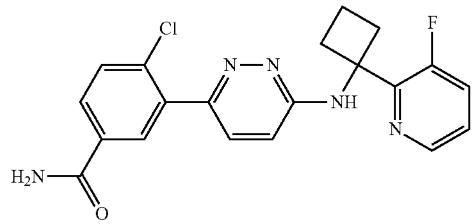 | 398.1 | B |
| [4-(6-{[(4-fluorophenyl)cyclobutyl]amino}pyridazin-3-yl)(2-pyridyl)]-N-methylcarboxamide | 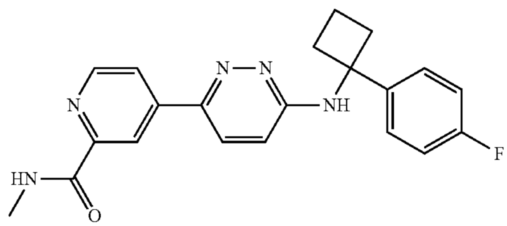 [SMILES: CNC(=O)c1cc(-c2ccc(NC3(c4ccc(F)cc4)CCC3)nn2)ccn1] | 378.2 | B |
| (6-(1H-indazol-5-yl)pyridazin-3-yl)[(3-fluoro(2-pyridyl))cyclobutyl]amine | 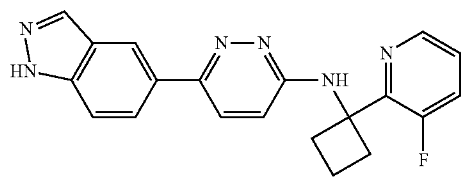 [SMILES: Fc1cccnc1C1(Nc2ccc(-c3ccc4[nH]ncc4c3)nn2)CCC1] | 361.1 | B |
| [6-(6-fluoro(1H-indazol-5-yl))pyndazin-3-yl][(3-fluoro(2-pyridyl))cyclobutyl]amine | 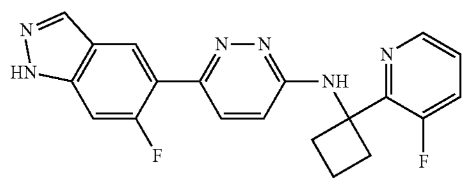 [SMILES: Fc1cc2[nH]ncc2cc1-c1ccc(NC2(c3ncccc3F)CCC2)nn1] | 379.1 | B |
| amino-N-[4-fluoro-3-(6-{[(3-fluoro(2-pyridyl))cyclobutyl]amino}pyridazin-3-yl)phenyl]amide | 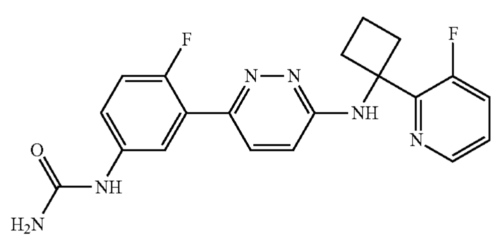 [SMILES: NC(=O)Nc1ccc(F)c(-c2ccc(NC3(c4ncccc4F)CCC3)nn2)c1] | 398.1 | B |
| amino[4-fluoro-3-(6-{[(3-fluoro(2-pyridyl))cyclobutyl]amino}pyridazin-3-yl)phenyl]sulfonamide | 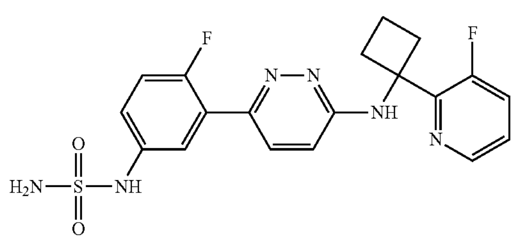 [SMILES: NS(=O)(=O)Nc1ccc(F)c(-c2ccc(NC3(c4ncccc4F)CCC3)nn2)c1] | 433.1 | B |
| amino[3-fluoro-4-(6-{[(3-fluoro(2-pyridyl))cyclobutyl]amino}pyridazin-3-yl)phenyl]sulfonamide | 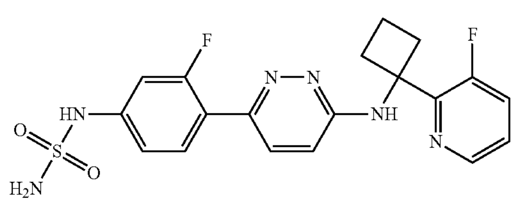 [SMILES: NS(=O)(=O)Nc1ccc(-c2ccc(NC3(c4ncccc4F)CCC3)nn2)c(F)c1] | 433.1 | B |

TABLE 2-continued

| Compound | Structure | m/z (M + H) | Mean AC1.4 |
|---|---|---|---|
| amino-N-[3-fluoro-4-(6-{[(3-fluoro(2-pyridyl))cyclobutyl]amino}pyridazin-3-yl)phenyl]amide | 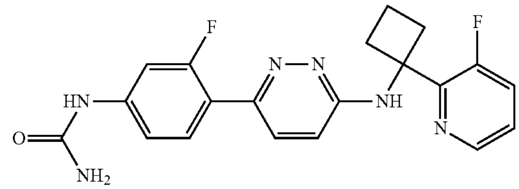 [SMILES: NC(=O)Nc1ccc(-c2ccc(NC3(c4ncccc4F)CCC3)nn2)c(F)c1] | 397.1 | B |
| 4-fluoro-3-(6-{[1-methyl-1-(6-oxo(2-hydropyridyl))ethyl]amino}pyridazin-3-yl)benzamide | 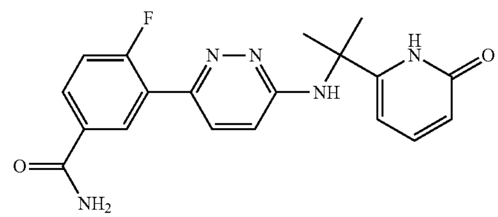 [SMILES: CC(C)(Nc1ccc(-c2cc(C(N)=O)ccc2F)nn1)c1cccc(=O)[nH]1] | 368.2 | D |
| 3-[6-({1-[6-(difluoromethoxy)(2-pyridyl)]-isopropyl}amino)pyridazin-3-yl]-4-fluorobenzamide | 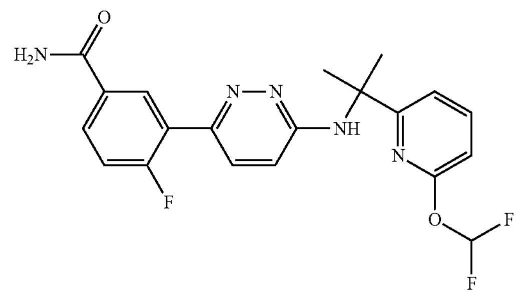 [SMILES: CC(C)(Nc1ccc(-c2cc(C(N)=O)ccc2F)nn1)c1cccc(OC(F)F)n1] | 418.1 | A |
| 3-[6-({1-[6-(difluoromethoxy)(2-pyridyl)]-isopropyl}amino)pyridazin-3-yl]benzamide | 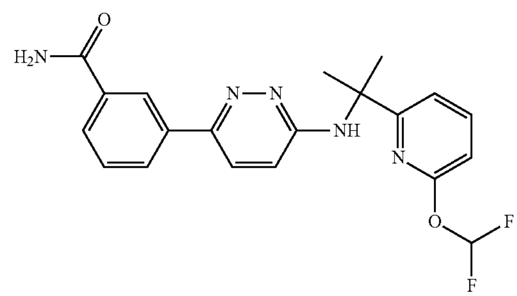 [SMILES: CC(C)(Nc1ccc(-c2cccc(C(N)=O)c2)nn1)c1cccc(OC(F)F)n1] | 400.2 | B |
| {3-[6-({1-[6-(difluoromethoxy)(2-pyridyl)]-isopropyl}amino)pyridazin-3-yl]phenyl}(methylsulfonyl)amine | 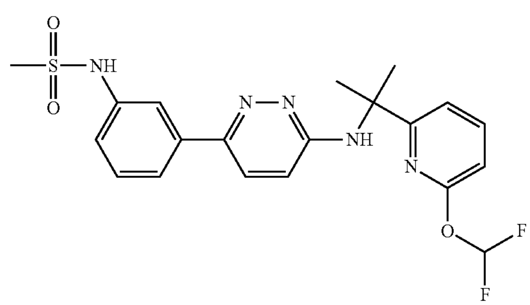 [SMILES: CC(C)(Nc1ccc(-c2cccc(NS(C)(=O)=O)c2)nn1)c1cccc(OC(F)F)n1] | 450.1 | A |
| 3-(6-{[(4-cyano(2-pyridyl))cyclobutyl]amino}pyridazin-3-yl)-4-fluorobenzamide | 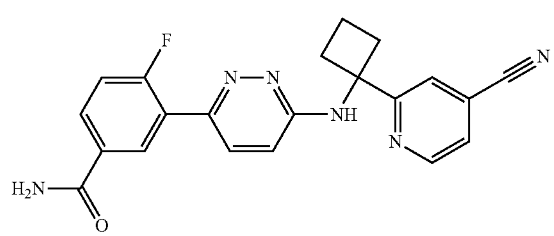 [SMILES: N#Cc1ccnc(C2(Nc3ccc(-c4cc(C(N)=O)ccc4F)nn3)CCC2)c1] | 389.1 | D |

TABLE 2-continued

| Compound | Structure | m/z (M + H) | Mean AC1.4 |
|---|---|---|---|
| 2-({[6-(3-carbamoyl-6-fluorophenyl)pyridazin-3-yl]amino}cyclobutyl)pyridine-4-carboxamide | 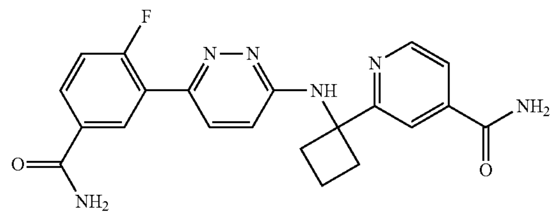 [SMILES: NC(=O)c1ccnc(C2(Nc3ccc(-c4cc(C(N)=O)ccc4F)nn3)CCC2)c1] | 407.1 | D |
| 3-(6-{[(5-cyano(2-pyridyl))cyclobutyl]amino}pyridazin-3-yl)-4-fluorobenzamide | 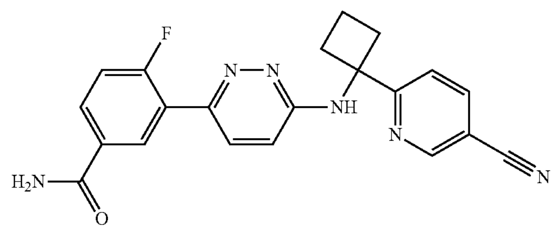 [SMILES: N#Cc1ccc(C2(Nc3ccc(-c4cc(C(N)=O)ccc4F)nn3)CCC2)nc1] | 389.2 | D |
| 3-(6-{[(6-cyano(2-pyridyl))cyclobutyl]amino}pyridazin-3-yl)-4-fluorobenzamide | 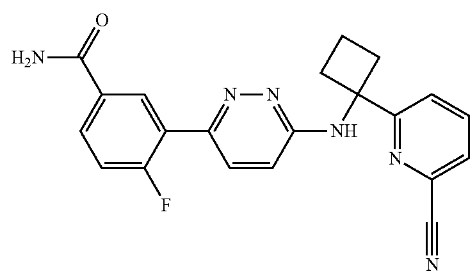 [SMILES: N#Cc1cccc(C2(Nc3ccc(-c4cc(C(N)=O)ccc4F)nn3)CCC2)n1] | 389.2 | B |
| 6-({[6-(3-carbamoyl-6-fluorophenyl)pyridazin-3-yl]amino}cyclobutyl)pyridine-2-carboxamide | 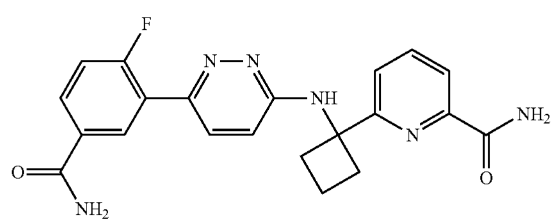 [SMILES: NC(=O)c1ccc(F)c(-c2ccc(NC3(c4cccc(C(N)=O)n4)CCC3)nn2)c1] | 407.2 | D |
| 4-fluoro-3-(6-{[(3-hydroxy(2-pyridyl))cyclobutyl]amino}pyridazin-3-yl)benzamide | 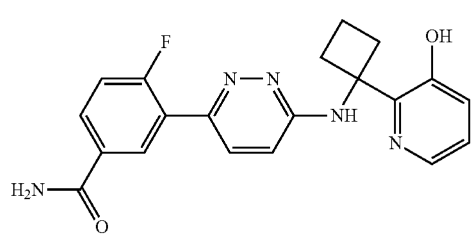 [SMILES: NC(=O)c1ccc(F)c(-c2ccc(NC3(c4ncccc4O)CCC3)nn2)c1] | 380.2 | D |
| 4-fluoro-3-(6-{[(3-methoxy(2-pyridyl))cyclobutyl]amino}pyridazin-3-yl)benzamide | 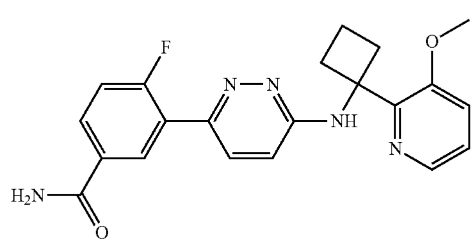 [SMILES: COc1cccnc1C1(Nc2ccc(-c3cc(C(N)=O)ccc3F)nn2)CCC1] | 394.2 | C |

TABLE 2-continued

| Compound | Structure | m/z (M + H) | Mean AC1.4 |
|---|---|---|---|
| 3-[6-({[3-(difluoromethoxy)(2-pyridyl)]cyclobutyl}amino)pyridazin-3-yl]-4-fluorobenzamide | 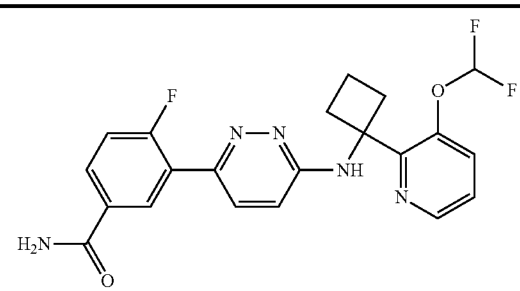 | 430.2 | C |
| 3-[6-({[3-(difluoromethoxy)-2-pyridyl]cyclobutyl}amino)pyridazin-3-yl]benzamide | 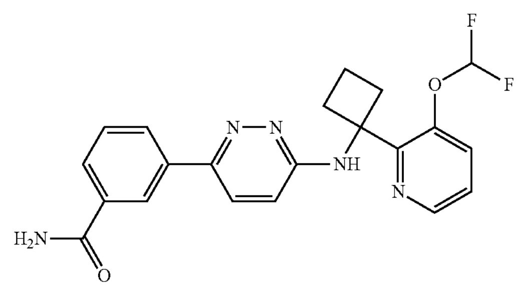 [SMILES: NC(=O)c1cccc(-c2ccc(NC3(c4ncccc4OC(F)F)CCC3)nn2)c1] | 412.2 | D |
| {3-[6-({[3-(difluoromethoxy)pyridyl]cyclobutyl}amino)pyridazin-3-yl]phenyl}(methylsulfonyl)amine | | 462.2 | C |
| 4-fluoro-3-(6-{[(5-methoxy(2-pyridyl))cyclobutyl]amino}pyridazin-3-yl)benzamide | 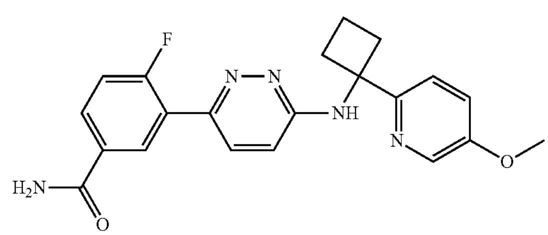 [SMILES: COc1ccc(C2(Nc3ccc(-c4cc(C(N)=O)ccc4F)nn3)CCC2)nc1] | 394.2 | D |
| 3-[6-({[5-(difluoromethoxy)(2-pyridyl)]cyclobutyl}amino)pyridazin-3-yl]-4-fluorobenzamide | 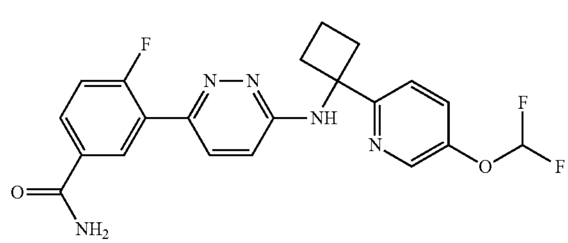 [SMILES: NC(=O)c1ccc(F)c(-c2ccc(NC3(c4ccc(OC(F)F)cn4)CCC3)nn2)c1] | 430.1 | D |
| 4-fluoro-3-(6-{[(5-hydroxy(2-pyridyl))cyclobutyl]amino}pyridazin-3-yl)benzamide | 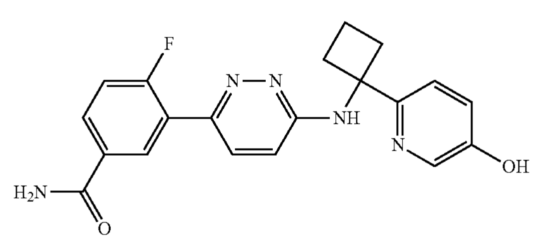 [SMILES: NC(=O)c1ccc(F)c(-c2ccc(NC3(c4ccc(O)cn4)CCC3)nn2)c1] | 380.1 | D |

TABLE 2-continued

| Compound | Structure | m/z (M + H) | Mean AC1.4 |
|---|---|---|---|
| [(3-fluoro(2-pyridyl))cyclobutyl](6-vinylpyridazin-3-yl)amine | 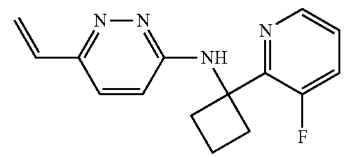 [SMILES: C=Cc1ccc(NC2(c3ncccc3F)CCC2)nn1] | 271.1 | D |
| 4-fluoro-3-(6-{[(3-fluoro(2-pyridyl))cyclobutyl]amino}pyridazin-3-yl)benzenecarbonitrile | 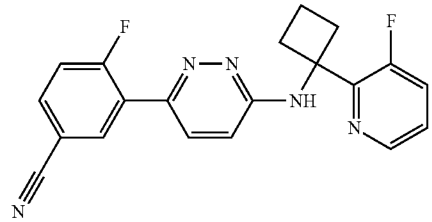 [SMILES: N#Cc1ccc(F)c(-c2ccc(NC3(c4ncccc4F)CCC3)nn2)c1] | 364.1 | B |
| [(3-fluoro(2-pyridyl))cyclobutyl](6-phenylpyridazin-3-yl)amine | 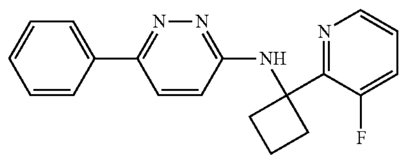 [SMILES: Fc1cccnc1C1(Nc2ccc(-c3ccccc3)nn2)CCC1] | 321.1 | B |
| (6-cyclohexylpyridazin-3-yl)[(3-fluoro(2-pyridyl))cyclobutyl]amine | 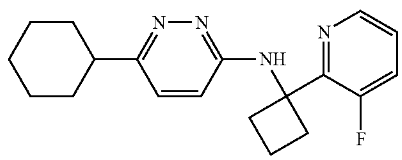 [SMILES: Fc1cccnc1C1(Nc2ccc(C3CCCCC3)nn2)CCC1] | 327.2 | C |
| (6-cyclohex-1-enylpyridazin-3-yl)[(3-fluoro(2-pyridyl))cyclobutyl]amine | 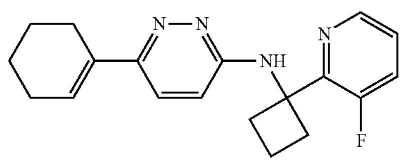 [SMILES: Fc1cccnc1C1(Nc2ccc(C3=CCCCC3)nn2)CCC1] | 325.2 | C |
| (6-cyclohex-1-enylpyridazin-3-yl){[(3-fluoro(2-pyridyl))cyclobutyl]methyl}amine | 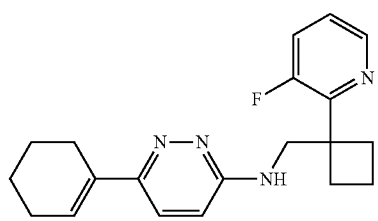 [SMILES: Fc1cccnc1C1(CNc2ccc(C3=CCCCC3)nn2)CCC1] | 339.2 | A |
| 4-fluoro-3-{6-[(methylcyclobutyl)amino]pyridazin-3-yl}benzamide | 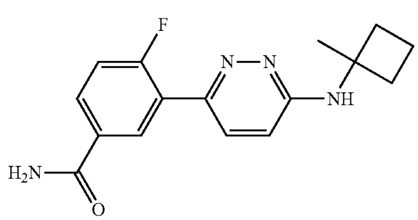 [SMILES: CC1(Nc2ccc(-c3cc(C(N)=O)ccc3F)nn2)CCC1] | 301.1 | D |
| (6-cyclohexylpyridazin-3-yl){[(3-fluoro(2-pyridyl))cyclobutyl]methyl}amine | 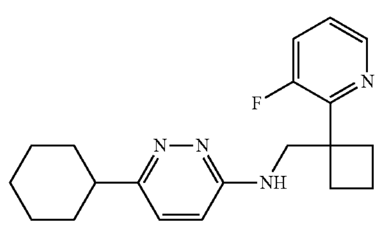 [SMILES: Fc1cccnc1C1(CNc2ccc(C3CCCCC3)nn2)CCC1] | 341.2 | B |

TABLE 2-continued

| Compound | Structure | m/z (M + H) | Mean AC1.4 |
|---|---|---|---|
| ethyl (2E)-3-[6-({[(3-fluoro(2-pyridyl))cyclobutyl]methyl}amino)pyridazin-3-yl]prop-2-enoate | 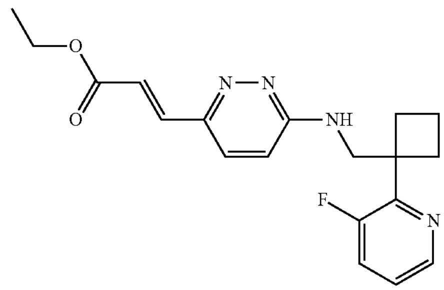 [SMILES: CCOC(=O)/C=C/c1ccc(NCC2(c3ncccc3F)CCC2)nn1] | 357.2 | D |
| ethyl (2E)-3-(6-{[(3-fluoro(2-pyridyl))cyclobutyl]amino}pyridazin-3-yl)prop-2-enoate | 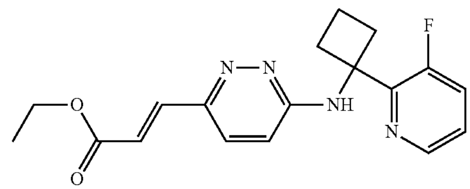 [SMILES: CCOC(=O)/C=C/c1ccc(NC2(c3ncccc3F)CCC2)nn1] | 343.1 | D |
| diethyl 2-[6-({[(3-fluoro-2-pyridyl)cyclobutyl]methyl}amino)pyridazin-3-yl]propane-1,3-dioate | 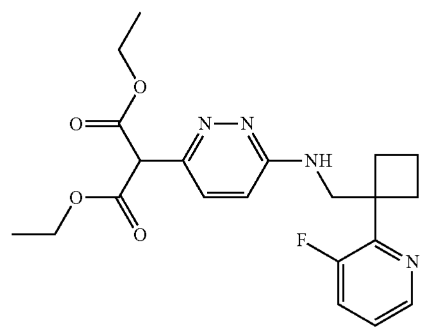 [SMILES: CCOC(=O)C(C(=O)OCC)c1ccc(NCC2(c3ncccc3F)CCC2)nn1] | 417.2 | D |
| (1S,2S)-2-[6-({[(3-fluoro(2-pyridyl))cyclobutyl]methyl}amino)pyridazin-3-yl]cyclopropanecarboxamide | 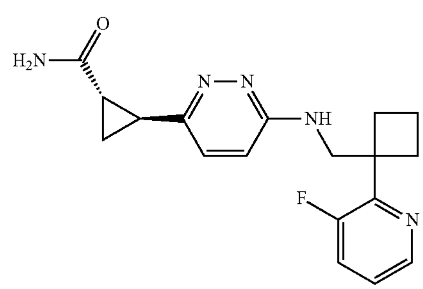 [SMILES: NC(=O)[C@H]1C[C@@H]1c1ccc(NCC2(c3ncccc3F)CCC2)nn1] | 342.2 | D |
| (2S,1R)-2-[6-({[(3-fluoro(2-pyridyl))cyclobutyl]methyl}amino)pyridazin-3-yl]cyclopropanecarboxamide | 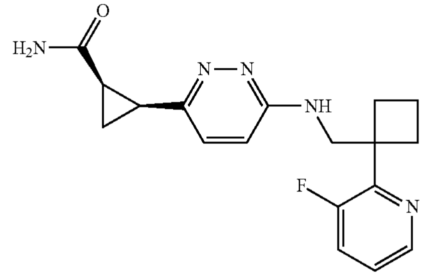 [SMILES: NC(=O)[C@@H]1C[C@@H]1c1ccc(NCC2(c3ncccc3F)CCC2)nn1] | 342.2 | D |

TABLE 2-continued

| Compound | Structure | m/z (M + H) | Mean AC1.4 |
|---|---|---|---|
| amino-N-{4-[6-({[(3-fluoro(2-pyridyl))cyclobutyl]methyl}amino)pyridazin-3-yl]cyclohexyl}amide | | 399.3 | B |
| amino-N-{4-[6-({[(3-fluoro(2-pyridyl))cyclobutyl]methyl}amino)pyridazin-3-yl]cyclohexyl}amide | | 399.2 | C |
| 4-fluoro-3-(6-{[(3-fluoro(2-pyridyl))cyclopentyl]amino}pyridazin-3-yl)benzamide | 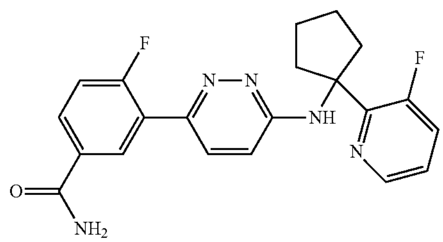 [SMILES: NC(=O)c1ccc(F)c(-c2ccc(NC3(c4ncccc4F)CCCC3)nn2)c1] | 396.2 | A |
| amino-N-{3-[6-({[(3-fluoro(2-pyridyl))cyclobutyl]methyl}amino)pyridazin-3-yl]cyclobutyl}amide | | 371.2 | C |
| amino-N-{3-[6-({[(3-fluoro(2-pyridyl))cyclobutyl]methyl}amino)pyridazin-3-yl]cyclobutyl}amide | | 371.2 | B |
| amino-N-{4-[6-({[(3-fluoro(2-pyridyl))cyclobutyl]methyl}amino)pyridazin-3-yl]cyclohex-3-enyl}amide | 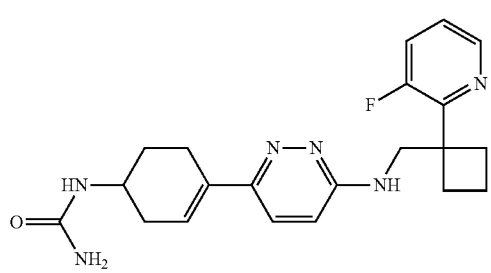 [SMILES: NC(=O)NC1CC=C(c2ccc(NCC3(c4ncccc4F)CCC3)nn2)CC1] | 397.2 | B |

TABLE 2-continued

| Compound | Structure | m/z (M + H) | Mean AC1.4 |
|---|---|---|---|
| phenylmethyl 3-[6-({[(3-fluoro-2-pyridyl)cyclobutyl]methyl}amino)pyridazin-3-yl]azetidinecarboxylate | 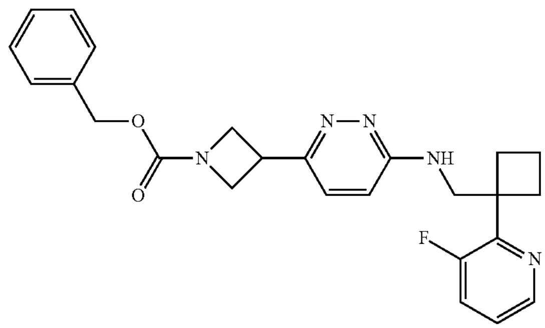 [SMILES: O=C(OCc1ccccc1)N1CC(c2ccc(NCC3(c4ncccc4F)CCC3)nn2)C1] | 448.2 | D |
| (6-azetidin-3-ylpyridazin-3-yl){[(3-fluoro(2-pyridyl))cyclobutyl]methyl}amine | 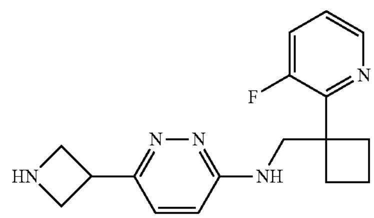 [SMILES: Fc1cccnc1C1(CNc2ccc(C3CNC3)nn2)CCC1] | 314.2 | D |
| methyl 3-[6-({[(3-fluoro-2-pyridyl)cyclobutyl]methyl}amino)pyridazin-3-yl]azetidinecarboxylate | 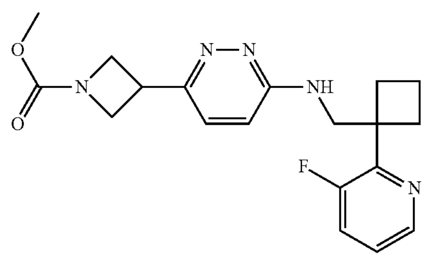 [SMILES: COC(=O)N1CC(c2ccc(NCC3(c4ncccc4F)CCC3)nn2)C1] | 372.2 | D |
| 3-[6-({[(3-fluoro-2-pyridyl)cyclobutyl]methyl}amino)pyridazin-3-yl]azetidinecarboxamide | 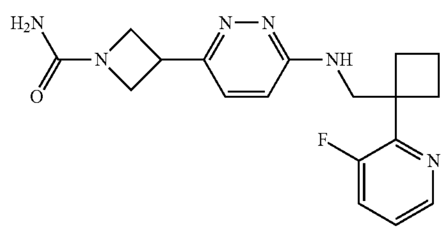 [SMILES: NC(=O)N1CC(c2ccc(NCC3(c4ncccc4F)CCC3)nn2)C1] | 357.2 | D |
| 1-acetyl-3-[6-({((3-fluoro(2-pyridyl))cyclobutyl]methyl}amino)pyridazin-3-yl]azetidine | 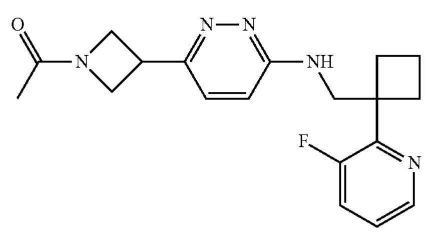 [SMILES: CC(=O)N1CC(c2ccc(NCC3(c4ncccc4F)CCC3)nn2)C1] | 356.2 | D |
| ethyl 5-[6-({[(3-fluoro-2-pyridyl)cyclobutyl]methyl}amino)pyridazin-3-yl]isoxazole-3-carboxylate | 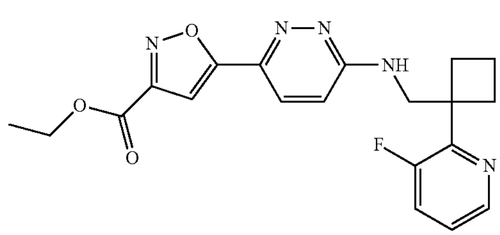 [SMILES: CCOC(=O)c1cc(-c2ccc(NCC3(c4ncccc4F)CCC3)nn2)on1] | 398.2 | D |

TABLE 2-continued

| Compound | Structure | m/z (M + H) | Mean AC1.4 |
|---|---|---|---|
| 5-[6-({[(3-fluoro-2-pyridyl)cyclobutyl]methyl}amino)pyridazin-3-yl]isoxazole-3-carboxylic acid | 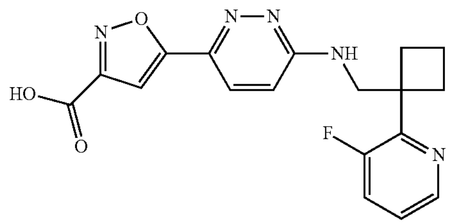 [SMILES: O=C(O)c1cc(-c2ccc(NCC3(c4ncccc4F)CCC3)nn2)on1] | 370.2 | D |
| 5-[6-({[(3-fluoro-2-pyridyl)cyclobutyl]methyl}amino)pyridazin-3-yl]isoxazole-3-carboxamide | 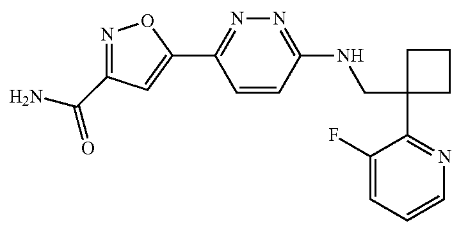 [SMILES: NC(=O)c1cc(-c2ccc(NCC3(c4ncccc4F)CCC3)nn2)on1] | 369.2 | B |
| amino-N-{5-[6-({[(3-fluoro(2-pyridyl))cyclobutyl]methyl}amino)pyridazin-3-yl](1H-indazol-3-yl)}amide | 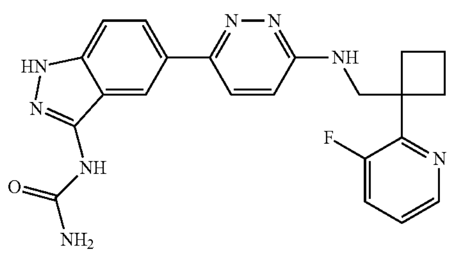 [SMILES: NC(=O)Nc1n[nH]c2ccc(-c3ccc(NCC4(c5ncccc5F)CCC4)nn3)cc12] | 433.3 | A |
| 4-[6-({[(3-fluoro(2-pyridyl))cyclobutyl]methyl}amino)pyridazin-3-yl]-1-methylimidazole-2-carboxamide | | 382.3 | D |
| 4-[6-({[(3-fluoro(2-pyridyl))cyclobutyl]methyl}amino)pyridazin-3-yl]-2-methoxybenzamide | 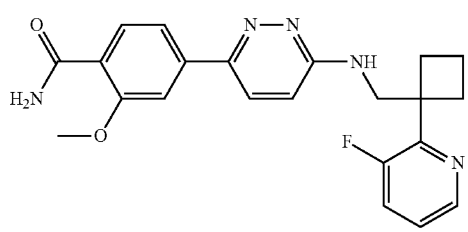 [SMILES: COc1cc(-c2ccc(NCC3(c4ncccc4F)CCC3)nn2)ccc1C(N)=O] | 408.2 | B |
| 4-[6-({[(3-fluoro(2-pyridyl))cyclobutyl]methyl}amino)pyridazin-3-yl]-2-hydroxybenzamide | 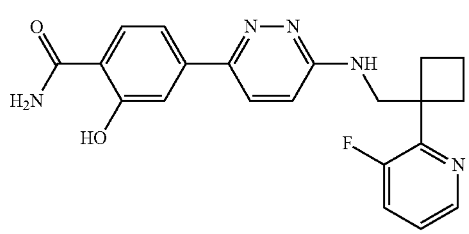 | 394.1 | B |

TABLE 2-continued

| Compound | Structure | m/z (M + H) | Mean AC1.4 |
|---|---|---|---|
| 5-[6-({[(3-fluoro(2-pyridyl))cyclobutyl]methyl}amino)pyridazin-3-yl]-2-methoxybenzamide | 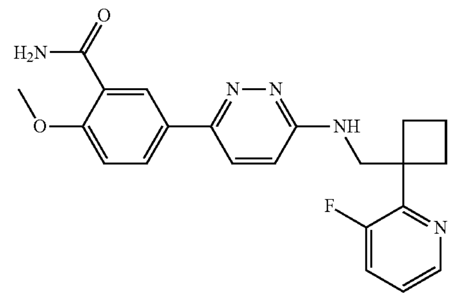 [SMILES: COc1ccc(-c2ccc(NCC3(c4ncccc4F)CCC3)nn2)cc1C(N)=O] | 408.2 | B |
| 5-[6-({[(3-fluoro(2-pyridyl))cyclobutyl]methyl}amino)pyridazin-3-yl]-2-hydroxybenzamide | 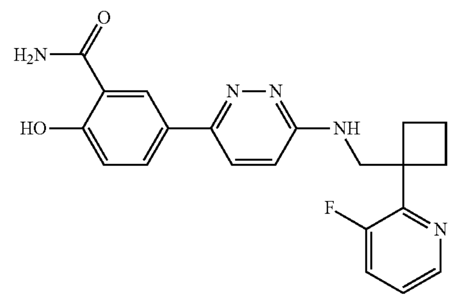 [SMILES: NC(=O)c1cc(-c2ccc(NCC3(c4ncccc4F)CCC3)nn2)ccc1O] | 394.1 | A |
| 4-[6-({[(3-fluoro(2-pyridyl))cyclobutyl]methyl}amino)pyridazin-3-yl]-2-methoxybenzoic acid | 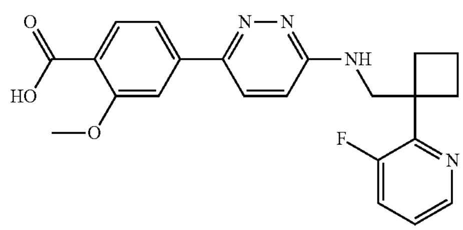 [SMILES: COc1cc(-c2ccc(NCC3(c4ncccc4F)CCC3)nn2)ccc1C(=O)O] | 409.2 | D |
| 5-[6-({[(3-fluoro(2-pyridyl))cyclobutyl]methyl}amino)pyridazin-3-yl]-2-methoxybenzoic acid | 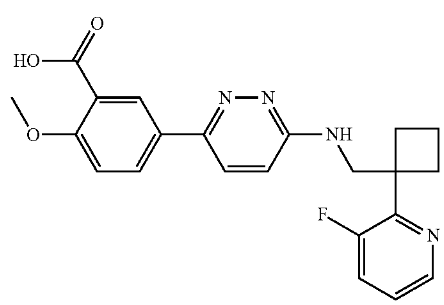 [SMILES: COc1ccc(-c2ccc(NCC3(c4ncccc4F)CCC3)nn2)cc1C(=O)O] | 409.2 | D |
| 5-[6-({[(3-fluoro-2-pyridyl)cyclobutyl]methyl}amino)pyridazin-3-yl]-1,3-oxazole-2-carboxamide | 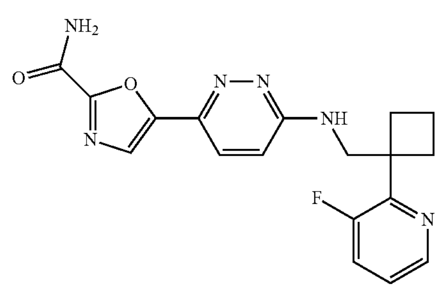 | 369.2 | B |

TABLE 2-continued

| Compound | Structure | m/z (M + H) | Mean AC1.4 |
|---|---|---|---|
| 4-[6-({[(3-fluoro-2-pyridyl)cyclobutyl]methyl}amino)pyridazin-3-yl]imidazole-2-carboxamide | 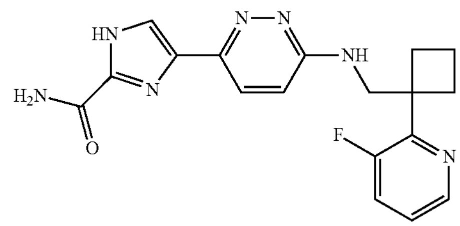 | 368.2 | C |
| 3-[6-({[(3-fluoro-2-pyridyl)cyclobutyl]methyl}amino)pyridazin-3-yl]isoxazole-5-carboxamide | 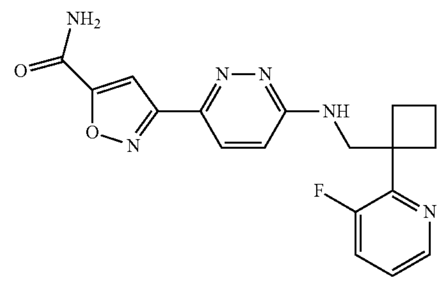 [SMILES: NC(=O)c1cc(-c2ccc(NCC3(c4ncccc4F)CCC3)nn2)no1] | 369.2 | A |
| 3-[6-({[(3-fluoro-2-pyridyl)cyclobutyl]methyl}amino)pyridazin-3-yl]pyrazole-5-carboxamide | 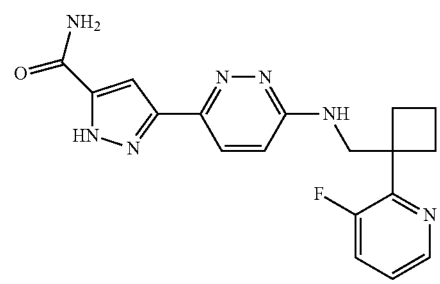 [SMILES: NC(=O)c1cc(-c2ccc(NCC3(c4ncccc4F)CCC3)nn2)n[nH]1] | 368.3 | B |
| 3-[6-({[(3-fluoro(2-pyridyl))cyclobutyl]methyl}amino)pyridazin-3-yl]-1-methylpyrazole-5-carboxamide | 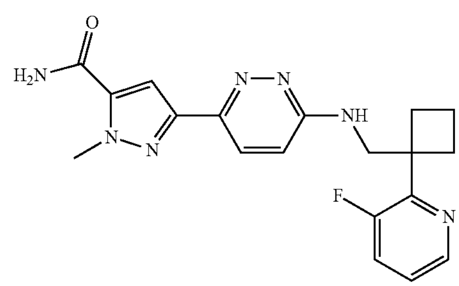 [SMILES: Cn1nc(-c2ccc(NCC3(c4ncccc4F)CCC3)nn2)cc1C(N)=O] | 382.3 | B |
| 5-[6-({[(3-fluoro(2-pyridyl))cyclobutyl]methyl}amino)pyridazin-3-yl]-1-methylpyrazole-3-carboxamide | 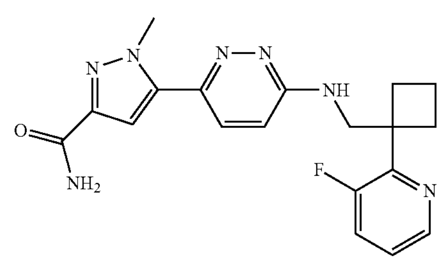 [SMILES: Cn1nc(C(N)=O)cc1-c1ccc(NCC2(c3ncccc3F)CCC2)nn1] | 382.3 | B |
| 2-[6-({[(3-fluoro-2-pyridyl)cyclobutyl]methyl}amino)pyridazin-3-yl]-1,3-oxazole-5-carboxamide | 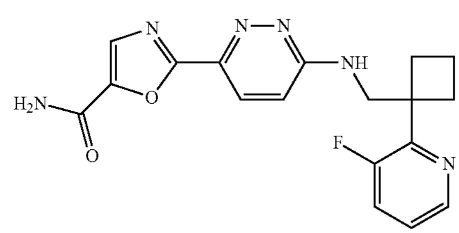 [SMILES: NC(=O)c1cnc(-c2ccc(NCC3(c4ncccc4F)CCC3)nn2)o1] | 369.1 | B |

TABLE 2-continued

| Compound | Structure | m/z (M + H) | Mean AC1.4 |
|---|---|---|---|
| 2-[6-({[(3-fluoro-2-pyridyl)cyclobutyl]methyl}amino)pyridazin-3-yl]-1,3-thiazole-4-carboxamide | 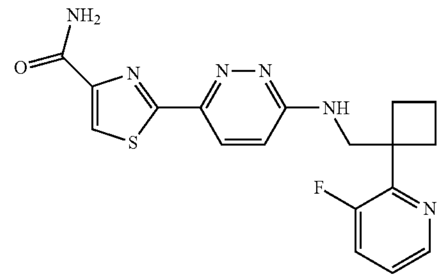 [SMILES: NC(=O)c1csc(-c2ccc(NCC3(c4ncccc4F)CCC3)nn2)n1] | 385.1 | D |
| 1-[(6-{[(3-fluoro-2-pyridyl)cyclobutyl]amino}pyridazin-3-yl)methyl]pyrazole-4-carboxamide | 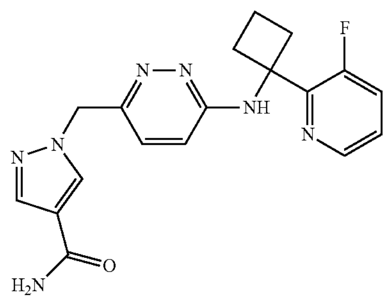 [SMILES: NC(=O)c1cnn(Cc2ccc(NC3(c4ncccc4F)CCC3)nn2)c1] | 368.1 | D |
| 5-[6-({[(3-fluoro-2-pyridyl)cyclobutyl]methyl}amino)pyridazin-3-yl]-1,2,4-oxadiazole-3-carboxamide | 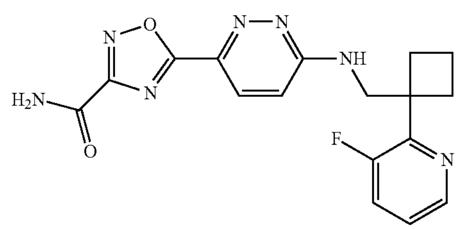 | 370.2 | B |
| 2-[6-({[(3-fluoro-2-pyridyl)cyclobutyl]methyl}amino)pyridazin-3-yl]-2-imidazoline-5-carboxamide | 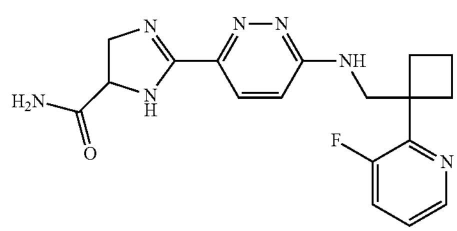 | 370.3 | D |
| methyl 2-[6-({[(3-fluoro-2-pyridyl)cyclobutyl]methyl}amino)pyridazin-3-yl]-2-imidazoline-5-carboxylate | 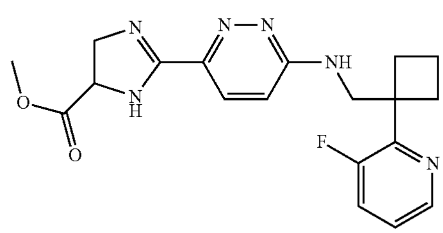 [SMILES: COC(=O)C1CN=C(c2ccc(NCC3(c4ncccc4F)CCC3)nn2)N1] | 385.3 | D |
| 2-[6-({[(3-fluoro-2-pyridyl)cyclobutyl]methyl}amino)pyridazin-3-yl]-2-imidazoline-5-carboxylic acid | 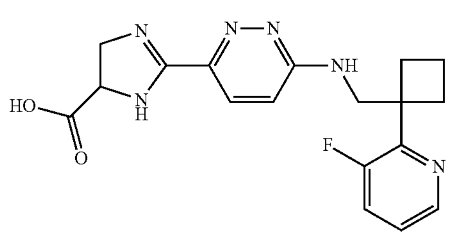 | 371.3 | D |

TABLE 2-continued

| Compound | Structure | m/z (M + H) | Mean AC1.4 |
|---|---|---|---|
| 2-[6-({[(3-fluoro-2-pyridyl)cyclobutyl]methyl}amino)pyridazin-3-yl]-1,3-oxazole-4-carboxamide | 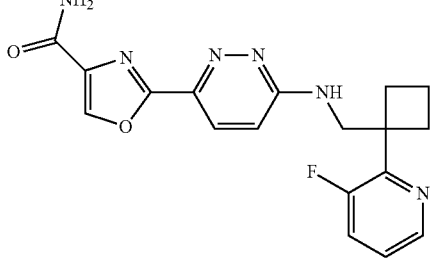 | 369.2 | D |
| 2-[6-({[(3-fluoro-2-pyridyl)cyclobutyl]methyl}amino)pyridazin-3-yl]-1,3-thiazole-5-carboxamide | 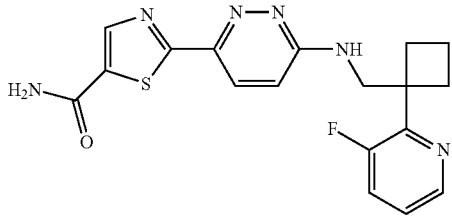 | 385.2 | A |
| methyl 2-[6-({[(3-fluoro-2-pyridyl)cyclobutyl]methyl}amino)pyridazin-3-yl]-1,3-oxazole-4-carboxylate | 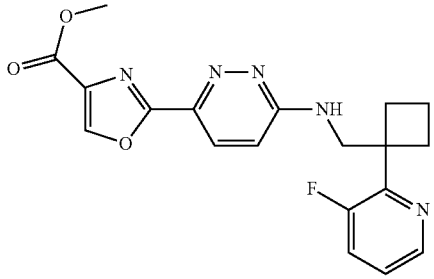 [SMILES: COC(=O)c1coc(-c2ccc(NCC3(c4ncccc4F)CCC3)nn2)n1] | 384.2 | D |
| {[(3-fluoro(2-pyridyl))cyclobutyl]methyl}{6-[6-({[(3-fluoro(2-pyridyl))cyclobutyl]methyl}amino)pyridazin-3-yl]pyridazin-3-yl}amine | 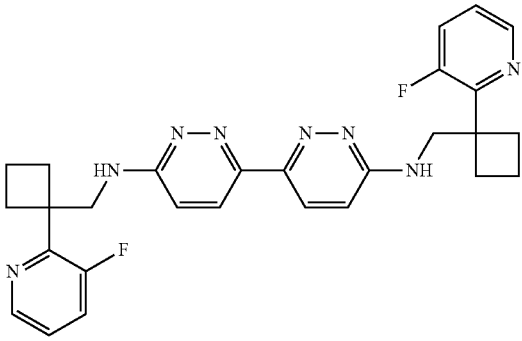 [SMILES: Fc1cccnc1C1(CNc2ccc(-c3ccc(NCC4(c5ncccc5F)CCC4)nn3)nn2)CCC1] | 515.4 | D |
| methyl 2-[6-({[(3-fluoro-2-pyridyl)cyclobutyl]methyl}amino)pyridazin-3-yl]-1,3-thiazole-4-carboxylate | 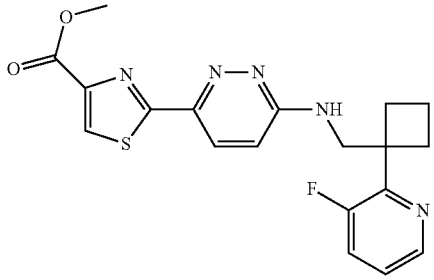 | 400.2 | D |

TABLE 2-continued

| Compound | Structure | m/z (M + H) | Mean AC1.4 |
|---|---|---|---|
| methyl 2-[6-({[(3-fluoro-2-pyridyl)cyclobutyl]methyl}amino)pyridazin-3-yl]-1,3-oxazole-5-carboxylate | 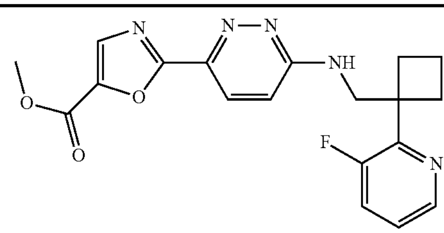 | 384.2 | D |
| 2-[6-({[(3-fluoro-2-pyridyl)cyclobutyl]methyl}amino)pyridazin-3-yl]imidazole-4-carboxamide | 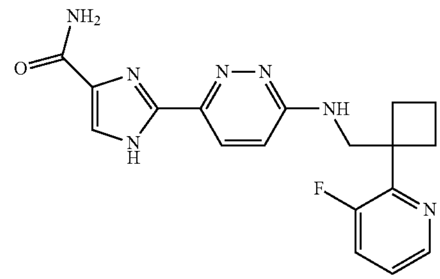 [SMILES: NC(=O)c1c[nH]c(-c2ccc(NCC3(c4ncccc4F)CCC3)nn2)n1] | 368.2 | B |
| methyl 2-[6-({[(3-fluoro-2-pyridyl)cyclobutyl]methyl}amino)pyridazin-3-yl]imidazole-4-carboxylate | 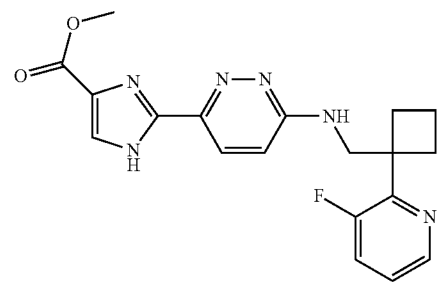 [SMILES: COC(=O)c1c[nH]c(-c2ccc(NCC3(c4ncccc4F)CCC3)nn2)n1] | 383.3 | D |
| 4-[6-({[(3-fluoro-2-pyridyl)cyclobutyl]methyl}amino)pyridazin-3-yl]-1,3-thiazole-2-carboxamide | 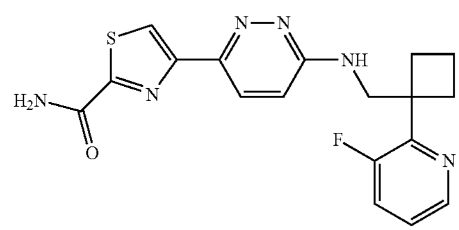 [SMILES: NC(=O)c1nc(-c2ccc(NCC3(c4ncccc4F)CCC3)nn2)cs1] | 385.2 | B |
| 5-[6-({[(3-fluoro-2-pyridyl)cyclobutyl]methyl}amino)pyridazin-3-yl]-1,3-thiazole-2-carboxamide | 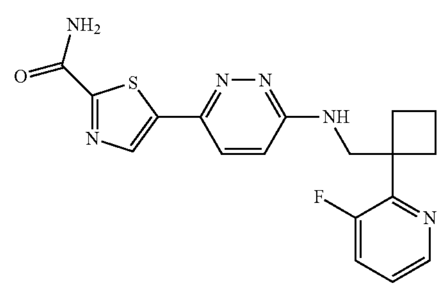 | 385.2 | B |
| 3-[6-({[(3-fluoro-2-pyridyl)cyclobutyl]methyl}amino)pyridazin-3-yl]-1,2,4-oxadiazole-5-carboxamide | 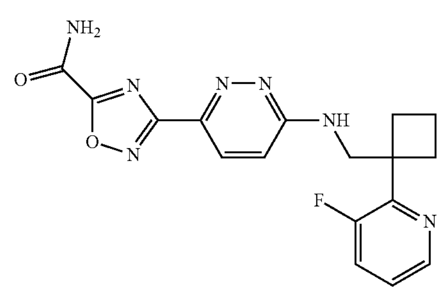 [SMILES: NC(=O)c1nc(-c2ccc(NCC3(c4ncccc4F)CCC3)nn2)no1] | 370.1 | B |

TABLE 2-continued

| Compound | Structure | m/z (M + H) | Mean AC1.4 |
|---|---|---|---|
| 5-[6-({[(3-fluoro-2-pyridyl)cyclobutyl]methyl}amino)pyridazin-3-yl]-4H-1,2,4-triazole-3-carboxamide | 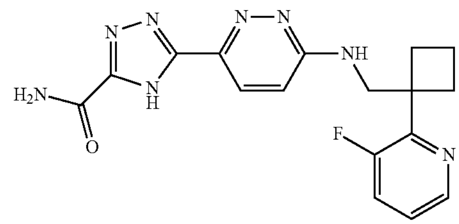 [SMILES: NC(=O)c1nnc(-c2ccc(NCC3(c4ncccc4F)CCC3)nn2)[nH]1] | 369.2 | C |
| methyl 2-[6-({[(3-fluoro(2-pyridyl))cyclobutyl]methyl}amino)pyridazin-3-yl]-1-methylimidazole-4-carboxylate | 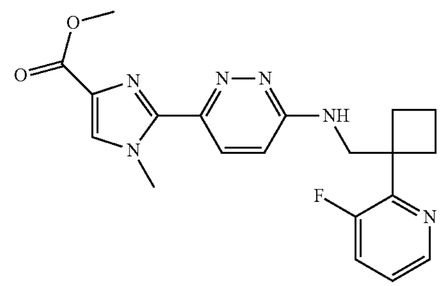 [SMILES: COC(=O)c1cn(C)c(-c2ccc(NCC3(c4ncccc4F)CCC3)nn2)n1] | 397.3 | D |
| 2-[6-({[(3-fluoro(2-pyridyl))cyclobutyl]methyl}amino)pyridazin-3-yl]-1-methylimidazole-4-carboxamide | 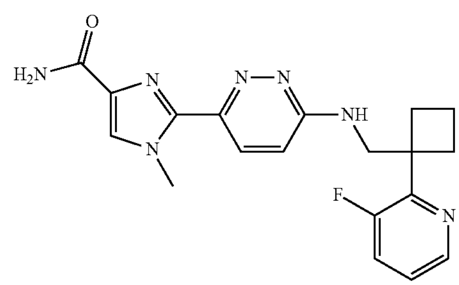 [SMILES: Cn1cc(C(N)=O)nc1-c1ccc(NCC2(c3ncccc3F)CCC2)nn1] | 382.3 | D |
| 2-[6-({[(3-fluoro(2-pyridyl))cyclobutyl]methyl}amino)pyridazin-3-yl]-1-methylimidazole-5-carboxamide | 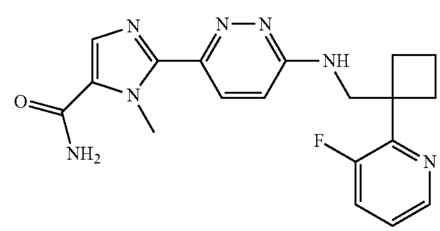 [SMILES: Cn1c(C(N)=O)cnc1-c1ccc(NCC2(c3ncccc3F)CCC2)nn1] | 382.3 | B |
| 2-(6-{[(3-fluoro-2-pyridyl)cyclobutyl]amino}pyridazin-3-yl)-1,3-thiazole-5-carboxamide | 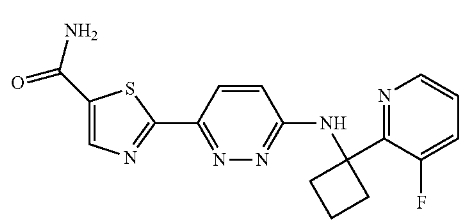 [SMILES: NC(=O)c1cnc(-c2ccc(NC3(c4ncccc4F)CCC3)nn2)s1] | 371.2 | B |
| 5-(6-{[(3-fluoro(2-pyridyl))cyclobutyl]amino}pyridazin-3-yl)-2-hydroxybenzamide | 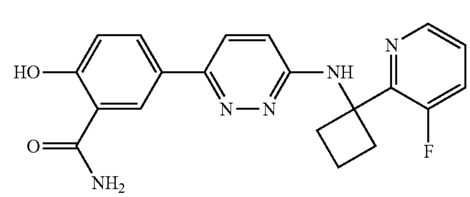 [SMILES: NC(=O)c1cc(-c2ccc(NC3(c4ncccc4F)CCC3)nn2)ccc1O] | 380.1 | B |

TABLE 2-continued

| Compound | Structure | m/z (M + H) | Mean AC1.4 |
|---|---|---|---|
| 5-[6-({[(3-fluoro-2-pyridyl)cyclobutyl]methyl}amino)pyridazin-3-yl]thiophene-2-carboxamide | 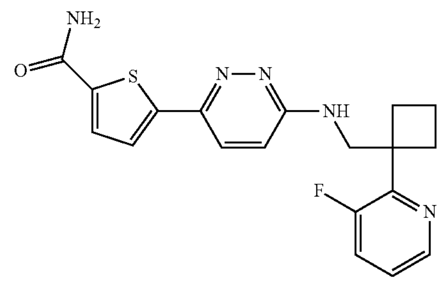 [SMILES: NC(=O)c1ccc(-c2ccc(NCC3(c4ncccc4F)CCC3)nn2)s1] | 384.1 | A |
| [6-(3-amino(1H-indazol-5-yl))pyridazin-3-yl][(3-fluoro(2-pyridyl))cyclobutyl]amine | 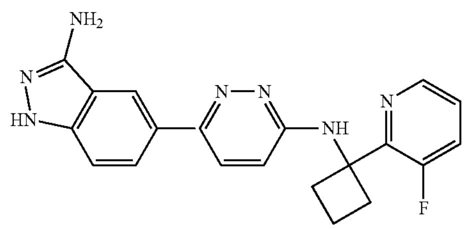 | 376.2 | B |
| 5-[6-({[(3-fluoro-2-pyridyl)cyclobutyl]methyl}amino)pyridazin-3-yl]-1,3,4-thiadiazole-2-carboxamide | 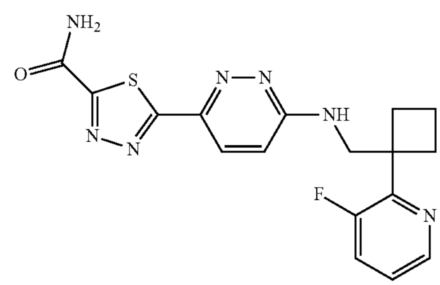 [SMILES: NC(=O)c1nnc(-c2ccc(NCC3(c4ncccc4F)CCC3)nn2)s1] | 386.1 | B |
| {[(3-fluoro(2-pyridyl))cyclobutyl]methyl}(6-(1,3-thiazol-2-yl)pyridazin-3-yl)amine | 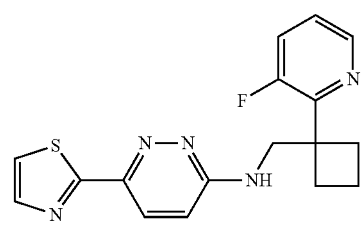 [SMILES: Fc1cccnc1C1(CNc2ccc(-c3nccs3)nn2)CCC1] | 342.1 | B |
| (6-(2H-1,2,3,4-tetraazol-5-yl)pyridazin-3-yl){[(3-fluoro(2-pyridyl))cyclobutyl]methyl}amine | 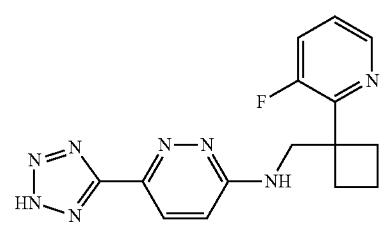 [SMILES: Fc1cccnc1C1(CNc2ccc(-c3nn[nH]n3)nn2)CCC1] | 327.2 | D |
| 5-[6-({[(3-fluoro-2-pyridyl)cyclobutyl]methyl}amino)pyridazin-3-yl]-1,3,4-oxadiazole-2-carboxamide | 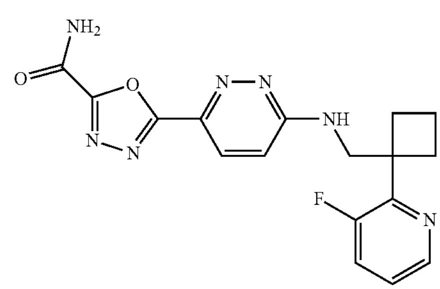 | 370.2 | C |

TABLE 2-continued

| Compound | Structure | m/z (M + H) | Mean AC1.4 |
|---|---|---|---|
| 2-[6-({[(3-fluoro(2-pyridyl))cyclobutyl]methyl}amino)pyridazin-3-yl]-4-methyl-1,3-thiazole-5-carboxamide | 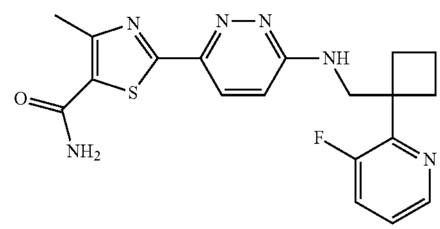 | 399.2 | B |
| 2-(6-{[(4-fluorophenyl)cyclobutyl]amino}pyridazin-3-yl)-1,3-thiazole-5-carboxamide | 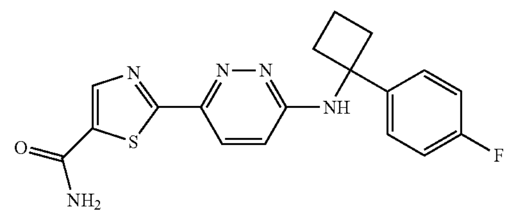 [SMILES: NC(=O)c1cnc(-c2ccc(NC3(c4ccc(F)cc4)CCC3)nn2)s1] | 370.2 | B |
| 2-[6-({[(3-fluoro-2-pyridyl)cyclobutyl]methyl}amino)pyridazin-3-yl]-1,3-thiazole-5-carboxylic acid | 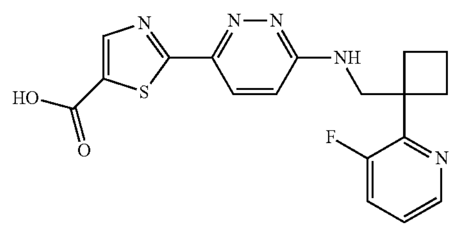 [SMILES: O=C(O)c1cnc(-c2ccc(NCC3(c4ncccc4F)CCC3)nn2)s1] | 386.2 | C |
| 5-(6-{[(3-fluoro-2-pyridyl)cyclobutyl]amino}pyridazin-3-yl)thiophene-2-carboxamide | 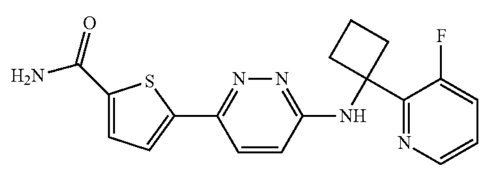 [SMILES: NC(=O)c1ccc(-c2ccc(NC3(c4ncccc4F)CCC3)nn2)s1] | 370.1 | B |
| 5-(6-{[(4-fluorophenyl)cyclobutyl]amino}pyridazin-3-yl)thiophene-2-carboxamide | 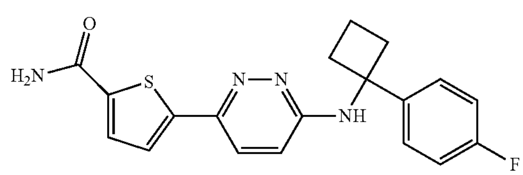 [SMILES: NC(=O)c1ccc(-c2ccc(NC3(c4ccc(F)cc4)CCC3)nn2)s1] | 369.1 | B |
| 5-(6-{[(3-fluoro-2-pyridyl)cyclobutyl]amino}pyridazin-3-yl)thiophene-2-carboxylic acid | 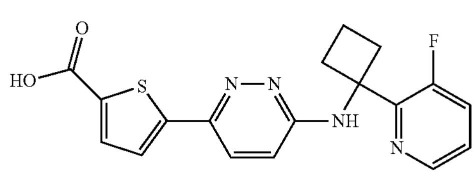 [SMILES: O=C(O)c1ccc(-c2ccc(NC3(c4ncccc4F)CCC3)nn2)s1] | 371.1 | D |
| 2-[6-({[(3-fluoro-2-pyridyl)cyclobutyl]methyl}amino)pyridazin-3-yl]-1,3-thiazole-5-carbonitrile | 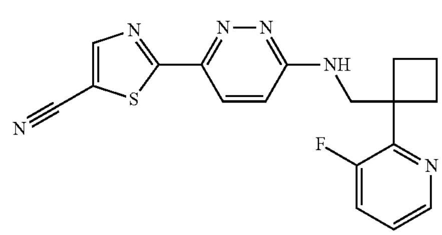 [SMILES: N#Cc1cnc(-c2ccc(NCC3(c4ncccc4F)CCC3)nn2)s1] | 367.1 | B |

TABLE 2-continued

| Compound | Structure | m/z (M + H) | Mean AC1.4 |
|---|---|---|---|
| 5-[6-({[(3-fluoro-2-pyridyl)cyclobutyl]methyl}amino)pyridazin-3-yl]thiophene-2-carboxylic acid | 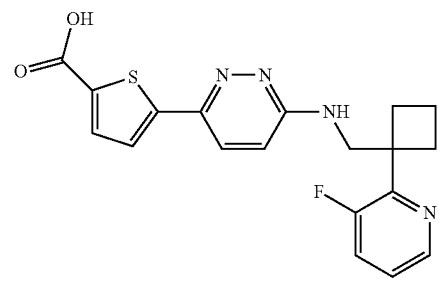 [SMILES: O=C(O)c1ccc(-c2ccc(NCC3(c4ncccc4F)CCC3)nn2)s1] | 385.0 | B |
| 2-[6-({[(3-fluoro(2-pyridyl))cyclobutyl]methyl}amino)pyridazin-3-yl]-4-hydroxy-1,3-thiazole-5-carboxamide | 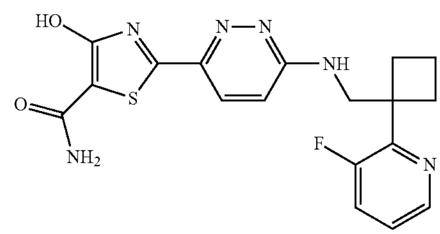 [SMILES: NC(=O)c1sc(-c2ccc(NCC3(c4ncccc4F)CCC3)nn2)nc1O] | 401.1 | B |
| 5-[6-({[(3-fluoro-2-pyridyl)cyclobutyl]methyl}amino)pyridazin-3-yl]-3-pyrazolino[3,4-d)1,3-thiazol-3-one | 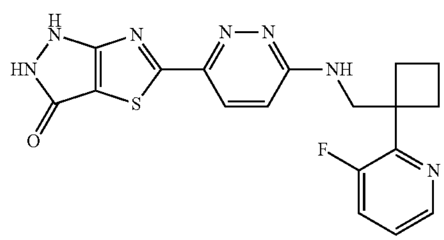 [SMILES: O=c1[nH][nH]c2nc(-c3ccc(NCC4(c5ncccc5F)CCC4)nn3)sc12] | 398.3 | D |
| 2-[6-({1-[6-(difluoromethoxy)(2-pyridyl)]-isopropyl}amino)pyridazin-3-yl]-1,3-thiazole-5-carboxamide | 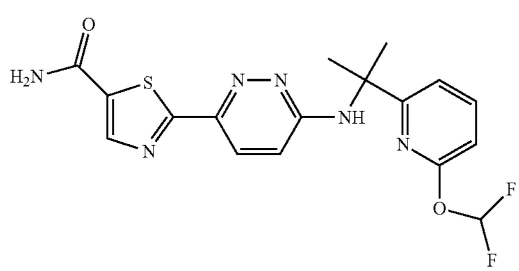 [SMILES: CC(C)(Nc1ccc(-c2ncc(C(N)=O)s2)nn1)c1cccc(OC(F)F)n1] | 407.1 | B |
| {2-[6-({[(3-fluoro-2-pyridyl)cyclobutyl]methyl}amino)pyridazin-3-yl]-1,3-thiazol-5-yl}methan-1-ol | 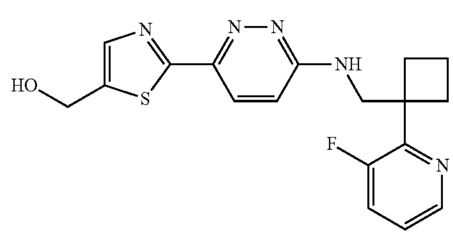 | 372.2 | B |
| [6-(5-(2H-1,2,3,4-tetraazol-5-yl)(1,3-thiazol-2-yl))pyridazin-3-yl]{[(3-fluoro(2-pyridyl))cyclobutyl]methyl}amine | 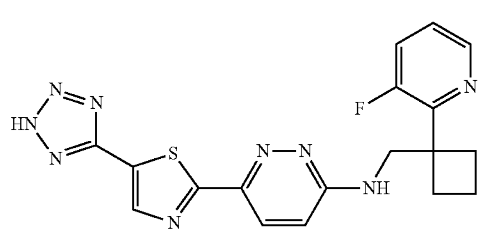 [SMILES: Fc1cccnc1C1(CNc2ccc(-c3ncc(-c4nn[nH]n4)s3)nn2)CCC1] | 410.2 | B |

TABLE 2-continued

| Compound | Structure | m/z (M + H) | Mean AC1.4 |
|---|---|---|---|
| 5-{2-[6-({[(3-fluoro-2-pyridyl)cyclobutyl]methyl}amino)pyridazin-3-yl]-1,3-thiazol-5-yl}-1,3,4-oxadiazolin-2-one | | 426.2 | B |
| ethyl 3-[6-({[(3-fluoro(2-pyridyl))cyclobutyl]methyl}amino)pyridazin-3-yl]-5-hydroxypyrazole-4-carboxylate | 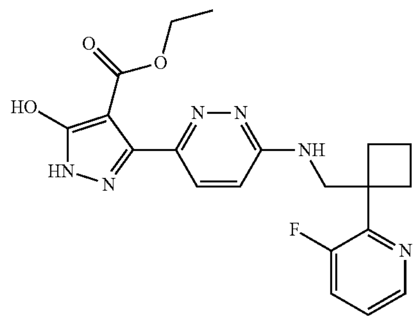 [SMILES: CCOC(=O)c1c(-c2ccc(NCC3(c4ncccc4F)CCC3)nn2)n[nH]c1O] | 413.1 | D |
| 3-[6-({[(3-fluoro-2-pyridyl)cyclobutyl]methyl}amino)pyridazin-3-yl]-3-pyrazolin-5-one | 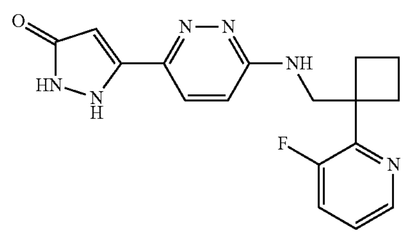 [SMILES: O=c1cc(-c2ccc(NCC3(c4ncccc4F)CCC3)nn2)[nH][nH]1] | 341.1 | B |
| 3-{2-[6-({[(3-fluoro-2-pyridyl)cyclobutyl)methyl}amino)pyridazin-3-yl]-1,3-thiazol-5-yl}-1,2,4-triazolin-5-one | 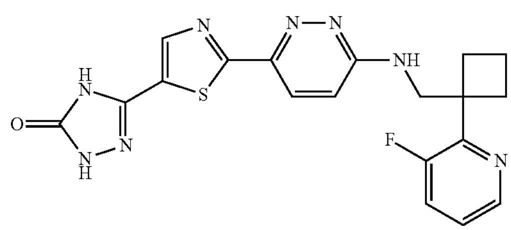 [SMILES: O=c1[nH]nc(-c2cnc(-c3ccc(NCC4(c5ncccc5F)CCC4)nn3)s2)[nH]1] | 425.2 | A |
| 3-{2-[6-({[(3-fluoro-2-pyridyl)cyclobulyl]rnethyl}amino)pyridazin-3-yl]-1,3-thiazol-5-yl}-1,2,4-oxadiazolin-5-one | 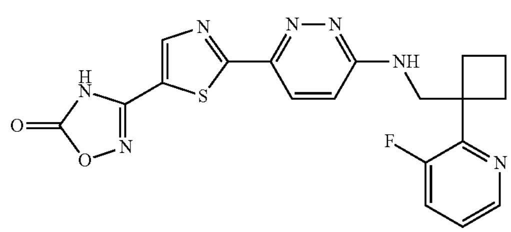 [SMILES: O=c1[nH]c(-c2cnc(-c3ccc(NCC4(c5ncccc5F)CCC4)nn3)s2)no1] | 426.2 | B |
| ethyl 2-[6-({[(3-fluoro(2-pyridyl))cyclobutyl]methyl}amino)pyridazin-3-yl]-4-hydroxy-1,3-thiazole-5-carboxylate | 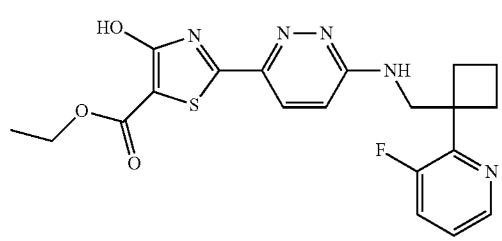 [SMILES: CCOC(=O)c1sc(-c2ccc(NCC3(c4ncccc4F)CCC3)nn2)nc1O] | 430.1 | D |

TABLE 2-continued

| Compound | Structure | m/z (M + H) | Mean AC1.4 |
|---|---|---|---|
| 2-(6-{[2-(3-fluoro(2-pyridyl))-2-methylpropyl)amino}pyridazin-3-yl)-1,3-thiazole-5-carboxamide | 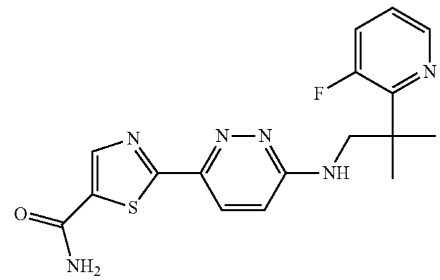 [SMILES: CC(C)(CNc1ccc(-c2ncc(C(N)=O)s2)nn1)c1ncccc1F] | 373.2 | A |
| 2-[6-({[(3-fluoro(2-pyridyl))cyclobutyl]methyl}amino)pyridazin-3-yl]-4-methoxy-1,3-thiazole-5-carboxamide | 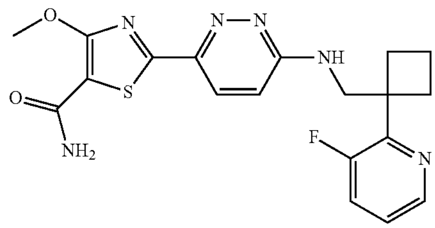 [SMILES: COc1nc(-c2ccc(NCC3(c4ncccc4F)CCC3)nn2)sc1C(N)=O] | 415.1 | A |
| 2-[6-({[(3-fluoro(2-pyridyl))cyclobutyl]methyl}amino)pyridazin-3-yl]-4-methoxy-1,3-thiazole-5-carboxylic acid | 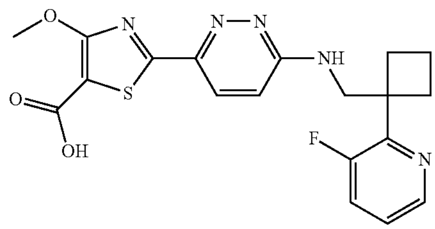 [SMILES: COc1nc(-c2ccc(NCC3(c4ncccc4F)CCC3)nn2)sc1C(=O)O] | 416.2 | C |
| 1-{2-[6-({[(3-fluoro-2-pyridyl)cyclobutyl]methyl}amino)pyridazin-3-yl]-1,3-thiazol-5-yl}ethan-1-ol | 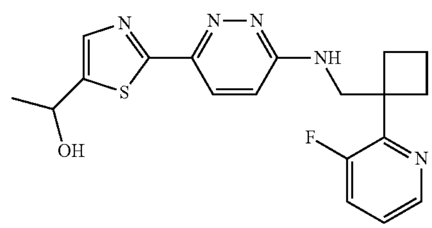 [SMILES: CC(O)c1cnc(-c2ccc(NCC3(c4ncccc4F)CCC3)nn2)s1] | 386.2 | B |
| 2,2,2-trifluoro-1-{2-[6-({[(3-fluoro(2-pyridyl))cyclobutyl]methyl}amino)pyridazin-3-yl](1,3-thiazol-5-yl)}ethan-1-ol | 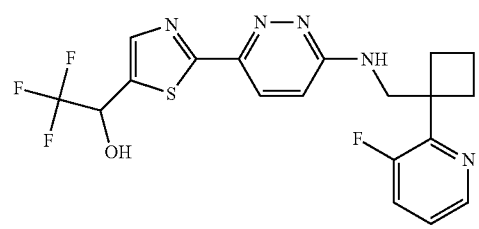 [SMILES: OC(c1cnc(-c2ccc(NCC3(c4ncccc4F)CCC3)nn2)s1)C(F)(F)F] | 440.2 | B |
| {2-[6-({[(3-fluoro(2-pyridyl))cyclobutyl]methyl}amino)pyridazin-3-yl](1,3-thiazol-5-yl)}-N-(methylethyl)carboxamide | 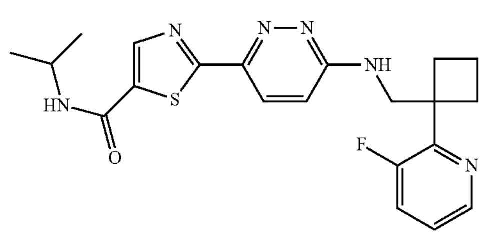 [SMILES: CC(C)NC(=O)c1cnc(-c2ccc(NCC3(c4ncccc4F)CCC3)nn2)s1] | 427.3 | B |

TABLE 2-continued

| Compound | Structure | m/z (M + H) | Mean AC1.4 |
|---|---|---|---|
| ethyl 2-[6-({[(3-fluoro-2-pyridyl)cyclobutyl]methyl}amino)pyridazin-3-yl]-1,3-thiazole-4-carboxylate | 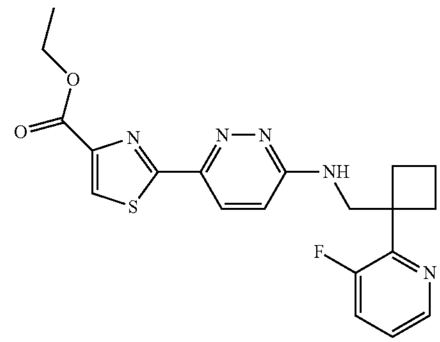 [SMILES: CCOC(=O)c1csc(-c2ccc(NCC3(c4ncccc4F)CCC3)nn2)n1] | 514.0 | D |
| 2-[6-({[(3-fluoro-2-pyridyl)cyclobutyl]methyl}amino)pyridazin-3-yl]-3-pyrrolino[3,4-d]1,3-thiazol-6-one | 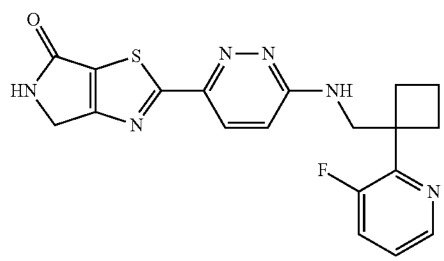 [SMILES: O=C1NCc2nc(-c3ccc(NCC4(c5ncccc5F)CCC4)nn3)sc21] | 396.1 | B |
| 1-{2-[6-({[(3-fluoro-2-pyridyl)cyclobutyl]methyl}amino)pyridazin-3-yl]-1,3-thiazol-5-yl}ethan-1-one | 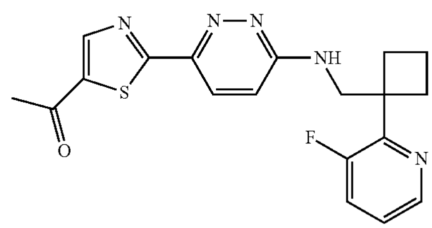 [SMILES: CC(=O)c1cnc(-c2ccc(NCC3(c4ncccc4F)CCC3)nn2)s1] | 384.2 | C |
| 2-{2-[6-({[(3-fluoro-2-pyridyl)cyclobutyl]methyl}amino)pyridazin-3-yl]-1,3-thiazol-5-yl}propan-2-ol | 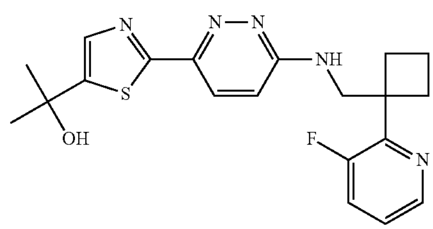 [SMILES: CC(C)(O)c1cnc(-c2ccc(NCC3(c4ncccc4F)CCC3)nn2)s1] | 400.3 | C |
| 1,1,1-trifluoro-2-{2-[6-({[(3-fluoro(2-pyridyl))cyclobutyl]methyl}amino)pyridazin-3-yl](1,3-thiazol-5-yl)}propan-2-ol | 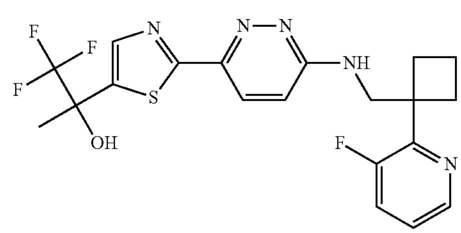 [SMILES: CC(O)(c1cnc(-c2ccc(NCC3(c4ncccc4F)CCC3)nn2)s1)C(F)(F)F] | 454.2 | C |
| {2-[6-({[(3-fluoro(2-pyridyl))cyclobutyl]methyl}amino)pyridazin-3-yl](1,3-thiazol-5-yl)}-N-methylcarboxamide | 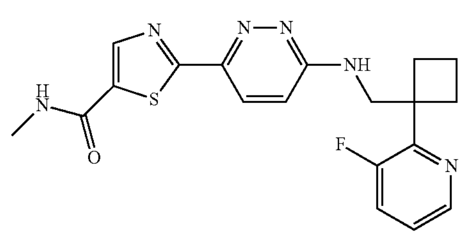 [SMILES: CNC(=O)c1cnc(-c2ccc(NCC3(c4ncccc4F)CCC3)nn2)s1] | 399.3 | A |

TABLE 2-continued

| Compound | Structure | m/z (M + H) | Mean AC1.4 |
|---|---|---|---|
| 3-(6-{[(2-pyridylcyclobutyl)methyl]amino}pyridazin-3-yl)benzenecarbonitrile | 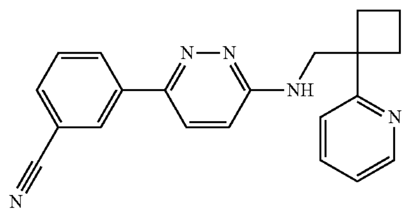 [SMILES: N#Cc1cccc(-c2ccc(NCC3(c4ccccn4)CCC3)nn2)c1] | 342.1 | B |
| 3-(6-{methyl[(2-pyridylcyclobutyl)methyl]amino}pyridazin-3-yl)benzamide | 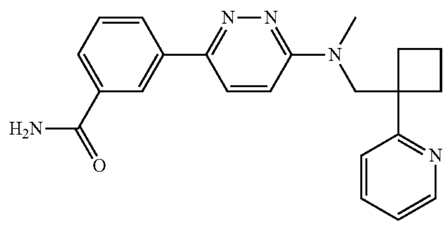 [SMILES: CN(CC1(c2ccccn2)CCC1)c1ccc(-c2cccc(C(N)=O)c2)nn1] | 374.2 | D |
| 6-[6-({[(3-fluoro-2-pyridyl)cyclobutyl]methyl}amino)pyridazin-3-yl]pyrazine-2-carbonitrile | 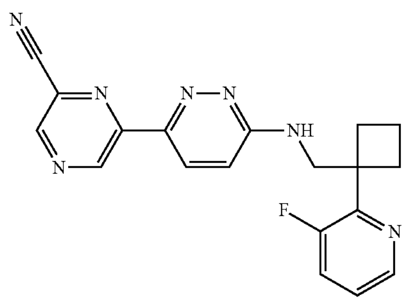 [SMILES: N#Cc1cncc(-c2ccc(NCC3(c4ncccc4F)CCC3)nn2)n1] | 362.1 | B |
| 6-[6-({[(3-fluoro-2-pyridyl)cyclobutyl]methyl}amino)pyridazin-3-yl]pyrazine-2-carboxamide | 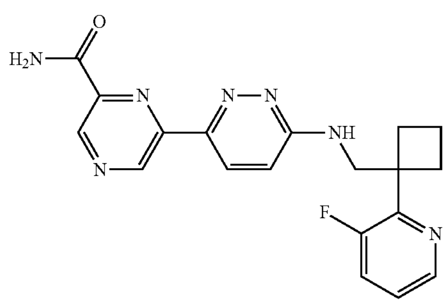 [SMILES: NC(=O)c1cncc(-c2ccc(NCC3(c4ncccc4F)CCC3)nn2)n1] | 380.2 | C |
| 2-[6-({[(3-fluoro(2-pyridyl))cyclobutyl]methyl}amino)pyridazin-3-yl]-4-hydroxy-1,3-thiazole-5-carbonitrile | 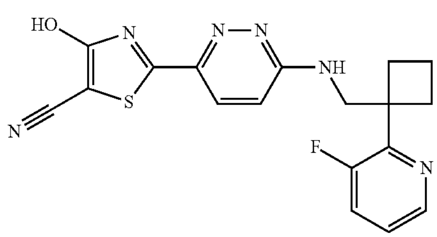 [SMILES: N#Cc1sc(-c2ccc(NCC3(c4ncccc4F)CCC3)nn2)nc1O] | 383.1 | D |
| 2-(6-{[(2-pyridylcyclobutyl)methyl]amino}pyridazin-3-yl)-1,3-thiazole-5-carboxamide | 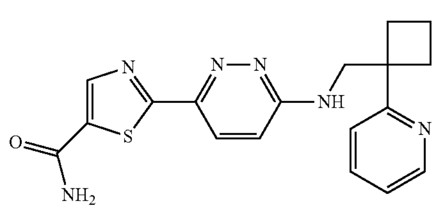 [SMILES: NC(=O)c1cnc(-c2ccc(NCC3(c4ccccn4)CCC3)nn2)s1] | 367.1 | A |

TABLE 2-continued

| Compound | Structure | m/z (M + H) | Mean AC1.4 |
|---|---|---|---|
| 2-(6-{[(2-pyridylcyclobutyl)methyl]amino}pyridazin-3-yl)-1,3-thiazole-5-carboxylic acid | 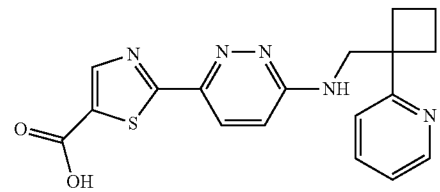 [SMILES: O=C(O)c1cnc(-c2ccc(NCC3(c4ccccn4)CCC3)nn2)s1] | 368.1 | C |
| 3-{5-[6-({[(3-fluoro-2-pyridyl)cyclobutyl]methyl}amino)pyridazin-3-yl]-2-thienyl}-1,2,4-triazolin-5-one | 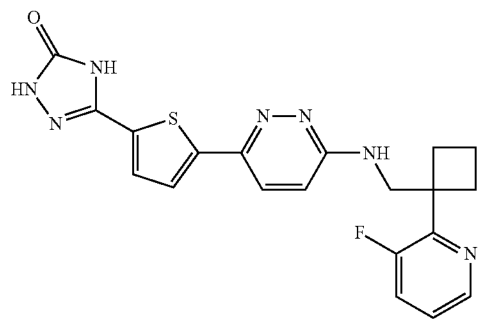 [SMILES: O=c1[nH]nc(-c2ccc(-c3ccc(NCC4(c5ncccc5F)CCC4)nn3)s2)[nH]1] | 424.1 | A |
| 3-[6-({[(3-fluoro-2-pyridyl)cyclobutyl]methyl}amino)pyridazin-3-yl]-1,2,4-triazolin-5-one | 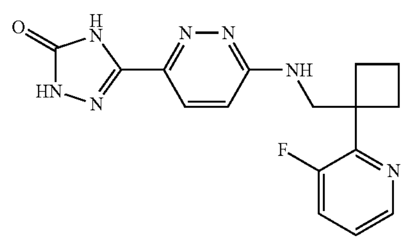 [SMILES: O=c1[nH]nc(-c2ccc(NCC3(c4ncccc4F)CCC3)nn2)[nH]1] | 342.2 | C |
| amino{2-[6-({[(3-fluoro(2-pyridyl))cyclobutyl]methyl}amino)pyridazin-3-yl](1,3-thiazol-5-yl)}methane-1-thione | 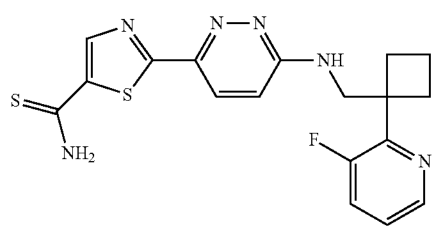 [SMILES: NC(=S)c1cnc(-c2ccc(NCC3(c4ncccc4F)CCC3)nn2)s1] | 401.2 | A |
| 2,2,2-trifluoro-1-{2-[6-({[(3-fluoro(2-pyridyl))cyclobutyl]methyl}amino)pyridazin-3-yl](1,3-thiazol-5-yl)}ethane-1,1-diol | 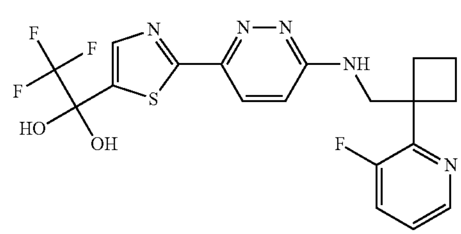 [SMILES: OC(O)(c1cnc(-c2ccc(NCC3(c4ncccc4F)CCC3)nn2)s1)C(F)(F)F] | 456.2 | B |
| {[(3-fluoro(2-pyridyl))cyclobutyl]methyl}{6-[5-(2,2,2-trifluoroethyl)(1,3-thiazol-2-yl)]pyridazin-3-yl}amine | 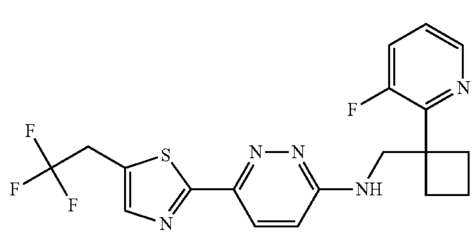 [SMILES: Fc1cccnc1C1(CNc2ccc(-c3ncc(CC(F)(F)F)s3)nn2)CCC1] | 424.2 | B |

TABLE 2-continued

| Compound | Structure | m/z (M + H) | Mean AC1.4 |
|---|---|---|---|
| 5-[6-({[(3-fluoro-2-pyridyl)cyclobutyl]methyl}amino)pyridazin-3-yl)thiophene-2-carbonitrile | 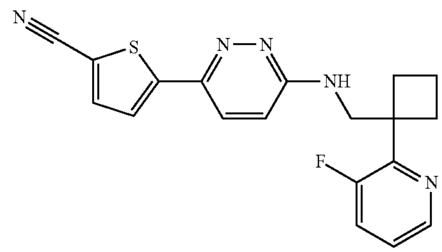 [SMILES: N#Cc1ccc(-c2ccc(NCC3(c4ncccc4F)CCC3)nn2)s1] | 366.2 | B |
| 2-[6-({[(3-fluoro-2-pyridyl)cyclobutyl]methyl}amino)pyridazin-3-yl]thiopheno[2,3-c]3-pyrrolin-6-one | 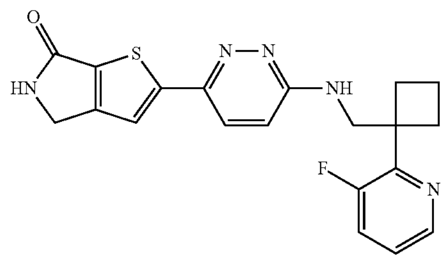 [SMILES: O=C1NCc2cc(-c3ccc(NCC4(c5ncccc5F)CCC4)nn3)sc21] | 396.2 | B |
| {6-[5-(1-amino-2,2,2-trifluoroethyl)(1,3-thiazol-2-yl)]pyridazin-3-yl}{[(3-fluoro(2-pyridyl))cyclobutyl]methyl}amine | 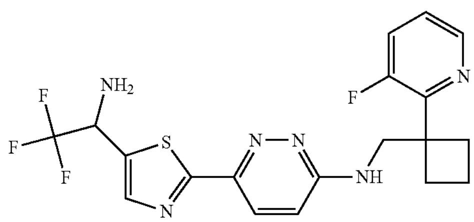 [SMILES: NC(c1cnc(-c2ccc(NCC3(c4ncccc4F)CCC3)nn2)s1)C(F)(F)F] | 439.2 | B |
| [6-(2-aminopyrimidin-4-yl)pyridazin-3-yl]{[(3-fluoro(2-pyridyl))cyclobutyl]methyl}amine | 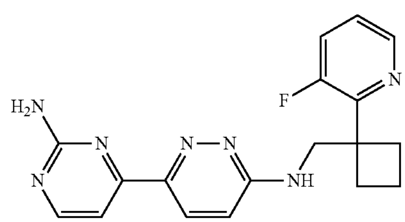 [SMILES: Nc1nccc(-c2ccc(NCC3(c4ncccc4F)CCC3)nn2)n1] | 352.3 | B |
| 2-{5-[6-({[(3-fluoro-2-pyridyl)cyclobutyl]methyl}amino)pyridazin-3-yl]-1,2,3,4-tetraazol-2-yl}acetamide | 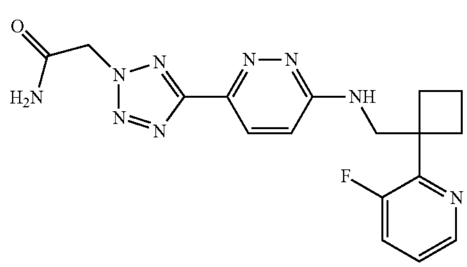 [SMILES: NC(=O)Cn1nnc(-c2ccc(NCC3(c4ncccc4F)CCC3)nn2)n1] | 384.3 | D |
| {6-[2-(2-aminoethyl)(1,2,3,4-tetraazol-5-yl)]pyridazin-3-yl}{[(3-fluoro(2-pyridyl))cyclobutyl]methyl}amine | 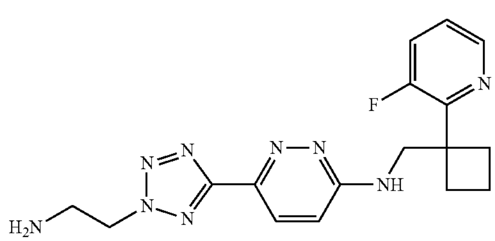 [SMILES: NCCn1nnc(-c2ccc(NCC3(c4ncccc4F)CCC3)nn2)n1] | 370.3 | D |

TABLE 2-continued

| Compound | Structure | m/z (M + H) | Mean AC1.4 |
|---|---|---|---|
| [6-(3-(2H-1,2,3,4-tetraazol-5-yl)phenyl)pyridazin-3-yl]{[(3-fluoro(2-pyridyl))cyclobutyl]methyl}amine | 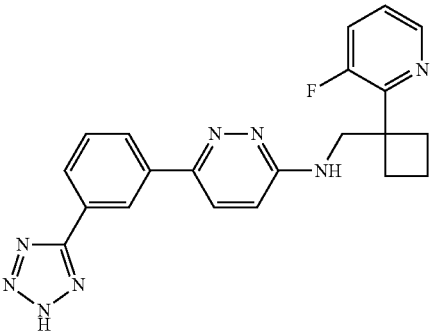 [SMILES: Fc1cccnc1C1(CNc2ccc(-c3cccc(-c4nn[nH]n4)c3)nn2)CCC1] | 403.1 | A |
| phenylmethyl 2-{[6-({[(3-fluoro-2-pyridyl)cyclobutyl]methyl}amino)pyridazin-3-yl]carbonylamino}acetate | 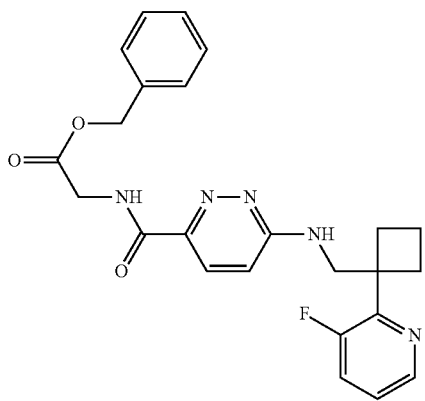 [SMILES: O=C(CNC(=O)c1ccc(NCC2(c3ncccc3F)CCC2)nn1)OCc1ccccc1] | 450.1 | D |
| 3-{3-[6-({[(3-fluoro-2-pyridyl)cyclobutyl]rnethyl}amino)pyridazin-3-yl]phenyl}-1,2,4-triazolin-5-one | 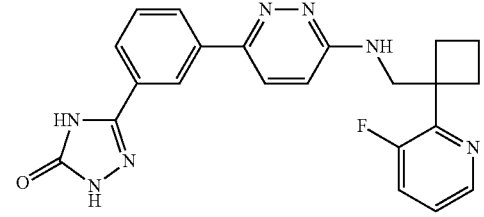 [SMILES: O=c1[nH]nc(-c2cccc(-c3ccc(NCC4(c5ncccc5F)CCC4)nn3)c2)[nH]1] | 418.3 | B |
| 3-{4-fluoro-3-[6-({[(3-fluoro(2-pyridyl))cyclobutyl]methyl}amino)pyridazin-3-yl]phenyl}-1,2,4-triazolin-5-one | 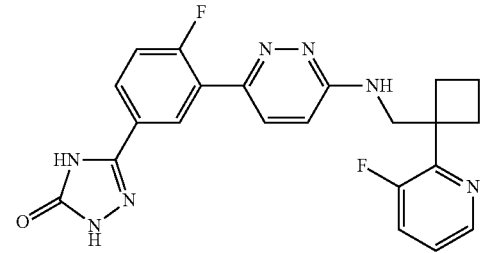 [SMILES: O=c1[nH]nc(-c2ccc(F)c(-c3ccc(NCC4(c5ncccc5F)CCC4)nn3)c2)[nH]1] | 436.3 | A |
| {6-[5-(aminomethyl)(1,3-thiazol-2-yl)]pyridazin-3-yl}{[(3-fluoro(2-pyridyl))cyclobutyl]methyl}amine | 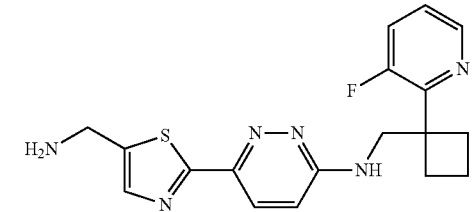 [SMILES: NCc1cnc(-c2ccc(NCC3(c4ncccc4F)CCC3)nn2)s1] | 371.3 | B |

TABLE 2-continued

| Compound | Structure | m/z (M + H) | Mean AC1.4 |
|---|---|---|---|
| N-((2-(6-((1-(3-fluoropyridin-2-yl)cyclobutyl)methylamino)pyridazin-3-yl)thiazol-5-yl)methyl)-2-methylpropane-2-sulfinamide | 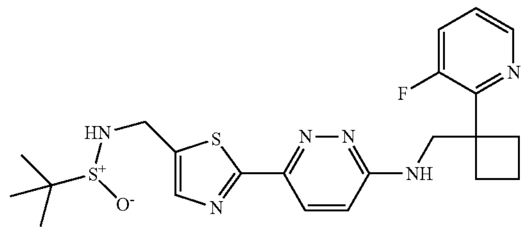 [SMILES: CC(C)(C)[S+]([O-])NCc1cnc(-c2ccc(NCC3(c4ncccc4F)CCC3)nn2)s1] | 475.3 | B |
| {6-[5-(aminoethyl)(1,3-thiazol-2-yl)]pyridazin-3-yl}{[(3-fluoro(2-pyridyl))cyclobutyl]methyl}amine | 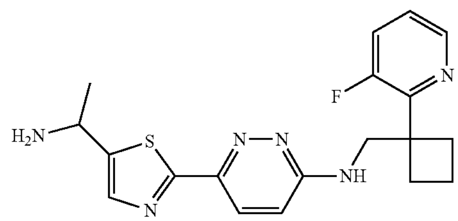 [SMILES: CC(N)c1cnc(-c2ccc(NCC3(c4ncccc4F)CCC3)nn2)s1] | 385.3 | B |
| {6-[5-(3-aminooxetan-3-yl)(1,3-thiazol-2-yl)]pyridazin-3-yl}{[(3-fluoro(2-pyridyl))cyclobutyl]methyl}amine | 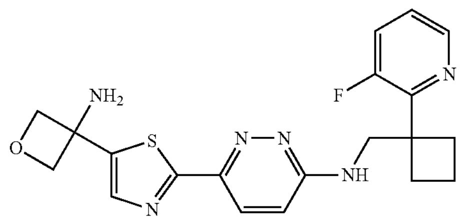 [SMILES: NC1(c2cnc(-c3ccc(NCC4(c5ncccc5F)CCC4)nn3)s2)COC1] | 413.2 | D |
| 2-[6-({[(3-fluoro-2-pyridyl)cyclobutyl]methyl}amino)pyridazin-3-yl]pyrimidine-4-carboxamide | 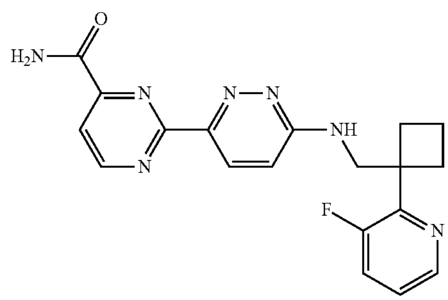 [SMILES: NC(=O)c1ccnc(-c2ccc(NCC3(c4ncccc4F)CCC3)nn2)n1] | 380.3 | A |
| {2-[6-({[(3-fluoro(2-pyridyl))cyclobutyl]methyl}amino)pyridazin-3-yl](1,3-thiazol-5-yl)}-N-(2-hydroxyethyl)carboxamide | 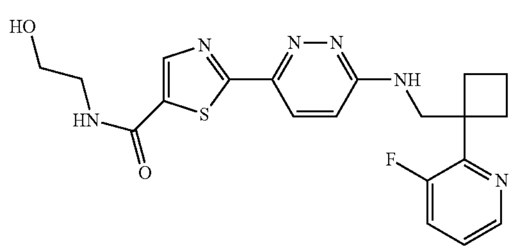 [SMILES: O=C(NCCO)c1cnc(-c2ccc(NCC3(c4ncccc4F)CCC3)nn2)s1] | 429.2 | A |
| ethyl 5-chloro-2-[5-chloro-6-({[(3-fluoro(2-pyridyl))cyclobutyl]methyl}amino)pyridazin-3-yl]-1,3-thiazole-4-carboxylate | 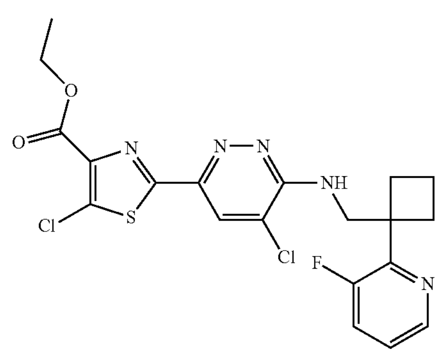 [SMILES: CCOC(=O)c1nc(-c2cc(Cl)c(NCC3(c4ncccc4F)CCC3)nn2)sc1Cl] | 482.2 | D |

TABLE 2-continued

| Compound | Structure | m/z (M + H) | Mean AC1.4 |
|---|---|---|---|
| N-{4-[6-({[(3-fluoro-2-pyridyl)cyclobutyl]methyl}amino)pyridazin-3-yl]pyrimidin-2-yl}acetamide | 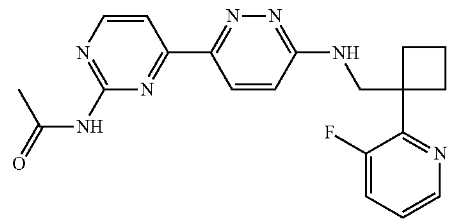 [SMILES: CC(=O)Nc1nccc(-c2ccc(NCC3(c4ncccc4F)CCC3)nn2)n1] | 394.3 | C |
| {4-(6-({[(3-fluoro(2-pyridyl))cyclobutyl]methyl}amino)pyridazin-3-yl]pyrimidin-2-yl}(methylsulfonyl)amine | 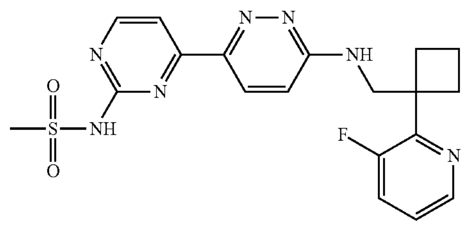 [SMILES: CS(=O)(=O)Nc1nccc(-c2ccc(NCC3(c4ncccc4F)CCC3)nn2)n1] | 430.3 | D |
| (2E)-3-amino-3-{2-[6-({[(3-fluoro(2-pyridyl))cyclobutyl]methyl}amino)pyridazin-3-yl](1,3-thiazol-5-yl)}-2-azaprop-2-enenitrile | 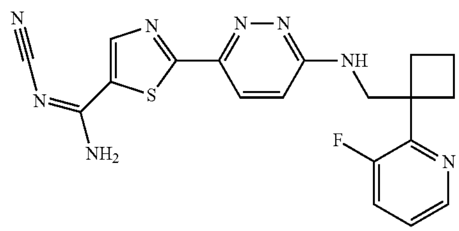 [SMILES: N#C/N=C(/N)c1cnc(-c2ccc(NCC3(c4ncccc4F)CCC3)nn2)s1] | 409.1 | B |
| N-({2-[6-({[(3-fluoro-2-pyridyl)cyclobutyl]methyl}amino)pyridazin-3-yl]-1,3-thiazol-5-yl}methyl)acetamide | 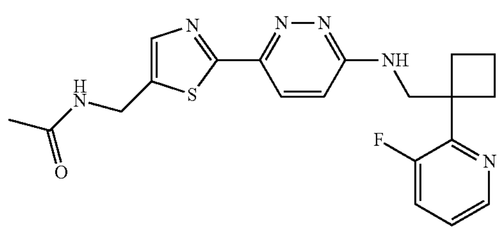 [SMILES: CC(=O)NCc1cnc(-c2ccc(NCC3(c4ncccc4F)CCC3)nn2)s1] | 413.3 | A |
| ({2-[6-({[(3-fluoro(2-pyridyl))cyclobutyl]methyl}amino)pyridazin-3-yl](1,3-thiazol-5-yl)}methyl)(methylsulfonyl)amine | 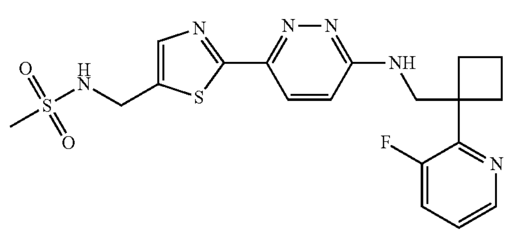 [SMILES: CS(=O)(=O)NCc1cnc(-c2ccc(NCC3(c4ncccc4F)CCC3)nn2)s1] | 449.2 | B |
| N-({2-[6-({[(3-fluoro(2-pyridyl))cyclobutyl]methyl}amino)pyridazin-3-yl](1,3-thiazol-5-yl)}methyl)methoxycarboxamide | 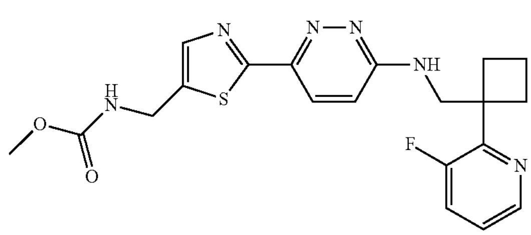 [SMILES: COC(=O)NCc1cnc(-c2ccc(NCC3(c4ncccc4F)CCC3)nn2)s1] | 429.2 | B |

TABLE 2-continued

| Compound | Structure | m/z (M + H) | Mean AC1.4 |
|---|---|---|---|
| 2,2-difluoro-1-{2-[6-({[(3-fluoro(2-pyridyl))cyclobutyl]methyl}amino)pyridazin-3-yl](1,3-thiazol-5-yl)}ethan-1-ol | 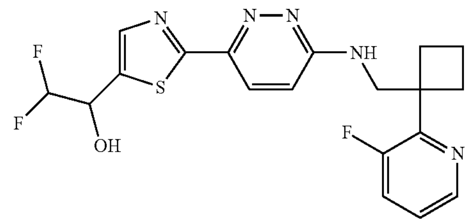 [SMILES: OC(c1cnc(-c2ccc(NCC3(c4ncccc4F)CCC3)nn2)s1)C(F)F] | 422.2 | B |
| N-(carbamoylmethyl)[6-({[(3-fluoro(2-pyridyl))cyclobutyl]methyl}amino)pyridazin-3-yl]carboxamide | 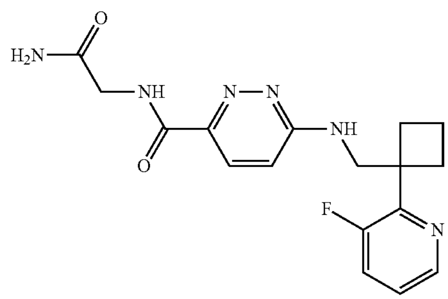 [SMILES: NC(=O)CNC(=O)c1ccc(NCC2(c3ncccc3F)CCC2)nn1] | 359.1 441.3 | D |
| 2-[6-({[(3-fluoro(2-pyridyl))cyclobutyl]methyl}amino)pyridazin-3-yl](1,3-thiazol-5-yl) morpholin-4-yl ketone | 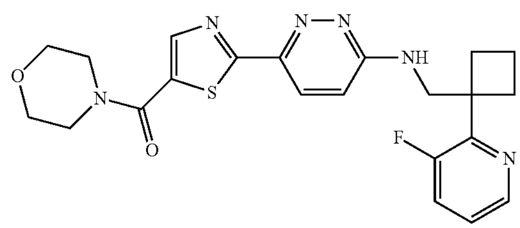 [SMILES: O=C(c1cnc(-c2ccc(NCC3(c4ncccc4F)CCC3)nn2)s1)N1CCOCC1] | 455.3 | C |
| N-(2-aminoethyl){2-[6-({[(3-fluoro(2-pyridyl))cyclobutyl]methyl}amino)pyridazin-3-yl](1,3-thiazol-5-yl)}carboxamide | 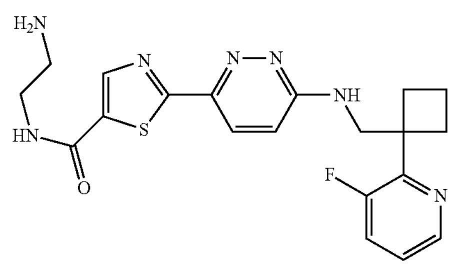 [SMILES: NCCNC(=O)c1cnc(-c2ccc(NCC3(c4ncccc4F)CCC3)nn2)s1] | 428.4 | A |
| N-(2,3-dihydroxypropyl){2-[6-({[(3-fluoro(2-pyridyl))cyclobutyl]methyl}amino)pyridazin-3-yl](1,3-thiazol-5-yl)}carboxamide | 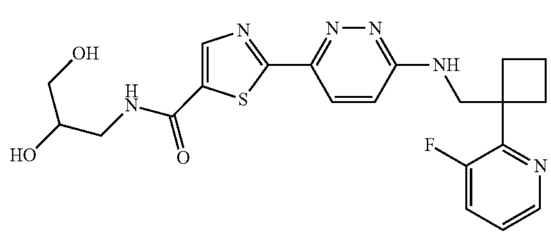 [SMILES: O=C(NCC(O)CO)c1cnc(-c2ccc(NCC3(c4ncccc4F)CCC3)nn2)s1] | 459.3 | A |
| {2-[6-({[(3-fluoro(2-pyridyl))cyclobutyl]methyl}amino)pyridazin-3-yl](1,3-thiazol-5-yl)}-N-pyrrolidin-3-ylcarboxamide | 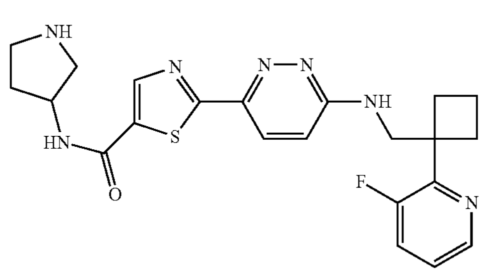 [SMILES: O=C(NC1CCNC1)c1cnc(-c2ccc(NCC3(c4ncccc4F)CCC3)nn2)s1] | 454.3 | A |

TABLE 2-continued

| Compound | Structure | m/z (M + H) | Mean AC1.4 |
|---|---|---|---|
| 2-{2-[6-({[(3-fluoro-2-pyridyl)cyclobutyl]methyl}amino)pyridazin-3-yl]-1,3-thiazol-5-yl}acetamide | 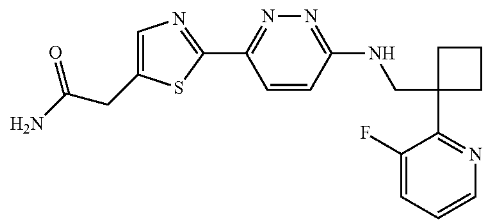 [SMILES: NC(=O)Cc1cnc(-c2ccc(NCC3(c4ncccc4F)CCC3)nn2)s1] | 399.3 | B |
| {[(3-fluoro(2-pyridyl))cyclobutyl]methyl}[6-(5-pyrazol-4-yl(1,3-thiazol-2-yl))pyridazin-3-yl]amine | 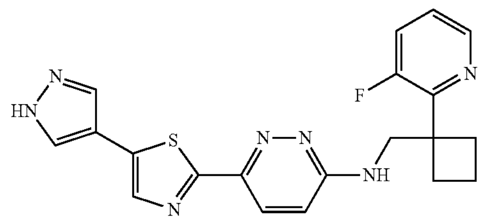 [SMILES: Fc1cccnc1C1(CNc2ccc(-c3ncc(-c4cn[nH]c4)s3)nn2)CCC1] | 408.3 | A |
| {[(3-fluoro(2-pyridyl))cyclobutyl]methyl}[6-(5-pyrazol-3-yl(1,3-thiazol-2-yl))pyridazin-3-yl]amine | 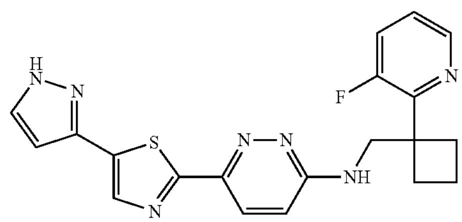 [SMILES: Fc1cccnc1C1(CNc2ccc(-c3ncc(-c4cc[nH]n4)s3)nn2)CCC1] | 408.3 | A |
| 4-[6-({[(3-fluoro-2-pyridyl)cyclobutyl]methyl}amino)pyridazin-3-yl]pyrimidine-2-carboxamide | 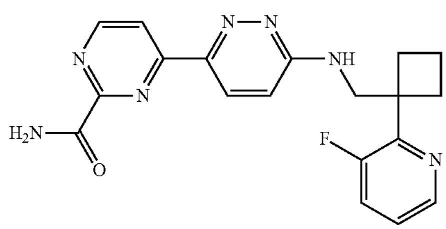 | 380.3 | D |
| 6-[6-({[(3-fluoro-2-pyridyl)cyclobutyl]methyl}amino)pyridazin-3-yl]pyrimidine-4-carboxamide | 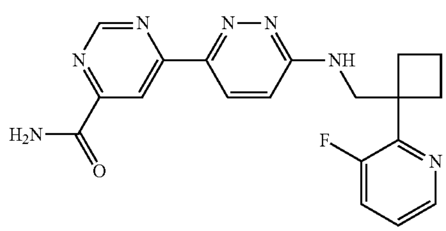 [SMILES: NC(=O)c1cc(-c2ccc(NCC3(c4ncccc4F)CCC3)nn2)ncn1] | 380.3 | B |
| [6-({[(3-fluoro(2-pyridyl))cyclobutyl]methyl}amino)pyridazin-3-yl]-N-pyrazol-5-ylcarboxamide | 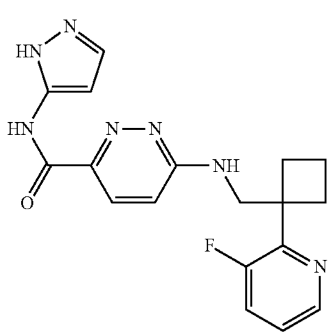 [SMILES: O=C(Nc1ccn[nH]1)c1ccc(NCC2(c3ncccc3F)CCC2)nn1] | 368.1 | B |

TABLE 2-continued

| Compound | Structure | m/z (M + H) | Mean AC1.4 |
|---|---|---|---|
| N-(carbamoylmethyl){2-[6-({[(3-fluoro(2-pyridyl))cyclobutyl]methyl}amino)pyridazin-3-yl](1,3-thiazol-5-yl)}carboxamide | 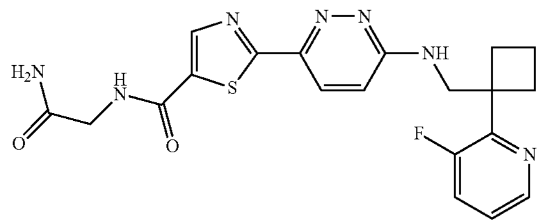 [SMILES: NC(=O)CNC(=O)c1cnc(-c2ccc(NCC3(c4ncccc4F)CCC3)nn2)s1] | 442.3 | A |
| 4-({2-[6-({[(3-fluoro-2-pyridyl)cyclobutyl]methyl}amino)pyridazin-3-yl]-1,3-thiazol-5-yl}carbonyl)piperazine-2-carboxamide | 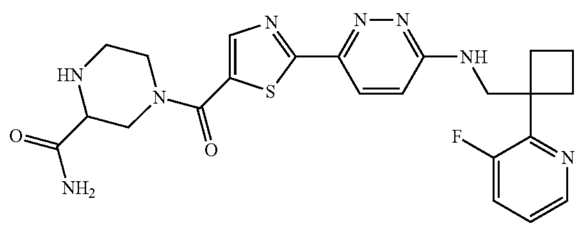 [SMILES: NC(=O)C1CN(C(=O)c2cnc(-c3ccc(NCC4(c5ncccc5F)CCC4)nn3)s2)CCN1] | 497.3 | B |
| [6-(5-chloro(1,3-thiazolino[5,4-b]pyridin-2-yl))pyridazin-3-yl]{[(3-fluoro(2-pyridyl))cyclobutyl]methyl}amine | 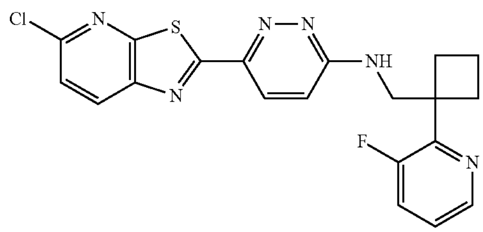 [SMILES: Fc1cccnc1C1(CNc2ccc(-c3nc4ccc(Cl)nc4s3)nn2)CCC1] | 427.1 | C |
| {[(3-fluoro(2-pyridyl))cyclobutyl]methyl}(6-(1,3-thiazolino[5,4-b]pyridin-2-yl)pyridazin-3-yl)amine | 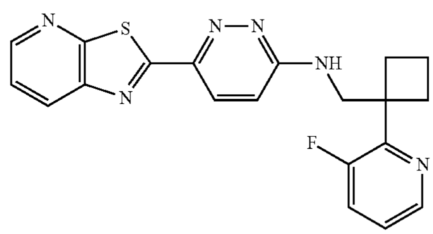 [SMILES: Fc1cccnc1C1(CNc2ccc(-c3nc4cccnc4s3)nn2)CCC1] | 393.1 | B |
| [6-(5-amino(1,3-thiazolino[5,4-b]pyridin-2-yl))pyridazin-3-yl]{[(3-fluoro(2-pyridyl))cyclobutyl]methyl}amine | 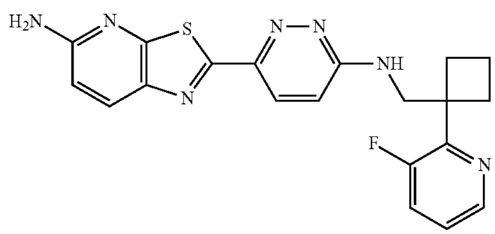 [SMILES: Nc1ccc2nc(-c3ccc(NCC4(c5ncccc5F)CCC4)nn3)sc2n1] | 408.1 | B |
| amino{4-fluoro-3-[6-({[(3-fluoro(2-pyridyl))cyclobutyl]methyl}amino)pyridazin-3-yl]phenyl}sulfonamide | 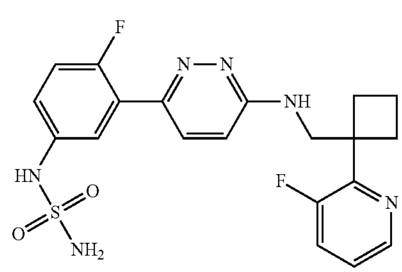 [SMILES: NS(=O)(=O)Nc1ccc(F)c(-c2ccc(NCC3(c4ncccc4F)CCC3)nn2)c1] | 447.2 | A |

TABLE 2-continued

| Compound | Structure | m/z (M + H) | Mean AC1.4 |
|---|---|---|---|
| 2-[6-({[(3-fluoro(2-pyridyl))cyclobutyl]methyl}amino)pyridazin-3-yl](1,3-thiazol-5-yl)3-hydroxypyrrolidinyl ketone | 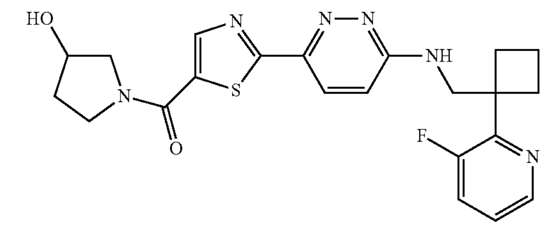 [SMILES: O=C(c1cnc(-c2ccc(NCC3(c4ncccc4F)CCC3)nn2)s1)N1CCC(O)C1] | 455.3 | C |
| 4-({2-[6-({[(3-fluoro2-pyridyl)cyclobutyl]methyl}amino)pyridazin-3-yl]-1,3-thiazol-5-yl}carbonyl)-1,4-thiazaperhydroine-1,1-dione | 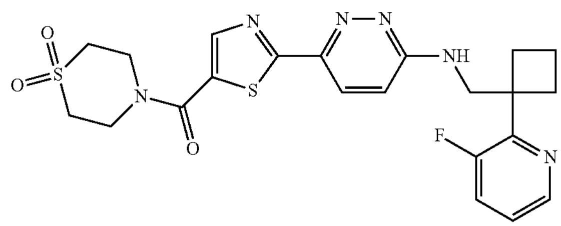 [SMILES: O=C(c1cnc(-c2ccc(NCC3(c4ncccc4F)CCC3)nn2)s1)N1CCS(=O)(=O)CC1] | 503.3 | B |
| N-(1,1-dioxothiolan-3-yl){2-[6-({[(3-fluoro(2-pyridyl))cyclobutyl]methyl}amino)pyridazin-3-yl](1,3-thiazol-5-yl)}carboxamide | 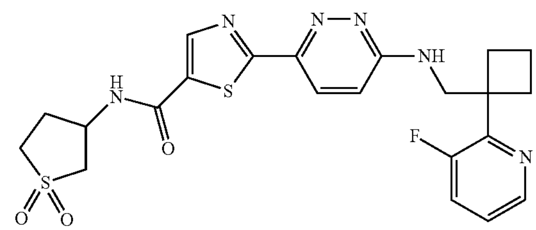 [SMILES: O=C(NC1CCS(=O)(=O)C1)c1cnc(-c2ccc(NCC3(c4ncccc4F)CCC3)nn2)s1] | 503.3 | A |
| {2-[6-({[(3-fluoro(2-pyridyl))cyclobutyl]methyl}amino)pyridazin-3-yl](1,3-thiazol-5-yl)}-N-[2-(methylsulfonyl)ethyl]carboxamide | 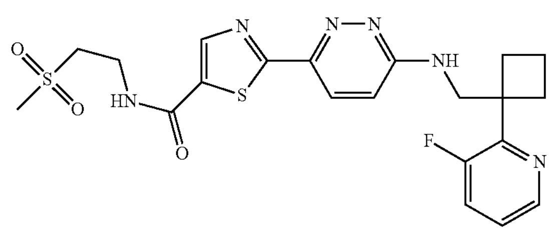 [SMILES: CS(=O)(=O)CCNC(=O)c1cnc(-c2ccc(NCC3(c4ncccc4F)CCC3)nn2)s1] | 491.2 | A |
| 2-[6-({[(3-fluoro(2-pyridyl))cyclobutyl]methyl}amino)pyridazin-3-yl](1,3-thiazol-5-yl) 3-hydroxypiperidyl ketone | 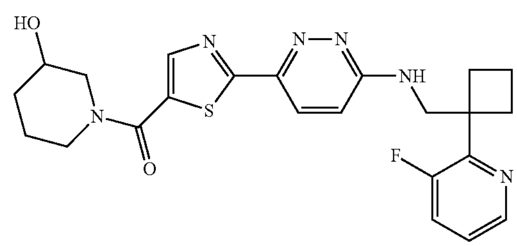 [SMILES: O=C(c1cnc(-c2ccc(NCC3(c4ncccc4F)CCC3)nn2)s1)N1CCCC(O)C1] | 469.3 | C |
| {[(3-fluoro(2-pyridyl))cyclobutyl]methyl}(6-pyrazolo[5,4-d]1,3-thiazol-5-ylpyridazin-3-yl)amine | 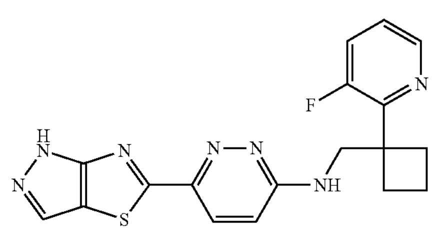 [SMILES: Fc1cccnc1C1(CNc2ccc(-c3nc4[nH]ncc4s3)nn2)CCC1] | 382.1 | A |

TABLE 2-continued

| Compound | Structure | m/z (M + H) | Mean AC1.4 |
|---|---|---|---|
| 2-[6-({[(3-fluoro(2-pyridyl))cyclobutyl]methyl}amino)pyridazin-3-yl](1,3-thiazol-5-yl) 4-hydroxypiperidyl ketone | 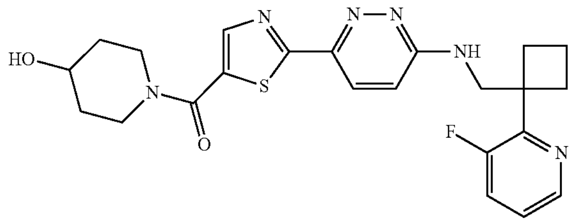 [SMILES: O=C(c1cnc(-c2ccc(NCC3(c4ncccc4F)CCC3)nn2)s1)N1CCC(O)CC1] | 469.3 | C |
| 4-({2-[6-({[(3-fluoro-2-pyridyl)cyclobutyl]methyl}amino)pyridazin-3-yl]-1,3-thiazol-5-yl}carbonyl)piperazin-2-one | 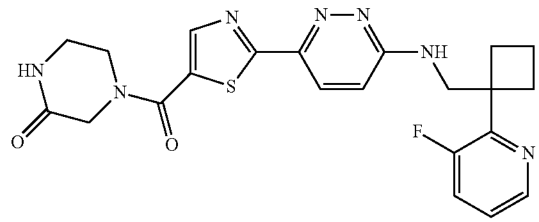 [SMILES: O=C1CN(C(=O)c2cnc(-c3ccc(NCC4(c5ncccc5F)CCC4)nn3)s2)CCN1] | 468.3 | C |
| {2-[6-({[(3-fluoro(2-pyridyl))cyclobutyl]methyl}amino)pyridazin-3-yl](1,3-thiazol-5-yl)}-N-(oxolan-2-ylmethyl)carboxamide | 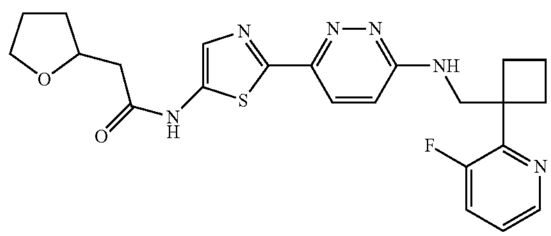 [SMILES: O=C(CC1CCCO1)Nc1cnc(-c2ccc(NCC3(c4ncccc4F)CCC3)nn2)s1] | 469.3 | B |
| 1-({2-[6-({[(3-fluoro-2-pyridyl)cyclobutyl]methyl}amino)pyridazin-3-yl]-1,3-thiazol-5-yl}carbonyl)piperidine-3-carboxamide | 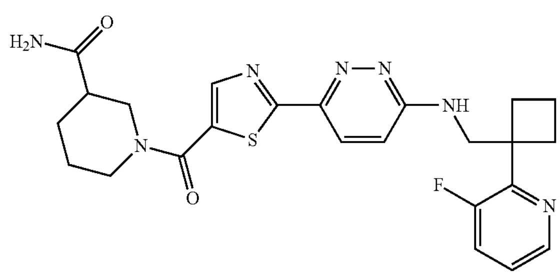 [SMILES: NC(=O)C1CCCN(C(=O)c2cnc(-c3ccc(NCC4(c5ncccc5F)CCC4)nn3)s2)C1] | 496.3 | C |
| [6-(3-(2H-1,2,3,4-tetraazol-5-yl)phenyl)pyridazin-3-yl][2-(3-fluoro(2-pyridyl))-2-methylpropyl]amine | 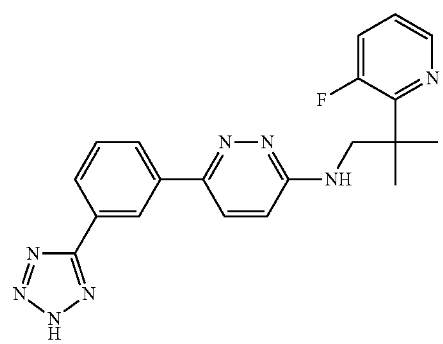 [SMILES: CC(C)(CNc1ccc(-c2cccc(-c3nn[nH]n3)c2)nn1)c1ncccc1F] | 391.3 | B |
| 2-[6-({[(3-fluoro-2-pyridyl)cyclobutyl]methyl}amino)pyridazin-3-yl]-1,3-thiazolino[5,4-b]pyridine-5-carboxamide | 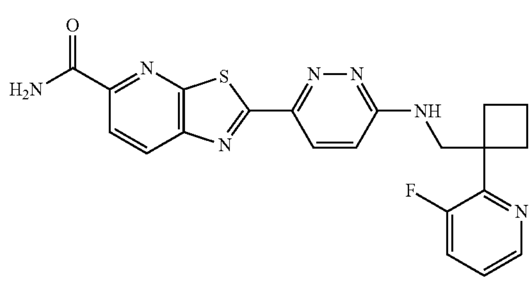 [SMILES: NC(=O)c1ccc2nc(-c3ccc(NCC4(c5ncccc5F)CCC4)nn3)sc2n1] | 436.1 | D |

TABLE 2-continued

| Compound | Structure | m/z (M + H) | Mean AC1.4 |
|---|---|---|---|
| {[(3-fluoro(2-pyridyl))cyclobutyl]methyl}[6-(5-methoxy(1,3-thiazolino[5,4-b]pyridin-2-yl))pyridazin-3-yl]amine | 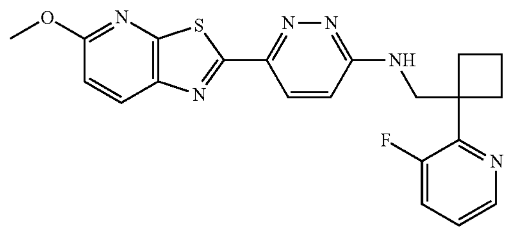 [SMILES: COc1ccc2nc(-c3ccc(NCC4(c5ncccc5F)CCC4)nn3)sc2n1] | 423.1 | D |
| 2-[6-({[(3-fluoro-2-pyridyl)cyclobutyl]methyl}amino)pyridazin-3-yl]-1,3-thiazolino[5,4-b]pyridin-5-ol | | 409.1 | B |
| N-((2R)-2,3-dihydroxypropyl){2-[6-({[(3-fluoro(2-pyridyl))cyclobutyl]methyl}amino)pyridazin-3-yl](1,3-thiazol-5-yl)}carboxamide | 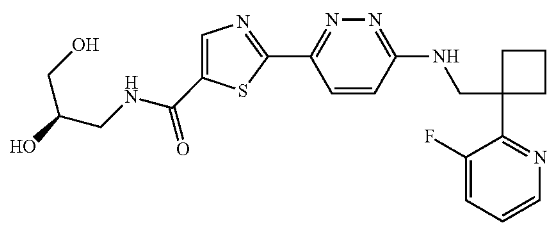 [SMILES: O=C(NC[C@@H](O)CO)c1cnc(-c2ccc(NCC3(c4ncccc4F)CCC3)nn2)s1] | 459.3 | B |
| N-((2S)-2,3-dihydroxypropyl){2-[6-({[(3-fluoro(2-pyridyl))cyclobutyl]methyl}amino)pyridazin-3-yl](1,3-thiazol-5-yl)}carboxamide | 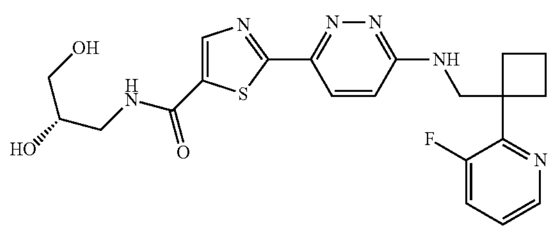 [SMILES: O=C(NC[C@H](O)CO)c1cnc(-c2ccc(NCC3(c4ncccc4F)CCC3)nn2)s1] | 459.3 | A |
| N-(2-amino-3,3,3-trifluoropropyl){2-[6-({[(3-fluoro(2-pyridyl))cyclobutyl]methyl}amino)pyridazin-3-yl](1,3-thiazol-5-yl)}carboxamide | | 496.3 | B |
| N-(3-amino-2,2-difluoropropyl){2-[6-({[(3-fluoro(2-pyridyl))cyclobutyl]methyl}amino)pyridazin-3-yl](1,3-thiazol-5-yl)}carboxamide | 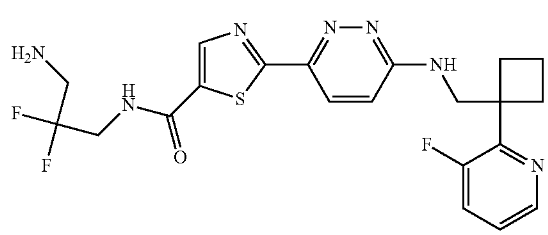 [SMILES: NCC(F)(F)CNC(=O)c1cnc(-c2ccc(NCC3(c4ncccc4F)CCC3)nn2)s1] | 478.3 | A |

//

TABLE 2-continued

| Compound | Structure | m/z (M + H) | Mean AC1.4 |
|---|---|---|---|
| {2-[6-({[(3-fluoro(2-pyridyl))cyclobutyl]methyl}amino)pyridazin-3-yl](1,3-thiazol-5-yl)}-NfN-dimethylcarboxamide | 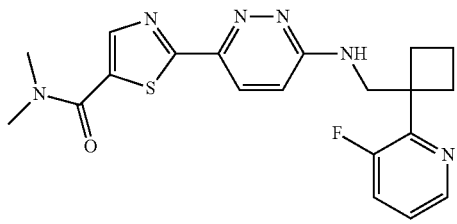 [SMILES: CN(C)C(=O)c1cnc(-c2ccc(NCC3(c4ncccc4F)CCC3)nn2)s1] | 414.3 | C |
| N-(2.2-difluoro-3-hydroxypropyl){2-[6-({[(3-fluoro(2-pyridyl))cyclobutyl]methyl}amino)pyridazin-3-yl](1,3-thiazol-5-yl)}carboxamide | 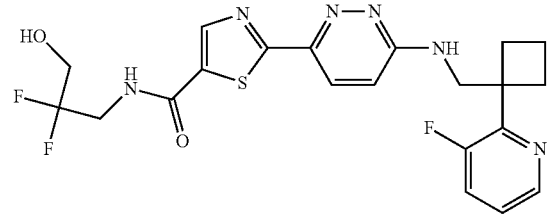 [SMILES: O=C(NCC(F)(F)CO)c1cnc(-c2ccc(NCC3(c4ncccc4F)CCC3)nn2)s1] | 479.3 | A |
| {2-[6-({[(3-fluoro(2-pyridyl))cyclobutyl]methyl}amino)pyridazin-3-yl](1,3-thiazol-5-yl)}-N-(2-oxopyrrolidin-3-yl)carboxamide | 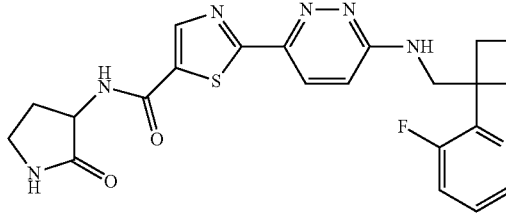 | 468.3 | B |
| 3-[6-({[3-fluoro-1-(3-fluoro(2-pyridyl))cyclobutyl]methyl}amino)pyridazin-3-yl]benzamide | 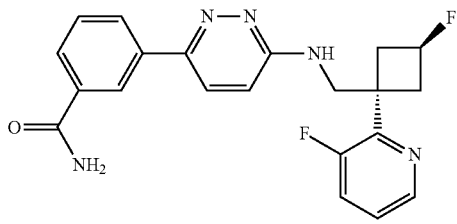 [SMILES: NC(=O)c1cccc(-c2ccc(NC[C@]3(c4ncccc4F)C[C@H](F)C3)nn2)c1] | 396.3 | A |
| 4-fluoro-3-[6-({[3-fluoro-1-(3-fluoro(2-pyridyl))cyclobutyl]methyl}amino)pyridazin-3-yl]benzamide | 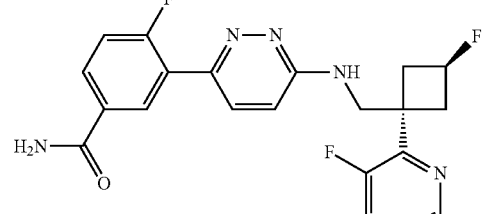 | 414.3 | A |
| 2-amino-N-({2-[6-({[(3-fluoro(2-pyridyl))cyclobutyl]methyl}amino)pyridazin-3-yl](1,3-thiazol-5-yl)}tnethyl)acetamide | 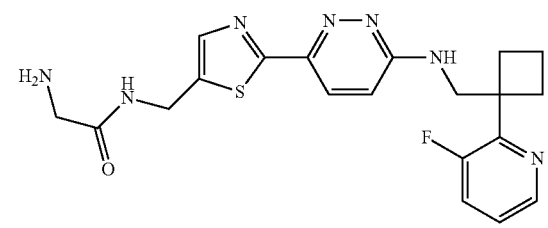 [SMILES: NCC(=O)NCc1cnc(-c2ccc(NCC3(c4ncccc4F)CCC3)nn2)s1] | 428.1 | A |

TABLE 2-continued

| Compound | Structure | m/z (M + H) | Mean AC1.4 |
|---|---|---|---|
| ((2S)pyrrolidin-2-yl)-N-({2-[6-({[(3-fluoro(2-pyridyl))cyclobutyl]methyl}amino)pyridazin-3-yl](1,3-thiazol-5-yl)}methyl)carboxamide | 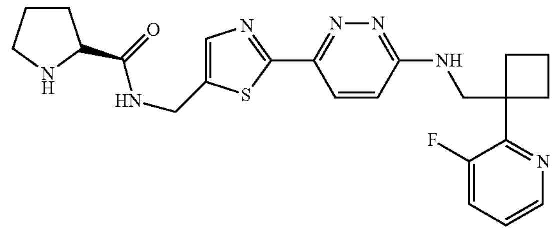 | | A |
| ((2R)pyrrolidin-2-yl)-N-({2-[6-({[(3-fluoro(2-pyridyl))cyclobutyl]methyl}amino)pyridazin-3-yl](1,3-thiazol-5-yl)}methyl)carboxamide | 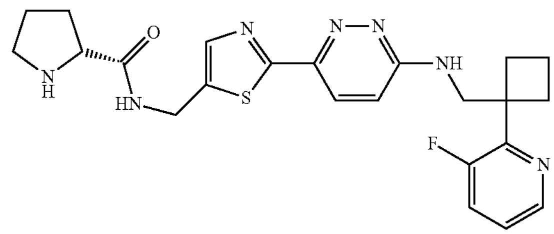 | 468.2 | A |
| {[(3-fluoro(2-pyridyl))cyclobutyl]methyl}(6-(3-pyrrolino[3,4-d]1,3-thiazol-2-yl)pyridazin-3-yl)amine | 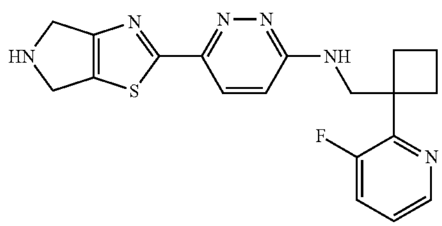 [SMILES: Fc1cccnc1C1(CNc2ccc(-c3nc4c(s3)CNC4)nn2)CCC1] | 383.1 | D |
| 2-[6-({[(3-fluoro(2-pyridyl))cyclobutyl]methyl}amino)pyridazin-3-yl]-5-(methylsulfonyl)-3-pyrrolino[3,4-d]1,3-thiazole | 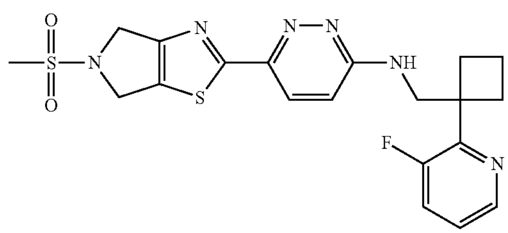 [SMILES: CS(=O)(=O)N1Cc2nc(-c3ccc(NCC4(c5ncccc5F)CCC4)nn3)sc2C1] | 461.1 | D |
| N-({2-[6-({[(3-fluoro(2-pyridyl))cyclobutyl]methyl}amino)pyridazin-3-yl](1,3-thiazol-5-yl)}methyl)-2-hydroxyacetamide | 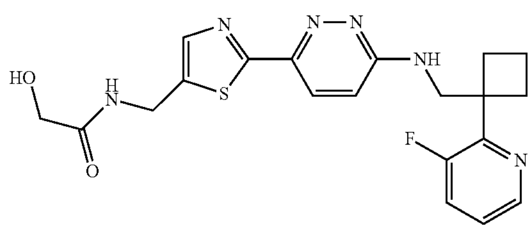 [SMILES: O=C(CO)NCc1cnc(-c2ccc(NCC3(c4ncccc4F)CCC3)nn2)s1] | 429.1 | A |
| 2-[({2-[6-({[(3-fluoro-2-pyridyl)cyclobutyl]methyl}amino)pyridazin-3-yl]-1,3-thiazol-5-yl}methyl)amino]acetamide | 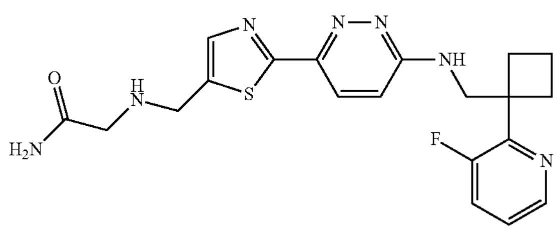 [SMILES: NC(=O)CNCc1cnc(-c2ccc(NCC3(c4ncccc4F)CCC3)nn2)s1] | 428.1 | B |

TABLE 2-continued

| Compound | Structure | m/z (M + H) | Mean AC1.4 |
|---|---|---|---|
| ((2S)-5-oxopyrrolidin-2-yl)-N-({2-[6-({[(3-fluoro(2-pyridyl))cyclobutyl]methyl}amino)pyridazin-3-yl](1,3-thiazol-5-yl)}methyl)carboxamide | 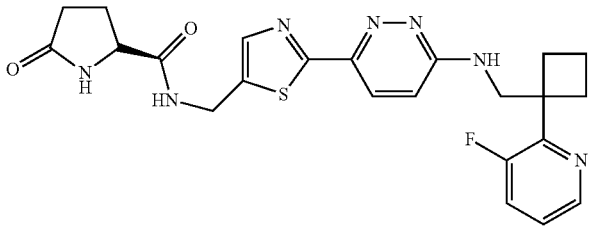 | 482.1 | A |
| N-({2-[6-({[(3-fluoro(2-pyridyl))cyclobutyl]methyl}amino)pyridazin-3-yl](1,3-thiazol-5-yl)}methyl)-2-hydroxy-2-methylpropanamide | 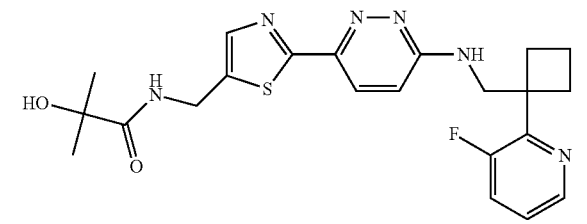 [SMILES: CC(C)(O)C(=O)NCc1cnc(-c2ccc(NCC3(c4ncccc4F)CCC3)nn2)s1] | 457.1 | A |
| N-((3S)pyrrolidin-3-yl){2-[6-({[(3-fluoro(2-pyridyl))cyclobutyl]methyl}amino)pyridazin-3-yl](1,3-thiazol-5-yl)}carboxamide | 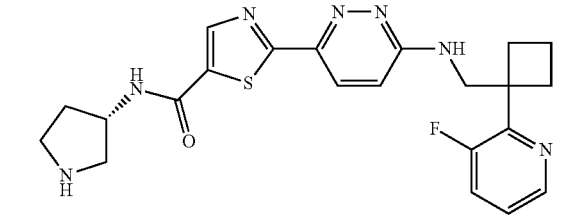 [SMILES: O=C(N[C@H]1CCNC1)c1cnc(-c2ccc(NCC3(c4ncccc4F)CCC3)nn2)s1] | 454.3 | A |
| N-((3R)pyrrolidin-3-yl){2-[6-({[(3-fluoro(2-pyridyl))cyclobutyl]methyl}amino)pyridazin-3-yl](1,3-thiazol-5-yl)}carboxamide | 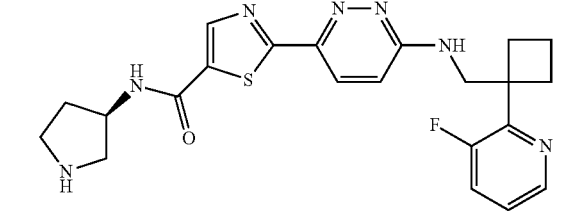 [SMILES: O=C(N[C@@H]1CCNC1)c1cnc(-c2ccc(NCC3(c4ncccc4F)CCC3)nn2)s1] | 454.3 | A |
| 2-[2-[6-{[1-(3-fluoro(2-pyridyl))-isopropyl]amino}pyridazin-3-yl)-1,3-thiazol-5-yl]acetamide | 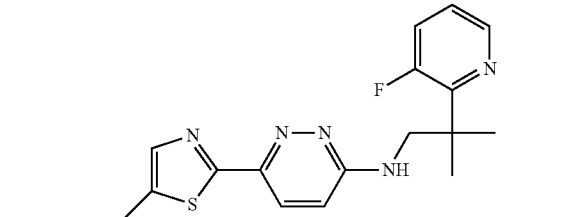 | 373.2 | D |
| ((3S)morpholin-3-yl)-N-({2-[6-({[(3-fluoro(2-pyridyl))cyclobutyl]methyl}amino)pyridazin-3-yl](1,3-thiazol-5-yl)}methyl)carboxamide | 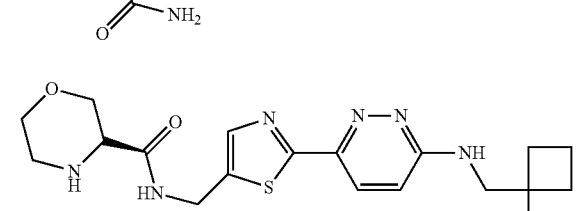 | 484.3 | A |

TABLE 2-continued

| Compound | Structure | m/z (M + H) | Mean AC1.4 |
|---|---|---|---|
| N-({2-[6-({[(3-fluoro(2-pyridyl))cyclobutyl]methyl}amino)pyridazin-3-yl](1,3-thiazol-5-yl)}methyl)pyrazol-5-ylcarboxamide | 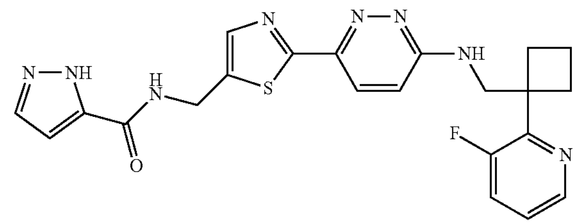 [SMILES: O=C(NCc1cnc(-c2ccc(NCC3(c4ncccc4F)CCC3)nn2)s1)c1ccn[nH]1] | 465.3 | A |
| N-({2-[6-({[(3-fluoro(2-pyridyl))cyclobutyl]methyl}amino)pyridazin-3-yl](1,3-thiazol-5-yl)}methyl)imidazol-2-ylcarboxamide | 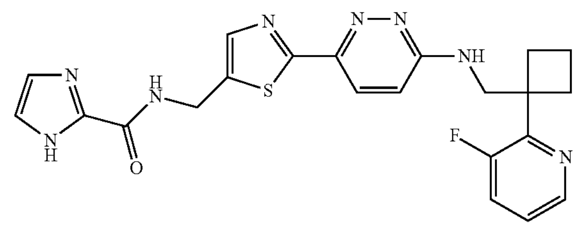 [SMILES: O=C(NCc1cnc(-c2ccc(NCC3(c4ncccc4F)CCC3)nn2)s1)c1ncc[nH]1] | 465.3 | A |
| N-({2-[6-({[(3-fluoro(2-pyridyl))cyclobutyl]methyl}amino)pyridazin-3-yl](1,3-thiazol-5-yl)}methyl)pyrazol-4-ylcarboxamide | 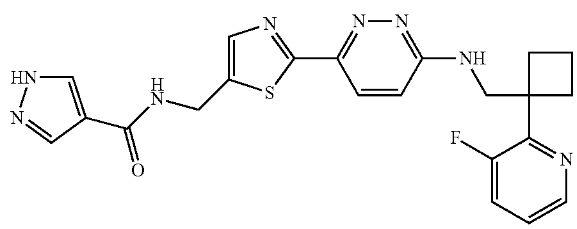 [SMILES: O=C(NCc1cnc(-c2ccc(NCC3(c4ncccc4F)CCC3)nn2)s1)c1cn[nH]c1] | 465.3 | A |
| ((4S)-2-oxoimidazolidin-4-yl)-N-({2-[6-({[(3-fluoro(2-pyridyl))cyclobutyl]methyl}amino)pyridazin-3-yl](1,3-thiazol-5-yl)}methyl)carboxamide | 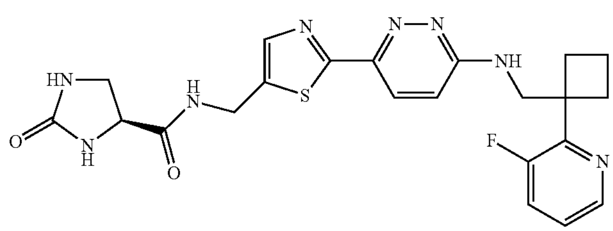 [SMILES: O=C1NC[C@@H](C(=O)NCc2cnc(-c3ccc(NCC4(c5ncccc5F)CCC4)nn3)s2)N1] | 483.3 | A |
| ((3S)-6-oxo(3-piperidyl))-N-({2-[6-({[(3-fluoro(2-pyridyl))cyclobutyl]methyl}amino)pyridazin-3-yl](1,3-thiazol-5-yl)}methyl)carboxamide | 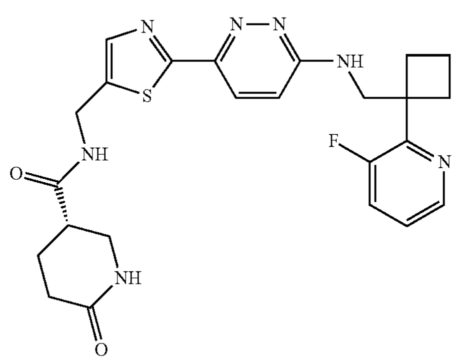 [SMILES: O=C1CC[C@H](C(=O)NCc2cnc(-c3ccc(NCC4(c5ncccc5F)CCC4)nn3)s2)CN1] | 496.3 | A |
| 2H-1,2,3-triazol-4-yl-N-({2-[6-({[(3-fluoro(2-pyridyl))cyclobutyl]methyl}amino)pyridazin-3-yl](1,3-thiazol-5-yl)}methyl)carboxamide | 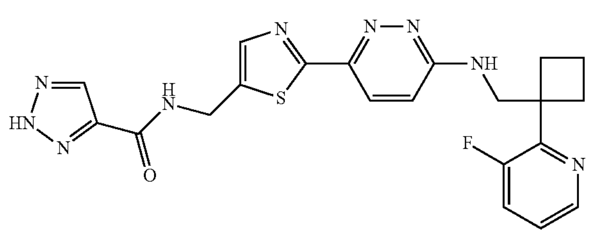 [SMILES: O=C(NCc1cnc(-c2ccc(NCC3(c4ncccc4F)CCC3)nn2)s1)c1cn[nH]n1] | 466.3 | A |

TABLE 2-continued

| Compound | Structure | m/z (M + H) | Mean AC1.4 |
|---|---|---|---|
| (2S)-2-amino-N-({2-[6-({[(3-fluoro(2-pyridyl))cyclobutyl]methyl}amino)pyridazin-3-yl](1,3-thiazol-5-yl)}methyl)-3-hydroxypropanamide | 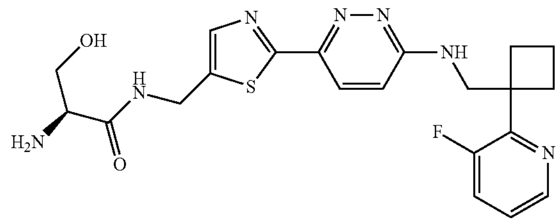 | 458.3 | A |
| (2R)-2-amino-N-({2-[6-({[(3-fluoro(2-pyridyl))cyclobutyl]methyl}amino)pyridazin-3-yl](1,3-thiazol-5-yl)}methyl)-3-hydroxypropanamide | 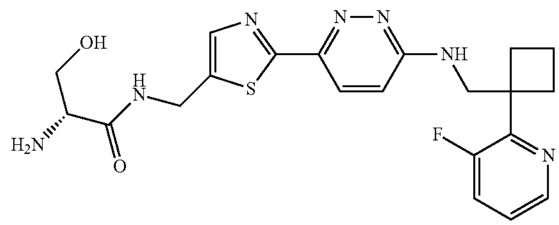 [SMILES: N[C@H](CO)C(=O)NCc1cnc(-c2ccc(NCC3(c4ncccc4F)CCC3)nn2)s1] | 458.3 | A |
| ((2S)-4-acetylpiperazin-2-yl)-N-({2-[6-({[(3-fluoro(2-pyridyl))cyclobutyl]methyl}amino)pyridazin-3-yl](1,3-thiazol-5-yl)}methyl)carboxamide | 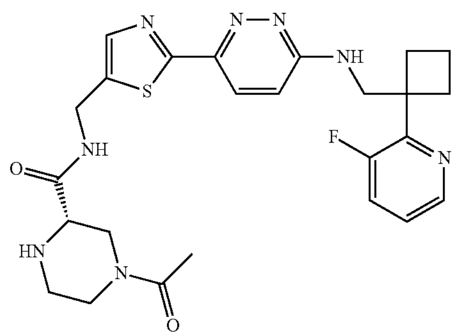 [SMILES: CC(=O)N1CCN[C@H](C(=O)NCc2cnc(-c3ccc(NCC4(c5ncccc5F)CCC4)nn3)s2)C1] | 525.3 | A |
| [(2S)-4-(methylsulfonyl)piperazin-2-yl]-N-({2-[6-({[(3-fluoro(2-pyridyl))cyclobutyl]methyl}amino)pyridazin-3-yl](1,3-thiazol-5-yl)}methyl)carboxamide | 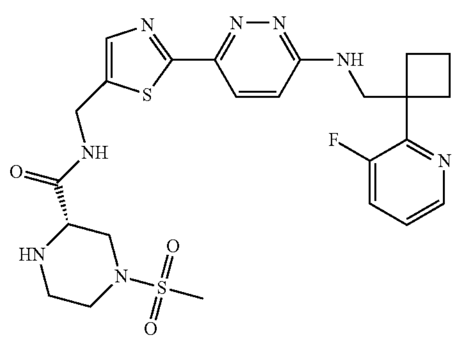 [SMILES: CS(=O)(=O)N1CCN[C@H](C(=O)NCc2cnc(-c3ccc(NCC4(c5ncccc5F)CCC4)nn3)s2)C1] | 562.3 | A |
| ((3S)morpholin-3-yl)-N-({2-[6-({[(3-fluoro(2-pyridyl))cyclobutyl]methyl}amino)pyridazin-3-yl](1,3-thiazol-5-yl)}methyl)carboxamide | 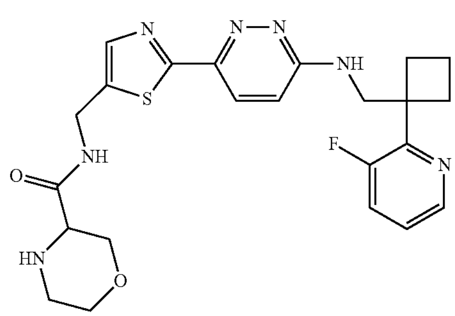 [SMILES: O=C(NCc1cnc(-c2ccc(NCC3(c4ncccc4F)CCC3)nn2)s1)C1COCCN1] | 484.2 | A |

TABLE 2-continued

| Compound | Structure | m/z (M + H) | Mean AC1.4 |
|---|---|---|---|
| 1H-1,2,4-triazol-5-yl-N-({2-[6-({[(3-fluoro(2-pyridyl))cyclobutyl]methyl}amino)pyridazin-3-yl](1,3-thiazol-5-yl)}methyl)carboxamide | 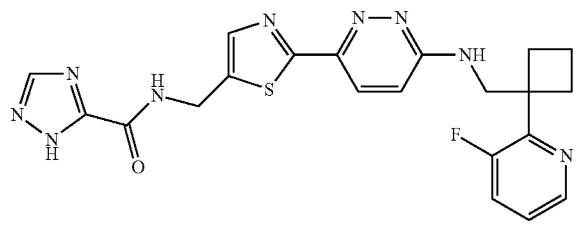 [SMILES: O=C(NCc1cnc(-c2ccc(NCC3(c4ncccc4F)CCC3)nn2)s1)c1ncn[nH]1] | 466.2 | A |
| ((2R)-6-oxo(2-piperidyl))-N-({2-[6-({[(3-fluoro(2-pyridyl))cyclobutyl]methyl}amino)pyridazin-3-yl](1,3-thiazol-5-yl)}methyl)carboxamide | 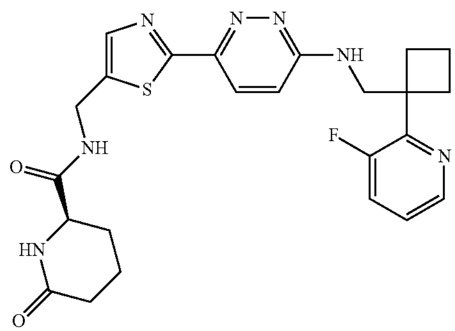 [SMILES: O=C1CCC[C@H](C(=O)NCc2cnc(-c3ccc(NCC4(c5ncccc5F)CCC4)nn3)s2)N1] | 495.2 | A |
| N-({2-[6-({[(3-fluoro(2-pyridyl))cyclobutyl]methyl}amino)pyridazin-3-yl](1,3-thiazol-5-yl)}methyl)imidazol-5-ylcarboxamide | 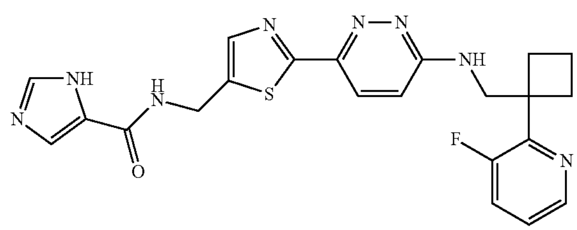 [SMILES: O=C(NCc1cnc(-c2ccc(NCC3(c4ncccc4F)CCC3)nn2)s1)c1cnc[nH]1] | 465.2 | A |
| 2-amino-N-({2-[6-({[(3-fluoro(2-pyridyl))cyclobutyl]methyl}amino)pyridazin-3-yl](1,3-thiazol-5-yl)}methyl)-2-methylpropanamide | 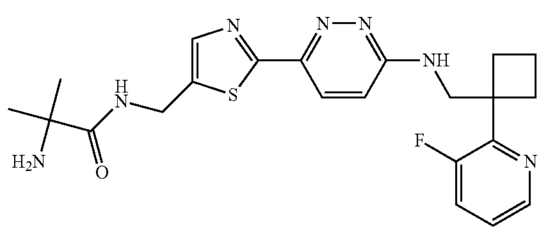 [SMILES: CC(C)(N)C(=O)NCc1cnc(-c2ccc(NCC3(c4ncccc4F)CCC3)nn2)s1] | 456.2 | A |
| (2S)-2-amino-N-({2-[6-({[(3-fluoro(2-pyridyl))cyclobutyl]methyl}amino)pyridazin-3-yl](1,3-thiazol-5-yl)}methyl)propanamide | 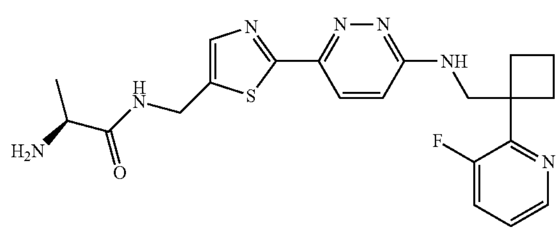 [SMILES: C[C@H](N)C(=O)NCc1cnc(-c2ccc(NCC3(c4ncccc4F)CCC3)nn2)s1] | 442.2 | A |
| N-({2-[6-({[(3-fluoro(2-pyridyl))cyclobutyl]methyl}amino)pyridazin-3-yl](1,3-thiazol-5-yl)}methyl)(2-hydroxyimidazol-5-yl)carboxamide | 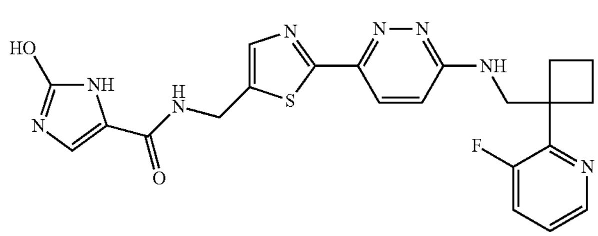 [SMILES: O=C(NCc1cnc(-c2ccc(NCC3(c4ncccc4F)CCC3)nn2)s1)c1cnc(O)[nH]1] | 481.2 | A |

TABLE 2-continued

| Compound | Structure | m/z (M + H) | Mean AC1.4 |
|---|---|---|---|
| (2S)-2-amino-N-({2-[6-({[(3-fluoro(2-pyridyl))cyclobutyl]methyl}amino)pyridazin-3-yl](1,3-thiazol-5-yl)}methyl)-3-hydroxy-3-methylbutanamide | 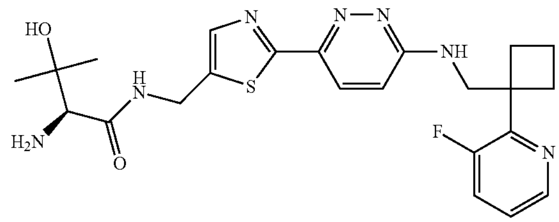 [SMILES: CC(C)(O)[C@H](N)C(=O)NCc1cnc(-c2ccc(NCC3(c4ncccc4F)CCC3)nn2)s1] | 486.3 | A |
| (2R)-2-amino-N-({2-[6-({[(3-fluoro(2-pyridyl))cyclobutyl]methyl}amino)pyridazin-3-yl](1,3-thiazol-5-yl)}methyl)propanamide | 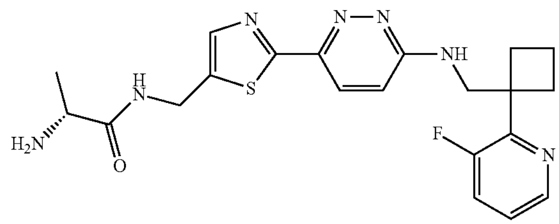 [SMILES: C[C@@H](N)C(=O)NCc1cnc(-c2ccc(NCC3(c4ncccc4F)CCC3)nn2)s1] | 442.2 | A |
| ((3R)-1,1-dioxo(1,4-thiazaperhydroin-3-yl))-N-({2-[6-({[(3-fluoro(2-pyridyl))cyclobutyl]methyl}amino)pyridazin-3-yl](1,3-thiazol-5-yl)}methyl)carboxamide | 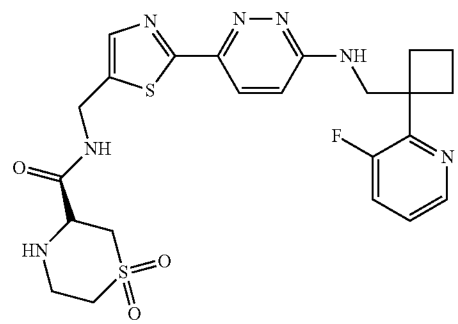 | 532.1 | A |
| ((2S)-4,4-difluoropyrrolidin-2-yl)-N-({2-[6-({[(3-fluoro(2-pyridyl))cyclobutyl]methyl}amino)pyridazin-3-yl](1,3-thiazol-5-yl)}methyl)carboxamide | 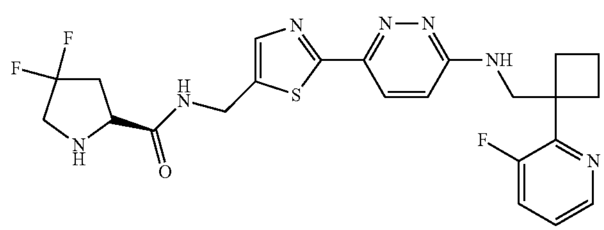 | 504.2 | A |
| tert-butyl (2S)-4,4-difluoro-2-[N-({2-[6-({[(3-fluoro(2-pyridyl))cyclobutyl]methyl}amino)pyridazin-3-yl](1,3-thiazol-5-yl)}methyl)carbamoyl]pyrrolidine-carboxylate | | 604.2 | B |
| ((2S)-4,4-difluoro-1-formylpyrrolidin-2-yl)-N-({2-[6-({[(3-fluoro(2-pyridyl))cyclobutyl]methyl}amino)pyridazin-3-yl](1,3-thiazol-5-yl)}methyl)carboxamide | 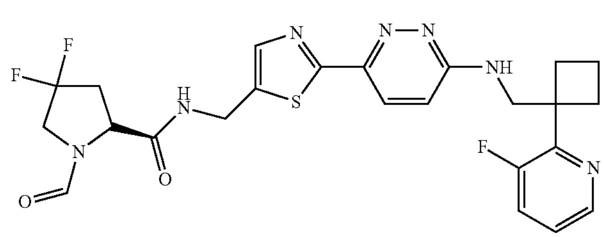 | 532.1 | A |

TABLE 2-continued

| Compound | Structure | m/z (M + H) | Mean AC1.4 |
|---|---|---|---|
| ((2R,4R)-4-fluoropyrrolidin-2-yl)-N-({2-[6-({[(3-fluoro(2-pyridyl))cyclobutyl]methyl}amino)pyridazin-3-yl](1,3-thiazol-5-yl)}methyl)carboxamide | 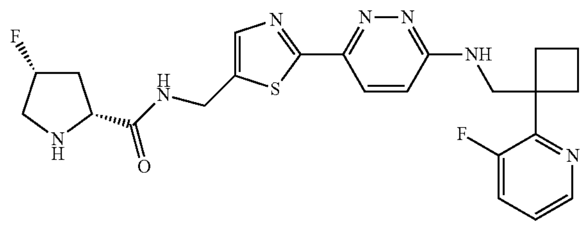 [SMILES: O=C(NCc1cnc(-c2ccc(NCC3(c4ncccc4F)CCC3)nn2)s1)[C@H]1C[C@@H](F)CN1] | 486.1 | A |
| N-({2-[6-({[(3-fluoro(2-pyridyl))cyclobutyl]methyl}amino)pyridazin-3-yl](1,3-thiazol-5-yl)}methyl)-2-methylpropanamide | 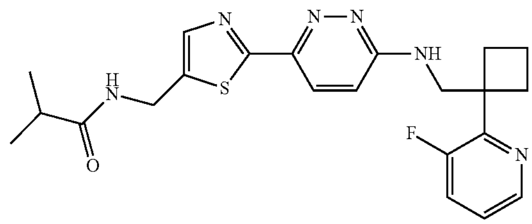 | 441.3 | A |
| 4-fluoro-3-(6-{[1-(3-fluoro(2-pyridyl))isopropyl]amino}pyridazin-3-yl)benzamide | | 370.2 | B |
| amino-N-({2-[6-({[(3-fluoro(2-pyridyl))cyclobutyl]methyl}amino)pyridazin-3-yl](1,3-thiazol-5-yl)}methyl)amide | 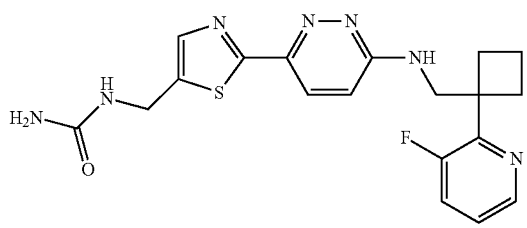 [SMILES: NC(=O)NCc1cnc(-c2ccc(NCC3(c4ncccc4F)CCC3)nn2)s1] | 414.1 | A |
| ((3S)-1,1-dioxo(1,4-thiazaperhydroin-3-yl))-N-({2-[6-({[(3-fluoro(2-pyridyl))cyclobutyl]methyl}amino)pyridazin-3-yl](1,3-thiazol-5-yl)}methyl)carboxamide | 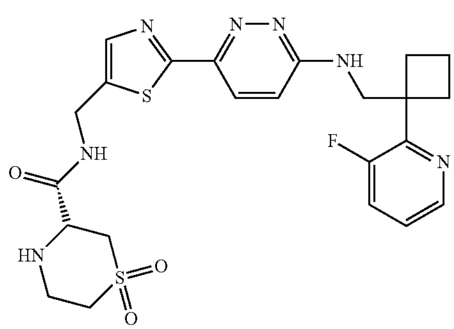 | 532.3 | A |
| N-({2-[6-({[3-fluoro-1-(3-fluoro(2-pyridyl))cyclobutyl]methyl}amino)pyridazin-3-yl]-1,3-thiazol-5-yl}methyl)acetamide | 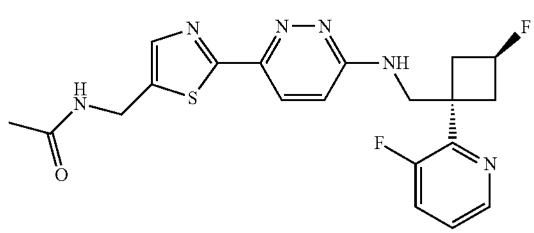 [SMILES: CC(=O)NCc1cnc(-c2ccc(NC[C@]3(c4ncccc4F)C[C@H](F)C3)nn2)s1] | 431.3 | B |

TABLE 2-continued

| Compound | Structure | m/z (M + H) | Mean AC1.4 |
|---|---|---|---|
| N-({2-[6-({[3-fluoro-1-(3-fluoro(2-pyridyl))cyclobutyl]methyl}amino)pyridazin-3-yl]-1,3-thiazol-5-yl}methyl)acetamide | 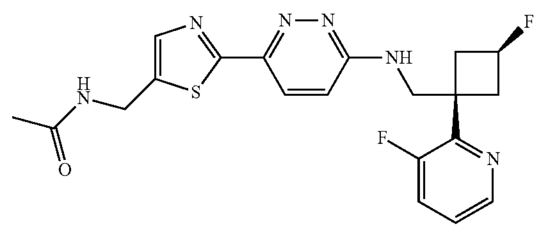 [SMILES: CC(=O)NCc1cnc(-c2ccc(NC[C@]3(c4ncccc4F)C[C@@H](F)C3)nn2)s1] | 431.2 | B |
| ((2S)pyrrolidin-2-yl)-N-{[2-(6-{[2-(3-fluoro(2-pyridyl))-2-methylpropyl]amino}pyridazin-3-yl)(1,3-thiazol-5-yl)]methyl}carboxamide | 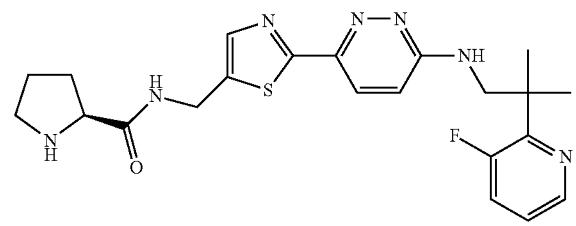 [SMILES: CC(C)(CNc1ccc(-c2ncc(CNC(=O)[C@@H]3CCCN3)s2)nn1)c1ncccc1F] | 456.3 | B |
| 2-(6-{[1-(3-chloro(2-pyridyl))-isopropyl]amino}pyridazin-3-yl)-1,3-thiazole-5-carboxamide | 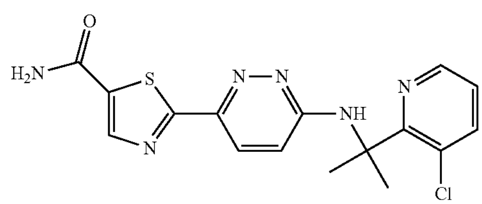 [SMILES: CC(C)(Nc1ccc(-c2ncc(C(N)=O)s2)nn1)c1ncccc1Cl] | 375.2 | B |
| 4-fluoro-3-[6-({[3-fluoro-1-(3-fluoro(2-pyridyl))cyclobutyl]methyl}amino)pyridazin-3-yl]benzamide | 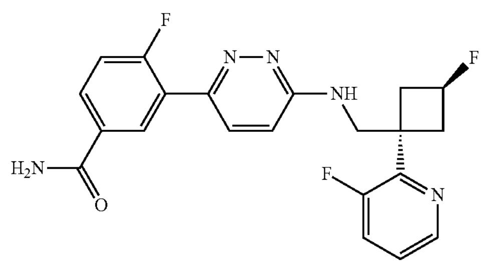 | 414.3 | B |
| 4-fluoro-3-[6-({[3-fluoro-1-(3-fluoro(2-pyridyl))cyclobutyl]methyl}amino)pyridazin-3-yl]benzenecarbonitrile | | 396.3 | B |
| 3-[6-({[3-fluoro-1-(3-fluoro(2-pyridyl))cyclobutyl]methyl}amino)pyridazin-3-yl]-4-hydroxybenzamide | 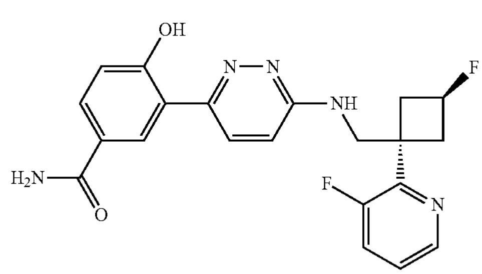 [SMILES: NC(=O)c1ccc(F)c(-c2ccc(NC[C@]3(c4ncccc4F)C[C@H](F)C3)nn2)c1] | 412.3 | B |

TABLE 2-continued

| Compound | Structure | m/z (M + H) | Mean AC1.4 |
|---|---|---|---|
| 4-fluoro-3-[6-({[3-fluoro-1-(3-fluoro(2-pyridyl))cyclobutyl]methyl}amino)pyridazin-3-yl]benzoic acid | 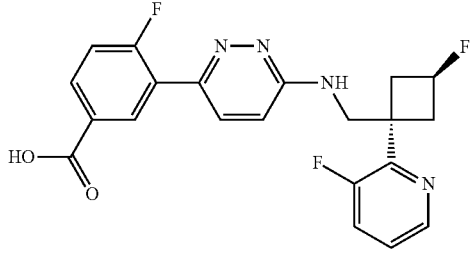 [SMILES: O=C(O)c1ccc(F)c(-c2ccc(NC[C@]3(c4ncccc4F)C[C@H](F)C3)nn2)c1] | 415.3 | A |
| 3-(6-{[2-(3-chloro(2-pyridyl))-2-methylpropyl]amino}pyridazin-3-yl)benzamide | 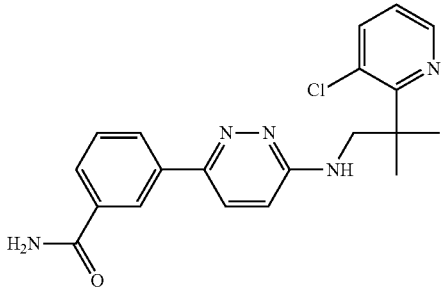 | 382.2 | A |
| 3-(6-{[2-(3-chloro(2-pyridyl))-2-methylpropyl]amino}pyridazin-3-yl)-4-fluorobenzamide | 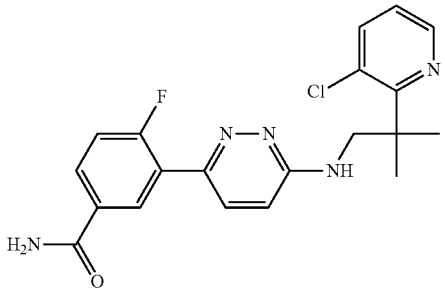 [SMILES: CC(C)(CNc1ccc(-c2cc(C(N)=O)ccc2F)nn1)c1ncccc1Cl] | 400.3 | A |
| N-((2R)-2,3-dihydroxypropyl){4-fluoro-3-[6-({[3-fluoro-1-(3-fluoro(2-pyridyl))cyclobutyl]methyl}amino)pyridazin-3-yl]phenyl}carboxamide | 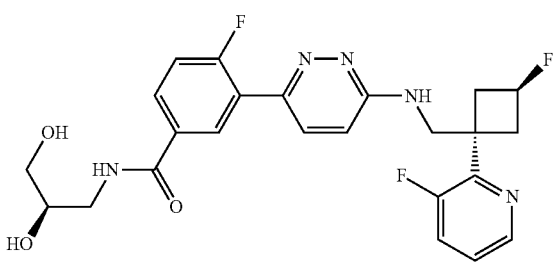 [SMILES: O=C(NC[C@@H](O)CO)c1ccc(F)c(-c2ccc(NC[C@]3(c4ncccc4F)C[C@H](F)C3)nn2)c1] | 488.3 | A |
| N-((3R)pyrrolidin-3-yl){4-fluoro-3-[6-({[3-fluoro-1-(3-fluoro(2-pyridyl))cyclobutyl]methyl}amino)pyridazin-3-yl]phenyl}carboxamide | 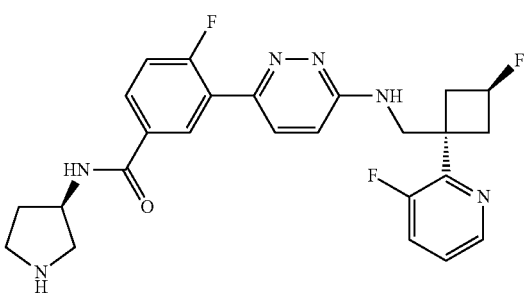 [SMILES: O=C(N[C@@H]1CCNC1)c1ccc(F)c(-c2ccc(NC[C@]3(c4ncccc4F)C[C@H](F)C3)nn2)c1] | 483.3 | B |

TABLE 2-continued

| Compound | Structure | m/z (M + H) | Mean AC1.4 |
|---|---|---|---|
| N-((3S)pyrrolidin-3-yl){4-fluoro-3-[6-({[3-fluoro-1-(3-fluoro(2-pyridyl))cyclobutyl]methyl}amino)pyridazin-3-yl]phenyl}carboxamide | 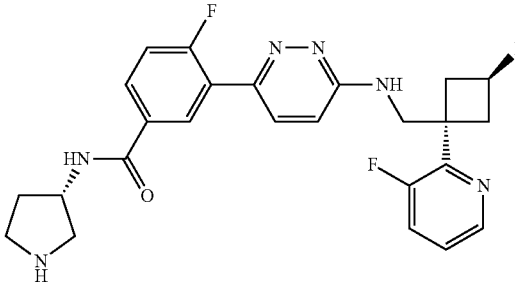 | 483.3 | B |
| [6-(3-(2H-1,2,3,4-tetraazol-5-yl)phenyl)pyridazin-3-yl]{[3-fluoro-1-(3-fluoro(2-pyridyl))cyclobutyl]methyl}amine | 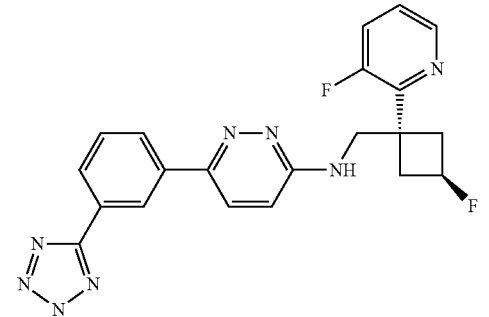 | 421.1 | A |
| 3-(6-{[2-(3-chloro(2-pyridyl))-2-methylpropyl]amino}pyridazin-3-yl)benzenecarbonitrile | 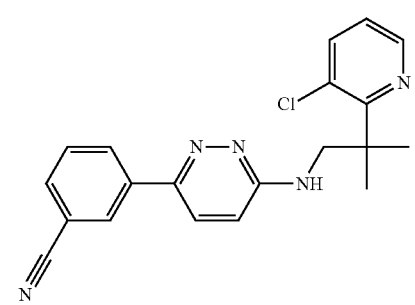 [SMILES: CC(C)(CNc1ccc(-c2cccc(C#N)c2)nn1)c1ncccc1Cl] | 364.2 | B |
| 3-(6-{[2-(3-chloro(2-pyridyl))-2-methylpropyl]amino}pyridazin-3-yl)-4-fluorobenzenecarbonitrile | 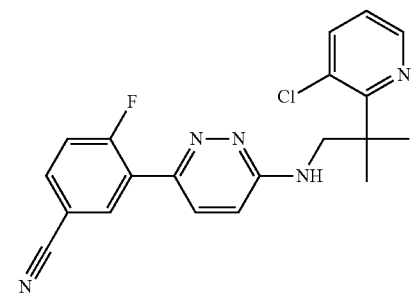 [SMILES: CC(C)(CNc1ccc(-c2cc(C#N)ccc2F)nn1)c1ncccc1Cl] | 382.2 | B |
| 2-[6-({[(3-fluoro-2-pyridyl)cyclobutyl]methyl}amino)pyridazin-3-yl]-1,3-thiazole-5-sulfonamide | 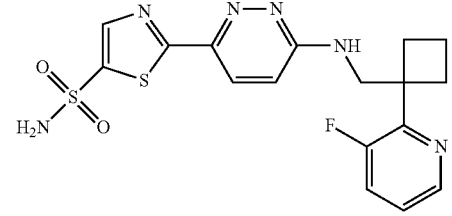 [SMILES: NS(=O)(=O)c1cnc(-c2ccc(NCC3(c4ncccc4F)CCC3)nn2)s1] | 421.2 | B |

TABLE 2-continued

| Compound | Structure | m/z (M + H) | Mean AC1.4 |
|---|---|---|---|
| (aminocyclopropyl)-N-({2-[6-({[(3-fluoro(2-pyridyl))cyclobutyl]methyl}amino)pyridazin-3-yl](1,3-thiazol-5-yl)}methyl)carboxamide | 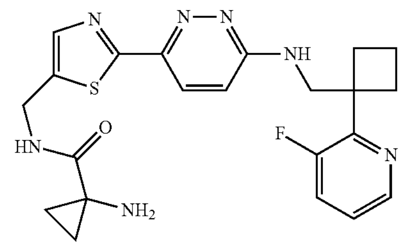 [SMILES: NC1(C(=O)NCc2cnc(-c3ccc(NCC4(c5ncccc5F)CCC4)nn3)s2)CC1] | 454.2 | A |
| (N-{1-[N-({2-[6-({[(3-fluoro(2-pyridyl))cyclobutyl]methyl}amino)pyridazin-3-yl](1,3-thiazol-5-yl)}methyl)carbamoyl]-isopropyl}carbamoyloxy)ethyl 2-methylpropanoate | 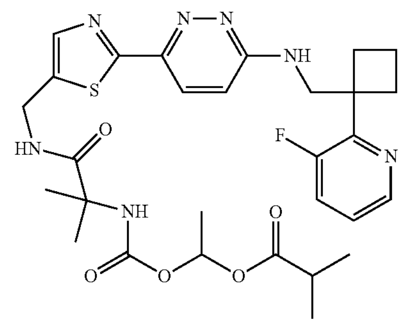 [SMILES: CC(OC(=O)NC(C)(C)C(=O)NCc1cnc(-c2ccc(NCC3(c4ncccc4F)CCC3)nn2)s1)OC(=O)C(C)C] | 614.1 | A |
| 3-[6-({[3-fluoro-1-(3-fluoro(2-pyridyl))cyclobutyl]methyl}amino)pyridazin-3-yl]benzoic acid | 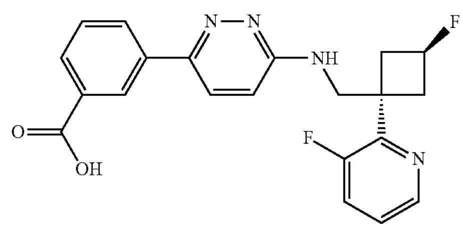 | 397.2 | A |
| 3-(6-{[(3-fluoro-1-(2-pyridyl)cyclobutyl)methyl]amino}pyridazin-3-yl)benzoic acid | | 379.3 | A |
| 3-(6-{[(3-fluoro-1-(2-pyridyl)cyclobutyl)methyl]amino}pyridazin-3-yl)benzoic acid | | 379.3 | B |
| 3-[6-({[3-fluoro-1-(3-fluoro(2-pyridyl))cyclobutyl]methyl}amino)pyridazin-3-yl]benzenecarbonitrile | 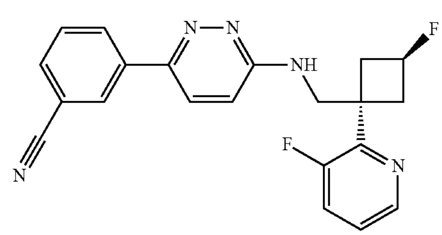 [SMILES: N#Cc1cccc(-c2ccc(NC[C@]3(c4ncccc4F)C[C@H](F)C3)nn2)c1] | 378.2 | B |

TABLE 2-continued

| Compound | Structure | m/z (M + H) | Mean AC1.4 |
|---|---|---|---|
| N-((2S)-2,3-dihydroxypropyl){4-fluoro-3-[6-({[3-fluoro-1-(3-fluoro(2-pyridyl))cyclobutyl]methyl}amino)pyridazin-3-yl]phenyl}carboxamide | | 488.3 | A |
| methyl 4-fluoro-3-[6-({[3-fluoro-1-(3-fluoro(2-pyridyl))cyclobutyl]methyl}amino)pyridazin-3-yl]benzoate | | 429.3 | B |
| {4-fluoro-3-[6-({[3-fluoro-1-(3-fluoro(2-pyridyl))cyclobutyl]methyl}amino)pyridazin-3-yl]phenyl}-N-methylcarboxamide | | 428.3 | A |
| {4-fluoro-3-[6-({[3-fluoro-1-(3-fluoro(2-pyridyl))cyclobutyl]methyl}amino)pyridazin-3-yl]phenyl}-N-(methylethyl)carboxamide | | 456.3 | A |
| methyl 3-[6-({[3-fluoro-1-(3-fluoro(2-pyridyl))cyclobutyl]methyl}amino)pyridazin-3-yl]benzoate | | 411.3 | B |
| methylethyl 4-fluoro-3-[6-({[3-fluoro-1-(3-fluoro(2-pyridyl))cyclobutyl]methyl}amino)pyridazin-3-yl]benzoate | | 457.3 | B |

TABLE 2-continued

| Compound | Structure | m/z (M + H) | Mean AC1.4 |
|---|---|---|---|
| 6-[6-({[(3-fluoro-2-pyridyl)cyclobutyl]methyl}amino)pyridazin-3-yl]imidazo[2,1-b]1,3-thiazoline-3-carboxamide | 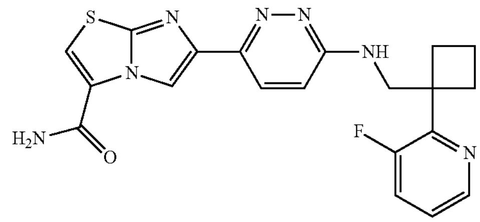 [SMILES: NC(=O)c1csc2nc(-c3ccc(NCC4(c5ncccc5F)CCC4)nn3)cn12] | 424.1 | A |
| 6-[6-({[(3-fluoro-2-pyridyl)cyclobutyl]methyl}amino)pyridazin-3-yl]imidazo[2,1-b]1,3-thiazoline-3-carboxylic acid | 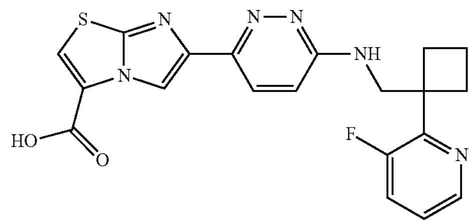 [SMILES: O=C(O)c1csc2nc(-c3ccc(NCC4(c5ncccc5F)CCC4)nn3)cn12] | 425.1 | A |
| 6-[6-({[3-fluoro-1-(3-fluoro(2-pyridyl))cyclobutyl]methyl}amino)pyridazin-3-yl]imidazo[2(1-b]1,3-thiazoline-3-carboxamide | 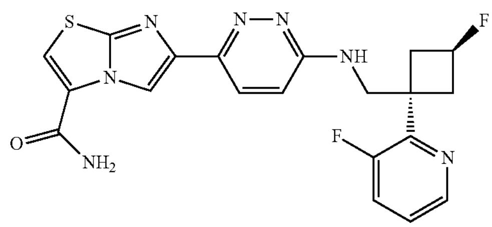 [SMILES: NC(=O)c1csc2nc(-c3ccc(NC[C@]4(c5ncccc5F)C[C@H](F)C4)nn3)cn12] | 442.1 | A |
| N-({2-[6-({[(3-fluoro(2-pyridyl))cyclobutyl]methyl}amino)pyridazin-3-yl](1,3-thiazol-5-yl)}methyl){3-[benzylamino]oxetan-3-yl}carboxamide | 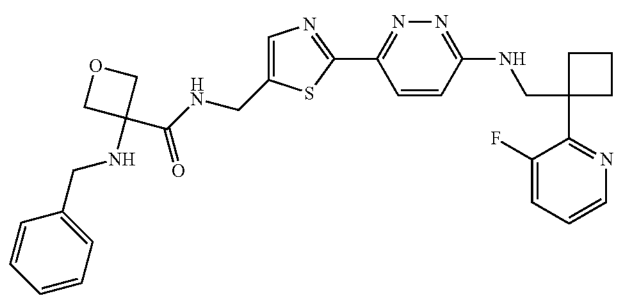 [SMILES: O=C(NCc1cnc(-c2ccc(NCC3(c4ncccc4F)CCC3)nn2)s1)C1(NCc2ccccc2)COC1] | 560.2 | A |
| 3-[6-({[3-fluoro-1-(3-fluoro(2-pyridyl))cyclobutyl]methyl}amino)pyridazin-3-yl]benzenesulfonamide | | 432.2 | B |
| {5-[6-({[3-fluoro-1-(3-fluoro(2-pyridyl))cyclobutyl]methyl}amino)pyridazin-3-yl](1H-indazol-3-yl)}(methylsulfonyl)amine | 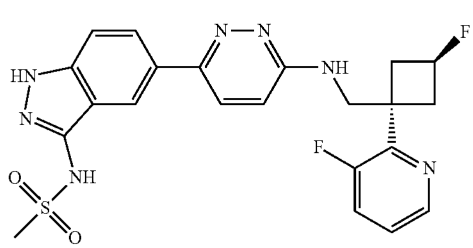 [SMILES: CS(=O)(=O)Nc1n[nH]c2ccc(-c3ccc(NC[C@]4(c5ncccc5F)C[C@H](F)C4)nn3)cc12] | 486.3 | A |

TABLE 2-continued

| Compound | Structure | m/z (M + H) | Mean AC1.4 |
|---|---|---|---|
| {[3-fluoro-1-(3-fluoro(2-pyridyl))cyclobutyl]methyl}{6-[3-(methylamino)(1H-indazol-5-yl)]pyridazin-3-yl}amine | 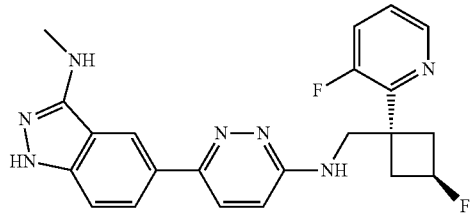 [SMILES: CNc1n[nH]c2ccc(-c3ccc(NC[C@]4(c5ncccc5F)C[C@H](F)C4)nn3)cc12] | 422.3 | A |
| {6-[3-(ethylamino)(1H-indazol-5-yl)]pyridazin-3-yl}{[3-fluoro-1-(3-fluoro(2-pyridyl))cyclobutyl]methyl}amine | 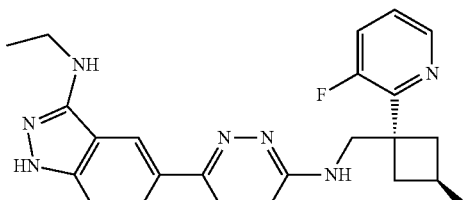 | 434.3 | A |
| [6-(3-amino(1H-indazol-5-yl))pyridazin-3-yl]{[3-fluoro-1-(3-fluoro(2-pyridyl))cyclobutyl]methyl}amine | 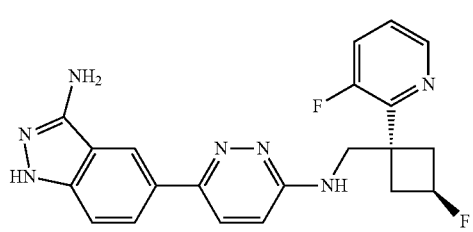 [SMILES: Nc1n[nH]c2ccc(-c3ccc(NC[C@]4(c5ncccc5F)C[C@H](F)C4)nn3)cc12] | 408.3 | A |
| ethyl 2-fluoro-5-[6-({[3-fluoro-1-(3-fluoro(2-pyridyl))cyclobutyl]methyl}amino)pyridazin-3-yl]benzoate | 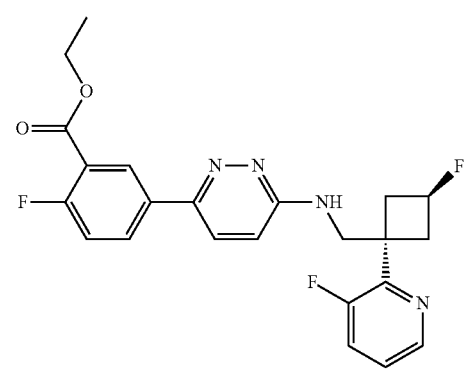 [SMILES: CCOC(=O)c1cc(-c2ccc(NC[C@]3(c4ncccc4F)C[C@H](F)C3)nn2)ccc1F] | 443.3 | C |
| 2-fluoro-5-[6-({[3-fluoro-1-(3-fluoro(2-pyridyl))cyclobutyl]methyl}amino)pyridazin-3-yl]benzoic acid | 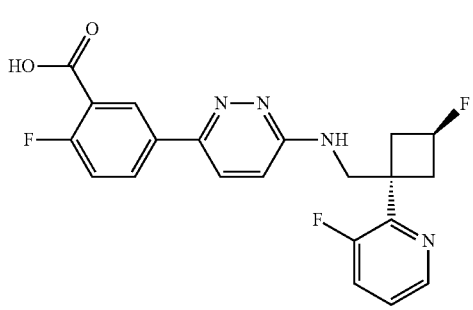 [SMILES: O=C(O)c1cc(-c2ccc(NC[C@]3(c4ncccc4F)C[C@H](F)C3)nn2)ccc1F] | 415.3 | B |

TABLE 2-continued

| Compound | Structure | m/z (M + H) | Mean AC1.4 |
|---|---|---|---|
| 2-{4-fluoro-3-[6-({[(3-fluoro(2-pyridyl))cyclobutyl]methyl}amino)pyridazin-3-yl]phenyl}acetamide | 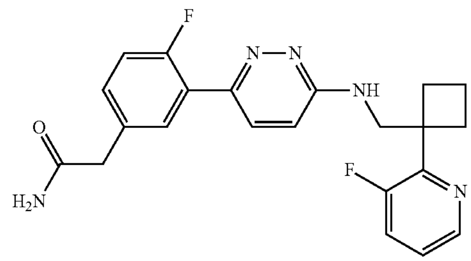 [SMILES: NC(=O)Cc1ccc(F)c(-c2ccc(NCC3(c4ncccc4F)CCC3)nn2)c1] | 410.1 | B |
| methyl 2-{4-fluoro-3-[6-({[(3-fluoro(2-pyridyl))cyclobutyl]methyl}amino)pyridazin-3-yl]phenyl}acetate | | 425.1 | B |
| N-({4-fluoro-3-[6-({[3-fluoro-1-(3-fluoro(2-pyridyl))cyclobutyl]methyl}amino)pyridazin-3-yl]phenyl}methyl)acetamide | 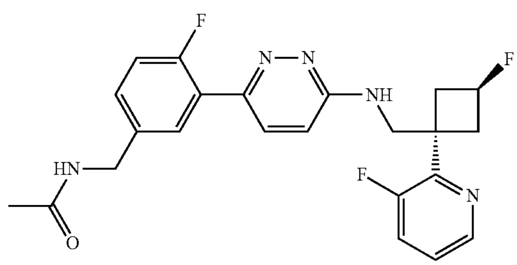 [SMILES: CC(=O)NCc1ccc(F)c(-c2ccc(NC[C@]3(c4ncccc4F)C[C@H](F)C3)nn2)c1] | 442.4 | B |
| N-({3-[6-({[3-fluoro-1-(3-fluoro(2-pyridyl))cyclobutyl]methyl}amino)pyridazin-3-yl]phenyl}methyl)acetamide | 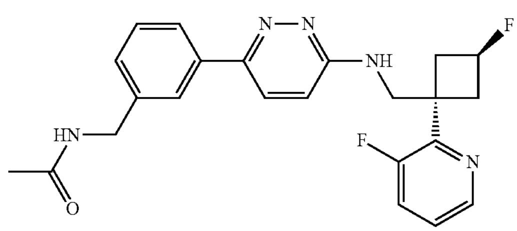 [SMILES: CC(=O)NCc1cccc(-c2ccc(NC[C@]3(c4ncccc4F)C[C@H](F)C3)nn2)c1] | 424.3 | B |
| {2-fluoro-5-[6-({[3-fluoro-1-(3-fluoro(2-pyridyl))cyclobutyl]methyl}amino)pyridazin-3-yl]phenyl}-N-methylcarboxamide | 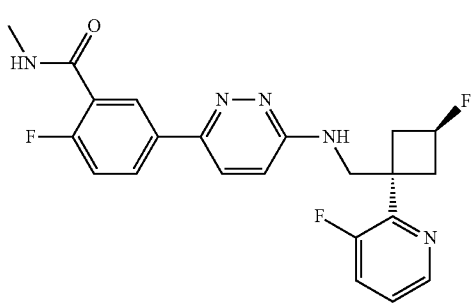 [SMILES: CNC(=O)c1cc(-c2ccc(NC[C@]3(c4ncccc4F)C[C@H](F)C3)nn2)ccc1F] | 428.3 | C |

TABLE 2-continued

| Compound | Structure | m/z (M + H) | Mean AC1.4 |
|---|---|---|---|
| N-ethyl{2-fluoro-5-[6-({[3-fluoro-1-(3-fluoro(2-pyridyl))cyclobutyl]methyl}amino)pyridazin-3-yl]phenyl}carboxamide | 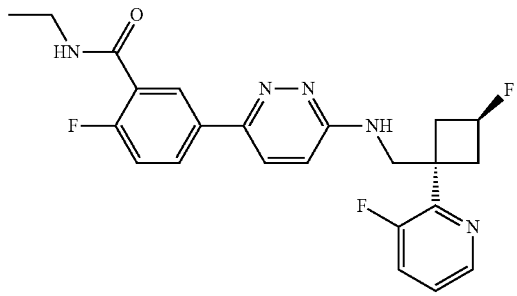 [SMILES: CCNC(=O)c1cc(-c2ccc(NC[C@]3(c4ncccc4F)C[C@H](F)C3)nn2)ccc1F] | 442.3 | C |
| methyl 5-[6-({[3-fluoro-1-(3-fluoro(2-pyridyl))cyclobutyl]methyl}amino)pyridazin-3-yl]-2-(methylamino)benzoate | 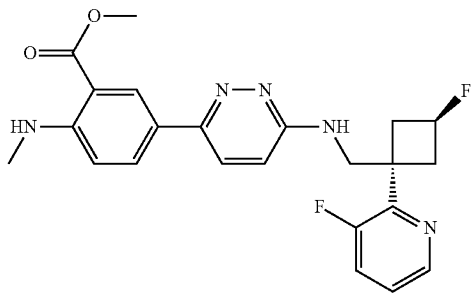 [SMILES: CNc1ccc(-c2ccc(NC[C@]3(c4ncccc4F)C[C@H](F)C3)nn2)cc1C(=O)OC] | 440.3 | B |
| ethyl 5-[6-({[3-fluoro-1-(3-fluoro(2-pyridyl))cyclobutyl]methyl}amino)pyridazin-3-yl]-2-(methylamino)benzoate | 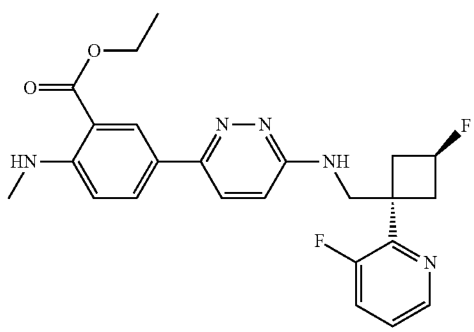 [SMILES: CCOC(=O)c1cc(-c2ccc(NC[C@]3(c4ncccc4F)C[C@H](F)C3)nn2)ccc1NC] | 454.3 | A |
| {3-[6-({[3-fluoro-1-(3-fluoro(2-pyridyl))cyclobutyl]methyl}amino)pyridazin-3-yl]phenyl}methan-1-ol | 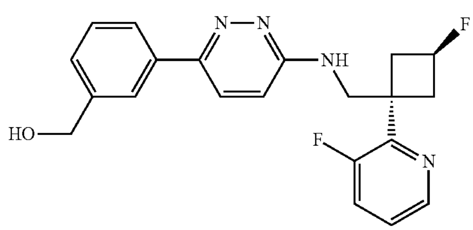 [SMILES: OCc1cccc(-c2ccc(NC[C@]3(c4ncccc4F)C[C@H](F)C3)nn2)c1] | 383.2 | B |
| 2-[2-(6-{[2-(3-chloro(2-pyridyl))-2-methylpropyl]amino}pyridazin-3-yl)-1,3-thiazol-5-yl]acetamide | 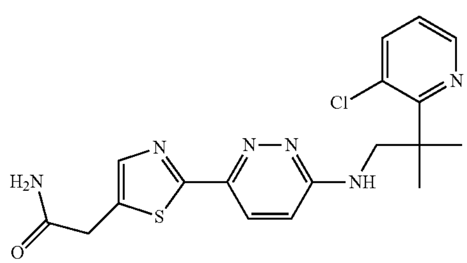 [SMILES: CC(C)(CNc1ccc(-c2ncc(CC(N)=O)s2)nn1)c1ncccc1Cl] | 403.2 | B |

TABLE 2-continued

| Compound | Structure | m/z (M + H) | Mean AC1.4 |
|---|---|---|---|
| 2-amino-N-{[2-(6-{[2-(3-chloro(2-pyridyl))-2-methylpropyl]amino}pyridazin-3-yl)(1,3-thiazol-5-yl)]methyl}-2-methylpropanamide | 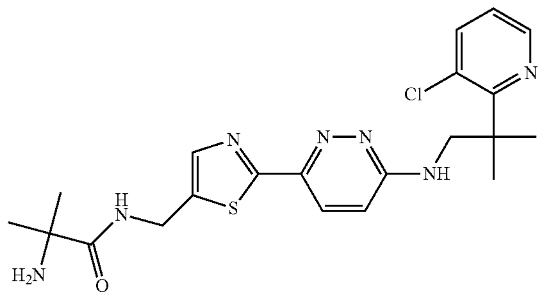 [SMILES: CC(C)(N)C(=O)NCc1cnc(-c2ccc(NCC(C)(C)c3ncccc3Cl)nn2)s1] | 460.1 | A |
| ((2S)azetidin-2-yl)-N-({2-[6-({[(3-fluoro(2-pyridyl))cyclobutyl]methyl}amino)pyridazin-3-yl](1,3-thiazol-5-yl)}methyl)carboxamide | 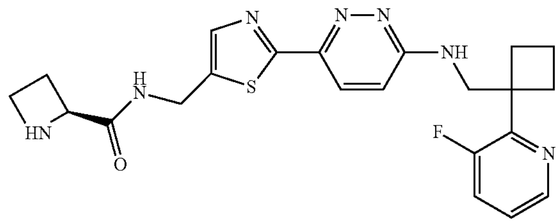 [SMILES: O=C(NCc1cnc(-c2ccc(NCC3(c4ncccc4F)CCC3)nn2)s1)[C@@H]1CCN1] | 454.1 | A |
| ethyl 2-{2-[6-({[(3-fluoro-2-pyridyl)cyclobutyl]methyl}amino)pyridazin-3-yl]-1(3-thiazol-4-yl}acetate | 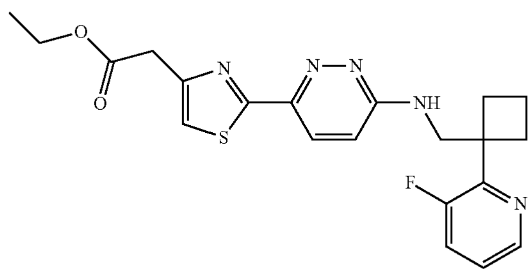 [SMILES: CCOC(=O)Cc1csc(-c2ccc(NCC3(c4ncccc4F)CCC3)nn2)n1] | 428.1 | C |
| 2-{2-[6-({[(3-fluoro-2-pyridyl)cyclobutyl)methyl}amino)pyridazin-3-yl]-1,3-thiazol-4-yl}acetamide | 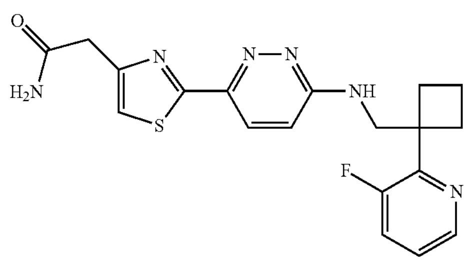 [SMILES: NC(=O)Cc1csc(-c2ccc(NCC3(c4ncccc4F)CCC3)nn2)n1] | 399.2 | D |
| 6-(6-{[1-(3-chloro(2-pyridyl))-isopropyl]amino}pyridazin-3-yl)imidazo[2,1-b]1,3-thiazoline-3-carboxamide | 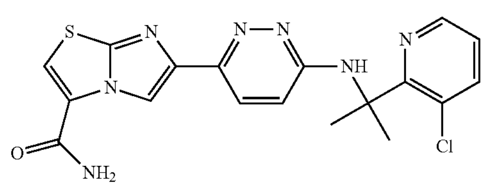 [SMILES: CC(C)(Nc1ccc(-c2cn3c(C(N)=O)csc3n2)nn1)c1ncccc1Cl] | 414.1 | B |
| 6-(6-{[2-(3-chloro(2-pyridyl))-2-methylpropyl]amino}pyridazin-3-yl)imidazo[2,1-b]1,3-thiazoline-3-carboxamide | 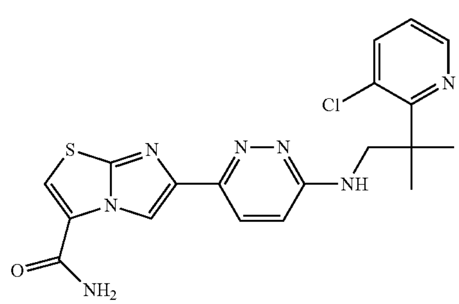 [SMILES: CC(C)(CNc1ccc(-c2cn3c(C(N)=O)csc3n2)nn1)c1ncccc1Cl] | 428.1 | A |

TABLE 2-continued

| Compound | Structure | m/z (M + H) | Mean AC1.4 |
|---|---|---|---|
| 6-({[(3-fluoro-2-pyridyl)cyclobutyl]methyl}amino)pyridazine-3-carboxamide | 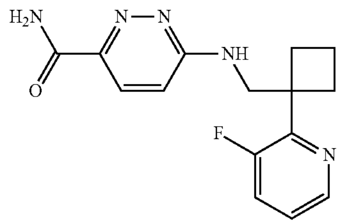 [SMILES: NC(=O)c1ccc(NCC2(c3ncccc3F)CCC2)nn1] | 302.2 | D |
| 2-{2-[6-({[(3-fluoro(2-pyridyl))cyclobutyl]methyl}amino)pyridazin-3-yl](1,3-thiazol-5-yl)}-2-methylpropanenitrile | 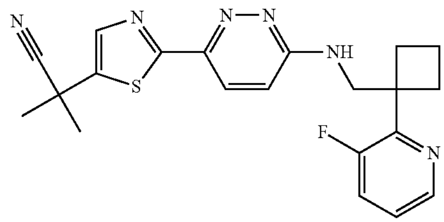 [SMILES: CC(C)(C#N)c1cnc(-c2ccc(NCC3(c4ncccc4F)CCC3)nn2)s1] | 409.1 | D |
| 2-{2-[6-({[(3-fluoro(2-pyridyl))cyclobutyl]methyl}amino)pyridazin-3-yl](1,3-thiazol-5-yl)}-2-methylpropanamide | 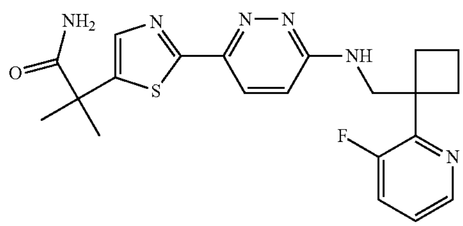 [SMILES: CC(C)(C(N)=O)c1cnc(-c2ccc(NCC3(c4ncccc4F)CCC3)nn2)s1] | 427.1 | D |
| 3-{2-[6-({[(3-fluoro-2-pyridyl)cyclobutyl]methyl}amino)pyridazin-3-yl]-1,3-thiazol-5-yl}propanamide | 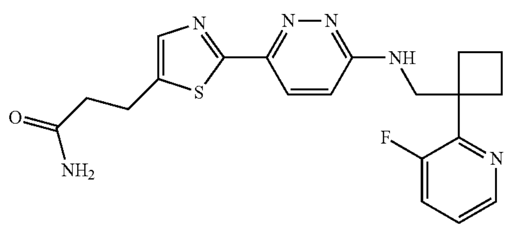 [SMILES: NC(=O)CCc1cnc(-c2ccc(NCC3(c4ncccc4F)CCC3)nn2)s1] | 413.1 | B |
| 3-{2-[6-({[(3-fluoro-2-pyridyl)cyclobutyl]methyl}amino)pyridazin-3-yl]-1,3-thiazol-5-yl}propanoic acid | | 414.1 | B |
| methyl 3-{2-[6-({[(3-fluoro-2-pyridyl)cyclobutyl]methyl}amino)pyridazin-3-yl]-1,3-thiazol-5-yl}propanoate | 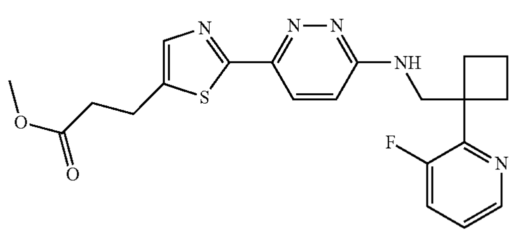 [SMILES: COC(=O)CCc1cnc(-c2ccc(NCC3(c4ncccc4F)CCC3)nn2)s1] | 428.1 | B |

| Compound | Structure | m/z (M + H) | Mean AC1.4 |
|---|---|---|---|
| 6-({[(3-fluoro-2-pyridyl)cyclobutyl]methyl}amino)pyridazine-3-carboxylic acid | 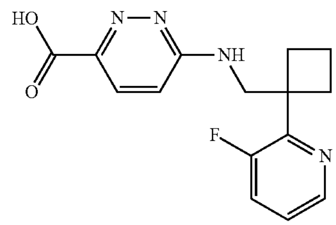 [SMILES: O=C(O)c1ccc(NCC2(c3ncccc3F)CCC2)nn1] | 303.2 | D |
| [6-({[(3-fluoro(2-pyridyl))cyclobutyl]methyl}amino)pyridazin-3-yl]-N-methylcarboxamide | 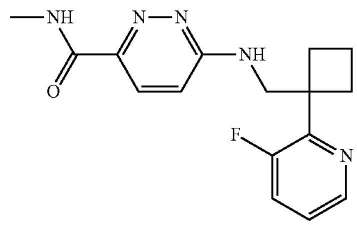 [SMILES: CNC(=O)c1ccc(NCC2(c3ncccc3F)CCC2)nn1] | 316.2 | D |
| [6-({[(3-fluoro(2-pyridyl))cyclobulyl)methyl}amino)pyridazin-3-yl]-N,N-dimethylcarboxamide | | 330.3 | D |
| 2-amino-N-({2-[6-({[(3-fluoro(2-pyridyl))cyclobutyl]methyl}amino)pyridazin-3-yl](1,3-thiazol-5-yl)}methyl)-2-methyl-N-methylpropanamide | 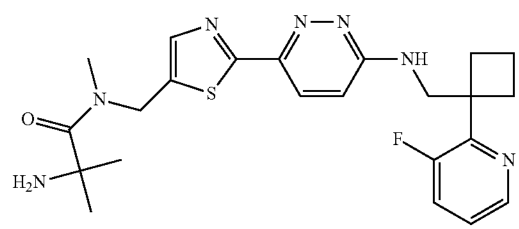 [SMILES: CN(Cc1cnc(-c2ccc(NCC3(c4ncccc4F)CCC3)nn2)s1)C(=O)C(C)(C)N] | 470.2 | A |
| 2-{2-[6-({[3-fluoro-1-(3-fluoro(2-pyridyl))cyclobutyl]methyl}amino)pyridazin-3-yl]-1,3-thiazol-5-yl}acetamide | | 417.1 | B |
| 2-{2-[6-({[3-fluoro-1-(3-fluoro(2-pyridyl))cyclobutyl]methyl}amino)pyridazin-3-yl]-1,3-thiazol-5-yl}acetic acid | 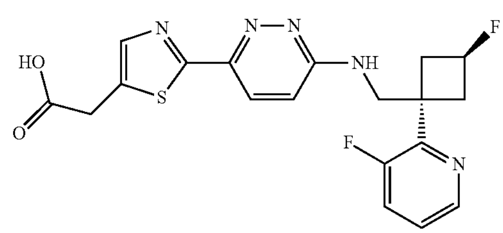 | 418.1 | B |
| 2-[2-(6-{[1-(3-chloro(2-pyridyl))isopropyl]amino}pyridazin-3-yl)-1,3-thiazol-5-yl]acetamide | | 389.1 | D |

TABLE 2-continued

| Compound | Structure | m/z (M + H) | Mean AC1.4 |
|---|---|---|---|
| (3-aminooxetan-3-yl)-N-({2-[6-({[(3-fluoro(2-pyridyl))cyclobutyl]methyl}amino)pyridazin-3-yl](1,3-thiazol-5-yl)}methyl)carboxamide | 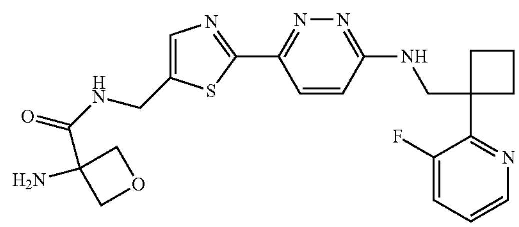 [SMILES: NC1(C(=O)NCc2cnc(-c3ccc(NCC4(c5ncccc5F)CCC4)nn3)s2)COC1] | 470.1 | A |
| {3-[6-({[(3-fluoro(2-pyridyl))cyclobutyl]methyl}amino)pyridazin-3-yl]phenyl}-N-methylcarboxamide | 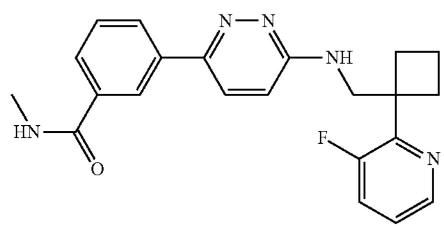 [SMILES: CNC(=O)c1cccc(-c2ccc(NCC3(c4ncccc4F)CCC3)nn2)c1] | 392.3 | B |
| {4-fluoro-3-[6-({[(3-fluoro(2-pyridyl))cyclobutyl]methyl}amino)pyridazin-3-yl]phenyl}-N-methylcarboxamide | 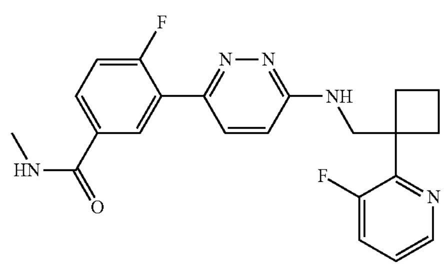 [SMILES: CNC(=O)c1ccc(F)c(-c2ccc(NCC3(c4ncccc4F)CCC3)nn2)c1] | 410.3 | A |
| N-({5-[6-({[(3-fluoro-2-pyridyl)cyclobutyl]methyl}amino)pyridazin-3-yl]-1,3-thiazol-2-yl}methyl)acetamide | 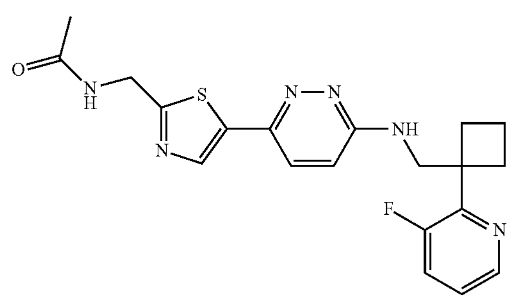 [SMILES: CC(=O)NCc1ncc(-c2ccc(NCC3(c4ncccc4F)CCC3)nn2)s1] | 413.3 | B |
| N-({4-[6-({[(3-fluoro-2-pyridyl)cyclobutyl]methyl}amino)pyridazin-3-yl]-1,3-thiazol-2-yl}methyl)acetamide | 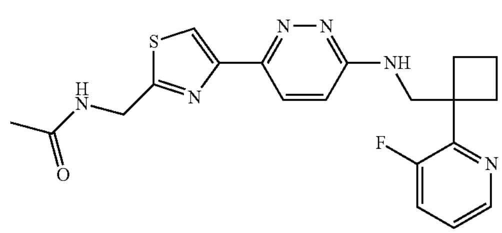 [SMILES: CC(=O)NCc1nc(-c2ccc(NCC3(c4ncccc4F)CCC3)nn2)cs1] | 413.3 | D |
| 2-{2-[6-({[1-(3-chloro(2-pyridyl))-3-fluorocyclobutyl]methyl}amino)pyridazin-3-yl]-1,3-thiazol-5-yl}acetamide | 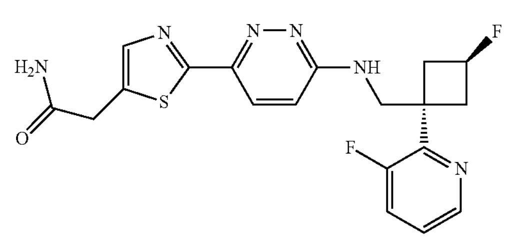 [SMILES: NC(=O)Cc1cnc(-c2ccc(NC[C@]3(c4ncccc4F)C[C@H](F)C3)nn2)s1] | 433.2 | B |

TABLE 2-continued

| Compound | Structure | m/z (M + H) | Mean AC1.4 |
|---|---|---|---|
| {3-[6-({[3-fluoro-1-(3-fluoro(2-pyridyl))cyclobutyl]methyl}amino)pyridazin-3-yl]phenyl}-N-methylcarboxamide | 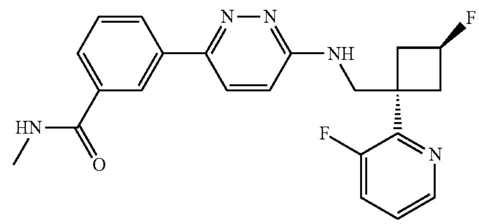 [SMILES: CNC(=O)c1cccc(-c2ccc(NC[C@]3(c4ncccc4F)C[C@H](F)C3)nn2)c1] | 410.1 | A |
| 2-{2-[6-({[(3-chloro-2-pyridyl)cyclobutyl]methyl}amino)pyridazin-3-yl]-1,3-thiazol-5-yl}acetamide | 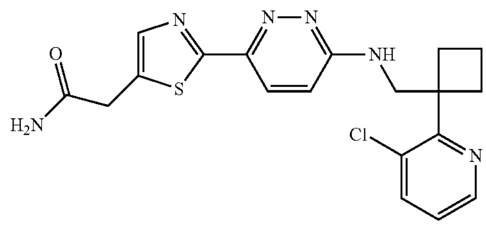 [SMILES: NC(=O)Cc1cnc(-c2ccc(NCC3(c4ncccc4Cl)CCC3)nn2)s1] | 415.3 | A |
| 2-{2-[6-({[(3-fluoro-2-pyridyl)cyclobutyl]methyl}amino)pyridazin-3-yl]-1,3-thiazol-5-yl}acetic acid | 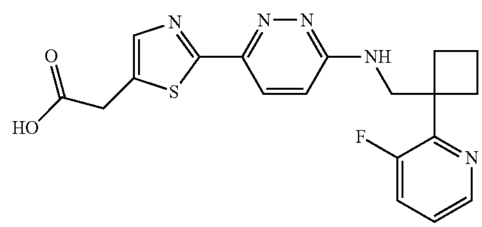 [SMILES: O=C(O)Cc1cnc(-c2ccc(NCC3(c4ncccc4F)CCC3)nn2)s1] | 400.3 | B |
| 2-{2-[6-({[(3-fluoro(2-pyridyl))cyclobutyl]methyl}amino)pyridazin-3-yl](1,3-thiazol-5-yl)}-N-methylacetamide | 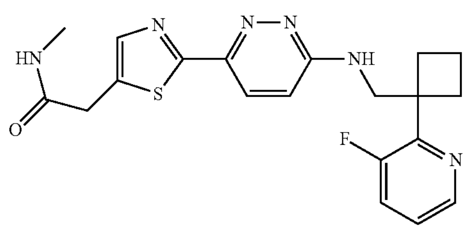 | 413.3 | B |
| 2-{2-[6-({[(3-fluoro(2-pyridyl))cyclobutyl]methyl}amino)pyridazin-3-yl](1,3-thiazol-5-yl)}-N,N-dimethylacetamide | 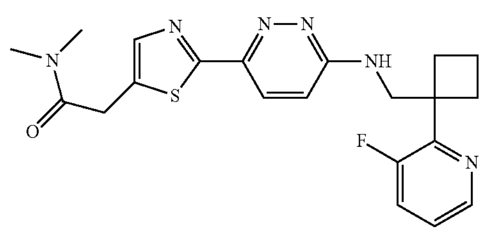 [SMILES: CN(C)C(=O)Cc1cnc(-c2ccc(NCC3(c4ncccc4F)CCC3)nn2)s1] | 427.3 | B |
| [6-({[(3-fluoro(2-pyridyl))cyclobutyl]methyl}amino)pyridazin-3-yl]-N-isoxazol-3-ylcarboxamide | 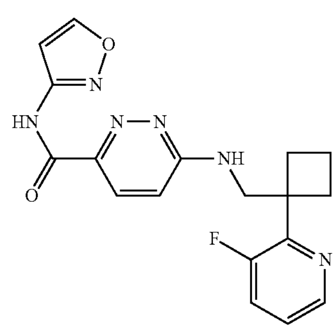 [SMILES: O=C(Nc1ccon1)c1ccc(NCC2(c3ncccc3F)CCC2)nn1] | 369.2 | B |

TABLE 2-continued

| Compound | Structure | m/z (M + H) | Mean AC1.4 |
|---|---|---|---|
| [6-({[(3-fluoro(2-pyridyl))cyclobutyl]methyl}amino)pyridazin-3-yl]-N-(1,3-oxazol-2-yl)carboxamide | 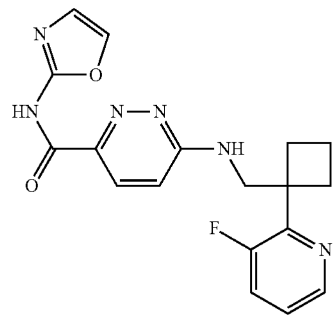 [SMILES: O=C(Nc1ncco1)c1ccc(NCC2(c3ncccc3F)CCC2)nn1] | 369.2 | D |
| [6-({[(3-fluoro(2-pyridyl))cyclobutyl]methyl}amino)pyridazin-3-yl]-N-(1,3-thiazol-2-yl)carboxamide | 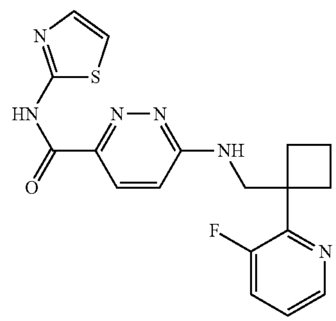 [SMILES: O=C(Nc1nccs1)c1ccc(NCC2(c3ncccc3F)CCC2)nn1] | 385.2 | A |
| [6-({[(3-fluoro(2-pyridyl))cyclobutyl]methyl}amino)pyridazin-3-yl]-N-(1,3,4-thiadiazol-2-yl)carboxamide | 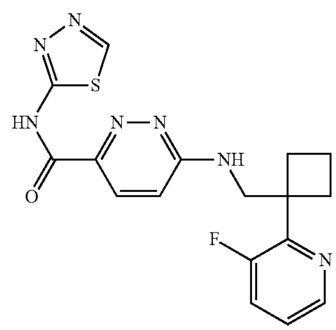 [SMILES: O=C(Nc1nncs1)c1ccc(NCC2(c3ncccc3F)CCC2)nn1] | 386.2 | B |
| [6-({[(3-fluoro(2-pyridyl))cyclobutyl]methyl}amino)pyridazin-3-yl]-N-imidazol-2-ylcarboxamide | 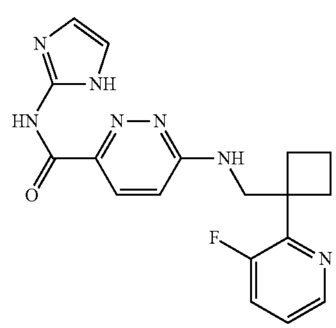 [SMILES: O=C(Nc1ncc[nH]1)c1ccc(NCC2(c3ncccc3F)CCC2)nn1] | 368.3 | C |
| N-({2-[6-({[(3-fluoro(2-pyridyl))cyclobutyl]methyl}amino)pyridazin-3-yl](1,3-thiazol-5-yl)}methyl)-2-methyl-2-(methylamino)propanamide | 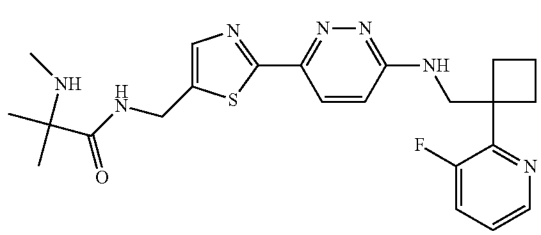 [SMILES: CNC(C)(C)C(=O)NCc1cnc(-c2ccc(NCC3(c4ncccc4F)CCC3)nn2)s1] | 470.3 | A |

TABLE 2-continued

| Compound | Structure | m/z (M + H) | Mean AC1.4 |
|---|---|---|---|
| [6-({[(3-fluoro(2-pyridyl))cyclobutyl]methyl}amino)pyridazin-3-yl]-N-(1-methylpyrazol-3-yl)carboxamide | 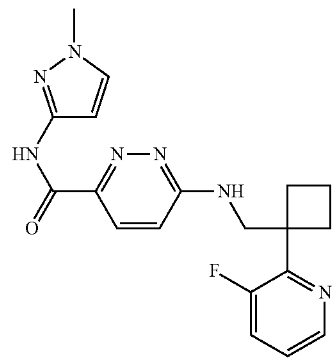 [SMILES: Cn1ccc(NC(=O)c2ccc(NCC3(c4ncccc4F)CCC3)nn2)n1] | 382.1 | C |
| N-(1H-1,2,4-triazol-5-yl)[6-({[(3-fluoro(2-pyridyl))cyclobutyl]methyl}amino)pyridazin-3-yl]carboxamide | 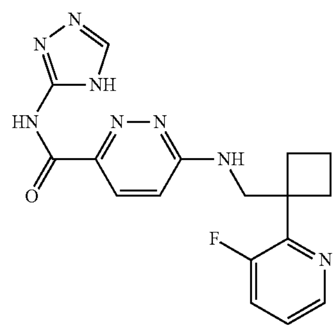 [SMILES: O=C(Nc1nnc[nH]1)c1ccc(NCC2(c3ncccc3F)CCC2)nn1] | 369.3 | D |
| N-(4-cyanoimidazol-5-yl)[6-({[(3-fluoro(2-pyridyl))cyclobutyl]methyl}amino)pyridazin-3-yl]carboxamide | 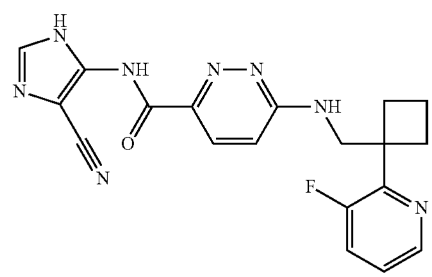 [SMILES: N#Cc1nc[nH]c1NC(=O)c1ccc(NCC2(c3ncccc3F)CCC2)nn1] | 393.3 | C |
| N-(4-cyanopyrazol-5-yl)[6-({[(3-fluoro(2-pyridyl))cyclobutyl]methyl}amino)pyridazin-3-yl]carboxamide | 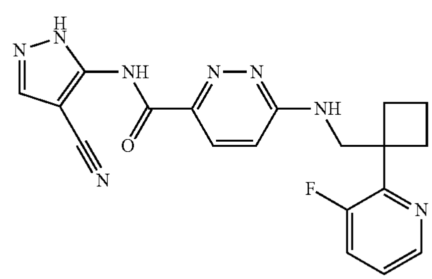 [SMILES: N#Cc1cn[nH]c1NC(=O)c1ccc(NCC2(c3ncccc3F)CCC2)nn1] | 393.3 | B |
| ethyl 4-{[6-({[(3-fluoro(2-pyridyl))cyclobutyl]methyl}amino)pyridazin-3-yl]carbonylamino}-1-methylimidazole-2-carboxylate | 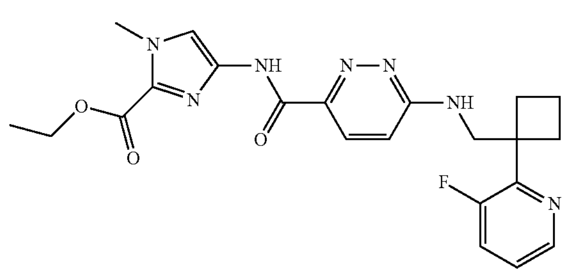 [SMILES: CCOC(=O)c1nc(NC(=O)c2ccc(NCC3(c4ncccc4F)CCC3)nn2)cn1C] | 454.3 | D |

TABLE 2-continued

| Compound | Structure | m/z (M + H) | Mean AC1.4 |
|---|---|---|---|
| ethyl 2-{[6-({[(3-fluoro-2-pyridyl)cyclobutyl]methyl}amino)pyridazin-3-yl]carbonylamino}-1,3-oxazole-4-carboxylate | 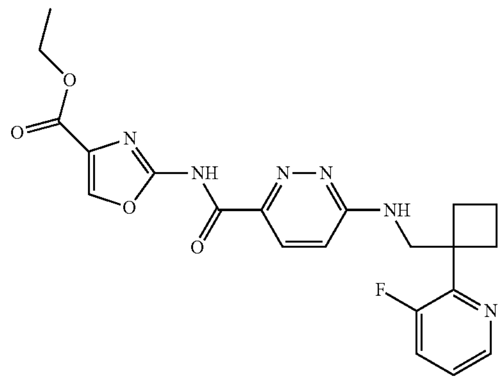 [SMILES: CCOC(=O)c1coc(NC(=O)c2ccc(NCC3(c4ncccc4F)CCC3)nn2)n1] | 441.3 | D |
| N-((3S)-2-oxopyrrolidin-3-yl)[6-({[(3-fluoro(2-pyridyl))cyclobutyl]methyl}amino)pyridazin-3-yl]carboxamide | 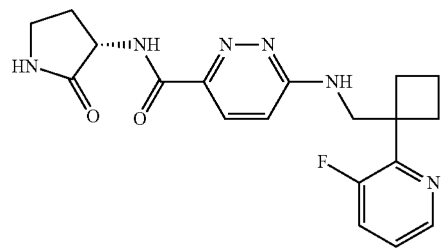 [SMILES: O=C(N[C@H]1CCNC1=O)c1ccc(NCC2(c3ncccc3F)CCC2)nn1] | 385.3 | D |
| N-((3R)-2-oxopyrrolidin-3-yl)[6-({[(3-fluoro(2-pyridyl))cyclobutyl]methyl}amino)pyridazin-3-yl]carboxamide | 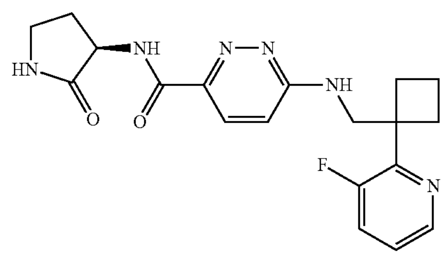 [SMILES: O=C(N[C@@H]1CCNC1=O)c1ccc(NCC2(c3ncccc3F)CCC2)nn1] | 385.3 | D |
| N-ethyl{4-fluoro-3-[6-({[3-fluoro-1-(3-fluoro(2-pyridyl))cyclobutyl]methyl}amino)pyridazin-3-yl]phenyl}carboxamide | 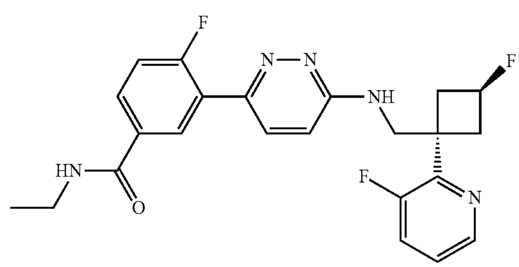 | 442.3 | B |
| N-(2-fluoroethyl){4-fluoro-3-[6-({[3-fluoro-1-(3-fluoro(2-pyridyl))cyclobutyl]methyl}amino)pyridazin-3-yl]phenyl}carboxamide | 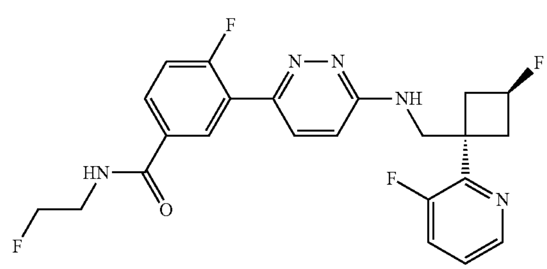 [SMILES: O=C(NCCF)c1ccc(F)c(-c2ccc(NC[C@]3(c4ncccc4F)C[C@H](F)C3)nn2)c1] | 460.3 | B |

TABLE 2-continued

| Compound | Structure | m/z (M + H) | Mean AC1.4 |
|---|---|---|---|
| N-(2,2-difluoroethyl){4-fluoro-3-[6-({[3-fluoro-1-(3-fluoro(2-pyridyl))cyclobutyl]methyl}amino)pyridazin-3-yl]phenyl}carboxamide | 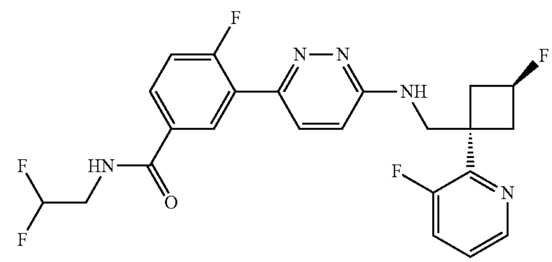 [SMILES: O=C(NCC(F)F)c1ccc(F)c(-c2ccc(NC[C@]3(c4ncccc4F)C[C@H](F)C3)nn2)c1] | 478.3 | B |
| {4-fluoro-3-[6-({[3-fluoro-1-(3-fluoro(2-pyridyl))cyclobutyl]methyl}amino)pyridazin-3-yl]phenyl}-N-(2,2,2-trifluoroethyl)carboxamide | 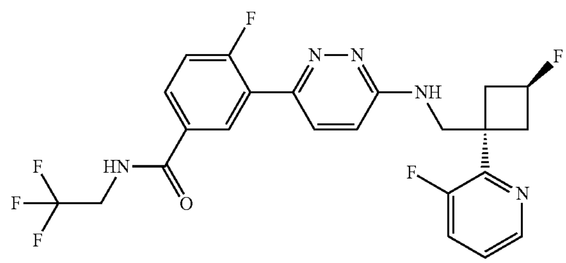 [SMILES: O=C(NCC(F)(F)F)c1ccc(F)c(-c2ccc(NC[C@]3(c4ncccc4F)C[C@H](F)C3)nn2)c1] | 496.3 | B |
| {4-fluoro-3-[6-({[3-fluoro-1-(3-fluoro(2-pyridyl))cyclobutyl]methyl}amino)pyridazin-3-yl]phenyl}-N,N-dimethylcarboxamide | 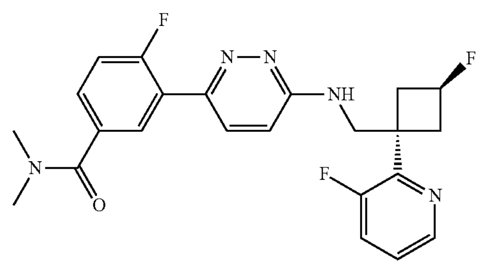 [SMILES: CN(C)C(=O)c1ccc(F)c(-c2ccc(NC[C@]3(c4ncccc4F)C[C@H](F)C3)nn2)c1] | 442.3 | B |
| 3-[6-({[(3-fluoro(2-pyridyl))cyclobutyl]methyl}amino)pyridazin-3-yl]-4-hydroxybenzoic acid | 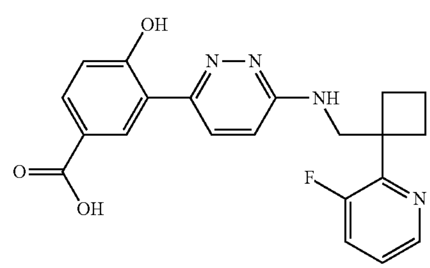 [SMILES: O=C(O)c1ccc(O)c(-c2ccc(NCC3(c4ncccc4F)CCC3)nn2)c1] | 395.2 | C |
| 2-{[6-({[(3-fluoro-2-pyridyl)cyclobutyl]methyl}amino)pyridazin-3-yl]carbonylamino}cyclopentanecarboxamide | 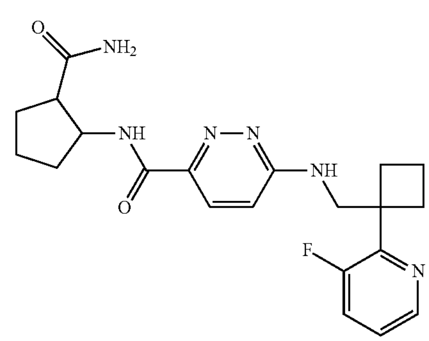 [SMILES: NC(=O)C1CCCC1NC(=O)c1ccc(NCC2(c3ncccc3F)CCC2)nn1] | 413.3 | D |

TABLE 2-continued

| Compound | Structure | m/z (M + H) | Mean AC1.4 |
|---|---|---|---|
| [6-({[(3-fluoro(2-pyridyl))cyclobutyl]methyl}amino)pyridazin-3-yl]-N-[(5-oxopyrrolidin-2-yl)methyl]carboxamide | 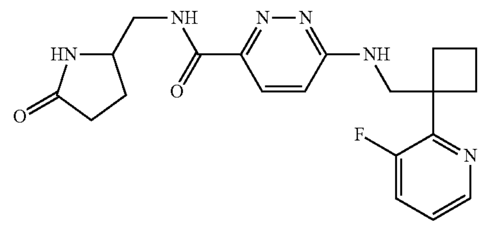 [SMILES: O=C1CCC(CNC(=O)c2ccc(NCC3(c4ncccc4F)CCC3)nn2)N1] | 399.3 | D |
| [6-({[(3-fluoro(2-pyridyl))cyclobutyl]methyl}amino)pyridazin-3-yl]-N-(2-oxo(3-piperidyl))carboxamide | 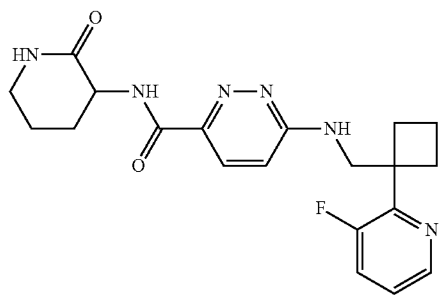 [SMILES: O=C(NC1CCCNC1=O)c1ccc(NCC2(c3ncccc3F)CCC2)nn1] | 399.3 | D |
| 4-{[6-({[(3-fluoro(2-pyridyl))cyclobutyl]methyl}amino)pyridazin-3-yl]carbonylamino}-1-methylimidazole-2-carboxamide | 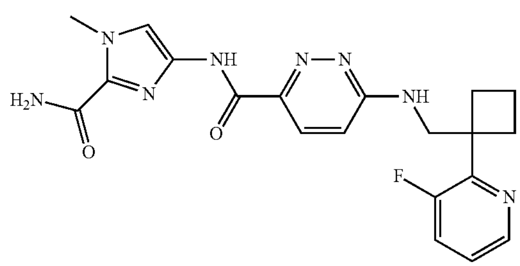 [SMILES: Cn1cc(NC(=O)c2ccc(NCC3(c4ncccc4F)CCC3)nn2)nc1C(N)=O] | 425.3 | D |
| 2-{[6-({[(3-fluoro-2-pyridyl)cyclobutyl]methyl}amino)pyridazin-3-yl]carbonylamino}-1,3-oxazole-4-carboxamide | 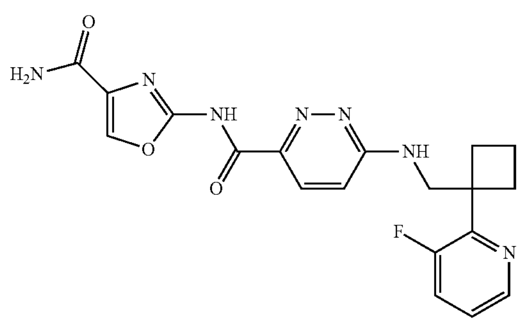 [SMILES: NC(=O)c1coc(NC(=O)c2ccc(NCC3(c4ncccc4F)CCC3)nn2)n1] | 412.3 | D |
| {3-[6-({[(3-fluoro(2-pyridyl))cyclobutyl]methyl}amino)pyridazin-3-yl]-4-hydroxyphenyl}-N-methylcarboxamide | 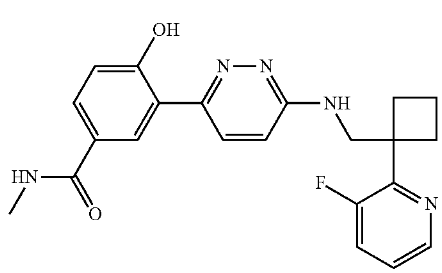 [SMILES: CNC(=O)c1ccc(O)c(-c2ccc(NCC3(c4ncccc4F)CCC3)nn2)c1] | 408.3 | B |

TABLE 2-continued

| Compound | Structure | m/z (M + H) | Mean AC1.4 |
|---|---|---|---|
| 3-[6-({[(3-fluoro(2-pyridyl))cyclobutyl]methyl}amino)pyridazin-3-yl]-4-hydroxybenzamide | 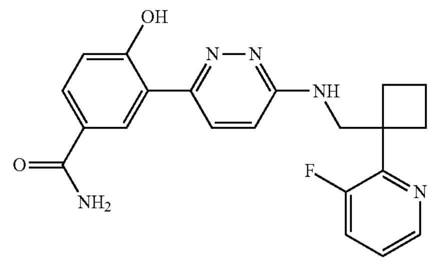 | 394.3 | B |
| 5-{[6-({[(3-fluoro-2-pyridyl)cyclobutyl]methyl}amino)pyridazin-3-yl]carbonylamino}pyrazole-4-carboxamide | 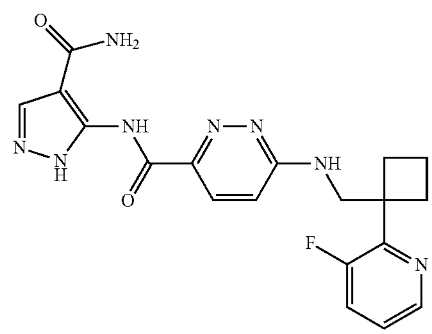 [SMILES: NC(=O)c1cn[nH]c1NC(=O)c1ccc(NCC2(c3ncccc3F)CCC2)nn1] | 411.3 | C |
| 5-[6-({[(3-fluoro(2-pyridyl))cyclobutyl]methyl}amino)pyridazin-3-yl]-2-methoxypyridine-3-carbonitrile | 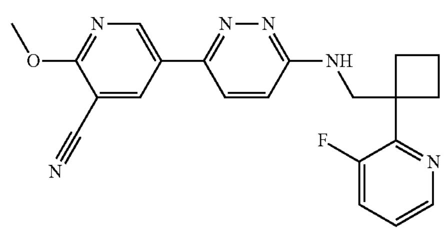 [SMILES: COc1ncc(-c2ccc(NCC3(c4ncccc4F)CCC3)nn2)cc1C#N] | 391.1 | D |
| 5-[6-({[(3-fluoro(2-pyridyl))cyclobutyl]methyl}amino)pyridazin-3-yl]-2-methoxypyridine-3-carboxamide | 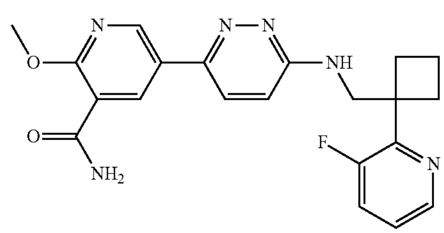 [SMILES: COc1ncc(-c2ccc(NCC3(c4ncccc4F)CCC3)nn2)cc1C(N)=O] | 409.2 | C |
| 5-[6-({[(3-fluoro(2-pyridyl))cyclobutyl]methyl}amino)pyridazin-3-yl]-2-oxohydropyridine-3-carboxylic acid | 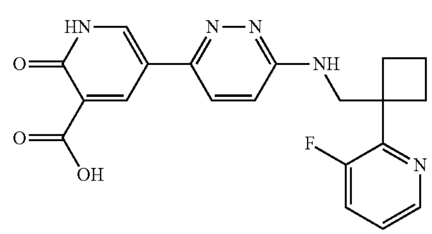 [SMILES: O=C(O)c1cc(-c2ccc(NCC3(c4ncccc4F)CCC3)nn2)c[nH]c1=O] | 396.1 | D |
| 5-[6-({[(3-fluoro(2-pyridyl))cyclobutyl]methyl}amino)pyridazin-3-yl]-2-oxohydropyridine-3-carboxamide | 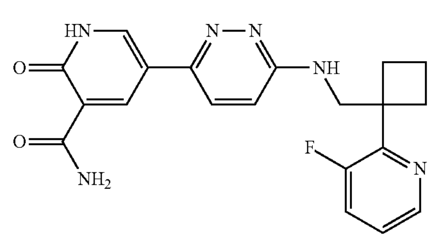 [SMILES: NC(=O)c1cc(-c2ccc(NCC3(c4ncccc4F)CCC3)nn2)c[nH]c1=O] | 395.1 | C |

TABLE 2-continued

| Compound | Structure | m/z (M + H) | Mean AC1.4 |
|---|---|---|---|
| [6-({[(3-fluoro(2-pyridyl))cyclobutyl]methyl}amino)pyridazin-3-yl]-N-(pyrazol-5-ylmethyl)carboxamide | 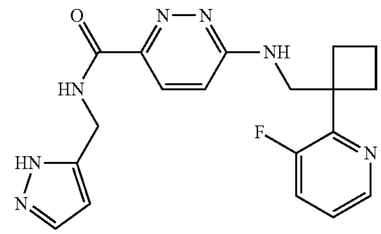 [SMILES: O=C(NCc1ccn[nH]1)c1ccc(NCC2(c3ncccc3F)CCC2)nn1] | 382.3 | D |
| [6-({[(3-fluoro(2-pyridyl))cyclobutyl]methyl}amino)pyridazin-3-yl]-N-[(1-methylpyrazol-5-yl)methyl]carboxamide | 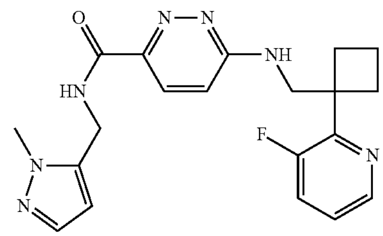 [SMILES: Cn1nccc1CNC(=O)c1ccc(NCC2(c3ncccc3F)CCC2)nn1] | 396.3 | D |
| [6-({[(3-fluoro(2-pyridyl))cyclobutyl]methyl}amino)pyridazin-3-yl]-N-[(1-methylpyrazol-3-yl)methyl]carboxamide | 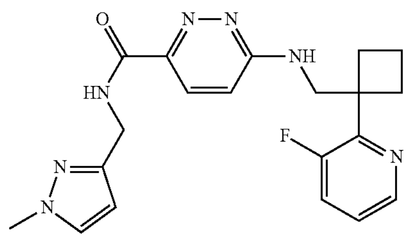 [SMILES: Cn1ccc(CNC(=O)c2ccc(NCC3(c4ncccc4F)CCC3)nn2)n1] | 396.3 | D |
| [6-({[(3-fluoro(2-pyridyl))cyclobutyl]methyl}amino)pyridazin-3-yl]-N-[(5-oxopyrrolidin-3-yl)methyl]carboxamide | 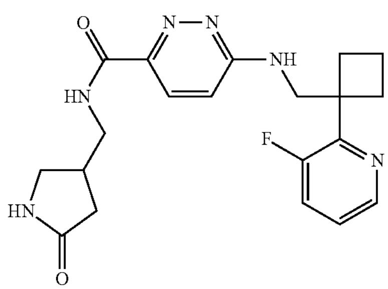 [SMILES: O=C1CC(CNC(=O)c2ccc(NCC3(c4ncccc4F)CCC3)nn2)CN1] | 385.3 | D |
| N-((3S)-6-oxo(3-piperidyl))[6-({[(3-fluoro(2-pyridyl))cyclobutyl]methyl}amino)pyridazin-3-yl]carboxamide | 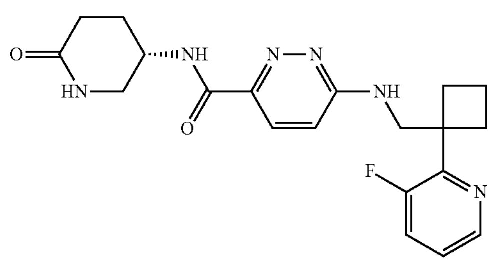 [SMILES: O=C1CC[C@H](NC(=O)c2ccc(NCC3(c4ncccc4F)CCC3)nn2)CN1] | 399.3 | D |
| N-((3R)-6-oxo(3-piperidyl))[6-({[(3-fluoro(2-pyridyl))cyclobutyl]methyl}amino)pyridazin-3-yl]carboxamide | 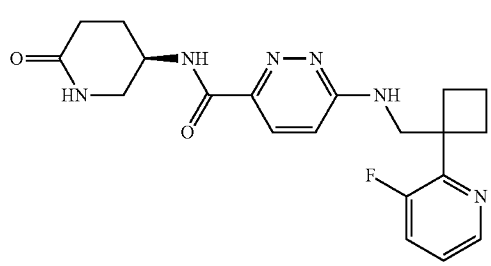 [SMILES: O=C1CC[C@@H](NC(=O)c2ccc(NCC3(c4ncccc4F)CCC3)nn2)CN1] | 399.3 | D |

TABLE 2-continued

| Compound | Structure | m/z (M + H) | Mean AC1.4 |
|---|---|---|---|
| [6-({[(3-fluoro(2-pyridyl))cyclobutyl]methyl}amino)pyridazin-3-yl]-N-(2-pyridylmethyl)carboxamide | 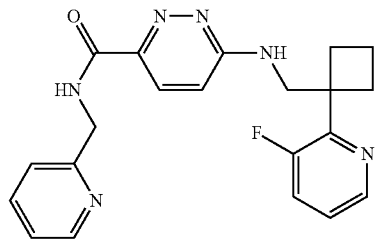 [SMILES: O=C(NCc1ccccn1)c1ccc(NCC2(c3ncccc3F)CCC2)nn1] | 393.3 | D |
| [6-({[(3-fluoro(2-pyridyl))cyclobutyl]methyl}amino)pyridazin-3-yl]-N-(3-pyridylmethyl)carboxamide | 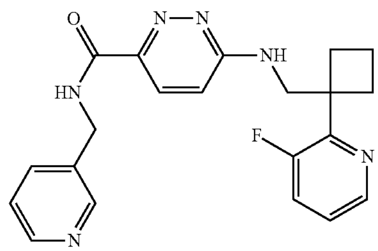 [SMILES: O=C(NCc1cccnc1)c1ccc(NCC2(c3ncccc3F)CCC2)nn1] | 393.3 | C |
| [6-({[(3-fluoro(2-pyridyl))cyclobutyl]methyl}amino)pyridazin-3-yl]-N-(4-pyridylmethyl)carboxamide | 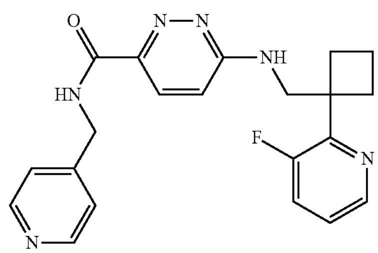 [SMILES: O=C(NCc1ccncc1)c1ccc(NCC2(c3ncccc3F)CCC2)nn1] | 393.3 | D |
| [6-({[(3-fluoro(2-pyridyl))cyclobutyl]methyl}amino)pyridazin-3-yl]-N-(1,3-thiazol-2-ylmethyl)carboxamide | 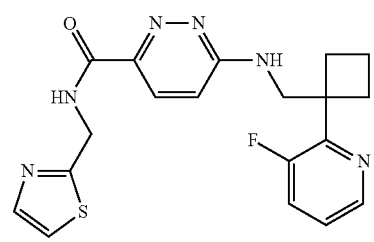 | 399.3 | D |
| [6-({[(3-fluoro(2-pyridyl))cyclobutyl]methyl}amino)pyridazin-3-yl]-N-methyl-N-(1,3-thiazol-2-ylmethyl)carboxamide | 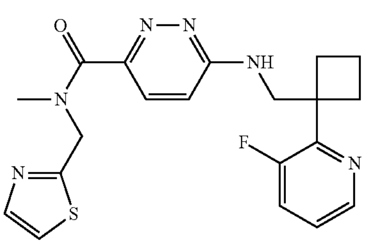 [SMILES: CN(Cc1nccs1)C(=O)c1ccc(NCC2(c3ncccc3F)CCC2)nn1] | 413.2 | D |
| ethyl 2-{[6-({[(3-fluoro-2-pyridyl)cyclobutyl]methyl}amino)pyridazin-3-yl]carbonylamino}-1,3-thiazole-5-carboxylate | 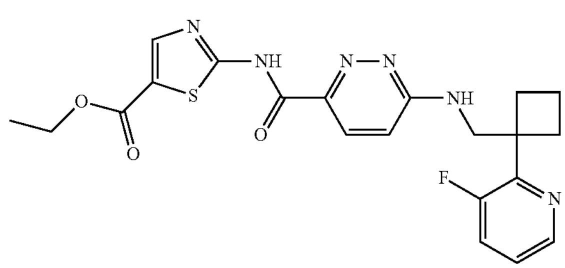 [SMILES: CCOC(=O)c1cnc(NC(=O)c2ccc(NCC3(c4ncccc4F)CCC3)nn2)s1] | 457.3 | D |

TABLE 2-continued

| Compound | Structure | m/z (M + H) | Mean AC1.4 |
|---|---|---|---|
| methyl 2-{[6-({[(3-fluoro-2-pyridyl)cyclobutyl]methyl}amino)pyridazin-3-yl]carbonylamino}-1,3-thiazole-4-carboxylate | 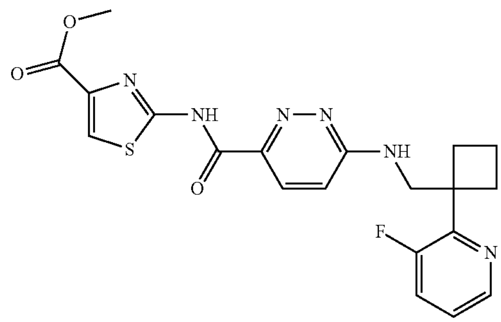 [SMILES: COC(=O)c1csc(NC(=O)c2ccc(NCC3(c4ncccc4F)CCC3)nn2)n1] | 443.2 | B |
| ethyl 2-(2-{[6-({[(3-fluoro-2-pyridyl)cyclobutyl]methyl}amino)pyridazin-3-yl]carbonylamino}-1,3-thiazol-4-yl)acetate | 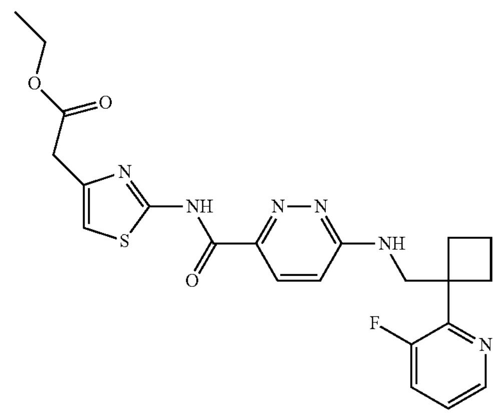 [SMILES: CCOC(=O)Cc1csc(NC(=O)c2ccc(NCC3(c4ncccc4F)CCC3)nn2)n1] | 471.3 | A |
| 5-[6-({[3-fluoro-1-(3-fluoro(2-pyridyl))cyclobutyl]methyl}amino)pyridazin-3-yl]-2-hydroxybenzoic acid | 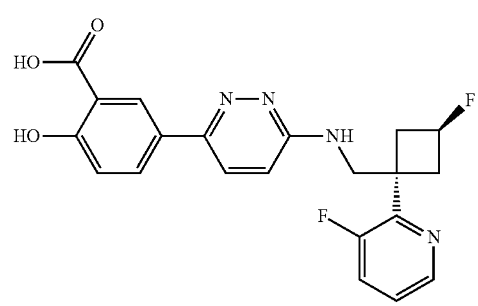 [SMILES: O=C(O)c1cc(-c2ccc(NC[C@]3(c4ncccc4F)C[C@H](F)C3)nn2)ccc1O] | 413.1 | B |
| {3-[6-({[3-fluoro-1-(3-fluoro(2-pyridyl))cyclobutyl]methyl}amino)pyridazin-3-yl]phenyl}-N-[2-hydroxy-1-(hydroxymethyl)ethyl]carboxamide | 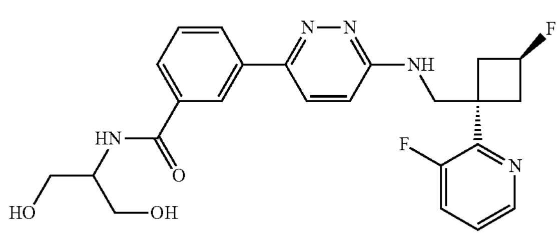 [SMILES: O=C(NC(CO)CO)c1cccc(-c2ccc(NC[C@]3(c4ncccc4F)C[C@H](F)C3)nn2)c1] | 470.2 | B |
| {5-[6-({[3-fluoro-1-(3-fluoro(2-pyridyl))cyclobutyl]methyl}amino)pyridazin-3-yl]-2-hydroxyphenyl}-N-methylcarboxamide | 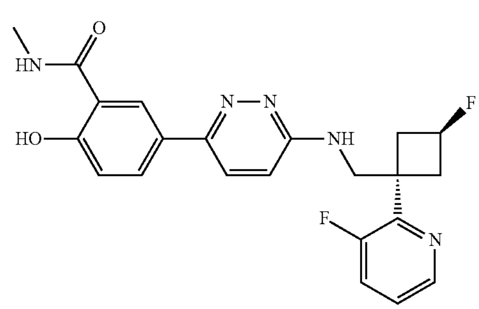 [SMILES: CNC(=O)c1cc(-c2ccc(NC[C@]3(c4ncccc4F)C[C@H](F)C3)nn2)ccc1O] | 426.1 | B |

TABLE 2-continued

| Compound | Structure | m/z (M + H) | Mean AC1.4 |
|---|---|---|---|
| 5-[6-({[3-fluoro-1-(3-fluoro(2-pyridyl))cyclobutyl]methyl}amino)pyridazin-3-yl]-2-hydroxybenzamide | 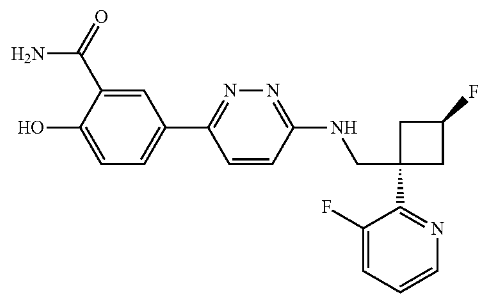 [SMILES: NC(=O)c1cc(-c2ccc(NC[C@]3(c4ncccc4F)C[C@H](F)C3)nn2)ccc1O] | 412.1 | A |
| {3-[6-({[3-fluoro-1-(3-fluoro(2-pyridyl))cyclobutyl]methyl}amino)pyridazin-3-yl]-4-hydroxyphenyl}-N-methylcarboxamide | 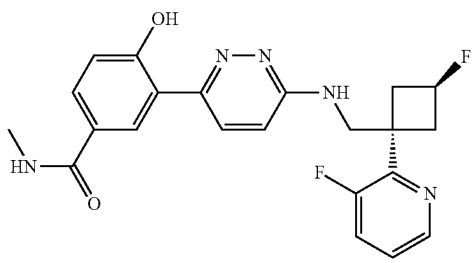 [SMILES: CNC(=O)c1ccc(O)c(-c2ccc(NC[C@]3(c4ncccc4F)C[C@H](F)C3)nn2)c1] | 426.2 | B |
| 2-{[6-({[(3-fluoro-2-pyridyl)cyclobutyl]methyl}amino)pyridazin-3-yl]carbonylamino}-1,3-thiazole-4-carboxamide | | 428.1 | A |
| {5-[6-({[(3-fluoro(2-pyridyl))cyclobutyl]methyl}amino)pyridazin-3-yl](2-thienyl)}-N-methylcarboxamide | | 398.1 | B |
| 2-[6-({[(3-fluoro-2-pyridyl)cyclobutyl]methyl}amino)pyridazin-3-yl]-4,5,6-trihydrocyclopenta[1,2-d]1,3-thiazole-4-carboxamide | 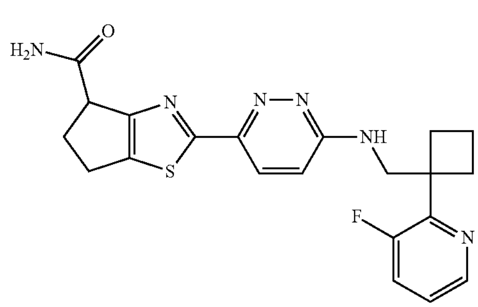 [SMILES: NC(=O)C1CCc2sc(-c3ccc(NCC4(c5ncccc5F)CCC4)nn3)nc21] | 425.3 | D |

TABLE 2-continued

| Compound | Structure | m/z (M + H) | Mean AC1.4 |
|---|---|---|---|
| 2-[6-({[(3-fluoro-2-pyridyl)cyclobutyl]methyl}amino)pyridazin-3-yl]-4,5,6-trihydrocyclopenta[1,2-d]1,3-thiazole-4-carboxylic acid | 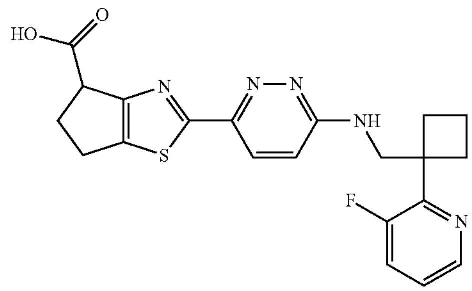 [SMILES: O=C(O)C1CCc2sc(-c3ccc(NCC4(c5ncccc5F)CCC4)nn3)nc21] | 426.3 | D |
| {[(3-fluoro(2-pyridyl))cyclobutyl]methyl}(6-(4,5,6,7-tetrahydro-1,3-thiazolo[5,4-c]pyridin-2-yl)pyridazin-3-yl)amine | 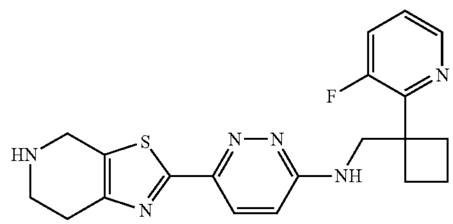 [SMILES: Fc1cccnc1C1(CNc2ccc(-c3nc4c(s3)CNCC4)nn2)CCC1] | 397.5 | D |
| N-{2-[6-({[(3-fluoro(2-pyridyl))cyclobutyl]methyl}amino)pyridazin-3-yl](4,5,6-trihydrocyclopenta[2,3-d]1,3-thiazol-4-yl)}methoxycarboxamide | 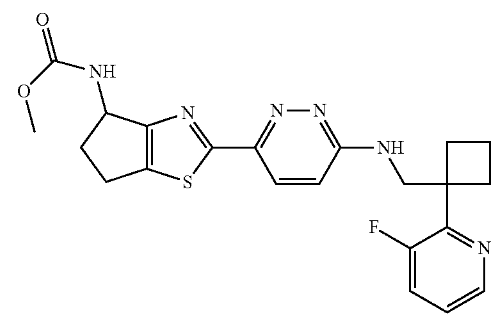 [SMILES: COC(=O)NC1CCc2sc(-c3ccc(NCC4(c5ncccc5F)CCC4)nn3)nc21] | 455.1 | D |
| 2-[6-({[(3-fluoro-2-pyridyl)cyclobutyl]methyl}amino)pyridazin-3-yl]-4,5,6,7-tetrahydro-1,3-thiazolo[5,4-c]pyridine-5-carboxamide | 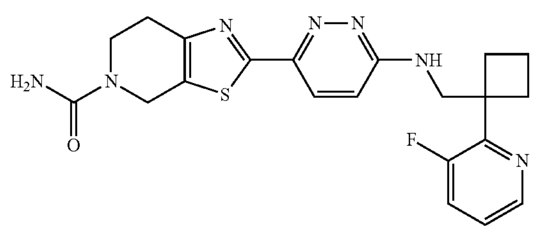 [SMILES: NC(=O)N1CCc2nc(-c3ccc(NCC4(c5ncccc5F)CCC4)nn3)sc2C1] | 440.1 | D |
| 5-acetyl-2-[6-({[(3-fluoro(2-pyridyl))cyclobutyl]methyl}amino)pyridazin-3-yl]-4,5,6,7-tetrahydro-1,3-thiazolo[5,4-c]pyridine | 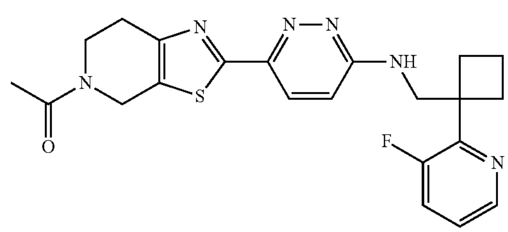 [SMILES: CC(=O)N1CCc2nc(-c3ccc(NCC4(c5ncccc5F)CCC4)nn3)sc2C1] | 439.3 | D |
| 2-[6-({[(3-fluoro(2-pyridyl))cyclobutyl]methyl}amino)pyridazin-3-yl]-5-(methylsulfonyl)-4,5,6,7-tetrahydro-1,3-thiazolo(5,4-c]pyridine | 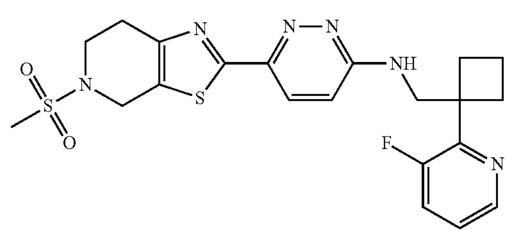 [SMILES: CS(=O)(=O)N1CCc2nc(-c3ccc(NCC4(c5ncccc5F)CCC4)nn3)sc2C1] | 475.3 | D |

TABLE 2-continued

| Compound | Structure | m/z (M + H) | Mean AC1.4 |
|---|---|---|---|
| {5-[6-({[3-fluoro-1-(3-fluoro(2-pyridyl))cyclobutyl]methyl}amino)pyridazin-3-yl]-2-hydroxyphenyl}-N,N-dimethylcarboxamide | 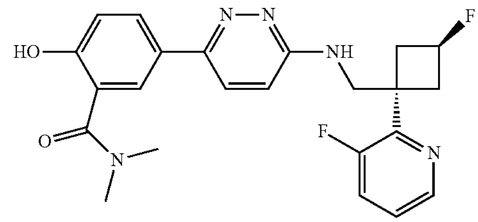 [SMILES: CN(C)C(=O)c1cc(-c2ccc(NC[C@]3(c4ncccc4F)C[C@H](F)C3)nn2)ccc1O] | 440.1 | B |
| 4-[6-({[3-fluoro-1-(3-fluoro(2-pyridyl))cyclobutyl]methyl}amino)pyridazin-3-yl]isoindolin-1-one | | 408.1 | B |
| 5-[6-({[3-fluoro-1-(3-fluoro(2-pyridyl))cyclobutyl]methyl}amino)pyridazin-3-yl]isoindolin-1-one | 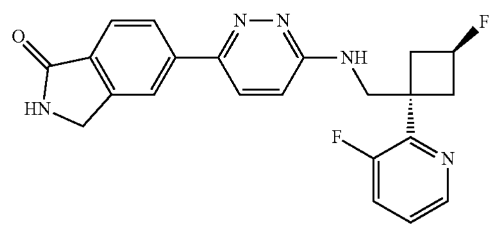 [SMILES: O=C1NCc2cc(-c3ccc(NC[C@]4(c5ncccc5F)C[C@H](F)C4)nn3)ccc21] | 408.1 | C |
| 6-[6-({[3-fluoro-1-(3-fluoro(2-pyridyl))cyclobutyl]methyl}amino)pyridazin-3-yl]isoindolin-1-one | | 408.1 | B |
| [6-(6-amino(4,5,6,7-tetrahydrobenzothiazol-2-yl))pyridazin-3-yl]{[(3-fluoro(2-pyridyl))cyclobutyl]methyl}amine | 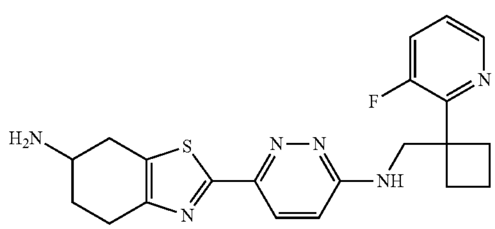 [SMILES: NC1CCc2nc(-c3ccc(NCC4(c5ncccc5F)CCC4)nn3)sc2C1] | 411.5 | D |
| amino-N-{2-[6-({[(3-fluoro(2-pyridyl))cyclobutyl]methyl}amino)pyridazin-3-yl](4,5,6,7-tetrahydrobenzothiazol-6-yl)}amide | 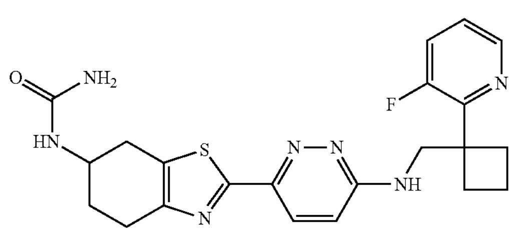 [SMILES: NC(=O)NC1CCc2nc(-c3ccc(NCC4(c5ncccc5F)CCC4)nn3)sc2C1] | 454.3 | D |

TABLE 2-continued

| Compound | Structure | m/z (M + H) | Mean AC1.4 |
|---|---|---|---|
| N-{3-fluoro-4-[6-({[3-fluoro-1-(3-fluoro(2-pyridyl))cyclobutyl]methyl}amino)pyridazin-3-yl]phenyl}(methylamino)carboxamide | 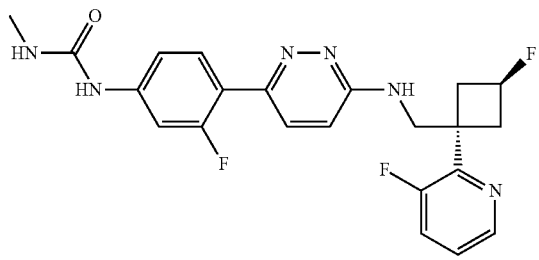 | 443.3 | A |
| N-{4-[6-({[3-fluoro-1-(3-fluoro(2-pyridyl))cyclobutyl]methyl}amino)pyridazin-3-yl]phenyl}-N-methyl(methylamino)carboxamide | 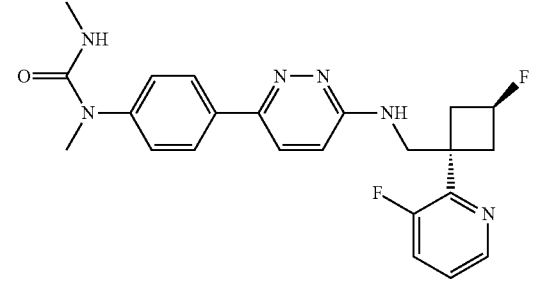 [SMILES: CNC(=O)N(C)c1ccc(-c2ccc(NC[C@]3(c4ncccc4F)C[C@H](F)C3)nn2)cc1] | 439.3 | D |
| N-[4-(carbamoylmethyl)(1,3-thiazol-2-yl)][6-({[(3-fluoro(2-pyridyl))cyclobutyl]methyl}amino)pyridazin-3-yl]carboxamide | 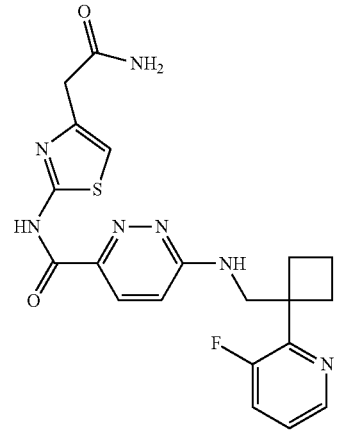 [SMILES: NC(=O)Cc1csc(NC(=O)c2ccc(NCC3(c4ncccc4F)CCC3)nn2)n1] | 442.1 | A |
| 2-(2-{[6-({[(3-fluoro(2-pyridyl))cyclobutyl]methyl}amino)pyridazin-3-yl]carbonylamino}(1,3-thiazol-4-yl))-N-methylacetamide | 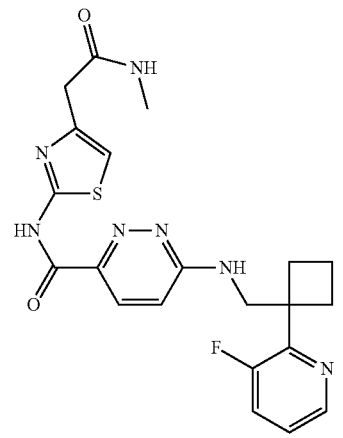 [SMILES: CNC(=O)Cc1csc(NC(=O)c2ccc(NCC3(c4ncccc4F)CCC3)nn2)n1] | 456.2 | A |

TABLE 2-continued

| Compound | Structure | m/z (M + H) | Mean AC1.4 |
|---|---|---|---|
| 2-{2-[6-({[1-(3-chloro(2-pyridyl))-3-fluorocyclobutyl]methyl}amino)pyridazin-3-yl](1,3-thiazol-5-yl)}-N-methylacetamide | 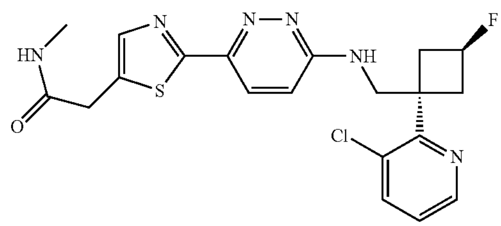 [SMILES: CNC(=O)Cc1cnc(-c2ccc(NC[C@]3(c4ncccc4Cl)C[C@H](F)C3)nn2)s1] | 447.3 | B |
| 3-{6-[4-(3-fluoro(2-pyridyl))-2-azabicyclo[2.1.1]hex-2-yl]pyridazin-3-yl}-4-hydroxybenzamide | 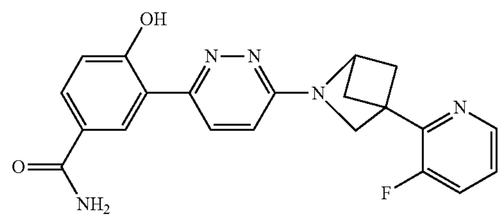 [SMILES: NC(=O)c1ccc(O)c(-c2ccc(N3CC4(c5ncccc5F)CC3C4)nn2)c1] | 392.1 | D |
| ethyl 2-(5-{[6-({[(3-fluoro-2-pyridyl)cyclobutyl]methyl}amino)pyridazin-3-yl]carbonylamino}-1,3,4-thiadiazol-2-yl)acetate | 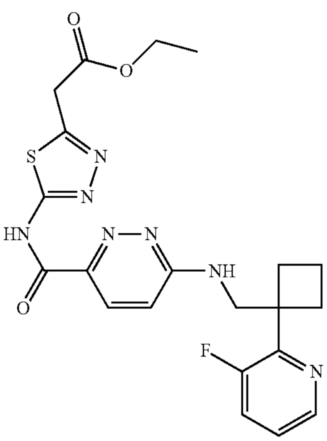 [SMILES: CCOC(=O)Cc1nnc(NC(=O)c2ccc(NCC3(c4ncccc4F)CCC3)nn2)s1] | 472.3 | D |
| N-[5-(carbamoylmethyl)(1,3,4-thiadiazol-2-yl)][6-({[(3-fluoro(2-pyridyl))cyclobutyl]methyl}amino)pyridazin-3-yl]carboxamide | 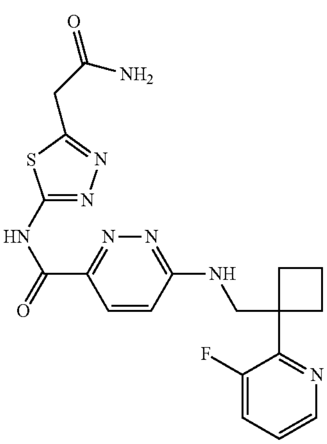 [SMILES: NC(=O)Cc1nnc(NC(=O)c2ccc(NCC3(c4ncccc4F)CCC3)nn2)s1] | 443.2 | D |
| N-{4-[6-({[3-fluoro-1-(3-fluoro(2-pyridyl))cyclobutyl]methyl}amino)pyridazin-3-yl]phenyl}(methylamino)carboxamide | 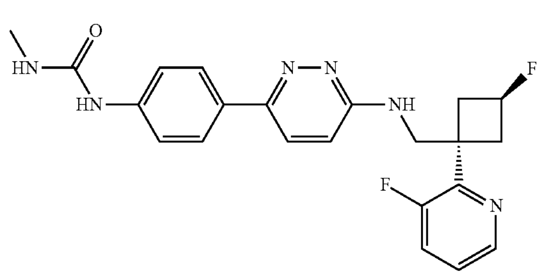 [SMILES: CNC(=O)Nc1ccc(-c2ccc(NC[C@]3(c4ncccc4F)C[C@H](F)C3)nn2)cc1] | 425.3 | A |

TABLE 2-continued

| Compound | Structure | m/z (M + H) | Mean AC1.4 |
|---|---|---|---|
| 2-{2-[6-({[(3-chloro(2-pyridyl))cyclobutyl]methyl}amino)pyridazin-3-yl](1,3-thiazol-5-yl)}-N-methylacetamide | | 429.2 | A |
| N-cyclopropyl{4-fluoro-3-[6-({[3-fluoro-1-(3-fluoro(2-pyridyl))cyclobutyl]methyl}amino)pyridazin-3-yl]phenyl}carboxamide | | 454.3 | A |
| 5-[6-({[(3-fluoro-2-pyridyl)cyclobutyl]methyl}amino)pyridazin-3-yl]-8-hydro-3-pyrazolino[1,5-a]pyrimidin-7-one | | 392.1 | B |
| 7-[6-({[(3-fluoro-2-pyridyl)cyclobutyl]methyl}amino)pyridazin-3-yl]-4-hydro-4-imidazolino[1,2-a]pyrimidin-5-one | | 392.3 | B |
| {4-fluoro-5-[6-({[3-fluoro-1-(3-fluoro(2-pyridyl))cyclobutyl]methyl}amino)pyridazin-3-yl]-2-hydroxyphenyl}-N-methylcarboxamide | | 444.1 | A |

TABLE 2-continued

| Compound | Structure | m/z (M + H) | Mean AC1.4 |
|---|---|---|---|
| 4-fluoro-5-[6-({[3-fluoro-1-(3-fluoro(2-pyridyl))cyclobutyl]methyl}amino)pyridazin-3-yl]-2-hydroxybenzamide | 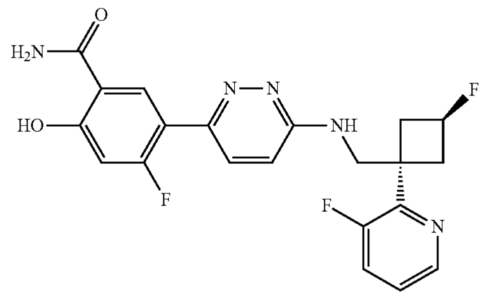 [SMILES: NC(=O)c1cc(-c2ccc(NC[C@]3(c4ncccc4F)C[C@H](F)C3)nn2)c(F)cc1O] | 430.1 | A |
| 3-[6-({[(3-fluoro(2-pyridyl))cyclobutyl]methyl}amino)pyridazin-3-yl]-4-methyl-3-pyrazolin-5-one | 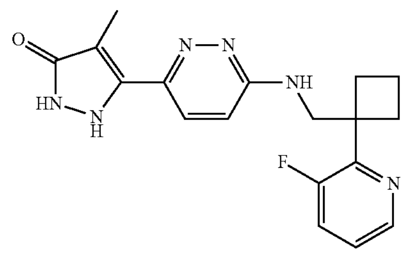 [SMILES: Cc1c(-c2ccc(NCC3(c4ncccc4F)CCC3)nn2)[nH][nH]c1=O] | 355.1 | D |
| 3-[6-({[(3-fluoro(2-pyridyl))cyclobutyl]methyl}amino)pyridazin-3-yl]-4,4-dimethyl-2-pyrazolin-5-one | 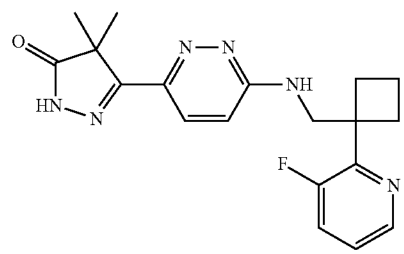 [SMILES: CC1(C)C(=O)NN=C1c1ccc(NCC2(c3ncccc3F)CCC2)nn1] | 369.2 | D |
| {[(3-fluoro(2-pyridyl))cyclobutyl]methyl}[6-benzylpyridazin-3-yl]amine | 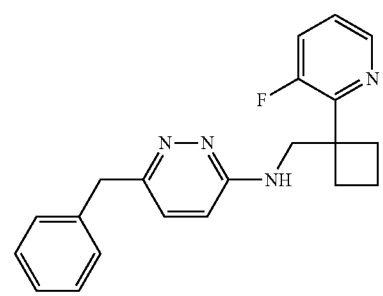 [SMILES: Fc1cccnc1C1(CNc2ccc(Cc3ccccc3)nn2)CCC1] | 349.3 | D |
| 3-[6-({[(3-fluoro(2-pyridyl))cyclobutyl]methyl}amino)-4-methylpyridazin-3-yl]benzenecarbonitrile | 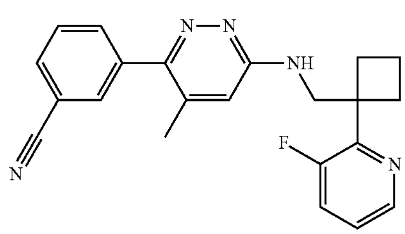 [SMILES: Cc1cc(NCC2(c3ncccc3F)CCC2)nnc1-c1cccc(C#N)c1] | 374.1 | C |
| 3-[6-({[(3-fluoro(2-pyridyl))cyclobutyl]methyl}amino)-4-methylpyridazin-3-yl]benzamide | 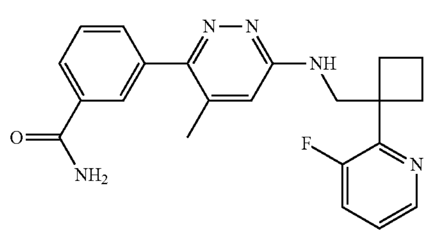 [SMILES: Cc1cc(NCC2(c3ncccc3F)CCC2)nnc1-c1cccc(C(N)=O)c1] | 392.1 | C |

TABLE 2-continued

| Compound | Structure | m/z (M + H) | Mean AC1.4 |
|---|---|---|---|
| N-cyclobutyl{4-fluoro-3-[6-({[3-fluoro-1-(3-fluoro(2-pyridyl))cyclobutyl]methyl}amino)pyridazin-3-yl]phenyl}carboxamide | 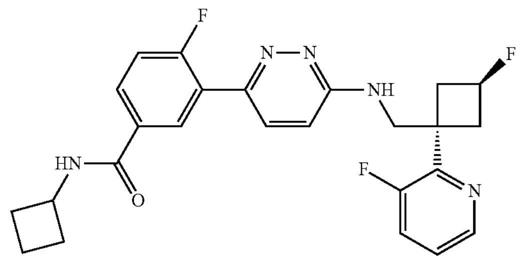 [SMILES: O=C(NC1CCC1)c1ccc(F)c(-c2ccc(NC[C@]3(c4ncccc4F)C[C@H](F)C3)nn2)c1] | 468.3 | A |
| 4-fluoro-3-[6-({[(3-fluoro(2-pyridyl))cyclobutyl]methyl}amino)-4-methylpyridazin-3-yl]benzamide | 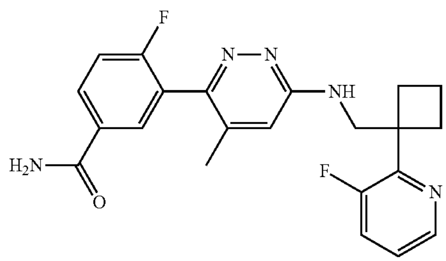 [SMILES: Cc1cc(NCC2(c3ncccc3F)CCC2)nnc1-c1cc(C(N)=O)ccc1F] | 410.1 | C |
| N-(3,3-difluorocyclobutyl){4-fluoro-3-[6-({[3-fluoro-1-(3-fluoro(2-pyridyl))cyclobutyl]methyl}amino)pyridazin-3-yl]phenyl}carboxamide | 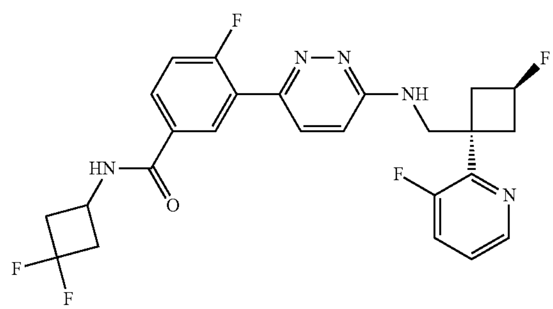 [SMILES: O=C(NC1CC(F)(F)C1)c1ccc(F)c(-c2ccc(NC[C@]3(c4ncccc4F)C[C@H](F)C3)nn2)c1] | 504.3 | A |
| 4-fluoro-3-[6-({[3-fluoro-1-(3-fluoro(2-pyridyl))cyclobutyl]methyl}amino)pyridazin-3-yl]-2-hydroxybenzamide | 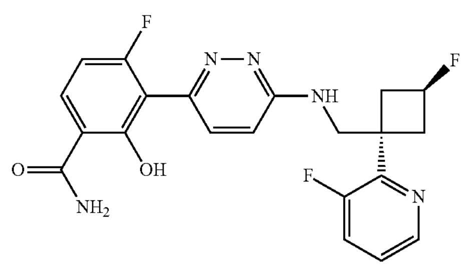 [SMILES: NC(=O)c1ccc(F)c(-c2ccc(NC[C@]3(c4ncccc4F)C[C@H](F)C3)nn2)c1O] | 430.0 | A |
| 2-[6-({[(3-fluoro(2-pyridyl))cyclobutyl]methyl}amino)-4-methylpyridazin-3-yl]-1,3-thiazole-5-carboxamide | 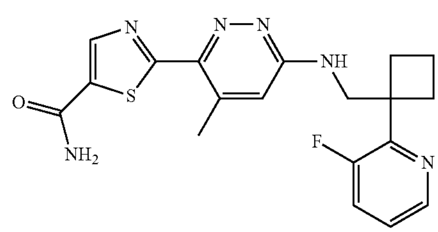 [SMILES: Cc1cc(NCC2(c3ncccc3F)CCC2)nnc1-c1ncc(C(N)=O)s1] | 399.1 | A |
| 3-[6-({[(3-fluoro(2-pyridyl))cyclobutyl]methyl}amino)-5-methylpyridazin-3-yl]benzamide | 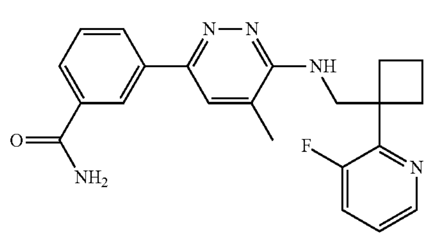 [SMILES: Cc1cc(-c2cccc(C(N)=O)c2)nnc1NCC1(c2ncccc2F)CCC1] | 392.1 | D |

TABLE 2-continued

| Compound | Structure | m/z (M + H) | Mean AC1.4 |
|---|---|---|---|
| N-cyclopropyl{3-[6-({[3-fluoro-1-(3-fluoro(2-pyridyl))cyclobutyl]methyl}amino)pyridazin-3-yl]phenyl}carboxamide | 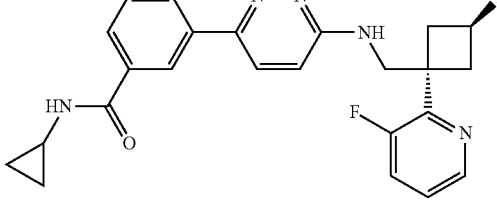 | 436.3 | B |
| [6-(2-aminopyrimidin-5-yl)pyridazin-3-yl]{[3-fluoro-1-(3-fluoro(2-pyridyl))cyclobutyl]methyl}amine | 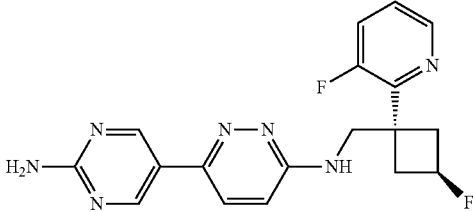 [SMILES: Nc1ncc(-c2ccc(NC[C@]3(c4ncccc4F)C[C@H](F)C3)nn2)cn1] | 370.1 | B |
| N-azetidin-3-yl{3-[6-({[3-fluoro-1-(3-fluoro(2-pyridyl))cyclobutyl]methyl}amino)pyridazin-3-yl]phenyl}carboxamide | 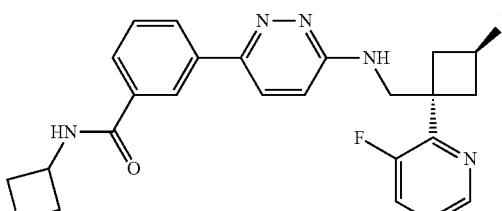 | 451.2 | B |
| N-(1-acetylazetidin-3-yl){3-[6-({[3-fluoro-1-(3-fluoro(2-pyridyl))cyclobutyl]methyl}amino)pyridazin-3-yl]phenyl}carboxamide | 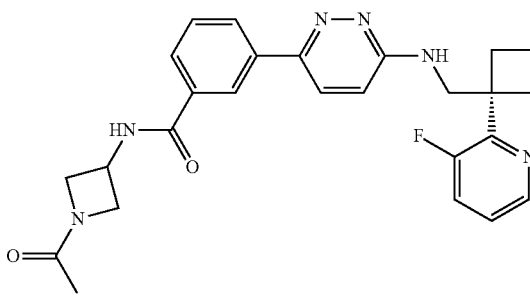 | 493.3 | B |
| {3-[6-({[3-fluoro-1-(3-fluoro(2-pyridyl))cyclobutyl]methyl}amino)pyridazin-3-yl]phenyl}-N-[1-(methylsulfonyl)azetidin-3-yl]carboxamide | 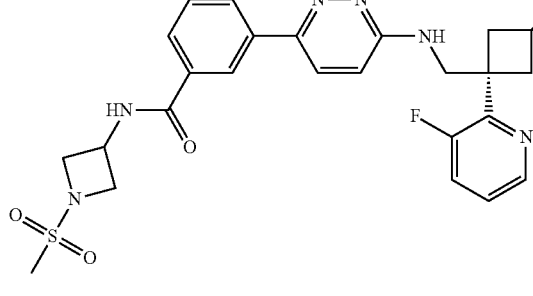 | 529.3 | B |
| {3-(6-({[3-fluoro-1-(3-fluoro(2-pyridyl))cyclobutyl]methyl}amino)pyridazin-3-yl]phenyl}-N-(2-hydroxy-2-methylpropyl)carboxamide | 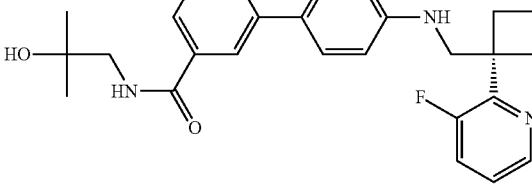 | 468.3 | B |

TABLE 2-continued

| Compound | Structure | m/z (M + H) | Mean AC1.4 |
|---|---|---|---|
| {3-[6-({[3-fluoro-1-(3-fluoro(2-pyridyl))cyclobutyl]methyl}amino)pyridazin-3-yl]phenyl}-N-(1-methylazetidin-3-yl)carboxamide | 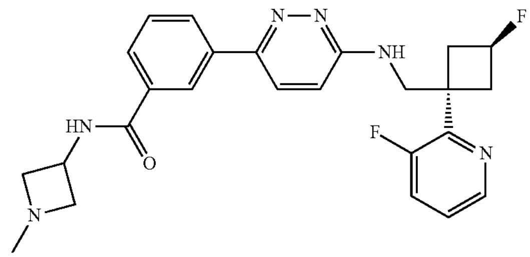 [SMILES: CN1CC(NC(=O)c2cccc(-c3ccc(NC[C@]4(c5ncccc5F)C[C@H](F)C4)nn3)c2)C1] | 465.3 | B |
| {3-[6-({[3-fluoro-1-(3-fluoro(2-pyridyl))cyclobutyl]methyl}amino)pyridazin-3-yl]phenyl}-N-oxetan-3-ylcarboxamide | 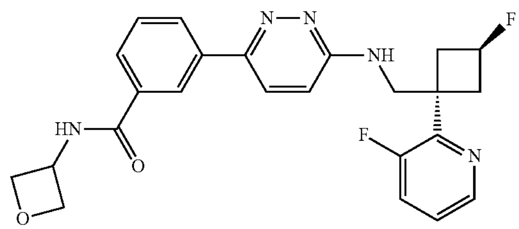 [SMILES: O=C(NC1COC1)c1cccc(-c2ccc(NC[C@]3(c4ncccc4F)C[C@H](F)C3)nn2)c1] | 452.3 | B |
| 2-{2-[6-({[(3-fluoro(2-pyridyl))cyclobutyl]methyl}amino)-4-methylpyridazin-3-yl]-1,3-thiazol-5-yl}acetic acid | 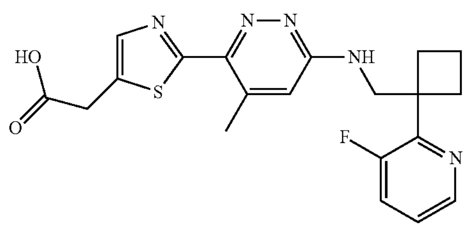 [SMILES: Cc1cc(NCC2(c3ncccc3F)CCC2)nnc1-c1ncc(CC(=O)O)s1] | 414.1 | B |
| {2-[6-({[(3-fluoro(2-pyridyl))cyclobutyl]methyl}amino)-4-methylpyridazin-3-yl]-1,3-thiazol-5-yl}methan-1-ol | 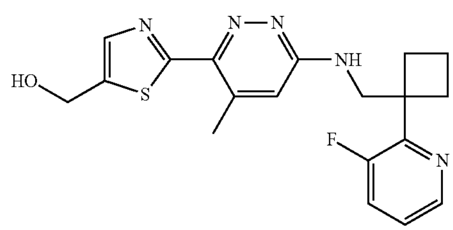 [SMILES: Cc1cc(NCC2(c3ncccc3F)CCC2)nnc1-c1ncc(CO)s1] | 386.1 | B |
| 2-{2-[6-({[(3-fluoro(2-pyridyl))cyclobutyl]methyl}amino)-4-methylpyridazin-3-yl](1,3-thiazol-5-yl)}-N-methylacelamide | 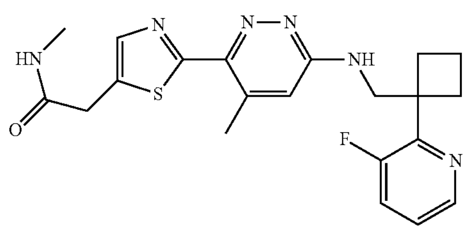 | 427.2 | B |
| 2-{2-[6-({[(3-fluoro(2-pyridyl))cyclobutyl]methyl}amino)-4-methylpyridazin-3-yl]-1,3-thiazol-5-yl}acetamide | 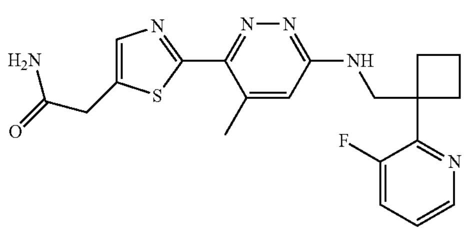 [SMILES: Cc1cc(NCC2(c3ncccc3F)CCC2)nnc1-c1ncc(CC(N)=O)s1] | 413.1 | B |

TABLE 2-continued

| Compound | Structure | m/z (M + H) | Mean AC1.4 |
|---|---|---|---|
| {4-fluoro-3-[6-({[3-fluoro-1-(3-ftuoro(2-pyridyl))cyclobutyl]methyl}amino)pyridazin-3-yl]phenyl}-N-(1-methylazetidin-3-yl)carboxamide | | 483.3 | B |
| N-(1-acetylazetidin-3-yl){4-fluoro-3-[6-({[3-fluoro-1-(3-fluoro(2-pyridyl))cyclobutyl]methyl}amino)pyridazin-3-yl]phenyl}carboxamide | 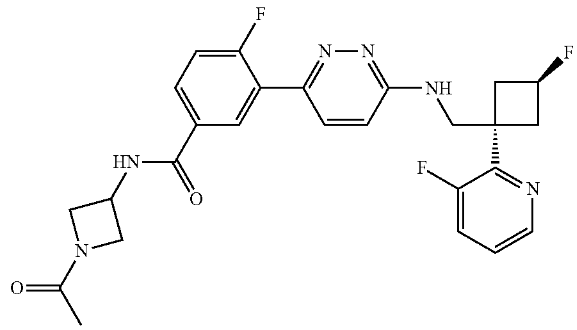 [SMILES: CC(=O)N1CC(NC(=O)c2ccc(F)c(-c3ccc(NC[C@]4(c5ncccc5F)C[C@H](F)C4)nn3)c2)C1] | 511.3 | A |
| {3-[6-({[3-fluoro-1-(3-fluoro(2-pyridyl))cyclobutyl]methyl}amino)pyridazin-3-yl]phenyl}-N-(3-hydroxycyclobutyl)carboxamide | 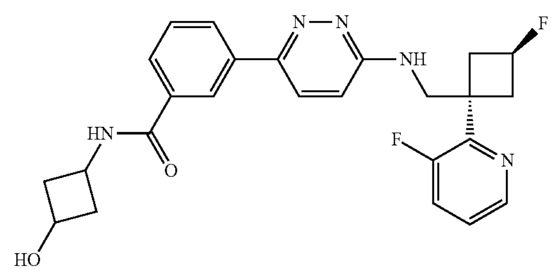 [SMILES: O=C(NC1CC(O)C1)c1cccc(-c2ccc(NC[C@]3(c4ncccc4F)C[C@H](F)C3)nn2)c1] | 466.3 | B |
| {[(3-fluoro(2-pyridyl))cyclobulyl]methyl}{6-[5-(piperazinylmethyl)(1,3-thiazol-2-yl)]pyridazin-3-yl}amine | 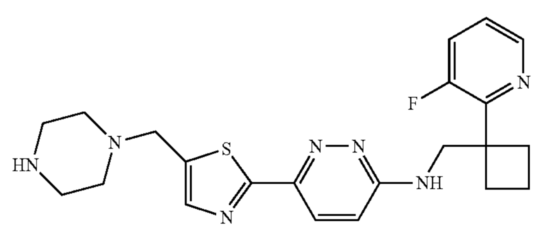 [SMILES: Fc1cccnc1C1(CNc2ccc(-c3ncc(CN4CCNCC4)s3)nn2)CCC1] | 440.3 | B |
| {[(3-fluoro(2-pyridyl))cyclobutyl]methyl}{6-[5-(morpholin-4-ylmethyl)(1,3-thiazol-2-yl)]pyridazin-3-yl}amine | 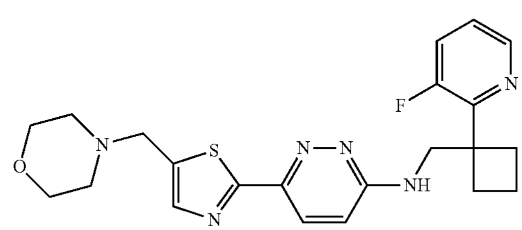 [SMILES: Fc1cccnc1C1(CNc2ccc(-c3ncc(CN4CCOCC4)s3)nn2)CCC1] | 441.3 | B |
| 4-({2-[6-({[(3-fluoro-2-pyridyl)cyclobutyl]methyl}amino)pyridazin-3-yl]-1,3-thiazol-5-yl}methyl)-1,4-thiazaperhydroine-1,1-dione | 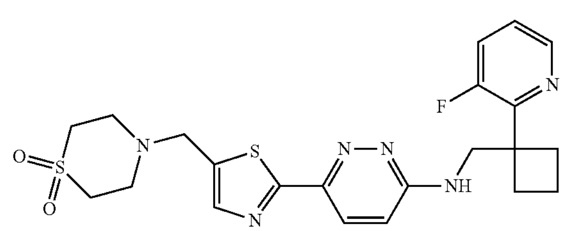 [SMILES: O=S1(=O)CCN(Cc2cnc(-c3ccc(NCC4(c5ncccc5F)CCC4)nn3)s2)CC1] | 489.3 | D |

TABLE 2-continued

| Compound | Structure | m/z (M + H) | Mean AC1.4 |
|---|---|---|---|
| {[(3-fluoro(2-pyridyl))cyclobutyl]methyl}(6-{5-[(4-methylpiperazinyl)methyl](1,3-thiazol-2-yl)}pyridazin-3-yl)amine | 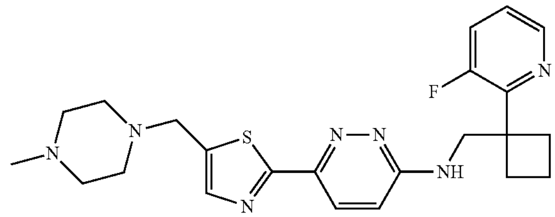 [SMILES: CN1CCN(Cc2cnc(-c3ccc(NCC4(c5ncccc5F)CCC4)nn3)s2)CC1] | 454.3 | B |
| {[(3-fluoro(2-pyridyl))cyclobutyl]methyl}[6-(5-{[4-(2,2,2-trifluoroethyl)piperazinyl]methyl}(1,3-thiazol-2-yl))pyridazin-3-yl]amine | 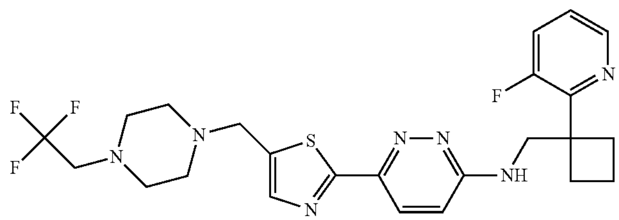 [SMILES: Fc1cccnc1C1(CNc2ccc(-c3ncc(CN4CCN(CC(F)(F)F)CC4)s3)nn2)CCC1] | 522.2 | B |
| 1-acetyl-4-({2-[6-({[(3-fluoro(2-pyridyl))cyclobutyl]methyl}amino)pyridazin-3-yl](1,3-thiazol-5-yl)}methyl)piperazine | 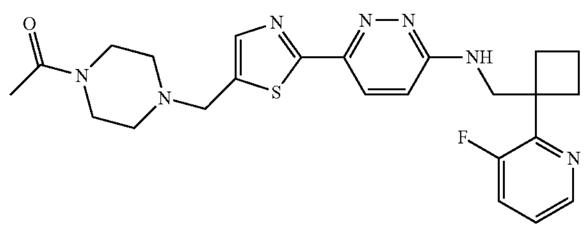 [SMILES: CC(=O)N1CCN(Cc2cnc(-c3ccc(NCC4(c5ncccc5F)CCC4)nn3)s2)CC1] | 482.3 | D |
| 1-({2-[6-({[(3-fluoro(2-pyridyl))cyclobutyl]methyl}amino)pyridazin-3-yl](1,3-thiazol-5-yl)}methyl)-4-(methylsulfonyl)piperazine | 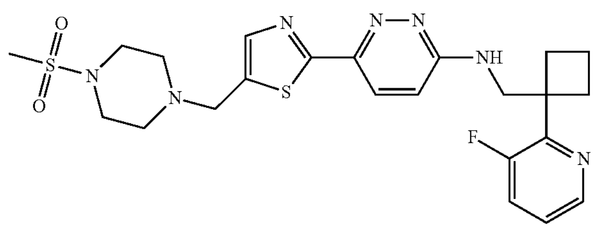 [SMILES: CS(=O)(=O)N1CCN(Cc2cnc(-c3ccc(NCC4(c5ncccc5F)CCC4)nn3)s2)CC1] | 518.3 | D |
| [(2S)-1-({2-[6-({[(3-fluoro(2-pyridyl))cyclobutyl]methyl}amino)pyridazin-3-yl](1,3-thiazol-5-yl)}methyl)piperazin-2-yl]methan-1-ol | 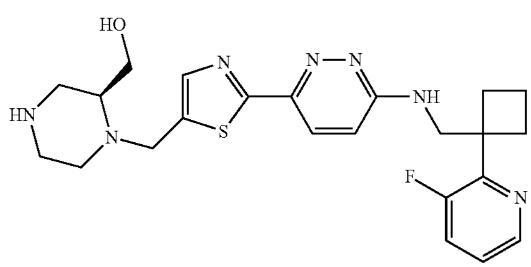 [SMILES: OC[C@@H]1CNCCN1Cc1cnc(-c2ccc(NCC3(c4ncccc4F)CCC3)nn2)s1] | 470.3 | B |
| [(2R)-1-({2-[6-({[(3-fluoro(2-pyridyl))cyclobutyl]methyl}amino)pyridazin-3-yl](1,3-thiazol-5-yl)}methyl)piperazin-2-yl]methan-1-ol | | 470.3 | C |

TABLE 2-continued

| Compound | Structure | m/z (M + H) | Mean AC1.4 |
|---|---|---|---|
| N-(2H-3,4,5,6-tetrahydropyran-4-yl){3-[6-({[3-fluoro-1-(3-fluoro(2-pyridyl))cyclobutyl]methyl}amino)pyridazin-3-yl]phenyl}carboxamide | 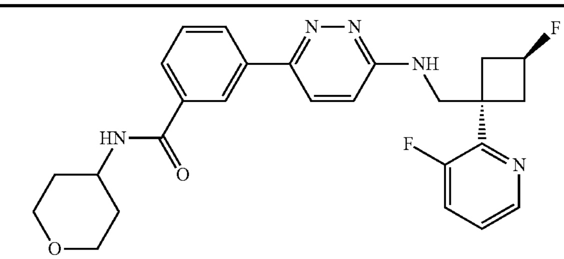 | 480.3 | B |
| {3-[6-({[3-fluoro-1-(3-fluoro(2-pyridyl))cyclobutyl]methyl}amino)pyridazin-3-yl]phenyl}-N-(3-hydroxy-3-methylcyclobutyl)carboxamide | 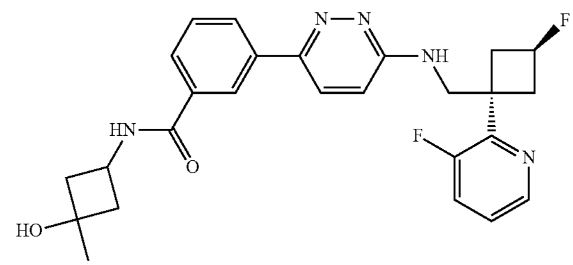 [SMILES: CC1(O)CC(NC(=O)c2cccc(-c3ccc(NC[C@]4(c5ncccc5F)C[C@H](F)C4)nn3)c2)C1] | 480.3 | B |
| N-((3S)oxolan-3-yl){3-[6-({[3-fluoro-1-(3-fluoro(2-pyridyl))cyclobutyl]methyl}amino)pyridazin-3-yl]phenyl}carboxamide | 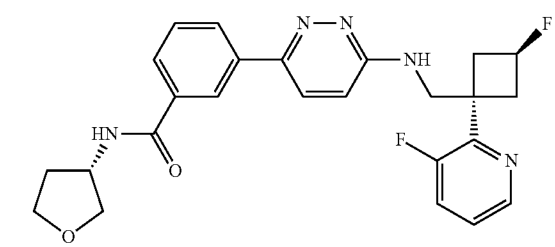 [SMILES: O=C(N[C@H]1CCOC1)c1cccc(-c2ccc(NC[C@]3(c4ncccc4F)C[C@H](F)C3)nn2)c1] | 466.3 | B |
| N-((3R)oxolan-3-yl){3-[6-({[3-fluoro-1-(3-fluoro(2-pyridyl))cyclobutyl]methyl}amino)pyridazin-3-yl]phenyl}carboxamide | 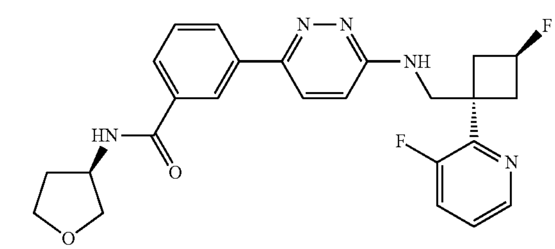 [SMILES: O=C(N[C@@H]1CCOC1)c1cccc(-c2ccc(NC[C@]3(c4ncccc4F)C[C@H](F)C3)nn2)c1] | 466.3 | B |
| N-((3S,4S)-4-hydroxy-1,1-dioxothiolan-3-yl){3-[6-({[3-fluoro-1-(3-fluoro(2-pyridyl))cyclobutyl]methyl}amino)pyridazin-3-yl]phenyl}carboxamide | 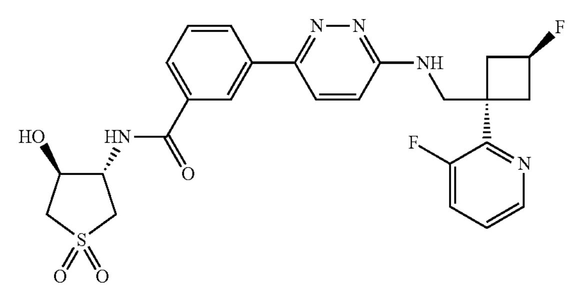 [SMILES: O=C(N[C@@H]1CS(=O)(=O)C[C@H]1O)c1cccc(-c2ccc(NC[C@]3(c4ncccc4F)C[C@H](F)C3)nn2)c1] | 530.3 | B |
| N-(1,1-dioxothiolan-3-yl){3-[6-({[3-fluoro-1-(3-fluoro(2-pyridyl))cyclobutyl]methyl}amino)pyridazin-3-yl]phenyl}carboxamide | 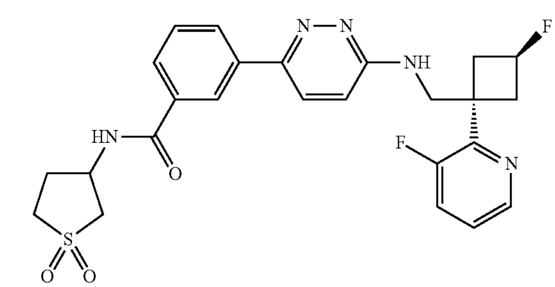 [SMILES: O=C(NC1CCS(=O)(=O)C1)c1cccc(-c2ccc(NC[C@]3(c4ncccc4F)C[C@H](F)C3)nn2)c1] | 514.3 | B |

TABLE 2-continued

| Compound | Structure | m/z (M + H) | Mean AC1.4 |
|---|---|---|---|
| 3-[6-({[3-fluoro-1-(3-fluoro(2-pyridyl))cyclobutyl]methyl}amino)pyridazin-3-yl]-2-hydroxybenzamide | 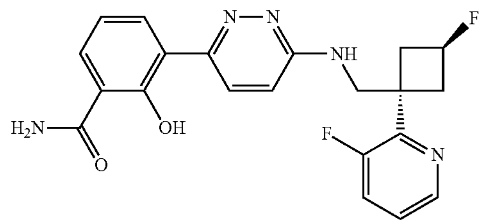 | 412.1 | A |
| 3-[6-({[(3-fluoro(2-pyridyl))cyclobutyl]methyl}amino)pyridazin-3-yl]-2-hydroxybenzamide | 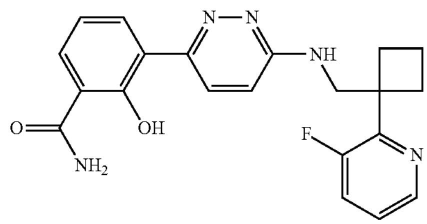 [SMILES: NC(=O)c1cccc(-c2ccc(NCC3(c4ncccc4F)CCC3)nn2)c1O] | 394.2 | A |
| 5-amino-3-[6-({[3-fluoro-1-(3-fluoro(2-pyridyl))cyclobutyl]methyl}amino)pyridazin-3-yl]benzenecarbonitrile | 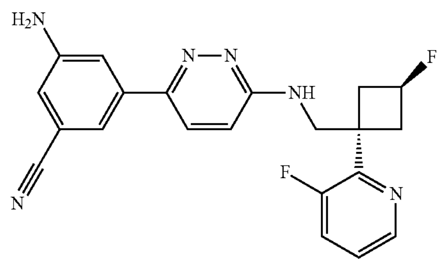 [SMILES: N#Cc1cc(N)cc(-c2ccc(NC[C@]3(c4ncccc4F)C[C@H](F)C3)nn2)c1] | 393.1 | A |
| 3-[6-({[3-fluoro-1-(3-fluoro(2-pyridyl))cyclobutyl]methyl}amino)pyridazin-3-yl]-5-(trifluoromethyl)benzamide | 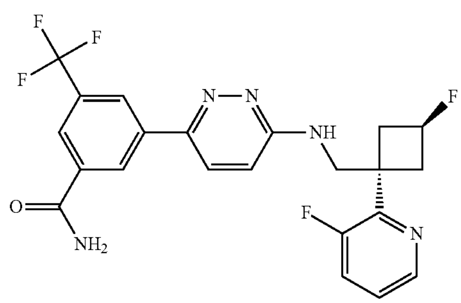 [SMILES: NC(=O)c1cc(-c2ccc(NC[C@]3(c4ncccc4F)C[C@H](F)C3)nn2)cc(C(F)(F)F)c1] | 464.1 | B |
| 5-chloro-3-[6-({[3-fluoro-1-(3-fluoro(2-pyridyl))cyclobutyl]methyl}amino)pyridazin-3-yl]benzamide | 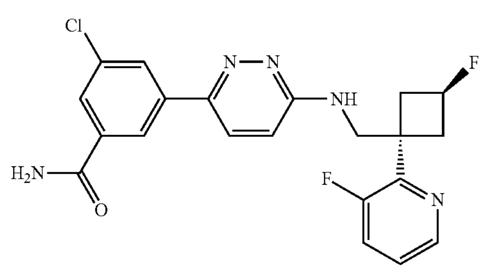 | 430.1 | B |
| 3-[6-({[3-fluoro-1-(3-fluoro(2-pyridyl))cyclobutyl]methyl}amino)pyridazin-3-yl]-5-hydroxybenzamide | 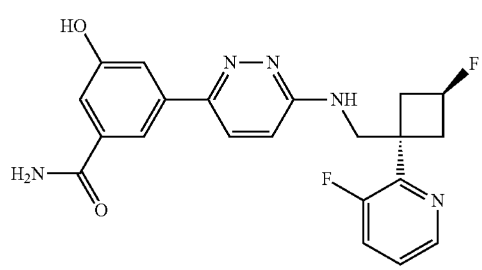 [SMILES: NC(=O)c1cc(Cl)cc(-c2ccc(NC[C@]3(c4ncccc4F)C[C@H](F)C3)nn2)c1] | 412.1 | A |

TABLE 2-continued

| Compound | Structure | m/z (M + H) | Mean AC1.4 |
|---|---|---|---|
| 5-amino-3-[6-({[3-fluoro-1-(3-fluoro(2-pyridyl))cyclobutyl]methyl}amino)pyridazin-3-yl]benzamide | 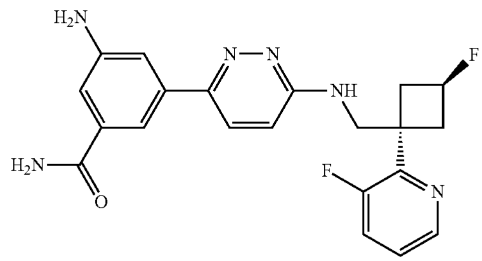 | 411.2 | B |
| {3-[6-({[3-fluoro-1-(3-fluoro(2-pyridyl))cyclobutyl]methyl}amino)pyridazin-3-yl]-2-hydroxyphenyl}-N-methylcarboxamide | | 426.2 | A |
| 3-[6-({(3-fluoro-1-(3-fluoro(2-pyridyl))cyclobutyl]methyl}amino)pyridazin-3-yl]-2-hydroxybenzenecarbonitrile | 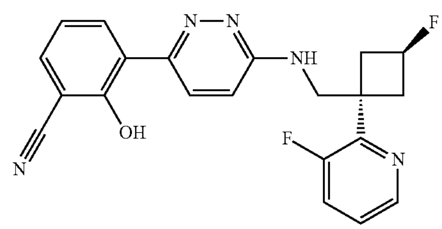 | 394.1 | B |
| 3-[6-({[3-fluoro-1-(3-fluoro(2-pyridyl))cyclobutyl]methyl}amino)pyridazin-3-yl]-2-methoxybenzenecarbonitrile | 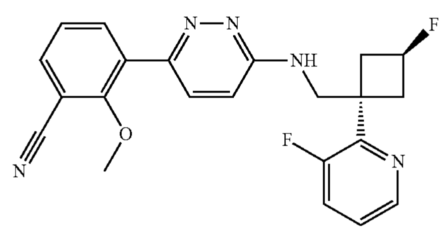 [SMILES: COc1c(C#N)cccc1-c1ccc(NC[C@]2(c3ncccc3F)C[C@H](F)C2)nn1] | 408.1 | C |
| 3-[6-({[3-fluoro-1-(3-fluoro(2-pyridyl))cyclobutyl]methyl}amino)pyridazin-3-yl]-2-hydroxybenzoic acid | 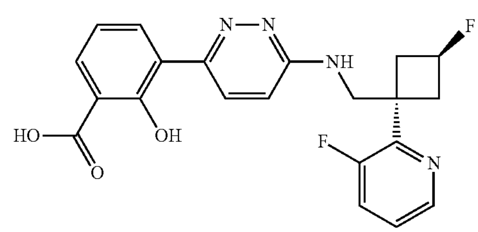 [SMILES: O=C(O)c1cccc(-c2ccc(NC[C@]3(c4ncccc4F)C[C@H](F)C3)nn2)c1O] | 413.1 | C |
| 5-[6-({[3-fluoro-1-(3-fluoro(2-pyridyl))cyclobutyl]methyl}amino)pyridazin-3-yl]-2-methoxybenzamide | | 426.1 | B |

TABLE 2-continued

| Compound | Structure | m/z (M + H) | Mean AC1.4 |
|---|---|---|---|
| N-(1,1-dioxothietan-3-yl){3-[6-({[3-fluoro-1-(3-fluoro(2-pyridyl))cyclobutyl]methyl}amino)pyridazin-3-yl]phenyl}carboxamide | 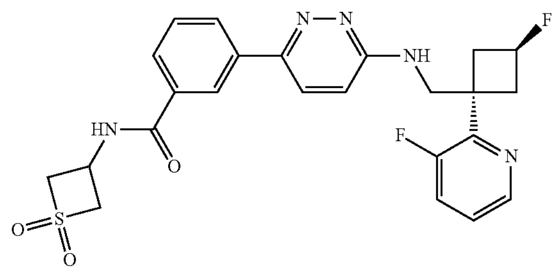 [SMILES: O=C(NC1CS(=O)(=O)C1)c1cccc(-c2ccc(NC[C@]3(c4ncccc4F)C[C@H](F)C3)nn2)c1] | 500.3 | B |
| 4-fluoro-3-[6-({[(3-fluoro(2-pyridyl))cyclobutyl]methyl}amino)pyridazin-3-yl]-2-hydroxybenzamide | 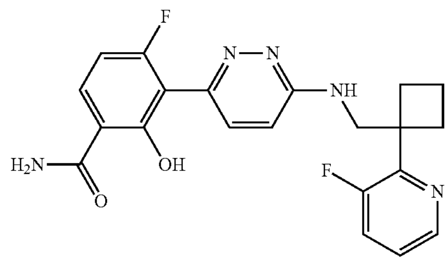 [SMILES: NC(=O)c1ccc(F)c(-c2ccc(NCC3(c4ncccc4F)CCC3)nn2)c1O] | 412.1 | A |
| 4-fluoro-5-[6-({[(3-fluoro(2-pyridyl))cyclobutyl]methyl}amino)pyridazin-3-yl]-2-hydroxybenzamide | 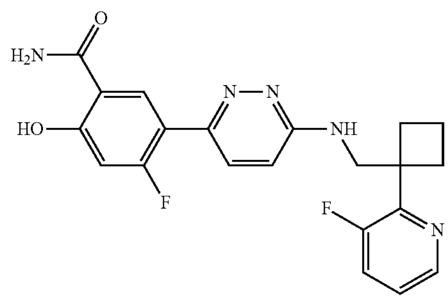 [SMILES: NC(=O)c1cc(-c2ccc(NCC3(c4ncccc4F)CCC3)nn2)c(F)cc1O] | 412.1 | A |
| {3-[6-({[3-fluoro-1-(3-fluoro(2-pyridyl))cyclobutyl]methyl}amino)pyridazin-3-yl]phenyl}-N-[(hydroxycyclopropyl)methyl]carboxamide | 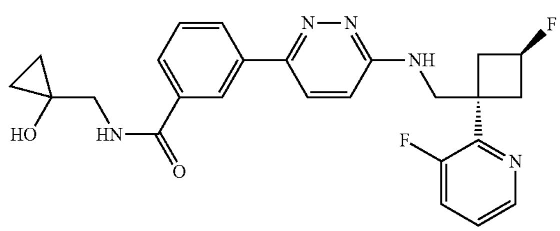 [SMILES: O=C(NCC1(O)CC1)c1cccc(-c2ccc(NC[C@]3(c4ncccc4F)C[C@H](F)C3)nn2)c1] | 466.1 | A |
| {3-[6-({[3-fluoro-1-(3-fluoro(2-pyridyl))cyclobutyl]methyl}amino)pyridazin-3-yl]-5-methylphenyl}-N-methylcarboxamide | 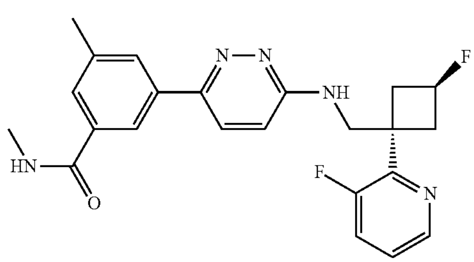 [SMILES: CNC(=O)c1cc(C)cc(-c2ccc(NC[C@]3(c4ncccc4F)C[C@H](F)C3)nn2)c1] | 424.1 | B |
| 3-[6-({[3-fluoro-1-(3-fluoro(2-pyridyl))cyclobutyl]methyl}amino)pyridazin-3-yl]-5-methylbenzamide | 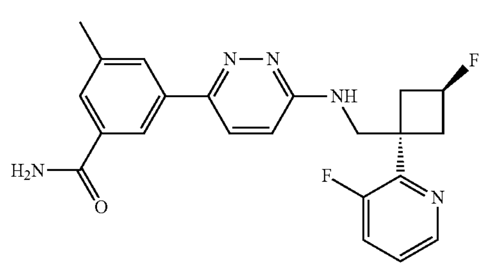 [SMILES: Cc1cc(C(N)=O)cc(-c2ccc(NC[C@]3(c4ncccc4F)C[C@H](F)C3)nn2)c1] | 410.0 | B |

TABLE 2-continued

| Compound | Structure | m/z (M + H) | Mean AC1.4 |
|---|---|---|---|
| 3-[6-({[(3-fluoro(2-pyridyl))cyclobutyl]methyl}amino)pyridazin-3-yl]-2-hydroxy-5-methylbenzamide | 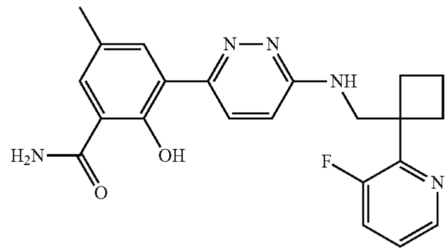 [SMILES: Cc1cc(C(N)=O)c(O)c(-c2ccc(NCC3(c4ncccc4F)CCC3)nn2)c1] | 408.2 | B |
| 3-[6-({[(3-fluoro(2-pyridyl))cyclobutyl]methyl}amino)pyridazin-3-yl]-2-hydroxy-5-methylbenzenecarbonitrile | 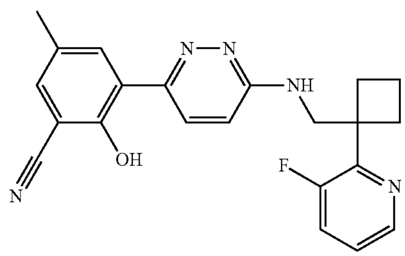 [SMILES: Cc1cc(C#N)c(O)c(-c2ccc(NCC3(c4ncccc4F)CCC3)nn2)c1] | 390.2 | B |
| 5-bromo-3-[6-({[(3-fluoro(2-pyridyl))cyclobutyl]methyl}amino)pyridazin-3-yl]-2-hydroxybenzenecarbonitrile | 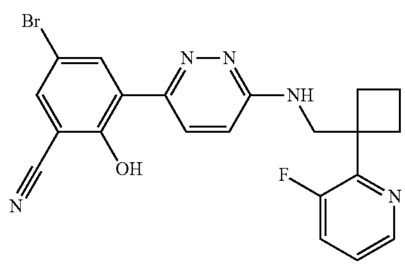 [SMILES: N#Cc1cc(Br)cc(-c2ccc(NCC3(c4ncccc4F)CCC3)nn2)c1O] | 454.0 | A |
| 3-[6-({[3-fluoro-1-(3-fluoro(2-pyridyl))cyclobutyl]methyl}amino)pyridazin-3-yl]-2-methoxybenzamide | 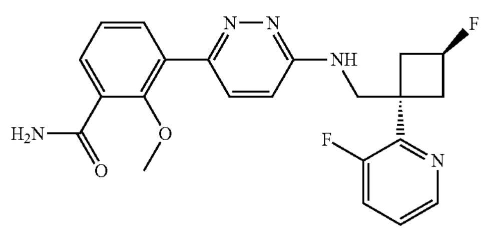 [SMILES: COc1c(C(N)=O)cccc1-c1ccc(NC[C@]2(c3ncccc3F)C[C@H](F)C2)nn1] | 426.2 | D |
| {5-bromo-3-[6-({[3-fluoro-1-(3-fluoro(2-pyridyl))cyclobutyl]methyl}amino)pyridazin-3-yl]-2-hydroxyphenyl}-N-methylcarboxamide | 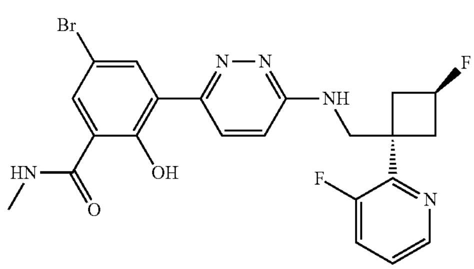 [SMILES: CNC(=O)c1cc(Br)cc(-c2ccc(NC[C@]3(c4ncccc4F)C[C@H](F)C3)nn2)c1O] | 507.0 | B |
| {3-[6-({[3-fluoro-1-(3-fluoro(2-pyridyl))cyclobutyl]methyl}amino)pyridazin-3-yl]-2-hydroxy-5-methylphenyl}-N-methylcarboxamide | 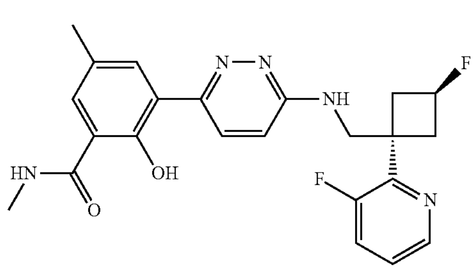 [SMILES: CNC(=O)c1cc(C)cc(-c2ccc(NC[C@]3(c4ncccc4F)C[C@H](F)C3)nn2)c1O] | 440.2 | B |

TABLE 2-continued

| Compound | Structure | m/z (M + H) | Mean AC1.4 |
|---|---|---|---|
| methyl 5-[6-({[3-fluoro-1-(3-fluoro(2-pyridyl))cyclobutyl]methyl}amino)pyridazin-3-yl]indole-2-carboxylate | 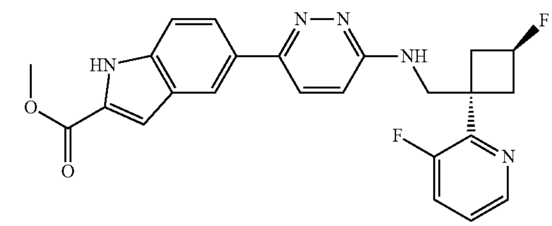 [SMILES: COC(=O)c1cc2cc(-c3ccc(NC[C@]4(c5ncccc5F)C[C@H](F)C4)nn3)ccc2[nH]1] | 450.2 | A |
| 5-[6-({[3-fluoro-1-(3-fluoro(2-pyridyl))cyclobutyl]methyl}amino)pyridazin-3-yl]indole-2-carboxamide | 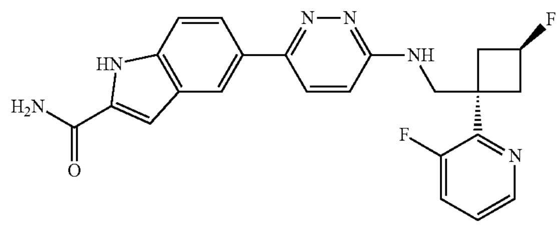 [SMILES: NC(=O)c1cc2cc(-c3ccc(NC[C@]4(c5ncccc5F)C[C@H](F)C4)nn3)ccc2[nH]1] | 435.2 | A |
| 5-[6-({[3-fluoro-1-(3-fluoro(2-pyridyl))cyclobutyl]methyl}amino)pyridazin-3-yl]indole-2-carboxylic acid | 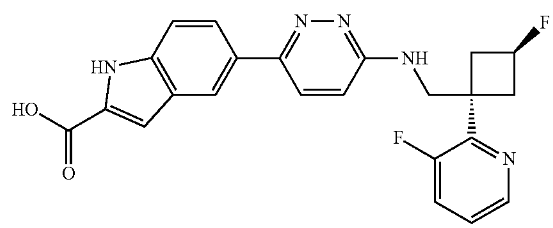 [SMILES: O=C(O)c1cc2cc(-c3ccc(NC[C@]4(c5ncccc5F)C[C@H](F)C4)nn3)ccc2[nH]1] | 436.2 | B |
| {5-[6-({[3-fluoro-1-(3-fluoro(2-pyridyl))cyclobutyl]methyl}amino)pyridazin-3-yl]indol-2-yl}-N-methylcarboxamide | 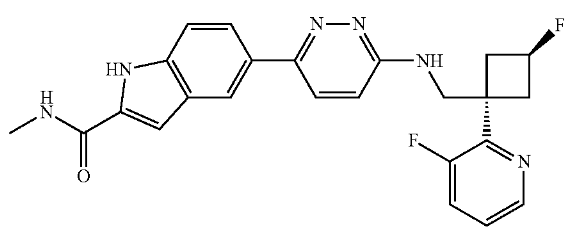 [SMILES: CNC(=O)c1cc2cc(-c3ccc(NC[C@]4(c5ncccc5F)C[C@H](F)C4)nn3)ccc2[nH]1] | 449.1 | A |
| [6-(6-amino(3-pyridyl))pyridazin-3-yl]{[3-fluoro-1-(3-fluoro(2-pyridyl))cyclobutyl]methyl}amine | 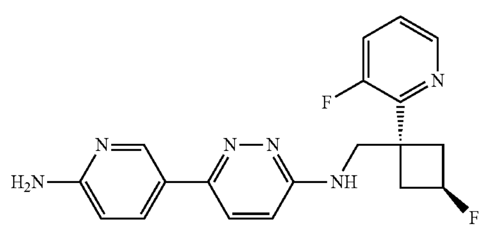 [SMILES: Nc1ccc(-c2ccc(NC[C@]3(c4ncccc4F)C[C@H](F)C3)nn2)cn1] | 369.3 | A |
| {[3-fluoro-1-(3-fluoro(2-pyridyl))cyclobutyl]methyl}{6-[6-(methylamino)(3-pyridyl)]pyridazin-3-yl}amine | 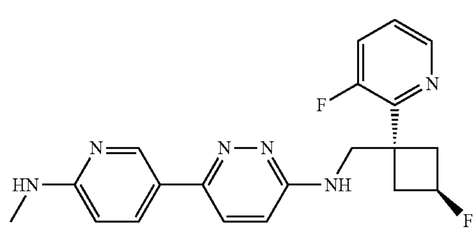 [SMILES: CNc1ccc(-c2ccc(NC[C@]3(c4ncccc4F)C[C@H](F)C3)nn2)cn1] | 383.3 | B |

TABLE 2-continued

| Compound | Structure | m/z (M + H) | Mean AC1.4 |
|---|---|---|---|
| {6-[6-(cyclopropylamino)(3-pyridyl)]pyridazin-3-yl}{[3-fluoro-1-(3-fluoro(2-pyridyl))cyclobutyl]methyl}amine | 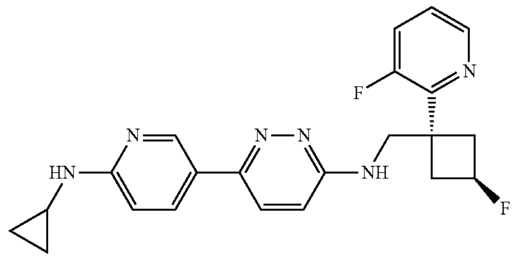 [SMILES: Fc1cccnc1[C@]1(CNc2ccc(-c3ccc(NC4CC4)nc3)nn2)C[C@@H](F)C1] | 409.3 | D |
| {6-[6-amino-5-(trifluoromethyl)(3-pyridyl)]pyridazin-3-yl}{[3-fluoro-1-(3-fluoro(2-pyridyl))cyclobutyl]methyl}amine | 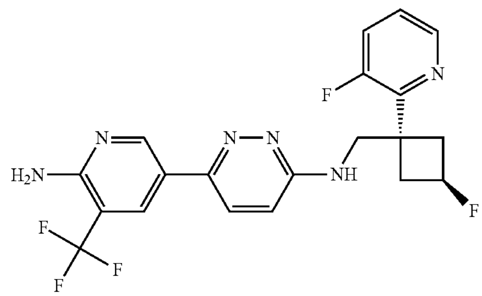 [SMILES: Nc1ncc(-c2ccc(NC[C@]3(c4ncccc4F)C[C@H](F)C3)nn2)cc1C(F)(F)F] | 437.0 | B |
| [N-({2-[6-({[(3-fluoro-2-pyridyl)cyclobutyl]methyl}amino)pyridazin-3-yl]-1,3-thiazol-5-yl}methyl)carbamoyl]methyl acetate | 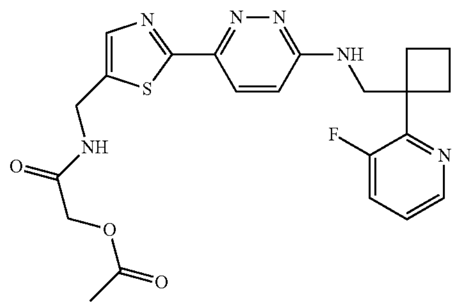 [SMILES: CC(=O)OCC(=O)NCc1cnc(-c2ccc(NCC3(c4ncccc4F)CCC3)nn2)s1] | 470.1 | A |
| [N-({2-[6-({[(3-fluoro-2-pyridyl)cyclobutyl]methyl}amino)pyridazin-3-yl]-1,3-thiazol-5-yl}methyl)carbamoyl]methyl(2S)-2-amino-3-methylbutanoate | 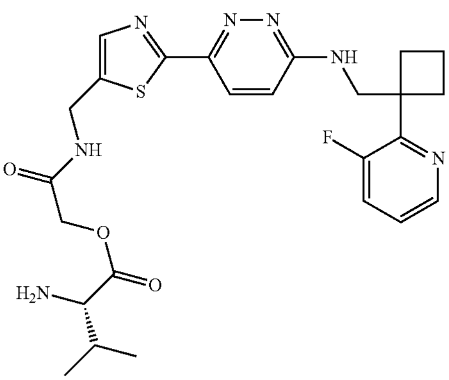 [SMILES: CC(C)[C@H](N)C(=O)OCC(=O)NCc1cnc(-c2ccc(NCC3(c4ncccc4F)CCC3)nn2)s1] | 528.2 | A |
| [N-({2-[6-({[(3-fluoro-2-pyridyl)cyclobutyl]methyl}amino)pyridazin-3-yl]-1,3-thiazol-5-yl}methyl)carbamoyl]methyl (2S)-2-aminopropanoate | 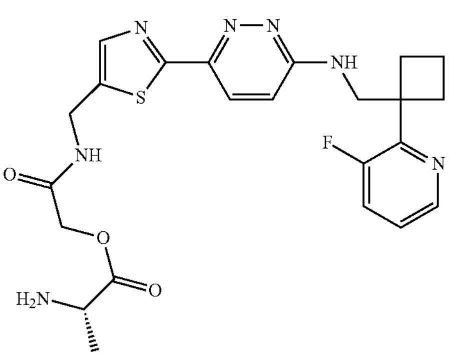 [SMILES: C[C@H](N)C(=O)OCC(=O)NCc1cnc(-c2ccc(NCC3(c4ncccc4F)CCC3)nn2)s1] | 500.2 | A |

TABLE 2-continued

| Compound | Structure | m/z (M + H) | Mean AC1.4 |
|---|---|---|---|
| {[3-fluoro-1-(3-fluoro(2-pyridyl))cyclobutyl]methyl}[6-(6-methoxy-5-methyl(3-pyridyl))pyridazin-3-yl]amine | 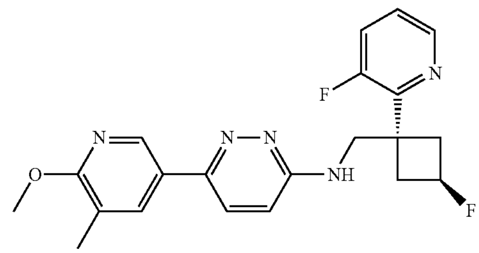 [SMILES: COc1ncc(-c2ccc(NC[C@]3(c4ncccc4F)C[C@H](F)C3)nn2)cc1C] | 398.3 | D |
| [6-(6-amino-5-methyl(3-pyridyl))pyridazin-3-yl]{[3-fluoro-1-(3-fluoro(2-pyridyl))cyclobutyl]methyl}amine | 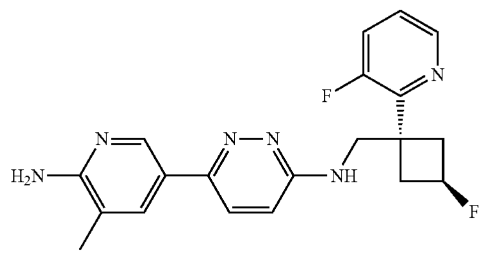 [SMILES: Cc1cc(-c2ccc(NC[C@]3(c4ncccc4F)C[C@H](F)C3)nn2)cnc1N] | 383.3 | B |
| (2S)-N-({2-[6-({[(3-fluoro(2-pyridyl))cyclobutyl]methyl}amino)pyridazin-3-yl](1,3-thiazol-5-yl)}methyl)-2-hydroxypropanamide | 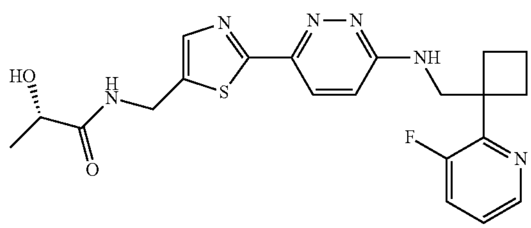 | 443.1 | A |
| (2R)-N-({2-[6-({[(3-fluoro(2-pyridyl))cyclobutyl]methyl}amino)pyridazin-3-yl](1,3-thiazol-5-yl)}methyl)-2-hydroxypropanamide | 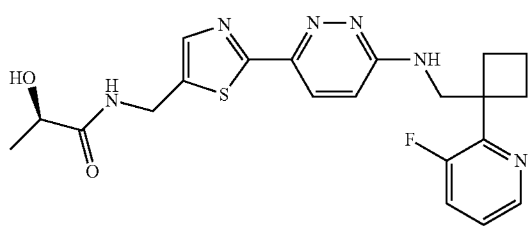 [SMILES: C[C@@H](O)C(=O)NCc1cnc(-c2ccc(NCC3(c4ncccc4F)CCC3)nn2)s1] | 443.1 | A |
| 2-[({2-[6-({[(3-fluoro-2-pyridyl)cyclobutyl]methyl}amino)pyridazin-3-yl]-1,3-thiazol-5-yl}methyl)amino]ethan-1-ol | 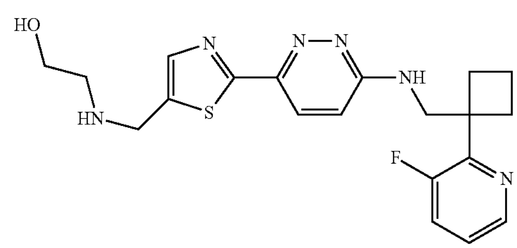 [SMILES: OCCNCc1cnc(-c2ccc(NCC3(c4ncccc4F)CCC3)nn2)s1] | 415.1 | B |
| N-({2-[6-({[(3-fluoro(2-pyridyl))cyclobutyl]methyl}amino)pyridazin-3-yl](1,3-thiazol-5-yl)}methyl)-2-hydroxy-N-methylacetamide | 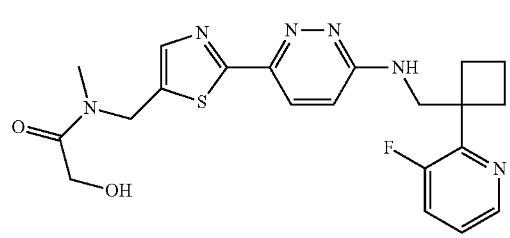 [SMILES: CN(Cc1cnc(-c2ccc(NCC3(c4ncccc4F)CCC3)nn2)s1)C(=O)CO] | 443.1 | B |

TABLE 2-continued

| Compound | Structure | m/z (M + H) | Mean AC1.4 |
|---|---|---|---|
| [N-({2-[6-({[(3-fluoro-2-pyridyl)cyclobutyl]methyl}amino)pyridazin-3-yl]-1,3-thiazol-5-yl}methyl)carbamoyl]methyl (2S)-2-((2S)-2-aminopropanoylamino)propanoate | 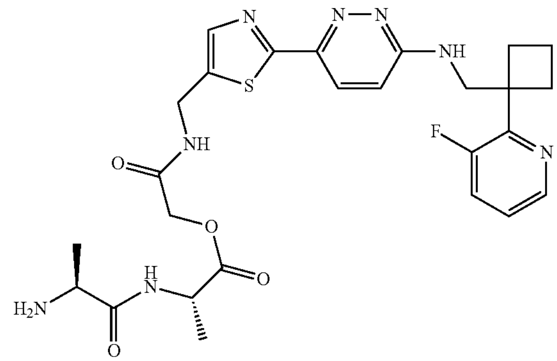 [SMILES: C[C@H](N)C(=O)N[C@@H](C)C(=O)OCC(=O)NCc1cnc(-c2ccc(NCC3(c4ncccc4F)CCC3)nn2)s1] | 571.1 | A |
| [N-({2-[6-({[(3-fluoro-2-pyridyl)cyclobutyl]methyl}amino)pyridazin-3-yl]-1,3-thiazol-5-yl}methyl)carbamoyl]methyl (2S)-2-((2S)-2-amino-3-methylbutanoylamino)-3-methylbutanoate | 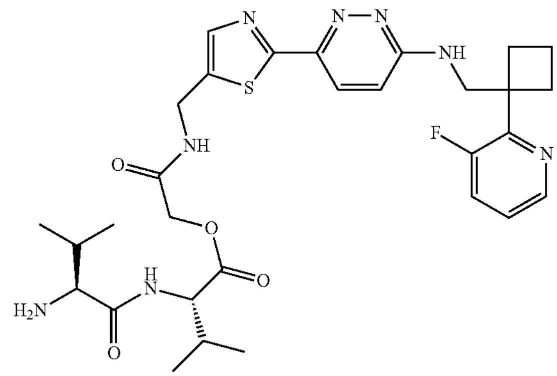 [SMILES: CC(C)[C@H](N)C(=O)N[C@H](C(=O)OCC(=O)NCc1cnc(-c2ccc(NCC3(c4ncccc4F)CCC3)nn2)s1)C(C)C] | 627.3 | A |

While the present invention has been described with reference to the specific embodiments described herein, it should be understood by those skilled in the art that various changes may be made and equivalents may be substituted without departing from the true spirit and scope of the invention. In addition, modifications may be made to adapt a particular situation, material, composition of matter and/or process to the objective, spirit and scope of the present invention. All such modifications are intended to be within the scope of the claims appended hereto.

What is claimed is:

1. A compound of Formula I:

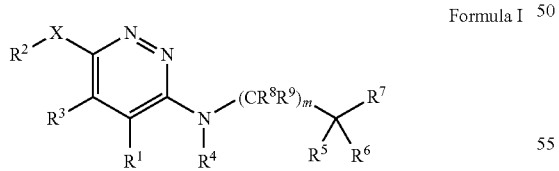

Formula I or a pharmaceutically acceptable salt thereof, wherein:
$R^1$ is selected from hydrogen, halogen, CN, $C_{1-6}$ alkyl, $C_{1-6}$ haloalkyl, $C(O)OR^a$, $C(O)NR^bR^c$, $OR^a$, $NR^bR^c$, $C_{6-10}$ aryl and 5-10 membered heteroaryl;
$R^2$ is selected from $C_{6-10}$ aryl and 5-10 membered heteroaryl each optionally substituted with 1, 2, 3, 4 or 5 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl groups is optionally substituted with 1, 2, 3, 4 or 5 $R^f$ substituents;
$R^3$ is selected from hydrogen, halogen, CN, $C_{1-6}$ alkyl, $C_{1-6}$ haloalkyl, $C(O)OR^a$, $C(O)NR^bR^c$, $OR^a$, $NR^bR^c$, $C_{6-10}$ aryl and 5-10 membered heteroaryl;
$R^4$ is selected from hydrogen, $C_{1-6}$ alkyl, $C_{1-6}$ haloalkyl, $C(O)R^a$, $C(O)OR^a$, $C(O)NR^bR^c$ and $SO_2R^a$;
$R^5$ and $R^6$ together with the carbon atom to which they are bound form a group selected from $C_{3-8}$ cycloalkyl, $C_{3-8}$ cycloalkenyl, 3-8 membered heterocycloalkyl and 3-8 membered heterocycloalkenyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl;
$R^7$ is selected from $C_{6-10}$ aryl and 5-10 membered heteroaryl, each optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents;

$R^8$ and $R^9$, at each occurrence, are each independently selected from hydrogen, halogen and $C_{1-6}$ alkyl;

X is a bond;

$R^a$, at each occurrence, is independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents;

$R^b$ and $R^c$, at each occurrence, are each independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, 5-10 membered heteroaryl, $C(O)R^g$, $C(O)OR^g$, $C(O)NR^iR^j$ and $SO_2R^g$, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents;

$R^d$, at each occurrence, is independently selected from hydrogen and $C_{1-6}$ alkyl;

$R^e$, at each occurrence, is independently selected from hydrogen, CN, OH, $C_{1-6}$ alkoxy, $C_{1-6}$ alkyl and $C_{1-6}$ haloalkyl;

$R^f$, at each occurrence, is independently selected from halogen, CN, $OR^h$, $OC(O)R^h$, $OC(O)OR^h$, $OC(O)NR^iR^j$, $NR^dC(O)R^h$, $NR^dC(O)OR^h$, $NR^dC(O)NR^iR^j$, $NR^dC(O)C(O)NR^iR^j$, $NR^dC(S)R^h$, $NR^dC(S)OR^h$, $NR^dC(S)NR^iR^j$, $NR^dC(NR^e)NR^iR^j$, $NR^dS(O)R^h$, $NR^dSO_2R^h$, $NR^dSO_2NR^iR^j$, $C(O)R^h$, $C(O)OR^h$, $C(O)NR^iR^j$, $C(S)R^h$, $C(S)OR^h$, $C(S)NR^iR^j$, $C(NR^e)NR^iR^j$, $SR^h$, $S(O)R^h$, $SO_2R^h$, $SO_2NR^iR^j$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^k$ substituents;

or two $R^f$ substituents bound to a single carbon atom, together with the carbon atom to which they are both bound, form a group selected from oxo, $C_{3-8}$ cycloalkyl and 3-8 membered heterocycloalkyl;

$R^g$, at each occurrence, is independently selected from $C_{1-6}$ alkyl, $C_{1-6}$ haloalkyl, phenyl, naphthyl, and $C_{7-11}$ aralkyl, each optionally substituted with 1, 2, 3, 4 or 5 substituents selected from halogen, CN, OH, $C_{1-6}$ alkoxy, $C_{1-6}$ alkyl and $C_{1-6}$ haloalkyl;

$R^h$, at each occurrence, is independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^k$ substituents;

$R^i$ and $R^j$, at each occurrence, are each independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, 5-10 membered heteroaryl, $C(O)R^g$, and $C(O)OR^g$, wherein each of the $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 substituents selected from halogen, CN, OH, $C_{1-6}$ alkoxy, $C_{1-6}$ alkyl and $C_{1-6}$ haloalkyl;

$R^k$, at each occurrence, is independently selected from halogen, CN, OH, $C_{1-6}$ alkoxy, $NH_2$, $NH(C_{1-6}$ alkyl), $N(C_{1-6}$ alkyl$)_2$, $NHC(O)C_{1-6}$ alkyl, $NHC(O)C_{7-11}$ aralkyl, $NHC(O)OC_{1-6}$ alkyl, $NHC(O)OC_{7-11}$ aralkyl, $OC(O)C_{1-6}$ alkyl, $OC(O)C_{7-11}$ aralkyl, $OC(O)OC_{1-6}$ alkyl, $OC(O)OC_{7-11}$ aralkyl, $C(O)C_{1-6}$ alkyl, $C(O)C_{7-11}$ aralkyl, $C(O)OC_{1-6}$ alkyl, $C(O)OC_{7-11}$ aralkyl, $C_{1-6}$ alkyl, $C_{1-6}$ haloalkyl, $C_{2-6}$ alkenyl, and $C_{2-6}$ alkynyl, wherein each $C_{1-6}$ alkyl, $C_{2-6}$ alkenyl, $C_{2-6}$ alkynyl, and $C_{7-11}$ aralkyl substituent is optionally substituted with 1, 2 or 3 substituents selected from OH, $C_{1-6}$ alkoxy, $NH_2$, $NH(C_{1-6}$ alkyl), $N(C_{1-6}$ alkyl$)_2$, $NHC(O)C_{1-6}$ alkyl, $NHC(O)C_{7-11}$ aralkyl, $NHC(O)OC_{1-6}$ alkyl, and $NHC(O)OC_{7-11}$ aralkyl;

or two $R^k$ substituents bound to a single carbon atom, together with the carbon atom to which they are both bound, form a oxo group;

m is 0, 1 or 2;

n, at each occurrence, independently is 0, 1 or 2;

p is 0, 1 or 2; and q is 0, 1 or 2.

2. The compound of claim 1, or a pharmaceutically acceptable salt thereof, wherein $R^5$ and $R^6$ together with the carbon atom to which they are bound form $C_{3-8}$ cycloalkyl optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

3. The compound of claim 2, or a pharmaceutically acceptable salt thereof, wherein $R^5$ and $R^6$ together with the carbon atom to which they are bound form a group selected from cyclopropyl, cyclobutyl, cyclopentyl and cyclohexyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

4. The compound of claim 3, or a pharmaceutically acceptable salt thereof, wherein $R^5$ and $R^6$ together with the carbon atom to which they are bound form cyclobutyl optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

5. The compound of claim 4, or a pharmaceutically acceptable salt thereof, wherein $R^5$ and $R^6$ together with the carbon atom to which they are bound form cyclobutyl optionally substituted with one or two halogens.

6. The compound of claim 5, or a pharmaceutically acceptable salt thereof, wherein $R^5$ and $R^6$ together with the carbon atom to which they are bound form a group selected from cyclobutyl, 3-fluorocyclobutyl and 3,3-difluorocyclobutyl.

7. The compound of claim 4, wherein the compound is of Formula V(a) or Formula V(b), or a pharmaceutically acceptable salt thereof:

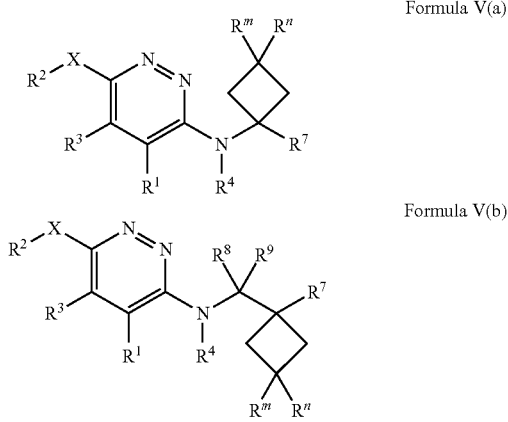

Formula V(a)

Formula V(b)

wherein $R^m$ and $R^n$ are each independently selected from hydrogen, halogen and $C_{1-6}$ alkyl.

8. The compound of claim 7, wherein one of $R^m$ and $R^n$ is hydrogen and the other is halogen.

9. The compound of claim 8, wherein the halogen and $R^7$ are in a trans configuration with respect to one another on the cyclobutyl ring.

10. The compound of claim 8, wherein the halogen and $R^7$ are in a cis configuration with respect to one another on the cyclobutyl ring.

11. The compound of claim 7, wherein one of $R^m$ and $R^n$ is hydrogen and the other is fluorine.

12. The compound of claim 1, or a pharmaceutically acceptable salt thereof, wherein $R^2$ is 5-10 membered heteroaryl optionally substituted with 1, 2, 3, 4 or 5 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

13. The compound of claim 12, or a pharmaceutically acceptable salt thereof, wherein $R^2$ is selected from pyridyl, pyrimidyl, pyrazyl, pyridazyl, triazyl, furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with 1, 2, 3 or 4 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

14. The compound of claim 13, or a pharmaceutically acceptable salt thereof, wherein $R^2$ is selected from pyridyl, pyrimidyl, pyrazyl, pyridazyl, triazyl, furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with a substituent selected from $(CH_2)_nC(O)OR^a$ and $(CH_2)_nC(O)NR^bR^c$; and optionally substituted with 1, 2 or 3 additional substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

15. The compound of claim 14, or a pharmaceutically acceptable salt thereof, wherein $R^2$ is selected from furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with $(CH_2)_nC(O)NR^bR^c$.

16. The compound of claim 13, or a pharmaceutically acceptable salt thereof, wherein $R^2$ is selected from pyridyl, pyrimidyl, pyrazyl, pyridazyl, triazyl, furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with $(CH_2)_nNR^dC(O)R^a$, wherein $R^a$ is $C_{1-6}$ alkyl or 3-8 membered heterocycloalkyl, each optionally substituted with 1, 2 or 3 additional substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

17. The compound of claim 16, or a pharmaceutically acceptable salt thereof, wherein $R^2$ is selected from furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with $(CH_2)_nNR^dC(O)R^a$, wherein $R^a$ is selected from $C_{1-6}$ alkyl, $C_{1-6}$ alkyl-OH and $C_{1-6}$ alkyl-NH$_2$, each optionally substituted with 1, 2 or 3 additional substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl.

18. The compound of claim 12, or a pharmaceutically acceptable salt thereof, wherein $R^2$ is selected from indolyl, indazolyl, benzimidazolyl, benzoxazolyl and benzoisoxazolyl, each optionally substituted with 1, 2, 3 or 4 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

19. The compound of claim 1, or a pharmaceutically acceptable salt thereof, wherein $R^7$ is 5-10 membered heteroaryl optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

20. The compound of claim 19, or a pharmaceutically acceptable salt thereof, wherein $R^7$ is pyridyl optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-6}$ cycloalkyl, $C_{3-6}$ cycloalkenyl, 3-6 membered heterocycloalkyl, 3-6 membered heterocycloalkenyl, phenyl, naphthyl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

21. The compound of claim 20, or a pharmaceutically acceptable salt thereof, wherein $R^7$ is 2-pyridyl optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-6}$ cycloalkyl, $C_{3-6}$ cycloalkenyl, 3-6 membered heterocycloalkyl, 3-6 membered heterocycloalkenyl, phenyl, naphthyl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

22. The compound of claim 1, or a pharmaceutically acceptable salt thereof, wherein m is 1.

23. The compound of claim 22, wherein $R^8$ and $R^9$ are each hydrogen.

24. The compound of claim 1, or a pharmaceutically acceptable salt thereof, wherein $R^1$ is selected from hydrogen, halogen, CN, $CF_3$ and methyl.

25. The compound of claim 24, or a pharmaceutically acceptable salt thereof, wherein $R^1$ is hydrogen.

26. The compound of claim 1, or a pharmaceutically acceptable salt thereof, wherein $R^3$ is selected from hydrogen, halogen, CN, $CF_3$ and methyl.

27. The compound of claim 26, or a pharmaceutically acceptable salt thereof, wherein $R^3$ is hydrogen.

28. The compound of claim 1, or a pharmaceutically acceptable salt thereof, wherein:

m is 0;

$R^2$ is selected from phenyl and 5-10 membered heteroaryl optionally substituted with 1, 2, 3, 4 or 5 substituents selected from halogen, CN, oxo, $(CH_2)_nOR^a$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, and $C_{2-6}$ alkynyl, wherein each of the $C_{1-6}$ alkyl, $C_{2-6}$ alkenyl, and $C_{2-6}$ alkynyl groups is optionally substituted with 1, 2, 3, 4 or 5 $R^f$ substituents;

$R^4$ is hydrogen;

$R^5$ and $R^6$ together with the carbon atom to which they are bound form cyclobutyl optionally substituted with one or two halogens; and $R^7$ is selected from phenyl and pyridyl, each optionally substituted with 1, 2 or 3 substituents selected from halogen, CN, $OR^a$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, and $C_{2-6}$ alkynyl.

29. The compound of claim 28, or a pharmaceutically acceptable salt thereof, wherein $R^1$ is hydrogen and $R^3$ is hydrogen.

30. The compound of claim 1, or a pharmaceutically acceptable salt thereof, wherein:

m is 1;

$R^2$ is selected from phenyl and 5-10 membered heteroaryl optionally substituted with 1, 2, 3, 4 or 5 substituents selected from halogen, CN, oxo, $(CH_2)_nOR^a$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, and $C_{2-6}$ alkynyl, wherein each of the $C_{1-6}$ alkyl, $C_{2-6}$ alkenyl, and $C_{2-6}$ alkynyl groups is optionally substituted with 1, 2, 3, 4 or 5 $R^f$ substituents;

$R^4$ is hydrogen;

$R^5$ and $R^6$ together with the carbon atom to which they are bound form cyclobutyl optionally substituted with one or two halogens;

$R^7$ is selected from phenyl and pyridyl, each optionally substituted with 1, 2 or 3 substituents selected from halogen, CN, $OR^a$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, and $C_{2-6}$ alkynyl;

$R^8$ is hydrogen; and $R^9$ is hydrogen.

31. The compound of claim 30, or a pharmaceutically acceptable salt thereof, wherein $R^1$ is hydrogen and $R^3$ is hydrogen.

32. The compound of claim 1, or a pharmaceutically acceptable salt thereof, wherein m is 0.

33. The compound of claim 1, or a pharmaceutically acceptable salt thereof, wherein $R^7$ is phenyl optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

34. The compound of claim 1, or a pharmaceutically acceptable salt thereof, wherein $R^2$ is phenyl optionally substituted with 1, 2, 3, 4 or 5 substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

35. The compound of claim 1, or a pharmaceutically acceptable salt thereof, wherein $R^4$ is hydrogen.

36. The compound of claim 1, wherein the compound is 4-fluoro-3-[6-({[3-fluoro-1-(3-fluoro(2-pyridyl))cyclobutyl]methyl}amino)pyridazin-3-yl]benzamide, or a pharmaceutically acceptable salt thereof.

37. The compound of claim 1, wherein the compound is 4-fluoro-3-[6-({[(trans)-3-fluoro-1-(3-fluoro(2-pyridyl))cyclobutyl]methyl}amino)pyridazin-3-yl]benzamide, or a pharmaceutically acceptable salt thereof.

38. The compound of claim 1, wherein the compound is 4-fluoro-3-[6-({[(3-fluoro(2-pyridyl))cyclobutyl]methyl}amino)pyridazin-3-yl]benzamide, or a pharmaceutically acceptable salt thereof.

39. The compound of claim 1, wherein the compound is [6-(3-amino(1H-indazol-5-yl))pyridazin-3-yl]{[(3-fluoro(2-pyridyl))cyclobutyl]methyl}amine, or a pharmaceutically acceptable salt thereof.

40. The compound of claim 1, wherein the compound is [6-(3-amino(1H-indazol-5-yl))pyridazin-3-yl]{[3-fluoro-1-(3-fluoro(2-pyridyl))cyclobutyl]methyl}amine, or a pharmaceutically acceptable salt thereof.

41. The compound of claim 1, wherein the compound is [6-(3-amino(1H-indazol-5-yl))pyridazin-3-yl]{[(trans)-3-fluoro-1-(3-fluoro(2-pyridyl))cyclobutyl]methyl}amine, or a pharmaceutically acceptable salt thereof.

42. The compound of claim 1, wherein the compound is N-({2-[6-({[(3-fluoro(2-pyridyl))cyclobutyl]methyl}amino)pyridazin-3-yl](1,3-thiazol-5-yl)}methyl)-2-hydroxyacetamide, or a pharmaceutically acceptable salt thereof.

43. The compound of claim 1, wherein the compound is 2-amino-N-({2-[6-({[(3-fluoro(2-pyridyl))cyclobutyl]methyl}amino)pyridazin-3-yl](1,3-thiazol-5-yl)}methyl)-2-methylpropanamide, or a pharmaceutically acceptable salt thereof.

44. The compound of claim 1, wherein the compound is (2S)-2-amino-N-({2-[6-({[(3-fluoro(2-pyridyl))cyclobutyl]methyl}amino)pyridazin-3-yl](1,3-thiazol-5-yl)}methyl)propanamide, or a pharmaceutically acceptable salt thereof.

45. The compound of claim 1, wherein the compound is (2R)-2-amino-N-({2-[6-({[(3-fluoro(2-pyridyl))cyclobutyl]methyl}amino)pyridazin-3-yl](1,3-thiazol-5-yl)}methyl)propanamide, or a pharmaceutically acceptable salt thereof.

46. The compound of claim 1, wherein the compound is (2S)-2-amino-N-({2-[6-({[(3-fluoro(2-pyridyl))cyclobutyl]methyl}amino)pyridazin-3-yl](1,3-thiazol-5-yl)}methyl)-3-hydroxy-3-methylbutanamide, or a pharmaceutically acceptable salt thereof.

47. The compound of claim 1, wherein the compound is selected from:

3-(6-{[(4-fluorophenyl)cyclobutyl]amino}pyridazin-3-yl)benzamide;
(6-(1H-indazol-5-yl)pyridazin-3-yl][(4-fluorophenyl)cyclobutyl]amine;
[6-(2-aminopyrimidin-5-yl)pyridazin-3-yl][(4-fluorophenyl)cyclobutyl]amine;
amino-N-[4-(6-{[(4-fluorophenyl)cyclobutyl]amino}pyridazin-3-yl)phenyl]amide;
3-(6-{[(2-fluorophenyl)cyclobutyl]amino}pyridazin-3-yl)benzamide;
3-(6-{[(3-fluorophenyl)cyclobutyl]amino}pyridazin-3-yl)benzamide;
3-{6-[(2-pyridylcyclobutyl)amino]pyridazin-3-yl}benzamide;
(phenylcyclobutyl)(6-phenylpyridazin-3-yl)amine;
3-{6-[(phenylcyclobutyl)amino]pyridazin-3-yl}benzamide;
3-(6-{[(3-fluoro-2-pyridyl)cyclobutyl]amino}pyridazin-3-yl)benzamide;
3-(6-{[(5-fluoro-2-pyridyl)cyclobutyl]amino}pyridazin-3-yl)benzamide;
4-fluoro-3-(6-{[(4-fluorophenyl)cyclobutyl]amino}pyridazin-3-yl)benzamide;
[(4-fluorophenyl)cyclobutyl][6-(6-methoxy(2-pyridyl))pyridazin-3-yl]amine;
(6-benzimidazol-5-ylpyridazin-3-yl)[(4-fluorophenyl)cyclobutyl]amine;
[(4-fluorophenyl)cyclobutyl](6-pyrazol-4-ylpyridazin-3-yl)amine;
3-{6-[(1,3-thiazol-2-ylcyclobutyl)amino]pyridazin-3-yl}benzamide;
4-fluoro-3-(6-{[(3-fluoro(2-pyridyl))cyclobutyl]amino}pyridazin-3-yl)benzamide;
3-(6-{[(4-methoxy-2-pyridyl)cyclobutyl]amino}pyridazin-3-yl)benzamide;
[6-(3-fluoro(4-pyridyl))pyridazin-3-yl][(4-fluorophenyl)cyclobutyl]amine;
[(4-fluorophenyl)cyclobutyl](6-(4-pyridyl)pyridazin-3-yl)amine;
4-(6-{[(4-fluorophenyl)cyclobutyl]amino}pyridazin-3-yl)pyridine-2-carbonitrile;
4-(6-{[(4-fluorophenyl)cyclobutyl]amino}pyridazin-3-yl)pyridine-2-carboxamide;
[4-(6-{[(4-fluorophenyl)cyclobutyl]amino}pyridazin-3-yl)phenyl](methylsulfonyl)amine;
[(4-fluorophenyl)cyclobutyl][6-(2-methoxy(3-pyridyl))pyridazin-3-yl]amine;
[(4-fluorophenyl)cyclobutyl]{6-[2-(2,2,2-trifluoroethoxy)(3-pyridyl)]pyridazin-3-yl}amine;
3-(6-{[(4-chlorophenyl)cyclobutyl]amino}pyridazin-3-yl)benzamide;
3-(6-{[(4-cyanophenyl)cyclobutyl]amino}pyridazin-3-yl)benzamide;
3-(6-{[(3-chloro(2-pyridyl))cyclobutyl]amino}pyridazin-3-yl)-4-fluorobenzamide;
[3-(6-{[(4-fluorophenyl)cyclobutyl]amino}pyridazin-3-yl)phenyl](methylsulfonyl)amine;
3-(6-{[(4-carbamoylphenyl)cyclobutyl]amino}pyridazin-3-yl)benzamide;
[(4-fluorophenyl)cyclobutyl][6-(2-methyl(4-pyridyl))pyridazin-3-yl]amine;
[(4-fluorophenyl)cyclobutyl][6-(2-methoxy(4-pyridyl))pyridazin-3-yl]amine;
3-(6-{[(6-methoxy-2-pyridyl)cyclobutyl]amino}pyridazin-3-yl)benzamide;
4-fluoro-3-(6-{[(6-methoxy(2-pyridyl))cyclobutyl]amino}pyridazin-3-yl)benzamide;
[3-(6-{[(6-methoxy(2-pyridyl))cyclobutyl]amino}pyridazin-3-yl)phenyl](methylsulfonyl)amine;
[3-(6-{[(3-fluoro(2-pyridyl))cyclobutyl]amino}pyridazin-3-yl)phenyl](methylsulfonyl)amine;
amino-N-[4-(6-{[(3-fluoro(2-pyridyl))cyclobutyl]amino}pyridazin-3-yl)phenyl]amide;
(6-(1H-indazol-6-yl)pyridazin-3-yl)[(3-fluoro(2-pyridyl))cyclobutyl]amine;
(6-benzimidazol-6-ylpyridazin-3-yl)[(3-fluoro(2-pyridyl))cyclobutyl]amine;
3-[6-({[6-(difluoromethoxy)-2-pyridyl]cyclobutyl}amino)pyridazin-3-yl]benzamide;
3-[6-({[6-(difluoromethoxy)(2-pyridyl)]cyclobutyl}amino)pyridazin-3-yl]-4-fluorobenzamide;
{3-[6-({[6-(difluoromethoxy)(2-pyridyl)]cyclobutyl}amino)pyridazin-3-yl]phenyl}(methylsulfonyl)amine;
4-fluoro-3-(6-{[(4-fluorophenyl)cyclobutyl]amino}pyridazin-3-yl)benzoic acid;
[4-fluoro-3-(6-{[(4-fluorophenyl)cyclobutyl]amino}pyridazin-3-yl)phenyl]-N-(2-hydroxy-2-methylpropyl)carboxamide;
3-(6-{[(3-bromo(2-pyridyl))cyclobutyl]amino}pyridazin-3-yl)-4-fluorobenzamide;
4-chloro-3-(6-{[(3-fluoro(2-pyridyl))cyclobutyl]amino}pyridazin-3-yl)benzamide;
[4-(6-{[(4-fluorophenyl)cyclobutyl]amino}pyridazin-3-yl)(2-pyridyl)]-N-methylcarboxamide;
(6-(1H-indazol-5-yl)pyridazin-3-yl)[(3-fluoro(2-pyridyl))cyclobutyl]amine;
[6-(6-fluoro(1H-indazol-5-yl))pyridazin-3-yl][(3-fluoro(2-pyridyl))cyclobutyl]amine;
amino-N-[4-fluoro-3-(6-{[(3-fluoro(2-pyridyl))cyclobutyl]amino}pyridazin-3-yl)phenyl]amide;
amino[4-fluoro-3-(6-{[(3-fluoro(2-pyridyl))cyclobutyl]amino}pyridazin-3-yl)phenyl]sulfonamide;
amino[3-fluoro-4-(6-{[(3-fluoro(2-pyridyl))cyclobutyl]amino}pyridazin-3-yl)phenyl]sulfonamide;
amino-N-[3-fluoro-4-(6-{[(3-fluoro(2-pyridyl))cyclobutyl]amino}pyridazin-3-yl)phenyl]amide;
3-(6-{[(4-cyano(2-pyridyl))cyclobutyl]amino}pyridazin-3-yl)-4-fluorobenzamide;
2-({[6-(3-carbamoyl-6-fluorophenyl)pyridazin-3-yl]amino}cyclobutyl)pyridine-4-carboxamide;
3-(6-{[(5-cyano(2-pyridyl))cyclobutyl]amino}pyridazin-3-yl)-4-fluorobenzamide;
3-(6-{[(6-cyano(2-pyridyl))cyclobutyl]amino}pyridazin-3-yl)-4-fluorobenzamide;
6-({[6-(3-carbamoyl-6-fluorophenyl)pyridazin-3-yl]amino}cyclobutyl)pyridine-2-carboxamide;
4-fluoro-3-(6-{[(3-hydroxy(2-pyridyl))cyclobutyl]amino}pyridazin-3-yl)benzamide;
4-fluoro-3-(6-{[(3-methoxy(2-pyridyl))cyclobutyl]amino}pyridazin-3-yl)benzamide;

3-[6-({[3-(difluoromethoxy)(2-pyridyl)]
cyclobutyl}amino)pyridazin-3-yl]-4-fluorobenzamide;
3-[6-({[3-(difluoromethoxy)-2-pyridyl]
cyclobutyl}amino)pyridazin-3-yl]benzamide;
{3-[6-({[3-(difluoromethoxy)(2-pyridyl)]
cyclobutyl}amino)pyridazin-3-yl]phenyl}(methylsulfonyl)amine;
4-fluoro-3-(6-{[(5-methoxy(2-pyridyl))cyclobutyl]
amino}pyridazin-3-yl)benzamide;
3-[6-({[5-(difluoromethoxy)(2-pyridyl)]
cyclobutyl}amino)pyridazin-3-yl]-4-fluorobenzamide;
4-fluoro-3-(6-{[(5-hydroxy(2-pyridyl))cyclobutyl]
amino}pyridazin-3-yl)benzamide;
4-fluoro-3-(6-{[(3-fluoro(2-pyridyl))cyclobutyl]
amino}pyridazin-3-yl)benzenecarbonitrile;
[(3-fluoro(2-pyridyl))cyclobutyl](6-phenylpyridazin-3-yl)amine;
(6-cyclohexylpyridazin-3-yl)[(3-fluoro(2-pyridyl))cyclobutyl]amine;
(6-cyclohex-1-enylpyridazin-3-yl)[(3-fluoro(2-pyridyl))cyclobutyl]amine;
4-fluoro-3-(6-{[(3-fluoro(2-pyridyl))cyclopentyl]
amino}pyridazin-3-yl)benzamide;
2-(6-{[(3-fluoro-2-pyridyl)cyclobutyl]amino}pyridazin-3-yl)-1,3-thiazole-5-carboxamide;
5-(6-{[(3-fluoro(2-pyridyl))cyclobutyl]amino}pyridazin-3-yl)-2-hydroxybenzamide;
[6-(3-amino(1H-indazol-5-yl))pyridazin-3-yl][(3-fluoro(2-pyridyl))cyclobutyl]amine;
2-(6-{[(4-fluorophenyl)cyclobutyl]amino}pyridazin-3-yl)-1,3-thiazole-5-carboxamide;
5-(6-{[(3-fluoro-2-pyridyl)cyclobutyl]amino}pyridazin-3-yl)thiophene-2-carboxamide;
5-(6-{[(4-fluorophenyl)cyclobutyl]amino}pyridazin-3-yl)thiophene-2-carboxamide; and
5-(6-{[(3-fluoro-2-pyridyl)cyclobutyl]amino}pyridazin-3-yl)thiophene-2-carboxylic acid;
or a pharmaceutically acceptable salt thereof.

48. The compound of claim 1, wherein the compound is selected from:
3-[6-({[(4-fluorophenyl)cyclopropyl]methyl}amino)pyridazin-3-yl]benzamide;
5-[6-({[(4-fluorophenyl)cyclopropyl]methyl}amino)pyridazin-3-yl]pyridine-3-carboxamide
5-[6-({[(4-fluorophenyl)cyclopropyl]methyl}amino)pyridazin-3-yl]pyridine-3-carbonitrile;
3-[6-({[(2-chlorophenyl)cyclopropyl]methyl}amino)pyridazin-3-yl]benzamide;
5-[6-({[(4-fluorophenyl)cyclopropyl]methyl}amino)pyridazin-3-yl]-3-hydrobenzimidazol-2-one;
[6-(3-amino(1H-indazol-5-yl))pyridazin-3-yl]{[(4-fluorophenyl)cyclopropyl]methyl}amine;
[6-(3-amino(1H-indazol-5-yl))pyridazin-3-yl]{[(2-fluorophenyl)cyclopropyl]methyl}amine;
[6-(3-amino(1H-indazol-5-yl))pyridazin-3-yl]{[(2-fluorophenyl)cyclobutyl]methyl}amine;
[6-(3-amino(1H-indazol-5-yl))pyridazin-3-yl]{[(4-fluorophenyl)cyclobutyl]methyl}amine;
[6-(3-amino(1H-indazol-5-yl))pyridazin-3-yl]{[(2-fluorophenyl)cyclopentyl]methyl}amine;
[6-(3-amino(1H-indazol-5-yl))pyridazin-3-yl]{[(4-fluorophenyl)cyclohexyl]methyl}amine;
[6-(3-amino(1H-indazol-5-yl))pyridazin-3-yl][(phenylcyclopropyl)methyl]amine;
[6-(3-amino(1H-indazol-5-yl))pyridazin-3-yl][(phenylcyclobutyl)methyl]amine;
[6-(3-amino(1H-indazol-5-yl))pyridazin-3-yl][(2,2-dimethyl-1-phenylcyclopropyl)methyl]amine;
[6-(3-amino(1H-indazol-5-yl))pyridazin-3-yl]{[(4-fluorophenyl)cyclopentyl]methyl}amine;
[6-(3-amino(1H-indazol-5-yl))pyridazin-3-yl]{[(3-fluoro(2-pyridyl))cyclobutyl]methyl}amine;
3-[6-({[(3-fluoro-2-pyridyl)cyclobutyl]methyl}amino)pyridazin-3-yl]benzamide;
{[(4-fluorophenyl)cyclobutyl]methyl}[6-(2-methoxypyrimidin-5-yl)pyridazin-3-yl]amine;
[6-(3-amino(1H-indazol-5-yl))pyridazin-3-yl]{[(5-fluoro(2-pyridyl))cyclobutyl]methyl}amine;
3-[6-({[(5-fluoro-2-pyridyl)cyclobutyl]methyl}amino)pyridazin-3-yl]benzamide;
4-[6-({[(3-fluoro-2-pyridyl)cyclobutyl]methyl}amino)pyridazin-3-yl]benzamide;
4-fluoro-3-[6-({[(3-fluoro(2-pyridyl))cyclobutyl]methyl}amino)pyridazin-3-yl]benzamide;
(6-(1H-indazol-5-yl)pyridazin-3-yl){[(3-fluoro(2-pyridyl))cyclobutyl]methyl}amine;
(6-(1H-indazol-6-yl)pyridazin-3-yl){[(3-fluoro(2-pyridyl))cyclobutyl]methyl}amine;
(6-(1H-indazol-6-yl)pyridazin-3-yl){[(6-methoxy(2-pyridyl))cyclobutyl]methyl}amine;
(6-(1H-indazol-5-yl)pyridazin-3-yl){[(6-methoxy(2-pyridyl))cyclobutyl]methyl}amine;
4-fluoro-3-[6-({[(6-methoxy(2-pyridyl))cyclobutyl]methyl}amino)pyridazin-3-yl]benzamide;
4-fluoro-3-(6-{[(2-pyridylcyclobutyl)methyl]amino}pyridazin-3-yl)benzamide;
(6-(1H-indazol-5-yl)pyridazin-3-yl)[(2-pyridylcyclobutyl)methyl]amine;
(6-(1H-indazol-6-yl)pyridazin-3-yl)[(2-pyridylcyclobutyl)methyl]amine;
2-fluoro-3-[6-({[(3-fluoro(2-pyridyl))cyclobutyl]methyl}amino)pyridazin-3-yl]benzamide;
3-fluoro-4-[6-({[(3-fluoro(2-pyridyl))cyclobutyl]methyl}amino)pyridazin-3-yl]benzamide;
6-({[(6-(1H-indazol-5-yl)pyridazin-3-yl)amino]methyl}cyclobutyl)pyridin-2-ol;
6-({[(6-(1H-indazol-6-yl)pyridazin-3-yl)amino]methyl}cyclobutyl)pyridin-2-ol;
4-fluoro-3-[6-({[(6-hydroxy(2-pyridyl))cyclobutyl]methyl}amino)pyridazin-3-yl]benzamide;
2-({[(6-(1H-indazol-5-yl)pyridazin-3-yl)amino]methyl}cyclobutyl)pyridin-4-ol;
4-fluoro-3-[6-({[(4-methoxy(2-pyridyl))cyclobutyl]methyl}amino)pyridazin-3-yl]benzamide;
(6-(1H-indazol-5-yl)pyridazin-3-yl){[(4-methoxy(2-pyridyl))cyclobutyl]methyl}amine;
(6-(1H-indazol-6-yl)pyridazin-3-yl){[(4-methoxy(2-pyridyl))cyclobutyl]methyl}amine;
2-({[(6-(1H-indazol-6-yl)pyridazin-3-yl)amino]methyl}cyclobutyl)pyridin-4-ol;
4-fluoro-3-[6-({[(4-hydroxy(2-pyridyl))cyclobutyl]methyl}amino)pyridazin-3-yl]benzamide;
5-[6-({[(3-fluoro-2-pyridyl)cyclobutyl]methyl}amino)pyridazin-3-yl]-3-hydrobenzimidazol-2-one;
{[(3-fluoro(2-pyridyl))cyclobutyl]methyl}(6-pyrazol-4-ylpyridazin-3-yl)amine;
{[(3-fluoro(2-pyridyl))cyclobutyl]methyl}[6-(1-methylpyrazol-4-yl)pyridazin-3-yl]amine;
3-[6-({[(3-fluoro-2-pyridyl)cyclobutyl]methyl}amino)pyridazin-3-yl]benzenesulfonamide;
{4-[6-({[(3-fluoro-2-pyridyl)cyclobutyl]methyl}amino)pyridazin-3-yl]phenyl}(methylsulfonyl)amine;

{3-[6-({[(3-fluoro(2-pyridyl))cyclobutyl]methyl}amino)pyridazin-3-yl]phenyl}(methylsulfonyl)amine;
4-fluoro-3-[6-({[(3-methoxy(2-pyridyl))cyclobutyl]methyl}amino)pyridazin-3-yl]benzamide;
(6-(1H-indazol-5-yl)pyridazin-3-yl){[(3-methoxy(2-pyridyl))cyclobutyl]methyl}amine;
(6-(1H-indazol-6-yl)pyridazin-3-yl){[(3-methoxy(2-pyridyl))cyclobutyl]methyl}amine;
4-fluoro-3-[6-({[(5-methoxy(2-pyridyl))cyclobutyl]methyl}amino)pyridazin-3-yl]benzamide;
(6-(1H-indazol-5-yl)pyridazin-3-yl){[(5-methoxy(2-pyridyl))cyclobutyl]methyl}amine;
(6-(1H-indazol-6-yl)pyridazin-3-yl){[(5-methoxy(2-pyridyl))cyclobutyl]methyl}amine;
3-{[(6-(1H-indazol-6-yl)pyridazin-3-yl)amino]methyl}-3-(2-pyridyl)cyclobutan-1-ol;
3-{[(6-(1H-indazol-6-yl)pyridazin-3-yl)amino]methyl}-3-(2-pyridyl)cyclobutan-1-ol;
3-[6-({[(4-fluorophenyl)cyclobutyl]methyl}amino)pyridazin-3-yl]benzamide;
3-[6-({[(3-fluoro(2-pyridyl))cyclobutyl]methyl}amino)pyridazin-3-yl]-4-methylbenzamide;
6-({[(6-(1H-indazol-5-yl)pyridazin-3-yl)amino]methyl}cyclobutyl)pyridine-3-carbonitrile;
6-[6-({[(3-fluoro(2-pyridyl))cyclobutyl]methyl}amino)pyridazin-3-yl]-3,3-dimethylindolin-2-one;
3-[6-({[(4-cyano-2-pyridyl)cyclobutyl]methyl}amino)pyridazin-3-yl]benzamide;
2-[({[6-(3-carbamoylphenyl)pyridazin-3-yl]amino}methyl)cyclobutyl]pyridine-4-carboxamide;
3-[6-({[(4-cyano(2-pyridyl))cyclobutyl]methyl}amino)pyridazin-3-yl]-4-fluorobenzamide;
2-[({[6-(3-carbamoyl-6-fluorophenyl)pyridazin-3-yl]amino}methyl)cyclobutyl]pyridine-4-carboxamide;
2-({[(6-(1H-indazol-5-yl)pyridazin-3-yl)amino]methyl}cyclobutyl)pyridine-4-carbonitrile;
2-({[(6-(1H-indazol-5-yl)pyridazin-3-yl)amino]methyl}cyclobutyl)pyridine-4-carboxamide;
3-[6-({[(6-cyano-2-pyridyl)cyclobutyl]methyl}amino)pyridazin-3-yl]benzamide;
6-[({[6-(3-carbamoylphenyl)pyridazin-3-yl]amino}methyl)cyclobutyl]pyridine-2-carboxamide;
6-({[(6-(1H-indazol-5-yl)pyridazin-3-yl)amino]methyl}cyclobutyl)pyridine-2-carbonitrile;
6-({[(6-(1H-indazol-5-yl)pyridazin-3-yl)amino]methyl}cyclobutyl)pyridine-2-carboxamide;
(6-(1H-indazol-6-yl)pyridazin-3-yl){[(4-fluorophenyl)cyclobutyl]methyl}amine;
(6-(1H-indazol-5-yl)pyridazin-3-yl){[(4-fluorophenyl)cyclobutyl]methyl}amine;
3-{6-{[(2-pyridylcyclobutyl)methyl]amino}pyridazin-3-yl}benzamide;
methyl 3-(3-fluoro(2-pyridyl))-3-{[(6-(1H-indazol-5-yl)pyridazin-3-yl)amino]methyl}azetidinecarboxylate;
methyl 3-({[6-(3-carbamoylphenyl)pyridazin-3-yl]amino}methyl)-3-(3-fluoro(2-pyridyl))azetidinecarboxylate;
{[(3-fluoro(2-pyridyl))cyclobutyl]methyl}{6-[3-(methylamino)(1H-indazol-5-yl)]pyridazin-3-yl}amine;
2-fluoro-5-[6-({[(3-fluoro(2-pyridyl))cyclobutyl]methyl}amino)pyridazin-3-yl]benzoic acid;
{2-fluoro-5-[6-({[(3-fluoro(2-pyridyl))cyclobutyl]methyl}amino)pyridazin-3-yl]phenyl}-N-methylcarboxamide;
N-{5-[6-({[(3-fluoro-2-pyridyl)cyclobutyl]methyl}amino)pyridazin-3-yl]-1H-indazol-3-yl}acetamide;
2-amino-N-{5-[6-({[(3-fluoro(2-pyridyl))cyclobutyl]methyl}amino)pyridazin-3-yl](1H-indazol-3-yl)}acetamide;
{5-[6-({[(3-fluoro(2-pyridyl))cyclobutyl]methyl}amino)pyridazin-3-yl](1H-indazol-3-yl)}(methylsulfonyl)amine;
3-amino-5-[6-({[(3-fluoro(2-pyridyl))cyclobutyl]methyl}amino)pyridazin-3-yl]-1H-indazolecarboxamide;
[6-(3-aminophenyl)pyridazin-3-yl]{[(3-fluoro(2-pyridyl))cyclobutyl]methyl}amine;
[6-(4-aminophenyl)pyridazin-3-yl]{[(3-fluoro(2-pyridyl))cyclobutyl]methyl}amine;
(6-{3-[(2-aminoethyl)amino](1H-indazol-5-yl)}pyridazin-3-yl){[(3-fluoro(2-pyridyl))cyclobutyl]methyl}amine;
amino{3-[6-({[(3-fluoro(2-pyridyl))cyclobutyl]methyl}amino)pyridazin-3-yl]phenyl}carboxamidine;
amino{4-[6-({[(3-fluoro(2-pyridyl))cyclobutyl]methyl}amino)pyridazin-3-yl]phenyl}carboxamidine;
3-(6-{[(pyrazin-2-ylcyclobutyl)methyl]amino}pyridazin-3-yl)benzamide;
(6-(1H-indazol-6-yl)pyridazin-3-yl)[(pyrazin-2-ylcyclobutyl)methyl]amine;
(6-(1H-indazol-5-yl)pyridazin-3-yl)[(pyrazin-2-ylcyclobutyl)methyl]amine;
amino-N-{3-[6-({[(3-fluoro(2-pyridyl))cyclobutyl]methyl}amino)pyridazin-3-yl]phenyl}amide;
5-[6-({[(3-fluoro-2-pyridyl)cyclobutyl]methyl}amino)pyridazin-3-yl]benzene-1,3-dicarboxylic acid;
5-[6-({[(3-fluoro-2-pyridyl)cyclobutyl]methyl}amino)pyridazin-3-yl]benzene-1,3-dicarboxamide;
3-[6-({[(3-fluoro-2-pyridyl)cyclobutyl]methyl}amino)pyridazin-3-yl]benzenecarboxamidine;
3-[6-({[1-acetyl-3-(3-fluoro(2-pyridyl))azetidin-3-yl]methyl}amino)pyridazin-3-yl]benzamide;
1-acetyl-3-(3-fluoro(2-pyridyl))-3-{[(6-(1H-indazol-5-yl)pyridazin-3-yl)amino]methyl}azetidine;
(6-(1H-indazol-5-yl)pyridazin-3-yl){[3-(3-fluoro(2-pyridyl))azetidin-3-yl]methyl}amine;
3-[6-({[3-(3-fluoro-2-pyridyl)azetidin-3-yl]methyl}amino)pyridazin-3-yl]benzamide;
3-(3-fluoro(2-pyridyl))-3-{[(6-(1H-indazol-5-yl)pyridazin-3-yl)amino]methyl}-1-(methylsulfonyl)azetidine;
3-[6-({[3-(3-fluoro(2-pyridyl))-1-(methylsulfonyl)azetidin-3-yl]methyl}amino)pyridazin-3-yl]benzamide;
(6-(1H-indazol-5-yl)pyridazin-3-yl){[3-(3-fluoro(2-pyridyl))azetidin-3-yl]methyl}(methylsulfonyl)amine;
amino{5-[6-({[(3-fluoro(2-pyridyl))cyclobutyl]methyl}amino)pyridazin-3-yl](1H-indazol-3-yl)}carboxamidine;
3-[6-({[3-(4-fluorophenyl)oxetan-3-yl]methyl}amino)pyridazin-3-yl]benzamide;
{6-[3-(ethylamino)(1H-indazol-5-yl)]pyridazin-3-yl}{[(3-fluoro(2-pyridyl))cyclobutyl]methyl}amine;
N-{4-[6-({[(3-fluoro-2-pyridyl)cyclobutyl]methyl}amino)pyridazin-3-yl]imidazol-2-yl}acetamide;
[6-(2-aminoimidazol-4-yl)pyridazin-3-yl]{[(3-fluoro(2-pyridyl))cyclobutyl]methyl}amine;
{[(3-fluoro(2-pyridyl))cyclobutyl]methyl}(6-{3-[(methylethyl)amino](1H-indazol-5-yl)}pyridazin-3-yl)amine;
{6-[3-(ethylamino)(1H-indazol-5-yl)]pyridazin-3-yl}[(2-pyridylcyclobutyl)methyl]amine;

{[(3-fluoro(2-pyridyl))cyclobutyl]methyl}{6-[2-(trifluoromethoxy)phenyl]pyridazin-3-yl}amine;
{2-[6-({[(3-fluoro-2-pyridyl)cyclobutyl]methyl}amino)pyridazin-3-yl]phenyl}methan-1-ol;
[6-(5-amino(2-pyridyl))pyridazin-3-yl]{[(3-fluoro(2-pyridyl))cyclobutyl]methyl}amine;
[6-(6-amino(3-pyridyl))pyridazin-3-yl]{[(3-fluoro(2-pyridyl))cyclobutyl]methyl}amine;
[6-(4-amino-3-fluorophenyl)pyridazin-3-yl]{[(3-fluoro(2-pyridyl))cyclobutyl]methyl}amine;
(6-benzotnazol-6-ylpyridazin-3-yl){[(3-fluoro(2-pyridyl))cyclobutyl]methyl}amine;
4-[6-({[(3-fluoro-2-pyridyl)cyclobutyl]methyl}amino)pyridazin-3-yl]indolin-2-one;
(6-benzimidazol-5-ylpyridazin-3-yl){[(3-fluoro(2-pyridyl))cyclobutyl]methyl}amine;
N-{3-[6-({[(3-fluoro-2-pyridyl)cyclobutyl]methyl}amino)pyridazin-3-yl]phenyl}acetamide;
{[(3-fluoro(2-pyridyl))cyclobutyl]methyl}[6-(4-morpholin-4-ylphenyl)pyridazin-3-yl]amine,
{[(3-fluoro(2-pyridyl))cyclobutyl]methyl}[6-(2-methylpyrimidin-5-yl)pyridazin-3-yl]amine;
{[(3-fluoro(2-pyridyl))cyclobutyl]methyl}(6-pyrimidin-2-ylpyridazin-3-yl)amine;
{[(3-fluoro(2-pyridyl))cyclobutyl]methyl}(6-pyrazin-2-ylpyridazin-3-yl)amine;
{[(3-fluoro(2-pyridyl))cyclobutyl]methyl}(6-phenylpyridazin-3-yl)amine;
N-{4-[6-({[(3-fluoro-2-pyridyl)cyclobutyl]methyl}amino)pyridazin-3-yl]phenyl}acetamide;
[6-(2-aminopyrimidin-5-yl)pyridazin-3-yl]{[(3-fluoro(2-pyridyl))cyclobutyl]methyl}amine;
N-{5-[6-({[(3-fluoro-2-pyridyl)cyclobutyl]methyl}amino)pyridazin-3-yl]pyrimidin-2-yl}acetamide;
N-{5-[6-({[(3-fluoro(2-pyridyl))cyclobutyl]methyl}amino)pyridazin-3-yl]pyrimidin-2-yl}methoxycarboxamide;
{[(3-fluoro(2-pyridyl))cyclobutyl]methyl}[6-(5-methoxy(2-pyridyl))pyridazin-3-yl]amine;
6-[6-({[(3-fluoro-2-pyridyl)cyclobutyl]methyl}amino)pyridazin-3-yl]pyridin-3-ol;
{5-[6-({[(3-fluoro(2-pyridyl))cyclobutyl]methyl}amino)pyridazin-3-yl]pyrimidin-2-yl}(methylsulfonyl)amine;
[6-(2,3-difluorophenyl)pyridazin-3-yl]{[(3-fluoro(2-pyridyl))cyclobutyl]methyl}amine;
{[(3-fluoro(2-pyridyl))cyclobutyl]methyl}[6-(3-fluoro(2-pyridyl))pyridazin-3-yl]amine;
5-[6-({[(3-fluoro(2-pyridyl))cyclobutyl]methyl}amino)pyridazin-3-yl]indolin-2-one;
5-[6-({[(3-fluoro(2-pyridyl))cyclobutyl]methyl}amino)pyridazin-3-yl]-1H-2-hydroindazol-3-one;
N-{3-[6-({[(3-fluoro(2-pyridyl))cyclobutyl]methyl}amino)pyridazin-3-yl]phenyl}(methylamino)carboxamide;
N-{4-[6-({[(3-fluoro(2-pyridyl))cyclobutyl]methyl}amino)pyridazin-3-yl]phenyl}(methylamino)carboxamide;
tert-butyl 4-{5-[6-({[(3-fluoro-2-pyridyl)cyclobutyl]methyl}amino)pyridazin-3-yl]pyrimidin-2-yl}piperazinecarboxylate;
2-({5-[6-({[(3-fluoro(2-pyridyl))cyclobutyl]methyl}amino)pyridazin-3-yl]pyrimidin-2-yl}amino)acetamide;
{6-[2-(aminomethyl)-5-fluorophenyl]pyridazin-3-yl}{[(3-fluoro(2-pyridyl))cyclobutyl]methyl}amine;
{6-[2-(aminomethyl)phenyl]pyridazin-3-yl}{[(3-fluoro(2-pyridyl))cyclobutyl]methyl}amine;
{6-[4-(aminomethyl)phenyl]pyridazin-3-yl}{[(3-fluoro(2-pyridyl))cyclobutyl]methyl}amine;
{[(3-fluoro(2-pyridyl))cyclobutyl]methyl}[6-(2-piperazinylpyrimidin-5-yl)pyridazin-3-yl]amine;
[6-(3-chloro(2-pyridyl))pyridazin-3-yl]{[(3-fluoro(2-pyridyl))cyclobutyl]methyl}amine;
{[(3-fluoro(2-pyridyl))cyclobutyl]methyl}[6-(2-methyl(3-pyridyl))pyridazin-3-yl]amine;
3-[6-({[(3-fluoro-2-pyridyl)cyclobutyl]methyl}amino)pyridazin-3-yl]pyridine-2-carbonitrile;
3-[6-({[(3-fluoro-2-pyridyl)cyclobutyl]methyl}amino)pyridazin-3-yl]pyridine-2-carboxamide;
methyl 3-[6-({[(3-fluoro-2-pyridyl)cyclobutyl]methyl}amino)pyridazin-3-yl]pyridine-2-carboxylate;
2-{3-[6-({[(3-fluoro-2-pyridyl)cyclobutyl]methyl}amino)pyridazin-3-yl]-2-pyridyl}propan-2-ol;
amino-N-{4-[6-({[(3-fluoro(2-pyridyl))cyclobutyl]methyl}amino)pyridazin-3-yl]phenyl}amide;
2-amino-2-{3-[6-({[(3-fluoro(2-pyridyl))cyclobutyl]methyl}amino)pyridazin-3-yl]phenyl}acetamide;
{[(3-fluoro(2-pyridyl))cyclobutyl]methyl}(6-pyridazin-4-ylpyridazin-3-yl)amine;
3-[6-({[3,3-difluoro-1-(3-fluoro(2-pyridyl))cyclobutyl]methyl}amino)pyridazin-3-yl]benzamide;
(6-(1H-indazol-5-yl)pyridazin-3-yl){[3,3-difluoro-1-(3-fluoro(2-pyridyl))cyclobutyl]methyl}amine;
5-[6-({[(3-fluoro(2-pyridyl))cyclobutyl]methyl}amino)pyridazin-3-yl]-2-(methylethyl)-1H-2-hydroindazol-3-one;
5-[6-({[(3-fluoro(2-pyridyl))cyclobutyl]methyl}amino)pyridazin-3-yl]-1-(methylethyl)-1H-2-hydroindazol-3-one;
{[(3-fluoro(2-pyridyl))cyclobutyl]methyl}(6-(2-pyridyl)pyridazin-3-yl)amine;
{3-[6-({[(3-fluoro-2-pyridyl)cyclobutyl]methyl}amino)pyridazin-3-yl]-2-pyridyl}methan-1-ol;
amino-N-{5-[6-({[(3-fluoro(2-pyridyl))cyclobutyl]methyl}amino)pyridazin-3-yl](2-pyridyl)}amide;
1-amino-1-{4-[6-({[(3-fluoro(2-pyridyl))cyclobutyl]methyl}amino)pyridazin-3-yl]phenyl}-2-methylpropan-2-ol;
amino-N-{5-[6-({[(3-fluoro(2-pyridyl))cyclobutyl]methyl}amino)pyridazin-3-yl]pyrimidin-2-yl}amide;
(6-(1H-indazol-6-yl)pyridazin-3-yl){[3,3-difluoro-1-(3-fluoro(2-pyridyl))cyclobutyl]methyl}amine;
[6-(2-amino(3-pyridyl))pyridazin-3-yl]{[(3-fluoro(2-pyridyl))cyclobutyl]methyl}amine;
[6-(6-amino-5-fluoro(3-pyridyl))pyridazin-3-yl]{[(3-fluoro(2-pyridyl))cyclobutyl]methyl}amine;
6-[6-({[(3-fluoro-2-pyridyl)cyclobutyl]methyl}amino)pyridazin-3-yl]indolin-2-one;
amino-N-{4-[6-({[3,3-difluoro-1-(3-fluoro(2-pyridyl))cyclobutyl]methyl}amino)pyridazin-3-yl]phenyl}amide;
ethyl 5-[6-({[(3-fluoro-2-pyridyl)cyclobutyl]methyl}amino)pyridazin-3-yl]isoxazole-3-carboxylate;
5-[6-({[(3-fluoro-2-pyridyl)cyclobutyl]methyl}amino)pyridazin-3-yl]isoxazole-3-carboxylic acid;
5-[6-({[(3-fluoro-2-pyridyl)cyclobutyl]methyl}amino)pyridazin-3-yl]isoxazole-3-carboxamide;
amino-N-{5-[6-({[(3-fluoro(2-pyridyl))cyclobutyl]methyl}amino)pyridazin-3-yl](1H-indazol-3-yl)}amide;

4-[6-({[(3-fluoro(2-pyridyl))cyclobutyl]methyl}amino)pyridazin-3-yl]-1-methylimidazole-2-carboxamide;
4-[6-({[(3-fluoro(2-pyridyl))cyclobutyl]methyl}amino)pyridazin-3-yl]-2-methoxybenzamide;
4-[6-({[(3-fluoro(2-pyridyl))cyclobutyl]methyl}amino)pyridazin-3-yl]-2-hydroxybenzamide;
5-[6-({[(3-fluoro(2-pyridyl))cyclobutyl]methyl}amino)pyridazin-3-yl]-2-methoxybenzamide;
5-[6-({[(3-fluoro(2-pyridyl))cyclobutyl]methyl}amino)pyridazin-3-yl]-2-hydroxybenzamide;
4-[6-({[(3-fluoro(2-pyridyl))cyclobutyl]methyl}amino)pyridazin-3-yl]-2-methoxybenzoic acid;
5-[6-({[(3-fluoro(2-pyridyl))cyclobutyl]methyl}amino)pyridazin-3-yl]-2-methoxybenzoic acid;
5-[6-({[(3-fluoro-2-pyridyl)cyclobutyl]methyl}amino)pyridazin-3-yl]-1,3-oxazole-2-carboxamide;
4-[6-({[(3-fluoro-2-pyridyl)cyclobutyl]methyl}amino)pyridazin-3-yl]imidazole-2-carboxamide;
3-[6-({[(3-fluoro-2-pyridyl)cyclobutyl]methyl}amino)pyridazin-3-yl]isoxazole-5-carboxamide;
3-[6-({[(3-fluoro-2-pyridyl)cyclobutyl]methyl}amino)pyridazin-3-yl]pyrazole-5-carboxamide;
3-[6-({[(3-fluoro(2-pyridyl))cyclobutyl]methyl}amino)pyridazin-3-yl]-1-methylpyrazole-5-carboxamide;
5-[6-({[(3-fluoro(2-pyridyl))cyclobutyl]methyl}amino)pyridazin-3-yl]-1-methylpyrazole-3-carboxamide;
2-[6-({[(3-fluoro-2-pyridyl)cyclobutyl]methyl}amino)pyridazin-3-yl]-1,3-oxazole-5-carboxamide;
2-[6-({[(3-fluoro-2-pyridyl)cyclobutyl]methyl}amino)pyridazin-3-yl]-1,3-thiazole-4-carboxamide;
5-[6-({[(3-fluoro-2-pyridyl)cyclobutyl]methyl}amino)pyridazin-3-yl]-1,2,4-oxadiazole-3-carboxamide;
2-[6-({[(3-fluoro-2-pyridyl)cyclobutyl]methyl}amino)pyridazin-3-yl]-1,3-oxazole-4-carboxamide;
2-[6-({[(3-fluoro-2-pyridyl)cyclobutyl]methyl}amino)pyridazin-3-yl]-1,3-thiazole-5-carboxamide;
methyl 2-[6-({[(3-fluoro-2-pyridyl)cyclobutyl]methyl}amino)pyridazin-3-yl]-1,3-oxazole-4-carboxylate;
methyl 2-[6-({[(3-fluoro-2-pyridyl)cyclobutyl]methyl}amino)pyridazin-3-yl]-1,3-thiazole-4-carboxylate;
methyl 2-[6-({[(3-fluoro-2-pyridyl)cyclobutyl]methyl}amino)pyridazin-3-yl]-1,3-oxazole-5-carboxylate;
2-[6-({[(3-fluoro-2-pyridyl)cyclobutyl]methyl}amino)pyridazin-3-yl]imidazole-4-carboxamide;
methyl 2-[6-({[(3-fluoro-2-pyridyl)cyclobutyl]methyl}amino)pyridazin-3-yl]imidazole-4-carboxylate;
4-[6-({[(3-fluoro-2-pyridyl)cyclobutyl]methyl}amino)pyridazin-3-yl]-1,3-thiazole-2-carboxamide;
5-[6-({[(3-fluoro-2-pyridyl)cyclobutyl]methyl}amino)pyridazin-3-yl]-1,3-thiazole-2-carboxamide;
3-[6-({[(3-fluoro-2-pyridyl)cyclobutyl]methyl}amino)pyridazin-3-yl]-1,2,4-oxadiazole-5-carboxamide;
5-[6-({[(3-fluoro-2-pyridyl)cyclobutyl]methyl}amino)pyridazin-3-yl]-4H-1,2,4-triazole-3-carboxamide;
methyl 2-[6-({[(3-fluoro(2-pyridyl))cyclobutyl]methyl}amino)pyridazin-3-yl]-1-methyl imidazole-4-carboxylate;
2-[6-({[(3-fluoro(2-pyridyl))cyclobutyl]methyl}amino)pyridazin-3-yl]-1-methyl imidazole-4-carboxamide;
2-[6-({[(3-fluoro(2-pyridyl))cyclobutyl]methyl}amino)pyridazin-3-yl]-1-methyl imidazole-5-carboxamide;
5-[6-({[(3-fluoro-2-pyridyl)cyclobutyl]methyl}amino)pyridazin-3-yl]thiophene-2-carboxamide;
5-[6-({[(3-fluoro-2-pyridyl)cyclobutyl]methyl}amino)pyridazin-3-yl]-1,3,4-thiadiazole-2-carboxamide;
{[(3-fluoro(2-pyridyl))cyclobutyl]methyl}(6-(1,3-thiazol-2-yl)pyridazin-3-yl)amine;
(6-(2H-1,2,3,4-tetraazol-5-yl)pyridazin-3-yl){[(3-fluoro(2-pyridyl))cyclobutyl]methyl}amine;
5-[6-({[(3-fluoro-2-pyridyl)cyclobutyl]methyl}amino)pyridazin-3-yl]-1,3,4-oxadiazole-2-carboxamide;
2-[6-({[(3-fluoro(2-pyridyl)cyclobutyl]methyl}amino)pyridazin-3-yl]-4-methyl-1,3-thiazole-5-carboxamide;
2-[6-({[(3-fluoro(2-pyridyl)cyclobutyl]methyl}amino)pyridazin-3-yl]-1,3-thiazole-5-carboxylic acid;
2-[6-({[(3-fluoro(2-pyridyl)cyclobutyl]methyl}amino)pyridazin-3-yl]-1,3-thiazole-5-carbonitrile;
5-[6-({[(3-fluoro-2-pyridyl)cyclobutyl]methyl}amino)pyridazin-3-yl]thiophene-2-carboxylic acid;
2-[6-({[(3-fluoro(2-pyridyl))cyclobutyl]methyl}amino)pyridazin-3-yl]-4-hydroxy-1,3-thiazole-5-carboxamide;
5-[6-({[(3-fluoro-2-pyridyl)cyclobutyl]methyl}amino)pyridazin-3-yl]-3-pyrazolino[3,4-d]1,3-thiazol-3-one;
{2-[6-({[(3-fluoro-2-pyridyl)cyclobutyl]methyl}amino)pyridazin-3-yl]-1,3-thiazol-5-yl}methan-1-ol;
[6-(5-(2H-1,2,3,4-tetraazol-5-yl)(1,3-thiazol-2-yl))pyridazin-3-yl]{[(3-fluoro(2-pyridyl))cyclobutyl]methyl}amine;
5-{2-[6-({[(3-fluoro-2-pyridyl)cyclobutyl]methyl}amino)pyridazin-3-yl]-1,3-thiazol-5-yl}-1,3,4-oxadiazolin-2-one;
ethyl 3-[6-({[(3-fluoro(2-pyridyl))cyclobutyl]methyl}amino)pyridazin-3-yl]-5-hydroxypyrazole-4-carboxylate;
3-{2-[6-({[(3-fluoro-2-pyridyl)cyclobutyl]methyl}amino)pyridazin-3-yl]-1,3-thiazol-5-yl}-1,2,4-triazolin-5-one;
3-{2-[6-({[(3-fluoro-2-pyridyl)cyclobutyl]methyl}amino)pyridazin-3-yl]-1,3-thiazol-5-yl}-1,2,4-oxadiazolin-5-one;
ethyl 2-[6-({[(3-fluoro(2-pyridyl))cyclobutyl]methyl}amino)pyridazin-3-yl]-4-hydroxy-1,3-thiazole-5-carboxylate;
2-[6-({[(3-fluoro(2-pyridyl))cyclobutyl]methyl}amino)pyridazin-3-yl]-4-methoxy-1,3-thiazole-5-carboxamide;
2-[6-({[(3-fluoro(2-pyridyl))cyclobutyl]methyl}amino)pyridazin-3-yl]-4-methoxy-1,3-thiazole-5-carboxylic acid;
1-{2-[6-({[(3-fluoro-2-pyridyl)cyclobutyl]methyl}amino)pyridazin-3-yl]-1,3-thiazol-5-yl}ethan-1-ol;
2,2,2-trifluoro-1-{2-[6-({[(3-fluoro(2-pyridyl))cyclobutyl]methyl}amino)pyridazin-3-yl](1,3-thiazol-5-yl)}ethan-1-ol;
{2-[6-({[(3-fluoro(2-pyridyl))cyclobutyl]methyl}amino)pyridazin-3-yl](1,3-thiazol-5-yl)}-N-(methylethyl)carboxamide;
ethyl 2-[6-({[(3-fluoro-2-pyridyl)cyclobutyl]methyl}amino)pyridazin-3-yl]-1,3-thiazole-4-carboxylate;
2-[6-({[(3-fluoro-2-pyridyl)cyclobutyl]methyl}amino)pyridazin-3-yl]-3-pyrrolino[3,4-d]1,3-thiazol-6-one;
1-{2-[6-({[(3-fluoro-2-pyridyl)cyclobutyl]methyl}amino)pyridazin-3-yl]-1,3-thiazol-5-yl}ethan-1-one;
2-{2-[6-({[(3-fluoro-2-pyridyl)cyclobutyl]methyl}amino)pyridazin-3-yl]-1,3-thiazol-5-yl}propan-2-ol;

1,1,1-trifluoro-2-{2-[6-({[(3-fluoro(2-pyridyl))cyclobutyl]methyl}amino)pyridazin-3-yl](1,3-thiazol-5-yl)}propan-2-ol;
{2-[6-({[(3-fluoro(2-pyridyl))cyclobutyl]methyl}amino)pyridazin-3-yl](1,3-thiazol-5-yl)}-N-methylcarboxamide;
3-(6-{[(2-pyridylcyclobutyl)methyl]amino}pyridazin-3-yl)benzenecarbonitrile;
3-(6-{methyl[(2-pyridylcyclobutyl)methyl]amino}pyridazin-3-yl)benzamide;
6-[6-({[(3-fluoro-2-pyridyl)cyclobutyl]methyl}amino)pyridazin-3-yl]pyrazine-2-carbonitrile;
6-[6-({[(3-fluoro-2-pyridyl)cyclobutyl]methyl}amino)pyridazin-3-yl]pyrazine-2-carboxamide;
2-[6-({[(3-fluoro(2-pyridyl))cyclobutyl]methyl}amino)pyridazin-3-yl]-4-hydroxy-1,3-thiazole-5-carbonitrile;
2-(6-{[(2-pyridylcyclobutyl)methyl]amino}pyridazin-3-yl)-1,3-thiazole-5-carboxamide;
2-(6-{[(2-pyridylcyclobutyl)methyl]amino}pyridazin-3-yl)-1,3-thiazole-5-carboxylic acid;
3-{5-[6-({[(3-fluoro-2-pyridyl)cyclobutyl]methyl}amino)pyridazin-3-yl]-2-thienyl}-1,2,4-triazolin-5-one;
amino{2-[6-({[(3-fluoro(2-pyridyl))cyclobutyl]methyl}amino)pyridazin-3-yl](1,3-thiazol-5-yl)}methane-1-thione;
2,2,2-trifluoro-1-{2-[6-({[(3-fluoro(2-pyridyl))cyclobutyl]methyl}amino)pyridazin-3-yl](1,3-thiazol-5-yl)}ethane-1,1-diol;
{[(3-fluoro(2-pyridyl))cyclobutyl]methyl}{6-[5-(2,2,2-trifluoroethyl)(1,3-thiazol-2-yl)]pyridazin-3-yl}amine;
5-[6-({[(3-fluoro-2-pyridyl)cyclobutyl]methyl}amino)pyridazin-3-yl]thiophene-2-carbonitrile;
2-[6-({[(3-fluoro-2-pyridyl)cyclobutyl]methyl}amino)pyridazin-3-yl]thiopheno[2,3-c]3-pyrrolin-6-one;
{6-[5-(1-amino-2,2,2-trifluoroethyl)(1,3-thiazol-2-yl)]pyridazin-3-yl}{[(3-fluoro(2-pyridyl))cyclobutyl]methyl}amine;
[6-(2-aminopyrimidin-4-yl)pyridazin-3-yl]{[(3-fluoro(2-pyridyl))cyclobutyl]methyl}amine;
2-{5-[6-({[(3-fluoro-2-pyridyl)cyclobutyl]methyl}amino)pyridazin-3-yl]-1,2,3,4-tetraazol-2-yl}acetamide;
{6-[2-(2-aminoethyl)(1,2,3,4-tetraazol-5-yl)]pyridazin-3-yl}{[(3-fluoro(2-pyridyl))cyclobutyl]methyl}amine;
[6-(3-(2H-1,2,3,4-tetraazol-5-yl)phenyl)pyridazin-3-yl]{[(3-fluoro(2-pyridyl))cyclobutyl]methyl}amine;
3-{3-[6-({[(3-fluoro-2-pyridyl)cyclobutyl]methyl}amino)pyridazin-3-yl]phenyl}-1,2,4-triazolin-5-one;
3-{4-fluoro-3-[6-({[(3-fluoro(2-pyridyl))cyclobutyl]methyl}amino)pyridazin-3-yl]phenyl}-1,2,4-triazolin-5-one;
{6-[5-(aminomethyl)(1,3-thiazol-2-yl)]pyridazin-3-yl}{[(3-fluoro(2-pyridyl))cyclobutyl]methyl}amine;
N-((2-(6-((1-(3-fluoropyridin-2-yl)cyclobutyl)methylamino)pyridazin-3-yl)thiazol-5-yl)methyl)-2-methylpropane-2-sulfinamide;
{6-[5-(aminoethyl)(1,3-thiazol-2-yl)]pyridazin-3-yl}{[(3-fluoro(2-pyridyl))cyclobutyl]methyl}amine;
{6-[5-(3-aminooxetan-3-yl)(1,3-thiazol-2-yl)]pyridazin-3-yl}{[(3-fluoro(2-pyridyl))cyclobutyl]methyl}amine;
2-[6-({[(3-fluoro-2-pyridyl)cyclobutyl]methyl}amino)pyridazin-3-yl]pyrimidine-4-carboxamide;
{2-[6-({[(3-fluoro(2-pyridyl))cyclobutyl]methyl}amino)pyridazin-3-yl](1,3-thiazol-5-yl)}-N-(2-hydroxyethyl)carboxamide;
ethyl 5-chloro-2-[5-chloro-6-({[(3-fluoro(2-pyridyl))cyclobutyl]methyl}amino)pyridazin-3-yl]-1,3-thiazole-4-carboxylate;
N-{4-[6-({[(3-fluoro-2-pyridyl)cyclobutyl]methyl}amino)pyridazin-3-yl]pyrimidin-2-yl}acetamide;
{4-[6-({[(3-fluoro(2-pyridyl))cyclobutyl]methyl}amino)pyridazin-3-yl]pyrimidin-2-yl}(methylsulfonyl)amine;
(2E)-3-amino-3-{2-[6-({[(3-fluoro(2-pyridyl))cyclobutyl]methyl}amino)pyridazin-3-yl](1,3-thiazol-5-yl)}-2-azaprop-2-enenitrile;
N-({2-[6-({[(3-fluoro-2-pyridyl)cyclobutyl]methyl}amino)pyridazin-3-yl]-1,3-thiazol-5-yl}methyl)acetamide;
({2-[6-({[(3-fluoro(2-pyridyl))cyclobutyl]methyl}amino)pyridazin-3-yl](1,3-thiazol-5-yl)}methyl)(methylsulfonyl)amine;
N-({2-[6-({[(3-fluoro(2-pyridyl))cyclobutyl]methyl}amino)pyridazin-3-yl](1,3-thiazol-5-yl)}methyl)methoxycarboxamide;
2,2-difluoro-1-{2-[6-({[(3-fluoro(2-pyridyl))cyclobutyl]methyl}amino)pyridazin-3-yl](1,3-thiazol-5-yl)}ethan-1-ol;
2-[6-({[(3-fluoro(2-pyridyl))cyclobutyl]methyl}amino)pyridazin-3-yl](1,3-thiazol-5-yl)morpholin-4-yl ketone;
N-(2-aminoethyl){2-[6-({[(3-fluoro(2-pyridyl))cyclobutyl]methyl}amino)pyridazin-3-yl](1,3-thiazol-5-yl)}carboxamide;
N-(2,3-dihydroxypropyl){2-[6-({[(3-fluoro(2-pyridyl))cyclobutyl]methyl}amino)pyridazin-3-yl](1,3-thiazol-5-yl)}carboxamide;
{2-[6-({[(3-fluoro(2-pyridyl))cyclobutyl]methyl}amino)pyridazin-3-yl](1,3-thiazol-5-yl)}-N-pyrrolidin-3-yl-carboxamide;
2-{2-[6-({[(3-fluoro-2-pyridyl)cyclobutyl]methyl}amino)pyridazin-3-yl]-1,3-thiazol-5-yl}acetamide;
{[(3-fluoro(2-pyridyl))cyclobutyl]methyl}[6-(5-pyrazol-4-yl(1,3-thiazol-2-yl))pyridazin-3-yl]amine;
{[(3-fluoro(2-pyridyl))cyclobutyl]methyl}[6-(5-pyrazol-3-yl(1,3-thiazol-2-yl))pyridazin-3-yl]amine;
4-[6-({[(3-fluoro-2-pyridyl)cyclobutyl]methyl}amino)pyridazin-3-yl]pyrimidine-2-carboxamide;
6-[6-({[(3-fluoro-2-pyridyl)cyclobutyl]methyl}amino)pyridazin-3-yl]pyrimidine-4-carboxamide;
N-(carbamoylmethyl){2-[6-({[(3-fluoro(2-pyridyl))cyclobutyl]methyl}amino)pyridazin-3-yl](1,3-thiazol-5-yl)}carboxamide;
4-({2-[6-({[(3-fluoro-2-pyridyl)cyclobutyl]methyl}amino)pyridazin-3-yl]-1,3-thiazol-5-yl}carbonyl)piperazine-2-carboxamide;
[6-(5-chloro(1,3-thiazolino[5,4-b]pyridin-2-yl))pyridazin-3-yl]{[(3-fluoro(2-pyridyl))cyclobutyl]methyl}amine;
{[(3-fluoro(2-pyridyl))cyclobutyl]methyl}(6-(1,3-thiazolino[5,4-b]pyridin-2-yl)pyridazin-3-yl)amine;
[6-(5-amino(1,3-thiazolino[5,4-b]pyridin-2-yl))pyridazin-3-yl]{[(3-fluoro(2-pyridyl))cyclobutyl]methyl}amine;
amino{4-fluoro-3-[6-({[(3-fluoro(2-pyridyl))cyclobutyl]methyl}amino)pyridazin-3-yl]phenyl}sulfonamide;
2-[6-({[(3-fluoro(2-pyridyl))cyclobutyl]methyl}amino)pyridazin-3-yl](1,3-thiazol-5-yl)3-hydroxypyrrolidinyl ketone;

4-({2-[6-({[(3-fluoro-2-pyridyl)cyclobutyl]methyl}amino)pyridazin-3-yl]-1,3-thiazol-5-yl}carbonyl)-1,4-thiazaperhydroine-1,1-dione;
N-(1,1-dioxothiolan-3-yl){2-[6-({[(3-fluoro(2-pyridyl))cyclobutyl]methyl}amino)pyridazin-3-yl](1,3-thiazol-5-yl)}carboxamide;
{2-[6-({[(3-fluoro(2-pyridyl))cyclobutyl]methyl}amino)pyridazin-3-yl](1,3-thiazol-5-yl)}-N-[2-(methylsulfonyl)ethyl]carboxamide;
2-[6-({[(3-fluoro(2-pyridyl))cyclobutyl]methyl}amino)pyridazin-3-yl](1,3-thiazol-5-yl)3-hydroxypiperidyl ketone;
{[(3-fluoro(2-pyridyl))cyclobutyl]methyl}(6-pyrazolo[5,4-d]1,3-thiazol-5-ylpyridazin-3-yl)amine;
2-[6-({[(3-fluoro(2-pyridyl))cyclobutyl]methyl}amino)pyridazin-3-yl](1,3-thiazol-5-yl)4-hydroxypiperidyl ketone;
4-({2-[6-({[(3-fluoro-2-pyridyl)cyclobutyl]methyl}amino)pyridazin-3-yl]-1,3-thiazol-5-yl}carbonyl)piperazin-2-one;
{2-[6-({[(3-fluoro(2-pyridyl))cyclobutyl]methyl}amino)pyridazin-3-yl](1,3-thiazol-5-yl)}-N-(oxolan-2-ylmethyl)carboxamide;
1-({2-[6-({[(3-fluoro-2-pyridyl)cyclobutyl]methyl}amino)pyridazin-3-yl]-1,3-thiazol-5-yl}carbonyl)piperidine-3-carboxamide;
2-[6-({[(3-fluoro-2-pyridyl)cyclobutyl]methyl}amino)pyridazin-3-yl]-1,3-thiazolino[5,4-b]pyridine-5-carboxamide;
{[(3-fluoro(2-pyridyl))cyclobutyl]methyl}[6-(5-methoxy(1,3-thiazolino[5,4-b]pyridin-2-yl))pyridazin-3-yl]amine;
2-[6-({[(3-fluoro-2-pyridyl)cyclobutyl]methyl}amino)pyridazin-3-yl]-1,3-thiazolino[5,4-b]pyridin-5-ol;
N-((2R)-2,3-dihydroxypropyl){2-[6-({[(3-fluoro(2-pyridyl))cyclobutyl]methyl}amino)pyridazin-3-yl](1,3-thiazol-5-yl)}carboxamide;
N-((2S)-2,3-dihydroxypropyl){2-[6-({[(3-fluoro(2-pyridyl))cyclobutyl]methyl}amino)pyridazin-3-yl](1,3-thiazol-5-yl)}carboxamide;
N-(2-amino-3,3,3-trifluoropropyl){2-[6-({[(3-fluoro(2-pyridyl))cyclobutyl]methyl}amino)pyridazin-3-yl](1,3-thiazol-5-yl)}carboxamide;
N-(3-amino-2,2-difluoropropyl){2-[6-({[(3-fluoro(2-pyridyl))cyclobutyl]methyl}amino)pyridazin-3-yl](1,3-thiazol-5-yl)}carboxamide;
{2-[6-({[(3-fluoro(2-pyridyl))cyclobutyl]methyl}amino)pyridazin-3-yl](1,3-thiazol-5-yl)}-N,N-dimethylcarboxamide;
N-(2,2-difluoro-3-hydroxypropyl){2-[6-({[(3-fluoro(2-pyridyl))cyclobutyl]methyl}amino)pyridazin-3-yl](1,3-thiazol-5-yl)}carboxamide;
{2-[6-({[(3-fluoro(2-pyridyl))cyclobutyl]methyl}amino)pyridazin-3-yl](1,3-thiazol-5-yl)}-N-(2-oxopyrrolidin-3-yl)carboxamide;
3-[6-({[3-fluoro-1-(3-fluoro(2-pyridyl))cyclobutyl]methyl}amino)pyridazin-3-yl]benzamide;
4-fluoro-3-[6-({[3-fluoro-1-(3-fluoro(2-pyridyl))cyclobutyl]methyl}amino)pyridazin-3-yl]benzamide;
2-amino-N-({2-[6-({[(3-fluoro(2-pyridyl))cyclobutyl]methyl}amino)pyridazin-3-yl](1,3-thiazol-5-yl)}methyl)acetamide;
((2S)pyrrolidin-2-yl)-N-({2-[6-({[(3-fluoro(2-pyridyl))cyclobutyl]methyl}amino)pyridazin-3-yl](1,3-thiazol-5-yl)}methyl)carboxamide;
((2R)pyrrolidin-2-yl)-N-({2-[6-({[(3-fluoro(2-pyridyl))cyclobutyl]methyl}amino)pyridazin-3-yl](1,3-thiazol-5-yl)}methyl)carboxamide;
{[(3-fluoro(2-pyridyl))cyclobutyl]methyl}(6-(3-pyrrolino[3,4-d]1,3-thiazol-2-yl)pyridazin-3-yl)amine;
2-[6-({[(3-fluoro(2-pyridyl))cyclobutyl]methyl}amino)pyridazin-3-yl]-5-(methylsulfonyl)-3-pyrrolino[3,4-d]1,3-thiazole;
N-({2-[6-({[(3-fluoro(2-pyridyl))cyclobutyl]methyl}amino)pyridazin-3-yl](1,3-thiazol-5-yl)}methyl)-2-hydroxyacetamide;
2-[({2-[6-({[(3-fluoro-2-pyridyl)cyclobutyl]methyl}amino)pyridazin-3-yl]-1,3-thiazol-5-yl}methyl)amino]acetamide;
((2S)-5-oxopyrrolidin-2-yl)-N-({2-[6-({[(3-fluoro(2-pyridyl))cyclobutyl]methyl}amino)pyridazin-3-yl](1,3-thiazol-5-yl)}methyl)carboxamide;
N-({2-[6-({[(3-fluoro(2-pyridyl))cyclobutyl]methyl}amino)pyridazin-3-yl](1,3-thiazol-5-yl)}methyl)-2-hydroxy-2-methylpropanamide;
N-((3S)pyrrolidin-3-yl){2-[6-({[(3-fluoro(2-pyridyl))cyclobutyl]methyl}amino)pyridazin-3-yl](1,3-thiazol-5-yl)}carboxamide;
N-((3R)pyrrolidin-3-yl){2-[6-({[(3-fluoro(2-pyridyl))cyclobutyl]methyl}amino)pyridazin-3-yl](1,3-thiazol-5-yl)}carboxamide;
((3S)morpholin-3-yl)-N-({2-[6-({[(3-fluoro(2-pyridyl))cyclobutyl]methyl}amino)pyridazin-3-yl](1,3-thiazol-5-yl)}methyl)carboxamide;
N-({2-[6-({[(3-fluoro(2-pyridyl))cyclobutyl]methyl}amino)pyridazin-3-yl](1,3-thiazol-5-yl)}methyl)pyrazol-5-ylcarboxamide;
N-({2-[6-({[(3-fluoro(2-pyridyl))cyclobutyl]methyl}amino)pyridazin-3-yl](1,3-thiazol-5-yl)}methyl)imidazol-2-ylcarboxamide;
N-({2-[6-({[(3-fluoro(2-pyridyl))cyclobutyl]methyl}amino)pyridazin-3-yl](1,3-thiazol-5-yl)}methyl)pyrazol-4-ylcarboxamide;
((4S)-2-oxoimidazolidin-4-yl)-N-({2-[6-({[(3-fluoro(2-pyridyl))cyclobutyl]methyl}amino)pyridazin-3-yl](1,3-thiazol-5-yl)}methyl)carboxamide;
((3S)-6-oxo(3-piperidyl))-N-({2-[6-({[(3-fluoro(2-pyridyl))cyclobutyl]methyl}amino)pyridazin-3-yl](1,3-thiazol-5-yl)}methyl)carboxamide;
2H-1,2,3-triazol-4-yl-N-({2-[6-({[(3-fluoro(2-pyridyl))cyclobutyl]methyl}amino)pyridazin-3-yl](1,3-thiazol-5-yl)}methyl)carboxamide;
(2S)-2-amino-N-({2-[6-({[(3-fluoro(2-pyridyl))cyclobutyl]methyl}amino)pyridazin-3-yl](1,3-thiazol-5-yl)}methyl)-3-hydroxypropanamide;
(2S)-2-amino-N-({2-[6-({[(3-fluoro(2-pyridyl))cyclobutyl]methyl}amino)pyridazin-3-yl](1,3-thiazol-5-yl)}methyl)-3-hydroxypropanamide;
((2S)-4-acetylpiperazin-2-yl)-N-({2-[6-({[(3-fluoro(2-pyridyl))cyclobutyl]methyl}amino)pyridazin-3-yl](1,3-thiazol-5-yl)}methyl)carboxamide;
[(2S)-4-(methylsulfonyl)piperazin-2-yl]-N-({2-[6-({[(3-fluoro(2-pyridyl))cyclobutyl]methyl}amino)pyridazin-3-yl](1,3-thiazol-5-yl)}methyl)carboxamide;
((3S)morpholin-3-yl)-N-({2-[6-({[(3-fluoro(2-pyridyl))cyclobutyl]methyl}amino)pyridazin-3-yl](1,3-thiazol-5-yl)}methyl)carboxamide;
1H-1,2,4-triazol-5-yl-N-({2-[6-({[(3-fluoro(2-pyridyl))cyclobutyl]methyl}amino)pyridazin-3-yl](1,3-thiazol-5-yl)}methyl)carboxamide;

((2R)-6-oxo(2-piperidyl))-N-({2-[6-({[(3-fluoro(2-pyridyl))cyclobutyl]methyl}amino)pyridazin-3-yl](1,3-thiazol-5-yl)}methyl)carboxamide;

N-({2-[6-({[(3-fluoro(2-pyridyl))cyclobutyl]methyl}amino)pyridazin-3-yl](1,3-thiazol-5-yl)}methyl)imidazol-5-ylcarboxamide;

2-amino-N-({2-[6-({[(3-fluoro(2-pyridyl))cyclobutyl]methyl}amino)pyridazin-3-yl](1,3-thiazol-5-yl)}methyl)-2-methylpropanamide;

(2S)-2-amino-N-({2-[6-({[(3-fluoro(2-pyridyl))cyclobutyl]methyl}amino)pyridazin-3-yl](1,3-thiazol-5-yl)}methyl)propanamide;

N-({2-[6-({[(3-fluoro(2-pyridyl))cyclobutyl]methyl}amino)pyridazin-3-yl](1,3-thiazol-5-yl)}methyl)(2-hydroxyimidazol-5-yl)carboxamide;

(2S)-2-amino-N-({2-[6-({[(3-fluoro(2-pyridyl))cyclobutyl]methyl}amino)pyridazin-3-yl](1,3-thiazol-5-yl)}methyl)-3-hydroxy-3-methylbutanamide;

(2S)-2-amino-N-({2-[6-({[(3-fluoro(2-pyridyl))cyclobutyl]methyl}amino)pyridazin-3-yl](1,3-thiazol-5-yl)}methyl)propanamide;

((3R)-1,1-dioxo(1,4-thiazaperhydroin-3-yl))-N-({2-[6-({[(3-fluoro(2-pyridyl))cyclobutyl]methyl}amino)pyridazin-3-yl](1,3-thiazol-5-yl)}methyl)carboxamide;

((2S)-4,4-difluoropyrrolidin-2-yl)-N-({2-[6-({[(3-fluoro(2-pyridyl))cyclobutyl]methyl}amino)pyridazin-3-yl](1,3-thiazol-5-yl)}methyl)carboxamide;

tert-butyl (2S)-4,4-difluoro-2-[N-({2-[6-({[(3-fluoro(2-pyridyl))cyclobutyl]methyl}amino)pyridazin-3-yl](1,3-thiazol-5-yl)}methyl)carbamoyl]pyrrolidinecarboxylate;

((2S)-4,4-difluoro-1-formylpyrrolidin-2-yl)-N-({2-[6-({[(3-fluoro(2-pyridyl))cyclobutyl]methyl}amino)pyridazin-3-yl](1,3-thiazol-5-yl)}methyl)carboxamide;

((2R,4R)-4-fluoropyrrolidin-2-yl)-N-({2-[6-({[(3-fluoro(2-pyridyl))cyclobutyl]methyl}amino)pyridazin-3-yl](1,3-thiazol-5-yl)}methyl)carboxamide;

N-({2-[6-({[(3-fluoro(2-pyridyl))cyclobutyl]methyl}amino)pyridazin-3-yl](1,3-thiazol-5-yl)}methyl)-2-methylpropanamide;

amino-N-({2-[6-({[(3-fluoro(2-pyridyl))cyclobutyl]methyl}amino)pyridazin-3-yl](1,3-thiazol-5-yl)}methyl)amide;

((3S)-1,1-dioxo(1,4-thiazaperhydroin-3-yl))-N-({2-[6-({[(3-fluoro(2-pyridyl))cyclobutyl]methyl}amino)pyridazin-3-yl](1,3-thiazol-5-yl)}methyl)carboxamide;

N-({2-[6-({[3-fluoro-1-(3-fluoro(2-pyridyl))cyclobutyl]methyl}amino)pyridazin-3-yl]-1,3-thiazol-5-yl}methyl)acetamide;

N-({2-[6-({[3-fluoro-1-(3-fluoro(2-pyridyl))cyclobutyl]methyl}amino)pyridazin-3-yl]-1,3-thiazol-5-yl}methyl)acetamide;

4-fluoro-3-[6-({[3-fluoro-1-(3-fluoro(2-pyridyl))cyclobutyl]methyl}amino)pyridazin-3-yl]benzamide;

4-fluoro-3-[6-({[3-fluoro-1-(3-fluoro(2-pyridyl))cyclobutyl]methyl}amino)pyridazin-3-yl]benzenecarbonitrile;

3-[6-({[3-fluoro-1-(3-fluoro(2-pyridyl))cyclobutyl]methyl}amino)pyridazin-3-yl]-4-hydroxybenzamide;

4-fluoro-3-[6-({[3-fluoro-1-(3-fluoro(2-pyridyl))cyclobutyl]methyl}amino)pyridazin-3-yl]benzoic acid;

N-((2R)-2,3-dihydroxypropyl){4-fluoro-3-[6-({[3-fluoro-1-(3-fluoro(2-pyridyl))cyclobutyl]methyl}amino)pyridazin-3-yl]phenyl}carboxamide;

N-((3R)pyrrolidin-3-yl){4-fluoro-3-[6-({[3-fluoro-1-(3-fluoro(2-pyridyl))cyclobutyl]methyl}amino)pyridazin-3-yl]phenyl}carboxamide;

N-((3S)pyrrolidin-3-yl){4-fluoro-3-[6-({[3-fluoro-1-(3-fluoro(2-pyridyl))cyclobutyl]methyl}amino)pyridazin-3-yl]phenyl}carboxamide;

[6-3-(2H-1,2,3,4-tetraazol-5-yl)phenyl)pyridazin-3-yl]{[3-fluoro-1-(3-fluoro(2-pyridyl))cyclobutyl]methyl}amine;

2-[6-({[(3-fluoro-2-pyridyl)cyclobutyl]methyl}amino)pyridazin-3-yl]-1,3-thiazole-5-sulfonamide;

(aminocyclopropyl)-N-({2-[6-({[(3-fluoro(2-pyridyl))cyclobutyl]methyl}amino)pyridazin-3-yl](1,3-thiazol-5-yl)}methyl)carboxamide;

(N-{1-[N-({2-[6-({[(3-fluoro(2-pyridyl))cyclobutyl]methyl}amino)pyridazin-3-yl](1,3-thiazol-5-yl)}methyl)carbamoyl]-isopropyl}carbamoyloxy)ethyl 2-methylpropanoate;

3-[6-({[3-fluoro-1-(3-fluoro(2-pyridyl))cyclobutyl]methyl}amino)pyridazin-3-yl]benzoic acid;

3-(6-{[(3-fluoro-1-(2-pyridyl)cyclobutyl)methyl]amino}pyridazin-3-yl)benzoic acid;

3-(6-{[(3-fluoro-1-(2-pyridyl)cyclobutyl)methyl]amino}pyridazin-3-yl)benzoic acid;

3-[6-({[3-fluoro-1-(3-fluoro(2-pyridyl))cyclobutyl]methyl}amino)pyridazin-3-yl]benzenecarbonitrile;

N-((2S)-2,3-dihydroxypropyl){4-fluoro-3-[6-({[3-fluoro-1-(3-fluoro(2-pyridyl))cyclobutyl]methyl}amino)pyridazin-3-yl]phenyl}carboxamide;

methyl 4-fluoro-3-[6-({[3-fluoro-1-(3-fluoro(2-pyridyl))cyclobutyl]methyl}amino)pyridazin-3-yl]benzoate;

{4-fluoro-3-[6-({[3-fluoro-1-(3-fluoro(2-pyridyl))cyclobutyl]methyl}amino)pyridazin-3-yl]phenyl}-N-methylcarboxamide;

{4-fluoro-3-[6-({[3-fluoro-1-(3-fluoro(2-pyridyl))cyclobutyl]methyl}amino)pyridazin-3-yl]phenyl}-N-(methylethyl)carboxamide;

methyl 3-[6-({[3-fluoro-1-(3-fluoro(2-pyridyl))cyclobutyl]methyl}amino)pyridazin-3-yl]benzoate;

methylethyl 4-fluoro-3-[6-({[3-fluoro-1-(3-fluoro(2-pyridyl))cyclobutyl]methyl}amino)pyridazin-3-yl]benzoate;

6-[6-({[(3-fluoro-2-pyridyl)cyclobutyl]methyl}amino)pyridazin-3-yl]imidazo[2,1-b]1,3-thiazoline-3-carboxamide;

6-[6-({[(3-fluoro-2-pyridyl)cyclobutyl]methyl}amino)pyridazin-3-yl]imidazo[2,1-b]1,3-thiazoline-3-carboxylic acid;

6-[6-({[3-fluoro-1-(3-fluoro(2-pyridyl))cyclobutyl]methyl}amino)pyridazin-3-yl]imidazo[2,1-b]1,3-thiazoline-3-carboxamide;

3-[6-({[3-fluoro-1-(3-fluoro(2-pyridyl))cyclobutyl]methyl}amino)pyridazin-3-yl]benzenesulfonamide;

{5-[6-({[3-fluoro-1-(3-fluoro(2-pyridyl))cyclobutyl]methyl}amino)pyridazin-3-yl](1H-indazol-3-yl)}(methylsulfonyl)amine;

{[3-fluoro-1-(3-fluoro(2-pyridyl))cyclobutyl]methyl}{6-[3-(methylamino)(1H-indazol-5-yl)]pyridazin-3-yl}amine;

{6-[3-(ethylamino)(1H-indazol-5-yl)]pyridazin-3-yl}{[3-fluoro-1-(3-fluoro(2-pyridyl))cyclobutyl]methyl}amine;

[6-(3-amino(1H-indazol-5-yl))pyridazin-3-yl]{[3-fluoro-1-(3-fluoro(2-pyridyl))cyclobutyl]methyl}amine;

ethyl 2-fluoro-5-[6-({[3-fluoro-1-(3-fluoro(2-pyridyl))cyclobutyl]methyl}amino)pyridazin-3-yl]benzoate;

2-fluoro-5-[6-({[3-fluoro-1-(3-fluoro(2-pyridyl))cyclobutyl]methyl}amino)pyridazin-3-yl]benzoic acid;

2-{4-fluoro-3-[6-({[(3-fluoro(2-pyridyl))cyclobutyl]methyl}amino)pyridazin-3-yl]phenyl}acetamide;

methyl 2-{4-fluoro-3-[6-({[(3-fluoro(2-pyridyl))cyclobutyl]methyl}amino)pyridazin-3-yl]phenyl}acetate;
N-({4-fluoro-3-[6-({[3-fluoro-1-(3-fluoro(2-pyridyl))cyclobutyl]methyl}amino)pyridazin-3-yl]phenyl}methyl)acetamide;
N-({3-[6-({[3-fluoro-1-(3-fluoro(2-pyridyl))cyclobutyl]methyl}amino)pyridazin-3-yl]phenyl}methyl)acetamide;
{2-fluoro-5-[6-({[3-fluoro-1-(3-fluoro(2-pyridyl))cyclobutyl]methyl}amino)pyridazin-3-yl]phenyl}-N-methylcarboxamide;
N-ethyl{2-fluoro-5-[6-({[3-fluoro-1-(3-fluoro(2-pyridyl))cyclobutyl]methyl}amino)pyridazin-3-yl]phenyl}carboxamide;
methyl 5-[6-({[3-fluoro-1-(3-fluoro(2-pyridyl))cyclobutyl]methyl}amino)pyridazin-3-yl]-2-(methylamino)benzoate;
ethyl 5-[6-({[3-fluoro-1-(3-fluoro(2-pyridyl))cyclobutyl]methyl}amino)pyridazin-3-yl]-2-(methylamino)benzoate;
{3-[6-({[3-fluoro-1-(3-fluoro(2-pyridyl))cyclobutyl]methyl}amino)pyridazin-3-yl]phenyl}methan-1-ol;
((2S)azetidin-2-yl)-N-({2-[6-({[(3-fluoro(2-pyridyl))cyclobutyl]methyl}amino)pyridazin-3-yl](1,3-thiazol-5-yl)}methyl)carboxamide;
ethyl 2-{2-[6-({[(3-fluoro-2-pyridyl)cyclobutyl]methyl}amino)pyridazin-3-yl]-1,3-thiazol-4-yl}acetate;
2-{2-[6-({[(3-fluoro-2-pyridyl)cyclobutyl]methyl}amino)pyridazin-3-yl]-1,3-thiazol-4-yl}acetamide;
2-{2-[6-({[(3-fluoro(2-pyridyl))cyclobutyl]methyl}amino)pyridazin-3-yl](1,3-thiazol-5-yl)}-2-methylpropanenitrile;
2-{2-[6-({[(3-fluoro(2-pyridyl))cyclobutyl]methyl}amino)pyridazin-3-yl](1,3-thiazol-5-yl)}-2-methylpropanamide;
3-{2-[6-({[(3-fluoro-2-pyridyl)cyclobutyl]methyl}amino)pyridazin-3-yl]-1,3-thiazol-5-yl}propanamide;
3-{2-[6-({[(3-fluoro-2-pyridyl)cyclobutyl]methyl}amino)pyridazin-3-yl]-1,3-thiazol-5-yl}propanoic acid;
methyl 3-{2-[6-({[(3-fluoro-2-pyridyl)cyclobutyl]methyl}amino)pyridazin-3-yl]-1,3-thiazol-5-yl}propanoate;
2-amino-N-({2-[6-({[(3-fluoro(2-pyridyl))cyclobutyl]methyl}amino)pyridazin-3-yl](1,3-thiazol-5-yl)}methyl)-2-methyl-N-methylpropanamide;
2-{2-[6-({[3-fluoro-1-(3-fluoro(2-pyridyl))cyclobutyl]methyl}amino)pyridazin-3-yl]-1,3-thiazol-5-yl}acetamide;
2-{2-[6-({[3-fluoro-1-(3-fluoro(2-pyridyl))cyclobutyl]methyl}amino)pyridazin-3-yl]-1,3-thiazol-5-yl}acetic acid;
(3-aminooxetan-3-yl)-N-({2-[6-({[(3-fluoro(2-pyridyl))cyclobutyl]methyl}amino)pyridazin-3-yl](1,3-thiazol-5-yl)}methyl)carboxamide;
{3-[6-({[(3-fluoro(2-pyridyl))cyclobutyl]methyl}amino)pyridazin-3-yl]phenyl}-N-methylcarboxamide;
{4-fluoro-3-[6-({[(3-fluoro(2-pyridyl))cyclobutyl]methyl}amino)pyridazin-3-yl]phenyl}-N-methylcarboxamide;
N-({5-[6-({[(3-fluoro-2-pyridyl)cyclobutyl]methyl}amino)pyridazin-3-yl]-1,3-thiazol-2-yl}methyl)acetamide;
N-({4-[6-({[(3-fluoro-2-pyridyl)cyclobutyl]methyl}amino)pyridazin-3-yl]-1,3-thiazol-2-yl}methyl)acetamide;
2-{2-[6-({[1-(3-chloro(2-pyridyl))-3-fluorocyclobutyl]methyl}amino)pyridazin-3-yl]-1,3-thiazol-5-yl}acetamide;
{3-[6-({[3-fluoro-1-(3-fluoro(2-pyridyl))cyclobutyl]methyl}amino)pyridazin-3-yl]phenyl}-N-methylcarboxamide;
2-{2-[6-({[(3-chloro-2-pyridyl)cyclobutyl]methyl}amino)pyridazin-3-yl]-1,3-thiazol-5-yl}acetamide;
2-{2-[6-({[(3-fluoro-2-pyridyl)cyclobutyl]methyl}amino)pyridazin-3-yl]-1,3-thiazol-5-yl}acetic acid;
2-{2-[6-({[(3-fluoro(2-pyridyl))cyclobutyl]methyl}amino)pyridazin-3-yl](1,3-thiazol-5-yl)}-N-methylacetamide;
2-{2-[6-({[(3-fluoro(2-pyridyl))cyclobutyl]methyl}amino)pyridazin-3-yl](1,3-thiazol-5-yl)}-N,N-dimethylacetamide;
N-({2-[6-({[(3-fluoro(2-pyridyl))cyclobutyl]methyl}amino)pyridazin-3-yl](1,3-thiazol-5-yl)}methyl)-2-methyl-2-(methylamino)propanamide;
N-ethyl{4-fluoro-3-[6-({[3-fluoro-1-(3-fluoro(2-pyridyl))cyclobutyl]methyl}amino)pyridazin-3-yl]phenyl}carboxamide;
N-(2-fluoroethyl){4-fluoro-3-[6-({[3-fluoro-1-(3-fluoro(2-pyridyl))cyclobutyl]methyl}amino)pyridazin-3-yl]phenyl}carboxamide;
N-(2,2-difluoroethyl){4-fluoro-3-[6-({[3-fluoro-1-(3-fluoro(2-pyridyl))cyclobutyl]methyl}amino)pyridazin-3-yl]phenyl}carboxamide;
{4-fluoro-3-[6-({[3-fluoro-1-(3-fluoro(2-pyridyl))cyclobutyl]methyl}amino)pyridazin-3-yl]phenyl}-N-(2,2,2-trifluoroethyl)carboxamide;
{4-fluoro-3-[6-({[3-fluoro-1-(3-fluoro(2-pyridyl))cyclobutyl]methyl}amino)pyridazin-3-yl]phenyl}-N,N-dimethylcarboxamide;
3-[6-({[(3-fluoro(2-pyridyl))cyclobutyl]methyl}amino)pyridazin-3-yl]-4-hydroxybenzoic acid;
{3-[6-({[(3-fluoro(2-pyridyl))cyclobutyl]methyl}amino)pyridazin-3-yl]-4-hydroxyphenyl}-N-methylcarboxamide;
3-[6-({[(3-fluoro(2-pyridyl))cyclobutyl]methyl}amino)pyridazin-3-yl]-4-hydroxybenzamide;
5-[6-({[(3-fluoro(2-pyridyl))cyclobutyl]methyl}amino)pyridazin-3-yl]-2-methoxypyridine-3-carbonitrile;
5-[6-({[(3-fluoro(2-pyridyl))cyclobutyl]methyl}amino)pyridazin-3-yl]-2-methoxypyridine-3-carboxamide;
5-[6-({[3-fluoro-1-(3-fluoro(2-pyridyl))cyclobutyl]methyl}amino)pyridazin-3-yl]-2-hydroxybenzoic acid;
{3-[6-({[3-fluoro-1-(3-fluoro(2-pyridyl))cyclobutyl]methyl}amino)pyridazin-3-yl]phenyl}-N-[2-hydroxy-1-(hydroxymethyl)ethyl]carboxamide;
{5-[6-({[3-fluoro-1-(3-fluoro(2-pyridyl))cyclobutyl]methyl}amino)pyridazin-3-yl]-2-hydroxyphenyl}-N-methylcarboxamide;
5-[6-({[3-fluoro-1-(3-fluoro(2-pyridyl))cyclobutyl]methyl}amino)pyridazin-3-yl]-2-hydroxybenzamide;
{3-[6-({[3-fluoro-1-(3-fluoro(2-pyridyl))cyclobutyl]methyl}amino)pyridazin-3-yl]-4-hydroxyphenyl}-N-methylcarboxamide;
{5-[6-({[(3-fluoro(2-pyridyl))cyclobutyl]methyl}amino)pyridazin-3-yl](2-thienyl)}-N-methylcarboxamide;

2-[6-({[(3-fluoro-2-pyridyl)cyclobutyl]methyl}amino) pyridazin-3-yl]-4,5,6-trihydrocyclopenta[1,2-d]1,3-thiazole-4-carboxamide;

2-[6-({[(3-fluoro-2-pyridyl)cyclobutyl]methyl}amino) pyridazin-3-yl]-4,5,6-trihydrocyclopenta[1,2-d]1,3-thiazole-4-carboxylic acid;

{[(3-fluoro(2-pyridyl))cyclobutyl]methyl}(6-(4,5,6,7-tetrahydro-1,3-thiazolo[5,4-c]pyridin-2-yl)pyridazin-3-yl)amine;

N-{2-[6-({[(3-fluoro(2-pyridyl))cyclobutyl] methyl}amino)pyridazin-3-yl](4,5,6-trihydrocyclopenta [2,3-d]1,3-thiazol-4-yl)}methoxycarboxamide;

2-[6-({[(3-fluoro-2-pyridyl)cyclobutyl]methyl}amino) pyridazin-3-yl]-4,5,6,7-tetrahydro-1,3-thiazolo[5,4-c] pyridine-5-carboxamide;

5-acetyl-2-[6-({[(3-fluoro(2-pyridyl))cyclobutyl] methyl}amino)pyridazin-3-yl]-4,5,6,7-tetrahydro-1,3-thiazolo[5,4-c]pyridine;

2-[6-({[(3-fluoro(2-pyridyl))cyclobutyl]methyl}amino) pyridazin-3-yl]-5-(methylsulfonyl)-4,5,6,7-tetrahydro-1,3-thiazolo[5,4-c]pyridine;

{5-[6-({[3-fluoro-1-(3-fluoro(2-pyridyl))cyclobutyl] methyl}amino)pyridazin-3-yl]-2-hydroxyphenyl}-N,N-dimethylcarboxamide;

4-[6-({[3-fluoro-1-(3-fluoro(2-pyridyl))cyclobutyl] methyl}amino)pyridazin-3-yl]isoindolin-1-one;

5-[6-({[3-fluoro-1-(3-fluoro(2-pyridyl))cyclobutyl] methyl}amino)pyridazin-3-yl]isoindolin-1-one;

6-[6-({[3-fluoro-1-(3-fluoro(2-pyridyl))cyclobutyl] methyl}amino)pyridazin-3-yl]isoindolin-1-one;

[6-(6-amino(4,5,6,7-tetrahydrobenzothiazol-2-yl))pyridazin-3-yl]{[(3-fluoro(2-pyridyl))cyclobutyl] methyl}amine;

amino-N-{2-[6-({[(3-fluoro(2-pyridyl))cyclobutyl] methyl}amino)pyridazin-3-yl](4,5,6,7-tetrahydrobenzothiazol-6-yl)}amide;

N-{3-fluoro-4-[6-({[3-fluoro-1-(3-fluoro(2-pyridyl))cyclobutyl]methyl}amino)pyridazin-3-yl]phenyl}(methylamino)carboxamide;

N-{4-[6-({[3-fluoro-1-(3-fluoro(2-pyridyl))cyclobutyl] methyl}amino)pyridazin-3-yl]phenyl}-N-methyl(methylamino)carboxamide;

2-{2-[6-({[1-(3-chloro(2-pyridyl))-3-fluorocyclobutyl] methyl}amino)pyridazin-3-yl](1,3-thiazol-5-yl)}-N-methylacetamide;

N-{4-[6-({[3-fluoro-1-(3-fluoro(2-pyridyl))cyclobutyl] methyl}amino)pyridazin-3-yl]phenyl}(methylamino) carboxamide;

2-{2-[6-({[(3-chloro(2-pyridyl))cyclobutyl] methyl}amino)pyridazin-3-yl](1,3-thiazol-5-yl)}-N-methylacetamide;

N-cyclopropyl{4-fluoro-3-[6-({[3-fluoro-1-(3-fluoro(2-pyridyl))cyclobutyl]methyl}amino)pyridazin-3-yl] phenyl}carboxamide;

{4-fluoro-5-[6-({[3-fluoro-1-(3-fluoro(2-pyridyl))cyclobutyl]methyl}amino)pyridazin-3-yl]-2-hydroxyphenyl}-N-methylcarboxamide;

4-fluoro-5-[6-({[3-fluoro-1-(3-fluoro(2-pyridyl))cyclobutyl]methyl}amino)pyridazin-3-yl]-2-hydroxybenzamide;

3-[6-({[(3-fluoro(2-pyridyl))cyclobutyl]methyl}amino)-4-methylpyridazin-3-yl]benzenecarbonitrile;

3-[6-({[(3-fluoro(2-pyridyl))cyclobutyl]methyl}amino)-4-methylpyridazin-3-yl]benzamide;

N-cyclobutyl{4-fluoro-3-[6-({[3-fluoro-1-(3-fluoro(2-pyridyl))cyclobutyl]methyl}amino)pyridazin-3-yl] phenyl}carboxamide;

4-fluoro-3-[6-({[3-fluoro(2-pyridyl))cyclobutyl] methyl}amino)-4-methylpyridazin-3-yl]benzamide;

N-(3,3-difluorocyclobutyl){4-fluoro-3-[6-({[3-fluoro-1-(3-fluoro(2-pyridyl))cyclobutyl]methyl}amino)pyridazin-3-yl]phenyl}carboxamide;

4-fluoro-3-[6-({[3-fluoro-1-(3-fluoro(2-pyridyl))cyclobutyl]methyl}amino)pyridazin-3-yl]-2-hydroxybenzamide;

2-[6-({[(3-fluoro(2-pyridyl))cyclobutyl]methyl}amino)-4-methylpyridazin-3-yl]-1,3-thiazole-5-carboxamide;

3-[6-({[(3-fluoro(2-pyridyl))cyclobutyl]methyl}amino)-5-methylpyridazin-3-yl]benzamide;

N-cyclopropyl{3-[6-({[3-fluoro-1-(3-fluoro(2-pyridyl)) cyclobutyl]methyl}amino)pyridazin-3-yl] phenyl}carboxamide;

[6-(2-aminopyrimidin-5-yl)pyridazin-3-yl]{[3-fluoro-1-(3-fluoro(2-pyridyl))cyclobutyl]methyl}amine;

N-azetidin-3-yl{3-[6-({[3-fluoro-1-(3-fluoro(2-pyridyl)) cyclobutyl]methyl}amino)pyridazin-3-yl] phenyl}carboxamide;

N-(1-acetylazetidin-3-yl){3-[6-({[3-fluoro-1-(3-fluoro(2-pyridyl))cyclobutyl]methyl}amino)pyridazin-3-yl] phenyl}carboxamide;

{3-[6-({[3-fluoro-1-(3-fluoro(2-pyridyl))cyclobutyl] methyl}amino)pyridazin-3-yl]phenyl}-N-[1-(methylsulfonyl)azetidin-3-yl]carboxamide;

{3-[6-({[3-fluoro-1-(3-fluoro(2-pyridyl))cyclobutyl] methyl}amino)pyridazin-3-yl]phenyl}-N-(2-hydroxy-2-methylpropyl)carboxamide;

{3-[6-({[3-fluoro-1-(3-fluoro(2-pyridyl))cyclobutyl] methyl}amino)pyridazin-3-yl]phenyl}-N-(1-methylazetidin-3-yl)carboxamide;

{3-[6-({[3-fluoro-1-(3-fluoro(2-pyridyl))cyclobutyl] methyl}amino)pyridazin-3-yl]phenyl}-N-oxetan-3-yl-carboxamide;

2-{2-[6-({[(3-fluoro(2-pyridyl))cyclobutyl] methyl}amino)-4-methylpyridazin-3-yl]-1,3-thiazol-5-yl}acetic acid;

{2-[6-({[(3-fluoro(2-pyridyl))cyclobutyl]methyl}amino)-4-methylpyridazin-3-yl]-1,3-thiazol-5-yl}methan-1-ol;

2-{2-[6-({[(3-fluoro(2-pyridyl))cyclobutyl] methyl}amino)-4-methylpyridazin-3-yl](1,3-thiazol-5-yl)}-N-methylacetamide;

2-{2-[6-({[(3-fluoro(2-pyridyl))cyclobutyl] methyl}amino)-4-methylpyridazin-3-yl]-1,3-thiazol-5-yl}acetamide;

{4-fluoro-3-[6-({[3-fluoro-1-(3-fluoro(2-pyridyl))cyclobutyl]methyl}amino)pyridazin-3-yl]phenyl}-N-(1-methylazetidin-3-yl)carboxamide;

N-(1-acetylazetidin-3-yl){4-fluoro-3-[6-({[3-fluoro-1-(3-fluoro(2-pyridyl))cyclobutyl]methyl}amino)pyridazin-3-yl]phenyl}carboxamide;

{3-[6-({[3-fluoro-1-(3-fluoro(2-pyridyl))cyclobutyl] methyl}amino)pyridazin-3-yl]phenyl}-N-(3-hydroxy-cyclobutyl)carboxamide;

{[(3-fluoro(2-pyridyl))cyclobutyl]methyl}{6-[5-(piperazinylmethyl)(1,3-thiazol-2-yl)]pyridazin-3-yl}amine;

{[(3-fluoro(2-pyridyl))cyclobutyl]methyl}{6-[5-(morpholin-4-ylmethyl)(1,3-thiazol-2-yl)]pyridazin-3-yl}amine;

4-({2-[6-({[(3-fluoro-2-pyridyl)cyclobutyl] methyl}amino)pyridazin-3-yl]-1,3-thiazol-5-yl}methyl)-1,4-thiazaperhydroine-1,1-dione;

{[(3-fluoro(2-pyridyl))cyclobutyl]methyl}(6-{5-[(4-methylpiperazinyl)methyl](1,3-thiazol-2-yl)}pyridazin-3-yl)amine;

{[(3-fluoro(2-pyridyl))cyclobutyl]methyl}[6-(5-{[4-(2,2,2-trifluoroethyl)piperazinyl]methyl}(1,3-thiazol-2-yl))pyridazin-3-yl]amine;

1-acetyl-4-({2-[6-({[(3-fluoro(2-pyridyl))cyclobutyl]methyl}amino)pyridazin-3-yl](1,3-thiazol-5-yl)}methyl)piperazine;

1-({2-[6-({[(3-fluoro(2-pyridyl))cyclobutyl]methyl}amino)pyridazin-3-yl](1,3-thiazol-5-yl)}methyl)-4-(methylsulfonyl)piperazine;

[(2S)-1-({2-[6-({[(3-fluoro(2-pyridyl))cyclobutyl]methyl}amino)pyridazin-3-yl](1,3-thiazol-5-yl)}methyl)piperazin-2-yl]methan-1-ol;

[(2R)-1-({2-[6-({[(3-fluoro(2-pyridyl))cyclobutyl]methyl}amino)pyridazin-3-yl](1,3-thiazol-5-yl)}methyl)piperazin-2-yl]methan-1-ol;

N-(2H-3,4,5,6-tetrahydropyran-4-yl){3-[6-({[3-fluoro-1-(3-fluoro(2-pyridyl))cyclobutyl]methyl}amino)pyridazin-3-yl]phenyl}carboxamide;

{3-[6-({[3-fluoro-1-(3-fluoro(2-pyridyl))cyclobutyl]methyl}amino)pyridazin-3-yl]phenyl}-N-(3-hydroxy-3-methylcyclobutyl)carboxamide;

N-((3S)oxolan-3-yl){3-[6-({[3-fluoro-1-(3-fluoro(2-pyridyl))cyclobutyl]methyl}amino)pyridazin-3-yl]phenyl}carboxamide;

N-((3R)oxolan-3-yl){3-[6-({[3-fluoro-1-(3-fluoro(2-pyridyl))cyclobutyl]methyl}amino)pyridazin-3-yl]phenyl}carboxamide;

N-((3S,4S)-4-hydroxy-1,1-dioxothiolan-3-yl){3-[6-({[3-fluoro-1-(3-fluoro(2-pyridyl))cyclobutyl]methyl}amino)pyridazin-3-yl]phenyl}carboxamide;

N-(1,1-dioxothiolan-3-yl){3-[6-({[3-fluoro-1-(3-fluoro(2-pyridyl))cyclobutyl]methyl}amino)pyridazin-3-yl]phenyl}carboxamide;

3-[6-({[3-fluoro-1-(3-fluoro(2-pyridyl))cyclobutyl]methyl}amino)pyridazin-3-yl]-2-hydroxybenzamide;

3-[6-({[(3-fluoro(2-pyridyl))cyclobutyl]methyl}amino)pyridazin-3-yl]-2-hydroxybenzamide;

5-amino-3-[6-({[3-fluoro-1-(3-fluoro(2-pyridyl))cyclobutyl]methyl}amino)pyridazin-3-yl]benzenecarbonitrile;

3-[6-({[3-fluoro-1-(3-fluoro(2-pyridyl))cyclobutyl]methyl}amino)pyridazin-3-yl]-5-(trifluoromethyl)benzamide;

5-chloro-3-[6-({[3-fluoro-1-(3-fluoro(2-pyridyl))cyclobutyl]methyl}amino)pyridazin-3-yl]benzamide;

3-[6-({[3-fluoro-1-(3-fluoro(2-pyridyl))cyclobutyl]methyl}amino)pyridazin-3-yl]-5-hydroxybenzamide;

5-amino-3-[6-({[3-fluoro-1-(3-fluoro(2-pyridyl))cyclobutyl]methyl}amino)pyridazin-3-yl]benzamide;

{3-[6-({[3-fluoro-1-(3-fluoro(2-pyridyl))cyclobutyl]methyl}amino)pyridazin-3-yl]-2-hydroxyphenyl}-N-methylcarboxamide;

3-[6-({[3-fluoro-1-(3-fluoro(2-pyridyl))cyclobutyl]methyl}amino)pyridazin-3-yl]-2-hydroxybenzenecarbonitrile;

3-[6-({[3-fluoro-1-(3-fluoro(2-pyridyl))cyclobutyl]methyl}amino)pyridazin-3-yl]-2-methoxybenzenecarbonitrile;

3-[6-({[3-fluoro-1-(3-fluoro(2-pyridyl))cyclobutyl]methyl}amino)pyridazin-3-yl]-2-hydroxybenzoic acid;

5-[6-({[3-fluoro-1-(3-fluoro(2-pyridyl))cyclobutyl]methyl}amino)pyridazin-3-yl]-2-methoxybenzamide;

N-(1,1-dioxothietan-3-yl){3-[6-({[3-fluoro-1-(3-fluoro(2-pyridyl))cyclobutyl]methyl}amino)pyridazin-3-yl]phenyl}carboxamide;

4-fluoro-3-[6-({[(3-fluoro(2-pyridyl))cyclobutyl]methyl}amino)pyridazin-3-yl]-2-hydroxybenzamide;

4-fluoro-5-[6-({[(3-fluoro(2-pyridyl))cyclobutyl]methyl}amino)pyridazin-3-yl]-2-hydroxybenzamide;

{3-[6-({[3-fluoro-1-(3-fluoro(2-pyridyl))cyclobutyl]methyl}amino)pyridazin-3-yl]phenyl}-N-[(hydroxycyclopropyl)methyl]carboxamide;

{3-[6-({[3-fluoro-1-(3-fluoro(2-pyridyl))cyclobutyl]methyl}amino)pyridazin-3-yl]-5-methylphenyl}-N-methylcarboxamide;

3-[6-({[3-fluoro-1-(3-fluoro(2-pyridyl))cyclobutyl]methyl}amino)pyridazin-3-yl]-5-methylbenzamide;

3-[6-({[(3-fluoro(2-pyridyl))cyclobutyl]methyl}amino)pyridazin-3-yl]-2-hydroxy-5-methylbenzamide;

3-[6-({[(3-fluoro(2-pyridyl))cyclobutyl]methyl}amino)pyridazin-3-yl]-2-hydroxy-5-methylbenzenecarbonitrile;

5-bromo-3-[6-({[(3-fluoro(2-pyridyl))cyclobutyl]methyl}amino)pyridazin-3-yl]-2-hydroxybenzenecarbonitrile;

3-[6-({[3-fluoro-1-(3-fluoro(2-pyridyl))cyclobutyl]methyl}amino)pyridazin-3-yl]-2-methoxybenzamide;

{5-bromo-3-[6-({[3-fluoro-1-(3-fluoro(2-pyridyl))cyclobutyl]methyl}amino)pyridazin-3-yl]-2-hydroxyphenyl}-N-methylcarboxamide;

{3-[6-({[3-fluoro-1-(3-fluoro(2-pyridyl))cyclobutyl]methyl}amino)pyridazin-3-yl]-2-hydroxy-5-methylphenyl}-N-methylcarboxamide;

methyl 5-[6-({[3-fluoro-1-(3-fluoro(2-pyridyl))cyclobutyl]methyl}amino)pyridazin-3-yl]indole-2-carboxylate;

5-[6-({[3-fluoro-1-(3-fluoro(2-pyridyl))cyclobutyl]methyl}amino)pyridazin-3-yl]indole-2-carboxamide;

5-[6-({[3-fluoro-1-(3-fluoro(2-pyridyl))cyclobutyl]methyl}amino)pyridazin-3-yl]indole-2-carboxylic acid;

{5-[6-({[3-fluoro-1-(3-fluoro(2-pyridyl))cyclobutyl]methyl}amino)pyridazin-3-yl]indol-2-yl}-N-methylcarboxamide;

[6-(6-amino(3-pyridyl))pyridazin-3-yl]{[3-fluoro-1-(3-fluoro(2-pyridyl))cyclobutyl]methyl}amine;

{[3-fluoro-1-(3-fluoro(2-pyridyl))cyclobutyl]methyl}{6-[6-(methylamino)(3-pyridyl)]pyridazin-3-yl}amine;

{6-[6-(cyclopropylamino)(3-pyridyl)]pyridazin-3-yl}{[3-fluoro-1-(3-fluoro(2-pyridyl))cyclobutyl]methyl}amine;

{6-[6-amino-5-(trifluoromethyl)(3-pyridyl)]pyridazin-3-yl}{[3-fluoro-1-(3-fluoro(2-pyridyl))cyclobutyl]methyl}amine;

[N-({2-[6-({[(3-fluoro-2-pyridyl)cyclobutyl]methyl}amino)pyridazin-3-yl]-1,3-thiazol-5-yl}methyl)carbamoyl]methyl acetate;

[N-({2-[6-({[(3-fluoro-2-pyridyl)cyclobutyl]methyl}amino)pyridazin-3-yl]-1,3-thiazol-5-yl}methyl)carbamoyl]methyl (2S)-2-amino-3-methylbutanoate;

[N-({2-[6-({[(3-fluoro-2-pyridyl)cyclobutyl]methyl}amino)pyridazin-3-yl]-1,3-thiazol-5-yl}methyl)carbamoyl]methyl (2S)-2-aminopropanoate;

{[3-fluoro-1-(3-fluoro(2-pyridyl))cyclobutyl]methyl}{6-[6-(methoxy-5-methyl(3-pyridyl))pyridazin-3-yl]amine;

[6-(6-amino-5-methyl(3-pyridyl))pyridazin-3-yl]{[3-fluoro-1-(3-fluoro(2-pyridyl))cyclobutyl]methyl}amine;

—N-({2-[6-({[(3-fluoro(2-pyridyl))cyclobutyl]methyl}amino)pyridazin-3-yl](1,3-thiazol-5-yl)}methyl)-2-hydroxypropanamide;

—N-({2-[6-({[(3-fluoro(2-pyridyl))cyclobutyl]
methyl}amino)pyridazin-3-yl](1,3-thiazol-5-yl)}me-
thyl)-2-hydroxypropanamide;

2-[({2-[6-({[(3-fluoro-2-pyridyl)cyclobutyl]
methyl}amino)pyridazin-3-yl]-1,3-thiazol-5-
yl}methyl)amino]ethan-1-ol;

N-({2-[6-({[(3-fluoro(2-pyridyl))cyclobutyl]
methyl}amino)pyridazin-3-yl](1,3-thiazol-5-yl)}me-
thyl)-2-hydroxy-N-methylacetamide;

[N-({2-[6-({[(3-fluoro-2-pyridyl)cyclobutyl]
methyl}amino)pyridazin-3-yl]-1,3-thiazol-5-
yl}methyl)carbamoyl]methyl (2S)-2-((2S)-2-amino-
propanoylamino)propanoate; and

[N-({2-[6-({[(3-fluoro-2-pyridyl)cyclobutyl]
methyl}amino)pyridazin-3-yl]-1,3-thiazol-5-
yl}methyl)carbamoyl]methyl (2S)-2-((2S)-2-amino-3-
methylbutanoylamino)-3-methylbutanoate;

or a pharmaceutically acceptable salt thereof.

49. A pharmaceutical composition comprising a compound of claim 1, or a pharmaceutically acceptable salt thereof.

50. The pharmaceutical composition of claim 49, wherein the pharmaceutical composition is formulated for oral, sublingual, subcutaneous, parenteral, intravenous, intranasal, topical, transdermal, intraperitoneal, intramuscular, intrapulmonary, vaginal, rectal, or intraocular administration.

51. The pharmaceutical composition of claim 50, wherein the pharmaceutical composition is formulated for oral administration.

* * * * *